US007625906B2

(12) United States Patent
Jones et al.

(10) Patent No.: US 7,625,906 B2
(45) Date of Patent: *Dec. 1, 2009

(54) FUSED-ARYL AND HETEROARYL DERIVATIVES AS MODULATORS OF METABOLISM AND THE PROPHYLAXIS AND TREATMENT OF DISORDERS RELATED THERETO

(75) Inventors: Robert M. Jones, San Diego, CA (US); Graeme Semple, San Diego, CA (US); Yifeng Xiong, San Diego, CA (US); Young-Jun Shin, San Digeo, CA (US); Albert S. Ren, San Diego, CA (US); Imelda Calderon, San Diego, CA (US); Beatriz Fioravanti, Tucson, AZ (US); Carleton R. Sage, Cardiff-by-the-Sea, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/355,785

(22) Filed: Feb. 16, 2006

(65) Prior Publication Data

US 2006/0142262 A1 Jun. 29, 2006

Related U.S. Application Data

(63) Continuation of application No. 10/890,549, filed on Jul. 13, 2004, now Pat. No. 7,132,426.

(60) Provisional application No. 60/487,443, filed on Jul. 14, 2003, provisional application No. 60/510,644, filed on Oct. 10, 2003.

(51) Int. Cl.
*A61K 31/519* (2006.01)
*C07D 487/00* (2006.01)

(52) U.S. Cl. .................... 514/262.1; 544/262
(58) Field of Classification Search .............. 544/262; 514/262.1
See application file for complete search history.

(56) References Cited

U.S. PATENT DOCUMENTS

| 4,139,705 | A | 2/1979 | Dunbar et al. |
|---|---|---|---|
| 4,189,579 | A | 2/1980 | Begin et al. |
| 4,343,804 | A | 8/1982 | Munison et al. |
| 5,952,504 | A | 9/1999 | Yoo et al. |
| 6,060,478 | A | 5/2000 | Gilligan |
| 6,107,301 | A | 8/2000 | Aldrich et al. |
| 6,350,750 | B1 | 2/2002 | Den Hartog et al. |
| 6,506,762 | B1 | 1/2003 | Horvath et al. |
| 6,552,192 | B1 | 4/2003 | Hanus et al. |
| 7,083,933 | B1 | 8/2006 | Griffin |
| 2005/0043327 | A1 | 2/2005 | Coe et al. |

FOREIGN PATENT DOCUMENTS

| EP | 1040831 | 10/2000 |
|---|---|---|
| EP | 1097709 | 5/2001 |
| EP | 1287133 | 3/2003 |
| EP | 1340749 A1 | 9/2003 |
| EP | 1475094 | 11/2004 |
| JP | 61 057587 | 3/1986 |
| JP | 2000-038350 | 2/2000 |
| JP | 2000 038350 | 2/2000 |
| JP | 200038350 | 2/2000 |
| JP | 2004-269468 | 9/2004 |
| JP | 2004-269469 | 9/2004 |
| WO | WO 94/13677 | 6/1994 |
| WO | WO 96/35689 | 11/1996 |
| WO | WO 97/29109 | 8/1997 |
| WO | WO 97/49706 | 12/1997 |
| WO | WO 98/08846 | 3/1998 |
| WO | WO 98/08847 | 3/1998 |
| WO | WO 98/35967 | 8/1998 |
| WO | WO 2004/062665 | 8/1998 |
| WO | WO 98/47874 | 10/1998 |
| WO | WO 98/47903 | 10/1998 |
| WO | WO 99/51599 | 10/1999 |
| WO | WO 00/11003 | 3/2000 |
| WO | WO 01/23387 | 4/2001 |
| WO | WO 01/23388 | 4/2001 |
| WO | WO 01/53263 | 7/2001 |
| WO | WO 01/87892 | 11/2001 |
| WO | WO 02/02549 | 1/2002 |
| WO | WO 02/19975 | 3/2002 |
| WO | WO0219975 A1 | 3/2002 |

(Continued)

OTHER PUBLICATIONS

Dubau-Assibat et al., 1995, 60(12): 3904-6, CAS: 123:8809.*
Huang et al., "Synthesis and antiplatelet activity of phenyl quinoiones," *Bioorganic & Medicinal Chemistry* (1998) 6:1657-1662.

(Continued)

*Primary Examiner*—Rei-tsang Shiao
(74) *Attorney, Agent, or Firm*—Fish & Richardson P.C.; Lyle W. Spruce

(57) ABSTRACT

The present invention relates to certain fused aryl and heteroaryl derivatives of Formula (I) that are modulators of metabolism.

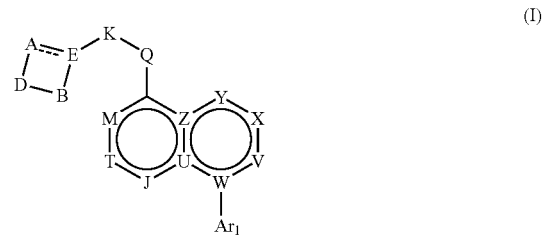

(I)

Accordingly, compounds of the present invention are useful in the prophylaxis or treatment of metabolic disorders and complications thereof, such as, diabetes and obesity.

50 Claims, 4 Drawing Sheets

FOREIGN PATENT DOCUMENTS

| | | |
|---|---|---|
| WO | WO 01/40480 | 5/2002 |
| WO | WO 02/40456 A1 | 5/2002 |
| WO | WO 02/40458 A1 | 5/2002 |
| WO | WO 02/072101 | 9/2002 |
| WO | WO 03/026661 A1 | 9/2002 |
| WO | WO 02/098878 | 12/2002 |
| WO | WO 03/000666 A1 | 1/2003 |
| WO | WO 03/032989 | 4/2003 |
| WO | WO 2004/000843 | 12/2003 |
| WO | WO2004/009596 | 1/2004 |
| WO | WO 2004/009597 | 1/2004 |
| WO | WO 2004/009602 | 1/2004 |
| WO | WO 2004/013633 A2 | 2/2004 |
| WO | WO 2004/035588 | 4/2004 |
| WO | WO2004037823 A1 | 5/2004 |
| WO | WO 2005/061489 A1 | 7/2005 |
| WO | WO2005063766 A2 | 7/2005 |
| WO | WO2005080330 | 9/2005 |
| WO | WO2006047516 | 5/2006 |

OTHER PUBLICATIONS

Chan et al., "Isoquinoline-6-Carboxamides as potent and selective anti-human cytomegalovirus (MCMV) inhibitors," *Bioorganic & Medicinal Chemistry Letter* (1999) 9:2583-2586.

Jia et al., "Design, synthesis and biological activity of novel non-amidine factor Xa inhibitors. Part I, P(1) structure-activity relationships of the substituted 1-(2-Naphthyl)-lH-pyrazole-5-carboxylamides," *Bioorganic & Medicinal Chemistry Letters* (2002)12:1651-1655.

Chen et al. "Optimization of 3-phenylpyrazolo[1,5-a]pyrimidines as potent corticotropin-releasing factor-1 antagonists with adequate lipophilicity and water solubility," *Bioorganic & Medicinal Chemistry Letters* (2004) 14:3669-3673.

Cocuzza, et al., "Use of the Suzuki reaction for the synthesis of aryl-substituted heterocycles as corticotropin-releasing hormone (CRH) antagonists," *Bioorganic & Medicinal Chemistry Letters* (1999) 9:1063-1066.

Quintela et al., "6 Dimethyalimino 1H-pyrazolo[3,4-d]pyrimidine derivatives as new inhibitors of inflammatory mediators in intact cells," *Bioorganic & Medicinal Chemistry Letters* (2003) 11:863-868.

Accession No. 2003-2415108 Chemicats. 1H-Pyrazolo [3,4-d]pyrimidin-4-amine, N-cyclohexyl-N-methyl-1-(3-methylphenyl)-, 2004 14:39:58.

Accession No. 2003-2415906 Chemicats, 1H-Pyrazolo [3,4-d]pyrimidin-4-amine, N-cyclohexyl-1- (4-methyoxphenyl) -N-methyl-, 2004 14:39:48.

Accession No. 2003-2416398 Chemicats, 1H-Pyrazolo [3,4-d]pyrimidin-4-amine,-N-cyclohexyl-1-1(2,4-dimethylphenyl)-N-methyl-, 2004 14:39:37.

Accession No. 2003-2416398 Chemicats, 1H-Pyrazolo [3,4-d]pyrimidin-4-amine,N-cyclohexyl-1-1(2,4-dimethylphenyl)N-methyl-, 2004 14:39:37.

Gilligan et al., "Corticotropin-releasing factor antagonists: recent advances and exciting prospects for the treatment of human diseases," *Current Opinion in Drug Discovery & Development* (2004) 7(4):487-497.

Quintela et al., "Pyrazolopyrimidines: synthesis, effect on histamine release from rat peritoneal mast cells and cytoxic activity," *Eur. J. Med. Chem.* (2001) 36:321-332.

Lanier et al., "Small molecule corticotrophin-releasing factor antanonists," *Expert Opin. Ther. Patents.* (2002 12(11):1619-1630.

Nesi et al., "New difunctionalized 4-nitroisoxazoles from alpha-nitroacetophenone oxime," *Heterocycles* (1985) 23(6):1465-1469.

Miyashita et al., "Preparation of heteroarenecarbonitriles by reaction of haloheteroarenes with potassium cyanide catalyzed by sodium p-toluenesulfinate," *Heterocycles* (1994) 39(1):345-350.

Robins et al., "Potential purine antagonists. IV. Synthesis of some 9-methyl-6-substituted- purines," *Department of Chemistry, New Mexico Highlands University* (1956) 79:490-494.

Baindur et al., "Solution-phase synthesis of a library of 3, 5, 7-trisubstituted 3H- [1,2,3]triazolo[4,5-d]pyrimidines," *J. Comb. Chem.* (2003) 5:653-659.

He et al., "4-(1,3-Dimethoxyprop-2-ylamino)-2,7-dimethyl-8-(2, 4-dichlorophenyl)pyrazolo[1,5-a]- 1,3,5-triazine: a potent, orally bioavailable CRF(1) receptor antagonist," *J. Med. Chem.* (2000) 43:449-456.

Giner-Sorolla et al., "The synthesis and properties of 6-mercaptomethylpurine and derivatives," *Division of Nucleoprotein Chemistry, Sloan-Kettering Institute for Cancer Research* (1965) 8:667-672.

Mueller et al., "7-Deaza-2-phenyladenines: structure-activity relationships of potent A1 selective adenosine receptor antagonists," *J. Med. Chem.* (1990) 33:2822-2828.

Thompson et al., "N6,9-disubstituted adenines: potent, selective antagonists at the A1 adenosine receptor," *J. Med. Chem.* (1991) 34:2877-2882.

Press et al., "Synthesis and SAR of 6-substituted purine derivatives as novel selective positive inotropes," *J. of Medicinal Chemistry* (1992) 35(24):4509-4515.

Rewcastle et al., "Tyrosine kinase inhibitors. 10. Isomeric 4-[(3-bromophenyl)amino]pyridod]- pyrimidines are potent ATP binding site inhibitors of the tyrosine kinase function of th eepidermal growth factor receptor," *J. Med. Chem.* (1996) 39(9):1823-1835.

Chen et al., "Design and synthesis of a series of non-peptide high-affinity human corticotropin-releasing factor1 receptor antagonists," *J. Med. Chem.* (1996) 39-4358-4360.

Betti et al., "Novel 3-aralkyl-7-(amino-substituted)-1,2,3-triazolo[4,5-d]pyrimidines with high affinity toward A1 adenosine receptors," *J. Med. Chem.* (1998) 41(5):668-673.

Chorvat et al., "Synthesis, corticotropin-releasing factor receptor binding affinity, and pharmacokinetic properties of triazolo-, imidazo-, and pyrrolopyrimidines and -pyridines," *J. Med. Chem.* (1999) 42(5):833-848.

Gilligan et al., "Corticotropin releasing factor (CRF) receptor modulators: progress and opportunities for new therapeutic agents," *Journal of Medicinal Chemistry* (2000) 43(9):1641-1660.

Hersperger et al., "Palladium-catalyzed cross-coupling reactions for the synthesis of 6, 8- disubstituted 1,7-napthyridines: a novel class of potent and selective phosphodiesterase type 4D inhibitors," *J. Med. Chem.* (2000) 43:675-682.

Gomtsyan et al., "Design, synthesis, and structure-activity relationship of 6-alkynylpyrimidines as potent adenosine kinase inhibitors," *J. Med. Chem.* (2002) 45:3639-3648.

Cohen et al., "The preparation and properties of 6-halomethylpurines," *Division of Nucleoprotein Chemistry, Sloan-Kettering Institute for Cancer Research* (1962) 27:3545-3549.

Yoon et al., "Reaction of diisobutylaluminum hydride with selected organic compounds containing representative functional groups," *J. Org. Chem.* (1985) 52:2443-2450.

Vice et al., "Concise formation of 4-benzyl piperidines and related derivatives using a Suzuki protocol," *J. Org. Chem.* (2001) 66:2487-2492.

Hocek et al., "An efficient synthesis of 2-substituted 6-methylpurine bases and nucleosides by Fe- or PD-catalyzed cross-coupling reactions of 2,6-dichloropurines," *J. Org. Chem.* (2003) 68:5773-5776.

Arvela et al., "Rapid, easy cyanation of aryl bromides and chlorides using nickel salts in conjunction with microwave promotion," *J. Org. Chem.* (2003) 68:9122-9125.

Hecht et al., "On the 'Activation of Cytokins'," *The Journal of Biological Chemistry* (1975) 250(18):7343-7351.

Lin et al., "Synthesis and antitumor activity of halogen-substituted 4-(3,3-dimethyl-1—triazeno)quinolines," *Journal of Medicinal Chemistry* (1978) 21(3):268-272.

Clark et al., "Synthesis and analgesic activity of 1,3-dihydro-3-(substituted phenyl)imidazo[4,5- b]pyridin-2-ones and 3-(substituted phenyl)-1,2,3-triazolo[4,5-b]pyridines," *Journal of Medicinal Chemistry* (1978) 21(9):665-978.

Vaughan et al., "The Reformatsky Reaction. I. Zinc and Ethyl Alpha-Bromoisobutyrate*," *Department of Chemistry, The University of Michigan* (1984) 30:1790-1795.

Sugimoto et al., "Preparation of nitrogen-containing pi-deficient heteroaromatic Grignard reagents: oxidative magnesiation of nitrogen-containing pi-deficient halogenoheteroaromatics using active magnesium," *J. Org. Chem.* (2003) 68:2054-2057.

Baskin et al., "An efficient copper catalyst for the formation of sulfones from sulfinic acid salts and aryl iodides," *Organic Letters* (2002) 4(25):4423-4425.

Wu et al., "One-pot two-step microwave-assisted reaction in constructing 4,5-disubstituted pyrazolopyrimidines," *Organic Letters* (2003) 5(20):3587-3590.

Silhar et al. "Facile and efficient synthesis of 6-(hydroxymethyl)purines," *Organic Letters* (2004) 6(19):3225-3228.

Arvela et al. "Rapid cyanation of aryl iodides in water using microwave promotion," *Org. Biomol. Chem.* (2003) 1:1119-1121.

Nakazoto et al., "Synthesis, SAR and biological activities of CRH: receptor: Novel 3- or 4- carbamoyl-1,2,5,6-tetrahydropyridinoquinoline derivative," *24th ACS National Meeting* (2002) 1p.

Kumagai et al., "Synthesis, SAR and biological activities of CRH: receptr: Novel 3- or 4- carbamoyl-1,2,5,6-tetrahydropyridinopyrrolopyrimidine derivative," *24th ACS National Meeting* (2002) 1p.

Pomorski "Synthesis of acids, derivatives of 4-hydroxy-1,5-naphthyridine," *Ann. Soc. Chim. Poolonorum* (1974) 48:321-324.

Litvinov et al., "Naphyridines, structure, physicochemical properties and general methods of synthesis," *Russian Chemical Reviews* (2000) 69 (3):201-220.

Sugimoto et al., "Lithiation of 1H-pyrazolo[3,4-d]pyrimidine derivative using lithium alkanetellorolate," *Tetrahedron Letters* (1999) 40:2139-2140.

Bakkestuen et al., "Regioselective N-9 arylation of purines employing arylboronic acids in the presence of Cu(II)," *Tetrahedron Letters* (2003) 44:3359:3362.

Chen et al., "Free radical method for the synthesis of spiropiperidinyl heterocycles," *Tetrahedron Letters* (1996) 37(30):5233-5234.

Colandrea et al., "Synthesis and regioselective alkylation of 1,6-and 1-7-naphthyridines," *Tetrahedron Letters* (2000) 41:8053-8057.

Gangloff et al., "Synthesis of 3,5-disubstituted-1,2,4-oxadiazoles using tetrabutylammonium fluoride as a mild and efficient catalyst," *Tetrahedron Letters* (2001) 42:1441-1443.

Baskin et al., "A mild, convenient synthesis of sulfinic acid salts and sulfonamides from alkyl and aryl halides," *Tetrahedron Letters* (2002) 43:8479-8483.

Bakkestuen et al., "Regioselective N-9 arylation of purines employing arylboronic acids in the presence of Cu(II)," *Tetrahedron Letters* (2003) 44:3359-3362.

Escher et al., "Cyclopentylamine substituted triazolo(4,5-d pyrimidine: implications for binding to the adenosine receptor," *Tetrahedron Letters* (1991) 32(29):3583-3584.

Desimoni et al., "Polynuclear isoxazole types-I isoxazolo[4,5,d]pyrimidines," *Tetrahedron* (1987) 23:675-680.

Prasad et al., "Convenient methods for the reduction of amides, nitriles, carboxylic esters, acids and hydroboration of alkenses using $NaBH_4/I_2$ System," *Tetrahedron* (1992) 48(22):4623-4628.

Baraldi et al., An efficient one-pot synthesis of 6-alkoxy-8,9-dialkylpurines via reaction of 5-amino-4-chloro-6-alkylaminopyrimidines with N,N-dimethylalkaneamides and alkoxide ions, *Tetrahedron* (2002) 58:7607-7611.

Kelly et al., "A synthesis of aaptamine," *Tetrahedron* (1965) 41(15):30333036.

Majeed et al., "Stannylation reacitons and cross-couplings in pyrimidines," *Tetrahedron* (1989) 45(4):993-1006.

Muci et al., "Practical palladium catalysts for C-N and C-O bond formation," *Department of Chemistry, Mass Institute of Technology* (2002) 219:133-209.

Zhang et al., "Preparation of 1-(tri-n-butylstannyl) furanoid glycols and their use in palladium-mediated coupling reactions," *Tetrahedron Letters* (1993) 34(10):1571-1574.

Accession No. 2003:2246300 Chemicats, 1H-Pyrazolo [3,4-d] pyrimidin-4-amine, N-cyclohexyl-1- (2,4-dimethiphenyl)-N-methyl-.

Accession No. 2003:2246299 Chemicats, 1H-Pyrazolo [3,4-d] pyrimidin-4-amine, N-cyclohexyl-N- methyl-1-(3-methyphenyl)-.

International Search Report dated May 9, 2005 for International Application No. PCT/US2004/022417.

Rotwein et al., "Polymorphism in the 5' flanking region of the human insulin gene: a genetic marker for non-insulin-dependent diabetes," *N Engl J Med.*, (1983) 308(2):65-71.

Rimoin et al., *Emery And Rimoin's Principles And Practice Of Medical Genetics*, 3rd Ed. 1:1401-1402 (1996).

Le Stunff et al., "Early changes in postprandial insulin secretion, not in insulin sensitivity, characterize juvenile obesity," *Diabetes*, (1989) 43:696-702.

Pederson, P., "The impact of obesity on the pathogenesis of non-insulin-dependent mellitus: a review of current hypotheses" *Diab. Metab. Rev.*, (1989) 5:505-509.

Brancati et al., "Body Weight Patterns From 20 to 49 Years of Age and Subsequent Risk for Diabetes Mellitus: The Johns Hopkins Precursors Study," *Arch Intern Med.* (1999) 159:957-963.

Hill et al., "Environmental contributions to the obesity epidemic," *Science*, (1998) 280(5368):1371-4.

Perry et al., "Prospective study of risk factors for development of non-insulin dependent diabetes in middle aged British men," *BMJ.* (1995) 310(6979):560-4.

Wolter et al., "Copper-Catalyzed Coupling of Aryl Iodides with Aliphatic Alcohols," *Organic Letters*, (2002) 4(6):973-976.

Groger et al., "Modern Methods Of The Suzuki Cross Coupling: The Long Expected General Synthetic Routes Using Aryl Chlorides," *Groger, Harald, Journal fuer Praktische Chemie*, (2000) 342(4):334-339.

Leadbeater et al., "First Examples Of Transition-Metal Free Sonogashira-Type Couplings," *Organic Letters*, (2003) 5(21):3919-3922.

Appukkuttan et al., "Transition-Metal-Free Sonogashira-Type Coupling Reactions In Water," *European Journal Of Organic Chemistry*, (2003) 24:4713-4716.

Baskin et al., "An Efficient Copper Catalyst for the Formation of Sulfones from Sulfinic Acid Salts and Aryl Iodides," *Organic Letters*, (2002) 4(25):4423-4425.

Reed et al., "In-vivo and in-vitro models of type 2 diabetes in pharmaceutical drug discovery," *Diabetes Obes Metab.* (1999) 1(2):75-86.

Collier et al., "Radiosynthesis and in-vivo evaluation of the pseudopeptide δ-opioid antagonist [$^{125}$I]-ITIPP(Ψ)" *J. Labeled Compd. Radiopharm.* (1999) 42:S264-S266.

Le Bas et al., "Radioiodinated analogs of EP 00652218 for the exploration of the tachykinin NK1 receptor by spect," *J. Labeled Compd. Radiopharm.*, (2001) 44:S280-S282.

Potenza et al., "A rapid quantitative bioassay for evaluating the effects of ligands upon receptors that molecule cAMP levels in a melanophore cell line," *Pigment Cell Res.* (1992) 5(6):372-8.

Higuchi et al., "Pro-drugs as Novel Delivery Systems," vol. 14 of the A.C.S. Symposium Series (1987).

Higuchi et al., *Bioreversible Carries in Drug Design*, ed. Edward B. Roche, American Pharmaceutical Association and Pergamon Press (1987).

Remington, The Science and Practice of Pharmacy, 20th Edition, (2000) Lippincott Williams & Wilkins, (Editors: Gennaro, A.R., et al.).

Wuts, *Protective Groups in Organic Synthesis*, 3rd edition, John Wiley & Sons, New York (1999).

Organic Chemistry of Sulfur; Oae S., Ed.; Plenum Press: New York (1977).

Chen et al., "Synthesis and Oral Efficacy of a 4-(Butylethylamino)pyrrolo[2,3-d]pyrimidine: A Centrally Active Corticotropin-Releasing Facton Receptor Antagonist," *J. Med. Chem.* (1997) 40:1749-1754.

Novinson et al., "Novel heterocyclic nitrofurfural hydrazones. In vivo antitrypanosomal activity," *J. Med. Chem.* (1976) 19(4):512-516.

Yuan et al., "3-Aryl pyrazolo[4,3-d]pyrimidine derivatives nonpeptide CRF-1 antagonists," *Bioorganic Medicinal Chemistry Lett.* (2002) 2133-2136.

Chapoulaud et al., "Synthesis of 4,8-Diarylcinnolines and Quinazolines with Potential Applications in Nonlinear Optics. Diazines. Part 28," *Tetrahedron* (2000) 56:5499.

Ding et al., "A Combinatorial Scaffold Approach toward Kinase-Directed Heterocycle Libraries," *J. Am. Chem. Soc.* (2002) 124:1594-1596.
Trejo et al., "Design and Synthesis of 4-Azaindoles as Inhibitors of p38 MAP Kinase," *J. Med. Chem.* (2003) 46:4702-4713.
Ozeki et al., "[Studies on antiallergy agent. I. Synthesis of 1,4-dihyrdo-4-oxo-3-quinolinecarboxylic acids,]" *Yakugaku Zasshi* (1987) 107(2):123-134.
Schafer et al., "Zur synthese von 4-aminochinolinen durch intramolekulare *Friedel-Cfafts-* Reaktion," *Montash fur Chemie* (1978) 109:527-535.
Estel et al., "Synthesis of *ortho*-substituted aminopyridines. Metalation of pivaloylamino derivatives," *J. Heterocyclic Chem.* (1989) 26:105-112.
Becalski et al., "Synthesis of carbolines by the graebe-ullmann method," *Acta Pol. Pharm.* (1984) 41:601-606.
Takei et al., "A new synthetic method for some pyrazolo[4m3-d]pyrimidines[11]" *Bull Chem. Soc.* Japan (1979) 52:208-211.
Gewald et al., "Synthase und Raektionen von 4-aminosothizolen," *Leibigs Ann. Chim* (1979) 10:1534-1546.
Bhatt et al., "Preparation and study of a nickel(II) ion selective electrode," *Indian J. Chem* (1994) 33B:436-437.
Accession No. 2003:2246300 Chemcats, 1H-Pyrazolo[3,4-d]pyrimidin-4-amine, N-cyclohexyl-1-(2, 4-dimethylphenyl)-N-methyl-.
Gundersen "Synthesis of purinecarbonitriles by Pd(0)-catalysed coupling of halopurines with zinc cyanide," *Acta Chemica Scandinavia* (1996) 50:58-63.
Spruce, Document, (2005) (1p.).
Sage, Document, (Feb. 2003) (9pp.).
Cheng, et al. Potential Purine Antagonist. VI. Synthesis of 1-Alkyl and 1-Aryl-4-Substituted Pyrazolo [3,4-d]pyrimidines, J.Org. Chem.,vol. 21, 1240-56(1956).
Berge et al., "Pharmaceutical Salts," *Journal of Pharmaceutical Sciences* (1977) 66(1):1-19.
Mosti, L, et al. Arzneimittel-Forschung 2000, 50(11), 963-972.
Mosti, L. et al. Farmaco 1990, 45(4), 415-29.
Press, Jeffery, B. et al. J. Med. Chem. 1992, 35(24), 4509-15.
Sarosotnikov, A. M. et al. Russian Chemical Bulletin 2003, 52(8), 1782-1709.
Vinogradov, V. M. et al. Mendeleev Communications 2002, (5), 198-200.
Chu et al., "A Role for Intestinal Endocrine Cell-Expressed GPR119 in Glycemic Control by Enhancing GLP-1 and GIP Release," (Arena Pharmaceuticals pre-publication document).
Abstract #107, p. 56, *Toward Understanding Islet Biology*, Jan. 21, 2003-Jan. 26, 2003, Keystone, Colorado.
Abstract #112, p. 42, *Diabetes Mellitus: Molecular Mechanism, Genetics and New Therapies*, Jan. 27, 2005-Feb. 2, 2005, Keystone, Colorado.
Abstract #228, p. 54, *Diabetes Mellitus: Molecular Mechanisms, Genetics and New Therapies*, Jan. 27, 2005-Feb. 2, 2005, Keystone, Colorado.
Abstract #117 & Poster, *Diabetes: Molecular Genetics, Signaling Pathways and Integrated Physiology*, Jan. 14, 2007-Jan. 19, 2007, Keystone, Colorado.
Abstract #230 & Poster, *Diabetes: Molecular Genetics, Signaling Pathways and Integrated Physiology*, Jan. 14, 2007-Jan. 19, 2007, Keystone, Colorado.
Chu et al., "A role for β-cell-expressed G protein-coupled receptor 119 in glycemic control by enhancing glucose-dependent insulin release," *Endocrinology* (2007) 148:2601-2609.
Fyfe et al., *Diabetes* (2007) 56(Supplement 1):A142 (Abstract #532-P).
Overton et al., "Deorphanization of a G protein-coupled receptor for oleoylethanolamide and its use in the discovery of small-molecule hypophagic agents," *Cell Metabolism* (2006) 3:167-175.
Soga et al., "Lysophosphatidylcholine enhances glucose-dependent insulin secretion via an orphan G-protein-coupled receptor," Biochem Biophys Res Commun (2005) 326:744-751.
Dubau-Assibat et al., "Lawesson's Reagent: An Efficient 1,3-Dipole Trapping Agent", J. Org. Chem. 1995, 60(12), 3904-3906 CAS: 123:8809.
Raffel et al., "Diabetes Mellitus", Principles and practice of medicinal Genetics, 3rd Ed 1:1401-40 (1996).

* cited by examiner

FUSED-ARYL AND HETEROARYL DERIVATIVES AS MODULATORS OF METABOLISM AND THE PROPHYLAXIS AND TREATMENT OF DISORDERS RELATED THERETO

CROSS REFERENCE TO RELATED APPLICATIONS

This application is a continuation of U.S. Ser. No. 10/890,549, filed Jul. 13, 2004, now U.S. Pat. No. 7,132,426, which in turn claims the benefit of U.S. Provisional Applications Ser. Nos. 60/487,443, filed Jul. 14, 2003 and 60/510,644, filed Oct. 10, 2003, the disclosures of each of which are incorporated herein by reference in their entireties.

FIELD OF THE INVENTION

The present invention relates to certain fused aryl and heteroaryl derivatives that are modulators of glucose metabolism. Accordingly, compounds of the present invention are useful in the prophylaxis or treatment of metabolic disorders and complications thereof, such as, diabetes and obesity.

BACKGROUND OF THE INVENTION

Diabetes mellitus is a serious disease afflicting over 100 million people worldwide. In the United States, there are more than 12 million diabetics, with 600,000 new cases diagnosed each year.

Diabetes mellitus is a diagnostic term for a group of disorders characterized by abnormal glucose homeostasis resulting in elevated blood sugar. There are many types of diabetes, but the two most common are Type I (also referred to as insulin-dependent diabetes mellitus or IDDM) and Type II (also referred to as non-insulin-dependent diabetes mellitus or NIDDM).

The etiology of the different types of diabetes is not the same; however, everyone with diabetes has two things in common: overproduction of glucose by the liver and little or no ability to move glucose out of the blood into the cells where it becomes the body's primary fuel.

People who do not have diabetes rely on insulin, a hormone made in the pancreas, to move glucose from the blood into the cells of the body. However, people who have diabetes either don't produce insulin or can't efficiently use the insulin they produce; therefore, they can't move glucose into their cells. Glucose accumulates in the blood creating a condition called hyperglycemia, and over time, can cause serious health problems.

Diabetes is a syndrome with interrelated metabolic, vascular, and neuropathic components. The metabolic syndrome, generally characterized by hyperglycemia, comprises alterations in carbohydrate, fat and protein metabolism caused by absent or markedly reduced insulin secretion and/or ineffective insulin action. The vascular syndrome consists of abnormalities in the blood vessels leading to cardiovascular, retinal and renal complications. Abnormalities in the peripheral and autonomic nervous systems are also part of the diabetic syndrome.

People with IDDM, which accounts for about 5% to 10% of those who have diabetes, don't produce insulin and therefore must inject insulin to keep their blood glucose levels normal. IDDM is characterized by low or undetectable levels of endogenous insulin production caused by destruction of the insulin-producing β cells of the pancreas, the characteristic that most readily distinguishes IDDM from NIDDM. IDDM, once termed juvenile-onset diabetes, strikes young and older adults alike.

Approximately 90 to 95% of people with diabetes have Type II (or NIDDM). NIDDM subjects produce insulin, but the cells in their bodies are insulin resistant: the cells don't respond properly to the hormone, so glucose accumulates in their blood. NIDDM is characterized by a relative disparity between endogenous insulin production and insulin requirements, leading to elevated blood glucose levels. In contrast to IDDM, there is always some endogenous insulin production in NMDDM; many NIDDM patients have normal or even elevated blood insulin levels, while other NIDDM patients have inadequate insulin production (Rotwein, R. et al. *N. Engl. J. Med.* 308, 65-71 (1983)). Most people diagnosed with NIDDM are age 30 or older, and half of all new cases are age 55 and older. Compared with whites and Asians, NIDDM is more common among Native Americans, African-Americans, Latinos, and Hispanics. In addition, the onset can be insidious or even clinically inapparent, making diagnosis difficult.

The primary pathogenic lesion on NIDDM has remained elusive. Many have suggested that primary insulin resistance of the peripheral tissues is the initial event. Genetic epidemiological studies have supported this view. Similarly, insulin secretion abnormalities have been argued as the primary defect in NIDDM. It is likely that both phenomena are important contributors to the disease process (Rimoin, D. L., et. al. Emery and Rimoin's Principles and Practice of Medical Genetics $3^{rd}$ Ed. 1:1401-1402 (1996)).

Many people with NIDDM have sedentery lifestyles and are obese; they weigh approximately 20% more than the recommended weight for their height and build. Furthermore, obesity is characterized by hyperinsulinemia and insulin resistance, a feature shared with NIDDM, hypertension and atherosclerosis.

Obesity and diabetes are among the most common human health problems in industrialized societies. In industrialized countries a third of the population is at least 20% overweight. In the United States, the percentage of obese people has increased from 25% at the end of the 1970s, to 33% at the beginning the 1990s. Obesity is one of the most important risk factors for NIDDM. Definitions of obesity differ, but in general, a subject weighing at least 20% more than the recommended weight for his/her height and build is considered obese. The risk of developing NIDDM is tripled in subjects 30% overweight, and three-quarters with NIDDM are overweight.

Obesity, which is the result of an imbalance between caloric intake and energy expenditure, is highly correlated with insulin resistance and diabetes in experimental animals and human. However, the molecular mechanisms that are involved in obesity-diabetes syndromes are not clear. During early development of obesity, increase insulin secretion balances insulin resistance and protects patients from hyperglycemia (Le Stunff, et al. *Diabetes* 43, 696-702 (1989)). However, after several decades, β cell function deteriorates and non-insulin-dependent diabetes develops in about 20% of the obese population (Pederson, P. *Diab. Metab. Rev.* 5, 505-509 (1989)) and (Brancati, F. L., et al., *Arch. Intern. Med.* 159, 957-963 (1999)). Given its high prevalence in modern societies, obesity has thus become the leading risk factor for NIDDM (Hill, J. O., et al., *Science* 280, 1371-1374 (1998)). However, the factors which predispose a fraction of patients to alteration of insulin secretion in response to fat accumulation remain unknown.

Whether someone is classified as overweight or obese is generally determined on the basis of their body mass index (BMI) which is calculated by dividing body weight (kg) by height squared (m$^2$). Thus, the units of BMI are kg/m$^2$ and it is possible to calculate the BMI range associated with minimum mortality in each decade of life. Overweight is defined as a BMI in the range 25-30 kg/m$^2$, and obesity as a BMI greater than 30 kg/m$^2$ (see TABLE below). There are problems with this definition in that it does not take into account the proportion of body mass that is muscle in relation to fat (adipose tissue). To account for this, obesity can also be defined on the basis of body fat content: greater than 25% and 30% in males and females, respectively.

| CLASSIFICATION OF WEIGHT BY BODY MASS INDEX (BMI) | |
|---|---|
| BMI | CLASSIFICATION |
| <18.5 | Underweight |
| 18.5-24.9 | Normal |
| 25.0-29.9 | Overweight |
| 30.0-34.9 | Obesity (Class I) |
| 35.0-39.9 | Obesity (Class II) |
| >40 | Extreme Obesity (Class III) |

As the BMI increases there is an increased risk of death from a variety of causes that is independent of other risk factors. The most common diseases with obesity are cardiovascular disease (particularly hypertension), diabetes (obesity aggravates the development of diabetes), gall bladder disease (particularly cancer) and diseases of reproduction. Research has shown that even a modest reduction in body weight can correspond to a significant reduction in the risk of developing coronary heart disease.

Compounds marketed as anti-obesity agents include Orlistat (XENICAL™) and Sibutramine. Orlistat (a lipase inhibitor) inhibits fat absorption directly and tends to produce a high incidence of unpleasant (though relatively harmless) side-effects such as diarrhea. Sibutramine (a mixed 5-HT/noradrenaline reuptake inhibitor) can increase blood pressure and heart rate in some patients. The serotonin releaser/reuptake inhibitors fenfluramine (Pondimin™) and dexfenfluramine (Redux™) have been reported to decrease food intake and body weight over a prolonged period (greater than 6 months). However, both products were withdrawn after reports of preliminary evidence of heart valve abnormalities associated with their use. Accordingly, there is a need for the development of a safer anti-obesity agent.

Obesity considerably increases the risk of developing cardiovascular diseases as well. Coronary insufficiency, atheromatous disease, and cardiac insufficiency are at the forefront of the cardiovascular complication induced by obesity. It is estimated that if the entire population had an ideal weight, the risk of coronary insufficiency would decrease by 25% and the risk of cardiac insufficiency and of cerebral vascular accidents by 35%. The incidence of coronary diseases is doubled in subjects less than 50 years of age who are 30% overweight. The diabetes patient faces a 30% reduced lifespan. After age 45, people with diabetes are about three times more likely than people without diabetes to have significant heart disease and up to five times more likely to have a stroke. These findings emphasize the inter-relations between risks factors for NIDDM and coronary heart disease and the potential value of an integrated approach to the prevention of these conditions based on the prevention of these conditions based on the prevention of obesity (Perry, I. J., et al., *BMJ* 310, 560-564 (1995)).

Diabetes has also been implicated in the development of kidney disease, eye diseases and nervous-system problems. Kidney disease, also called nephropathy, occurs when the kidney's "filter mechanism" is damaged and protein leaks into urine in excessive amounts and eventually the kidney fails. Diabetes is also a leading cause of damage to the retina at the back of the eye and increases risk of cataracts and glaucoma. Finally, diabetes is associated with nerve damage, especially in the legs and feet, which interferes with the ability to sense pain and contributes to serious infections. Taken together, diabetes complications are one of the nation's leading causes of death.

SUMMARY OF THE INVENTION

The present invention is drawn to compounds which bind to and modulate the activity of a GPCR referred to herein as RUP3, and uses thereof. The term RUP3 as used herein includes the human sequences found in GeneBank accession numbers XM_066873 and AY288416, and naturally-occurring allelic variants, mammalian orthologs, and recombinant mutants thereof. A preferred human RUP3 for use in screening and testing of the compounds of the invention is provided in the nucleotide sequence of Seq. ID. No:1 and the corresponding amino acid sequence in Seq. ID. No:2.

One aspect of the present invention encompasses certain fused aryl and heteroaryl derivatives as shown in Formula (I):

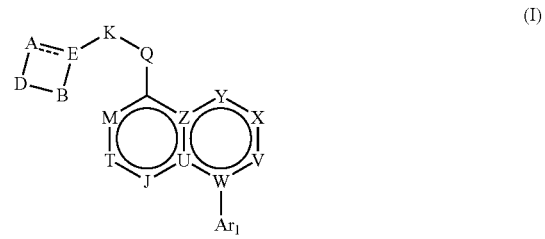

or a pharmaceutically acceptable salt, hydrate or solvate thereof;

wherein:

A and B are each independently C$_{1-3}$ alkylene optionally substituted with 1 to 4 substituents selected from the group consisting of C$_{1-3}$ alkyl, C$_{1-4}$ alkoxy, carboxy, cyano, C$_{1-3}$ haloalkyl and halogen;

D is O, S, S(O), S(O)$_2$, CR$_1$R$_2$ or N—R$_2$, wherein R$_1$ is selected from the group consisting of H, C$_{1-8}$ alkyl, C$_{1-4}$ alkoxy, halogen and hydroxyl;

E is N, C or CR$_3$, wherein R$_3$ is H or C$_{1-8}$ alkyl;

===== is a single bond when E is N or CR$_3$, or a double bond when E is C;

K is a C$_{3-6}$ cycloalkylene or C$_{1-3}$ alkylene wherein each are optionally substituted with 1 to 4 substituents selected from the group consisting of C$_{1-3}$ alkyl, C$_{1-4}$ alkoxy, carboxy, cyano, C$_{1-3}$ haloalkyl and halogen; or K is a bond;

Q is NR$_4$, O, S, S(O) or S(O)$_2$, wherein R$_4$ is H or C$_{1-8}$ alkyl and the C$_{1-8}$ alkyl is optionally substituted with C$_{2-8}$ dialkylamine;

T is N or CR$_5$;

M is N or CR$_6$;

J is N or CR$_7$;

U is C or N;

V is N, $CR_8$ or V is a bond;
W is N or C;
X is O, S, N, $CR_9$ or $NR_{11}$;
Y is O, S, N, $CR_{10}$ or $NR_{12}$;
Z is C or N;
$R_5$, $R_6$, $R_7$, $R_8$, $R_9$ and $R_{10}$ are each independently selected from the group consisting of H, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-4}$ alkylamino, $C_{2-8}$ dialkylamino, carboxamide, cyano, $C_{3-6}$ cycloalkyl, $C_{2-6}$ dialkylcarboxamide, $C_{2-6}$ dialkylsulfonamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, hydroxylamino and nitro; wherein said $C_{2-6}$ alkenyl, $C_{1-8}$ alkyl, $C_{2-6}$ alkynyl and $C_{3-6}$ cycloalkyl are optionally substituted with 1, 2, 3 or 4 substituents selected from the group consisting of $C_{1-5}$ acyl, $C_{1-5}$ acyloxy, $C_{1-4}$ alkoxy, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{2-8}$ dialkylamino, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, hydroxyl, hydroxylamino and nitro;

$R_{11}$ and $R_{12}$ are each independently selected from $C_{2-6}$ alkenyl, $C_{1-8}$ alkyl, $C_{2-6}$ alkynyl or $C_{3-6}$ cycloalkyl optionally each substituted with 1, 2, 3 or 4 substituents selected from the group consisting of $C_{1-5}$ acyl, $C_{1-5}$ acyloxy, $C_{1-4}$ alkoxy, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{2-8}$ dialkylamino, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, hydroxyl, hydroxylamino and nitro;

$Ar_1$ is aryl or heteroaryl each optionally substituted with $R_{13}$, $R_{14}$, $R_{15}$, $R_{16}$, and $R_{17}$; wherein $R_{13}$ is selected from the group consisting of $C_{1-5}$ acyl, $C_{1-6}$ acylsulfonamide, $C_{1-5}$ acyloxy, $C_{2-6}$ alkenyl, $C_{1-4}$ alkoxy, $C_{1-8}$ alkyl, $C_{1-4}$ alkylamino, $C_{1-6}$ alkylcarboxamide, $C_{1-4}$ alkylthiocarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, arylsulfonyl, carbamimidoyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, $C_{2-6}$ dialkylthiocarboxamide, guanidinyl, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heterocyclic, heterocyclic-oxy, heterocyclicsulfonyl, heterocyclic-carbonyl, heteroaryl, heteroarylcarbonyl, hydroxyl, nitro, $C_{4-7}$ oxo-cycloalkyl, phenoxy, phenyl, sulfonamide, sulfonic acid, and thiol, and wherein said $C_{1-5}$ acyl, $C_{1-6}$ acylsulfonamide, $C_{1-4}$ alkoxy, $C_{1-8}$ alkyl, $C_{1-4}$ alkylamino, $C_{1-6}$ alkylsulfonamide, $C_{1-4}$ alkylsulfonyl, $C_{1-4}$ alkylthio, arylsulfonyl, carbamimidoyl, $C_{2-6}$ dialkylamino, heterocyclic, heterocyclic-carbonyl, heteroaryl, phenoxy and phenyl are each optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heteroaryl, heterocyclic, hydroxyl, nitro, phenyl, and phosphonooxy, and wherein said $C_{1-7}$ alkyl and $C_{1-4}$ alkylcarboxamide are each optionally substituted with 1 to 5 substituents selected from the group consisting of $C_{1-4}$ alkoxy and hydroxy; or $R_{13}$ is a group of Formula (A):

(A)

wherein:
"p" and "r" are independently 0, 1, 2 or 3; and
$R_{18}$ is H, $C_{1-5}$ acyl, $C_{2-6}$ alkenyl, $C_{1-8}$ alkyl, $C_{1-4}$ alkylcarboxamide, $C_{2-6}$ alkynyl, $C_{1-4}$ alkylsulfonamide, carbo-$C_{1-6}$-alkoxy, carboxamide, carboxy, cyano, $C_{3-7}$ cycloalkyl, $C_{2-6}$ dialkylcarboxamide, halogen, heteroaryl or phenyl, and wherein said heteroaryl or phenyl optionally substituted with 1 to 5 substituents selected independently from the group consisting of $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl;

$R_{14}$, $R_{15}$, $R_{16}$, and $R_{17}$ are each independently selected form the group consisting of H, $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl and nitro; or two adjacent $R_{14}$, $R_{15}$, $R_{16}$ and $R_{17}$ together with the atoms to which they are attached form a 5, 6 or 7 member cycloalkyl, cycloalkenyl or heterocyclic group fused with $Ar_1$ wherein the 5, 6 or 7 member group is optionally substituted with halogen; and $R_2$ is selected from the group consisting of $C_{1-8}$ alkyl, $C_{2-6}$ alkynyl, amino, aryl, carboxamide, carboxy, cyano, $C_{3-6}$-cycloalkyl, $C_{1-4}$ haloalkoxy, $C_{1-4}$ haloalkyl, halogen, heteroaryl and hydroxyl; and wherein said $C_{1-8}$ alkyl, aryl and heteroaryl are each optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{3-6}$-cycloalkyl-$C_{1-3}$-heteroalkylene, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro; or $R_2$ is —$Ar_2$—$Ar_3$ wherein $Ar_2$ and $Ar_3$ are each independently aryl or heteroaryl each optionally substituted with 1 to 5 substituents selected from the group consisting of H, $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, $C_{1-4}$ alkylamino, carbo-$C_{1-6}$-alkoxy, carboxamide, carboxy, cyano, $C_{3-6}$-cycloalkyl, $C_{2-8}$ dialkylamino, $C_{2-6}$ dialkylcarboxamide, $C_{1-4}$ haloalkoxy, $C_{1-4}$ haloalkyl, halogen, hydroxyl and nitro; or $R_2$ is a group of Formula (B):

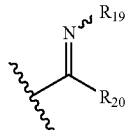

(B)

wherein:
$R_{19}$ is H, $C_{1-8}$ alkyl, $C_{3-7}$ cycloalkyl, aryl, heteroaryl or $OR_{21}$; and $R_{20}$ is F, Cl, Br, CN or $NR_{22}R_{23}$; where $R_{21}$ is H, $C_{1-8}$ alkyl or $C_{3-7}$ cycloalkyl, and $R_{22}$ and $R_{23}$ are independently H, $C_{1-8}$ alkyl, $C_{3-7}$ cycloalkyl, aryl or heteroaryl; or $R_2$ is a group of Formula (C):

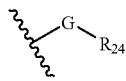

(C)

wherein:
G is:
i) —C(O)—, —C(O)NR$_{25}$—, —NR$_{25}$C(O)—, —NR$_{25}$—, —NR$_{25}$C(O)O—, —OC(O)NR$_{25}$—, —CR$_{25}$R$_{26}$NR$_{27}$C(O)—, —CR$_{25}$R$_{26}$C(O)NR$_{27}$—, —C(O)O—, —OC(O)—, —C(S)—, —C(S)NR$_{25}$—, —C(S)O—, —OC(S)—, —CR$_{25}$R$_{26}$—, —O—, —S—, —S(O)—, —S(O)$_2$— or a bond when D is CR$_2$R$_3$; or
ii) —CR$_{25}$R$_{26}$C(O)—, —C(O)—, —CR$_{25}$R$_{26}$C(O)NR$_{27}$—, —C(O)NR$_{25}$—, —C(O)O—, —C(S)—, —C(S)NR$_{25}$—, —C(S)O—, —CR$_{25}$R$_{26}$—, —S(O)$_2$—, or a bond when D is NR$_2$;
wherein $R_{25}$, $R_{26}$ and $R_{27}$ are each independently H or $C_{1-8}$ alkyl; and $R_{24}$ is H, $C_{1-8}$ alkyl, $C_{3-7}$ cycloalkyl, phenyl, heteroaryl, or heterocyclic each optionally substituted with 1 to 5 substituents selected from the group consisting of $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, heterocyclic, hydroxyl, hydroxylamino, nitro, phenyl, phenoxy, and sulfonic acid, wherein said $C_{1-4}$ alkoxy, $C_{1-7}$ alkyl, $C_{1-4}$ alkylamino, heteroaryl, phenyl and phenoxy are each optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino, nitro, and phenyl; provided that Z and U are not both N.

One aspect of the present invention pertains to pharmaceutical compositions comprising at least one compound of the present invention and a pharmaceutically acceptable carrier.

One aspect of the present invention pertains to methods for the treatment of a metabolic-related disorder in an individual comprising administering to the individual in need of such treatment a therapeutically effective amount of a compound of the present invention or a pharmaceutical composition thereof.

One aspect of the present invention pertains to methods of decreasing food intake of an individual comprising administering to the individual in need thereof a therapeutically effective amount of a compound of the present invention or pharmaceutical composition thereof.

One aspect of the present invention pertains to methods of inducing satiety in an individual comprising administering to the individual in need thereof a therapeutically effective amount of a compound of the present invention or pharmaceutical composition thereof.

One aspect of the present invention pertains to methods of controlling or decreasing weight gain of an individual comprising administering to the individual in need thereof a therapeutically effective amount of a compound of the present invention or pharmaceutical composition thereof.

One aspect of the present invention pertains to methods of modulating a RUP3 receptor in an individual comprising contacting the receptor with a compound of the present invention. In some embodiments, the compound is an agonist for the RUP3 receptor. In some embodiments, the modulation of the RUP3 receptor is the treatment of a metabolic-related disorder.

Some embodiments of the present invention include a method of modulating a RUP3 receptor in an individual comprising contacting the receptor with a compound of the present invention wherein the modulation of the RUP3 receptor reduces food intake of the individual.

Some embodiments of the present invention include a method of modulating a RUP3 receptor in an individual comprising contacting the receptor with a compound of the present invention wherein the modulation of the RUP3 receptor induces satiety in the individual.

Some embodiments of the present invention include a method of modulating a RUP3 receptor in an individual comprising contacting the receptor with a compound of the present invention wherein the modulation of the RUP3 receptor controls or reduces weight gain of the individual.

One aspect of the present invention pertains to use of a compound of the present invention for production of a medicament for use in the treatment of a metabolic-related disorder.

One aspect of the present invention pertains to use of a compound of the present invention for production of a medicament for use in decreasing food intake in an individual.

One aspect of the present invention pertains to use of a compound of the present invention for production of a medicament for use of inducing satiety in an individual.

One aspect of the present invention pertains to use of a compound of the present invention for production of a medicament for use in controlling or decreasing weight gain in an individual.

One aspect of the present invention pertains to a compound of the present invention for use in a method of treatment of the human or animal body by therapy.

One aspect of the present invention pertains to a compound of the present invention for use in a method of treatment of a metabolic-related disorder of the human or animal body by therapy.

One aspect of the present invention pertains to a compound of the present invention for use in a method of decreasing food intake of the human or animal body by therapy.

One aspect of the present invention pertains to a compound of the present invention for use in a method of inducing satiety of the human or animal body by therapy.

One aspect of the present invention pertains to a compound of the present invention for use in a method of controlling or decreasing weight gain of the human or animal body by therapy.

Some embodiments of the present invention pertain to methods wherein the human has a body mass index of about 18.5 to about 45. In some embodiments, the human has a body mass index of about 25 to about 45. In some embodiments, the human has a body mass index of about 30 to about 45. In some embodiments, the human has a body mass index of about 35 to about 45.

In some embodiments the individual is a mammal. In some embodiments the mammal is a human.

In some embodiments, the metabolic-related disorder is hyperlipidemia, type 1 diabetes, type 2 diabetes mellitus, idiopathic type 1 diabetes (Type 1b), latent autoimmune diabetes in adults (LADA), early-onset type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction (e.g. necrosis and apoptosis), dyslipidemia, post-prandial lipemia, conditions of impaired glucose tolerance (IGT), conditions of impaired fasting plasma glucose, metabolic acidosis, ketosis, arthritis, obesity, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, coronary heart disease, angina pectoris, thrombosis, atherosclerosis, myocardial infarction, transient ischemic attacks, stroke, vascular restenosis, hyperglycemia, hyperinsulinemia, hyperlipidemia, hypertryglicerdemia, insulin resistance, impaired glucose metabolism, conditions of impaired glucose tolerance, conditions of impaired fasting plasma glucose, obesity, erectile dysfunction, skin and connective tissue disorders, foot ulcerations and ulcerative colitis, endothelial dysfunction and impaired vascular compliance.

In some embodiments, the metabolic-related disorder is type I diabetes, type II diabetes, inadequate glucose tolerance, insulin resistance, hyperglycemia, hyperlipidemia, hypertriglyceridemia, hypercholesterolemia, dyslipidemia or syndrome X. In some embodiments, the metabolic-related disorder is type II diabetes. In some embodiments, the metabolic-related disorder is hyperglycemia. In some embodiments, the metabolic-related disorder is hyperlipidemia. In some embodiments, the metabolic-related disorder is hypertriglyceridemia. In some embodiments, the metabolic-related disorder is type I diabetes. In some embodiments, the metabolic-related disorder is dyslipidemia. In some embodiments, the metabolic-related disorder is syndrome X.

One aspect of the present invention pertains to a method of producing a pharmaceutical composition comprising admixing at least one compound, as described herein, and a pharmaceutically acceptable carrier.

This application is related to two U.S. Provisional Patent Applications, Ser. Nos. 60/487,443 filed Jul. 14, 2003; and 60/510,644 filed Oct. 10, 2003, both which are incorporated by reference in their entirety.

Applicant reserves the right to exclude any one or more of the compounds from any of the embodiments of the invention. Applicant additionally reserves the right to exclude any disease, condition or disorder from any of the embodiments of the invention.

DETAILED DESCRIPTION OF THE INVENTION

Definitions

Figure 1:
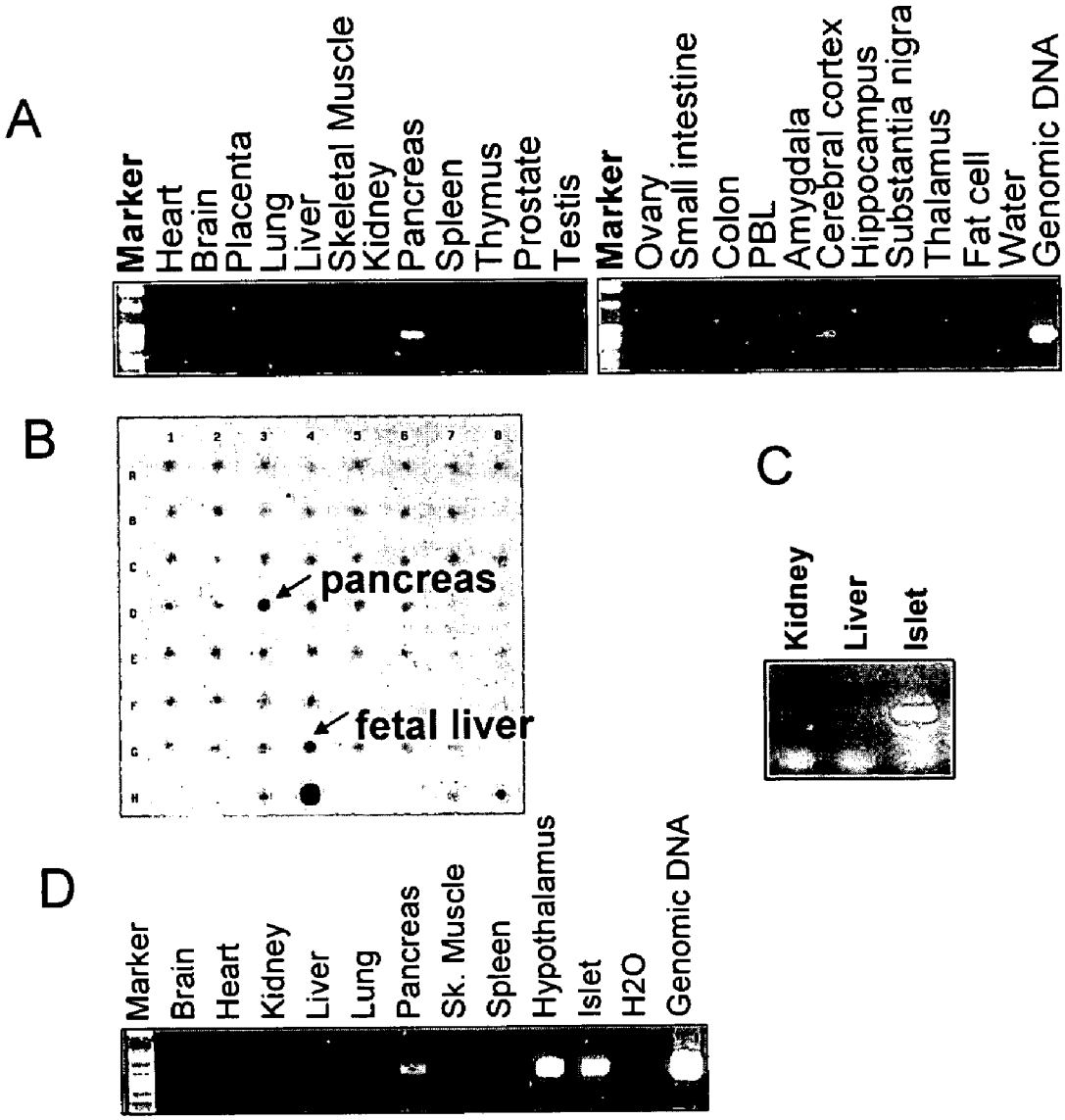
FIG. 1A shows RT-PCR analysis of RUP3 expression in human tissues. A total of twenty-two (22) human tissues were analyzed.
FIG. 1B shows the cDNA Dot-Blot analysis of RUP 3 expression in human tissues.
FIG. 1C shows analysis of RUP3 by RT-PCR with isolated human pancreatic islets of Langerhans.
FIG. 1D shows analysis of RUP3 expression with cDNAs of rat origin by RT-PCR.

The scientific literature that has evolved around receptors has adopted a number of terms to refer to ligands having various effects on receptors. For clarity and consistency, the following definitions will be used throughout this patent document.

AGONISTS shall mean moieties that interact and activate the receptor, such as the RUP3 receptor and initiates a physiological or pharmacological response characteristic of that receptor. For example, when moieties activate the intracellular response upon binding to the receptor, or enhance GTP binding to membranes.

AMINO ACID ABBREVIATIONS used herein are set out in TABLE 1:

TABLE 1

| | | |
|---|---|---|
| ALANINE | ALA | A |
| ARGININE | ARG | R |
| ASPARAGINE | ASN | N |
| ASPARTIC ACID | ASP | D |
| CYSTEINE | CYS | C |
| GLUTAMIC ACID | GLU | E |
| GLUTAMINE | GLN | Q |
| GLYCINE | GLY | G |
| HISTIDINE | HIS | H |
| ISOLEUCINE | ILE | I |
| LEUCINE | LEU | L |
| LYSINE | LYS | K |
| METHIONINE | MET | M |
| PHENYLALANINE | PHE | F |
| PROLINE | PRO | P |
| SERINE | SER | S |
| THREONINE | THR | T |
| TRYPTOPHAN | TRP | W |
| TYROSINE | TYR | Y |
| VALINE | VAL | V |
| ALANINE | ALA | A |

The term ANTAGONISTS is intended to mean moieties that competitively bind to the receptor at the same site as agonists (for example, the endogenous ligand), but which do not activate the intracellular response initiated by the active form of the receptor, and can thereby inhibit the intracellular responses by agonists or partial agonists. Antagonists do not diminish the baseline intracellular response in the absence of an agonist or partial agonist.

Chemical Group, Moiety or Radical:

The term "$C_{1-5}$ acyl" denotes a $C_{1-5}$ alkyl radical attached to a carbonyl wherein the definition of alkyl has the same definition as described herein; some examples include but not limited to, acetyl, propionyl, n-butanoyl, iso-butanoyl, sec-butanoyl, t-butanoyl (i.e., pivaloyl), pentanoyl and the like.

The term "$C_{1-5}$ acyloxy" denotes an acyl radical attached to an oxygen atom wherein acyl has the same definition has described herein; some examples include but not limited to acetyloxy, propionyloxy, butanoyloxy, iso-butanoyloxy, sec-butanoyloxy, t-butanoyloxy and the like.

The term "$C_{1-6}$ acylsulfonamide" refers to a $C_{1-6}$ acyl attached directly to the nitrogen of the sulfonamide, wherein the definitions for $C_{1-6}$ acyl and sulfonamide have the same meaning as described herein, and a $C_{1-6}$ acylsulfonamide can be represented by the following formula:

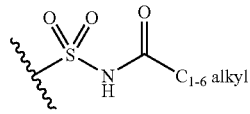

Some embodiments of the present invention are when acylsulfonamide is a $C_{1-5}$ acylsulfonamide, some embodiments are $C_{1-4}$ acylsulfonamide, some embodiments are $C_{1-3}$ acylsulfonamide, and some embodiments are $C_{1-2}$ acylsulfonamide. Examples of an acylsulfonamide include, but not limited to, acetylsulfamoyl [—S(=O)$_2$NHC(=O)Me], propionylsulfamoyl [—S(=O)$_2$NHC(=O)Et], isobutyrylsulfamoyl, butyrylsulfamoyl, 2-methyl-butyrylsulfamoyl, 3-methyl-butyrylsulfamoyl, 2,2-dimethyl-propionylsulfamoyl, pentanoylsulfamoyl, 2-methyl-pentanoylsulfamoyl, 3-methyl-pentanoylsulfamoyl, 4-methyl-pentanoylsulfamoyl, and the like.

The term "$C_{2-6}$ alkenyl" denotes a radical containing 2 to 6 carbons wherein at least one carbon-carbon double bond is present, some embodiments are 2 to 4 carbons, some embodiments are 2 to 3 carbons, and some embodiments have 2 carbons. Both E and Z isomers are embraced by the term "alkenyl." Furthermore, the term "alkenyl" includes di- and tri-alkenyls. Accordingly, if more than one double bond is present then the bonds may be all E or Z or a mixtures of E and Z. Examples of an alkenyl include vinyl, allyl, 2-butenyl, 3-butenyl, 2-pentenyl, 3-pentenyl, 4-pentenyl, 2-hexenyl, 3-hexenyl, 4-hexenyl, 5-hexanyl, 2,4-hexadienyl and the like.

The term "$C_{1-4}$ alkoxy" as used herein denotes a radical alkyl, as defined herein, attached directly to an oxygen atom. Examples include methoxy, ethoxy, n-propoxy, iso-propoxy, n-butoxy, t-butoxy, iso-butoxy, sec-butoxy and the like.

The term "$C_{1-8}$ alkyl" denotes a straight or branched carbon radical containing 1 to 8 carbons, some embodiments are 1 to 6 carbons, some embodiments are 1 to 3 carbons, and some embodiments are 1 or 2 carbons. Examples of an alkyl include, but not limited to, methyl, ethyl, n-propyl, iso-propyl, n-butyl, sec-butyl, iso-butyl, t-butyl, pentyl, iso-pentyl, t-pentyl, neo-pentyl, 1-methylbutyl [i.e., —CH(CH$_3$)CH$_2$CH$_2$CH$_3$], 2-methylbutyl [i.e., —CH$_2$CH(CH$_3$)CH$_2$CH$_3$], n-hexyl and the like.

The term "$C_{1-4}$ alkylcarboxamido" or "$C_{1-4}$ alkylcarboxamide" denotes a single $C_{1-4}$ alkyl group attached to the nitrogen of an amide group, wherein alkyl has the same definition as found herein. The $C_{1-5}$ alkylcarboxamido may be represented by the following:

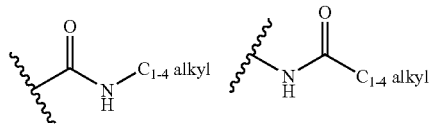

Examples include, but not limited to, N-methylcarboxamide, N-ethylcarboxamide, N-n-propylcarboxamide, N-iso-propylcarboxamide, N-n-butylcarboxamide, N-sec-butylcarboxamide, N-iso-butylcarboxamide, N-t-butylcarboxamide and the like.

The term "$C_{1-3}$ alkylene" refers to a $C_{1-3}$ divalent straight carbon group. In some embodiments $C_{1-3}$ alkylene refers to, for example, —CH$_2$—, —CH$_2$CH$_2$—, —CH$_2$CH$_2$CH$_2$—, and the like. In some embodiments, $C_{1-3}$ alkylene refers to —CH—, —CHCH$_2$—, —CHCH$_2$CH$_2$—, and the like wherein these examples relate generally to "A".

The term "$C_{1-4}$ alkylsulfinyl" denotes a $C_{1-4}$ alkyl radical attached to a sulfoxide radical of the formula: —S(O)— wherein the alkyl radical has the same definition as described herein. Examples include, but not limited to, methylsulfinyl, ethylsulfinyl, n-propylsulfinyl, iso-propylsulfinyl, n-butylsulfinyl, sec-butylsulfinyl, iso-butylsulfinyl, t-butyl, and the like.

The term "$C_{1-4}$ alkylsulfonamide" refers to the groups

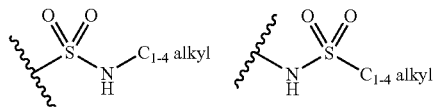

wherein $C_{1-4}$ alkyl has the same definition as described herein.

The term "$C_{1-4}$ alkylsulfonyl" denotes a $C_{1-4}$ alkyl radical attached to a sulfone radical of the formula: —S(O)$_2$— wherein the alkyl radical has the same definiti+on as described herein. Examples include, but not limited to, methylsulfonyl, ethylsulfonyl, n-propylsulfonyl, iso-propylsulfonyl, n-butylsulfonyl, sec-butylsulfonyl, iso-butylsulfonyl, t-butyl, and the like.

The term "$C_{1-4}$ alkylthio" denotes a $C_{1-4}$ alkyl radical attached to a sulfide of the formula: —S— wherein the alkyl radical has the same definition as described herein. Examples include, but not limited to, methylsulfanyl (i.e., CH$_3$S—), ethylsulfanyl, n-propylsulfanyl, iso-propylsulfanyl, n-butylsulfanyl, sec-butylsulfanyl, iso-butylsulfanyl, t-butyl, and the like.

The term "$C_{1-4}$ alkylthiocarboxamide" denotes a thioamide of the following formulae:

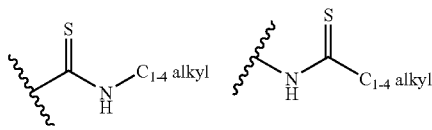

wherein $C_{1-4}$ alkyl has the same definition as described herein.

The term "$C_{1-4}$ alkylthioureyl" denotes the group of the formula: —NC(S)N— wherein one are both of the nitrogens are substituted with the same or different $C_{1-4}$ alkyl groups and alkyl has the same definition as described herein. Examples of an alkylthioureyl include, but not limited to, $CH_3NHC(S)NH$—, $NH_2C(S)NCH_3$—, $(CH_3)_2N(S)NH$—, $(CH_3)_2N(S)NH$—, $(CH_3)_2N(S)NCH_3$—, $CH_3CH_2NHC(S)NH$—, $CH_3CH_2NHC(S)NCH_3$—, and the like.

The term "$C_{1-4}$ alkylureyl" denotes the group of the formula: —NC(O)N— wherein one are both of the nitrogens are substituted with the same or different $C_{1-4}$ alkyl group wherein alkyl has the same definition as described herein. Examples of an alkylureyl include, but not limited to, $CH_3NHC(O)NH$—, $NH_2C(O)NCH_3$—, $(CH_3)_2N(O)NH$—, $(CH_3)_2N(O)NH$—, $(CH_3)_2N(O)NCH_3$—, $CH_3CH_2NHC(O)NH$—, $CH_3CH_2NHC(O)NCH_3$—, and the like.

The term "$C_{2-6}$ alkynyl" denotes a radical containing 2 to 6 carbons and at least one carbon-carbon triple bond, some embodiments are 2 to 4 carbons, some embodiments are 2 to 3 carbons, and some embodiments have 2 carbons. Examples of an alkynyl include, but not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. The term "alkynyl" includes di- and tri-ynes.

The term "amino" denotes the group —$NH_2$.

The term "$C_{1-4}$ alkylamino" denotes one alkyl radical attached to an amino radical wherein the alkyl radical has the same meaning as described herein. Some examples include, but not limited to, methylamino, ethylamino, n-propylamino, iso-propylamino, n-butylamino, sec-butylamino, iso-butylamino, t-butylamino, and the like. Some embodiments are "$C_{1-2}$ alkylamino."

The term "aryl" denotes an aromatic ring radical containing 6 to 10 ring carbons. Examples include phenyl and naphthyl.

The term "arylalkyl" defines a $C_1$-$C_4$ alkylene, such as —$CH_2$—, —$CH_2CH_2$— and the like, which is further substituted with an aryl group. Examples of an "arylalkyl" include benzyl, phenethylene and the like.

The term "arylcarboxamido" denotes a single aryl group attached to the nitrogen of an amide group, wherein aryl has the same definition as found herein. The example is N-phenylcarboxamide.

The term "arylureyl" denotes the group —NC(O)N— where one of the nitrogens are substituted with an aryl.

The term "benzyl" denotes the group —$CH_2C_6H_5$.

The term "carbo-$C_{1-6}$-alkoxy" refers to a $C_{1-6}$ alkyl ester of a carboxylic acid, wherein the alkyl group is as defined herein. In some embodiments, the carbo-$C_{1-6}$-alkoxy group is bonded to a nitrogen atom and together form a carbamate group (e.g., N—COO—$C_{1-6}$-alkyl). In some embodiments, the carbo-$C_{1-6}$-alkoxy group is an ester (e.g., —COO—$C_{1-6}$-alkyl). Examples include, but not limited to, carbomethoxy, carboethoxy, carbopropoxy, carboisopropoxy, carbobutoxy, carbo-sec-butoxy, carbo-iso-butoxy, carbo-t-butoxy, carbo-n-pentoxy, carbo-iso-pentoxy, carbo-t-pentoxy, carbo-neopentoxy, carbo-n-hexyloxy, and the like.

The term "carboxamide" refers to the group —$CONH_2$.

The term "carboxy" or "carboxyl" denotes the group —$CO_2H$; also referred to as a carboxylic acid group.

The term "cyano" denotes the group —CN.

The term "$C_{3-7}$ cycloalkenyl" denotes a non-aromatic ring radical containing 3 to 6 ring carbons and at least one double bond; some embodiments contain 3 to 5 carbons; some embodiments contain 3 to 4 carbons. Examples include cyclopropenyl, cyclobutenyl, cyclopentenyl, cyclopentenyl, cyclohexenyl, and the like.

The term "$C_{3-7}$ cycloalkyl" denotes a saturated ring radical containing 3 to 6 carbons; some embodiments contain 3 to 5 carbons; some embodiments contain 3 to 4 carbons. Examples include cyclopropyl, cyclobutyl, cyclopentyl, cyclopenyl, cyclohexyl, cycloheptyl and the like.

The term "$C_{4-8}$ diacylamino" denotes an amino group bonded with two acyl groups defined herein wherein the acyl groups may be the same or different, such as:

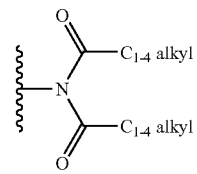

Examples of $C_{4-8}$ diacylamino groups include, but limited to, diacetylamino, dipropionylamino, acetylpropionylamino and the like.

The term "$C_{2-6}$ dialkylamino" denotes an amino substituted with two of the same or different alkyl radicals wherein alkyl radical has the same definition as described herein. Some examples include, but not limited to, dimethylamino, methylethylamino, diethylamino, methylpropylamino, methylisopropylamino, ethylpropylamino, ethylisopropylamino, dipropylamino, propylisopropylamino and the like. Some embodiments are "$C_{2-4}$ dialkylamino."

The term "$C_{1-4}$ dialkylcarboxamido" or "$C_{1-4}$ dialkylcarboxamide" denotes two alkyl radicals, that are the same or different, attached to an amide group, wherein alkyl has the same definition as described herein. A $C_{1-4}$ dialkylcarboxamido may be represented by the following groups:

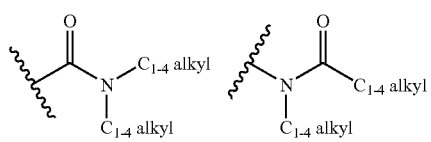

wherein $C_{1-4}$ has the same definition as described herein. Examples of a dialkylcarboxamide include, but not limited to, N,N-dimethylcarboxamide, N-methyl-N-ethylcarboxamide, N,N-diethylcarboxamide, N-methyl-N-isopropylcarboxamide, and the like.

The term "$C_{2-6}$ dialkylsulfonamide" refers to one of the following groups shown below:

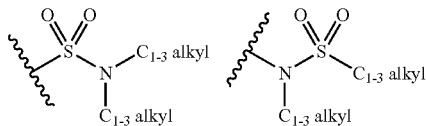

wherein $C_{1-3}$ has the same definition as described herein, for example but not limited to, methyl, ethyl, n-propyl, isopropyl, and the like.

The term "$C_{2-6}$ dialkylthiocarboxamido" or "$C_{2-6}$ dialkylthiocarboxamide" denotes two alkyl radicals, that are the same or different, attached to a thioamide group, wherein alkyl has the same definition as described herein. A $C_{1-4}$ dialkylthiocarboxamido may be represented by the following groups:

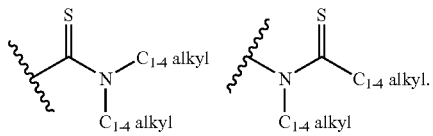

Examples of a dialkylthiocarboxamide include, but not limited to, N,N-dimethylthiocarboxamide, N-methyl-N-ethylthiocarboxamide and the like.

The term "$C_{2-6}$ dialkylsulfonylamino" refers to an amino group bonded with two $C_{1-3}$ alkylsulfonyl groups as defined herein.

The term "ethynylene" refers to the carbon-carbon triple bond group as represented below:

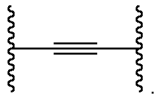

The term "formyl" refers to the group —CHO.

The term "$C_{1-4}$ haloalkoxy" denotes a haloalkyl, as defined herein, which is directly attached to an oxygen atom. Examples include, but not limited to, difluoromethoxy, trifluoromethoxy, 2,2,2-trifluoroethoxy, pentafluoroethoxy and the like.

The term "$C_{1-4}$ haloalkyl" denotes an $C_{1-4}$ alkyl group, defined herein, wherein the alkyl is substituted with one halogen up to fully substituted and a fully substituted $C_{1-4}$ haloalkyl can be represented by the formula $C_nL_{2n+1}$ wherein L is a halogen and "n" is 1, 2, 3 or 4; when more than one halogen is present then they may be the same or different and selected from the group consisting of F, Cl, Br and I, preferably F. Examples of $C_{1-4}$ haloalkyl groups include, but not limited to, fluoromethyl, difluoromethyl, trifluoromethyl, chlorodifluoromethyl, 2,2,2-trifluoroethyl, pentafluoroethyl and the like.

The term "$C_{1-4}$ haloalkylcarboxamide" denotes an alkylcarboxamide group, defined herein, wherein the alkyl is substituted with one halogen up to fully substituted represented by the formula $C_nL_{2n+1}$ wherein L is a halogen and "n" is 1, 2, 3 or 4. When more than one halogen is present they may be the same or different and selected from the group consisting of F, Cl, Br and I, preferably F.

The term "$C_{1-4}$ haloalkylsulfinyl" denotes a haloalkyl radical attached to a sulfoxide group of the formula: —S(O)— wherein the haloalkyl radical has the same definition as described herein. Examples include, but not limited to, trifluoromethylsulfinyl, 2,2,2-trifluoroethylsulfinyl, 2,2-difluoroethylsulfinyl and the like.

The term "$C_{1-4}$ haloalkylsulfonyl" denotes a haloalkyl radical attached to a sulfone group of the formula: —S(O)$_2$— wherein haloalkyl has the same definition as described herein. Examples include, but not limited to, trifluoromethylsulfonyl, 2,2,2-trifluoroethylsulfonyl, 2,2-difluoroethylsulfonyl and the like.

The term "$C_{1-4}$ haloalkylthio" denotes a haloalkyl radicaol directly attached to a sulfur wherein the haloalkyl has the same meaning as described herein. Examples include, but not limited to, trifluoromethylthio (i.e., $CF_3S$—), 1,1-difluoroethylthio, 2,2,2-trifluoroethylthio and the like.

The term "halogen" or "halo" denotes to a fluoro, chloro, bromo or iodo group.

The term "$C_{1-2}$ heteroalkylene" refers to a $C_{1-2}$ alkylene bonded to a heteroatom selected from O, S, S(O), S(O)$_2$ and NH. Some represented examples include, but not limited to, the groups of the following formulae:

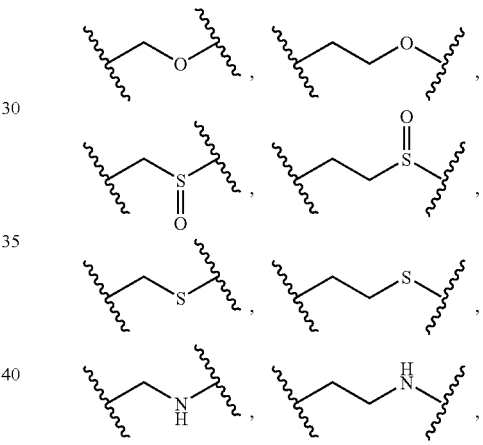

and the like.

The term "heteroaryl" denotes an aromatic ring system that may be a single ring, two fused rings or three fused rings wherein at least one ring carbon is replaced with a heteroatom selected from, but not limited to, the group consisting of O, S and N wherein the N can be optionally substituted with H, $C_{1-4}$ acyl or $C_{1-4}$ alkyl. Examples of heteroaryl groups include, but not limited to, pyridyl, benzofuranyl, pyrazinyl, pyridazinyl, pyrimidinyl, triazinyl, quinoline, benzoxazole, benzothiazole, 1H-benzimidazole, isoquinoline, quinazoline, quinoxaline and the like. In some embodiments, the heteroaryl atom is O, S, NH, examples include, but not limited to, pyrrole, indole, and the like. Other examples include, but not limited to, those in TABLE 2A, TABLE 4, and the like.

The term "heterocyclic" denotes a non-aromatic carbon ring (i.e., cycloalkyl or cycloalkenyl as defined herein) wherein one, two or three ring carbons are replaced by a heteroatom selected from, but not limited to, the group consisting of O, S, N, wherein the N can be optionally substituted with H, $C_{1-4}$ acyl or $C_{1-4}$ alkyl, and ring carbon atoms optionally substituted with oxo or a thiooxo thus forming a carbonyl or thiocarbonyl group. The heterocyclic group is a 3-, 4-, 5-, 6- or 7-membered containing ring. Examples of a heterocyclic group include but not limited to aziridin-1-yl, aziridin-2-yl, azetidin-1-yl, azetidin-2-yl, azetidin-3-yl, piperidin-1-yl, piperidin-4-yl, morpholin-4-yl, piperzin-1-yl, piperzin-4-yl, pyrrolidin-1-yl, pyrrolidin-3-yl, [1,3]-dioxolan-2-yl and the like. Additional examples of heterocyclic groups are shown in TABLES 2B, 2C, 2D, 2E, 2F and 2G, infra.

The term "heterocyclic-carbonyl" denotes a heterocyclic group, as defined herein, directly bonded to the carbon of a carbonyl group (i.e., C=O). In some embodiments, a ring nitrogen of the heterocyclic group is bonded to the carbonyl group forming an amide. Examples include, but not limited to,

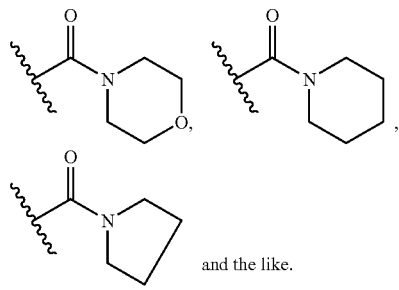

In some embodiments, a ring carbon is bonded to the carbonyl group forming a ketone group. Examples include, but not limited to,

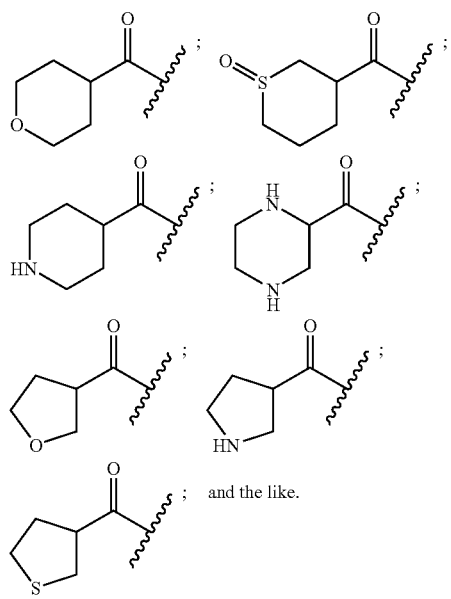

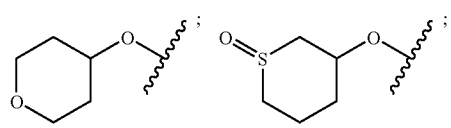

The term "heterocyclic-oxy" refers to a heterocyclic group, as defined herein, that is directly bonded to an oxygen atom. Examples include the following:

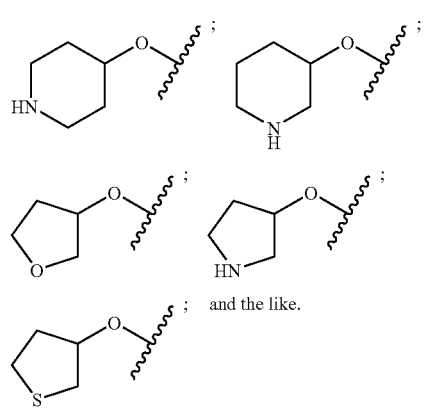

The term "heterocycliccarboxamido" denotes a heterocyclic group, as defined herein, with a ring nitrogen where the ring nitrogen is bonded directly to the carbonyl forming an amide. Examples include, but not limited to,

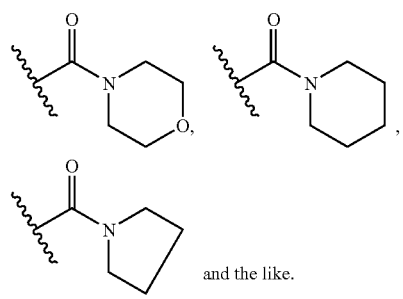

The term "heterocyclicsulfonyl" denotes a heterocyclic group, as defined herein, with a ring nitrogen where the ring nitrogen is bonded directly to an SO$_2$ group forming an sulfonamide. Examples include, but not limited to,

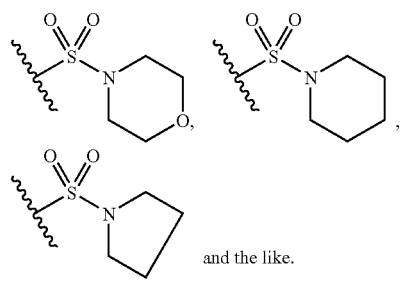

The term "hydroxyl" refers to the group —OH.
The term "hydroxylamino" refers to the group —NHOH.
The term "nitro" refers to the group —NO$_2$.
The term "C$_{4-7}$ oxo-cycloalkyl" refers to a C$_{4-7}$ cycloalkyl, as defined herein, wherein one of the ring carbons is replaced with a carbonyl. Examples of C$_{4-7}$ oxo-cycloalkyl include, but are not limited to, 2-oxo-cyclobutyl, 3-oxo-cyclobutyl, 3-oxo-cyclopentyl, 4-oxo-cyclohexyl, and the like and represented by the following structures respectively:

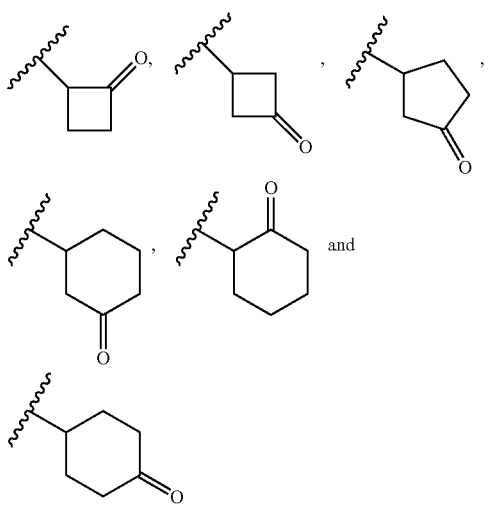

The term "perfluoroalkyl" denotes the group of the formula $-C_nF_{2n+1}$; stated differently, a perfluoroalkyl is an alkyl as defined herein wherein the alkyl is fully substituted with fluorine atoms and is therefore considered a subset of haloalkyl. Examples of perfluoroalkyls include $CF_3$, $CF_2CF_3$, $CF_2CF_2CF_3$, $CF(CF_3)_2$, $CF_2CF_2CF_2CF_3$, $CF_2CF(CF_3)_2$, $CF(CF_3)CF_2CF_3$ and the like.

The term "phenoxy" refers to the group $C_6H_5O-$.

The term "phenyl" refers to the group $C_6H_5-$.

The term "phosphonooxy" refers to a group with the following chemical structure:

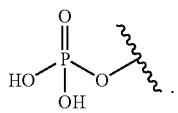

The term "sulfonamide" refers to the group $-SO_2NH_2$.

The term "sulfonic acid" refers to the group $-SO_3H$.

The term "tetrazolyl" refers to the five membered heteroaryl of the following formulae:

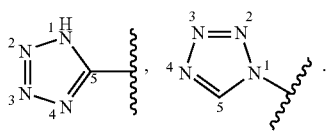

In some embodiments, the tetrazolyl group is further substituted at either the 1 or 5 position resepectively with a group selected from the group consisting of $C_{1-3}$ alkyl, $C_{1-3}$ haloalkyl and $C_{1-3}$ alkoxy.

The term "thiol" denotes the group $-SH$.

CODON shall mean a grouping of three nucleotides (or equivalents to nucleotides) which generally comprise a nucleoside (adenosine (A), guanosine (G), cytidine (C), uridine (U) and thymidine (T)) coupled to a phosphate group and which, when translated, encodes an amino acid.

COMPOSITION shall mean a material comprising at least two compounds or two components; for example, and without limitation, a Pharmaceutical Composition is a Composition comprising a compound of the present invention and a pharmaceutically acceptable carrier.

COMPOUND EFFICACY shall mean a measurement of the ability of a compound to inhibit or stimulate receptor functionality, as opposed to receptor binding affinity.

CONSTITUTIVELY ACTIVATED RECEPTOR shall mean a receptor subject to constitutive receptor activation.

CONSTITUTIVE RECEPTOR ACTIVATION shall mean stabilization of a receptor in the active state by means other than binding of the receptor with its endogenous ligand or a chemical equivalent thereof.

CONTACT or CONTACTING shall mean bringing the indicated moieties together, whether in an in vitro system or an in vivo system. Thus, "contacting" a RUP3 receptor with a compound of the invention includes the administration of a compound of the present invention to an individual, preferably a human, having a RUP3 receptor, as well as, for example, introducing a compound of the invention into a sample containing a cellular or more purified preparation containing a RUP3 receptor.

ENDOGENOUS shall mean a material that a mammal naturally produces. ENDOGENOUS in reference to, for example and not limitation, the term "receptor" shall mean that which is naturally produced by a mammal (for example, and not limitation, a human) or a virus.

In contrast, the term NON-ENDOGENOUS in this context shall mean that which is not naturally produced by a mammal (for example, and not limitation, a human) or a virus. For example, and not limitation, a receptor which is not constitutively active in its endogenous form, but when manipulated becomes constitutively active, is most preferably referred to herein as a "non-endogenous, constitutively activated receptor." Both terms can be utilized to describe both "in vivo" and "in vitro" systems. For example, and not a limitation, in a screening approach, the endogenous or non-endogenous receptor may be in reference to an in vitro screening system. As a further example and not limitation, where the genome of a mammal has been manipulated to include a non-endogenous constitutively activated receptor, screening of a candidate compound by means of an in vivo system is viable.

IN NEED OF PROPHYLAXIS OR TREATMENT as used herein refers to a judgment made by a caregiver (e.g. physician, nurse, nurse practitioner, etc. in the case of humans; veterinarian in the case of animals, including non-human mammals) that an individual or animal requires or will benefit from prophylaxis or treatment. This judgment is made based on a variety of factors that are in the realm of a caregiver's expertise, but that includes the knowledge that the individual or animal is ill, or will be ill, as the result of a disease, condition or disorder that is treatable by the compounds of the invention. In general, "in need of prophylaxis" refers to the judgment made by the caregiver that the individual will become ill. In this context, the compounds of the invention are used in a protective or preventive manner. However, "in need of treatment" refers to the judgment of the caregiver that the individual is already ill, therefore, the compounds of the present invention are used to alleviate, inhibit or ameliorate the disease, condition or disorder.

INDIVIDUAL as used herein refers to any animal, including mammals, preferably mice, rats, other rodents, rabbits, dogs, cats, swine, cattle, sheep, horses, or primates, and most preferably humans.

INHIBIT or INHIBITING, in relationship to the term "response" shall mean that a response is decreased or prevented in the presence of a compound as opposed to in the absence of the compound.

INVERSE AGONISTS shall mean moieties that bind the endogenous form of the receptor or to the constitutively activated form of the receptor, and which inhibit the baseline intracellular response initiated by the active form of the receptor below the normal base level of activity which is observed in the absence of agonists or partial agonists, or decrease GTP binding to membranes. Preferably, the baseline intracellular response is inhibited in the presence of the inverse agonist by at least 30%, more preferably by at least 50%, and most preferably by at least 75%, as compared with the baseline response in the absence of the inverse agonist.

LIGAND shall mean an endogenous, naturally occurring molecule specific for an endogenous, naturally occurring receptor.

As used herein, the terms MODULATE or MODULATING shall mean to refer to an increase or decrease in the amount, quality, response or effect of a particular activity, function or molecule.

PHARMACEUTICAL COMPOSITION shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

THERAPEUTICALLY EFFECTIVE AMOUNT as used herein refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) Preventing the disease; for example, preventing a disease, condition or disorder in an individual that may be predisposed to the disease, condition or disorder but does not yet experience or display the pathology or symptomatology of the disease, (2) Inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) Ameliorating the disease; for example, ameliorating a disease, condition or disorder in an individual that is experiencing or displaying the pathology or symptomatology of the disease, condition or disorder (i.e., reversing the pathology and/or symptomatology).

Compounds of the Present Invention:

One aspect of the present invention encompasses fused aryl and heteroaryl derivatives as shown in Formula (I):

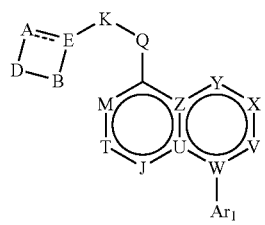

(I)

or a pharmaceutically acceptable salt, hydrate or solvate thereof; wherein $Ar_1$, M, T, J, Y, X, V, W, Z, U, Q, K, E, A, B, D, and ----- have the same definitions as described herein, supra and infra.

Some embodiments of the present invention encompass fused aryl and heteroaryl derivatives as shown in Formula (I) wherein:

A and B are independently $C_{1-3}$ alkylene optionally substituted with 1 to 4 substituents selected from the group consisting of $C_{1-3}$ alkyl, $C_{1-4}$ alkoxy, carboxy, cyano, $C_{1-3}$ haloalkyl and halogen;

D is O, S, S(O), $S(O)_2$, $CR_1R_2$ or N—$R_2$, wherein $R_1$ is selected from the group consisting of H, $C_{1-8}$ alkyl, $C_{1-4}$ alkoxy, halogen and hydroxyl;

E is N, C or $CR_3$, wherein $R_3$ is H or $C_{1-8}$ alkyl;

----- is a single bond when E is N or $CR_3$, or a double bond when E is C;

K is a $C_{1-3}$ alkylene group optionally substituted with 1 to 4 substituents selected from the group consisting of $C_{1-3}$ alkyl, $C_{1-4}$ alkoxy, carboxy, cyano, $C_{1-3}$ haloalkyl and halogen; or K is a bond;

Q is $NR_4$, O, S, S(O) or $S(O)_2$, wherein $R_4$ is H or $C_{1-8}$ alkyl;

T is N or $CR_5$;

M is N or $CR_6$;

J is N or $CR_7$;

U is C or N;

V is N, $CR_8$ or V is a bond;

W is N or C;

X is O, S, N, $CR_9$ or $NR_{11}$;

Y is O, S, N, $CR_{10}$ or $NR_{12}$;

Z is C or N;

$R_5$, $R_6$, $R_7$, $R_8$, $R_9$ and $R_{10}$ are independently selected from the group consisting of H, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-4}$ alkylamino, $C_{2-8}$ dialkylamino, carboxamide, cyano, $C_{3-6}$ cycloalkyl, $C_{2-6}$ dialkylcarboxamide, $C_{2-6}$ dialkylsulfonamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, hydroxylamino and nitro; wherein said $C_{2-6}$ alkenyl, $C_{1-8}$ alkyl, $C_{2-6}$ alkynyl and $C_{3-6}$ cycloalkyl are optionally substituted with 1, 2, 3 or 4 substituents selected from the group consisting of $C_{1-5}$ acyl, $C_{1-5}$ acyloxy, $C_{1-4}$ alkoxy, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{2-8}$ dialkylamino, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, hydroxyl, hydroxylamino and nitro;

$R_{11}$ and $R_{12}$ are independently selected from $C_{2-6}$ alkenyl, $C_{1-8}$ alkyl, $C_{2-6}$ alkynyl or $C_{3-6}$ cycloalkyl each optionally substituted with 1, 2, 3 or 4 substituents selected from the group consisting of $C_{1-5}$ acyl, $C_{1-5}$ acyloxy, $C_{1-4}$ alkoxy, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{2-8}$ dialkylamino, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, hydroxyl, hydroxylamino and nitro;

$Ar_1$ is aryl or heteroaryl optionally substituted with $R_{13}$, $R_{14}$, $R_{15}$, $R_{16}$ and $R_{17}$; wherein $R_{13}$ is selected from the group consisting of H, $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, arylsulfonyl, carbo-$C_{1-6}$-alkoxy, carboxamide, carboxy, cyano, $C_{3-7}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heterocyclic, heterocyclicsulfonyl, heteroaryl, hydroxyl, nitro, $C_{4-7}$ oxo-cycloalkyl, phenoxy, phenyl, sulfonamide and sulfonic acid, and wherein said $C_{1-5}$ acyl, $C_{1-4}$ alkoxy, $C_{1-8}$ alkyl, $C_{1-4}$ alkylsulfonamide, alkylsulfonyl, arylsulfonyl, heteroaryl, phenoxy or phenyl each optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkyltbio, $C_{1-4}$ alkylureyl, carbo-$C_{1-6}$-alkoxy, carboxamide, carboxy, cyano, $C_{3-7}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heteroaryl, heterocyclic, hydroxyl, nitro and phenyl; or $R_{13}$ is a group of Formula (A):

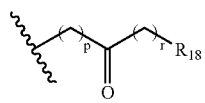

(A)

wherein:

"p" and "r" are independently 0, 1, 2 or 3; and $R_{18}$ is H, $C_{1-5}$ acyl, $C_{2-6}$ alkenyl, $C_{1-8}$ alkyl, $C_{1-4}$ alkylcarboxamide, $C_{2-6}$ alkynyl, $C_{1-4}$ alkylsulfonamide, carbo-$C_{1-6}$-alkoxy, carboxamide, carboxy, cyano, $C_{3-7}$ cycloalkyl, $C_{2-6}$ dialkylcarboxamide, halogen, heteroaryl or phenyl, and wherein the heteroaryl or phenyl optionally substituted with 1 to 5 substituents selected independently from the group consisting of $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl;

$R_{14}$-$R_{17}$ are independently selected form the group consisting of H, $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl and nitro; or two adjacent $R_{14}$, $R_{15}$, $R_{16}$ and $R_{17}$ together with the atoms to which they are attached form a 5, 6 or 7 membered cycloalkyl, cycloalkenyl or heterocyclic group fused with $Ar_1$ wherein the 5, 6 or 7 membered group is optionally substituted with halogen; and $R_2$ is selected from the group consisting of H, $C_{1-8}$ alkyl, $C_{2-6}$ alkynyl, amino, aryl, carboxamide, carboxy, cyano, $C_{3-6}$-cycloalkyl, $C_{1-4}$ haloalkoxy, $C_{1-4}$ haloalkyl, halogen, heteroaryl and hydroxyl; and wherein said $C_{1-8}$ alkyl, aryl and heteroaryl are each optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{3-6}$-cycloalkyl-$C_{1-3}$-heteroalkylene, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro; or $R_2$ is —$Ar_2$—$Ar_3$ wherein $Ar_2$ and $Ar_3$ are independently aryl or heteroaryl each optionally substituted with 1 to 5 substituents selected from the group consisting of H, $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, $C_{1-4}$ alkylamino, carbo-$C_{1-6}$-alkoxy, carboxamide, carboxy, cyano, $C_{3-6}$-cycloalkyl, $C_{2-8}$ dialkylamino, $C_{2-6}$ dialkylcarboxamide, $C_{1-4}$ haloalkoxy, $C_{1-4}$ haloalkyl, halogen, hydroxyl and nitro; or $R_2$ is a group of Formula (B):

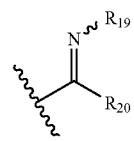

(B)

wherein:

$R_{19}$ is H, $C_{1-8}$ alkyl, $C_{3-7}$ cycloalkyl, aryl, heteroaryl or $OR_{21}$; and $R_{20}$ is F, Cl, Br, CN or $NR_{22}R_{23}$; where $R_{21}$ is H, $C_{1-8}$ alkyl or $C_{3-7}$ cycloalkyl, and $R_{22}$ and $R_{23}$ are independently H, $C_{1-8}$ alkyl, $C_{3-7}$ cycloalkyl, aryl or heteroaryl; or $R_2$ is a group of Formula (C):

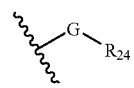

(C)

wherein:

G is selected from the group consisting of:

i) C(O), C(O)$NR_{25}$, C(O)O, OC(O), C(S), C(S)$NR_{25}$, C(S)O, OC(S), $CR_{25}R_{26}$, O, S, S(O) and S(O)$_2$ when D is $CR_1R_2$, or ii) C(O), C(O)$NR_{25}$, C(O)O, C(S), C(S)$NR_{25}$, C(S)O, $CR_{25}R_{26}$ and S(O)$_2$ when D is $NR_2$, wherein $R_{25}$ and $R_{26}$ are independently H or $C_{1-8}$ alkyl; and $R_{24}$ is $C_{1-8}$ alkyl, $C_{3-7}$ cycloalkyl, phenyl or heteroaryl optionally substituted with 1 to 5 substituents selected from the group consisting of $C_{1-5}$ acyl, $C_{1-5}$ acyloxy, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, hydroxyl, hydroxylamino and nitro; or a pharmaceutically acceptable salt, hydrate or solvate thereof; provided that Z and U are not both N.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

As used herein, "substituted" indicates that at least one hydrogen atom of the chemical group is replaced by a non-hydrogen substituent or group, the non-hydrogen substituent or group can be monovalent or divalent. When the substituent or group is divalent, then it is understood that this group is further substituted with another substituent or group. When a chemical group herein is "substituted" it may have up to the full valance of substitution; for example, a methyl group can be substituted by 1, 2, or 3 substituents, a methylene group can be substituted by 1 or 2 substituents, a phenyl group can be substituted by 1, 2, 3, 4, or 5 substituents, a naphthyl group can be substituted by 1, 2, 3, 4, 5, 6, or 7 substituents and the like. Likewise, "substituted with one or more substituents" refers to the substitution of a group with one substituent up to the total number of substituents physically allowed by the group. Further, when a group is substituted with more than one group they can be identical or they can be different.

It is understood and appreciated that compounds of the present invention may have one or more chiral centers, and therefore can exist as enantiomers and/or diastereomers. The invention is understood to extend to and embrace all such enantiomers, diastereomers and mixtures thereof, including but not limited, to racemates. Accordingly, some embodiments of the present invention pertain to compounds, such as those represented in Formula (I) and other formulae used throughout this disclosure, that are R enantiomers. Further, some embodiments of the present invention pertain to compounds, such as those represented in Formula (I) and other formulae used throughout this disclosure, that are S enantiomers. In examples where more than one chiral center is present, then, some embodiments of the present invention include compounds that are RS or SR enantiomers. In further embodiments, compounds of the present invention are RR or SS enantiomers. It is understood that compounds of Formula (I) and formulae used throughout this disclosure are intended to represent all individual enantiomers and mixtures thereof, unless stated or shown otherwise.

Compounds of the invention can also include tautomeric forms, such as keto-enol tautomers, and the like. Tautomeric forms can be in equilibrium or sterically locked into one form by appropriate substitution. It is understood that the various tautomeric forms are within the scope of the compounds of the present invention.

Compounds of the invention can also include all isotopes of atoms occurring in the intermediates and/or final compounds. Isotopes include those atoms having the same atomic number but different mass numbers. For example, isotopes of hydrogen include deuterium and tritium.

In some embodiments, compounds of the invention are not 4-[1-(2,4-Dimethyl-phenyl)-1H-pyrazolo[3,4-d]pyrimidin-4-ylamino]-piperidine-1-carboxylic acid ethyl ester; 4-(1-m-Tolyl-1H-pyrazolo[3,4-d]pyrimidin-4-ylamino)-piperidine-1-carboxylic acid ethyl ester; 4-[1-(4-Methoxy-phenyl)-1H-pyrazolo[3,4-d]pyrimidin-4-ylamino]-piperidine-1-carboxylic acid ethyl ester; 4-[1-(4-Chloro-phenyl)-1H-pyrazolo[3,4-d]pyrimidin-4-ylamino]-piperidine-1-carboxylic acid ethyl ester; and 4-(1-Phenyl-1H-pyrazolo[3,4-d]pyrimidin-4-ylamino)-piperidine-1-carboxylic acid ethyl ester.

In some embodiments of the present invention, ----- is a single bond.

Some embodiments of the present invention pertain to compounds wherein Q is $NR_4$. In some embodiments, $R_4$ is $C_{1-8}$ alkyl optionally substituted with $C_{2-8}$ dialkylamino. In some embodiments, $R_4$ is selected from the group consisting of methyl, ethyl, isopropyl, and 2-dimethylamino-ethyl. In some embodiments, $R_4$ is H (i.e., NH).

In some embodiments, compounds of the present invention can be represented by Formula (Ia) as illustrated below:

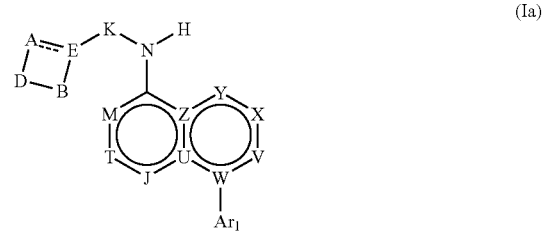

(Ia)

wherein each variable in Formula (Ia) has the same meaning as described herein, supra and infra.

In some embodiments, K is a bond.

In some embodiments, K is selected from the group consisting of —$CH_2$—, —$CH_2CH_2$—, and —$CH(CH_3)CH_2$—.

In some embodiments, K is —$CH_2$— or —$CH_2CH_2$—.

Some embodiments of the present invention pertain to compounds wherein Q is O. Some embodiments of the present invention can be represented by Formula (Ic) as illustrated below:

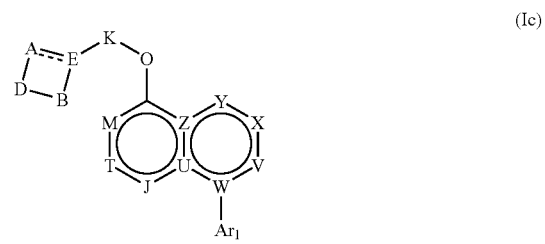

(Ic)

wherein each variable in Formula (Ic) has the same meaning as described herein, supra and infra. In some embodiments, K is —$CH_2$— or —$CH_2CH_2$—.

In some embodiments, compounds of the present invention are represented by Formula (Ic) and K is a bond; these embodiments can be represented by Formula (Id) as illustrated below:

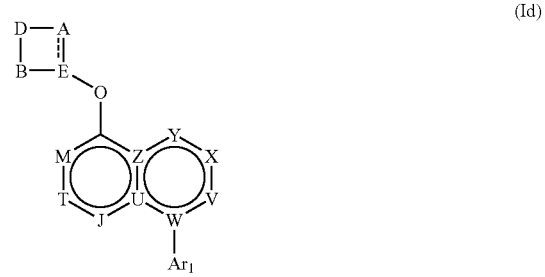

(Id)

wherein each variable in Formula (Id) has the same meaning as described herein, supra and infra.

Some embodiments of the present invention pertain to compounds wherein Q is S, S(O) or S(O)$_2$. In some embodiments, Q is S. In some embodiments, Q is S(O). In some embodiments, Q is S(O)$_2$. Some embodiments of the present invention can be represented by Formulae (Ie), (If) and (Ig) respectively as shown below:

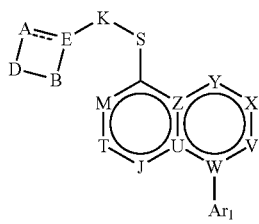
(Ie)

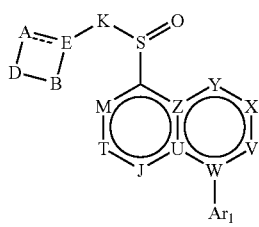
(If)

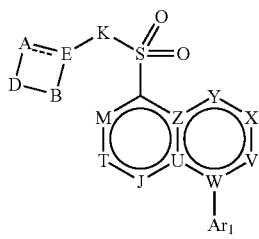
(Ig)

wherein each variable in Formulae (Ie), (If) and (Ig) has the same meaning as described herein, supra and infra.

Some embodiments of the present invention pertain to compounds wherein A and B are independently C$_{1-2}$ alkylene optionally substituted with 1 to 4 substituents selected from the group consisting of C$_{1-3}$ alkyl, C$_{1-4}$ alkoxy, carboxy, cyano, C$_{1-3}$ haloalkyl and halogen.

Some embodiments of the present invention pertain to compounds wherein both A and B are C$_1$ alkylene groups optionally substituted with 1 to 2 methyl groups.

In some embodiments, A and B are both —CH$_2$—. Some embodiments of the present invention and can be represented by Formula (Ik) as shown below:

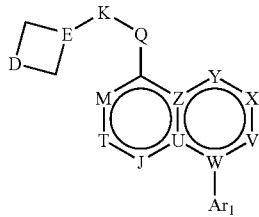
(Ik)

wherein each variable in Formula (Ik) has the same meaning as described herein, supra and infra.

In some embodiments, both A and B are —CH$_2$— and E is CH.

In some embodiments, both A and B are —CH$_2$—, E is CH, and D is N—R$_2$.

Some embodiments of the present invention pertain to compounds wherein A is a C$_1$ alkylene group and B is a C$_2$ alkylene group wherein A is optionally substituted with 1 to 2 methyl groups and B is optionally substituted with 1 to 4 methyl groups. In some embodiments, A is —CH$_2$— or —CH— and B is —CH$_2$CH$_2$—. It is understood that when ----- is a single bond there are two methods to describe the same ABED ring system, for examples, in some embodiments A is —CH$_2$—, B is —CH$_2$CH$_2$—, and for the same embodiments, A is —CH$_2$CH$_2$— and B is —CH$_2$—. Therefore, it is understood that either method is correct. Some embodiments of the present invention can be represented by Formulae (Im) and (In) respectively as shown below:

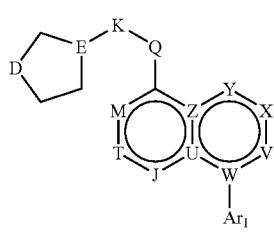
(Im)

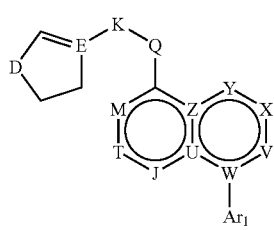
(In)

wherein each variable in Formulae (Im) and (In) has the same meaning as described herein, supra and infra. In some embodiments, A is —CH$_2$—, B is —CH$_2$CH$_2$—, and K is a —CH$_2$— or —CH$_2$CH$_2$—. In some embodiments, A is —CH$_2$—, B is —CH$_2$CH$_2$—, and K is a bond.

In some embodiments, A is —CH$_2$CH$_2$— and B is —CH$_2$—, and E is CH.

In some embodiments, A is —CH$_2$CH$_2$— and B is —CH$_2$—, E is CH and D is N—R$_2$.

Some embodiments of the present invention pertain to compounds wherein A is a C$_1$ alkylene group and B is a C$_3$ alkylene group wherein A is optionally substituted with 1 to 2 methyl groups and B is optionally substituted with 1 to 4 methyl groups. In some embodiments, A is —CH$_2$— or —CH— and B is —CH$_2$CH$_2$CH$_2$— and can be represented by Formulae (Ip) and (Iq) respectively as shown below:

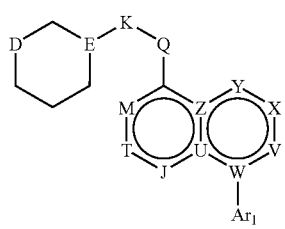
(Ip)

-continued

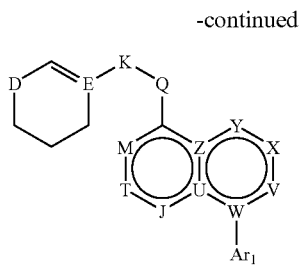

(Iq)

wherein each variable in Formulae (Ip) and (Iq) has the same meaning as described herein, supra and infra.

Some embodiments of the present invention pertain to compounds wherein A is a $C_2$ alkylene group and B is a $C_1$ alkylene group wherein A is optionally substituted with 1 to 4 methyl groups and B is optionally substituted with 1 to 2 methyl groups. In some embodiments, A is —CHCH$_2$— and B is —CH$_2$—; these embodiments can be represented by Formula (It) as shown below:

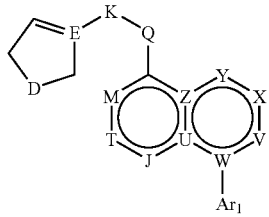

(It)

wherein each variable in Formula (It) has the same meaning as described herein, supra and infra.

Some embodiments of the present invention pertain to compounds wherein A is CH$_2$ and B is —CH$_2$CH$_2$—, —CH$_2$CH(CH$_3$)—, —CH(CH$_3$)CH$_2$—, —CH$_2$CH(CF$_3$)— or —CH(CF$_3$)CH$_2$—. In some embodiments, compounds of the invention are represented by Formulae (Iv), (Iw) and (Ix) as shown below:

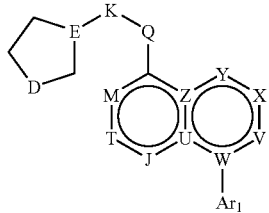

(Iv)

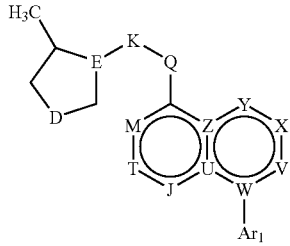

(Iw)

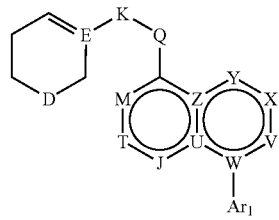

(Ix)

wherein each variable in Formulae (Iv), (Iw) and (Ix) has the same meaning as described herein, supra and infra. In some embodiments, D is N—R$_2$. In some embodiments, E is CR$_3$. In some embodiments, R$_3$ is H.

Some embodiments of the present invention pertain to compounds wherein A is a $C_3$ alkylene group and B is a $C_1$ alkylene group wherein A is optionally substituted with 1 to 4 methyl groups and B is optionally substituted with 1 to 2 methyl groups. In some embodiments, A is —CHCH$_2$CH$_2$— and B is —CH$_2$—. Some embodiments, compounds of the present invention can be represented by Formulae (IIa) as shown below:

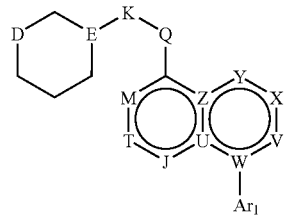

(IIa)

wherein each variable in Formulae (IIa) has the same meaning as described herein, supra and infra.

In some embodiments, A is —CH$_2$— and B is —CH$_2$CH$_2$CH$_2$—. Some embodiments, compounds of the present invention can be represented by Formulae (IIb) as shown below:

(IIb)

wherein each variable in Formulae (IIb) has the same meaning as described herein, supra and infra.

In some embodiments, A is —CH$_2$—, B is —CH$_2$CH$_2$CH$_2$— and E is CH.

In some embodiments, A is —CH$_2$—, B is —CH$_2$CH$_2$CH$_2$—, E is CH, and D is N—R$_2$.

Some embodiments of the present invention pertain to compounds wherein A and B are both $C_2$ alkylene groups optionally substituted with 1 to 4 methyl groups. In some embodiments, A is —CH$_2$CH$_2$— or —CHCH$_2$— and B is —CH$_2$CH$_2$—. In some embodiments, both A and B are —CH$_2$CH$_2$—. Some embodiments of the present invention can be represented by Formulae (IIc) and (IId) as shown below:

(IIc)

(IId)

wherein each variable in Formulae (IIc) and (IId) has the same meaning as described herein, supra and infra. In some embodiments, both A and B are —CH$_2$CH$_2$— and E is CH. In some embodiments, A and B are both —CH$_2$CH$_2$—, D is N—R$_2$, and E is CR$_3$. In some embodiments, both A and B are —CH$_2$CH$_2$—, E is CH, and D is N—R$_2$. Some embodiments of the present invention can be represented by Formula (IIf) as shown below:

(IIf)

wherein each variable in Formula (IIf) has the same meaning as described herein, supra and infra. In some embodiments, compounds have the Formula (IIf) and R$_3$ is H. In further embodiment, K is a bond. In still further embodiments, K is —CH$_2$— or —CH$_2$CH$_2$—.

Some embodiments of the present invention pertain to compounds of Formula (IIg) as shown below:

(IIg)

wherein each variable in Formula (IIg) has the same meaning as described herein, supra and infra. In some embodiments, R$_3$ is H and Q is O (i.e., oxygen).

Some embodiments of the present invention pertain to compounds wherein A is a C$_2$ alkylene group and B is a C$_3$ alkylene groups wherein A and B are optionally substituted with 1 to 4 methyl groups. In some embodiments, A is —CH$_2$CH$_2$— or —CHCH$_2$— and B is —CH$_2$CH$_2$CH$_2$— and can be represented by Formulae (IIh) and (IIi) as shown below:

(IIh)

(IIi)

wherein each variable in Formulae (IIh) and (IIi) has the same meaning as described herein, supra and infra.

Some embodiments of the present invention pertain to compounds wherein A is a C$_3$ alkylene group and B is a C$_2$ alkylene group wherein A and B are optionally substituted with 1 to 4 methyl groups. In some embodiments, A is —CHCH$_2$CH$_2$— and B is —CH$_2$CH$_2$—; these embodiments can be represented by Formula (IIk) as shown below:

(IIk)

wherein each variable in Formula (IIk) has the same meaning as described herein, supra and infra.

Some embodiments of the present invention pertain to compounds wherein A and B are both C$_3$ alkylene groups optionally substituted with 1 to 4 methyl groups. In some embodiments, A is —CH$_2$CH$_2$CH$_2$— or —CHCH$_2$CH$_2$— and B is —CH$_2$CH$_2$CH$_2$— and are represented by Formulae (IIm) and (IIn) respectively as shown below:

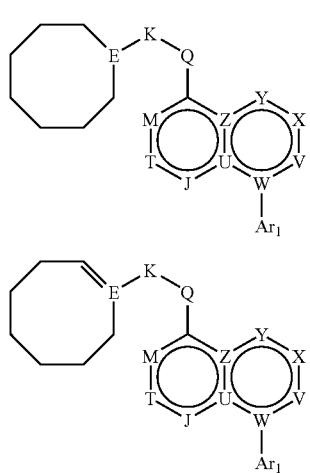

(IIm)

(IIn)

wherein each variable in Formulae (IIm) and (IIn) has the same meaning as described herein, supra and infra.

Some embodiments of the present invention pertain to compounds wherein ----- is a single bond, these embodiments are represented by Formula (IIo) as shown below:

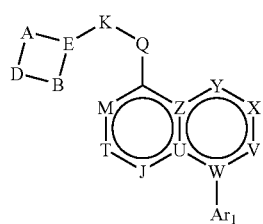

(IIo)

wherein each variable in Formula (IIo) has the same meaning as described herein, supra and infra.

Some embodiments of the present invention pertain to compounds wherein E is N.

Some embodiments of the present invention pertain to compounds wherein E is $CR_3$.

Some embodiments of the present invention pertain to compounds wherein $R_3$ is H.

In some embodiments, E is CH and D is N—$R_2$.

In some embodiments, E is CH and D is $CHR_2$.

Some embodiments of the present invention pertain to compounds wherein ----- is a double bond. It is understood that when ----- is a double bond then E is $CR_3$ (i.e., carbon atom) and E is not N (i.e., a nitrogen atom).

Some embodiments of the present invention pertain to compounds wherein K is a $C_{1-3}$ alkylene group optionally substituted with 1 to 4 substituents selected from the group consisting of $C_{1-3}$ alkyl, $C_{1-4}$ alkoxy, carboxy, cyano, $C_{1-3}$ haloalkyl and halogen. In some embodiments, K is a —$CH_2$— group. In some embodiments, K is a —$CH_2CH_2$— group.

Some embodiments of the present invention pertain to compounds wherein K is a bond; these embodiments are represented by Formula (IIq) as shown below:

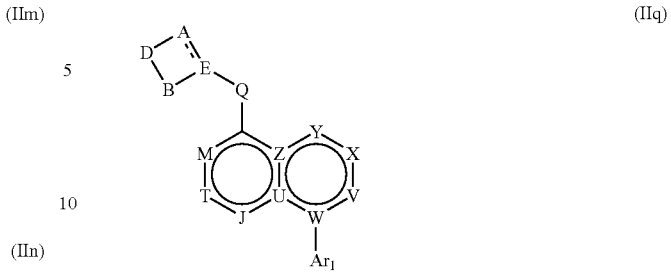

wherein each variable in Formula (IIq) has the same meaning as described herein, supra and infra. In some embodiments, Q is O (i.e., an oxygen atom).

Some embodiments of the present invention pertain to compounds wherein D is $CR_1R_2$ and can be represented by Formula (IIt) as shown below:

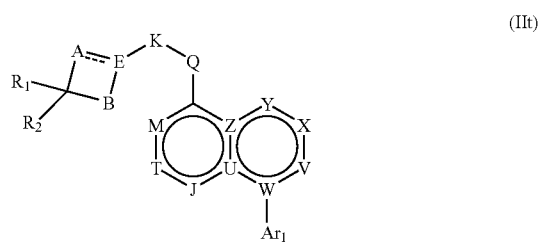

wherein each variable in Formula (IIt) has the same meaning as described herein, supra and infra. In some embodiments, $R_2$ is selected from the group consisting of H, amino, carboxamide, carboxy, cyano, $C_{3-6}$-cycloalkyl, $C_{1-4}$ haloalkoxy, $C_{1-4}$ haloalkyl, halogen and hydroxyl. In some embodiments, $R_2$ is selected from the group consisting of $OCH_3$, $OCH_2CH_3$, $OCH_2CH_2CH_3$, $OCH(CH_3)_2$, $OCH_2(CH_2)_2CH_3$, amino, carboxamide, carboxy, cyano, cyclopropyl, cyclobutyl, cyclopentyl, cyclohexyl, $OCF_3$, $OCHF_2$, $CF_3$, $CHF_2$ and F. In some embodiments, $R_2$ is $C_{1-8}$ alkyl, aryl or heteroaryl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{3-6}$-cycloalkyl-$C_{1-3}$-heteroalkylene, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro. In some embodiments, $R_2$ is selected from the group consisting of $CH_3$, $CH_2CH_3$, $CH_2CH_2CH_3$, $CH(CH_3)_2$, $CH(CH_3)(CH_2CH_3)$, $CH_2(CH_2)_2CH_3$, $CH_2(CH_2)_3CH_3$. In some embodiments, $R_2$ is selected from the group consisting of $CH_2OCH_3$, $CH_2CH_2OCH_3$, $CH_2OCH_2CH_3$, $CH_2OCH_2CH_2CH_3$, $CH_2CH_2OCH_2CH_3$, $CH_2CH_2OCH_2CH_2CH_3$, $CH_2OCH(CH_3)_2$, $CH_2OCH_2CH(CH_3)_2$, $CH_2CO_2H$, $CH_2CH_2CO_2H$, $CH_2OH$, $CH_2CH_2OH$ and $CH_2CH_2CH_2OH$. In some embodiments, $R_2$ is selected from the group consisting of $CH_2SCH_3$, $CH_2SCH_2CH_3$, $CH_2SCH_2CH_2CH_3$, $CH_2SCH(CH_3)_2$, $CH_2SCH_2(CH_2)_2CH_3$, $CH_2CH_2SCH_3$, $CH_2CH_2SCH_2CH_3$, CH$_2$CH$_2$SCH$_2$CH$_2$CH$_3$, CH$_2$CH$_2$SCH(CH$_3$)$_2$, CH$_2$CH$_2$SCH$_2$(CH$_2$)$_2$CH$_3$, CH$_2$S(O)CH$_3$, CH$_2$S(O)CH$_2$CH$_3$, CH$_2$S(O)CH$_2$CH$_2$CH$_3$, CH$_2$S(O)CH(CH$_3$)$_2$, CH$_2$S(O)CH$_2$(CH$_2$)$_2$CH$_3$, CH$_2$CH$_2$S(O)CH$_3$, CH$_2$CH$_2$S(O)CH$_2$CH$_3$, CH$_2$CH$_2$S(O)CH$_2$CH$_2$CH$_3$, CH$_2$CH$_2$S(O)CH(CH$_3$)$_2$, CH$_2$CH$_2$S(O)CH$_2$(CH$_2$)$_2$CH$_3$, CH$_2$S(O)$_2$CH$_3$, CH$_2$S(O)$_2$CH$_2$CH$_3$, CH$_2$S(O)$_2$CH$_2$CH$_2$CH$_3$, CH$_2$S(O)$_2$CH(CH$_3$)$_2$, CH$_2$S(O)$_2$CH$_2$(CH$_2$)$_2$CH$_3$, CH$_2$CH$_2$S(O)$_2$CH$_3$, CH$_2$CH$_2$S(O)$_2$CH$_2$CH$_3$, CH$_2$CH$_2$S(O)$_2$CH$_2$CH$_2$CH$_3$, CH$_2$CH$_2$S(O)$_2$CH(CH$_3$)$_2$ and CH$_2$CH$_2$S(O)$_2$CH$_2$(CH$_2$)$_2$CH$_3$. In some embodiments, R$_2$ is selected from the group consisting of CH$_2$OCH$_2$-cyclopropyl, CH$_2$OCH$_2$-cyclobutyl, CH$_2$OCH$_2$-cyclopentyl, CH$_2$OCH$_2$-cyclohexyl, CH$_2$OCH$_2$CH$_2$-cyclopropyl, CH$_2$OCH$_2$CH$_2$-cyclobutyl, CH$_2$OCH$_2$CH$_2$-cyclopentyl, CH$_2$OCH$_2$CH$_2$-cyclohexyl, CH$_2$CH$_2$OCH$_2$-cyclopropyl, CH$_2$CH$_2$OCH$_2$-cyclobutyl, CH$_2$CH$_2$OCH$_2$-cyclopentyl, CH$_2$CH$_2$OCH$_2$-cyclohexyl, CH$_2$CH$_2$OCH$_2$CH$_2$-cyclopropyl, CH$_2$CH$_2$OCH$_2$CH$_2$-cyclobutyl, CH$_2$CH$_2$OCH$_2$CH$_2$-cyclopentyl and CH$_2$CH$_2$OCH$_2$CH$_2$-cyclohexyl. In some embodiments, R$_2$ is selected from the group consisting of 1,2,4-oxadiazol-3-yl, 1,2,4-oxadiazol-5-yl, 1,3,4-oxadiazol-2-yl, 1,2,4-triazol-5-yl and 1,2,4-triazol-1-yl, 3-methyl-1,2,4-oxadiazol-5-yl, 3-methyl-1,2,4-oxadiazol-5-yl, 3-ethyl-1,2,4-oxadiazol-5-yl, 3-ethyl-1,2,4-oxadiazol-5-yl, 5-methyl-1,3,4-oxadiazol-2-yl, 5-ethyl-1,3,4-oxadiazol-2-yl, 3-methyl-1,2,4-triazol-5-yl, 3-ethyl-1,2,4-triazol-5-yl, 3-methyl-1,2,4-triazol-1-yl, 3-ethyl-1,2,4-triazol-1-yl, 5-methyl-1,2,4-triazol-1-yl and 5-ethyl-1,2,4-triazol-1-yl.

In some embodiments R$_2$ is a heteroaryl comprising 5-atoms in the aromatic ring and are represented by the following formulae:

TABLE 2A

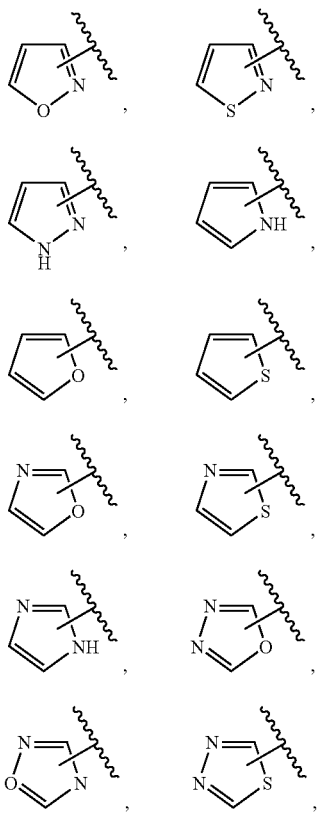

TABLE 2A-continued

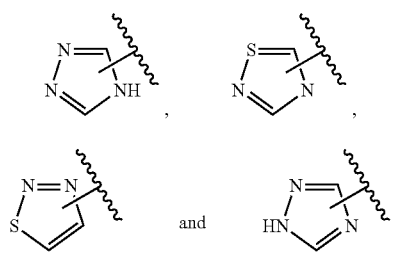

wherein the 5-membered heteroaryl is bonded at any available position of the ring, for example, a imidazolyl ring can be bonded at one of the ring nitrogens (i.e., imidazol-1-yl group) or at one of the ring carbons (i.e., imidazol-2-yl, imidazol-4-yl or imiadazol-5-yl group). In some embodiments R$_2$ is a 5-membered heteroaryl, for example but not limited to those shown in TABLE 2A, optionally substituted with 1 to 4 substituents selected from the group consisting of C$_{1-5}$ acyl, C$_{1-5}$ acyloxy, C$_{1-4}$ alkoxy, C$_{1-8}$ alkyl, C$_{1-4}$ alkylamino, C$_{1-4}$ alkylcarboxamide, C$_{1-4}$ alkylthiocarboxamide, C$_{1-4}$ alkylsulfonamide, C$_{1-4}$ alkylsulfinyl, C$_{1-4}$ alkylsulfonyl, C$_{1-4}$ alkylthio, C$_{1-4}$ alkylthioureyl, C$_{1-4}$ alkylureyl, amino, carbo-C$_{1-6}$-alkoxy, carboxamide, carboxy, cyano, C$_{3-6}$-cycloalkyl, C$_{3-6}$-cycloalkyl-C$_{1-3}$-heteroalkylene, C$_{2-8}$ dialkylamino, C$_{2-6}$ dialkylcarboxamide, C$_{2-6}$ dialkylthiocarboxamide, C$_{2-6}$ dialkylsulfonamide, C$_{1-4}$ alkylthioureyl, C$_{1-4}$ haloalkoxy, C$_{1-4}$ haloalkyl, C$_{1-4}$ haloalkylsulfinyl, C$_{1-4}$ haloalkylsulfonyl, C$_{1-4}$ haloalkyl, C$_{1-4}$ haloalkylthio, halogen, heterocyclic, hydroxyl, hydroxylamino and nitro.

In some embodiments R$_2$ is a heteroaryl comprising 5-atoms in the aromatic ring and are represented by the following formulae:

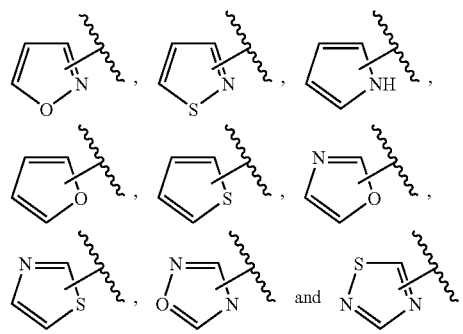

wherein the 5-membered heteroaryl is bonded at any available position of the ring as described above. In some embodiments, R$_2$ is a 5-membered heteroaryl optionally substituted with 1 to 4 substituents selected from the group consisting of C$_{1-5}$ acyl, C$_{1-5}$ acyloxy, C$_{1-4}$ alkoxy, C$_{1-8}$ alkyl, C$_{1-4}$ alkylamino, C$_{1-4}$ alkylcarboxamide, C$_{1-4}$ alkylthiocarboxamide, C$_{1-4}$ alkylsulfonamide, C$_{1-4}$ alkylsulfinyl, C$_{1-4}$ alkylsulfonyl, C$_{1-4}$ alkylthio, C$_{1-4}$ alkylthioureyl, C$_{1-4}$ alkylureyl, amino, carbo-C$_{1-6}$-alkoxy, carboxamide, carboxy, cyano, C$_{3-6}$-cycloalkyl-C$_{1-3}$-heteroalkylene, C$_{2-8}$ dialkylamino, C$_{2-6}$ dialkylcarboxamide, C$_{2-6}$ dialkylthiocarboxamide, C$_{2-6}$ dialkylsulfonamide, C$_{1-4}$ alkylthioureyl, C$_{1-4}$ haloalkoxy, C$_{1-4}$ haloalkyl, C$_{1-4}$ haloalkylsulfinyl, C$_{1-4}$ haloalkylsulfonyl, C$_{1-4}$ haloalkyl, $C_{1-4}$ haloalkylthio, halogen, heterocyclic, hydroxyl, hydroxylamino and nitro.

In some embodiments $R_2$ is a heterocyclic group represented, for example, by the formulae in TABLE 2B.

TABLE 2B

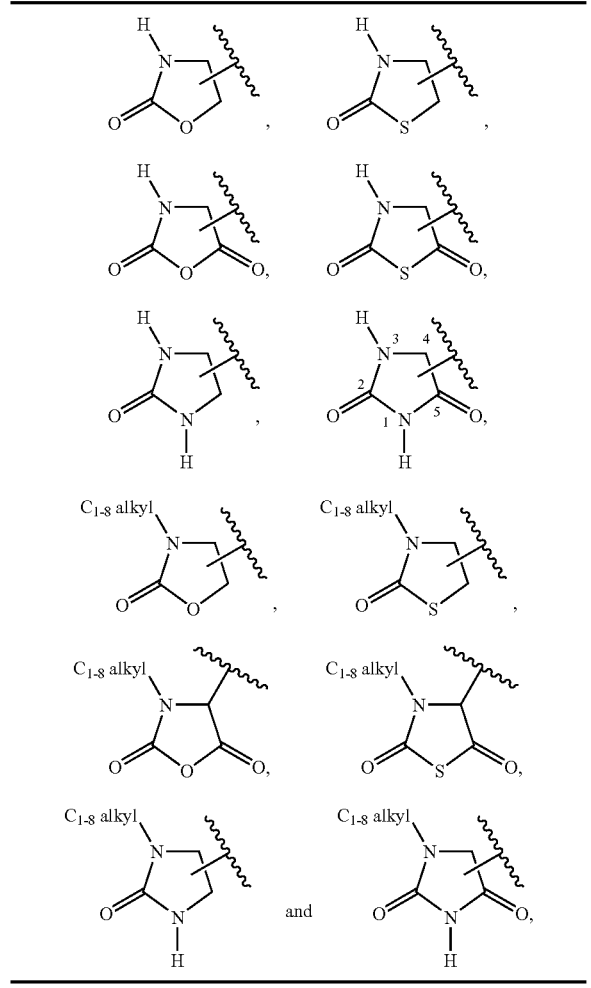

It is understood that any one of the heterocyclic groups shown in TABLES 2B to 2E may be bonded at any ring carbon or ring nitrogen as allowed by the respective formula unless otherwise specified. For example, a 2,5-dioxo-imidazolidinyl group may be bonded at the ring carbon or at either of the two ring nitrogens to give the following formulae respectively:

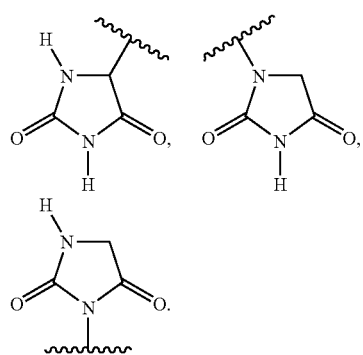

In some embodiments $R_2$ is a heterocyclic represented, for example, by the formulae in TABLE 2C.

TABLE 2C

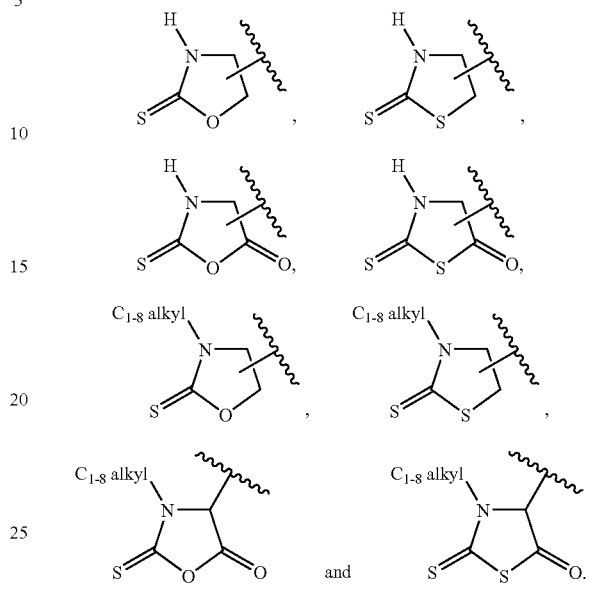

In some embodiments $R_2$ is a heterocyclic represented, for example, by the formulae in TABLE 2D.

TABLE 2D

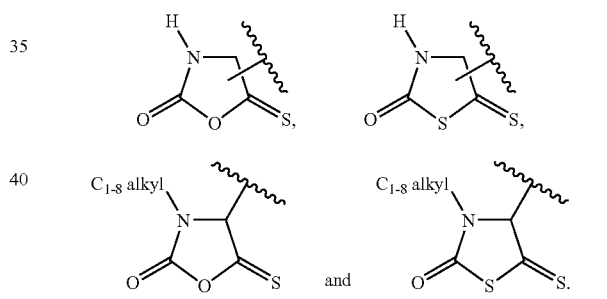

In some embodiments $R_2$ is a heterocyclic represented, for example, by the formulae in TABLE 2E.

TABLE 2E

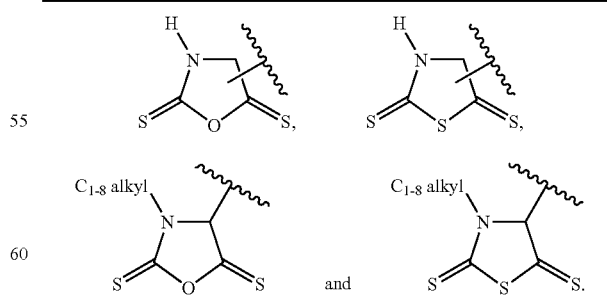

In some embodiments $R_2$ is a heterocyclic represented, for example, by the formulae in TABLE 2F wherein the $C_{1-6}$ alkyl group on the respective ring nitrogen atoms may be the same or different.

TABLE 2F

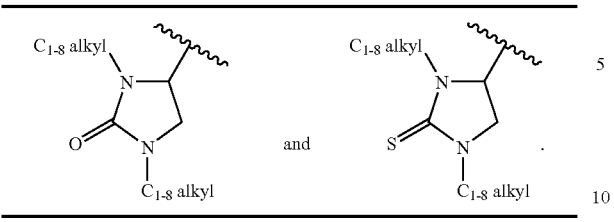

In some embodiments R$_2$ is a heterocyclic represented, for example, by the formulae in TABLE 2G wherein the C$_{1-6}$ alkyl group on the respective ring nitrogen atoms may be the same or different.

TABLE 2G

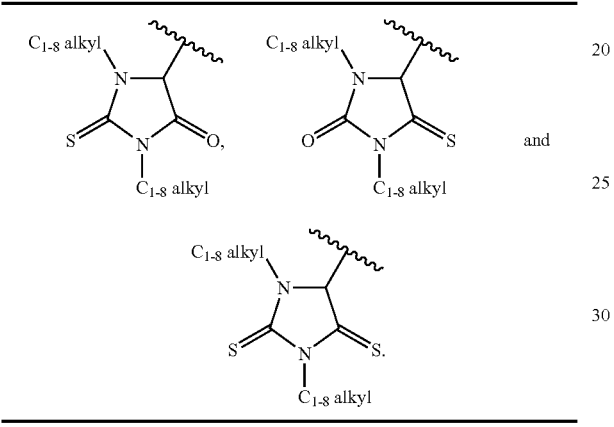

Some embodiments of the present invention pertain to compounds of Formula (IIt) wherein R$_2$ is —Ar$_2$—Ar$_3$ wherein Ar$_2$ and Ar$_3$ are independently aryl or heteroaryl optionally substituted with 1 to 5 substituents selected from the group consisting of H, C$_{1-5}$ acyl, C$_{1-5}$ acyloxy, C$_{1-4}$ alkoxy, C$_{1-8}$ alkyl, C$_{1-4}$ alkylcarboxamide, C$_{1-4}$ alkylthiocarboxamide, C$_{1-4}$ alkylsulfinyl, C$_{1-4}$ alkylsulfonyl, C$_{1-4}$ alkylthio, amino, carbo-C$_{1-6}$-alkoxy, carboxamide, carboxy, cyano, C$_{3-6}$-cycloalkyl, C$_{2-6}$ dialkylcarboxamide, C$_{1-4}$ haloalkoxy, C$_4$ haloalkyl, halogen, hydroxyl and nitro.

In some embodiments Ar$_2$ is a heteroaryl comprising 5-atoms in the aromatic ring and are represented by the following formulae shown in TABLE 3.

TABLE 3

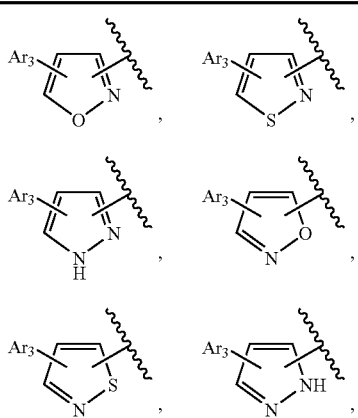

TABLE 3-continued

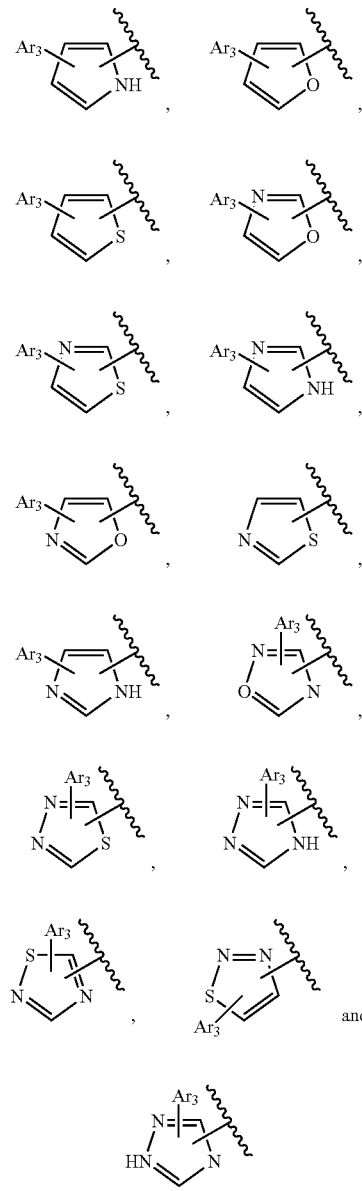

wherein the 5-membered heteroaryl is bonded at any position of the ring, for example, a imidazolyl ring can be bonded at one of the ring nitrogens (i.e., imidazol-1-yl group) or at one of the ring carbons (i.e., imidazol-2-yl, imidazol-4-yl or imiadazol-5-yl group) and Ar$_3$ is bonded to any remaining available ring atom. In some embodiments Ar$_2$ is a heteroaryl and Ar$_3$ is phenyl. In some embodiments, Ar$_2$ is a phenyl and Ar$_3$ is heteroaryl (such as a heteroaryl selected from TABLE 2A, supra). In some embodiments the heteroaryl and phenyl are optionally substituted with 1 to 5 substituents selected from the group consisting of H, C$_{1-4}$ alkoxy, C$_{1-8}$ alkyl, C$_{1-4}$ alkylcarboxamide, C$_{1-4}$ alkylsulfinyl, C$_{1-4}$ alkylsulfonyl, C$_{1-4}$ alkylthio, C$_{1-4}$ haloalkoxy, C$_{1-4}$ haloalkyl, halogen, hydroxyl and nitro.

Some embodiments of the present invention pertain to compounds of Formula (IIt) wherein $R_2$ is Formula (B):

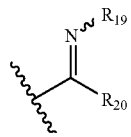

(B)

wherein:
$R_{19}$ is $C_{1-8}$ alkyl or $C_{3-7}$ cycloalkyl; and $R_{20}$ is F, Cl, Br or CN.

Some embodiments of the present invention pertain to compounds of Formula (IIt) wherein $R_2$ is Formula (C):

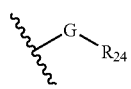

(C)

wherein:
G is selected from the group consisting of C(O), C(O)NR$_{25}$, C(O)O, OC(O), C(S), C(S)NR$_{25}$, C(S)O, OC(S), CR$_{25}$R$_{26}$, O, S, S(O) and S(O)$_2$; wherein $R_{25}$ and $R_{26}$ are independently H or $C_{1-8}$ alkyl; and $R_{24}$ is $C_{1-8}$ alkyl, $C_{3-7}$ cycloalkyl, phenyl or heteroaryl optionally substituted with 1 to 5 substituents selected from the group consisting of $C_{1-5}$ acyl, $C_{1-5}$ acyloxy, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, hydroxyl, hydroxylamino and nitro.

Some embodiments of the present invention pertain to compounds of Formula (IIt) wherein $R_2$ is Formula (C) and G is selected from the group consisting of C(O), C(O)NR$_{25}$, C(O)O, OC(O), C(S), C(S)NR$_{25}$, C(S)O, OC(S) and CR$_{25}$R$_{26}$. In some embodiments, $R_{24}$ is $C_{1-8}$ alkyl optionally substituted with 1 to 5 substituents selected from the group consisting of $C_{1-5}$ acyl, $C_{1-4}$ alkoxy, $C_{1-7}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carboxamide, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, halogen and hydroxyl.

Some embodiments of the present invention pertain to compounds of Formula (IIt) wherein $R_2$ is Formula (C) and G is selected from the group consisting of C(O), C(O)NR$_{25}$, C(O)O, OC(O), C(S), C(S)NR$_{25}$, C(S)O, OC(S) and CR$_{25}$R$_{26}$. In some embodiments, $R_{24}$ is phenyl optionally substituted with 1 to 5 substituents selected from the group consisting of $C_{1-5}$ acyl, $C_{1-4}$ alkoxy, $C_{1-7}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carboxamide, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, halogen and hydroxyl.

Some embodiments of the present invention pertain to compounds of Formula (IIt) wherein $R_2$ is Formula (C) and G is selected from the group consisting of C(O), C(O)NR$_{25}$, C(O)O, OC(O), C(S), C(S)NR$_{25}$, C(S)O, OC(S) and CR$_{25}$R$_{26}$. In some embodiments, $R_{24}$ is heteroaryl optionally substituted with 1 to 5 substituents selected from the group consisting of $C_{1-5}$ acyl, $C_{1-4}$ alkoxy, $C_{1-7}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carboxamide, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, halogen and hydroxyl. In some embodiments, $R_{24}$ is selected from the group consisting of pyridinyl, pyridazinyl, pyrimidinyl and pyrazinyl. In some embodiments, $R_{24}$ is pyridinyl.

Some embodiments of the present invention pertain to compounds wherein $R_{25}$ and $R_{26}$ are independently H or $C_{1-2}$ alkyl.

Some embodiments of the present invention pertain to compounds of Formula (IIt) wherein $R_2$ is Formula (C) and G is selected from the group consisting of O, S, S(O) and S(O)$_2$. In some embodiments, $R_{24}$ is $C_{1-8}$ alkyl optionally substituted with 1 to 5 substituents selected from the group consisting of $C_{1-5}$ acyl, $C_{1-4}$ alkoxy, $C_{1-7}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carboxamide, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, halogen and hydroxyl.

Some embodiments of the present invention pertain to compounds of Formula (IIt) wherein $R_2$ is Formula (C) and G is selected from the group consisting of O, S, S(O) and S(O)$_2$. In some embodiments, $R_{24}$ is phenyl optionally substituted with 1 to 5 substituents selected from the group consisting of $C_{1-5}$ acyl, $C_{1-4}$ alkoxy, $C_{1-7}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carboxamide, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, halogen and hydroxyl.

Some embodiments of the present invention pertain to compounds of Formula (IIt) wherein $R_2$ is Formula (C) and G is selected from the group consisting of O, S, S(O) and S(O)$_2$. In some embodiments, $R_{24}$ is heteroaryl optionally substituted with 1 to 5 substituents selected from the group consisting of $C_{1-5}$ acyl, $C_{1-4}$ alkoxy, $C_{1-7}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carboxamide, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, halogen and hydroxyl. In some embodiments, $R_{24}$ is selected from the group consisting of pyridinyl, pyridazinyl, pyrimidinyl and pyrazinyl. In some embodiments, $R_{24}$ is pyridinyl.

Some embodiments of the present invention pertain to compounds wherein $R_1$ is H.

Some embodiments of the present invention pertain to compounds wherein $R_2$ is a group of Formula (C):

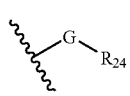

(C)

wherein G is:
—NHC(O)—, —NH—, —NHC(O)O—, —CH$_2$NHC(O)—, or a bond; and $R_{24}$ is H, $C_{1-8}$ alkyl, or heteroaryl, each optionally substituted with 1 to 2 substituents selected from the group consisting of $C_{1-4}$ alkoxy, and $C_{1-7}$ alkyl.

In some embodiments, $R_2$ is selected from the group consisting of the following:

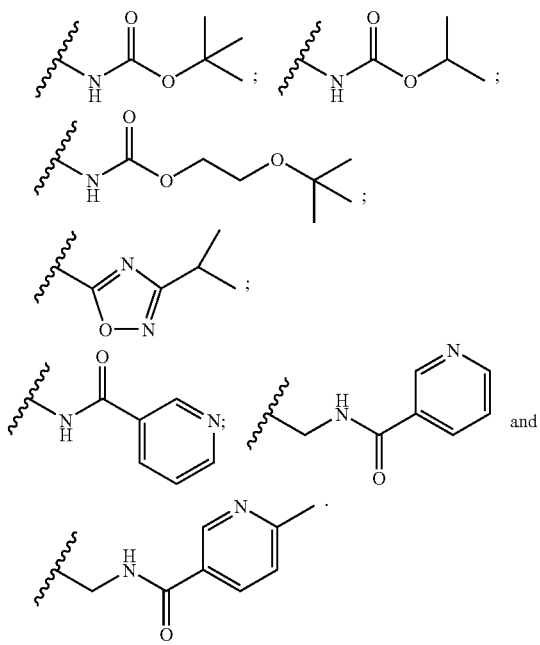

Some embodiments of the present invention pertain to compounds wherein $R_2$ is of Formula (C):

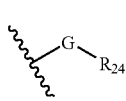

(C)

wherein:

G is $-CR_{25}R_{26}C(O)-$, $-C(O)-$, $-C(O)NR_{25}-$, $-C(O)O-$, $-C(S)NR_{25}-$, $-CR_{25}R_{26}-$, or a bond, wherein $R_{25}$, and $R_{26}$ are each independently H or $C_{1-8}$ alkyl; and $R_{24}$ is H, $C_{1-8}$ alkyl, $C_{3-7}$ cycloalkyl, phenyl, heteroaryl, or heterocyclic each optionally substituted with 1 to 5 substituents selected from the group consisting of $C_{1-4}$ alkoxy, $C_{1-7}$ alkyl, $C_{1-4}$ alkylamino, amino, carbo-$C_{1-6}$-alkoxy, carboxy, $C_{3-7}$ cycloalkyl, $C_{2-8}$ dialkylamino, $C_{1-4}$ haloalkoxy, $C_{1-4}$ haloalkyl, halogen, heteroaryl, heterocyclic, hydroxyl, and nitro, wherein said $C_{1-4}$ alkoxy, $C_{1-7}$ alkyl, $C_{1-4}$ alkylamino, heteroaryl, and phenyl are each optionally substituted with 1 to 5 substituents selected from the group consisting of $C_{1-4}$ alkoxy, carbo-$C_{1-6}$-alkoxy, carboxamide, carboxy, $C_{3-7}$ cycloalkyl, halogen, heterocyclic, and phenyl.

In some embodiments, Formula (C) is $-CR_{25}R_{26}C(O)R_{24}$.

In some embodiments, Formula (C) is $-C(O)R_{24}$.
In some embodiments, Formula (C) is $-C(O)NR_{25}R_{24}$.
In some embodiments, Formula (C) is $R_{24}$ (i.e., -G- is a bond).
In some embodiments, Formula (C) is $-C(O)OR_{24}$.
In some embodiments, Formula (C) is $-C(S)NR_{25}R_{24}$.
In some embodiments, Formula (C) is $-CR_{25}R_{26}R_{24}$.

Some embodiments of the present invention pertain to compounds wherein $R_2$ is $-C(O)OR_{24}$ and $R_{24}$ is $C_{1-8}$ alkyl, $C_{3-7}$ cycloalkyl, phenyl, heteroaryl, or heterocyclic each optionally substituted with 1 to 5 substituents selected from the group consisting of $C_{1-4}$ alkoxy, $C_{1-7}$ alkyl, $C_{1-4}$ alkylsulfonyl, amino, carbo-$C_{1-6}$-alkoxy, carboxy, cyano, $C_{3-7}$ cycloalkyl, $C_{2-8}$ dialkylamino, $C_{1-4}$ haloalkoxy, $C_{1-4}$ haloalkyl, halogen, heteroaryl, heterocyclic, hydroxyl, phenyl, phenoxy, and sulfonic acid, wherein said $C_{1-7}$ alkyl, phenyl and phenoxy are each optionally substituted with 1 to 5 substituents selected from the group consisting of amino, $C_{1-4}$ haloalkoxy, and heterocyclic.

Some embodiments of the present invention pertain to compounds wherein $R_2$ is $-C(O)OR_{24}$ and $R_{24}$ is $C_{1-8}$ alkyl, or $C_{3-7}$ cycloalkyl each optionally substituted with 1 to 5 substituents selected from the group consisting of $C_{1-4}$ alkoxy, $C_{1-7}$ alkyl, $C_{1-4}$ alkylsulfonyl, carboxy, cyano, $C_{3-7}$ cycloalkyl, $C_{2-8}$ dialkylamino, $C_{1-4}$ haloalkoxy, $C_{1-4}$ haloalkyl, halogen, heteroaryl, heterocyclic, hydroxyl, phenyl, phenoxy, and sulfonic acid.

Some embodiments of the present invention pertain to compounds wherein $R_2$ is $-C(O)OR_{24}$ and $R_{24}$ is $C_{1-8}$ alkyl, or $C_{3-7}$ cycloalkyl wherein said $C_{3-7}$ cycloalkyl is optionally substituted with 1 to 5 substituents selected from the group consisting of $C_{1-4}$ alkoxy, $C_{1-7}$ alkyl, carboxy, $C_{2-8}$ dialkylamino, and halogen.

Some embodiments of the present invention pertain to compounds wherein $R_2$ is $-C(O)OR_{24}$ and $R_{24}$ is $C_{1-8}$ alkyl, or $C_{3-7}$ cycloalkyl.

Some embodiments of the present invention pertain to compounds wherein $R_2$ is $-C(O)R_{24}$ and $R_{24}$ is $C_{1-8}$ alkyl, $C_{3-7}$ cycloalkyl, phenyl, heteroaryl, or heterocyclic each optionally substituted with 1 to 5 substituents selected from the group consisting of $C_{2-6}$ alkenyl, $C_{1-4}$ alkoxy, $C_{1-7}$ alkyl, $C_{1-4}$ alkylsulfonyl, amino, carbo-$C_{1-6}$-alkoxy, carboxy, cyano, $C_{3-7}$ cycloalkyl, $C_{2-8}$ dialkylamino, $C_{1-4}$ haloalkoxy, $C_{1-4}$ haloalkyl, halogen, heteroaryl, heterocyclic, hydroxyl, phenyl, phenoxy, and sulfonic acid, wherein said $C_{1-7}$ alkyl, phenyl and phenoxy are each optionally substituted with 1 to 5 substituents selected from the group consisting of amino, $C_{1-4}$ haloalkoxy, and heterocyclic.

Some embodiments of the present invention pertain to compounds wherein $R_2$ is $-C(O)R_{24}$ and $R_{24}$ is $C_{1-8}$ alkyl, heteroaryl, or heterocyclic each optionally substituted with 1 to 5 substituents selected from the group consisting of H, $C_{1-4}$ alkoxy, $C_{1-7}$ alkyl, amino, carboxy, halogen, heteroaryl, hydroxyl, phenoxy, and sulfonic acid, wherein said $C_{1-7}$ alkyl and phenoxy are optionally substituted with 1 to 5 substituents selected from the group consisting of amino, $C_{1-4}$ haloalkoxy, and heterocyclic.

Some embodiments of the present invention pertain to compounds wherein $R_2$ is $-CH_2R_{24}$, or $-R_{24}$ and $R_{24}$ is $C_{1-8}$ alkyl, $C_{3-7}$ cycloalkyl, phenyl, heteroaryl, or heterocyclic each optionally substituted with 1 to 5 substituents selected from the group consisting of $C_{1-5}$ acyl, $C_{2-6}$ alkenyl, $C_{1-4}$ alkoxy, $C_{1-7}$ alkyl, $C_{1-4}$ alkylsulfonyl, amino, carbo-$C_{1-6}$-alkoxy, carboxy, cyano, $C_{3-7}$ cycloalkyl, $C_{2-8}$ dialkylamino, $C_{1-4}$ haloalkoxy, $C_{1-4}$ haloalkyl, halogen, heteroaryl, heterocyclic, hydroxyl, phenyl, phenoxy, and sulfonic acid, wherein said $C_{1-7}$ alkyl, phenyl and phenoxy are each optionally substituted with 1 to 5 substituents selected from the group consisting of amino, $C_{1-4}$ haloalkoxy, and heterocyclic.

Some embodiments of the present invention pertain to compounds wherein $R_2$ is $-CH_2R_{24}$, or $-R_{24}$, and $R_{24}$ is $C_{1-8}$ alkyl, $C_{3-7}$ cycloalkyl, or heteroaryl each optionally substituted with 1 to 5 substituents selected from the group consisting of $C_{1-5}$ acyl, $C_{2-6}$ alkenyl, $C_{1-4}$ alkoxy, carbo-$C_{1-6}$-alkoxy, carboxy, cyano, $C_{3-7}$ cycloalkyl, and hydroxyl.

Some embodiments of the present invention pertain to compounds wherein $R_2$ is $-S(O)_2R_{24}$ and $R_{24}$ is $C_{1-8}$ alkyl, $C_{3-7}$ cycloalkyl, phenyl, heteroaryl, or heterocyclic each optionally substituted with 1 to 5 substituents selected from the group consisting of $C_{2-6}$ alkenyl, $C_{1-4}$ alkoxy, $C_{1-7}$ alkyl, $C_{1-4}$ alkylsulfonyl, amino, carbo-$C_{1-6}$-alkoxy, carboxy, cyano, $C_{3-7}$ cycloalkyl, $C_{2-8}$ dialkylamino, $C_{1-4}$ haloalkoxy, $C_{1-4}$ haloalkyl, halogen, heteroaryl, heterocyclic, hydroxyl, phenyl, phenoxy, and sulfonic acid, wherein said $C_{1-7}$ alkyl, phenyl and phenoxy are each optionally substituted with 1 to 5 substituents selected from the group consisting of amino, $C_{1-4}$ haloalkoxy, and heterocyclic.

Some embodiments of the present invention pertain to compounds wherein $R_2$ is —S(O)$_2$R$_{24}$ and $R_{24}$ is $C_{1-8}$ alkyl, or heteroaryl and said heteroaryl is optionally substituted with 1 to 5 $C_{1-7}$ alkyl.

Some embodiments of the present invention pertain to compounds wherein $R_2$ is —CH$_2$C(O)R$_{24}$ and $R_{24}$ is $C_{1-8}$ alkyl, $C_{3-7}$ cycloalkyl, phenyl, heteroaryl, or heterocyclic each optionally substituted with 1 to 5 substituents selected from the group consisting of $C_{2-6}$ alkenyl, $C_{1-4}$ alkoxy, $C_{1-7}$ alkyl, $C_{1-4}$ alkylsulfonyl, amino, carbo-$C_{1-6}$-alkoxy, carboxy, cyano, $C_{3-7}$ cycloalkyl, $C_{2-8}$ dialkylamino, $C_{1-4}$ haloalkoxy, $C_{1-4}$ haloalkyl, halogen, heteroaryl, heterocyclic, hydroxyl, phenyl, phenoxy, and sulfonic acid, wherein said $C_{1-7}$ alkyl, phenyl and phenoxy are each optionally substituted with 1 to 5 substituents selected from the group consisting of amino, $C_{1-4}$ haloalkoxy, and heterocyclic.

Some embodiments of the present invention pertain to compounds wherein $R_2$ is —CH$_2$C(O)R$_{24}$ and $R_{24}$ is phenyl, heteroaryl, or heterocyclic each optionally substituted with 1 to 5 substituents selected from the group consisting of $C_{1-4}$ alkoxy, $C_{1-7}$ alkyl, $C_{1-4}$ alkylsulfonyl, cyano, $C_{2-8}$ dialkylamino, $C_{1-4}$ haloalkoxy, $C_{1-4}$ haloalkyl, halogen, heteroaryl, and phenyl.

Some embodiments of the present invention pertain to compounds wherein $R_2$ is —CH$_2$C(O)NHR$_{24}$ and $R_{24}$ is $C_{1-8}$ alkyl, $C_{3-7}$ cycloalkyl, phenyl, heteroaryl, or heterocyclic each optionally substituted with 1 to 5 substituents selected from the group consisting of $C_{2-6}$ alkenyl, $C_{1-4}$ alkoxy, $C_{1-7}$ alkyl, $C_{1-4}$ alkylsulfonyl, amino, carbo-$C_{1-6}$-alkoxy, carboxy, cyano, $C_{3-7}$ cycloalkyl, $C_{2-8}$ dialkylamino, $C_{1-4}$ haloalkoxy, $C_{1-4}$ haloalkyl, halogen, heteroaryl, heterocyclic, hydroxyl, phenyl, phenoxy, and sulfonic acid, wherein said $C_{1-7}$ alkyl, phenyl and phenoxy are each optionally substituted with 1 to 5 substituents selected from the group consisting of amino, $C_{1-4}$ haloalkoxy, and heterocyclic.

Some embodiments of the present invention pertain to compounds wherein $R_2$ is —CH$_2$C(O)NHR$_{24}$ and wherein $R_{24}$ is phenyl optionally substituted with 1 to 5 substituents selected from the group consisting of $C_{1-4}$ alkoxy, $C_{1-8}$ alkyl, $C_{1-4}$ haloalkyl, and halogen.

Some embodiments of the present invention pertain to compounds wherein D is N—R$_2$ and is represented by Formula (IIv):

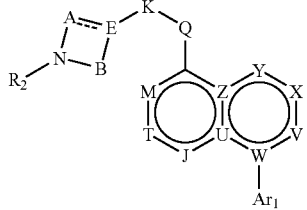

(IIv)

wherein each variable in Formula (IIv) has the same meaning as described herein, supra and infra. In some embodiments, $R_2$ is $C_{1-8}$ alkyl, aryl or heteroaryl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{3-6}$-cycloalkyl-$C_{1-3}$-heteroalkylene, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro. In some embodiments, $R_2$ is pyridyl. In some embodiments, $R_2$ is 2-pyridyl.

In some embodiments, $R_2$ is selected from the group consisting of CH$_2$CH$_2$C(CH$_3$)$_3$, CH$_2$CH$_2$CH(CH$_3$)$_2$ and CH$_2$(CH$_2$)$_4$CH$_3$. In some embodiments, $R_2$ is selected from the group consisting of: CH$_3$, CH$_2$CH$_3$, CH$_2$CH$_2$CH$_3$, CH(CH$_3$)$_2$, CH(CH$_3$)(CH$_2$CH$_3$), CH$_2$(CH$_2$)$_2$CH$_3$ and CH$_2$(CH$_2$)$_3$CH$_3$. In some embodiments, $R_2$ is selected from the group consisting of CH$_2$OCH$_3$, CH$_2$CH$_2$OCH$_3$, CH$_2$OCH$_2$CH$_3$, CH$_2$OCH$_2$CH$_2$CH$_3$, CH$_2$CH$_2$OCH$_2$CH$_3$, CH$_2$CH$_2$OCH$_2$CH$_2$CH$_3$, CH$_2$OCH(CH$_3$)$_2$, CH$_2$OCH$_2$CH(CH$_3$)$_2$, CH$_2$CO$_2$H, CH$_2$CH$_2$CO$_2$H, CH$_2$OH, CH$_2$CH$_2$OH and CH$_2$CH$_2$CH$_2$OH. In some embodiments, $R_2$ is selected from the group consisting of CH$_2$SCH$_3$, CH$_2$SCH$_2$CH$_3$, CH$_2$SCH$_2$CH$_2$CH$_3$, CH$_2$SCH(CH$_3$)$_2$, CH$_2$SCH$_2$(CH$_2$)$_2$CH$_3$, CH$_2$CH$_2$SCH$_3$, CH$_2$CH$_2$SCH$_2$CH$_3$, CH$_2$CH$_2$SCH$_2$CH$_2$CH$_3$, CH$_2$CH$_2$SCH(CH$_3$)$_2$, CH$_2$CH$_2$SCH$_2$(CH$_2$)$_2$CH$_3$, CH$_2$S(O)CH$_3$, CH$_2$S(O)CH$_2$CH$_3$, CH$_2$S(O)CH$_2$CH$_2$CH$_3$, CH$_2$S(O)CH(CH$_3$)$_2$, CH$_2$S(O)CH$_2$(CH$_2$)$_2$CH$_3$, CH$_2$CH$_2$S(O)CH$_3$, CH$_2$CH$_2$S(O)CH$_2$CH$_3$, CH$_2$CH$_2$S(O)CH$_2$CH$_2$CH$_3$, CH$_2$CH$_2$S(O)CH(CH$_3$)$_2$, CH$_2$CH$_2$S(O)CH$_2$(CH$_2$)$_2$CH$_3$, CH$_2$S(O)$_2$CH$_3$, CH$_2$S(O)$_2$CH$_2$CH$_3$, CH$_2$S(O)$_2$CH$_2$CH$_2$CH$_3$, CH$_2$S(O)$_2$CH(CH$_3$)$_2$, CH$_2$S(O)$_2$CH$_2$(CH$_2$)$_2$CH$_3$, CH$_2$CH$_2$S(O)$_2$CH$_3$, CH$_2$CH$_2$S(O)$_2$CH$_2$CH$_3$, CH$_2$CH$_2$S(O)$_2$CH$_2$CH$_2$CH$_3$, CH$_2$CH$_2$S(O)$_2$CH(CH$_3$)$_2$ and CH$_2$CH$_2$S(O)$_2$CH$_2$(CH$_2$)$_2$CH$_3$. In some embodiments, $R_2$ is CH$_2$-cyclopropyl. In some embodiments, $R_2$ is selected from the group consisting of CH$_2$OCH$_2$-cyclopropyl, CH$_2$OCH$_2$-cyclobutyl, CH$_2$OCH$_2$-cyclopentyl, CH$_2$OCH$_2$-cyclohexyl, CH$_2$OCH$_2$CH$_2$-cyclopropyl, CH$_2$OCH$_2$CH$_2$-cyclobutyl, CH$_2$OCH$_2$CH$_2$-cyclopentyl, CH$_2$OCH$_2$CH$_2$-cyclohexyl, CH$_2$CH$_2$OCH$_2$-cyclopropyl, CH$_2$CH$_2$OCH$_2$-cyclobutyl, CH$_2$CH$_2$OCH$_2$-cyclopentyl, CH$_2$CH$_2$OCH$_2$-cyclohexyl, CH$_2$CH$_2$OCH$_2$CH$_2$-cyclopropyl, CH$_2$CH$_2$OCH$_2$CH$_2$-cyclobutyl, CH$_2$CH$_2$OCH$_2$CH$_2$-cyclopentyl and CH$_2$CH$_2$OCH$_2$CH$_2$-cyclohexyl. In some embodiments, $R_2$ is selected from the group consisting of 1,2,4-oxadiazol-3-yl, 1,2,4-oxadiazol-5-yl, 1,3,4-oxadiazol-2-yl, 1,2,4-triazol-5-yl and 1,2,4-triazol-1-yl, 3-methyl-1,2,4-oxadiazol-5-yl, 3-methyl-1,2,4-oxadiazol-5-yl, 3-ethyl-1,2,4-oxadiazol-5-yl, 3-ethyl-1,2,4-oxadiazol-5-yl, 5-methyl-1,3,4-oxadiazol-2-yl, 5-ethyl-1,3,4-oxadiazol-2-yl, 3-methyl-1,2,4-triazol-5-yl, 3-ethyl-1,2,4-triazol-5-yl, 3-methyl-1,2,4-triazol-1-yl, 3-ethyl-1,2,4-triazol-1-yl, 5-methyl-1,2,4-triazol-1-yl and 5-ethyl-1,2,4-triazol-1-yl.

In some embodiments, compounds are of Formula (IIv) and $R_2$ is a heteroaryl comprising 5-atoms in the ring selected from the group shown in Table 2A. In some embodiments, $R_2$ is a 5-membered heteroaryl optionally substituted with 1 to 4 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl-$C_{1-3}$- heteroalkylene, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro.

In some embodiments $R_2$ is a heterocyclic group selected from the groups shown in TABLE 2B to TABLE 2G.

Some embodiments of the present invention pertain to compounds of Formula (IIv) wherein $R_2$ is —$Ar_2$—$Ar_3$ wherein $Ar_2$ and $Ar_3$ are independently aryl or heteroaryl optionally substituted with 1 to 5 substituents selected from the group consisting of H, $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, carbo-$C_{1-6}$-alkoxy, carboxamide, carboxy, cyano, $C_{3-6}$-cycloalkyl, $C_{2-6}$ dialkylcarboxamide, $C_{1-4}$ haloalkoxy, $C_{1-4}$ haloalkyl, halogen, hydroxyl and nitro. In some embodiments $Ar_2$ is a heteroaryl comprising 5-atoms in the aromatic ring and selected from the group shown in TABLE 3. In some embodiments $Ar_2$ is a heteroaryl and $Ar_3$ is phenyl. In some embodiments, $Ar_2$ is a phenyl and $Ar_3$ is heteroaryl (such as a heteroaryl selected from TABLE 2A or TABLE 4, supra). In some embodiments, the heteroaryl and the phenyl are optionally substituted with 1 to 5 substituents selected from the group consisting of $C_{1-4}$ alkoxy, $C_{1-8}$ alkyl, $C_{1-4}$ alkylcarboxamide, $C_{1-4}$ alkylsulfinyl, $C_{1-4}$ alkylsulfonyl, $C_{1-4}$ alkylthio, cyano, $C_{1-4}$ haloalkoxy, $C_{1-4}$ haloalkyl, halogen, hydroxyl and nitro.

Some embodiments of the present invention pertain to compounds wherein D is N—$R_2$. In some embodiments, $R_2$ is Formula (B):

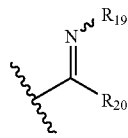

(B)

wherein $R_{19}$ is $C_{1-8}$ alkyl or $C_{3-7}$ cycloalkyl; and $R_{20}$ is F, Cl, Br or CN.

Some embodiments of the present invention pertain to compounds of Formula (IIv) wherein $R_2$ is Formula (C):

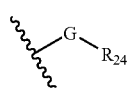

(C)

wherein G is selected from the group consisting of C(O), C(O)$NR_{25}$, C(O)O, C(S), C(S)$NR_{25}$, C(S)O, $CR_{25}R_{26}$ and S(O)$_2$, wherein $R_{25}$ and $R_{26}$ are independently H or $C_{1-8}$ alkyl; and $R_{24}$ is $C_{1-8}$ alkyl, $C_{3-7}$ cycloalkyl, phenyl or heteroaryl optionally substituted with 1 to 5 substituents selected from the group consisting of $C_{1-5}$ acyl, $C_{1-5}$ acyloxy, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, hydroxyl, hydroxylamino and nitro.

Some embodiments of the present invention pertain to compounds of Formula (IIv) wherein $R_2$ is Formula (C) and $R_{24}$ is $C_{1-8}$ alkyl optionally substituted with 1 to 5 substituents selected from the group consisting of $C_{1-5}$ acyl, $C_{1-4}$ alkoxy, $C_{1-7}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carboxamide, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, halogen and hydroxyl.

In some embodiments, the group -G-$R_{24}$ is selected from the group consisting of $C(O)CH_3$, $C(O)CH_2CH_3$, $C(O)CH_2CH_2CH_3$, $C(O)CH(CH_3)_2$, $C(O)CH_2CH_2CH_2CH_3$, $C(O)C(CH_3)_3$, $C(O)CH_2C(CH_3)_3$, $CH_3$, $CH_2CH_3$, $CH_2CH_2CH_3$, $CH(CH_3)_2$, $CH(CH_3)(CH_2CH_3)$, $CH_2(CH_2)_2CH_3$, $C(CH_3)_3$, $CH_2(CH_2)_3CH_3$, $C(O)NHCH_3$, $C(O)NHCH_2CH_3$, $C(O)NHCH_2CH_2CH_3$, $C(O)NHCH(CH_3)_2$, $C(O)NHCH_2(CH_2)_2CH_3$, $C(O)N(CH_3)_2$, $C(O)N(CH_3)CH_2CH_3$, $C(O)NH(CH_2CH_3)_2$, $CO_2CH_3$, $CO_2CH_2CH_3$, $CO_2CH_2CH_2CH_3$, $CO_2CH(CH_3)_2$, $CO_2CH_2(CH_2)_2CH_3$, $CO_2C(CH_3)_3$, $CO_2CH(CH_3)CH_2CH_3$, $CO_2CH_2CH(CH_3)_2$, $CO_2CH_2(CH_2)_3CH_3$, $CO_2CH(CH_3)CH_2CH_2CH_3$, $CO_2CH_2CH(CH_3)CH_2CH_3$, $CO_2CH_2CH_2CH(CH_3)_2$, and $CO_2CH_2C(CH_3)_3$.

Some embodiments of the present invention pertain to compounds of Formula (IIv) wherein $R_2$ is Formula (C) and $R_{24}$ is phenyl optionally substituted with 1 to 5 substituents selected from the group consisting of $C_{1-5}$ acyl, $C_{1-4}$ alkoxy, $C_{1-7}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carboxamide, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, halogen and hydroxyl.

Some embodiments of the present invention pertain to compounds of Formula (IIv) wherein $R_2$ is Formula (C) and $R_{24}$ is heteroaryl optionally substituted with 1 to 5 substituents selected from the group consisting of $C_{1-5}$ acyl, $C_{1-4}$ alkoxy, $C_{1-7}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carboxamide, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, halogen and hydroxyl. In some embodiments, $R_{24}$ is selected from the group consisting of pyridinyl, pyridazinyl, pyrimidinyl and pyrazinyl. In some embodiments, $R_{24}$ is pyridinyl.

Some embodiments of the present invention pertain to compounds wherein $R_{25}$ and $R_{26}$ are independently H or $C_{1-2}$ alkyl.

In some embodiments, A and B are both —$CH_2CH_2$—, D is $NR_2$, E is CH, ----- is a single bond, and K is a single bond; these embodiments can be represented by Formula (IIx) as shown below:

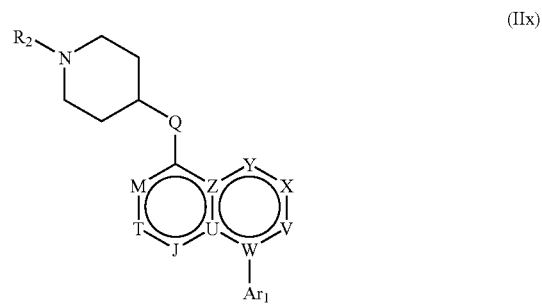

(IIx)

wherein each variable in Formula (IIx) has the same meaning as described herein, supra and infra. In some embodiments, compounds are of Formula (IIx) and Q is O (i.e., an oxygen atom) or NH.

In some embodiments, compounds of the present invention are of Formula (IIx) wherein $R_2$ is Formula (C); these embodiments can be represented by Formula (IIy) as shown below:

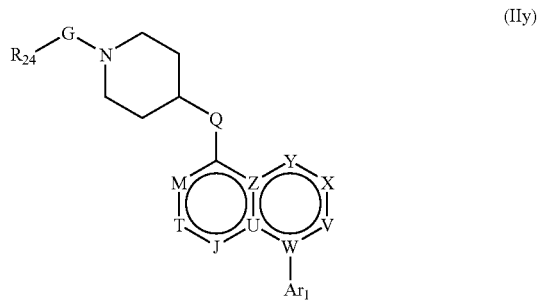

(IIy)

wherein each variable in Formula (IIy) has the same meaning as described herein, supra and infra. In some embodiments, G is C(O), C(O)NR$_{25}$, C(O)O, C(S), C(S)NR$_{25}$, C(S)O, CR$_{25}$R$_{26}$ or S(O)$_2$. In some embodiments, G is C(O) and can be represented by Formula (IIz) as shown below:

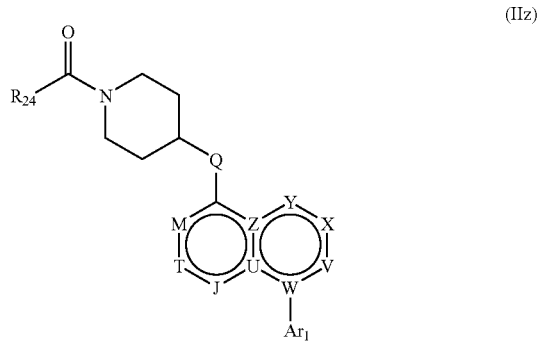

(IIz)

wherein each variable in Formula (IIz) has the same meaning as described herein, supra and infra. In some embodiments, G is C(O)O and can be represented by Formula (IIa) as shown below:

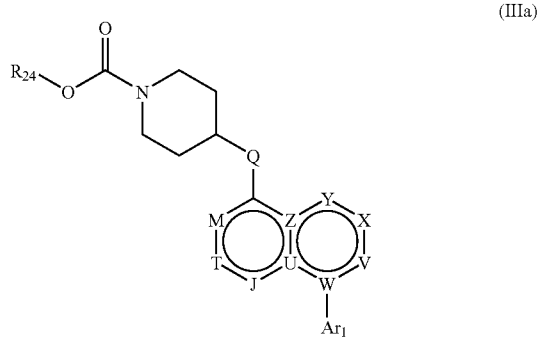

(IIIa)

wherein each variable in Formula (IIIa) has the same meaning as described herein, supra and infra.

In some embodiments, compounds are of either Formula (IIz) or (IIIa) and $R_{24}$ is $C_{1-8}$ alkyl, $C_{3-7}$ cycloalkyl, phenyl or heteroaryl optionally substituted with 1 to 5 substituents selected from the group consisting of $C_{1-5}$ acyl, $C_{1-5}$ acyloxy, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, hydroxyl, hydroxylamino and nitro.

In some embodiments, compounds are of either Formula (IIz) or (IIIa) and $R_{24}$ is $C_{1-8}$ alkyl optionally substituted with 1 to 5 substituents selected from the group consisting of $C_{1-5}$ acyl, $C_{1-5}$ acyloxy, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, hydroxyl, hydroxylamino and nitro.

In some embodiments, compounds are of either Formula (IIz) or (IIa) and $R_{24}$ is phenyl optionally substituted with 1 to 5 substituents selected from the group consisting of $C_{1-5}$ acyl, $C_{1-5}$ acyloxy, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, hydroxyl, hydroxylamino and nitro. In some embodiments, the phenyl is substituted with 1 to 4 substituents selected from the group consisting of $C_{1-5}$ acyl, $C_{1-4}$ alkoxy, $C_{1-7}$ alkyl, $C_{1-4}$ alkylsulfinyl, $C_{1-4}$ alkylsulfonyl, $C_{1-4}$ alkylthio, carboxamide, carboxy, $C_{3-7}$ cycloalkyl, $C_{2-8}$ dialkylamino, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio and halogen. In some embodiments, the phenyl is substituted with 1 to 4 substituents selected from the group consisting of $C_{1-4}$ alkylsulfonyl, $C_{1-4}$ haloalkylsulfonyl and halogen.

In some embodiments, compounds are of either Formula (IIz) or (IIIa) and $R_{24}$ is heteroaryl optionally substituted with 1 to 5 substituents selected from the group consisting of $C_{1-5}$ acyl, $C_{1-5}$ acyloxy, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, hydroxyl, hydroxylamino and nitro. In some embodiments, the heteroaryl is substituted with 1 to 4 substituents selected from the group consisting of $C_{1-5}$ acyl, $C_{1-4}$ alkoxy, $C_{1-7}$ alkyl, $C_{1-4}$ alkylsulfinyl, $C_{1-4}$ alkylsulfonyl, $C_{1-4}$ alkylthio, carboxamide, carboxy, $C_{3-7}$ cycloalkyl, $C_{2-8}$ dialkylamino, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio and halogen. In some embodiments, the heteroaryl is substituted with 1 to 4 substituents selected from the group consisting of $C_{1-4}$ alkylsulfonyl, $C_{1-4}$ haloalkylsulfonyl and halogen. In some embodiments, the heteroaryl is a 5-memebered heteroaryl, for example, as shown in TABLE 2A, supra. In some embodiments, the heteroaryl is a 6-membered heteroaryl, for example, as shown in TABLE 4, supra. In some embodiments, the heteroaryl is selected from the group consisting of pyridinyl, pyridazinyl, pyrimidinyl and pyrazinyl. In some embodiments, the heteroaryl is pyridinyl.

In some embodiments, $R_{24}$ is 1-methyl-1H-imidazole-4-yl, or 2,4-dimethyl-thiazole-5-yl.

In some embodiments, compounds are of Formula (IIy), (IIx) or (IIIa) and Q is $NR_4$, O, S, S(O) or $S(O)_2$. In still further embodiments, Q is NH or O.

Some embodiments of the present invention pertain to compounds wherein $Ar_1$ is aryl or heteroaryl optionally substituted with $R_{13}$, $R_{14}$, $R_{15}$, $R_{16}$, and $R_{17}$;

wherein $R_{13}$ is selected from the group consisting of $C_{1-6}$ acylsulfonamide, $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, amino, carbamimidoyl, carboxamide, carboxy, cyano, $C_{2-6}$ dialkylamino, halogen, heterocyclic, heterocyclic-oxy, heterocyclic-carbonyl, heteroaryl, heteroarylcarbonyl, and sulfonamide, and wherein said $C_{1-6}$ acylsulfonamide, $C_{1-4}$ alkoxy, $C_{1-8}$ alkyl, $C_{1-4}$ alkylamino, $C_{1-4}$ alkylsulfonamide, alkylsulfonyl, $C_{1-4}$ alkylthio, carbamimidoyl, $C_{2-6}$ dialkylamino, heterocyclic, heterocyclic-carbonyl, and heteroaryl are each optionally substituted with 1 to 5 substituents selected independently from the group consisting of $C_{1-6}$ acylsulfonamide, $C_{1-4}$ alkoxy, $C_{1-7}$ alkyl, $C_{1-4}$ alkylcarboxamide, $C_{1-4}$ alkylsulfonyl, carboxy, $C_{3-7}$ cycloalkyloxy, $C_{2-6}$ dialkylamino, $C_{2-6}$ dialkylcarboxamide, heteroaryl, heterocyclic, hydroxyl, phenyl, and phosphonooxy, and wherein said $C_{1-7}$ alkyl and $C_{1-4}$ alkylcarboxamide are each optionally substituted with 1 to 5 substituents selected from the group consisting of $C_{1-4}$ alkoxy and hydroxy; and $R_{14}$, $R_{15}$, $R_{16}$, and $R_{17}$ are each independently selected form the group consisting of $C_{1-6}$ acylsulfonamide, $C_{1-4}$ alkoxy, $C_{1-8}$ alkyl, $C_{1-4}$ alkylamino, $C_{1-4}$ alkylcarboxamide, $C_{1-4}$ alkylsulfonamide, $C_{1-4}$ alkylsulfonyl, $C_{1-4}$ alkylthio, amino, carbamimidoyl, carboxamide, cyano, $C_{2-6}$ dialkylamino, and halogen.

Some embodiments of the present invention pertain to compounds wherein $Ar_1$ is aryl.

Some embodiments of the present invention pertain to compounds wherein $Ar_1$ is heteroaryl.

Some embodiments of the present invention pertain to compounds wherein $Ar_1$ is phenyl optionally substituted with $R_{13}$, $R_{14}$, $R_{15}$, $R_{16}$, and $R_{17}$;

wherein $R_{13}$ is selected from the group consisting of $C_{1-6}$ acylsulfonamide, $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, amino, carbamimidoyl, carboxamide, carboxy, cyano, $C_{2-6}$ dialkylamino, $C_{1-4}$ haloalkyl, halogen, heterocyclic, heterocyclic-oxy, heterocyclic-carbonyl, heteroaryl, heteroarylcarbonyl, and sulfonamide, and wherein $C_{1-6}$ acylsulfonamide, $C_{1-4}$ alkoxy, $C_{1-8}$ alkyl, $C_{1-4}$ alkylamino, $C_{1-4}$ alkylsulfonamide, $C_{1-4}$ alkylsulfonyl, $C_{1-4}$ alkylthio, carbamimidoyl, $C_{2-6}$ dialkylamino, heterocyclic, heterocyclic-carbonyl, and heteroaryl are each optionally substituted with 1 to 5 substituents selected independently from the group consisting of $C_{1-6}$ acylsulfonamide, $C_{1-4}$ alkoxy, $C_{1-7}$ alkyl, $C_{1-4}$ alkylcarboxamide, $C_{1-4}$ alkylsulfonyl, carboxy, $C_{3-7}$ cycloalkyloxy, $C_{2-6}$ dialkylamino, $C_{2-6}$ dialkylcarboxamide, heteroaryl, heterocyclic, hydroxyl, phenyl, and phosphonooxy wherein said $C_{1-7}$ alkyl and $C_{1-4}$ alkylcarboxamide are each optionally substituted with 1 to 5 substituents selected from the group consisting of $C_{1-4}$ alkoxy and hydroxy; and $R_{14}$, $R_{15}$, $R_{16}$, and $R_{17}$ are each independently selected form the group consisting of $C_{1-6}$ acylsulfonamide, $C_{1-4}$ alkoxy, $C_{1-8}$ alkyl, $C_{1-4}$ alkylamino, $C_{1-4}$ alkylcarboxamide, $C_{1-4}$ alkylsulfonamide, $C_{1-4}$ alkylsulfonyl, $C_{1-4}$ alkylthio, amino, carbamimidoyl, carboxamide, cyano, $C_{2-6}$ dialkylamino, $C_{1-4}$ haloalkyl, and halogen.

Some embodiments of the present invention pertain to compounds wherein $Ar_1$ is phenyl optionally substituted with $R_{13}$, $R_{14}$, $R_{15}$, $R_{16}$, and $R_{17}$;

wherein $R_{13}$ is selected from the group consisting of $C_{1-6}$ acylsulfonamide, $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, carbamimidoyl, carboxamide, carboxy, cyano, $C_{2-6}$ dialkylamino, halogen, heterocyclic, heterocyclic-oxy, heterocyclic-carbonyl, heteroaryl, heteroarylcarbonyl, and sulfonamide, and wherein said $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, carbamimidoyl, $C_{2-6}$ dialkylamino, heterocyclic, heterocyclic-carbonyl, and heteroaryl are each optionally substituted with 1 to 5 substituents selected independently from the group consisting of $C_{1-6}$ acylsulfonamide, $C_{1-4}$ alkoxy, $C_{1-7}$ alkyl, $C_{1-4}$ alkylcarboxamide, $C_{1-4}$ alkylsulfonyl, carboxy, $C_{2-6}$ dialkylamino, $C_{2-6}$ dialkylcarboxamide, heteroaryl, heterocyclic, hydroxyl, phenyl, and phosphonooxy, and wherein said $C_{1-7}$ alkyl and $C_{1-4}$ alkylcarboxamide are each optionally substituted with 1 to 5 substituents selected from the group consisting of $C_{1-4}$ alkoxy and hydroxy; and $R_{14}$, $R_{15}$, $R_{16}$, and $R_{17}$ are each independently selected form the group consisting of $C_{1-8}$ alkyl, and halogen.

Some embodiments of the present invention pertain to compounds wherein $Ar_1$ is phenyl. In some embodiments, the phenyl is optionally substituted with $R_{13}$. In some embodiments, $R_{13}$ is selected from the group consisting of H, $C_{1-5}$ acyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, carboxamide, $C_{3-7}$ cycloalkyl, halogen and sulfonamide.

In some embodiments, $R_{13}$ is selected from the group consisting of $C(O)CH_3$, $C(O)CH_2CH_3$, $C(O)CH_2CH_2CH_3$, $C(O)CH(CH_3)_2$, $C(O)CH_2CH_2CH_2CH_3$, $OCH_3$, $OCH_2CH_3$, $OCH_2CH_2CH_3$, $OCH(CH_3)_2$, $OCH_2CH_2CH_2CH_3$, $CH_3$, $CH_2CH_3$, $CH_2CH_2CH_3$, $CH(CH_3)_2$, $CH(CH_3)(CH_2CH_3)$, $CH_2(CH_2)_2CH_3$, $CH_2(CH_2)_3CH_3$, $CH_2(CH_2)_4CH_3$, $CH_2(CH_2)_5CH_3$, $C(O)NHCH_3$, $C(O)NHCH_2CH_3$, $C(O)NHCH_2CH_2CH_3$, $C(O)NHCH(CH_3)_2$, $C(O)NHCH_2(CH_2)_2CH_3$, CCH, $S(O)_2NHCH_3$, $S(O)_2NHCH_2CH_3$, $S(O)_2NHCH_2CH_2CH_3$, $S(O)_2NHCH(CH_3)_2$, $S(O)_2NHCH_2(CH_2)_2CH_3$ and $S(O)_2NHCH(CH_3)CH_2CH_3$.

In some embodiments, $R_{13}$ is selected from the group consisting of $S(O)CH_3$, $S(O)CH_2CH_3$, $S(O)CH_2CH_2CH_3$, $S(O)CH(CH_3)_2$, $S(O)CH_2(CH_2)_2CH_3$, $S(O)CH(CH_3)CH_2CH_3$, $S(O)_2CH_3$, $S(O)_2CH_2CH_3$, $S(O)_2CH_2CH_2CH_3$, $S(O)_2CH(CH_3)_2$, $S(O)_2CH_2(CH_2)_2CH_3$, $S(O)_2CH(CH_3)CH_2CH_3$, $SCH_3$, $SCH_2CH_3$, $SCH_2CH_2CH_3$, $SCH(CH_3)_2$ and $SCH_2(CH_2)_2CH_3$.

In some embodiments, $R_{13}$ is selected from the group consisting of amino, arylsulfonyl, carboxy, cyano, $C_{3-7}$ cycloalkyl, halogen, $C_{1-4}$ haloalkoxy, $C_{1-4}$ haloalkyl and $C_{1-4}$ haloalkylthio. In some embodiments, $R_{13}$ is selected from the group consisting of phenylsulfonyl, cyclopropyl, cyclobutyl, cyclopentyl, cyclohexyl, Cl, F, Br, $OCF_3$, $OCHF_2$, $OCH_2CF_3$, $CF_3$, $CHF_2$, $CH_2CF_3$, $SCF_3$, $SCHF_2$ and $SCH_2CF_3$. In some embodiments, $R_{13}$ is selected from the group consisting of heterocyclic, heteroaryl, $C_{4-7}$ oxo-cycloalkyl, phenoxy and phenyl. In some embodiments, $R_{13}$ is selected from the group consisting of morpholin-4-yl, thiomorpholin-4-yl, 1-oxo-$1\lambda^4$-thiomorpholin-4-yl, 1,1-Dioxo-$1\lambda^6$-thiomorpholin-4-yl, piperazin-1-yl, 4-methyl-piperazin-1-yl, 4-ethyl-piperazin-1-yl, 4-propyl-piperazin-1-yl, piperidin-1-yl, pyrrolidin-1-yl, 2,5-dioxo-imidazolidin-4-yl, 2,4-dioxo-thiazolidin-5-yl, 4-oxo-2-thioxo-thiazolidin-5-yl, 3-methyl-2,5-dioxo-imidazolidin-4-yl, 3-methyl-2,4-dioxo-thiazolidin-5-yl, 3-methyl-4-oxo-2-thioxo-thiazolidin-5-yl, 3-ethyl-2,5-dioxo-imidazolidin-4-yl, 3-ethyl-2,4-dioxo-thiazolidin-5-yl, and 3-ethyl-4-oxo-2-thioxo-thiazolidin-5-yl. In some embodiments, $R_{13}$ is selected from the group consisting of 1H-imidazol-4-yl, [1,2,4]triazol-1-yl, [1,2,3]triazol-1-yl, [1,2,4]triazol-4-yl, pyrrol-1-yl, pyrazol-1-yl, 1H-pyrazol-3-yl, imidazol-1-yl, oxazol-5-yl, oxazol-2-yl, [1,3,4]oxadiazol-2-yl, [1,3,4]thiadiazol-2-yl, [1,2,4]oxadiazol-3-yl, [1,2,4]thiadiazol-3-yl, tetrazol-1-yl, pyrimidin-5-yl, pyrimidin-2-yl, pyrimidin-4-yl, pyridazin-3-yl, pyridazin-4-yl, pyrazin-2-yl, 1,3-dioxo-1,3-dihydro-isoindol-2-yl and [1,2,3]thiadiazol-4-yl. In some embodiments, $R_{13}$ is $C_{1-8}$ alkyl or $C_{1-4}$ alkoxy optionally substituted with 1 to 5 substituents selected independently from the group consisting of $C_{1-4}$ alkoxy, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carbo-$C_{1-6}$-alkoxy, carboxamide, carboxy, cyano, heterocyclic, hydroxyl and phenyl. In some embodiments, $R_{13}$ is $C_{1-4}$ alkylsulfonyl optionally substituted with 1 to 5 substituents selected independently from the group consisting of $C_{1-4}$ alkoxy, carboxamide, heteroaryl, heterocyclic and phenyl. In some embodiments, the $C_{1-4}$ alkylsulfonyl is substituted with the heteroaryl group. In some embodiments, the heteroaryl group is selected from the group consisting of 1H-imidazol-4-yl, [1,2,4]triazol-1-yl, [1,2,3]triazol-1-yl, [1,2,4]triazol-4-yl, pyrrol-1-yl, pyrazol-1-yl, 1H-pyrazol-3-yl, imidazol-1-yl, oxazol-5-yl, oxazol-2-yl, [1,3,4]oxadiazol-2-yl, [1,3,4]thiadiazol-2-yl, [1,2,4]oxadiazol-3-yl, [1,2,4]thiadiazol-3-yl, tetrazol-1-yl, pyrimidin-5-yl, pyrimidin-2-yl, pyrimidin-4-yl, pyridazin-3-yl, pyridazin-4-yl, pyrazin-2-yl, 1,3-dioxo-1,3-dihydro-isoindol-2-yl and [1,2,3]thiadiazol-4-yl. In some embodiments, $R_{13}$ is arylsulfonyl, heteroaryl, phenoxy or phenyl optionally substituted with 1 to 5 substituents selected independently from the group consisting of $C_{1-5}$ acyl, $C_{1-4}$ alkoxy, $C_{1-8}$ alkyl, $C_{1-4}$ alkylsulfonamide, $C_{1-4}$ alkylsulfinyl, $C_{1-4}$ alkylsulfonyl, $C_{1-4}$ alkylthio, carboxamide, carboxy, cyano, halogen, $C_{1-4}$ haloalkoxy, $C_{1-4}$ haloalkyl, $C_{1-4}$ haloalkylthio and hydroxyl. In some embodiments, $R_{13}$ is arylsulfonyl, heteroaryl, phenoxy or phenyl optionally substituted with 1 to 5 substituents selected independently from the group consisting of $C_{1-4}$ alkoxy, $C_{1-8}$ alkyl, cyano, halogen, $C_{1-4}$ haloalkoxy, $C_{1-4}$ haloalkyl and hydroxyl.

Some embodiments of the present invention pertain to compounds wherein $Ar_1$ is phenyl. In some embodiments, the phenyl is optionally substituted with $R_{13}$. In some embodiments, $R_{13}$ is a group of Formula (A):

(A)

wherein:

"p" and "r" are independently 0, 1, 2 or 3; and $R_{18}$ is H, $C_{1-5}$ acyl, $C_{2-6}$ alkenyl, $C_{1-8}$ alkyl, $C_{1-4}$ alkylcarboxamide, $C_{2-6}$ alkynyl, $C_{1-4}$ alkylsulfonamide, carbo-$C_{1-6}$-alkoxy, carboxamide, carboxy, cyano, $C_{3-7}$ cycloalkyl, $C_{2-6}$ dialkylcarboxamide, halogen, heteroaryl or phenyl, and wherein the heteroaryl or phenyl may be optionally substituted with 1 to 5 substituents selected independently from the group consisting of $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl. In some embodiments, p=0 and r=0. In some embodiments, $R_{18}$ is heteroaryl or phenyl each optionally substituted with 1 to 5 substituents selected independently from the group consisting of $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl. In some embodiments, the heteroaryl is selected from the group consisting of 1H-imidazol-4-yl, [1,2,4]triazol-1-yl, [1,2,3]triazol-1-yl, [1,2,4]triazol-4-yl, pyrrol-1-yl, pyrazol-1-yl, 1H-pyrazol-3-yl, imidazol-1-yl, oxazol-5-yl, oxazol-2-yl, [1,3,4]oxadiazol-2-yl, [1,3,4]thiadiazol-2-yl, [1,2,4]oxadiazol-3-yl, [1,2,4]thiadiazol-3-yl, tetrazol-1-yl, pyrimidin-5-yl, pyrimidin-2-yl, pyrimidin-4-yl, pyridazin-3-yl, pyridazin-4-yl, pyrazin-2-yl, 1,3-dioxo-1,3-dihydro-isoindol-2-yl and [1,2,3]thiadiazol-4-yl. In some embodiments, p=0 and r=1. In some embodiments, $R_{18}$ is carbo-$C_{1-6}$-alkoxy or carboxy. In some embodiments, p=2 and r=1. In some embodiments, $R_{18}$ is H, $C_{1-5}$ acyl or $C_{1-8}$ alkyl.

Some embodiments of the present invention pertain to compounds wherein $Ar_1$ is phenyl. In some embodiments, the phenyl is optionally substituted with $R_{14}$, $R_{15}$, $R_{16}$ and $R_{17}$. In some embodiments, $R_{14}$, $R_{15}$, $R_{16}$ and $R_{17}$ are independently selected from the group consisting of H, $C_{1-5}$ acyl, $C_{1-4}$ alkoxy, $C_{1-8}$ alkyl, $C_{1-4}$ alkylcarboxamide, $C_{1-4}$ alkylureyl, carbo-$C_{1-6}$-alkoxy, carboxamide, carboxy, cyano, $C_{3-7}$ cycloalkyl, halogen, $C_{1-4}$ haloalkoxy and $C_{1-4}$ haloalkyl. In some embodiments, one $R_{14}$, $R_{15}$, $R_{16}$ and $R_{17}$ is a halogen. In further embodiments, the halogen is a fluorine atom.

Some embodiments of the present invention pertain to compounds wherein $Ar_1$ is phenyl and $R_{13}$ is substituted at the para position on the phenyl; these embodiments can be represented by Formula (IIIc) as shown below:

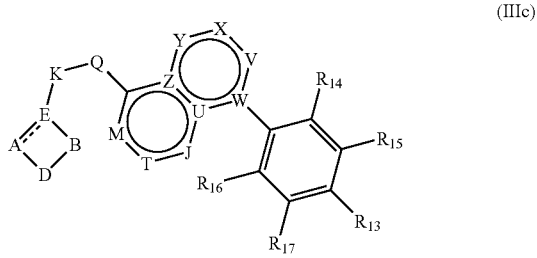

(IIIc)

wherein each variable in Formula (IIIc) has the same meaning as described herein, supra and infra.

Some embodiments of the present invention pertain to compounds wherein $Ar_1$ is phenyl and two adjacent $R_{14}$, $R_{15}$, $R_{16}$ and $R_{17}$ together with the atoms to which they are attached form a 5, 6 or 7 membered cycloalkyl, cycloalkenyl or heterocyclic group fused with the phenyl group wherein the 5, 6 or 7 membered group is optionally substituted with halogen. In some embodiments, the phenyl and two adjacent $R_{14}$, $R_{15}$, $R_{16}$ and $R_{17}$ groups form a 5, 6 or 7 membered fused cycloalkyl as represented in TABLE 5:

TABLE 5

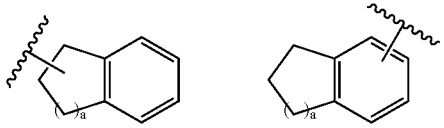

wherein "a" is 1, 2 or 3 to give a 5, 6 or 7 membered cycloalkyl fused together with the phenyl group where two of the ring carbons are shared between the cycloalkyl and phenyl group. In some embodiments, 1, 2, or 3 ring carbons are replaced by a heteroatom selected from, but not limited to, O, S, and N, wherein N is substituted with H or $C_{1-4}$ alkyl. In some embodiments, the two adjacent groups form a 5 membered heterocyclic group with the phenyl group. In some embodiments, the 5 membered heterocyclic group with the phenyl group together is a 2,3-dihydro-benzofuran-5-yl or benzo[1,3]dioxol-5-yl group. In some embodiments, the two adjacent groups form a 6 membered heterocyclic group with the phenyl group. In some embodiments, the 6 membered heterocyclic group with the phenyl group together is a 2,3-dihydro-benzo[1,4]dioxin-6-yl or 2,3-dihydro-benzo[1,4]dioxin-2-yl group. In some embodiments, the two adjacent groups form a 7 membered heterocyclic group with the phenyl group. In some embodiments, the 7 membered heterocyclic group with the phenyl group together is a 3,4-dihydro-2H-benzo[b][1,4]dioxepin-7-yl group.

Some embodiments of the present invention pertain to compounds wherein $Ar_1$ is pyridyl optionally substituted with $R_{13}$, $R_{14}$, $R_{15}$, and $R_{16}$;

wherein $R_{13}$ is selected from the group consisting of $C_{1-6}$ acylsulfonamide, $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, amino, carbamimidoyl, carboxamide, carboxy, cyano, $C_{2-6}$ dialkylamino, halogen, heterocyclic, heterocyclic-oxy, heterocyclic-carbonyl, heteroaryl, and sulfonamide, and wherein $C_{1-6}$ acylsulfonamide, $C_{1-4}$ alkoxy, $C_{1-8}$ alkyl, $C_{1-4}$ alkylamino, $C_{1-4}$ alkylsulfonamide, alkylsulfonyl, $C_{1-4}$ alkylthio, carbamimidoyl, $C_{2-6}$ dialkylamino, heterocyclic, heterocyclic-carbonyl, and heteroaryl are each optionally substituted with 1 to 5 substituents selected independently from the group consisting of $C_{1-6}$ acylsulfonamide, $C_{1-4}$ alkoxy, $C_{1-7}$ alkyl, $C_{1-4}$ alkylcarboxamide, $C_{1-4}$ alkylsulfonyl, carboxy, $C_{3-7}$ cycloalkyloxy, $C_{2-6}$ dialkylamino, $C_{2-6}$ dialkylcarboxamide, heteroaryl, heterocyclic, hydroxyl, phenyl, and phosphonooxy, and wherein said $C_{1-7}$ alkyl and $C_{1-4}$ alkylcarboxamide are each optionally substituted with 1 to 5 substituents selected from the group consisting of $C_{1-4}$ alkoxy and hydroxy; and $R_{14}$, $R_{15}$, and $R_{16}$ are each independently selected form the group consisting of $C_{1-6}$ acylsulfonamide, $C_{1-4}$ alkoxy, $C_{1-8}$ alkyl, $C_{1-4}$ alkylamino, $C_{1-4}$ alkylcarboxamide, $C_{1-4}$ alkylsulfonamide, $C_{1-4}$ alkylsulfonyl, $C_{1-4}$ alkylthio, amino, carbamimidoyl, carboxamide, cyano, $C_{2-6}$ dialkylamino, and halogen.

Some embodiments of the present invention pertain to compounds wherein $Ar_1$ is pyridyl optionally substituted with $R_{13}$, $R_{14}$, $R_{15}$, and $R_{16}$;

wherein $R_{13}$ is selected from the group consisting of $C_{1-6}$ acylsulfonamide, $C_{1-4}$ alkoxy, $C_{1-8}$ alkyl, $C_{1-4}$ alkylamino, $C_{1-4}$ alkylsulfonyl, $C_{1-4}$ alkylthio, amino, $C_{2-6}$ dialkylamino, halogen, heterocyclic, and sulfonamide, and wherein $C_{1-4}$ alkoxy, $C_{1-8}$ alkyl, $C_{1-4}$ alkylamino, alkylsulfonyl, $C_{1-4}$ alkylthio, $C_{2-6}$ dialkylamino, and heterocyclic are each optionally substituted with 1 to 5 substituents selected independently from the group consisting of $C_{1-6}$ acylsulfonamide, $C_{1-4}$ alkoxy, $C_{1-4}$ alkylsulfonyl, $C_{3-7}$ cycloalkyloxy, heteroaryl, hydroxyl, phenyl, and phosphonooxy; and $R_{14}$, $R_{15}$, and $R_{16}$ are each independently selected form the group consisting of $C_{1-6}$ acylsulfonamide, $C_{1-4}$ alkoxy, $C_{1-8}$ alkyl, $C_{1-4}$ alkylamino, $C_{1-4}$ alkylcarboxamide, $C_{1-4}$ alkylsulfonamide, $C_{1-4}$ alkylsulfonyl, $C_{1-4}$ alkylthio, amino, carbamimidoyl, carboxamide, cyano, $C_{2-6}$ dialkylamino, and halogen.

Some embodiments of the present invention pertain to compounds wherein $Ar_1$ is pyridyl optionally substituted with $R_{13}$, $R_{14}$, $R_{15}$, and $R_{16}$;

wherein $R_{13}$ is selected from the group consisting of $C_{1-6}$ acylsulfonamide, $C_{1-4}$ alkoxy, $C_{1-8}$ alkyl, $C_{1-4}$ alkylamino, $C_{1-4}$ alkylsulfonyl, $C_{1-4}$ alkylthio, amino, $C_{2-6}$ dialkylamino, halogen, heterocyclic, and sulfonamide, and wherein $C_{1-4}$ alkoxy, $C_{1-8}$ alkyl, $C_{1-4}$ alkylamino, alkylsulfonyl, $C_{1-4}$ alkylthio, $C_{2-6}$ dialkylamino, and heterocyclic are each optionally substituted with 1 to 5 substituents selected independently from the group consisting of $C_{1-6}$ acylsulfonamide, $C_{1-4}$ alkoxy, $C_{1-4}$ alkylsulfonyl, $C_{3-7}$ cycloalkyloxy, heteroaryl, hydroxyl, phenyl, and phosphonooxy; and $R_{14}$, $R_{15}$, and $R_{16}$ are each independently selected form the group consisting of $C_{1-8}$ alkyl, and halogen.

Some embodiments of the present invention pertain to compounds of Formula (IIId) as shown below:

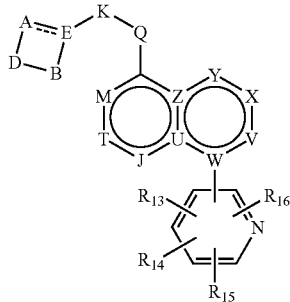
(IIId)

wherein each variable in Formula (IIId) has the same meaning as described herein, supra and infra.

Some embodiments of the present invention pertain to compounds of Formulae (IIId-1) and (IIId-2) as shown below:

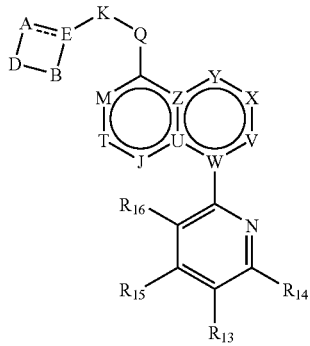
(IIId-1)

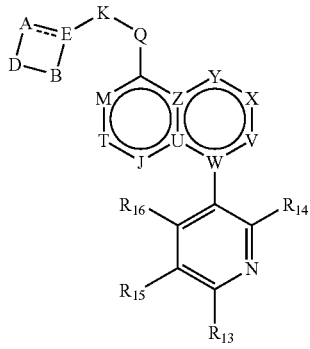
(IIId-2)

wherein each variable in Formulae (IIId-1) and (IIId-2) have the same meaning as described herein, supra and infra.

Some embodiments of the present invention pertain to compounds wherein $Ar_1$ is heteroaryl. In some embodiments, the heteroaryl is optionally substituted with $R_{13}$. In some embodiments, $R_{13}$ is selected from the group consisting of H, $C_{1-5}$ acyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, carboxamide, $C_{3-7}$ cycloalkyl, halogen and sulfonamide. In some embodiments, $R_{13}$ is selected from the group consisting of $C(O)CH_3$, $C(O)CH_2CH_3$, $C(O)CH_2CH_2CH_3$, $C(O)CH(CH_3)_2$, $C(O)CH_2CH_2CH_2CH_3$, $OCH_3$, $OCH_2CH_3$, $OCH_2CH_2CH_3$, $OCH(CH_3)_2$, $OCH_2CH_2CH_2CH_3$, $CH_3$, $CH_2CH_3$, $CH_2CH_2CH_3$, $CH(CH_3)_2$, $CH(CH_3)(CH_2CH_3)$, $CH_2(CH_2)_2CH_3$, $CH_2(CH_2)_3CH_3$, $CH_2(CH_2)_4CH_3$, $CH_2(CH_2)_5CH_3$, $C(O)NHCH_3$, $C(O)NHCH_2CH_3$, $C(O)NHCH_2CH_2CH_3$, $C(O)NHCH(CH_3)_2$, $C(O)NHCH_2(CH_2)_2CH_3$, CCH, $S(O)_2NHCH_3$, $S(O)_2NHCH_2CH_3$, $S(O)_2NHCH_2CH_2CH_3$, $S(O)_2NHCH(CH_3)_2$, $S(O)_2NHCH_2(CH_2)_2CH_3$ and $S(O)_2NHCH(CH_3)CH_2CH_3$.

In some embodiments, $R_{13}$ is selected from the group consisting of $S(O)CH_3$, $S(O)CH_2CH_3$, $S(O)CH_2CH_2CH_3$, $S(O)CH(CH_3)_2$, $S(O)CH_2(CH_2)_2CH_3$, $S(O)CH(CH_3)CH_2CH_3$, $S(O)_2CH_3$, $S(O)_2CH_2CH_3$, $S(O)_2CH_2CH_2CH_3$, $S(O)_2CH(CH_3)_2$, $S(O)_2CH_2(CH_2)_2CH_3$, $S(O)_2CH(CH_3)CH_2CH_3$, $SCH_3$, $SCH_2CH_3$, $SCH_2CH_2CH_3$, $SCH(CH_3)_2$ and $SCH_2(CH_2)_2CH_3$.

In some embodiments, $R_{13}$ is selected from the group consisting of amino, arylsulfonyl, carboxy, cyano, $C_{3-7}$ cycloalkyl, halogen, $C_{1-4}$ haloalkoxy, $C_{1-4}$ haloalkyl and $C_{1-4}$ haloalkylthio. In some embodiments, $R_{13}$ is selected from the group consisting of phenylsulfonyl, cyclopropyl, cyclobutyl, cyclopentyl, cyclohexyl, Cl, F, Br, $OCF_3$, $OCHF_2$, $OCH_2CF_3$, $CF_3$, $CHF_2$, $CH_2CF_3$, $SCF_3$, $SCHF_2$ and $SCH_2CF_3$. In some embodiments, $R_{13}$ is selected from the group consisting of heterocyclic, heteroaryl, $C_{4-7}$ oxo-cycloalkyl, phenoxy and phenyl. In some embodiments, $R_{13}$ is selected from the group consisting of morpholin-4-yl, thiomorpholin-4-yl, 1-oxo-$1\lambda^4$-thiomorpholin-4-yl, 1,1-Dioxo-$1\lambda^6$-thiomorpholin-4-yl, piperazin-1-yl, 4-methyl-piperazin-1-yl, 4-ethyl-piperazin-1-yl, 4-propyl-piperazin-1-yl, piperidin-1-yl, pyrrolidin-1-yl, 2,5-dioxo-imidazolidin-4-yl, 2,4-dioxo-thiazolidin-5-yl, 4-oxo-2-thioxo-thiazolidin-5-yl, 3-methyl-2,5-dioxo-imidazolidin-4-yl, 3-methyl-2,4-dioxo-thiazolidin-5-yl, 3-methyl-4-oxo-2-thioxo-thiazolidin-5-yl, 3-ethyl-2,5-dioxo-imidazolidin-4-yl, 3-ethyl-2,4-dioxo-thiazolidin-5-yl, and 3-ethyl-4-oxo-2-thioxo-thiazolidin-5-yl. In some embodiments, $R_{13}$ is selected from the group consisting of 1H-imidazol-4-yl, [1,2,4]triazol-1-yl, [1,2,3]triazol-1-yl, [1,2,4]triazol-4-yl, pyrrol-1-yl, pyrazol-1-yl, 1H-pyrazol-3-yl, imidazol-1-yl, oxazol-5-yl, oxazol-2-yl, [1,3,4]oxadiazol-2-yl, [1,3,4]thiadiazol-2-yl, [1,2,4]oxadiazol-3-yl, [1,2,4]thiadiazol-3-yl, tetrazol-1-yl, pyrimidin-5-yl, pyrimidin-2-yl, pyrimidin-4-yl, pyridazin-3-yl, pyridazin-4-yl, pyrazin-2-yl, 1,3-dioxo-1,3-dihydro-isoindol-2-yl and [1,2,3]thiadiazol-4-yl. In some embodiments, $R_{13}$ is $C_{1-8}$ alkyl or $C_{1-4}$ alkoxy, optionally substituted with 1 to 5 substituents selected independently from the group consisting of $C_{1-4}$ alkoxy, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carbo-$C_{1-6}$-alkoxy, carboxamide, carboxy, cyano, heterocyclic, hydroxyl and phenyl. In some embodiments, $R_{13}$ is $C_{1-4}$ alkylsulfonyl optionally substituted with 1 to 5 substituents selected independently from the group consisting of $C_{1-4}$ alkoxy, carboxamide, heteroaryl, heterocyclic and phenyl. In some embodiments, the $C_{1-4}$ alkylsulfonyl is substituted with the heteroaryl group. In some embodiments, the heteroaryl is selected from the group consisting of 1H-imidazol-4-yl, [1,2,4]triazol-1-yl, [1,2,3]triazol-1-yl, [1,2,4]triazol-4-yl, pyrrol-1-yl, pyrazol-1-yl, 1H-pyrazol-3-yl, imidazol-1-yl, oxazol-5-yl, oxazol-2-yl, [1,3,4]oxadiazol-2-yl, [1,3,4]thiadiazol-2-yl, [1,2,4]oxadiazol-3-yl, [1,2,4]thiadiazol-3-yl, tetrazol-1-yl, pyrimidin-5-yl, pyrimidin-2-yl, pyrimidin-4-yl, pyridazin-3-yl, pyridazin-4-yl, pyrazin-2-yl, 1,3-dioxo-1,3-dihydro-isoindol-2-yl and [1,2,3]thiadiazol-4-yl. In some embodiments, $R_{13}$ is arylsulfonyl, heteroaryl, phenoxy or phenyl optionally substituted with 1 to 5 substituents selected independently from the group consisting of $C_{1-5}$ acyl, $C_{1-4}$ alkoxy, $C_{1-8}$ alkyl, $C_{1-4}$ alkylsulfonamide, $C_{1-4}$ alkylsulfinyl, $C_{1-4}$ alkylsulfonyl, $C_{1-4}$ alkylthio, carboxamide, carboxy, cyano, halogen, $C_{1-4}$ haloalkoxy, $C_{1-4}$ haloalkyl, $C_{1-4}$ haloalkylthio and hydroxyl. In some embodiments, $R_{13}$ is arylsulfonyl, heteroaryl, phenoxy or phenyl optionally substituted with 1 to 5 substituents selected independently from the group consisting of $C_{1-4}$ alkoxy, $C_{1-8}$ alkyl, cyano, halogen, $C_{1-4}$ haloalkoxy, $C_{1-4}$ haloalkyl and hydroxyl.

Some embodiments of the present invention pertain to compounds wherein $Ar_1$ is heteroaryl. In some embodiments, the heteroaryl is optionally substituted with $R_{13}$. In some embodiments, $R_{13}$ is of Formula (A):

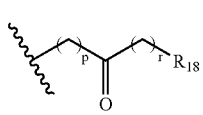

(A)

wherein:
"p" and "r" are independently 0, 1, 2 or 3; and $R_{18}$ is H, $C_{1-5}$ acyl, $C_{2-6}$ alkenyl, $C_{1-8}$ alkyl, $C_{1-4}$ alkylcarboxamide, $C_{2-6}$ alkynyl, $C_{1-4}$ alkylsulfonamide, carbo-$C_{1-6}$-alkoxy, carboxamide, carboxy, cyano, $C_{3-7}$ cycloalkyl, $C_{2-6}$ dialkylcarboxamide, halogen, heteroaryl or phenyl, and wherein the heteroaryl or phenyl may be optionally substituted with 1 to 5 substituents selected independently from the group consisting of $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl. In some embodiments, p=0 and r=0. In some embodiments, $R_{18}$ is heteroaryl or phenyl optionally substituted with 1 to 5 substituents selected independently from the group consisting of $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl. In some embodiments, the heteroaryl is selected from the group consisting of 1H-imidazol-4-yl, [1,2,4]triazol-1-yl, [1,2,3]triazol-1-yl, [1,2,4]triazol-4-yl, pyrrol-1-yl, pyrazol-1-yl, 1H-pyrazol-3-yl, imidazol-1-yl, oxazol-5-yl, oxazol-2-yl, [1,3,4]oxadiazol-2-yl, [1,3,4]thiadiazol-2-yl, [1,2,4]oxadiazol-3-yl, [1,2,4]thiadiazol-3-yl, tetrazol-1-yl, pyrimidin-5-yl, pyrimidin-2-yl, pyrimidin-4-yl, pyridazin-3-yl, pyridazin-4-yl, pyrazin-2-yl, 1,3-dioxo-1,3-dihydro-isoindol-2-yl and [1,2,3]thiadiazol-4-yl. In some embodiments, p=0 and r=1. In some embodiments, $R_{18}$ is carbo-$C_{1-6}$-alkoxy or carboxy. In some embodiments, p=2 and r=1. In some embodiments, $R_{18}$ is H, $C_{1-5}$ acyl or $C_{1-8}$ alkyl.

Some embodiments of the present invention pertain to compounds wherein $Ar_1$ is heteroaryl. In some embodiments, the heteroaryl is optionally substituted with $R_{14}$, $R_{15}$, $R_{16}$ and $R_{17}$. In some embodiments, $R_{14}$-$R_{17}$ are independently selected from the group consisting of H, $C_{1-5}$ acyl, $C_{1-4}$ alkoxy, $C_{1-8}$ alkyl, $C_{1-4}$ alkylcarboxamide, $C_{1-4}$ alkylureyl, carbo-$C_{1-6}$-alkoxy, carboxamide, carboxy, cyano, $C_{3-7}$ cycloalkyl, halogen, $C_{1-4}$ haloalkoxy and $C_{1-4}$ haloalkyl. In some embodiments, one $R_{14}$, $R_{15}$, $R_{16}$ and $R_{17}$ is halogen. In further embodiments, the halogen is fluorine.

Some embodiments of the present invention pertain to compounds wherein $Ar_1$ is heteroaryl. In some embodiments, the heteroaryl is optionally substituted with $R_{14}$, $R_{15}$, $R_{16}$ and $R_{17}$ wherein two adjacent $R_{14}$, $R_{15}$, $R_{16}$ and $R_{17}$ groups together with the atoms to which they are attached form a 5, 6 or 7 membered cycloalkyl, cycloalkenyl or heterocyclic group fused with the heteroaryl group wherein the 5, 6 or 7 membered group is optionally substituted with halogen. In some embodiments, the two adjacent groups form a 5 membered heterocyclic group fused with the heteroaryl group. In some embodiments, the two adjacent groups form a 6 membered heterocyclic group fused with the heteroaryl group. In some embodiments, the two adjacent groups form a 7 membered heterocyclic group fused with the heteroaryl group.

Some embodiments of the present invention pertain to compounds wherein $R_3$ and $R_4$ are independently H or $CH_3$.

Some embodiments of the present invention pertain to compounds wherein M and J are both N (i.e., nitrogen atom) and T is $CR_5$. In some embodiments, Z and U are both C (i.e., a carbon atom); these embodiments can be represented by Formula (IIIe) as shown below:

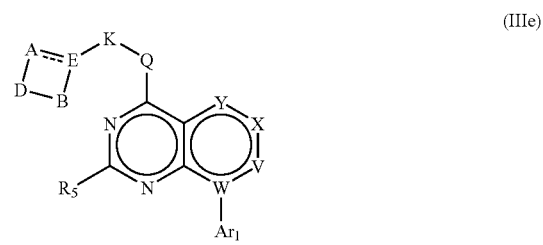

(IIIe)

wherein each variable in Formula (IIIe) has the same meaning as described herein, supra and infra.

Some embodiments of the present invention pertain to compounds wherein V is a bond; these embodiments are represented by Formula (IIIg) as shown below:

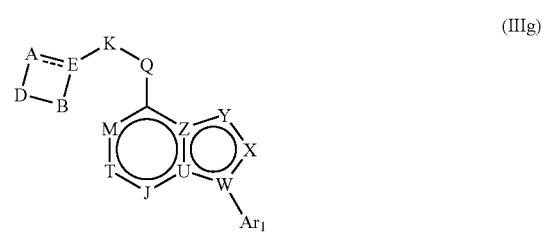

(IIIg)

wherein each variable in Formula (IIIg) has the same meaning as described herein, supra and infra.

Some embodiments of the present invention pertain to compounds wherein W is N.

Some embodiments of the present invention pertain to compounds wherein X is $CR_9$ and Y is $CR_{10}$. In some embodiments, V is a bond and represented by Formula (IIIi):

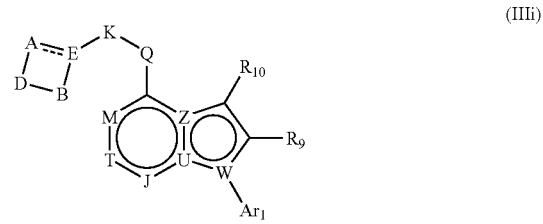

(IIIi)

wherein each variable in Formula (IIIi) has the same meaning as described herein, supra and infra. In some embodiments W is N (i.e., a nitrogen atom).

Some embodiments of the present invention pertain to compounds wherein X is N and Y is $CR_{10}$.

In some embodiments, V is a bond and represented by Formula (IIIk):

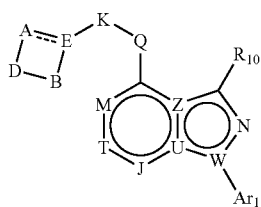

(IIIk)

wherein each variable in Formula (IIIk) has the same meaning as described herein, supra and infra. In some embodiments W is N (i.e., a nitrogen atom).

Some embodiments of the present invention pertain to compounds wherein X is $CR_9$ and Y is N. In some embodiments, V is a bond and represented by Formula (IIIm):

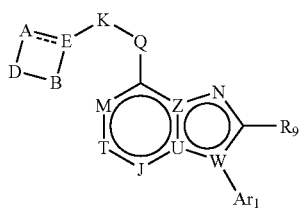

(IIIm)

wherein each variable in Formula (IIIm) has the same meaning as described herein, supra and infra. In some embodiments W is N (i.e., a nitrogen atom).

Some embodiments of the present invention pertain to compounds wherein X and Y are both N. In some embodiments, V is a bond and represented by Formula (IIIo):

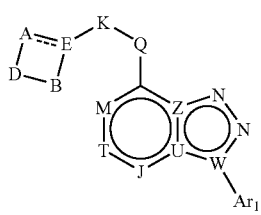

(IIIo)

wherein each variable in Formula (IIIo) has the same meaning as described herein, supra and infra. In some embodiments W is N (i.e., a nitrogen atom).

Some embodiments of the present invention pertain to compounds having the Formula (H7):

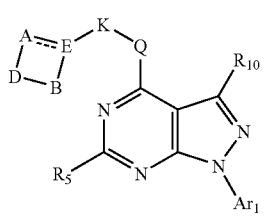

(H7)

wherein:
A is —$CH_2$—, or —$CH_2CH_2$—;
B is —$CH_2$—, —$CH_2CH_2$—, or —$CH_2CH_2CH_2$—;
E is CH;
----- is a single bond;
D is N—$R_2$;
K is —$CH_2$—, —$CH_2CH_2$—, —$CH(CH_3)CH_2$—, or a bond;
Q is O, S, S(O), S(O)$_2$, NH;
$R_5$ is H, $CH_3$ or $N(CH_3)_2$;
$R_{10}$ is H or $CH_3$;
$R_2$ is —$CR_{25}R_{26}C(O)R_{24}$, —$C(O)R_{24}$, —$C(O)NR_{25}R_{24}$, —$R_{24}$, —$C(O)OR_{24}$, —$C(S)NR_{25}R_{24}$, or —$CR_{25}R_{26}R_{24}$, wherein $R_{24}$ is $C_{1-8}$ alkyl, $C_{3-7}$ cycloalkyl, phenyl, heteroaryl, or heterocyclic each optionally substituted with 1 to 5 substituents selected from the group consisting of $C_{2-6}$ alkenyl, $C_{1-4}$ alkoxy, $C_{1-7}$ alkyl, $C_{1-4}$ alkylsulfonyl, amino, carbo-$C_{1-6}$-alkoxy, carboxy, cyano, $C_{3-7}$ cycloalkyl, $C_{2-8}$ dialkylamino, $C_{1-4}$ haloalkoxy, $C_{1-4}$ haloalkyl, halogen, heteroaryl, heterocyclic, hydroxyl, phenyl, phenoxy, and sulfonic acid, wherein said $C_{1-7}$ alkyl, phenyl and phenoxy are each optionally substituted with 1 to 5 substituents selected from the group consisting of amino, $C_{1-4}$ haloalkoxy, and heterocyclic; and $R_{25}$ and $R_{26}$ are each independently H or $C_{1-8}$ alkyl; and $Ar_1$ is aryl or heteroaryl optionally substituted with $R_{13}$, $R_{14}$, $R_{15}$, $R_{16}$, and $R_{17}$; wherein $R_{13}$ is selected from the group consisting of $C_{1-6}$ acylsulfonamide, $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, amino, carbamimidoyl, carboxamide, carboxy, cyano, $C_{2-6}$ dialkylamino, halogen, heterocyclic, heterocyclic-oxy, heterocyclic-carbonyl, heteroaryl, and sulfonamide, and wherein $C_{1-6}$ acylsulfonamide, $C_{1-4}$ alkoxy, $C_{1-8}$ alkyl, $C_{1-4}$ alkylamino, $C_{1-4}$ alkylsulfonamide, alkylsulfonyl, $C_{1-4}$ alkylthio, carbamimidoyl, $C_{2-6}$ dialkylamino, heterocyclic, heterocyclic-carbonyl, and heteroaryl are each optionally substituted with 1 to 5 substituents selected independently from the group consisting of $C_{1-6}$ acylsulfonamide, $C_{1-4}$ alkoxy, $C_{1-7}$ alkyl, $C_{1-4}$ alkylcarboxamide, $C_{1-4}$ alkylsulfonyl, carboxy, $C_{3-7}$ cycloalkyloxy, $C_{2-6}$ dialkylamino, $C_{2-6}$ dialkylcarboxamide, heteroaryl, heterocyclic, hydroxyl, phenyl, and phosphonooxy wherein said $C_{1-7}$ alkyl and $C_{1-4}$ alkylcarboxamide are each optionally substituted with 1 to 5 substituents selected from the group consisting of $C_{1-4}$ alkoxy and hydroxy; and $R_{14}$, $R_{15}$, $R_{16}$, and $R_{17}$ are each independently selected form the group consisting of $C_{1-6}$ acylsulfonamide, $C_{1-4}$ alkoxy, $C_{1-8}$ alkyl, $C_{1-4}$ alkylamino, $C_{1-4}$ alkylcarboxamide, $C_{1-4}$ alkylsulfonamide, $C_{1-4}$ alkylsulfonyl, $C_{1-4}$ alkylthio, amino, carbamimidoyl, carboxamide, cyano, $C_{2-6}$ dialkylamino, and halogen.

Some embodiments of the present invention pertain to compounds having the Formula (H7):
A and B are both —$CH_2CH_2$—;
E is CH;
----- is a single bond;
D is N—$R_2$;
K is a bond;
Q is O, or NH;
$R_5$ and $R_{10}$ are both H;
$R_2$ is —$C(O)OR_{24}$ wherein $R_{24}$ is $C_{1-8}$ alkyl, or $C_{3-7}$ cycloalkyl each optionally substituted with 1 to 5 substituents selected from the group consisting of $C_{1-4}$ alkoxy, $C_{1-7}$ alkyl, $C_{1-4}$ alkylsulfonyl, amino, carbo-$C_{1-6}$-alkoxy, carboxy, cyano, $C_{3-7}$ cycloalkyl, $C_{2-8}$ dialkylamino, $C_{1-4}$ haloalkoxy, $C_{1-4}$ haloalkyl, halogen, heteroaryl, heterocyclic, hydroxyl, phenyl, and phenoxy; and $Ar_1$ is aryl or heteroaryl optionally substituted with $R_{13}$, $R_{14}$, $R_{15}$, $R_{16}$, and $R_{17}$; wherein $R_{13}$ is selected from the group consisting of $C_{1-6}$ acylsulfonamide, $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, amino, carbamimidoyl, carboxamide, carboxy, cyano, $C_{2-6}$ dialkylamino, halogen, heterocyclic, heterocyclic-oxy, heterocyclic-carbonyl, heteroaryl, and sulfonamide, and wherein $C_{1-6}$ acylsulfonamide, $C_{1-4}$ alkoxy, $C_{1-8}$ alkyl, $C_{1-4}$ alkylamino, $C_{1-4}$ alkylsulfonamide, alkylsulfonyl, $C_{1-4}$ alkylthio, carbamimidoyl, $C_{2-6}$ dialkylamino, heterocyclic, heterocyclic-carbonyl, and heteroaryl are each optionally substituted with 1 to 5 substituents selected independently from the group consisting of $C_{1-6}$ acylsulfonamide, $C_{1-4}$ alkoxy, $C_{1-7}$ alkyl, $C_{1-4}$ alkylcarboxamide, $C_{1-4}$ alkylsulfonyl, carboxy, $C_{3-7}$ cycloalkyloxy, $C_{2-6}$ dialkylamino, $C_{2-6}$ dialkylcarboxamide, heteroaryl, heterocyclic, hydroxyl, phenyl, and phosphonooxy wherein said $C_{1-7}$ alkyl and $C_{1-4}$ alkylcarboxamide are each optionally substituted with 1 to 5 substituents selected from the group consisting of $C_{1-4}$ alkoxy and hydroxy; and $R_{14}$, $R_{15}$, $R_{16}$, and $R_{17}$ are each independently selected form the group consisting of $C_{1-4}$ alkoxy, $C_{1-8}$ alkyl, and halogen.

Some embodiments of the present invention pertain to compounds having the Formula (H7):

A and B are both —$CH_2CH_2$—;
E is CH;
----- is a single bond;
D is N—$R_2$
K is a bond;
Q is O, or NH;
$R_5$ and $R_{10}$ are both H;
$R_2$ is —C(O)O$R_{24}$ wherein $R_{24}$ is $C_{1-8}$ alkyl or $C_{3-7}$ cycloalkyl;
$Ar_1$ is phenyl, 3-pyridyl, or 2-pyridyl each optionally substituted with $R_{13}$, $R_{14}$, $R_{15}$, $R_{16}$, and $R_{17}$, wherein $R_{13}$ is selected from the group consisting of $C_{1-6}$ acylsulfonamide, $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, carbamimidoyl, carboxamide, carboxy, cyano, $C_{2-6}$ dialkylamino, halogen, heterocyclic, heterocyclic-oxy, heterocyclic-carbonyl, heteroaryl, heteroarylcarbonyl, and sulfonamide, and wherein $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, carbamimidoyl, $C_{2-6}$ dialkylamino, heterocyclic, heterocyclic-carbonyl, and heteroaryl are each optionally substituted with 1 to 5 substituents selected independently from the group consisting of $C_{1-6}$ acylsulfonamide, $C_{1-4}$ alkoxy, $C_{1-7}$ alkyl, $C_{1-4}$ alkylcarboxamide, $C_{1-4}$ alkylsulfonyl, carboxy, $C_{2-6}$ dialkylamino, $C_{2-6}$ dialkylcarboxamide, heteroaryl, heterocyclic, hydroxyl, phenyl, and phosphonooxy wherein said $C_{1-7}$ alkyl and $C_{1-4}$ alkylcarboxamide are each optionally substituted with 1 to 5 substituents selected from the group consisting of $C_{1-4}$ alkoxy and hydroxy; and $R_{14}$, $R_{15}$, $R_{16}$, and $R_{17}$ are each independently $CH_3$, or F.

In some embodiments, $R_2$ is selected from the group consisting of methoxycarbonyl, ethoxycarbonyl, iso-propoxycarbonyl, n-propoxycarbonyl, n-butoxycarbonyl, tert-butoxycarbonyl, iso-butoxycarbonyl, and n-pentyloxycarbonyl.

In some embodiments, $R_{11}$ is selected from the group consisting of
sulfamoyl [i.e., —S(O)$_2$NH$_2$],
acetylsulfamoyl [i.e., —S(O)$_2$NHC(O)CH$_3$],
propionylsulfamoyl [i.e., —S(O)$_2$NHC(O)CH$_2$CH$_3$],
butyrylsulfamoyl [i.e., —S(O)$_2$NHC(O)CH$_2$CH$_2$CH$_3$],
pentanoylsulfamoyl [i.e., —S(O)$_2$NHC(O)CH$_2$CH$_2$CH$_2$CH$_3$],
methanesulfonyl [i.e., —S(O)$_2$CH$_3$],
ethanesulfonyl [i.e., —S(O)$_2$CH$_2$CH$_3$],
propane-1-sulfonyl [i.e., —S(O)$_2$CH$_2$CH$_2$CH$_3$],
hydroxymethyl (i.e., —CH$_2$OH),
2-hydroxyethyl (i.e., —CH$_2$CH$_2$OH),
3-hydroxypropyl (i.e., —CH$_2$CH$_2$CH$_2$OH),
4-hydroxy-butyl (i.e., —CH$_2$CH$_2$CH$_2$CH$_2$OH),
phosphonooxymethyl [i.e., —CH$_2$OP(O)(OH)$_2$],
2-phosphonooxy-ethyl [i.e., —CH$_2$CH$_2$OP(O)(OH)$_2$],
3-phosphonooxy-propyl [i.e., —CH$_2$CH$_2$CH$_2$OP(O)(OH)$_2$], and
4-phosphonooxy-butyl [i.e., —CH$_2$CH$_2$CH$_2$CH$_2$OP(O)(OH)$_2$].

Inventors have discovered that a variety of fused aromatic rings can be utilized in the present invention. The fused ring system is generically represented by the ring designated by variables G, F, J, U, W, V, X, Y and Z in Formula (I) as well as other formulae disclosed herein. In some embodiments, the fused ring is a 6-6 fused ring wherein two ring atoms (i.e., U and Z) are mutually shared by both rings. In some embodiments, the fused ring system is a 6-5 fused ring wherein two ring atoms (i.e., U and Z) are mutally shared by both rings. Representative fused rings of the present invention include, but not limited to, those disclosed in TABLE 6 shown below:

TABLE 6

(I)

| No. | Fused Ring System | M | T | J | Y | X | V | W | Z | U |
|---|---|---|---|---|---|---|---|---|---|---|
| H1 | 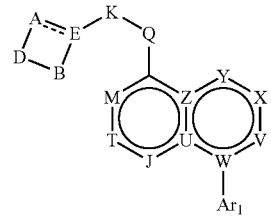 | N | $CR_5$ | N | $CR_{10}$ | $CR_9$ | $CR_8$ | C | C | C |

TABLE 6-continued

| No. | Fused Ring System | M | T | J | Y | X | V | W | Z | U |
|---|---|---|---|---|---|---|---|---|---|---|
| H2 | | N | $CR_5$ | N | $CR_{10}$ | $CR_9$ | N | C | C | C |
| H3 | | N | $CR_5$ | N | N | $CR_9$ | N | C | C | C |
| H4 | | N | $CR_5$ | N | N | $CR_9$ | $CR_8$ | C | C | C |
| H5 | | N | $CR_5$ | N | $CR_{10}$ | N | $CR_8$ | C | C | C |
| H6 | | N | $CR_5$ | N | $CR_{10}$ | $CR_9$ | A Bond | N | C | C |
| H7 | | N | $CR_5$ | N | $CR_{10}$ | N | A Bond | N | C | C |

TABLE 6-continued (I)

| No. | Fused Ring System | M | T | J | Y | X | V | W | Z | U |
|---|---|---|---|---|---|---|---|---|---|---|
| H8 | (structure) | N | CR$_5$ | N | N | CR$_9$ | A Bond | N | C | C |
| H9 | (structure) | N | CR$_5$ | N | N | N | A Bond | N | C | C |
| H10 | (structure) | N | CR$_5$ | N | NR$_{12}$ | CR$_9$ | A Bond | C | C | C |
| H11 | (structure) | N | CR$_5$ | N | NR$_{12}$ | N | A Bond | C | C | C |
| H12 | (structure) | N | CR$_5$ | N | O | N | A Bond | C | C | C |
| H13 | (structure) | N | CR$_5$ | N | S | N | A Bond | C | C | C |

TABLE 6-continued
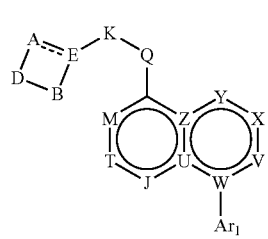
| No. | Fused Ring System | M | T | J | Y | X | V | W | Z | U |
|---|---|---|---|---|---|---|---|---|---|---|
| H14 | | N | CR$_5$ | N | O | CR$_9$ | A Bond | C | C | C |
| H15 | | N | CR$_5$ | N | S | CR$_9$ | A Bond | C | C | C |
| H16 | | CR$_6$ | CR$_5$ | N | CR$_{10}$ | CR$_9$ | CR$_8$ | C | C | C |
| H17 | | CR$_6$ | CR$_5$ | N | CR$_{10}$ | CR$_9$ | N | C | C | C |
| H18 | | CR$_6$ | CR$_5$ | N | N | CR$_9$ | N | C | C | C |
| H19 | | CR$_6$ | CR$_5$ | N | N | CR$_9$ | CR$_8$ | C | C | C |

TABLE 6-continued
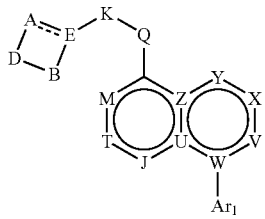
(I)
| No. | Fused Ring System | M | T | J | Y | X | V | W | Z | U |
|---|---|---|---|---|---|---|---|---|---|---|
| H20 | | $CR_6$ | $CR_5$ | N | $CR_{10}$ | N | $CR_8$ | C | C | C |
| H21 | | $CR_6$ | $CR_5$ | N | $CR_{10}$ | $CR_9$ | A Bond | N | C | C |
| H22 | | $CR_6$ | $CR_5$ | N | $CR_{10}$ | N | A Bond | N | C | C |
| H23 | | $CR_6$ | $CR_5$ | N | N | $CR_9$ | A Bond | N | C | C |
| H24 | | $CR_6$ | $CR_5$ | N | N | N | A Bond | N | C | C |
| H25 | | $CR_6$ | $CR_5$ | N | $NR_{12}$ | $CR_9$ | A Bond | C | C | C |

TABLE 6-continued
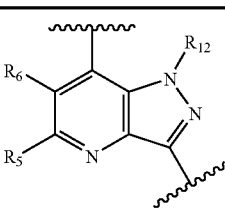
(I)
| No. | Fused Ring System | M | T | J | Y | X | V | W | Z | U |
|---|---|---|---|---|---|---|---|---|---|---|
| H26 | 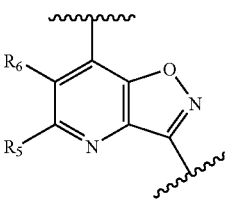 | $CR_6$ | $CR_5$ | N | $NR_{12}$ | N | A Bond | C | C | C |
| H27 | 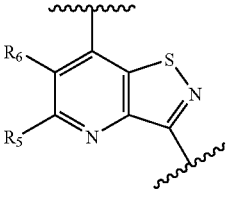 | $CR_6$ | $CR_5$ | N | O | N | A Bond | C | C | C |
| H28 | 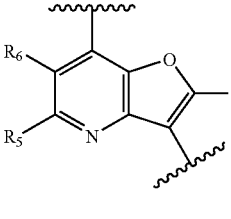 | $CR_6$ | $CR_5$ | N | S | N | A Bond | C | C | C |
| H29 | 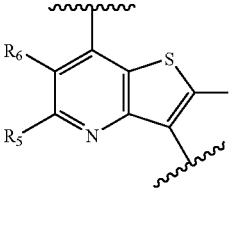 | $CR_6$ | $CR_5$ | N | O | $CR_9$ | A Bond | C | C | C |
| H30 | 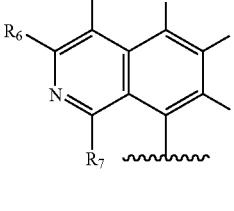 | $CR_6$ | $CR_5$ | N | S | $CR_9$ | A Bond | C | C | C |
| H31 |  | $CR_6$ | N | $CR_7$ | $CR_{10}$ | $CR_9$ | $CR_8$ | C | C | C |

TABLE 6-continued
(I)
| No. | Fused Ring System | M | T | J | Y | X | V | W | Z | U |
|---|---|---|---|---|---|---|---|---|---|---|
| H32 | 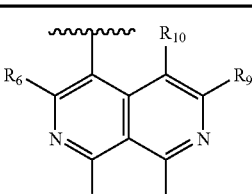 | CR$_6$ | N | CR$_7$ | CR$_{10}$ | CR$_9$ | N | C | C | C |
| H33 | 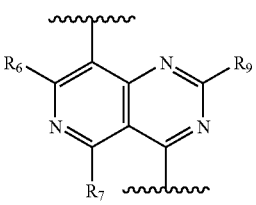 | CR$_6$ | N | CR$_7$ | N | CR$_9$ | N | C | C | C |
| H34 | 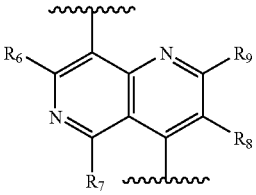 | CR$_6$ | N | CR$_7$ | N | CR$_9$ | CR$_8$ | C | C | C |
| H35 | 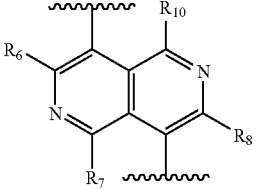 | CR$_6$ | N | CR$_7$ | CR$_{10}$ | N | CR$_8$ | C | C | C |
| H36 | 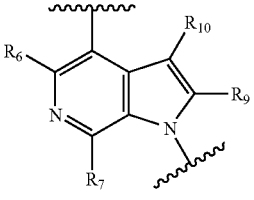 | CR$_6$ | N | CR$_7$ | CR$_{10}$ | CR$_9$ | A Bond | N | C | C |
| H37 | 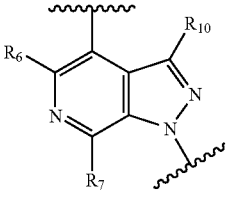 | CR$_6$ | N | CR$_7$ | CR$_{10}$ | N | A Bond | N | C | C |

TABLE 6-continued (I)

| No. | Fused Ring System | M | T | J | Y | X | V | W | Z | U |
|---|---|---|---|---|---|---|---|---|---|---|
| H38 | | $CR_6$ | N | $CR_7$ | N | $CR_9$ | A Bond | N | C | C |
| H39 | | $CR_6$ | N | $CR_7$ | N | N | A Bond | N | C | C |
| H40 | | $CR_6$ | N | $CR_7$ | $NR_{12}$ | $CR_9$ | A Bond | C | C | C |
| H41 | | $CR_6$ | N | $CR_7$ | $NR_{12}$ | N | A Bond | C | C | C |
| H42 | | $CR_6$ | N | $CR_7$ | O | N | A Bond | C | C | C |
| H43 | | $CR_6$ | N | $CR_7$ | S | N | A Bond | C | C | C |

TABLE 6-continued (I)

| No. | Fused Ring System | M | T | J | Y | X | V | W | Z | U |
|---|---|---|---|---|---|---|---|---|---|---|
| H44 | | $CR_6$ | N | $CR_7$ | O | $CR_9$ | A Bond | C | C | C |
| H45 | | $CR_6$ | N | $CR_7$ | S | $CR_9$ | A Bond | C | C | C |
| H46 | | N | $CR_5$ | N | $CR_{10}$ | S | A Bond | C | C | C |
| H47 | | N | $CR_5$ | N | $CR_{10}$ | O | A Bond | C | C | C |
| H48 | | N | $CR_5$ | N | $CR_{10}$ | $NR_{11}$ | A Bond | C | C | C |
| H49 | | N | $CR_5$ | N | N | S | A Bond | C | C | C |

TABLE 6-continued (I)

| No. | Fused Ring System | M | T | J | Y | X | V | W | Z | U |
|---|---|---|---|---|---|---|---|---|---|---|
| H50 | | N | CR$_5$ | N | N | O | A Bond | C | C | C |
| H51 | | N | CR$_5$ | N | N | NR$_{11}$ | A Bond | C | C | C |
| H52 | | N | CR$_5$ | N | CR$_{10}$ | CR$_9$ | A Bond | C | N | C |
| H53 | | N | CR$_5$ | N | N | CR$_9$ | A Bond | C | N | C |
| H54 | | N | CR$_5$ | N | CR$_{10}$ | N | A Bond | C | N | C |
| H55 | | CR$_6$ | CR$_5$ | N | CR$_{10}$ | S | A Bond | C | C | C |

TABLE 6-continued
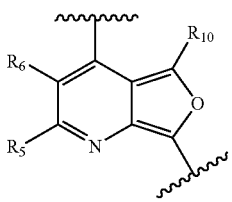
(I)
| No. | Fused Ring System | M | T | J | Y | X | V | W | Z | U |
|---|---|---|---|---|---|---|---|---|---|---|
| H56 | 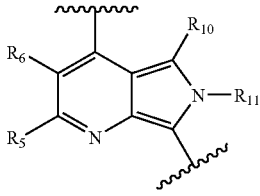 | $CR_6$ | $CR_5$ | N | $CR_{10}$ | O | A Bond | C | C | C |
| H57 | 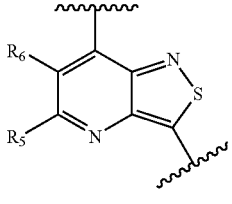 | $CR_6$ | $CR_5$ | N | $CR_{10}$ | $NR_{11}$ | A Bond | C | C | C |
| H58 | 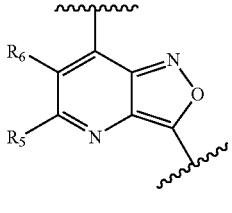 | $CR_6$ | $CR_5$ | N | N | S | A Bond | C | C | C |
| H59 | | $CR_6$ | $CR_5$ | N | N | O | A Bond | C | C | C |
| H60 | 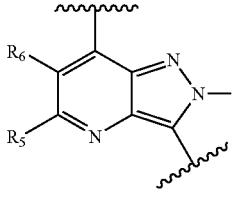 | $CR_6$ | $CR_5$ | N | N | $NR_9$ | A Bond | C | C | C |
| H61 | 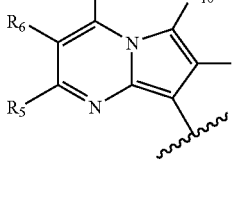 | $CR_6$ | $CR_5$ | N | $CR_{10}$ | $CR_9$ | A Bond | C | N | C |

TABLE 6-continued (I)

| No. | Fused Ring System | M | T | J | Y | X | V | W | Z | U |
|---|---|---|---|---|---|---|---|---|---|---|
| H62 | | $CR_6$ | $CR_5$ | N | N | $CR_9$ | A Bond | C | N | C |
| H63 | | $CR_6$ | $CR_5$ | N | $CR_{10}$ | N | A Bond | C | N | C |
| H64 | | $CR_6$ | N | $CR_7$ | $CR_{10}$ | S | A Bond | C | C | C |
| H65 | | $CR_6$ | N | $CR_7$ | $CR_{10}$ | O | A Bond | C | C | C |
| H66 | | $CR_6$ | N | $CR_7$ | $CR_{10}$ | $NR_{11}$ | A Bond | C | C | C |
| H67 | | $CR_6$ | N | $CR_7$ | N | S | A Bond | C | C | C |

TABLE 6-continued (I)

| No. | Fused Ring System | M | T | J | Y | X | V | W | Z | U |
|---|---|---|---|---|---|---|---|---|---|---|
| H68 | | $CR_6$ | N | $CR_7$ | N | O | A Bond | C | C | C |
| H69 | | $CR_6$ | N | $CR_7$ | N | $NR_{11}$ | A Bond | C | C | C |
| H70 | | $CR_6$ | N | $CR_7$ | $CR_{10}$ | $CR_9$ | A Bond | C | N | C |
| H71 | | $CR_6$ | N | $CR_7$ | N | $CR_9$ | A Bond | C | N | C |
| H72 | | $CR_6$ | N | $CR_7$ | $CR_{10}$ | N | A Bond | C | N | C |
| H73 | | N | $CR_5$ | N | $CR_{10}$ | $CR_9$ | A Bond | C | C | N |

TABLE 6-continued

| No. | Fused Ring System | M | T | J | Y | X | V | W | Z | U |
|-----|---|---|---|---|---|---|---|---|---|---|
| H74 | | N | CR$_5$ | N | N | CR$_9$ | A Bond | C | C | N |
| H75 | | N | CR$_5$ | N | CR$_{10}$ | N | A Bond | C | C | N |
| H76 | | N | CR$_5$ | N | N | N | A Bond | C | C | N |
| H77 | | CR$_6$ | CR$_5$ | N | CR$_{10}$ | CR$_9$ | A Bond | C | C | N |
| H78 | | CR$_6$ | CR$_5$ | N | N | CR$_9$ | A Bond | C | C | N |
| H79 | | CR$_6$ | CR$_5$ | N | CR$_{10}$ | N | A Bond | C | C | N |

TABLE 6-continued

| No. | Fused Ring System | M | T | J | Y | X | V | W | Z | U |
|---|---|---|---|---|---|---|---|---|---|---|
| H80 | | CR$_6$ | CR$_5$ | N | N | N | A Bond | C | C | N |
| H81 | | CR$_6$ | N | CR$_7$ | CR$_{10}$ | CR$_9$ | A Bond | C | C | N |
| H82 | | CR$_6$ | N | CR$_7$ | N | CR$_9$ | A Bond | C | C | N |
| H83 | | CR$_6$ | N | CR$_7$ | CR$_{10}$ | N | A Bond | C | C | N |
| H84 | | CR$_6$ | N | CR$_7$ | N | N | A Bond | C | C | N |
| H85 | | N | CR$_5$ | CR$_7$ | CR$_{10}$ | CR$_9$ | CR$_8$ | C | C | C |

TABLE 6-continued

| No. | Fused Ring System | M | T | J | Y | X | V | W | Z | U |
|---|---|---|---|---|---|---|---|---|---|---|
| H86 | | N | $CR_5$ | $CR_7$ | N | $CR_9$ | $CR_8$ | C | C | C |
| H87 | | N | $CR_5$ | $CR_7$ | $CR_{10}$ | N | $CR_8$ | C | C | C |
| H88 | | N | $CR_5$ | $CR_7$ | $CR_{10}$ | $CR_9$ | N | C | C | C |
| H89 | | N | $CR_5$ | $CR_7$ | N | N | $CR_8$ | C | C | C |
| H90 | | N | $CR_5$ | $CR_7$ | N | $CR_9$ | N | C | C | C |
| H91 | | N | $CR_5$ | $CR_7$ | $CR_{10}$ | $CR_9$ | A Bond | N | C | C |

TABLE 6-continued (I)

| No. | Fused Ring System | M | T | J | Y | X | V | W | Z | U |
|---|---|---|---|---|---|---|---|---|---|---|
| H92 | | N | CR$_5$ | CR$_7$ | CR$_{10}$ | N | A Bond | N | C | C |
| H93 | | N | CR$_5$ | CR$_7$ | N | CR$_9$ | A Bond | N | C | C |
| H94 | | N | CR$_5$ | CR$_7$ | N | N | A Bond | N | C | C |
| H95 | | N | CR$_5$ | CR$_7$ | NR$_{12}$ | CR$_9$ | A Bond | C | C | C |
| H96 | | N | CR$_5$ | CR$_7$ | NR$_{12}$ | N | A Bond | C | C | C |
| H97 | | N | CR$_5$ | CR$_7$ | O | CR$_9$ | A Bond | C | C | C |

TABLE 6-continued (I)

| No. | Fused Ring System | M | T | J | Y | X | V | W | Z | U |
|-----|---|---|---|---|---|---|---|---|---|---|
| H98 | | N | CR$_5$ | CR$_7$ | O | N | A Bond | C | C | C |
| H99 | | N | CR$_5$ | CR$_7$ | S | CR$_9$ | A Bond | C | C | C |
| H100 | | N | CR$_5$ | CR$_7$ | S | N | A Bond | C | C | C |
| H101 | | N | CR$_5$ | CR$_7$ | CR$_{10}$ | O | A Bond | C | C | C |
| H102 | | N | CR$_5$ | CR$_7$ | CR$_{10}$ | S | A Bond | C | C | C |
| H103 | | N | CR$_5$ | CR$_7$ | CR$_{10}$ | NR$_{11}$ | A Bond | C | C | C |

TABLE 6-continued
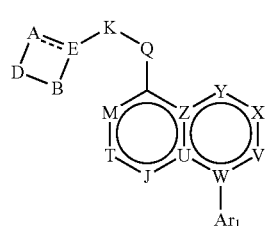
(I)
| No. | Fused Ring System | M | T | J | Y | X | V | W | Z | U |
|---|---|---|---|---|---|---|---|---|---|---|
| H104 | | N | CR$_5$ | CR$_7$ | N | O | A Bond | C | C | C |
| H105 | | N | CR$_5$ | CR$_7$ | N | S | A Bond | C | C | C |
| H106 | | N | CR$_5$ | CR$_7$ | N | NR$_{11}$ | A Bond | C | C | C |
| H107 | | N | CR$_5$ | CR$_7$ | CR$_{10}$ | CR$_9$ | A Bond | C | N | C |
| H108 | | N | CR$_5$ | CR$_7$ | N | CR$_9$ | A Bond | C | N | C |
| H109 | | N | CR$_5$ | CR$_7$ | CR$_{10}$ | N | A Bond | C | N | C |

TABLE 6-continued
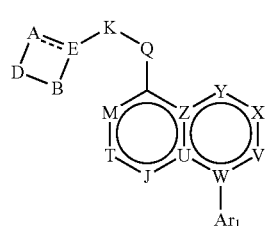
(I)
| No. | Fused Ring System | M | T | J | Y | X | V | W | Z | U |
|---|---|---|---|---|---|---|---|---|---|---|
| H110 | | N | CR$_5$ | CR$_7$ | CR$_{10}$ | CR$_9$ | A Bond | C | C | N |
| H111 | | N | CR$_5$ | CR$_7$ | CR$_{10}$ | N | A Bond | C | C | N |
| H112 | | N | CR$_5$ | CR$_7$ | N | CR$_9$ | A Bond | C | C | N |
| H113 | | N | CR$_5$ | CR$_7$ | N | N | A Bond | C | C | N |
| H114 | | CR$_6$ | CR$_5$ | N | N | N | A Bond | C | N | C |
| H115 | | CR$_6$ | N | CR$_7$ | N | N | A Bond | C | N | C |

TABLE 6-continued (I)

| No. | Fused Ring System | M | T | J | Y | X | V | W | Z | U |
|---|---|---|---|---|---|---|---|---|---|---|
| H116 | | N | CR$_5$ | CR$_7$ | N | N | A Bond | C | N | C |

Some embodiments of the present invention pertain to compounds wherein M, J, X, and W are all N; T is CR$_5$; Y is CR$_{10}$; V is a bond; and Z and U are both C.

Some embodiments of the present invention pertain to compounds wherein M, J, X, and W are all N; T is CR$_5$, wherein R$_5$ is —H, —CH$_3$, or —N(CH$_3$)$_2$; Y is CR$_{10}$, wherein R$_{10}$ is —H or —CH$_3$; V is a bond; and Z and U are both C.

Some embodiments of the present invention pertain to compounds wherein M, J, X, and W are all N; T is C—H; Y is C—H; V is a bond; and Z and U are both C.

In some embodiments of the present invention a compound is not one or more of the compounds illustrated in Table 7, infra.

TABLE 7

| Structure | Chemical Name |
|---|---|
| 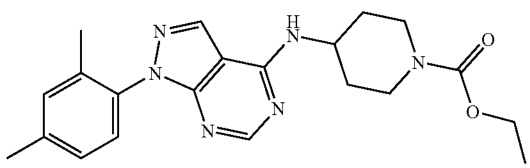 | 4-[1-(2,4-Dimethyl-phenyl)-1H-pyrazolo[3,4-d]pyrimidin-4-ylamino]-piperidine-1-carboxylic acid ethyl ester |
| 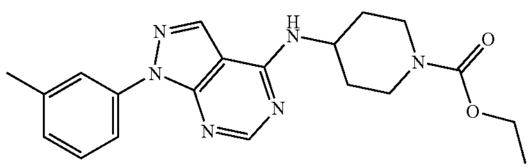 | 4-(1-m-Tolyl-1H-pyrazolo[3,4-d]pyrimidin-4-ylamino)-piperidine-1-carboxylic acid ethyl ester |
| 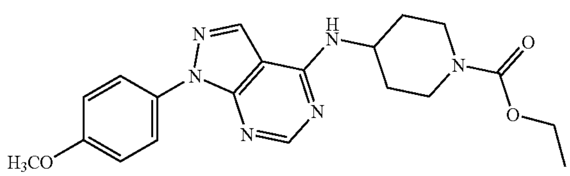 | 4-[1-(4-Methoxy-phenyl)-1H-pyrazolo[3,4-d]pyrimidin-4-ylamino]-piperidine-1-carboxylic acid ethyl ester |
| 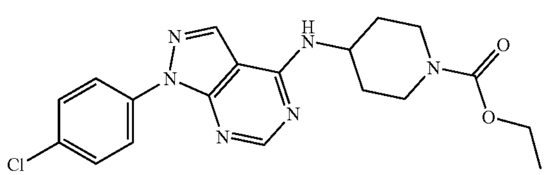 | 4-[1-(4-Chloro-phenyl)-1H-pyrazolo[3,4-d]pyrimidin-4-ylamino]-piperidine-1-carboxylic acid ethyl ester |

TABLE 7-continued

| Structure | Chemical Name |
|---|---|
| 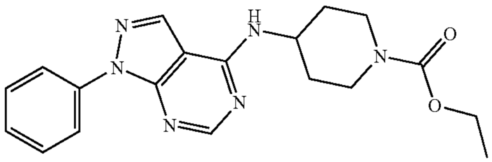 | 4-(1-Phenyl-1H-pyrazolo[3,4-d]pyrimidin-4-ylamino)-piperidine-1-carboxylic acid ethyl ester |

Some embodiments of the present invention pertain to compounds wherein $R_5$, $R_6$, $R_7$, $R_8$, $R_9$ and $R_{10}$ are independently selected from the group consisting of H, $C_{1-4}$ alkoxy, $C_{1-8}$ alkyl, $C_{2-6}$ alkynyl, amino, $C_{3-7}$ cycloalkyl and $C_{1-4}$ haloalkyl.

In some embodiments, $R_5$, $R_6$, $R_7$, $R_8$, $R_9$ and $R_{10}$ are independently H or $C_{1-8}$ alkyl.

In some embodiments, $R_5$, $R_6$, $R_7$, $R_8$, $R_9$ and $R_{10}$ are independently H or $CH_3$.

In some embodiments, $R_5$ is H.

Some embodiments of the present invention pertain to compounds wherein $R_{11}$ and $R_{12}$ are independently selected from the group consisting of H, $C_{1-8}$ alkyl, $C_{2-6}$ alkynyl, $C_{3-7}$ cycloalkyl and $C_{1-4}$ haloalkyl. In some embodiments, $R_{11}$ and $R_{12}$ are independently H or $C_{1-8}$ alkyl.

In some embodiments, $R_{11}$ and $R_{12}$ are independently H or $C_{1-8}$ alkyl.

In some embodiments, $R_{11}$ and $R_{12}$ are independently H or $CH_3$.

Some embodiments of the present invention include compounds illustrated in TABLES A, B, C, D, E, F, G, I, J, and K shown below.

TABLE A

| Cmpd# | Structure | Chemical Name |
|---|---|---|
| A1 | 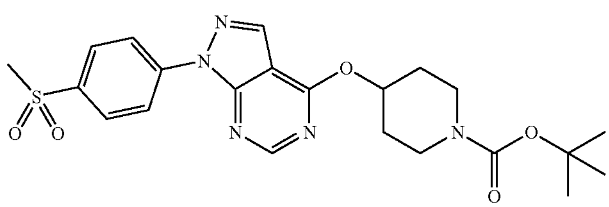 | 4-[1-(4-Methanesulfonyl-phenyl)-1H-pyrazolo[3,4-d]pyrimidin-4-yloxy]-piperidine-1-carboxylic acid tert-butyl ester |
| A2 | 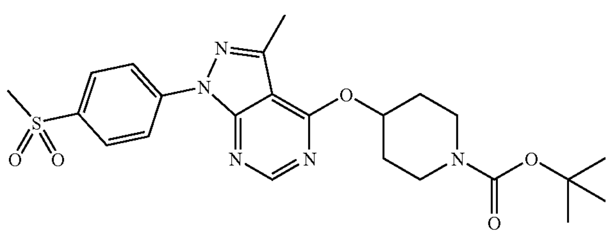 | 4-[1-(4-Methanesulfonyl-phenyl)-3-methyl-1H-pyrazolo[3,4-d]pyrimidin-4-yloxy]-piperidine-1-carboxylic acid tert-butyl ester |
| A3 | 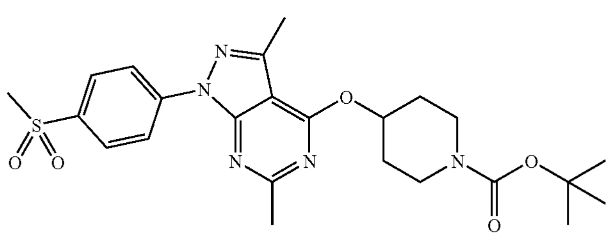 | 4-[1-(4-Methanesulfonyl-phenyl)-3,6-dimethyl-1H-pyrazolo[3,4-d]pyrimidin-4-yloxy]-piperidine-1-carboxylic acid tert-butyl ester |
| A4 | 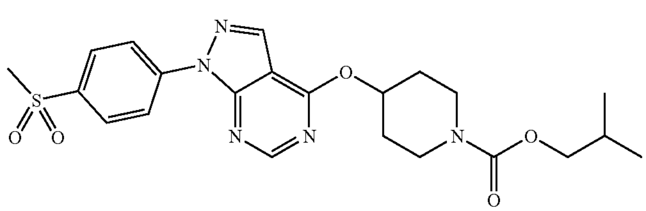 | 4-[1-(4-Methanesulfonyl-phenyl)-1H-pyrazolo[3,4-d]pyrimidin-4-yloxy]-piperidine-1-carboxylic acid isobutyl ester |

TABLE A-continued

| Cmpd# | Structure | Chemical Name |
|---|---|---|
| A5 | 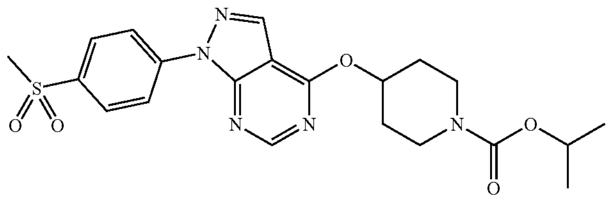 | 4-[1-(4-Methanesulfonyl-phenyl)-1H-pyrazolo[3,4-d]pyrimidin-4-yloxy]-piperidine-1-carboxylic acid isopropyl ester |
| A6 | 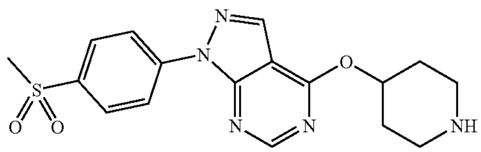 | 1-(4-Methanesulfonyl-phenyl)-4-(piperidin-4-yloxy)-1H-pyrazolo[3,4-d]pyrimidine |
| A7 | 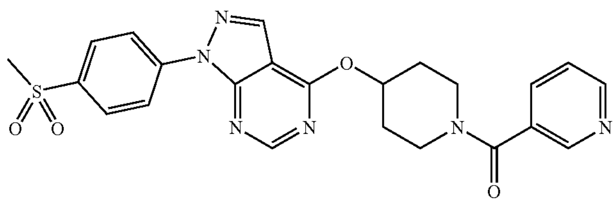 | {4-[1-(4-Methanesulfonyl-phenyl)-1H-pyrazolo[3,4-d]pyrimidin-4-yloxy]-piperidin-1-yl}-pyridin-3-yl-methanone |
| A8 | 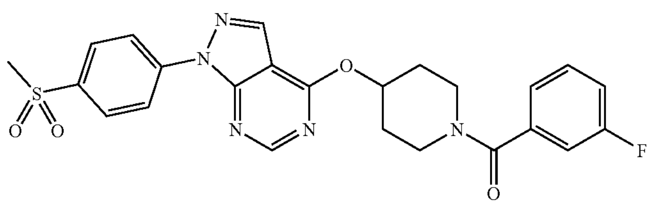 | (3-Fluoro-phenyl)-{4-[1-(4-methanesulfonyl-phenyl)-1H-pyrazolo[3,4-d]pyrimidin-4-yloxy]-piperidin-1-yl}-methanone |
| A9 | 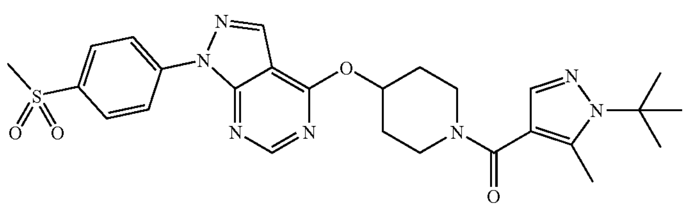 | (1-tert-Butyl-5-methyl-1H-pyrazol-4-yl)-{4-[1-(4-methanesulfonyl-phenyl)-1H-pyrazolo[3,4-d]pyrimidin-4-yloxy]-piperidin-1-yl}-methanone |
| A10 | 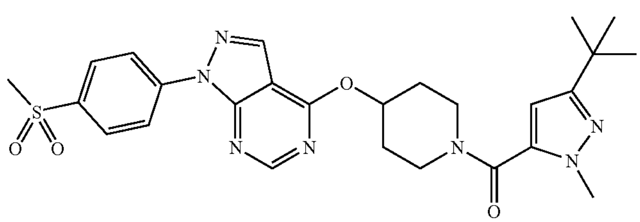 | (5-tert-Butyl-2-methyl-2H-pyrazol-3-yl)-{4-[1-(4-methanesulfonyl-phenyl)-1H-pyrazolo[3,4-d]pyrimidin-4-yloxy]-piperidin-1-yl}-methanone |
| A11 | 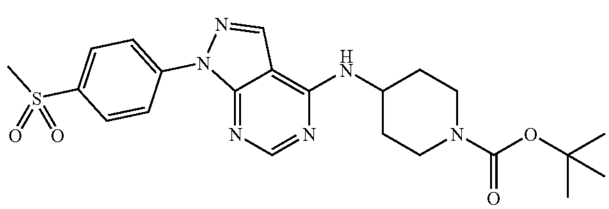 | 4-[1-(4-Methanesulfonyl-phenyl)-1H-pyrazolo[3,4-d]pyrimidin-4-ylamino]-piperidine-1-carboxylic acid tert-butyl ester |

TABLE A-continued

| Cmpd# | Structure | Chemical Name |
|---|---|---|
| A12 | 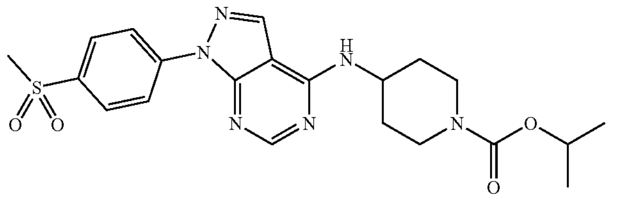 | 4-[1-(4-Methanesulfonyl-phenyl)-1H-pyrazolo[3,4-d]pyrimidin-4-ylamino]-piperidine-1-carboxylic acid isopropyl ester |
| A13 | 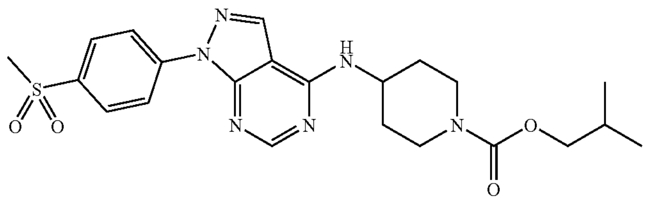 | 4-[1-(4-Methanesulfonyl-phenyl)-1H-pyrazolo[3,4-d]pyrimidin-4-ylamino]-piperidine-1-carboxylic acid isobutyl ester |
| A14 | 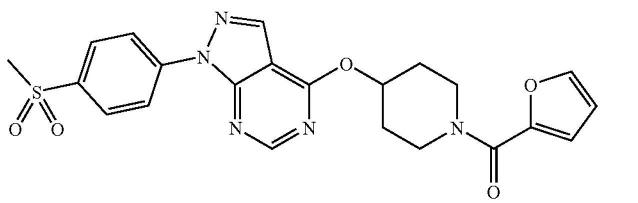 | Furan-2-yl-{4-[1-(4-methanesulfonyl-phenyl)-1H-pyrazolo[3,4-d]pyrimidin-4-yloxy]-piperidin-1-yl}-methanone |
| A15 | 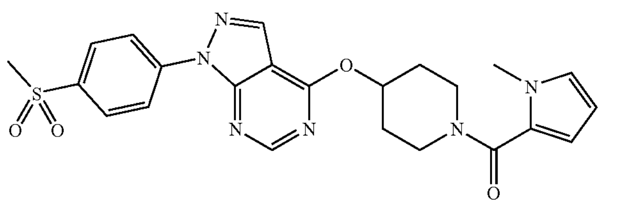 | {4-[1-(4-Methanesulfonyl-phenyl)-1H-pyrazolo[3,4-d]pyrimidin-4-yloxy]-piperidin-1-yl}-(1-methyl-1H-pyrrol-2-yl)-methanone |
| A16 | 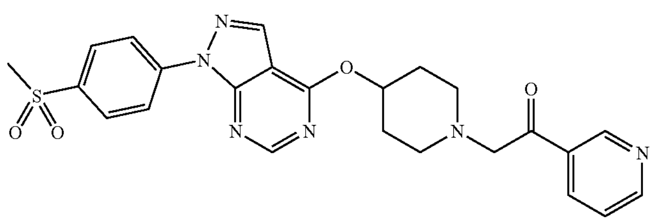 | 2-{4-[1-(4-Methanesulfonyl-phenyl)-1H-pyrazolo[3,4-d]pyrimidin-4-yloxy]-piperidin-1-yl}-1-pyridin-3-yl-ethanone |
| A17 | 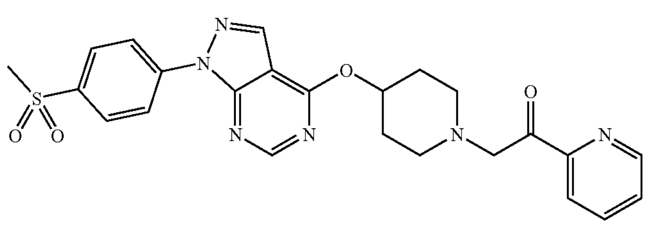 | 2-{4-[1-(4-Methanesulfonyl-phenyl)-1H-pyrazolo[3,4-d]pyrimidin-4-yloxy]-piperidin-1-yl}-1-pyridin-2-yl-ethanone |
| A18 | 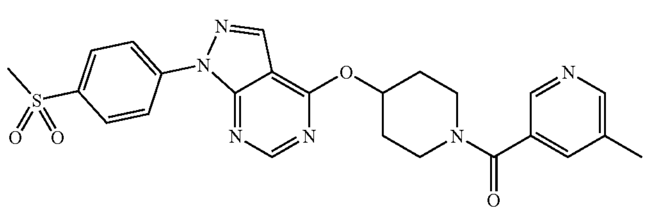 | {4-[1-(4-Methanesulfonyl-phenyl)-1H-pyrazolo[3,4-d]pyrimidin-4-yloxy]-piperidin-1-yl}-(5-methyl-pyridin-3-yl)-methanone |

TABLE A-continued

| Cmpd# | Structure | Chemical Name |
|---|---|---|
| A19 | 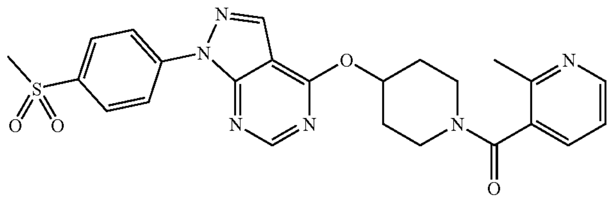 | {4-[1-(4-Methanesulfonyl-phenyl)-1H-pyrazolo[3,4-d]pyrimidin-4-yloxy]-piperidin-1-yl}-(2-methyl-pyridin-3-yl)-methanone |
| A20 | 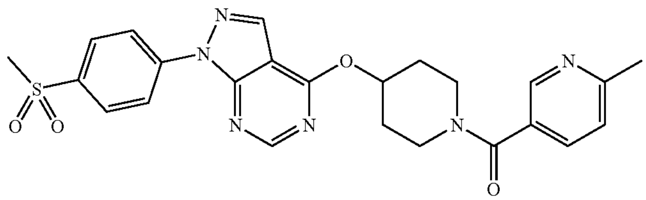 | {4-[1-(4-Methanesulfonyl-phenyl)-1H-pyrazolo[3,4-d]pyrimidin-4-yloxy]-piperidin-1-yl}-(6-methyl-pyridin-3-yl)-methanone |
| A21 | 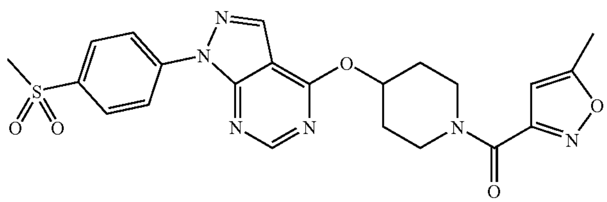 | {4-[1-(4-Methanesulfonyl-phenyl)-1H-pyrazolo[3,4-d]pyrimidin-4-yloxy]-piperidin-1-yl}-(5-methyl-isoxazol-3-yl)-methanone |
| A22 | 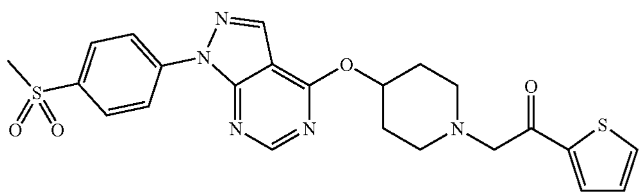 | 2-{4-[1-(4-Methanesulfonyl-phenyl)-1H-pyrazolo[3,4-d]pyrimidin-4-yloxy]-piperidin-1-yl}-1-thiophen-2-yl-ethanone |
| A23 | 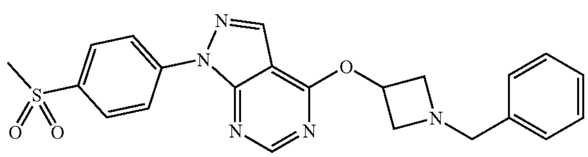 | 4-(1-Benzyl-azetidin-3-yloxy)-1-(4-methanesulfonyl-phenyl)-1H-pyrazolo[3,4-d]pyrimidine |
| A24 | 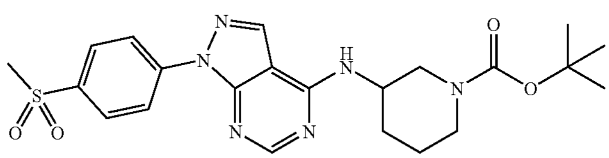 | 3-[1-(4-Methanesulfonyl-phenyl)-1H-pyrazolo[3,4-d]pyrimidin-4-ylamino]-piperidine-1-carboxylic acid tert-butyl ester |
| A25 | 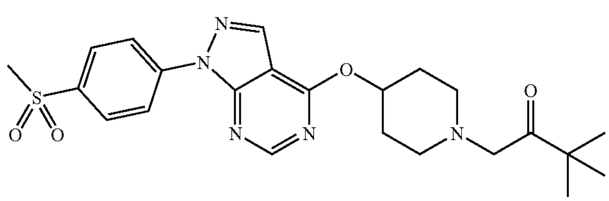 | 1-{4-[1-(4-Methanesulfonyl-phenyl)-1H-pyrazolo[3,4-d]pyrimidin-4-yloxy]-piperidin-1-yl}-3,3-dimethyl-butan-2-one |
| A26 | 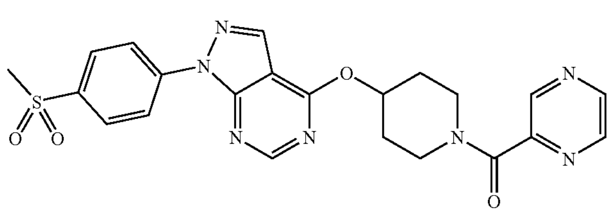 | {4-[1-(4-Methanesulfonyl-phenyl)-1H-pyrazolo[3,4-d]pyrimidin-4-yloxy]-piperidin-1-yl}-pyrazin-2-yl-methanone |

TABLE A-continued

| Cmpd# | Chemical Name |
|---|---|
| A27 | {4-[1-(4-Methanesulfonyl-phenyl)-1H-pyrazolo[3,4-d]pyrimidin-4-yloxy]-piperidin-1-yl}-(5-methyl-pyrazin-2-yl)-methanone |
| A28 | {4-[1-(4-Methanesulfonyl-phenyl)-1H-pyrazolo[3,4-d]pyrimidin-4-yloxy]-piperidin-1-yl}-pyrimidin-5-yl-methanone |
| A29 | {4-[1-(4-Methanesulfonyl-phenyl)-1H-pyrazolo[3,4-d]pyrimidin-4-yloxy]-piperidin-1-yl}-pyridazin-4-yl-methanone |
| A30 | {4-[1-(4-Methanesulfonyl-phenyl)-1H-pyrazolo[3,4-d]pyrimidin-4-yloxy]-piperidin-1-yl}-thiophen-2-yl-methanone |
| A31 | (3,4-Dimethyl-isoxazol-5-yl)-{4-[1-(4-methanesulfonyl-phenyl)-1H-pyrazolo[3,4-d]pyrimidin-4-yloxy]-piperidin-1-yl}-methanone |
| A32 | 3-tert-Butoxy-1-{4-[1-(4-methanesulfonyl-phenyl)-1H-pyrazolo[3,4-d]pyrimidin-4-yloxy]-piperidin-1-yl}-propan-1-one |
| A33 | (3-{4-[1-(4-Methanesulfonyl-phenyl)-1H-pyrazolo[3,4-d]pyrimidin-4-yloxy]-piperidin-1-yl}-3-oxo-propyl)-methyl-carbamic acid tert-butyl ester |

TABLE A-continued

| Cmpd# | Structure | Chemical Name |
|---|---|---|
| A34 | 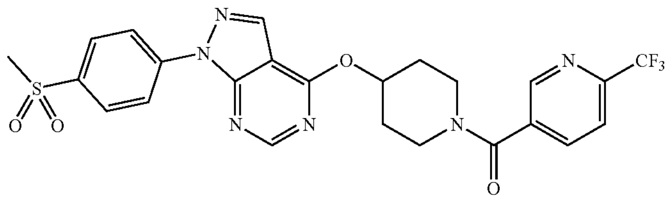 | {4-[1-(4-Methanesulfonyl-phenyl)-1H-pyrazolo[3,4-d]pyrimidin-4-trifluoromethyl-pyridin-3-yl)-methanone |
| A35 | 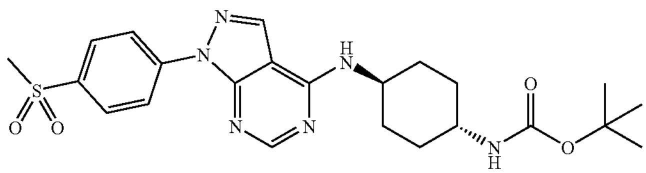 | {4-[1-(4-Methanesulfonyl-phenyl)-1H-pyrazolo[3,4-d]pyrimidin-4-ylamino]-cyclohexyl}-carbamic acid tert-butyl ester |
| A36 | 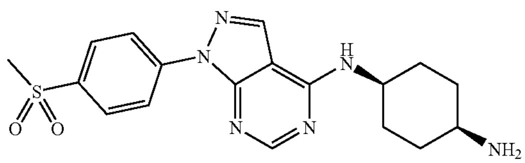 | N-[1-(4-Methanesulfonyl-phenyl)-1H-pyrazolo[3,4-d]pyrimidin-4-yl]-cyclohexane-1,4-diamine |
| A37 | 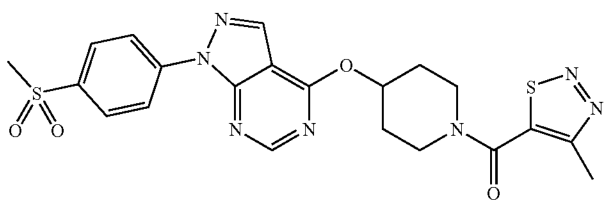 | {4-[1-(4-Methanesulfonyl-phenyl)-1H-pyrazolo[3,4-d]pyrimidin-4-yloxy]-piperidin-1-yl}-(4-methyl-[1,2,3]thiadiazol-5-yl)-methanone |
| A38 | 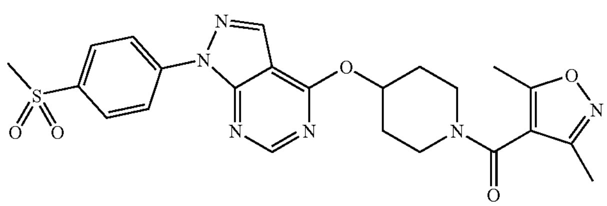 | (3,5-Dimethyl-isoxazol-4-yl)-{4-[1-(4-methanesulfonyl-phenyl)-1H-pyrazolo[3,4-d]pyrimidin-4-yloxy]-piperidin-1-yl}-methanone |
| A39 | 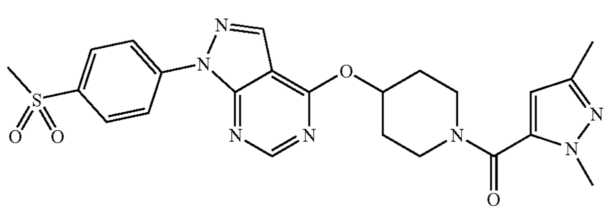 | (2,5-Dimethyl-2H-pyrazol-3-yl)-{4-[1-(4-methanesulfonyl-phenyl)-1H-pyrazolo[3,4-d]pyrimidin-4-yloxy]-piperidin-1-yl}-methanone |
| A40 | 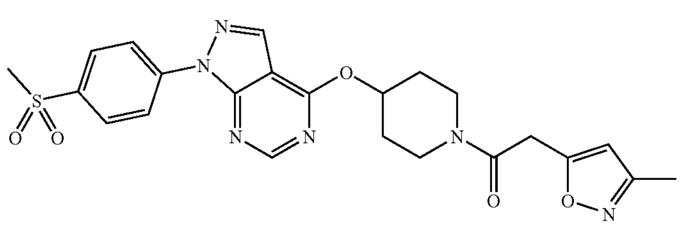 | 1-{4-[1-(4-Methanesulfonyl-phenyl)-1H-pyrazolo[3,4-d]pyrimidin-4-yloxy]-piperidin-1-yl}-2-(3-methyl-isoxazol-5-yl)-ethanone |

TABLE A-continued

| Cmpd# | Structure | Chemical Name |
|---|---|---|
| A41 | 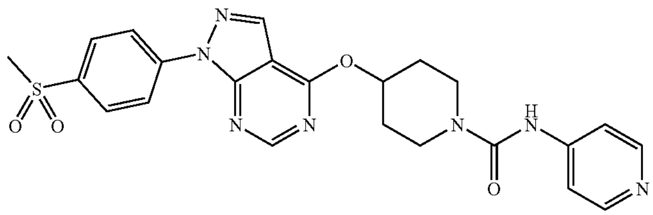 | 4-[1-(4-Methanesulfonyl-phenyl)-1H-pyrazolo[3,4-d]pyrimidin-4-yloxy]-piperidine-1-carbothioic acid pyridin-4-ylamide |
| A42 | 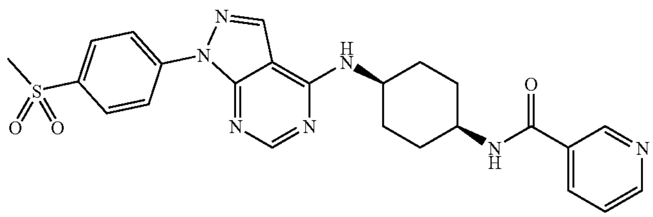 | N-{4-[1-(4-Methanesulfonyl-phenyl)-1H-pyrazolo[3,4-d]pyrimidin-4-ylamino]-cyclohexyl}-nicotinamide |
| A43 | 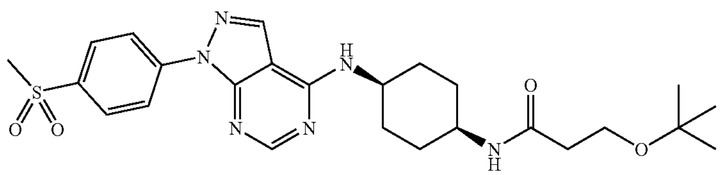 | 3-tert-Butoxy-N-{4-[1-(4-methanesulfonyl-phenyl)-1H-pyrazolo[3,4-d]pyrimidin-4-ylamino]-cyclohexyl}-propionamide |
| A44 | 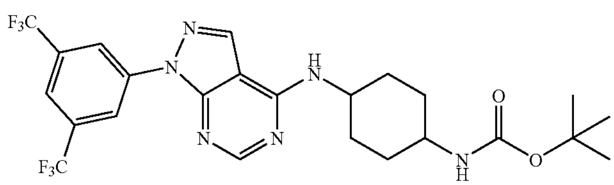 | {4-[1-(3,5-Bis-trifluoromethyl-phenyl)-1H-pyrazolo[3,4-d]pyrimidin-4-ylamino]-cyclohexyl}-carbamic acid tert-butyl ester |
| A45 | 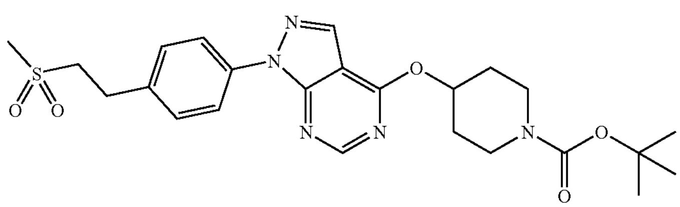 | 4-{1-[4-(2-Methanesulfonyl-ethyl)-phenyl]-1H-pyrazolo[3,4-d]pyrimidin-4-yloxy}-piperidine-1-carboxylic acid tert-butyl ester |
| A46 | 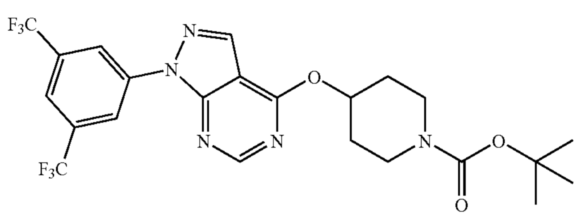 | 4-[1-(3,5-Bis-trifluoromethyl-phenyl)-1H-pyrazolo[3,4-d]pyrimidin-4-yloxy]-piperidine-1-carboxylic acid tert-butyl ester |
| A47 | 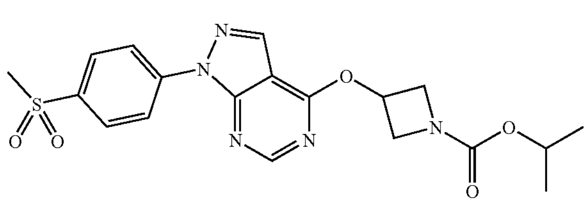 | 3-[1-(4-Methanesulfonyl-phenyl)-1H-pyrazolo[3,4-d]pyrimidin-4-yloxy]-azetidine-1-carboxylic acid isopropyl ester |

TABLE A-continued

| Cmpd# | Structure | Chemical Name |
|---|---|---|
| A48 | 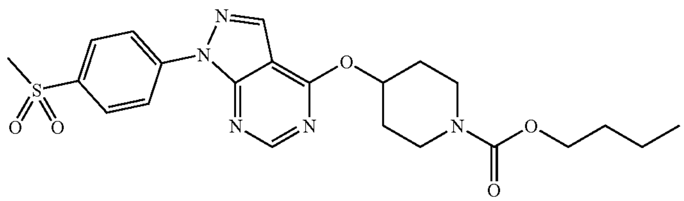 | 4-[1-(4-Methanesulfonyl-phenyl)-1H-pyrazolo[3,4-d]pyrimidin-4-yloxy]-piperidine-1-carboxylic acid butyl ester |
| A49 | 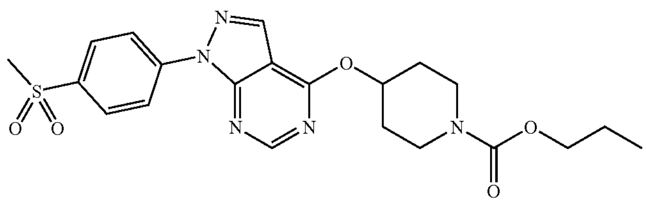 | 4-[1-(4-Methanesulfonyl-phenyl)-1H-pyrazolo[3,4-d]pyrimidin-4-yloxy]-piperidine-1-carboxylic acid propyl ester |
| A50 | 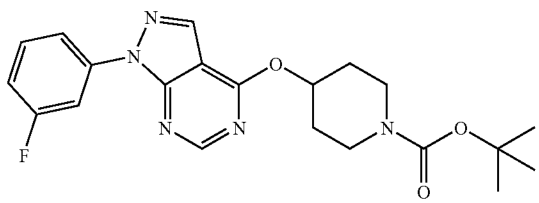 | 4-[1-(3-Fluoro-phenyl)-1H-pyrazolo[3,4-d]pyrimidin-4-yloxy]-piperidine-1-carboxylic acid tert butyl ester |
| A51 | 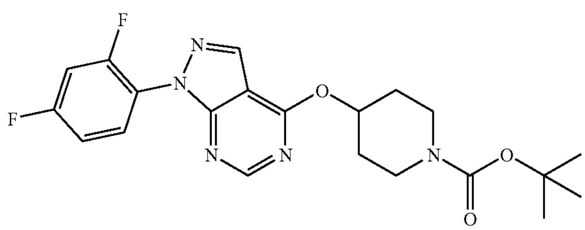 | 4-[1-(2,4-Difluoro-phenyl)-1H-pyrazolo[3,4-d]pyrimidin-4-yloxy]-piperidine-1-carboxylic acid tert-butyl ester |
| A52 | 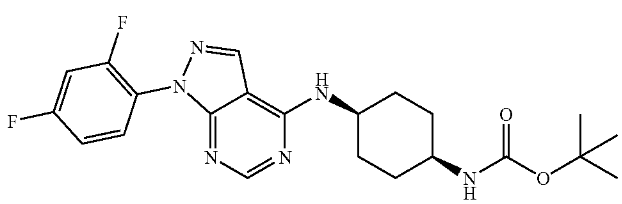 | {4-[1-(2,4-Difluoro-phenyl)-1H-pyrazolo[3,4-d]pyrimidin-4-ylamino]-cyclohexyl}-carbamic acid tert-butyl ester |
| A53 | 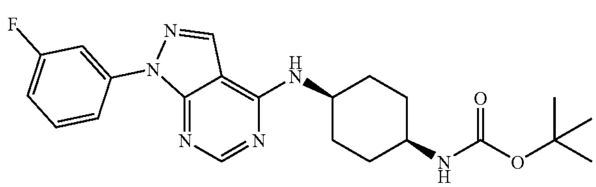 | {4-[1-(3-Fluoro-phenyl)-1H-pyrazolo[3,4-d]pyrimidin-4-ylamino]-cyclohexyl}-carbamic acid tert-butyl ester |
| A54 | 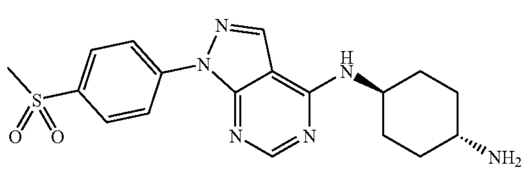 | N-[1-(4-Methanesulfonyl-phenyl)-1H-pyrazolo[3,4-d]pyrimidin-4-yl]-cyclohexane-1,4-diamine |
| A55 | 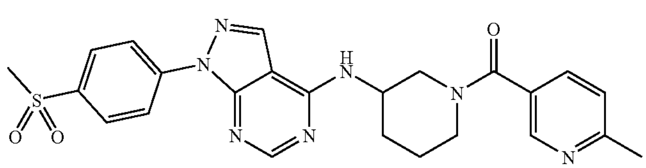 | {3-[1-(4-Methanesulfonyl-phenyl)-1H-pyrazolo[3,4-d]pyrimidin-4-ylamino]-piperidin-1-yl}-(6-methyl-pyridin-3-yl)-methanone |

TABLE A-continued

| Cmpd# | Structure | Chemical Name |
|---|---|---|
| A56 | 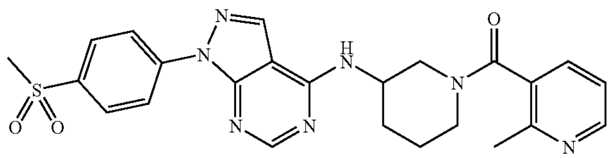 | {3-[1-(4-Methanesulfonyl-phenyl)-1H-pyrazolo[3,4-d]pyrimidin-4-ylamino]-piperidin-1-yl}-(2-methyl-pyridin-3-yl)-methanone |
| A57 | 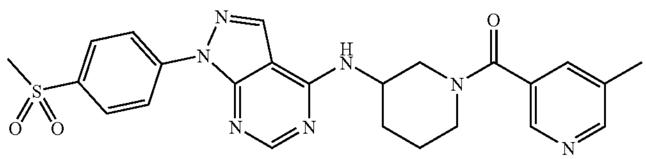 | {3-[1-(4-Methanesulfonyl-phenyl)-1H-pyrazolo[3,4-d]pyrimidin-4-ylamino]-piperidin-1-yl}-(5-methyl-pyridin-3-yl)-methanone |
| A58 | 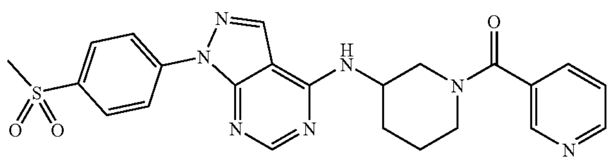 | {3-[1-(4-Methanesulfonyl-phenyl)-1H-pyrazolo[3,4-d]pyrimidin-4-ylamino]-piperidin-1-yl}-pyridin-3-yl-methanone |
| A59 | 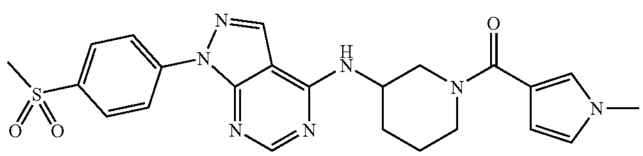 | {3-[1-(4-Methanesulfonyl-phenyl)-1H-pyrazolo[3,4-d]pyrimidin-4-ylamino]-piperidin-1-yl}-(1-methyl-1H-pyrrol-3-yl)-methanone |
| A60 | 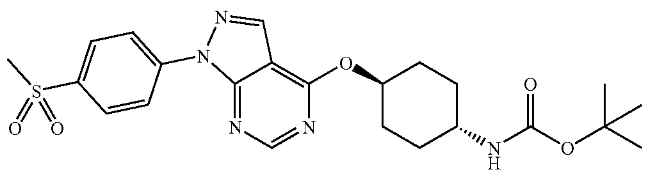 | {4-[1-(4-Methanesulfonyl-phenyl)-1H-pyrazolo[3,4-d]pyrimidin-4-yloxy]-cyclohexyl}-carbamic acid tert-butyl ester |
| A61 | 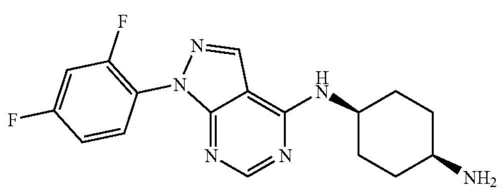 | N-[1-(2,4-Difluoro-phenyl)-1H-pyrazolo[3,4-d]pyrimidin-4-yl]-cyclohexane-1,4-diamine |
| A62 | 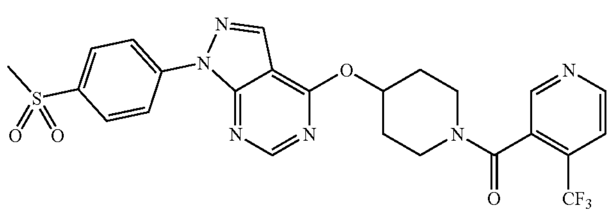 | {4-[1-(4-Methanesulfonyl-phenyl)-1H-pyrazolo[3,4-d]pyrimidin-4-yloxy]-piperidin-1-yl}-(4-trifluoromethyl-pyridin-3-yl)-methanone |
| A63 | 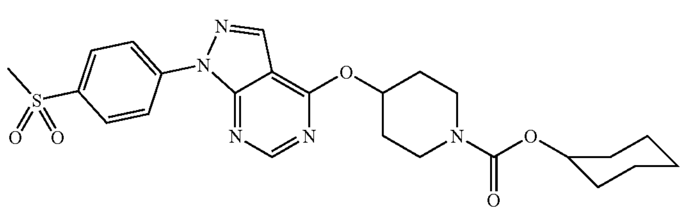 | 4-[1-(4-Methanesulfonyl-phenyl)-1H-pyrazolo[3,4-d]pyrimidin-4-yloxy]-piperidine-1-carboxylic acid cyclohexyl ester |

TABLE A-continued

| Cmpd# | Structure | Chemical Name |
|---|---|---|
| A64 | 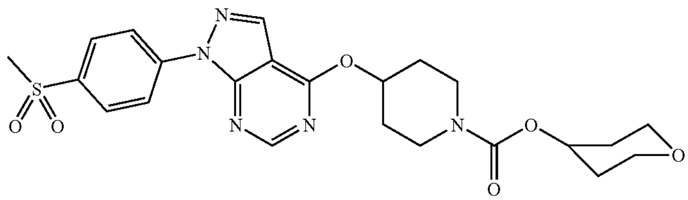 | 4-[1-(4-Methanesulfonyl-phenyl)-1H-pyrazolo[3,4-d]pyrimidin-4-yloxy]-piperidine-1-carboxylic acid tetrahydro-pyran-4-yl ester |
| A65 | 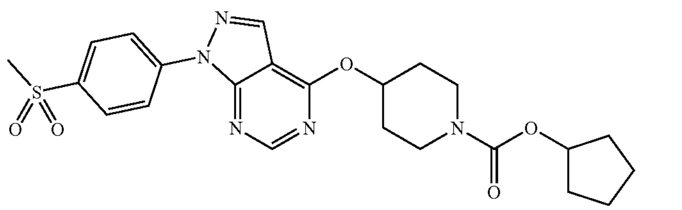 | 4-[1-(4-Methanesulfonyl-phenyl)-1H-pyrazolo[3,4-d]pyrimidin-4-yloxy]-piperidine-1-carboxylic acid cyclopentyl ester |
| A66 | 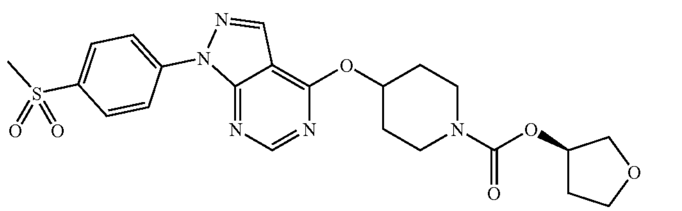 | 4-[1-(4-Methanesulfonyl-phenyl)-1H-pyrazolo[3,4-d]pyrimidin-4-yloxy]-piperidine-1-carboxylic acid tetrahydro-furan-3-yl ester |
| A67 | 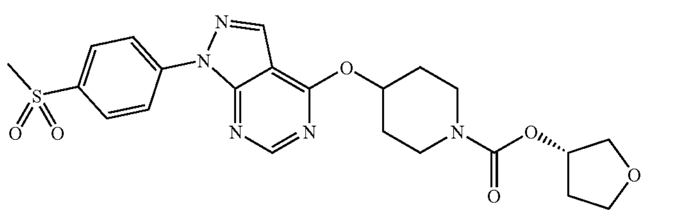 | 4-[1-(4-Methanesulfonyl-phenyl)-1H-pyrazolo[3,4-d]pyrimidin-4-yloxy]-piperidine-1-carboxylic acid tetrahydro-furan-3-yl ester |
| A68 | 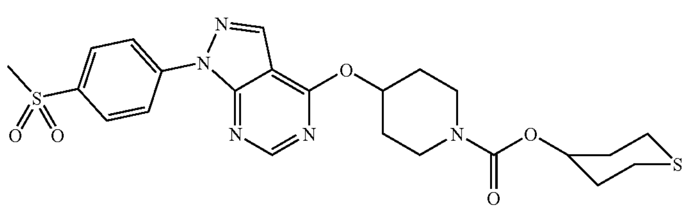 | 4-[1-(4-Methanesulfonyl-phenyl)-1H-pyrazolo[3,4-d]pyrimidin-4-yloxy]-piperidine-1-carboxylic acid tetrahydro-thiopyran-4-yl ester |
| A69 | 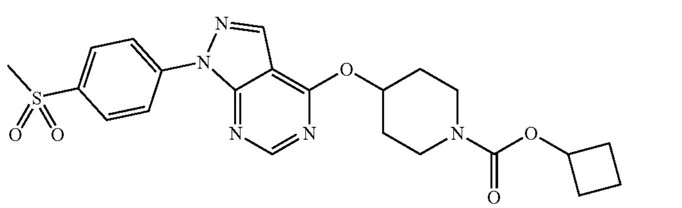 | 4-[1-(4-Methanesulfonyl-phenyl)-1H-pyrazolo[3,4-d]pyrimidin-4-yloxy]-piperidine-1-carboxylic acid cyclobutyl ester |
| A70 | 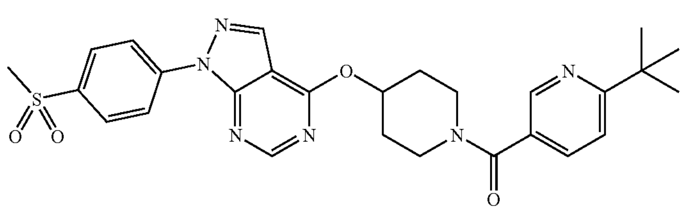 | (6-tert-Butyl-pyridin-3-yl)-{4-[1-(4-methanesulfonyl-phenyl)-1H-pyrazolo[3,4-d]pyrimidin-4-yloxy]-piperidin-1-yl}-methanone |

TABLE A-continued

| Cmpd# | Structure | Chemical Name |
|---|---|---|
| A71 | 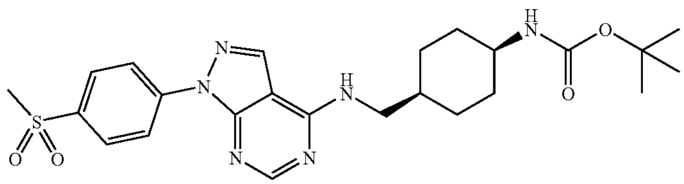 | (4-{[1-(4-Methanesulfonyl-phenyl)-1H-pyrazolo[3,4-d]pyrimidin-4-ylamino]-methyl}-cyclohexyl)-carbamic acid tert-butyl ester |
| A72 | 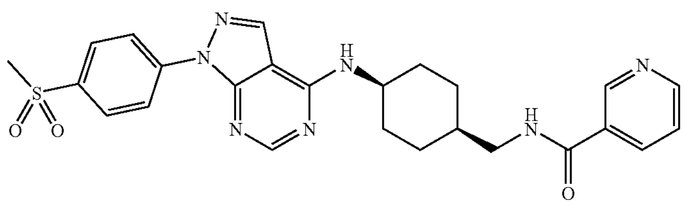 | N-{4-[1-(4-Methanesulfonyl-phenyl)-1H-pyrazolo[3,4-d]pyrimidin-4-ylamino]-cyclohexylmethyl}-nicotinamide |
| A73 | 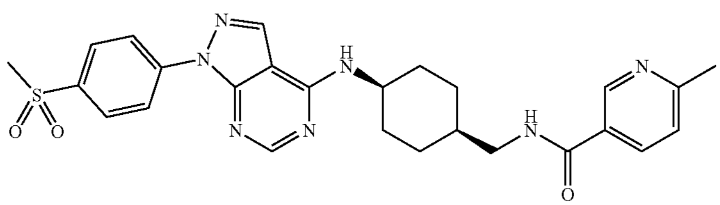 | N-{4-[1-(4-Methanesulfonyl-phenyl)-1H-pyrazolo[3,4-d]pyrimidin-4-ylamino]-cyclohexylmethyl}-6-methyl-nicotinamide |
| A74 | 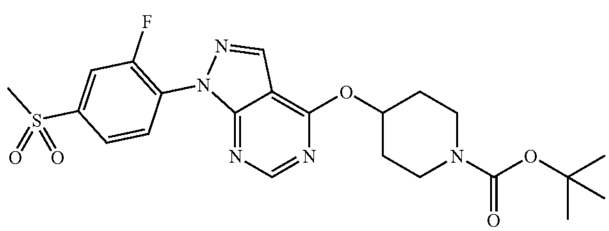 | 4-[1-(2-Fluoro-4-methanesulfonyl-phenyl)-1H-pyrazolo[3,4-d]pyrimidin-4-yloxy]-piperidine-1-carboxylic acid tert-butyl ester |
| A75 | 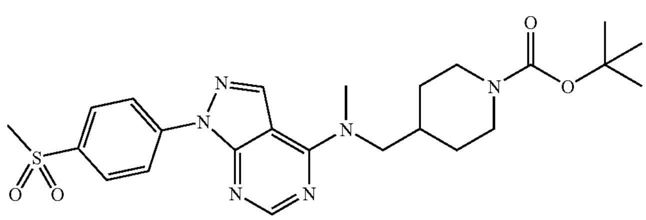 | 4-({[1-(4-Methanesulfonyl-phenyl)-1H-pyrazolo[3,4-d]pyrimidin-4-yl]-methyl-amino}-methyl)-piperidine-1-carboxylic acid tert-butyl ester |
| A76 | 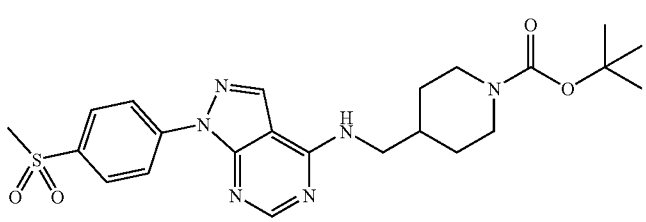 | 4-{[1-(4-Methanesulfonyl-phenyl)-H-pyrazolo[3,4-d]pyrimidin-4-ylamino]-methyl}-piperidine-1-carboxylic acid tert-butyl ester |
| A77 | 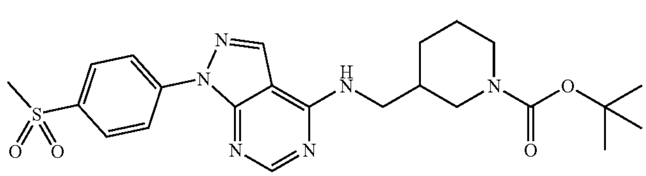 | 3-{[1-(4-Methanesulfonyl-phenyl)-1H-pyrazolo[3,4-d]pyrimidin-4-ylamino]-methyl}-piperidine-1-carboxylic acid tert-butyl ester |

TABLE A-continued

| Cmpd# | Structure | Chemical Name |
|---|---|---|
| A78 | 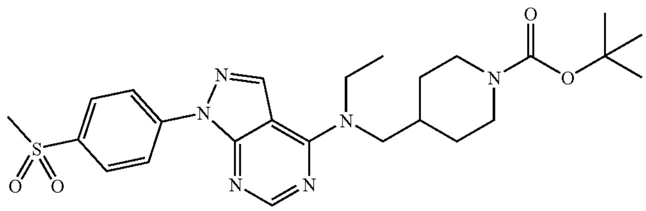 | 4-({Ethyl-[1-(4-methanesulfonyl-phenyl)-1H-pyrazolo[3,4-d]pyrimidin-4-yl]-amino}-methyl)-piperidine-1-carboxylic acid tert butyl ester |
| A79 | 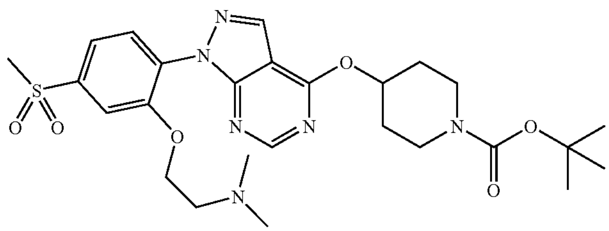 | 4-{1-[2-(2-Dimethylamino-ethoxy)-4-methanesulfonyl-phenyl]-1H-pyrazolo[3,4-d]pyrimidin-4-yloxy}-piperidine-1-carboxylic acid tert butyl ester |
| A80 | 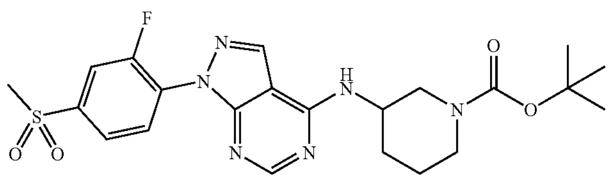 | 3-[1-(2-Fluoro-4-methanesulfonyl-phenyl)-1H-pyrazolo[3,4-d]pyrimidin-4-ylamino]-piperidine-1-carboxylic acid tert-butyl ester |
| A81 | 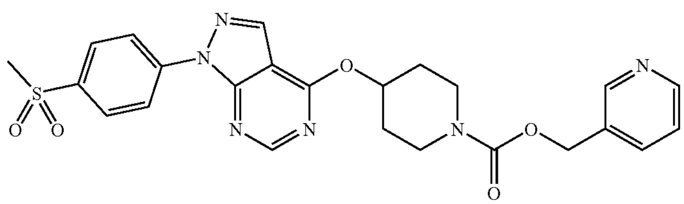 | 4-[1-(4-Methanesulfonyl-phenyl)-1H-pyrazolo[3,4-d]pyrimidin-4-yloxy]-piperidine-1-carboxylic acid pyridin-3-ylmethyl ester |
| A82 | 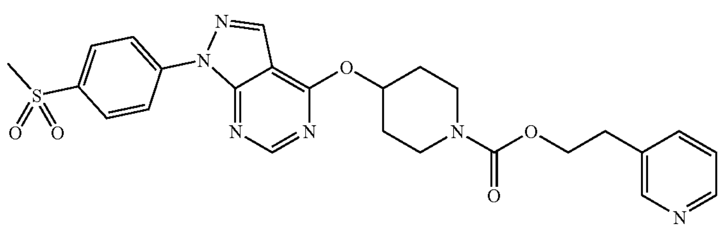 | 4-[1-(4-Methanesulfonyl-phenyl)-1H-pyrazolo[3,4-d]pyrimidin-4-yloxy]-piperidine-1-carboxylic acid 2-pyridin-3-yl-ethyl ester |
| A83 | 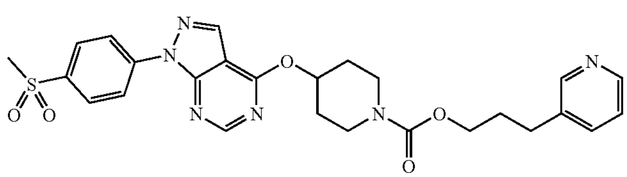 | 4-[1-(4-Methanesulfonyl-phenyl)-1H-pyrazolo[3,4-d]pyrimidin-4-yloxy]-piperidine-1-carboxylic acid 3-pyridin-3-yl-propyl ester |
| A84 | 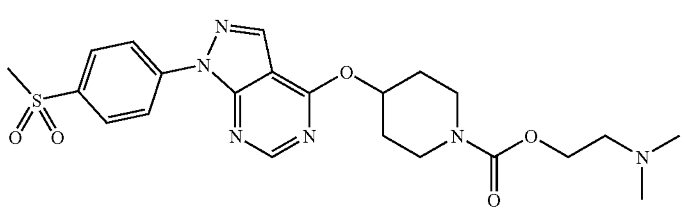 | 4-[1-(4-Methanesulfonyl-phenyl)-1H-pyrazolo[3,4-d]pyrimidin-4-yloxy]-piperidine-1-carboxylic acid 2-dimethylamino-ethyl ester |

TABLE A-continued

| Cmpd# | Structure | Chemical Name |
|---|---|---|
| A85 | 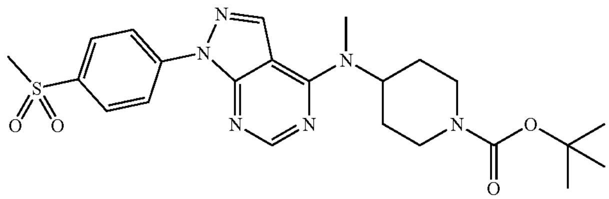 | 4-{[1-(4-Methanesulfonyl-phenyl)-1H-pyrazolo[3,4-d]pyrimidin-4-yl]-methyl-amino}-piperidine-1-carboxylic acid tert-butyl ester |
| A86 | 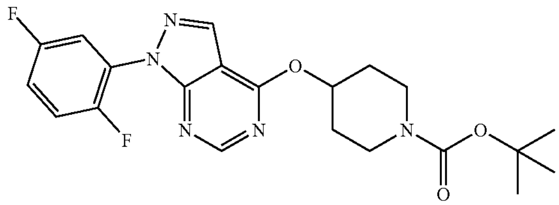 | 4-[1-(2,5-Difluoro-phenyl)-1H-pyrazolo[3,4-d]pyrimidin-4-yloxy]-piperidine-1-carboxylic acid tert-butyl ester |
| A87 | 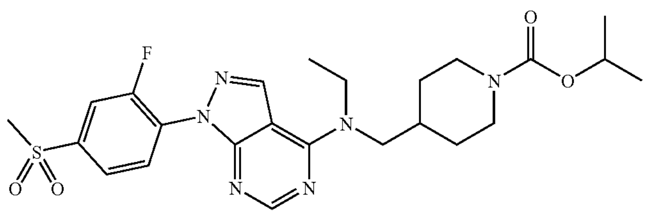 | 4-({Ethyl-[1-(2-fluoro-4-methanesulfonyl-phenyl)-1H-pyrazolo[3,4-d]pyrimidin-4-yl]-amino}-methyl)-piperidine-1-carboxylic acid isopropyl ester |
| A88 | 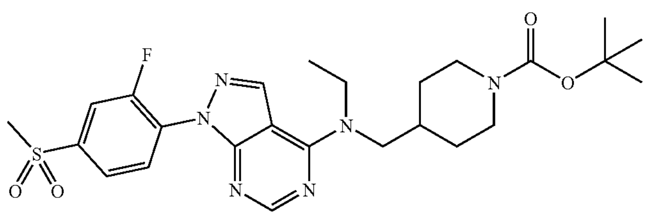 | 4-({Ethyl-[1-(2-fluoro-4-methanesulfonyl-phenyl)-1H-pyrazolo[3,4-d]pyrimidin-4-yl]-amino}-methyl)-piperidine-1-carboxylic acid tert-butyl ester |
| A89 | 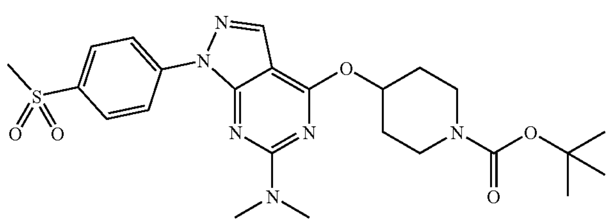 | 4-[6-Dimethylamino-1-(4-methanesulfonyl-phenyl)-1H-pyrazolo[3,4-d]pyrimidin-4-yloxy]-piperidine-1-carboxylic acid tert-butyl ester |
| A90 | 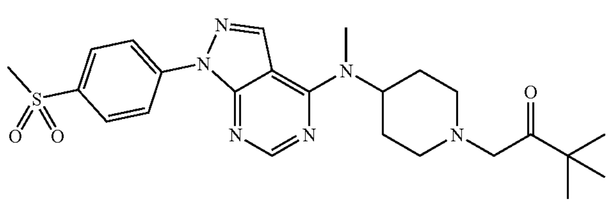 | 1-(4-{[1-(4-Methanesulfonyl-phenyl)-1H-pyrazolo[3,4-d]pyrimidin-4-yl]-methyl-amino}-piperidin-1-yl)-3,3-dimethyl-butan-2-one |
| A91 | 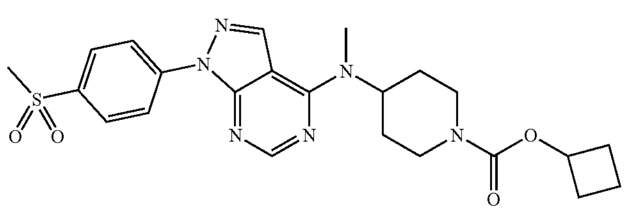 | 4-{[1-(4-Methanesulfonyl-phenyl)-1H-pyrazolo[3,4-d]pyrimidin-4-yl]-methyl-amino}-piperidine-1-carboxylic acid cyclobutyl ester |

TABLE A-continued

| Cmpd# | Structure | Chemical Name |
|---|---|---|
| A92 | 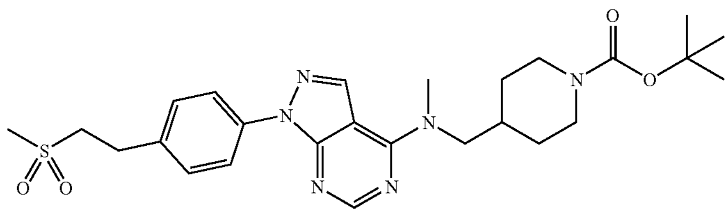 | 4-[({1-[4-(2-Methanesulfonyl-ethyl)-phenyl]-1H-pyrazolo[3,4-d]pyrimidin-4-yl}-methyl-amino)-methyl]-piperidine-1-carboxylic acid tert-butyl ester |
| A93 | 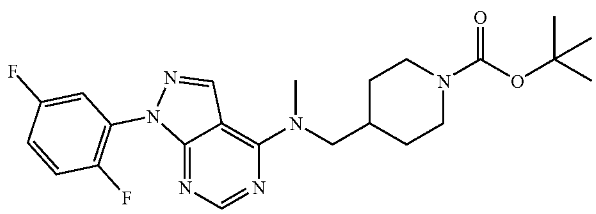 | 4-({[1-(2,5-Difluoro-phenyl)-1H-pyrazolo[3,4-d]pyrimidin-4-yl]-methyl-amino}-methyl)-piperidine-1-carboxylic acid tert-butyl ester |
| A94 | 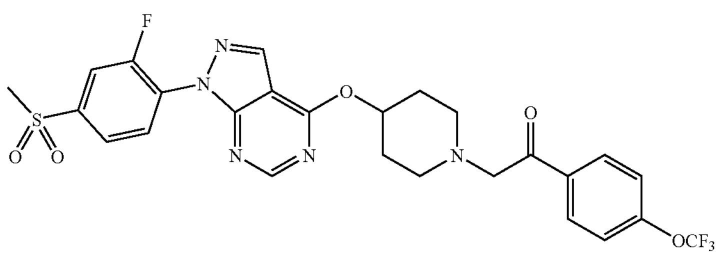 | 2-{4-[1-(2-Fluoro-4-methanesulfonyl-phenyl)-1H-pyrazolo[3,4-d]pyrimidin-4-yloxy]-piperidin-1-yl}-1-(4-trifluoromethoxy-phenyl)-ethanone |
| A95 | 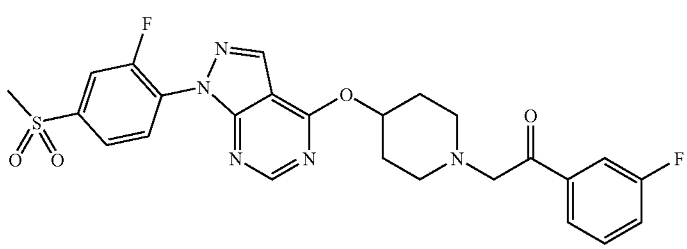 | 2-{4-[1-(2-Fluoro-4-methanesulfonyl-phenyl)-1H-pyrazolo[3,4-d]pyrimidin-4-yloxy]-piperidin-1-yl}-1-(3-fluoro-phenyl)-ethanone |
| A96 | 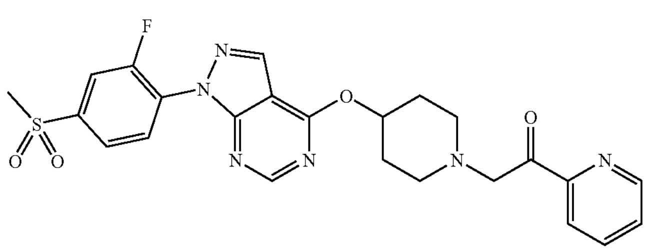 | 2-{4-[1-(2-Fluoro-4-methanesulfonyl-phenyl)-1H-pyrazolo[3,4-d]pyrimidin-4-yloxy]-piperidin-1-yl}-1-pyridin-2-yl-ethanone |
| A97 | 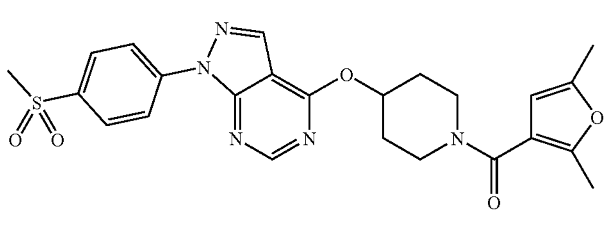 | (2,5-Dimethyl-furan-3-yl)-{4-[1-(4-methanesulfonyl-phenyl)-1H-pyrazolo[3,4-d]pyrimidin-4-yloxy]-piperidin-1-yl}-methanone |

TABLE A-continued

| Cmpd# | Structure | Chemical Name |
|---|---|---|
| A98 | 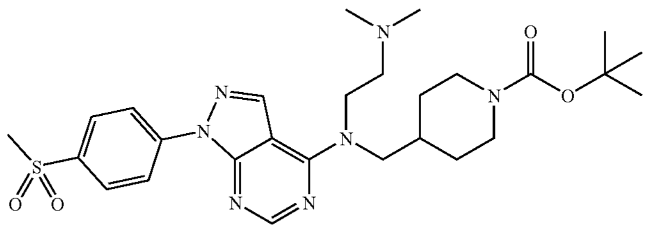 | 4-({(2-Dimethylamino-ethyl)-[1-(4-methanesulfonyl-phenyl)-1H-pyrazolo[3,4-d]pyrimidin-4-yl]-amino}-methyl)-piperidine-1-carboxylic acid tert-butyl ester |
| A99 | 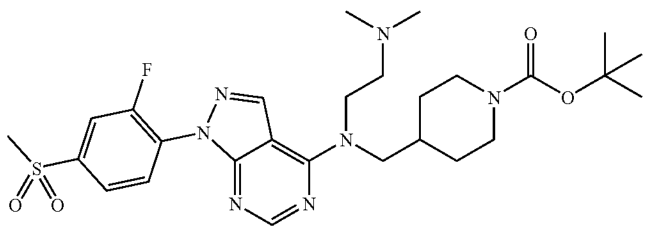 | 4-({(2-Dimethylamino-ethyl)-[1-(2-fluoro-4-methanesulfonyl-phenyl)-1H-pyrazolo[3,4-d]pyrimidin-4-yl]-amino}-methyl)-piperidine-1-carboxylic acid tert-butyl ester |
| A100 | 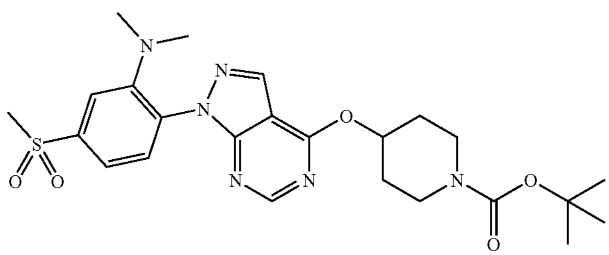 | 4-[1-(2-Dimethylamino-4-methanesulfonyl-phenyl)-1H-pyrazolo[3,4-d]pyrimidin-4-yloxy]-piperidine-1-carboxylic tert-butyl ester |
| A101 | 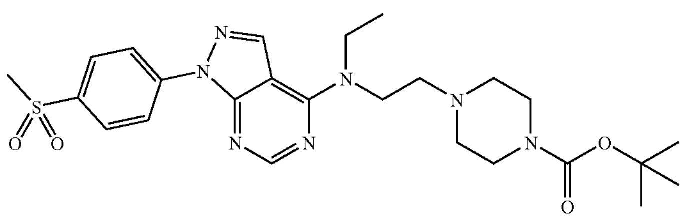 | 4-(2-{Ethyl-[1-(4-methanesulfonyl-phenyl)-1H-pyrazolo[3,4-d]pyrimidin-4-yl]-amino}-ethyl)-piperazine-1-carboxylic acid tert-butyl ester |
| A102 | 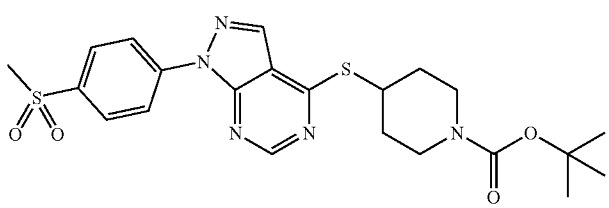 | 4-[1-(4-Methanesulfonyl-phenyl)-1H-pyrazolo[3,4-d]pyrimidin-4-ylsulfanyl]-piperidine-1-carboxylic acid tert-butyl ester |
| A103 | 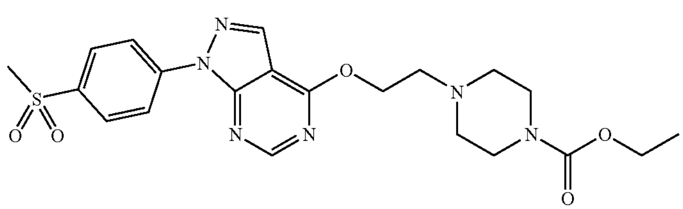 | 4-{2-[1-(4-Methanesulfonyl-phenyl)-1H-pyrazolo[3,4-d]pyrimidin-4-yloxy]-ethyl}-piperazine-1-carboxylic acid ethyl ester |
| A104 | 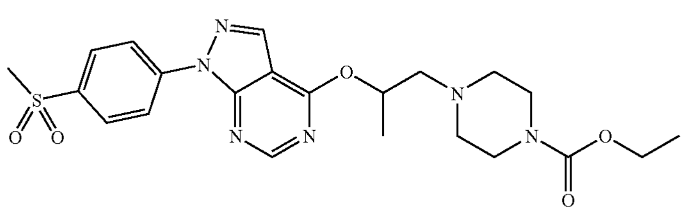 | 4-{2-[1-(4-Methanesulfonyl-phenyl)-1H-pyrazolo[3,4-d]pyrimidin-4-yloxy]-propyl}-piperazine-1-carboxylic acid ethyl ester |

TABLE A-continued

| Cmpd# | Structure | Chemical Name |
|---|---|---|
| A105 | 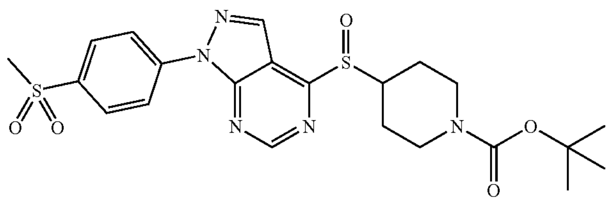 | 4-[1-(4-Methanesulfonyl-phenyl)-1H-pyrazolo[3,4-d]pyrimidine-4-sulfinyl]-piperidine-1-carboxylic acid tert-butyl ester |
| A106 | 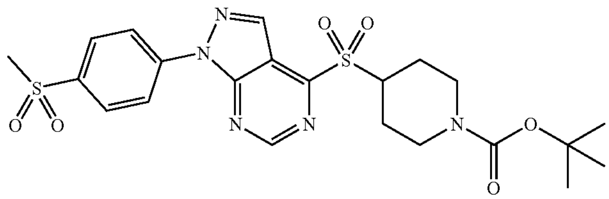 | 4-[1-(4-Methanesulfonyl-phenyl)-1H-pyrazolo[3,4-d]pyrimidine-4-sulfonyl]-piperidine-1-carboxylic acid tert-butyl ester |
| A107 | 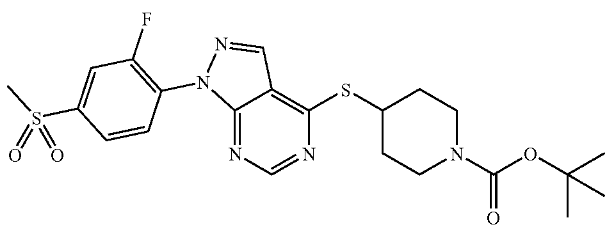 | 4-[1-(2-Fluoro-4-methanesulfonyl-phenyl)-1H-pyrazolo[3,4-d]pyrimidin-4-ylsulfanyl]-piperidine-1-carboxylic acid tert-butyl ester |
| A108 | 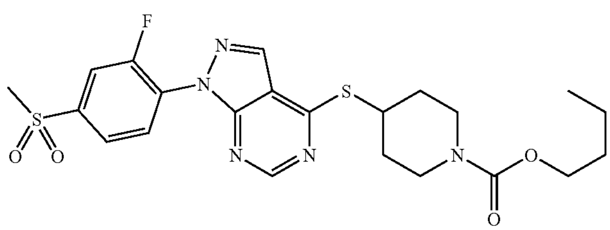 | 4-[1-(2-Fluoro-4-methanesulfonyl-phenyl)-1H-pyrazolo[3,4-d]pyrimidin-4-ylsulfanyl]-piperidine-1-carboxylic acid butyl ester |
| A109 | 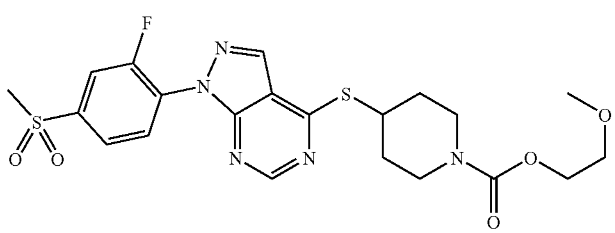 | 4-[1-(2-Fluoro-4-methanesulfonyl-phenyl)-1H-pyrazolo[3,4-d]pyrimidin-4-ylsulfanyl]-piperidine-1-carobyxlic acid 2-methoxy-ethyl ester |
| A110 | 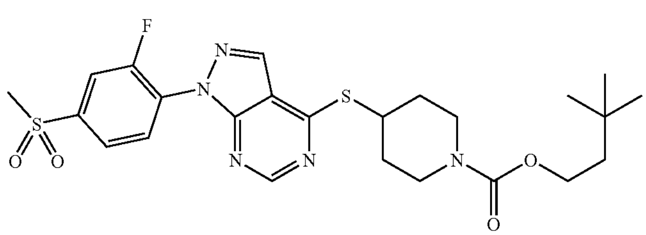 | 4-[1-(2-Fluoro-4-methanesulfonyl-phenyl)-1H-pyrazolo[3,4-d]pynimidin-4-ylsulfanyl]-piperidine-1-carboxylic acid 3,3-dimethyl-butyl ester |
| A111 | 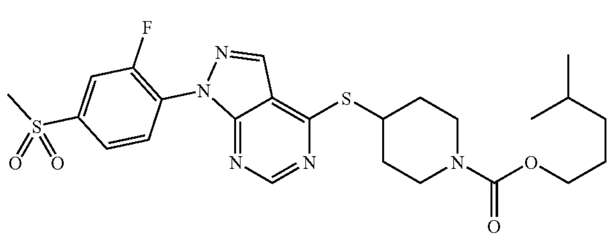 | 4-[1-(2-Fluoro-4-methanesulfonyl-phenyl)-1H-pyrazolo[3,4-d]pynimidin-4-ylsulfanyl]-piperidine-1-carboxylic acid 4-methyl-pentyl ester |

TABLE A-continued

| Cmpd# | Structure | Chemical Name |
|---|---|---|
| A112 | 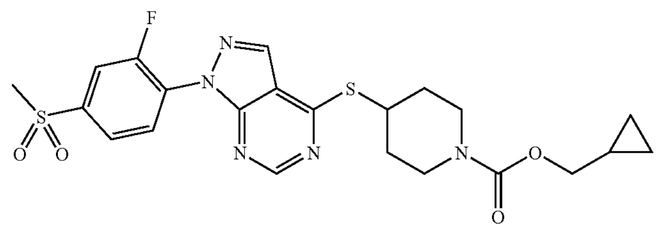 | 4-[1-(2-Fluoro-4-methanesulfonyl-phenyl)-1H-pyrazolo[3,4-d]pyrimidin-4-ylsulfanyl]-piperidine-1-carboxylic acid cyclopropylmethyl ester |
| A113 | 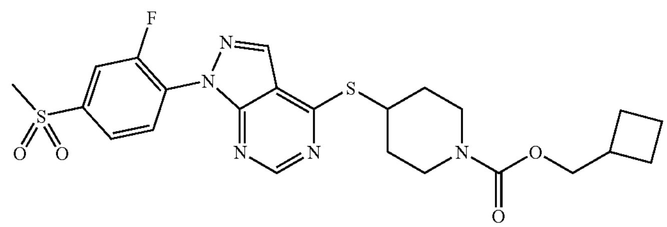 | 4-[1-(2-Fluoro-4-methanesulfonyl-phenyl)-1H-pyrazolo[3,4-d]pyrimidin-4-ylsulfanyl]-piperidine-1-carboxylic acid cyclobutylmethyl ester |
| A114 | 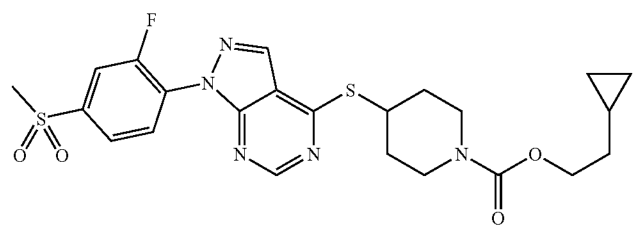 | 4-[1-(2-Fluoro-4-methanesulfonyl-phenyl)-1H-pyrazolo[3,4-d]pyrimidin-4-ylsulfanyl]-piperidine-1-carboxylic acid 2-cyclopropyl-ethyl ester |
| A115 | 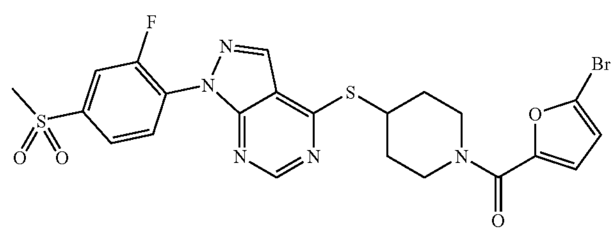 | (5-Bromo-furan-2-yl)-{4-[1-(2-fluoro-4-methanesulfonyl-phenyl)-1H-pyrazolo[3,4-d]pyrimidin-4-ylsulfanyl]-piperidin-1-yl}-methanone |
| A116 | 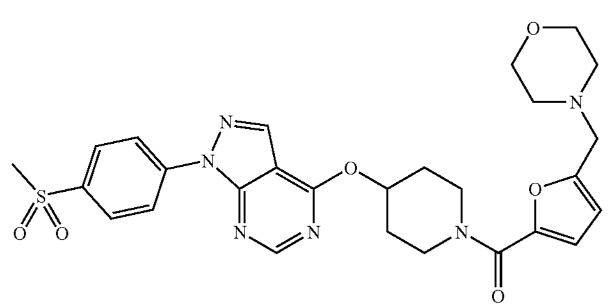 | {4-[1-(4-Methanesulfonyl-phenyl)-1H-pyrazolo[3,4-d]pyrimidin-4-yloxy]-piperidin-1-yl}-(5-morpholin-4-ylmethyl-furan-2-yl)-methanone |
| A117 | 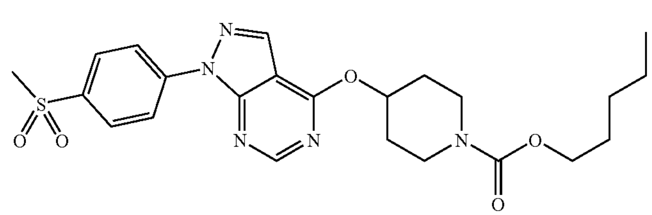 | 4-[1-(4-Methanesulfonyl-phenyl)-1H-pyrazolo[3,4-d]pyrimidin-4-yloxy]-piperidine-1-carboxylic acid pentyl ester |

TABLE A-continued

| Cmpd# | Structure | Chemical Name |
|---|---|---|
| A118 | 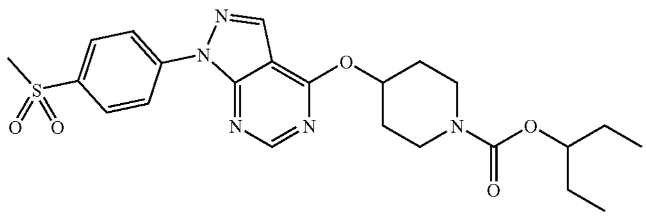 | 4-[1-(4-Methanesulfonyl-phenyl)-1H-pyrazolo[3,4-d]pyrimidin-4-yloxy]-piperidine-1-carboxylic acid 1-ethyl-propyl ester |
| A119 | 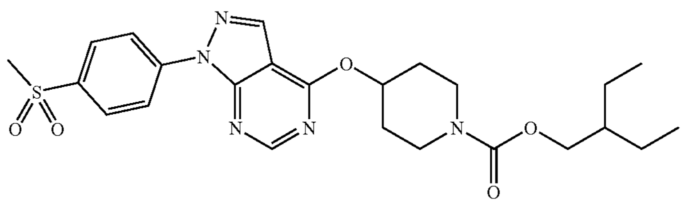 | 4-[1-(4-Methanesulfonyl-phenyl)-1H-pyrazolo[3,4-d]pyrimidin-4-yloxy]-piperidine-1-carboxylic acid 2-ethyl-butyl ester |
| A120 | 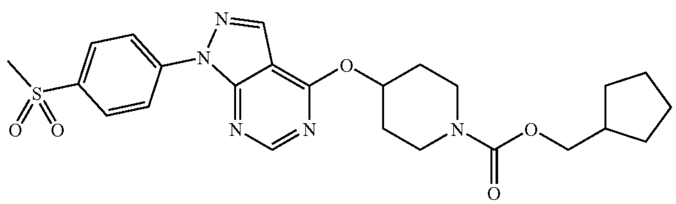 | 4-[1-(4-Methanesulfonyl-phenyl)-1H-pyrazolo[3,4-d]pyrimidin-4-yloxy]-piperidine-1-carboxylic acid cyclopentylmethyl ester |
| A121 | 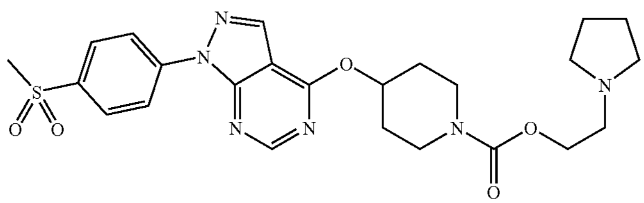 | 4-[1-(4-Methanesulfonyl-phenyl)-1H-pyrazolo[3,4-d]pyrimidin-4-yloxy]-piperidine-1-carboxylic acid 2-pyrrolidin-1-yl-ethyl ester |
| A122 | 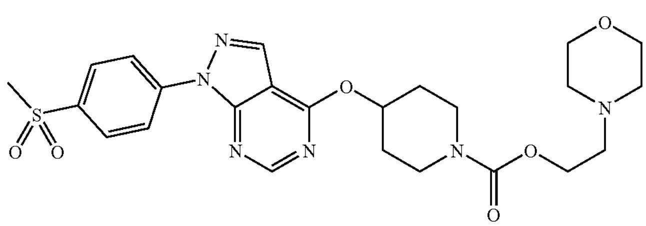 | 4-[1-(4-Methanesulfonyl-phenyl)-1H-pyrazolo[3,4-d]pyrimidin-4-yloxy]-piperidine-1-carboxylic acid 2-morpholin-4-yl-ethyl ester |
| A123 | 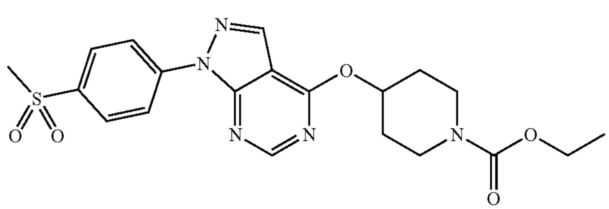 | 4-[1-(4-Methanesulfonyl-phenyl)-1H-pyrazolo[3,4-d]pyrimidin-4-yloxy]-piperidine-1-carboxylic acid ethyl ester |
| A124 | 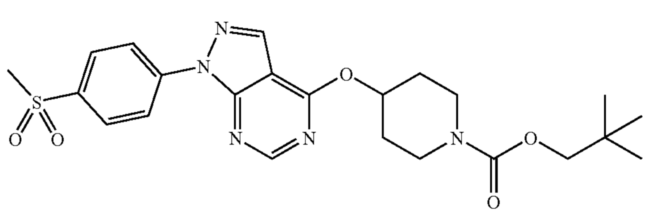 | 4-[1-(4-Methanesulfonyl-phenyl)-1H-pyrazolo[3,4-d]pyrimidin-4-yloxy]-piperidine-1-carboxylic acid 2,2-dimethyl-propyl ester |

TABLE A-continued

| Cmpd# | Structure | Chemical Name |
| --- | --- | --- |
| A125 | 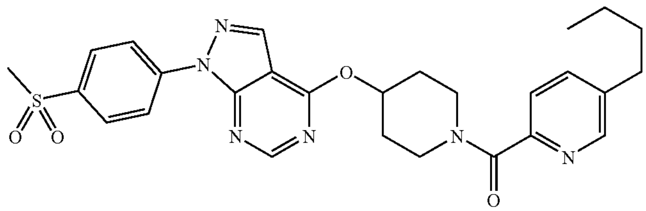 | (5-Butyl-pyridin-2-yl)-{4-[1-(4-methanesulfonyl-phenyl)-1H-pyrazolo[3,4-d]pyrimidin-4-yloxy]-piperidin-1-yl}-methanone |
| A126 | 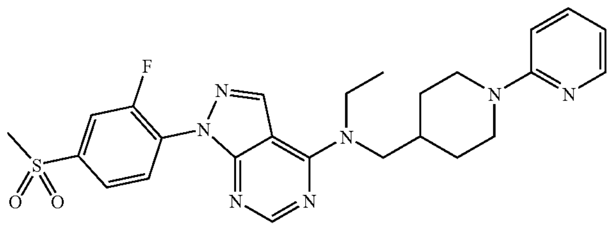 | Ethyl-[1-(2-fluoro-4-methanesulfonyl-phenyl)-1H-pyrazolo[3,4-d]pyrimidin-4-yl]-(3,4,5,6-tetrahydro-2H-[1,2']bipyridinyl-4-ylmethyl)-amine |
| A127 | 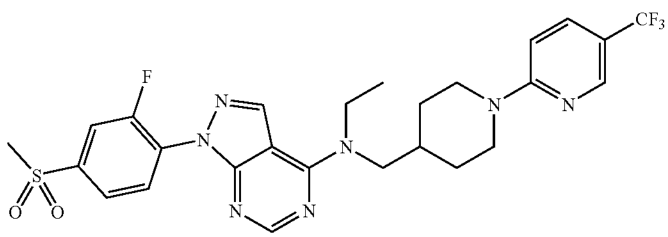 | Ethyl-[1-(2-fluoro-4-methanesulfonyl-phenyl)-1H-pyrazolo[3,4-d]pyrimidin-4-yl]-(5'-trifluoromethyl-3,4,5,6-tetrahydro-2H-[1,2']bipyridinyl-4-ylmethyl)-amine |
| A128 | 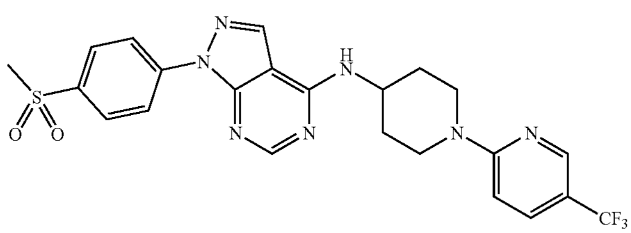 | [1-(4-Methanesulfonyl-phenyl)-1H-pyrazolo[3,4-d]pyrimidin-4-yl]-(5'-trifluoromethyl-3,4,5,6-tetrahydro-2H-[1,2']bipyridinyl-4-yl)-amine |
| A129 | 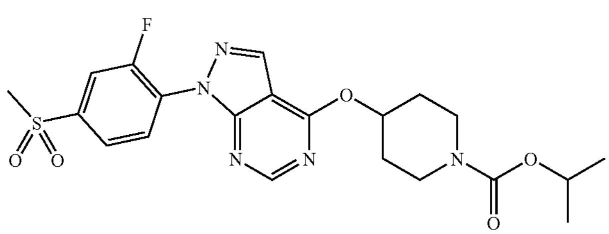 | 4-[1-(2-Fluoro-4-methanesulfonyl-phenyl)-1H-pyrazolo[3,4-d]pyrimidin-4-yloxy]-piperidine-1-carboxylic acid isopropyl ester |
| A130 | 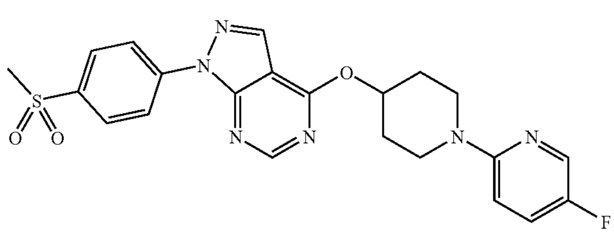 | 5'-Fluoro-4-[1-(4-methanesulfonyl-phenyl)-1H-pyrazolo[3,4-d]pyrimidin-4-yloxy]-3,4,5,6-tetrahydro-2H-[1,2']bipyridinyl |

TABLE A-continued

| Cmpd# | Structure | Chemical Name |
|---|---|---|
| A131 | 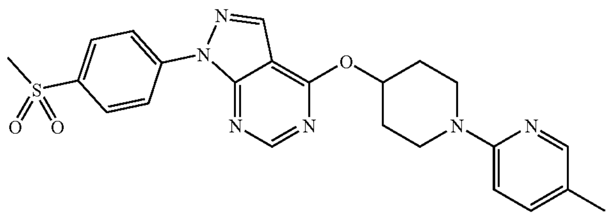 | 4-[1-(4-Methanesulfonyl-phenyl)-1H-pyrazolo[3,4-d]pyrimidin-4-yloxy]-5'-methyl-3,4,5,6-tetrahydro-2H-[1,2']bipyridinyl |
| A132 | 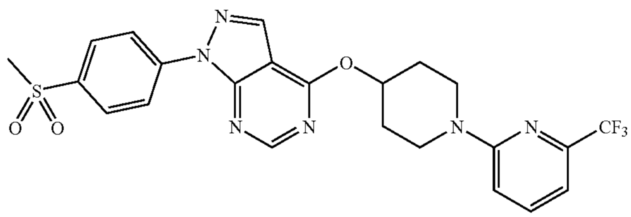 | 4-[1-(4-Methanesulfonyl-phenyl)-1H-pyrazolo[3,4-d]pyrimidin-4-yloxy]-6'-trifluoromethyl-3,4,5,6-tetrahydro-2H-[1,2']bipyridinyl |
| A133 | 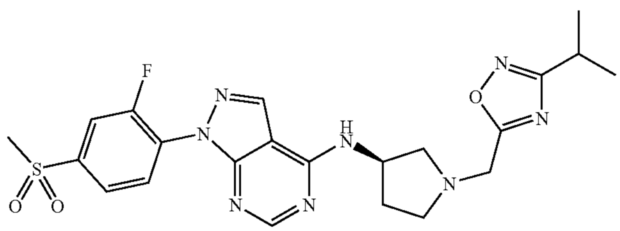 | [1-(2-Fluoro-4-methanesulfonyl-phenyl)-1H-pyrazolo[3,4-d]pyrimidin-4-yl]-[1-(3-isopropyl-[1,2,4]oxadiazol-5-ylmethyl)-pyrrolidin-3-yl]-amine |
| A134 | 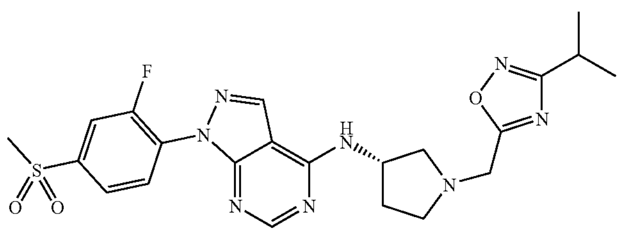 | [1-(2-Fluoro-4-methanesulfonyl-phenyl)-1H-pyrazolo[3,4-d]pyrimidin-4-yl]-[1-(3-isopropyl-[1,2,4]oxadiazol-5-ylmethyl)-pyrrolidin-3-yl]-amine |
| A135 | 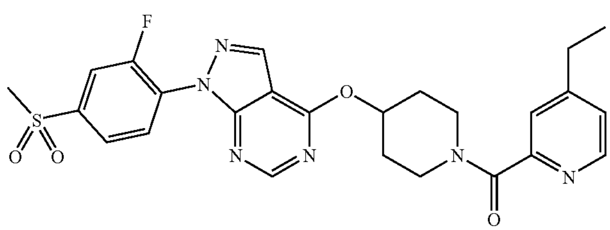 | (4-Ethyl-pyridin-2-yl)-{4-[1-(2-fluoro-4-methanesulfonyl-phenyl)-1H-pyrazolo[3,4-d]pyrimidin-4-yloxy]-piperidin-1-yl}-methanone |
| A136 | 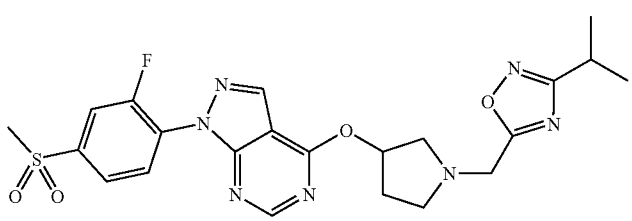 | 1-(2-Fluoro-4-methanesulfonyl-phenyl)-4-[1-(3-isopropyl-[1,2,4]oxadiazol-4-ylmethyl)-pyrrolidin-3-yloxy]-1H-pyrazolo[3,4-d]pyrimidine |
| A137 | 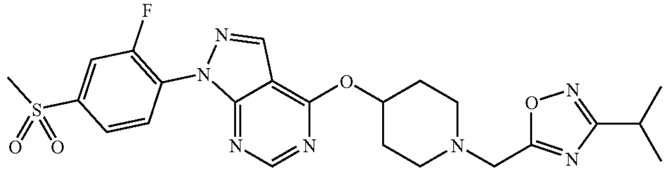 | 1-(2-Fluoro-4-methanesulfonyl-phenyl)-4-[1-(3-isopropyl-[1,2,4]oxadiazol-5-ylmethyl)-piperidin-4-yloxy]-1H-pyrazolo[3,4-d]pyrimidine |

TABLE A-continued

| Cmpd# | Structure | Chemical Name |
|---|---|---|
| A138 | 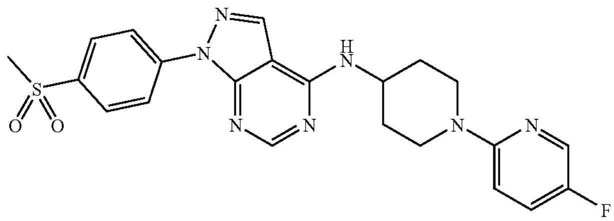 | (5'-Fluoro-3,4,5,6-tetrahydro-2H-[1,2']bipyridinyl-4-yl)-[1-(4-methanesulfonyl-phenyl)-1H-pyrazolo[3,4-d]pyrimidin-4-yl]-amine |
| A139 | 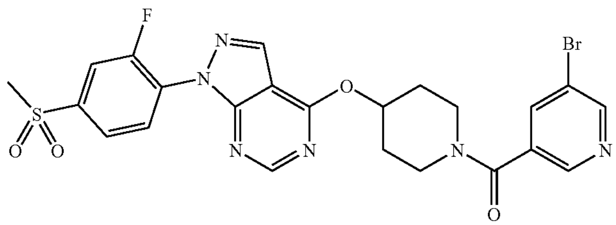 | (5-Bromo-pyridin-3-yl)-{4-[1-(2-fluoro-4-methanesulfonyl-phenyl)-1H-pyrazolo[3,4-d]pyrimidin-4-yloxy]-piperidin-1-yl}-methanone |
| A140 | 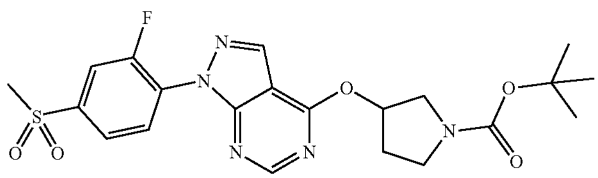 | 3-[1-(2-Fluoro-4-methanesulfonyl-phenyl)-1H-pyrazolo[3,4-d]pyrimidin-4-yloxy]-pyrrolidine-1-carboxylic acid tert-butyl ester |
| A141 | 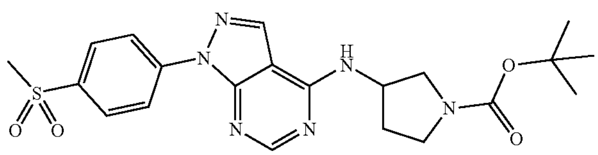 | 3-[1-(4-Methanesulfonyl-phenyl)-1H-pyrazolo[3,4-d]pyrimidin-4-ylamino]-pyrrolidine-1-carboxylic acid tert-butyl ester |
| A142 | 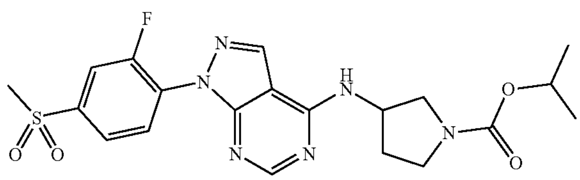 | 3-[1-(2-Fluoro-4-methanesulfonyl-phenyl)-1H-pyrazolo[3,4-d]pyrimidin-4-ylamino]-pyrrolidine-1-carboxylic acid isopropyl ester |
| A143 | 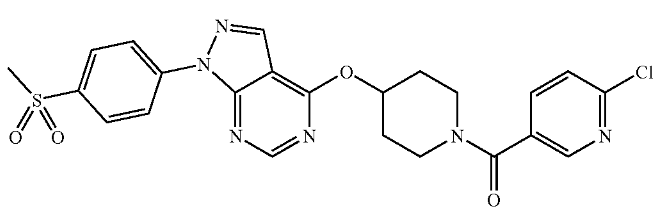 | (6-Chloro-pyridin-3-yl)-{4-[1-(4-methanesulfonyl-phenyl)-1H-pyrazolo[3,4-d]pyrimidin-4-yloxy]-piperidin-1-yl}-methanone |
| A144 | 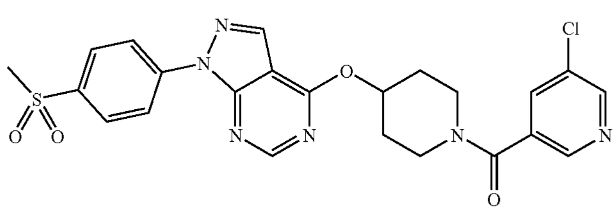 | (5-Chloro-pyridin-3-yl)-{4-[1-(4-methanesulfonyl-phenyl)-1H-pyrazolo[3,4-d]pyrimidin-4-yloxy]-piperidin-1-yl}-methanone |

TABLE A-continued

| Cmpd# | Structure | Chemical Name |
|---|---|---|
| A145 | 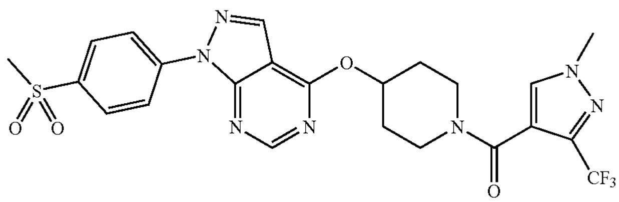 | {4-[1-(4-Methanesulfonyl-phenyl)-1H-pyrazolo[3,4-d]pyrimidin-4-yloxy]-piperidin-1-yl}-(1-methyl-3-trifluoromethyl-1H-pyrazol-4-yl)-methanone |
| A146 | 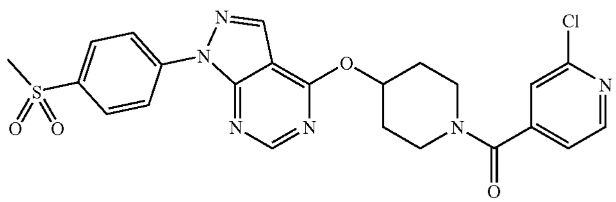 | (2-Chloro-pyridin-4-yl)-{4-[1-(4-methanesulfonyl-phenyl)-1H-pyrazolo[3,4-d]pyrimidin-4-yloxy]-piperidin-1-yl}-methanone |
| A147 | 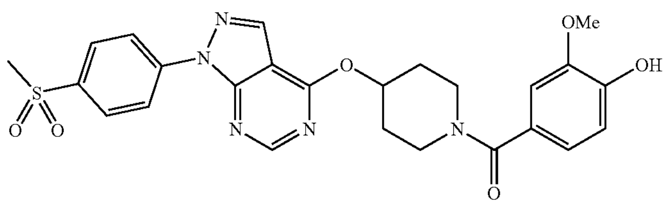 | (4-Hydroxy-3-methoxy-phenyl)-{4-[1-(4-methanesulfonyl-phenyl)-1-pyrazolo[3,4-d]pyrimidin-4-yloxy]-piperidin-1-yl}-methanone |
| A148 | 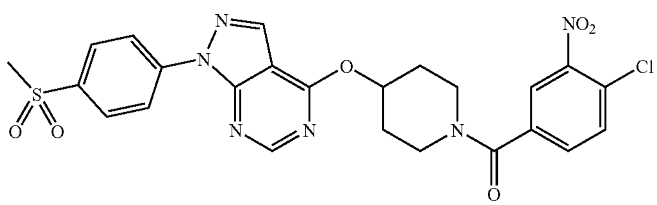 | (4-Chloro-3-nitro-phenyl)-{4-[1-(4-methanesulfonyl-phenyl)-1H-pyrazolo[3,4-d]pyrimidin-4-yloxy]-piperidin-1-yl}-methanone |
| A149 | 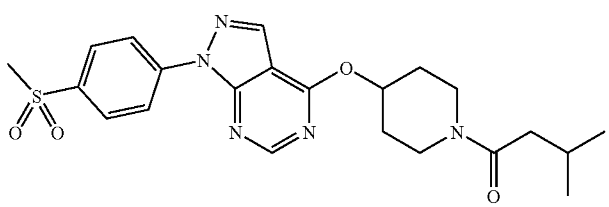 | 1-{4-[1-(4-Methanesulfonyl-phenyl)-1H-pyrazolo[3,4-d]pyrimidin-4-yloxyl]-piperidin-1-yl}-3-methyl-butan-1-one |
| A150 | 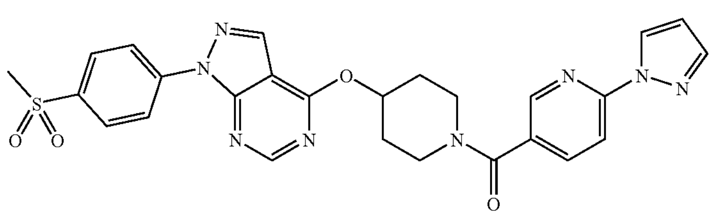 | {4-[1-(4-Methanesulfonyl-phenyl)-1H-pyrazolo[3,4-d]pyrimidin-4-yloxy]-piperidin-1-yl}-(6-pyrazol-1-yl-pyridin-3-yl)-methanone |
| A151 | 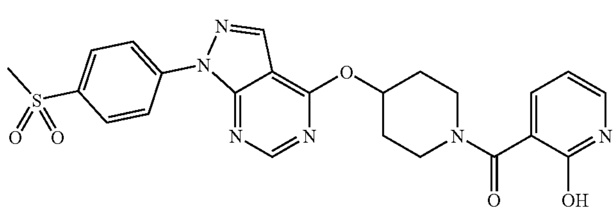 | (2-Hydroxy-pyridin-3-yl)-{4-[1-(4-methanesulfonyl-phenyl)-1H-pyrazolo[3,4-d]pyrimidin-4-yloxy]-piperidin-1-yl}-methanone |

TABLE A-continued

| Cmpd# | Structure | Chemical Name |
|---|---|---|
| A152 | 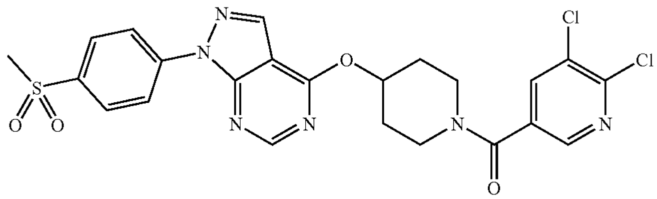 | (5,6-Dichloro-pyridin-3-yl)-{4-[1-(4-methanesulfonyl-phenyl)-1H-pyrazolo[3,4-d]pyrimidin-4-yloxy]-piperidin-1-yl}-methanone |
| A153 | 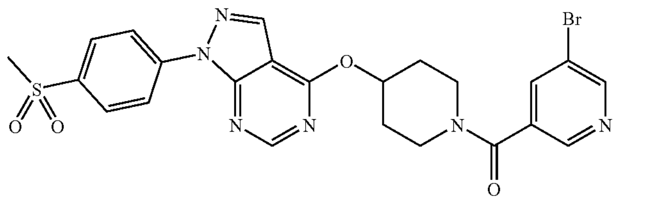 | (5-Bromo-pyridin-3-yl)-{4-[1-(4-methanesulfonyl-phenyl)-1H-pyrazolo[3,4-d]pyrimidin-4-yloxy]-piperidin-1-yl}-methanone |
| A154 | 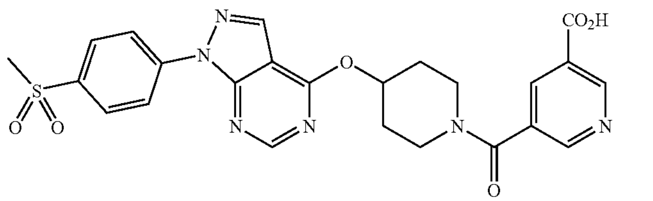 | 5-{4-[1-(4-Methanesulfonyl-phenyl)-1H-pyrazolo[3,4-d]pyrimidin-4-yloxy]-piperidine-1-carbonyl}-nicotinic acid |
| A155 | 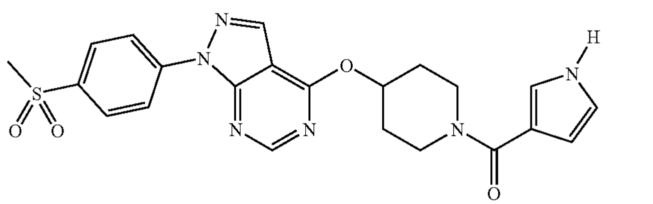 | (1H-Imidazol-4-yl)-{4-[1-(4-methanesulfonyl-phenyl)-1H-pyrazolo[3,4-d]pyrimidin-4-yloxyl]-piperidin-1-yl}-methanone |
| A156 | 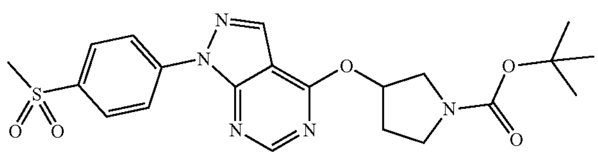 | 3-[1-(4-Methanesulfonyl-phenyl)-1H-pyrazolo[3,4-d]pyrimidin-4-yloxy]-pyrrolidine-1-carboxylic acid tert-butyl ester |
| A157 | 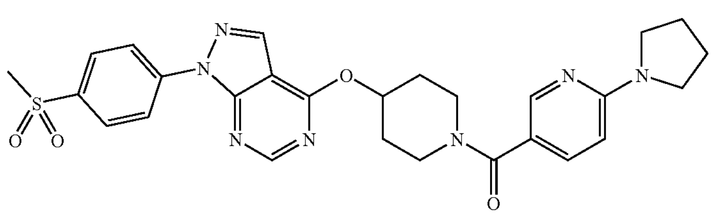 | {4-[1-(4-Methanesulfonyl-phenyl)-1H-pyrazolo[3,4-d]pyrimidin-4-yloxy]-piperidin-1-yl}-(6-pyrrolidin-1-yl-pyridin-3-yl)-methanone |
| A158 | 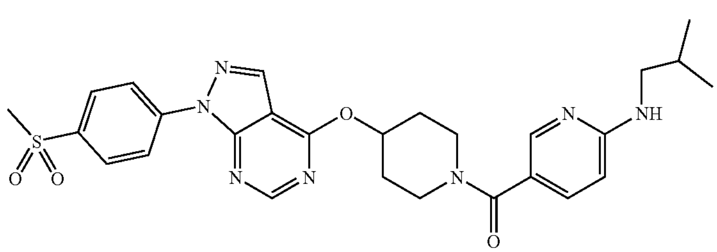 | (6-Isobutylamino-pyridin-3-yl)-{4-[1-(4-methanesulfonyl-phenyl)-1H-pyrazolo[3,4-d]pyrimidin-4-yloxy]-piperidin-1-yl}-methanone |

TABLE A-continued

| Cmpd# | Structure | Chemical Name |
|---|---|---|
| A159 | 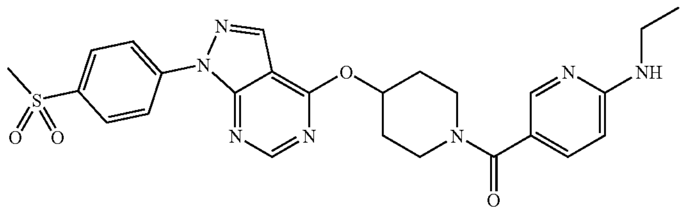 | (6-Ethylamino-pyridin-3-yl)-{4-[1-(4-methanesulfonyl-phenyl)-1H-pyrazolo[3,4-d]pyrimidin-4-yloxy]-piperidin-1-yl}-methanone |
| A160 | 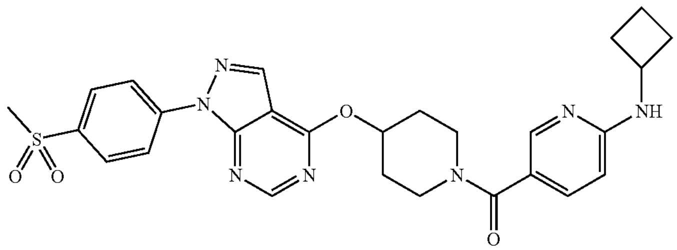 | (6-Cyclobutylamino-pyridin-3-yl)-{4-[1-(4-methanesulfonyl-phenyl)-1H-pyrazolo[3,4-d]pyrimidin-4-yloxy]-piperidin-1-yl}-methanone |
| A161 | 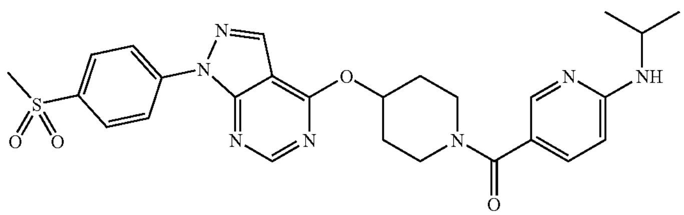 | (6-Isopropylamino-pyridin-3-yl)-{4-[1-(4-methanesulfonyl-phenyl)-1H-pyrazolo[3,4-d]pyrimidin-4-yloxy]-piperidin-1-yl}-methanone |
| A162 | 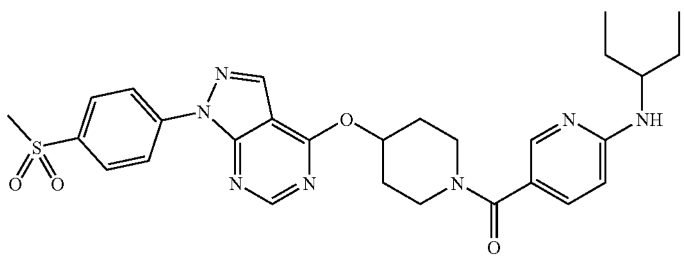 | [6-(1-Ethyl-propylamino)-pyridin-3-yl]-{4-[1-(4-methanesulfonyl-phenyl)-1H-pyrazolo[3,4-d]pyrimidin-4-yloxy]-piperidin-1-yl}-methanone |
| A163 | 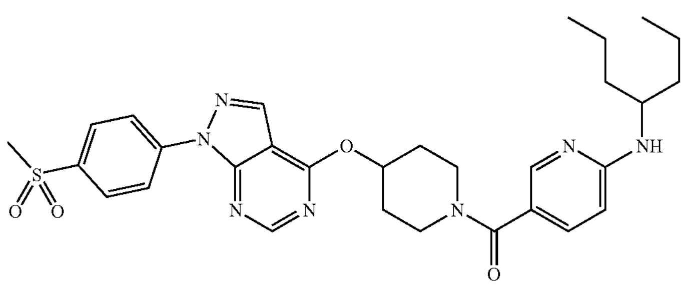 | {4-[1-(4-Methanesulfonyl-phenyl)-1H-pyrazolo[3,4-d]pyrimidin-4-yloxy]-piperidin-1-yl}-[6-(1-propyl-butylamino)-pyridin-3-yl]-methanone |
| A164 | 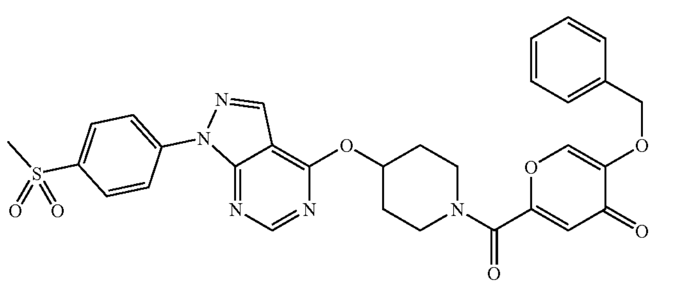 | 5-Benzyloxy-2-{4-[1-(4-methanesulfonyl-phenyl)-1H-pyrazolo[3,4-d]pyrimidin-4-yloxy]-piperidine-1-carbonyl}-pyran-4-one |

TABLE A-continued

| Cmpd# | Structure | Chemical Name |
|---|---|---|
| A165 | 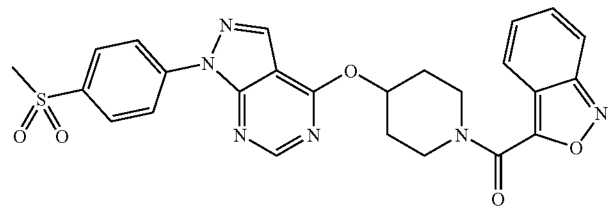 | Benzo[c]isoxazol-3-yl-{4-[1-(4-methanesulfonyl-phenyl)-1H-pyrazolo[3,4-d]pyrimidin-4-yloxy]-piperidin-1-yl}-methanone |
| A166 | 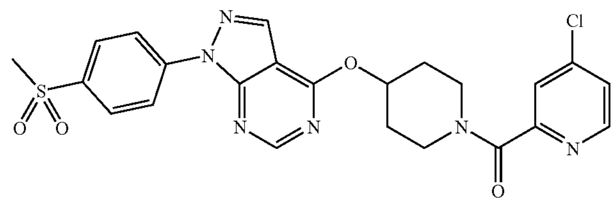 | (4-Chloro-pyridin-2-yl)-{4-[1-(4-methanesulfonyl-phenyl)-1H-pyrazolo[3,4-d]pyrimidin-4-yloxy]-piperidin-1-yl}-methanone |
| A167 | 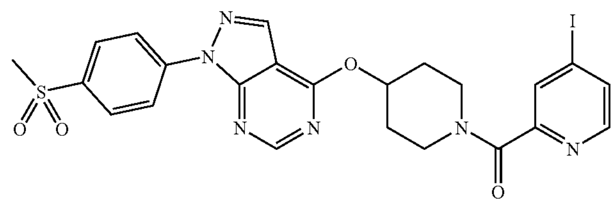 | (4-Iodo-pyridin-2-yl)-{4-[1-(4-methanesulfonyl-phenyl)-1H-pyrazolo[3,4-d]pyrimidin-4-yloxy]-piperidin-1-yl}-methanone |
| A168 | 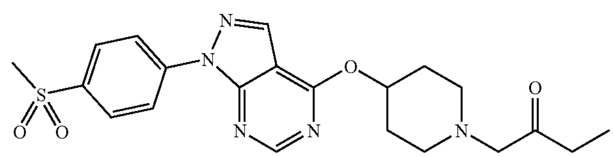 | 1-{4-[1-(4-Methanesulfonyl-phenyl)-1H-pyrazolo[3,4-d]pyrimidin-4-yloxy]-piperidin-1-yl}-butan-2-one |
| A169 | 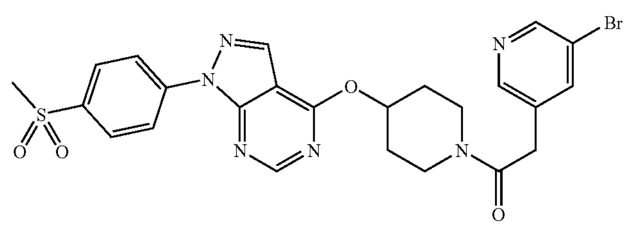 | 2-(5-Bromo-pyridin-3-yl)-1-{4-[1-(4-methanesulfonyl-phenyl)-1H-pyrazolo[3,4-d]pyrimidin-4-yloxy]-piperidin-1-yl}-ethanone |
| A170 | 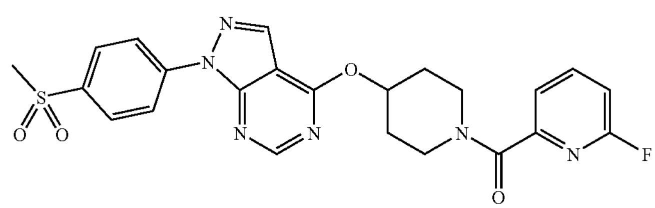 | (6-Fluoro-pyridin-2-yl)-{4-[1-(4-methanesulfonyl-phenyl)-1H-pyrazolo[3,4-d]pyrimidin-4-yloxy]-piperidin-1-yl}-methanone |
| A171 | 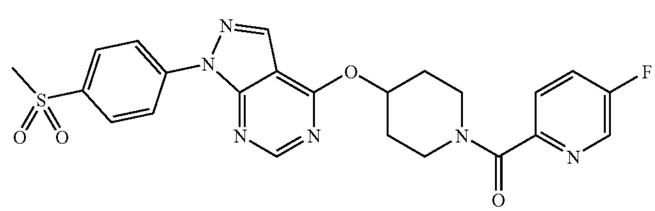 | (5-Fluoro-pyridin-2-yl)-{4-[1-(4-methanesulfonyl-phenyl)-1H-pyrazolo[3,4-d]pyrimidin-4-yloxy]-piperidin-1-yl}-methanone |

TABLE A-continued

| Cmpd# | Structure | Chemical Name |
|---|---|---|
| A172 | 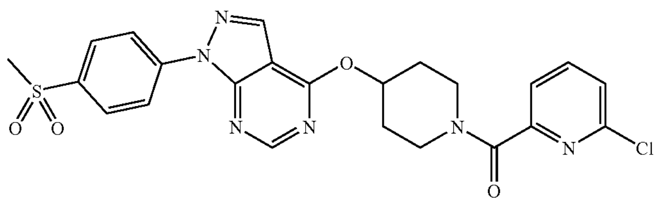 | (6-Chloro-pyridin-2-yl)-{4-[1-(4-methanesulfonyl-phenyl)-1H-pyrazolo[3,4-d]pyrimidin-4-yloxy]-piperidin-1-yl}-methanone |
| A173 | 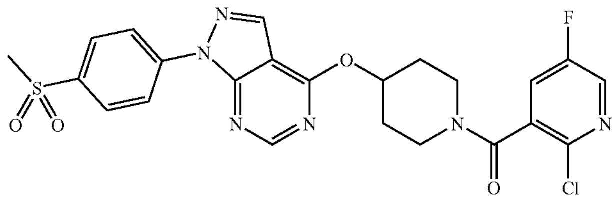 | (2-Chloro-5-fluoro-pyridin-3-yl)-{4-[1-(4-methanesulfonyl-phenyl)-1H-pyrazolo[3,4-d]pyrimidin-4-yloxy]-piperidin-1-yl}-methanone |
| A174 | 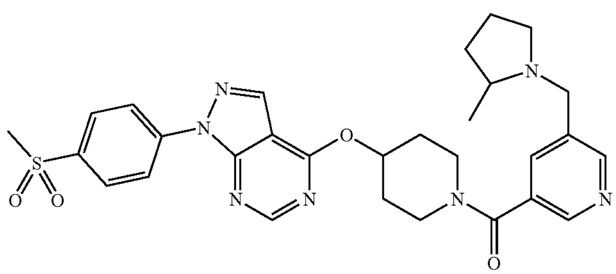 | {4-[1-(4-Methanesulfonyl-phenyl)-1H-pyrazolo[3,4-d]pyrimidin-4-yloxy]-piperidin-1-yl}-[5-(2-methyl-pyrrolidin-1-ylmethyl)-pyridin-3-yl]-methanone |
| A175 | 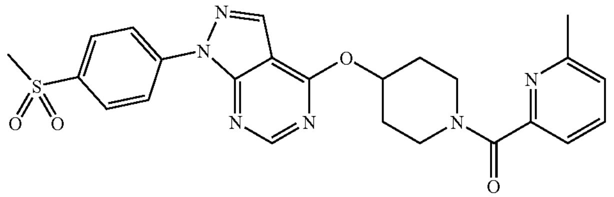 | {4-[1-(4-Methanesulfonyl-phenyl)-1H-pyrazolo[3,4-d]pyrimidin-4-yloxy]-piperidin-1-yl}-(6-methyl-pyridin-2-yl)-methanone |
| A176 | 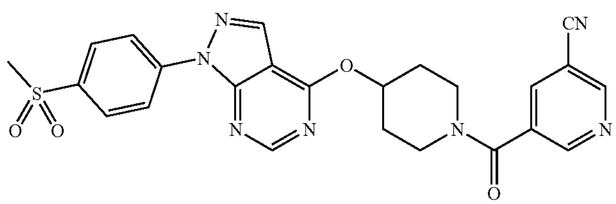 | 5-{4-[1-(4-Methanesulfonyl-phenyl)-1H-pyrazolo[3,4-d]pyrimidin-4-yloxy]-piperidine-1-carbonyl}-nicotinonitrile |
| A177 | 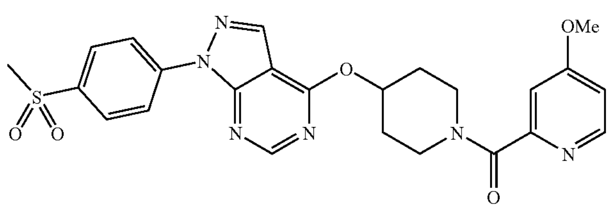 | {4-[1-(4-Methanesulfonyl-phenyl)-1H-pyrazolo[3,4-d]pyrimidin-4-yloxy]-piperidin-1-yl}-(4-methoxy-pyridin-2-yl)-methanone |
| A178 | 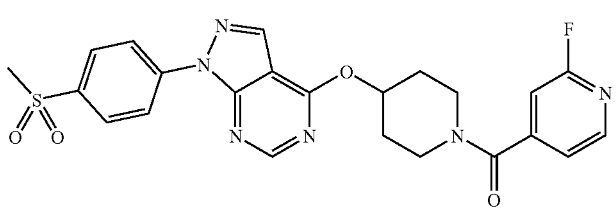 | (2-Fluoro-pyridin-4-yl)-{4-[1-(4-methanesulfonyl-phenyl)-1H-pyrazolo[3,4-d]pyrimidin-4-yloxy]-piperidin-1-yl}-methanone |

TABLE A-continued

| Cmpd# | Structure | Chemical Name |
|---|---|---|
| A179 | 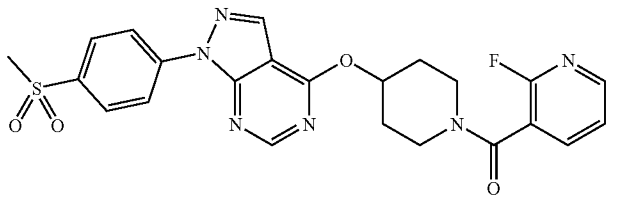 | (2-Fluoro-pyridin-3-yl)-{4-[1-(4-methanesulfonyl-phenyl)-1H-pyrazolo[3,4-d]pyrimidin-4-yloxy]-piperidin-1-yl}-methanone |
| A180 | 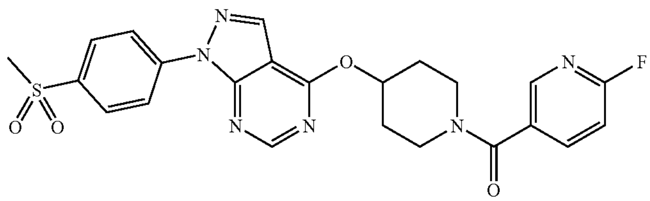 | (6-Fluoro-pyridin-3-yl)-{4-[1-(4-methanesulfonyl-phenyl)-1H-pyrazolo[3,4-d]pyrimidin-4-yloxy]-piperidin-1-yl}-methanone |
| A181 | 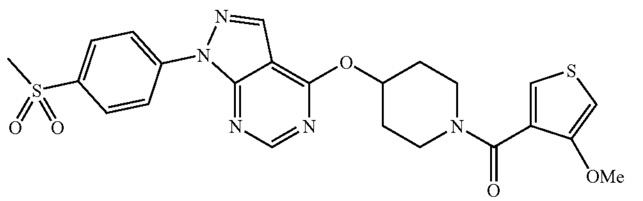 | {4-[1-(4-Methanesulfonyl-phenyl)-1H-pyrazolo[3,4-d]pyrimidin-4-yloxy]-piperidin-1-yl}-(4-methoxy-thiophen-3-yl)-methanone |
| A182 | 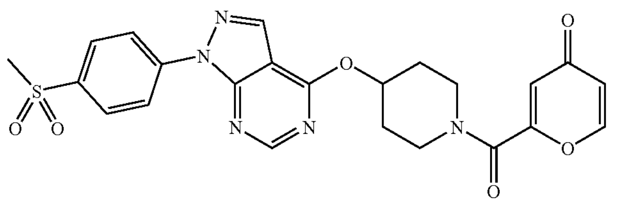 | 2-{4-[1-(4-Methanesulfonyl-phenyl)-1H-pyrazolo[3,4-d]pyrimidin-4-yloxy]-piperidine-1-carbonyl}-pyran-4-one |
| A183 | 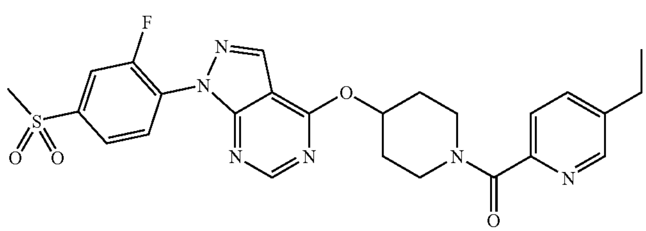 | (5-Ethyl-pyridin-2-yl)-{4-[1-(2-fluoro-4-methanesulfonyl-phenyl)-1H-pyrazolo[3,4-d]pyrimidin-4-yloxy]-piperidin-1-yl}-methanone |
| A184 | 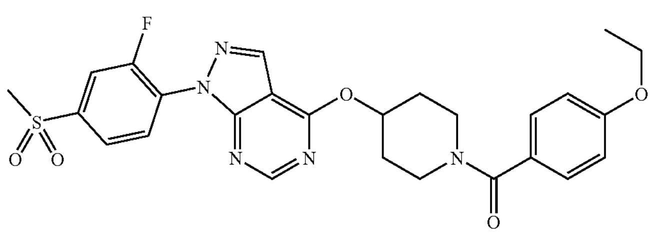 | (4-Ethoxy-phenyl)-{4-[1-(2-fluoro-4-methanesulfonyl-phenyl)-1H-pyrazolo[3,4-d]pyrimidin-4-yloxy]-piperidin-1-yl}-methanone |
| A185 | 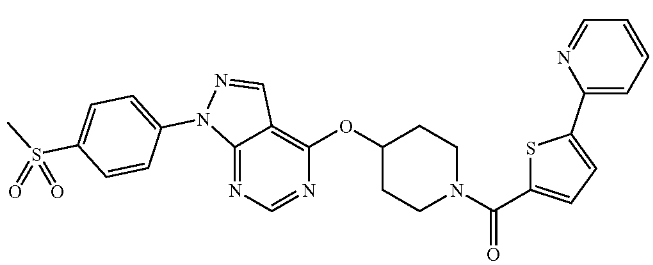 | {4-[1-(4-Methanesulfonyl-phenyl)-1H-pyrazolo[3,4-d]pyrimidin-4-yloxy]-piperidin-1-yl}-(5-pyridin-2-yl-thiophen-2-yl)-methanone |

TABLE A-continued

| Cmpd# | Structure | Chemical Name |
|---|---|---|
| A186 | 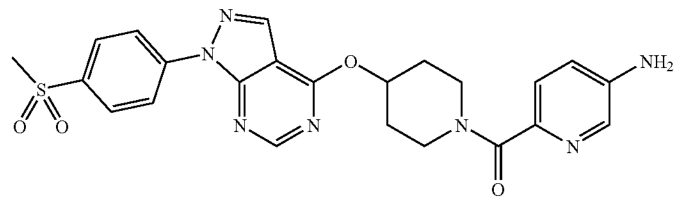 | (5-Amino-pyridin-2-yl)-{4-[1-(4-methanesulfonyl-phenyl)-1H-pyrazolo[3,4-d]pyrimidin-4-yloxy]-piperidin-1-yl}-methanone |
| A187 | 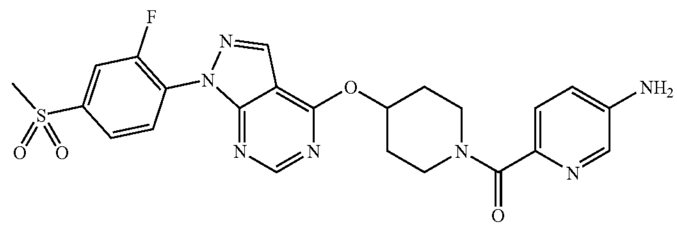 | (5-Amino-pyridin-2-yl)-{4-[1-(2-fluoro-4-methanesulfonyl-phenyl)-1H-pyrazolo[3,4-d]pyrimidin-4-yloxy]-piperidin-1-yl}-methanone |
| A188 | 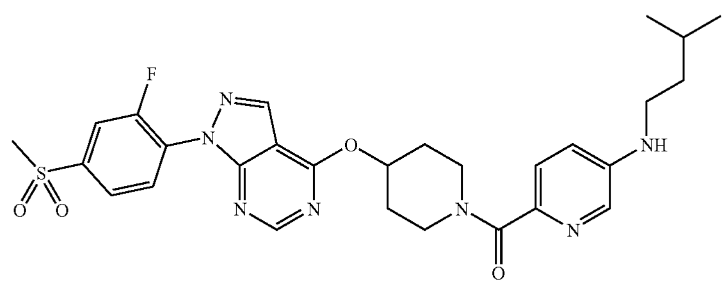 | {4-[1-(2-Fluoro-4-methanesulfonyl-phenyl)-1H-pyrazolo[3,4-d]pyrimidin-4-yloxy]-piperidin-1-yl}-[5-(3-methyl-butylamino)-pyridin-2-yl]-methanone |
| A189 | 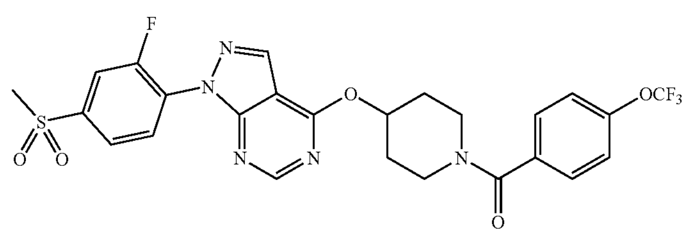 | {4-[1-(2-Fluoro-4-methanesulfonyl-phenyl)-1H-pyrazolo[3,4-d]pyrimidin-4-yloxy]-piperidin-1-yl}-(4-trifluoromethoxy-phenyl)-methanone |
| A190 | 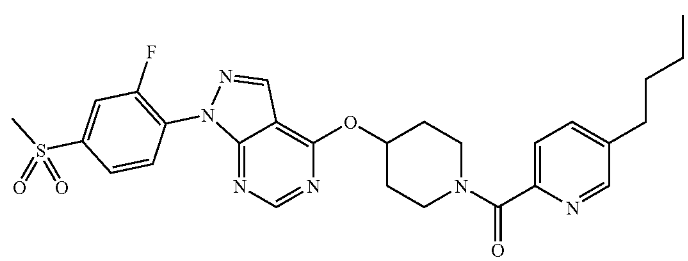 | (5-Butyl-pyridin-2-yl)-{4-[1-(2-fluoro-4-methanesulfonyl-phenyl)-1H-pyrazolo[3,4-d]pyrimidin-4-yloxy]-piperidin-1-yl}-methanone |
| A191 | 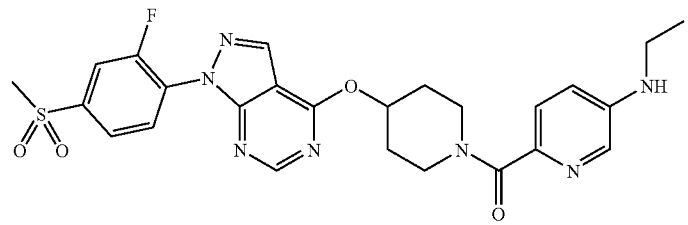 | (5-Ethylamino-pyridin-2-yl)-{4-[1-(2-fluoro-4-methanesulfonyl-phenyl)-1H-pyrazolol[3,4-d]pyrimidin-4-yloxy]-piperidin-1-yl}-methanone |

TABLE A-continued

| Cmpd# | Structure | Chemical Name |
|---|---|---|
| A192 | 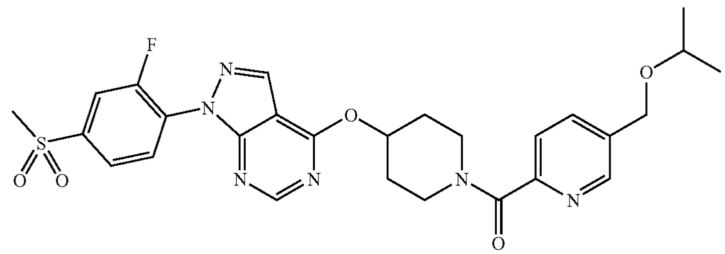 | {4-[1-(2-Fluoro-4-methanesulfonyl-phenyl)-1H-pyrazolo[3,4-d]pyrimidin-4-yloxy]-piperidin-1-yl}-(5-isopropoxymethyl-pyridin-2-yl)-methanone |
| A193 | 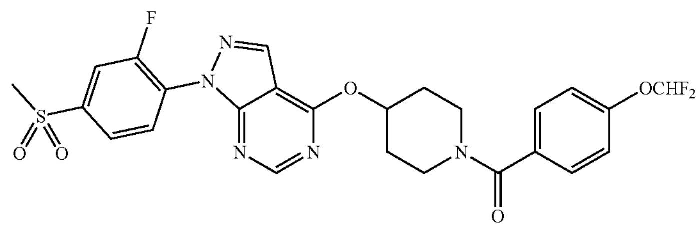 | (4-Difluoromethoxy-phenyl)-{4-[1-(2-fluoro-4-methanesulfonyl-phenyl)-1H-pyrazolo[3,4-d]pyrimidin-4-yloxy]-piperidin-1-yl}-methanone |
| A194 | 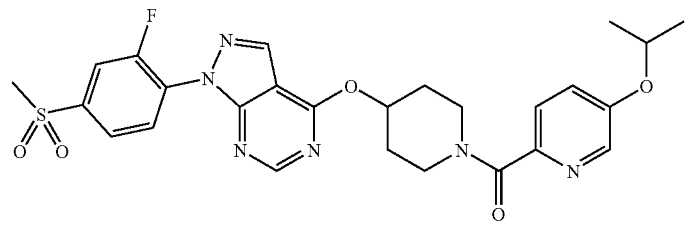 | {4-[1-(2-Fluoro-4-methanesulfonyl-phenyl)-1H-pyrazolo[3,4-d]pyrimidin-4-yloxy]-piperidin-1-yl}-(5-isopropoxy-pyridin-2-yl)-methanone |
| A195 | 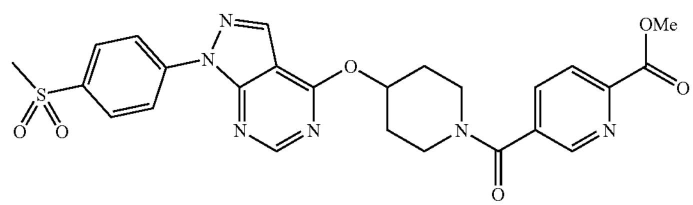 | 5-{4-[1-(4-Methanesulfonyl-phenyl)-1H-pyrazolol[3,4-d]pyrimidin-4-yloxy]-piperidine-1-carbonyl}-pyridine-2-carboxylic acid methyl ester |
| A196 | 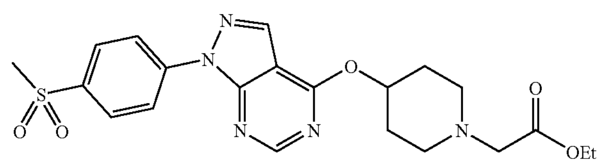 | {4-[1-(4-Methanesulfonyl-phenyl)-1H-pyrazolo[3,4-d]pyrimidin-4-yloxy]-piperidin-1-yl}-acetic acid ethyl ester |
| A197 | 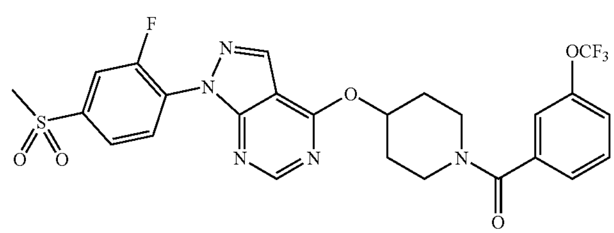 | {4-[1-(2-Fluoro-4-methanesulfonyl-phenyl)-1H-pyrazolo[3,4-d]pyrimidin-4-yloxy]-piperidin-1-yl}-(3-trifluoromethoxy-phenyl)-methanone |
| A198 | 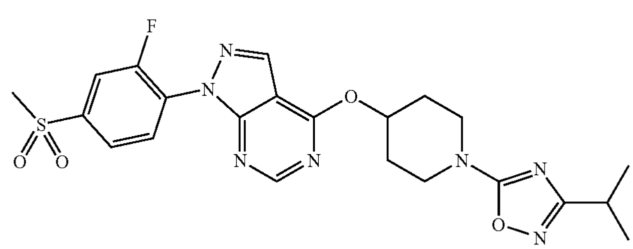 | 1-(2-Fluoro-4-methanesulfonyl-phenyl)-4-[1-(3-isopropyl-[1,2,4]oxadiazol-5-yl)-piperidin-4-yloxy]-1H-pyrazolo[3,4-d]pyrimidine |

TABLE A-continued

| Cmpd# | Structure | Chemical Name |
|---|---|---|
| A199 | 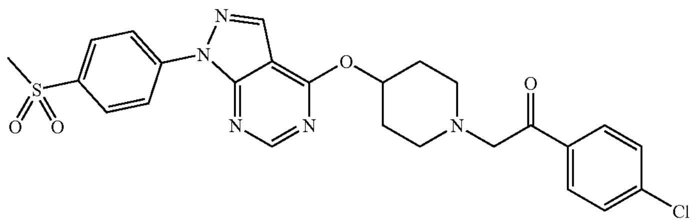 | 1-(4-Chloro-phenyl)-2-{4-[1-(4-methanesulfonyl-phenyl)-1H-pyrazolo[3,4-d]pyrimidin-4-yloxy]-piperidin-1-yl}-ethanone |
| A200 | 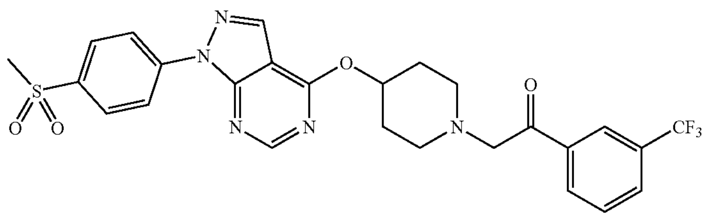 | 2-{4-[1-(4-Methanesulfonyl-phenyl)-1H-pyrazolo[3,4-d]pyrimidin-4-yloxy]-piperidin-1-yl}-1-(3-trifluoromethyl-phenyl)-ethanone |
| A201 | 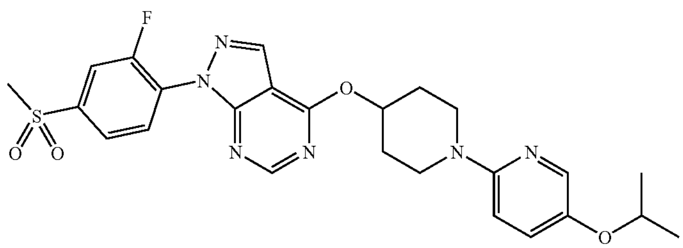 | 4-[1-(2-Fluoro-4-methanesulfonyl-phenyl)-1H-pyrazolo[3,4-d]pyrimidin-4-yloxy]-5'-isopropoxy-3,4,5,6-tetrahydro-2H-[1,2']bipyridinyl |
| A202 | 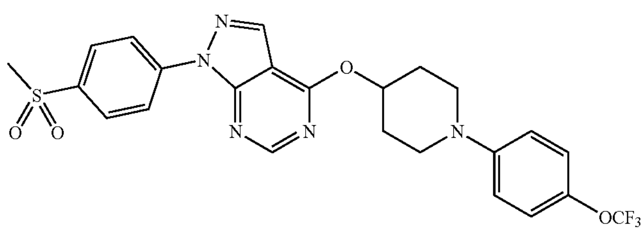 | 1-(4-Methanesulfonyl-phenyl)-4-[1-(4-trifluoromethoxy-phenyl)-piperidin-4-yloxy]-1H-pyrazolo[3,4-d]pyrimidine |
| A203 | 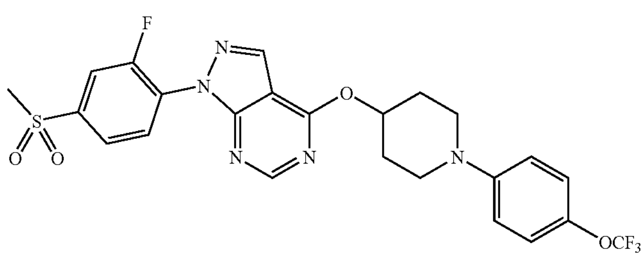 | 1-(2-Fluoro-4-methanesulfonyl-phenyl)-4-[1-(4-trifluoromethoxy-phenyl)-piperidin-4-yloxy]-1H-pyrazolo[3,4-d]pyrimidine |
| A204 | 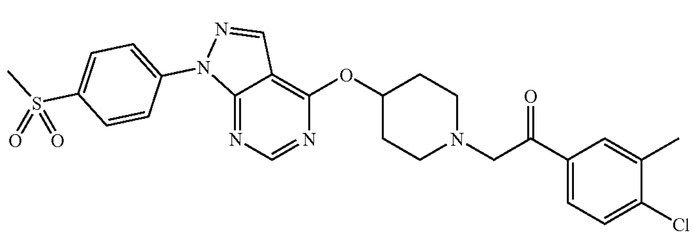 | 1-(4-Chloro-3-methyl-phenyl)-2-{4-[1-(4-methanesulfonyl-phenyl)-1H-pyrazolo[3,4-d]pyrimidin-4-yloxy]-piperidin-1-yl}-ethanone |

TABLE A-continued

| Cmpd# | Structure | Chemical Name |
|---|---|---|
| A205 | 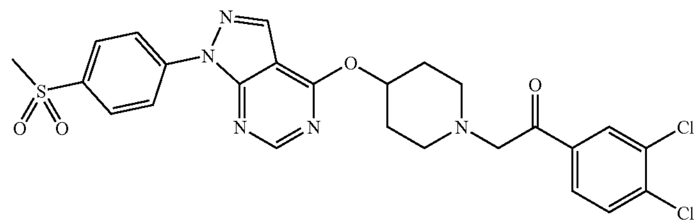 | 1-(3,4-Dichloro-phenyl)-2-{4-[1-(4-methanesulfonyl-phenyl)-1H-pyrazolo[3,4-d]pyrimidin-4-yloxy]-piperidin-1-yl}-ethanone |
| A206 | 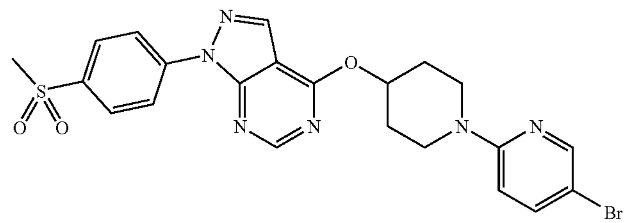 | 5'-Bromo-4-[1-(4-methanesulfonyl-phenyl)-1H-pyrazolo[3,4-d]pyrimidin-4-yloxy]-3,4,5,6-tetrahydro-2H-[1,2']bipyridinyl |
| A207 | 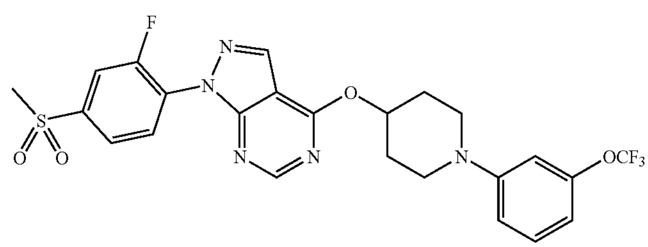 | 1-(2-Fluoro-4-methanesulfonyl-phenyl)-4-[1-(3-trifluoromethoxy-phenyl)-piperidin-4-yloxy]-1H-pyrazolo[3,4-d]pyrimidine |
| A208 | 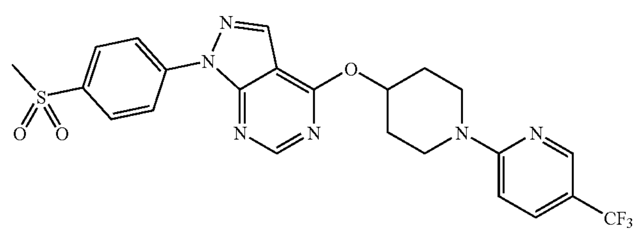 | 4-[1-(4-Methanesulfonyl-phenyl)-1H-pyrazolo[3,4-d]pyrimidin-4-yloxy]-5'-trifluoromethyl-3,4,5,6-tetrahydro-2H-[1,2']bipyridinyl |
| A209 | 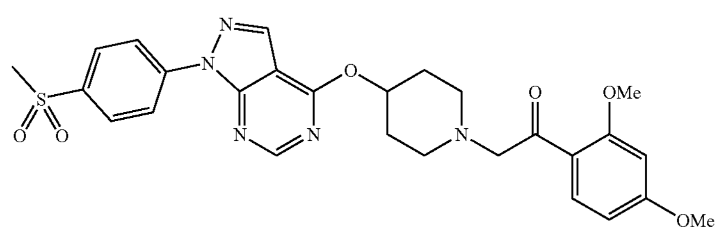 | 1-(2,4-Dimethoxy-phenyl)-2-{4-[1-(4-methanesulfonyl-phenyl)-1H-pyrazolo[3,4-d]pyrimidin-4-yloxy]-piperidin-1-yl}-ethanone |
| A210 | 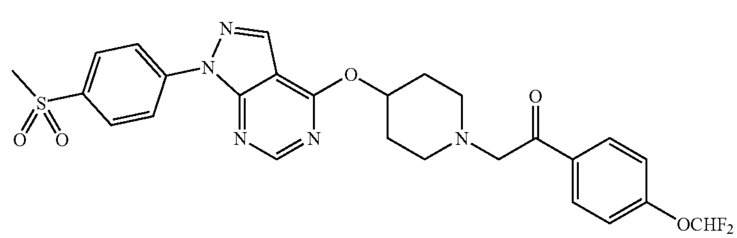 | 1-(4-Difluoromethoxy-phenyl)-2-{4-[1-(4-methanesulfonyl-phenyl)-1H-pyrazolo[3,4-d]pyrimidin-4-yloxy]-piperidin-1-yl}-ethanone |

TABLE A-continued

| Cmpd# | Structure | Chemical Name |
|---|---|---|
| A211 | 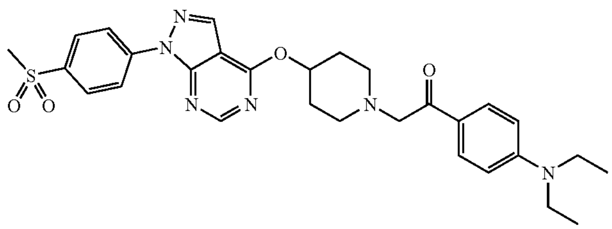 | 1-(4-Diethylamino-phenyl)-2-{4-[1-(4-methanesulfonyl-phenyl)-1H-pyrazolo[3,4-d]pyrimidin-4-yloxy]-piperidin-1-yl}-ethanone |
| A212 | 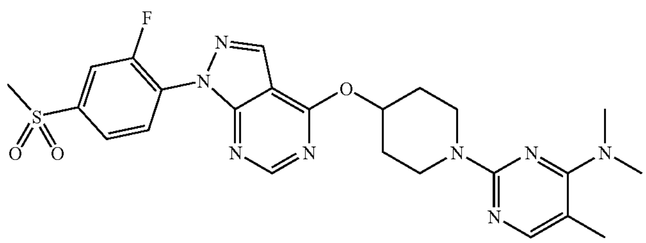 | (2-{4-[1-(2-Fluoro-4-methanesulfonyl-phenyl)-1H-pyrazolo[3,4-d]pyrimidin-4-yloxy]-piperidin-1-yl}-5-methyl-pyrimidin-4-yl)-dimethyl-amine |
| A213 | 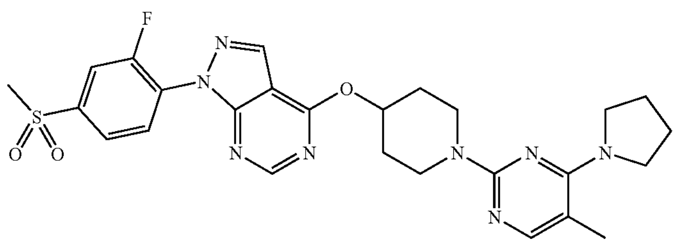 | 1-(2-Fluoro-4-methanesulfonyl-phenyl)-4-[1-(5-methyl-4-pyrrolidin-1-yl-pyrimidin-2-yl)-piperidin-4-yloxy]-1H-pyrazolo[3,4-d]pyrimidine |
| A214 | 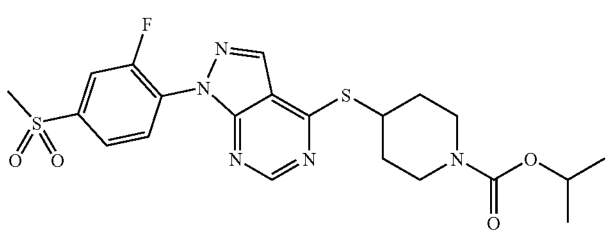 | 4-[1-(2-Fluoro-4-methanesulfonyl-phenyl)-1H-pyrazolo[3,4-d]pyrimidin-4-ylsulfanyl]-piperidine-1-carboxylic acid isopropyl ester |
| A215 | 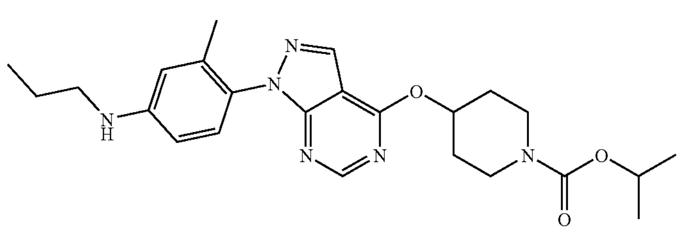 | 4-[1-(2-Methyl-4-propylamino-phenyl)-1H-pyrazolo[3,4-d]pyrimidin-4-yloxy]-piperidine-1-carboxylic acid isopropyl ester |
| A216 | 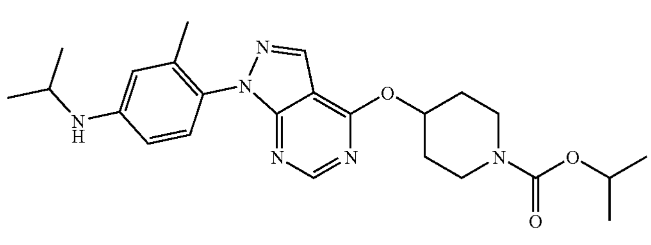 | 4-[1-(4-Isopropylamino-2-methyl-phenyl)-1H-pyrazolo[3,4-d]pyrimidin-4-yloxy]-piperidine-1-carboxylic acid isopropyl ester |

TABLE A-continued

| Cmpd# | Structure | Chemical Name |
|---|---|---|
| A217 | 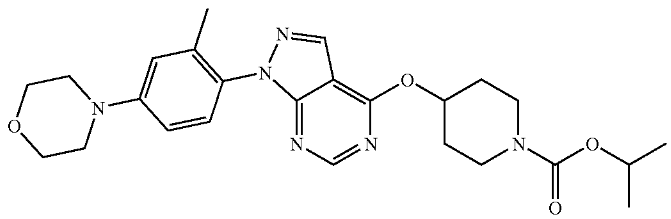 | 4-[1-(2-Methyl-4-morpholin-4-yl-phenyl)-1H-pyrazolo[3,4-d]pyrimidin-4-yloxy]-piperidine-1-carboxylic acid isopropyl ester |
| A218 | 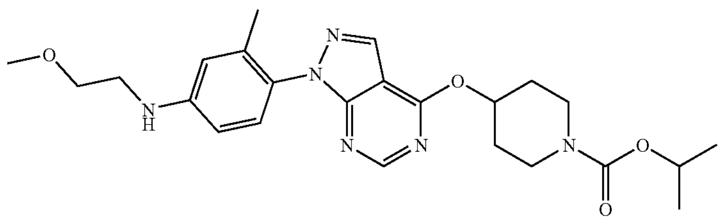 | 4-{1-[4-(2-Methoxy-ethylamino)-2-methyl-phenyl]-1H-pyrazolo[3,4-d]pyrimidin-4-yloxy}-piperidine-1-carboxylic acid isopropyl ester |
| A219 | 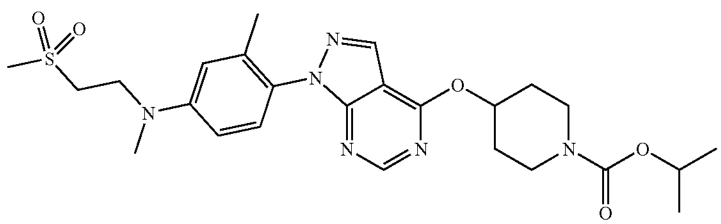 | 4-(1-{4-[(2-Methanesulfonyl-ethyl)-methyl-amino]-2-methyl-phenyl}-1H-pyrazolo[3,4-d]pyrimidin-4-yloxy)-piperidine-1-carboxylic acid isopropyl ester |
| A220 | 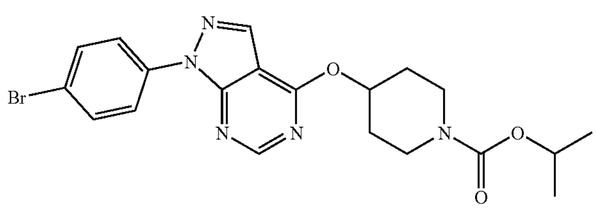 | 4-[1-(4-Bromo-phenyl)-1H-pyrazolo[3,4-d]pyrimidin-4-yloxy]-piperidine-1-carboxylic acid isopropyl ester |
| A221 | 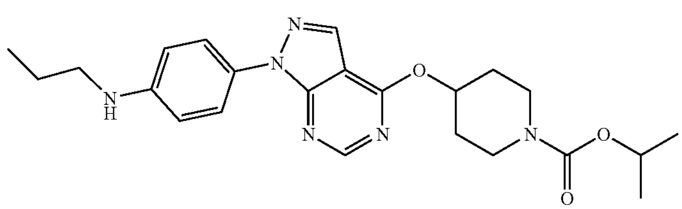 | 4-[1-(4-Propylamino-phenyl)-1H-pyrazolo[3,4-d]pyrimidin-4-yloxy]-piperidine-1-carboxylic acid isopropyl ester |
| A222 | 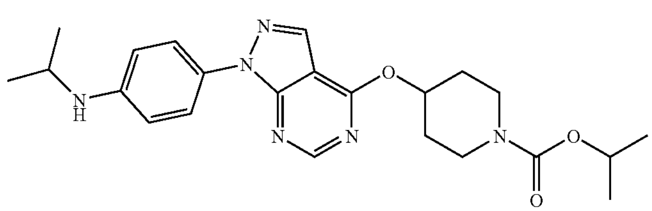 | 4-[1-(4-Isopropylamino-phenyl)-1H-pyrazolo[3,4-d]pyrimidin-4-yloxy]-piperidine-1-carboxylic acid isopropyl ester |
| A223 | 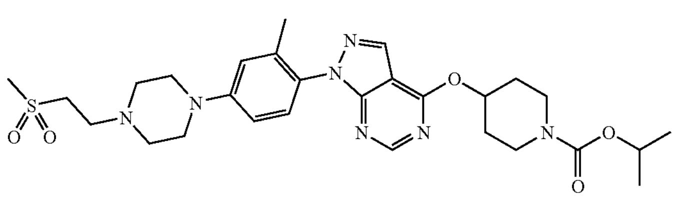 | 4-(1-{4-[4-(2-Methanesulfonyl-ethyl)-piperazin-1-yl]-2-methyl-phenyl}-1H-pyrazolo[3,4-d]pyrimidin-4-yloxy)-piperidine-1-carboxylic acid isopropyl ester |

TABLE A-continued

| Cmpd# | Structure | Chemical Name |
|---|---|---|
| A224 | 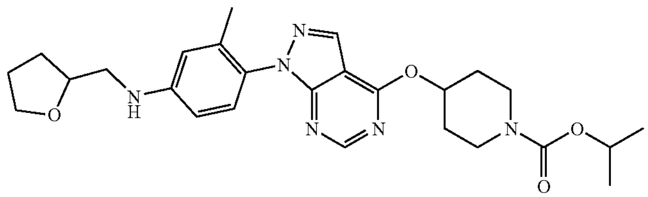 | 4-(1-{2-Methyl-4-[(tetrahydro-furan-2-ylmethyl)-amino]-phenyl}-1H-pyrazolo[3,4-d]pyrimidin-4-yloxy)-piperidine-1-carboxylic acid isopropyl ester |
| A225 | 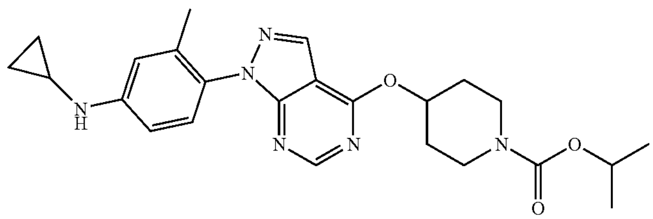 | 4-[1-(4-Cyclopropylamino-2-methyl-phenyl)-1H-pyrazolo[3,4-d]pyrimidin-4-yloxy]-piperidine-1-carboxylic acid isopropyl ester |
| A226 | 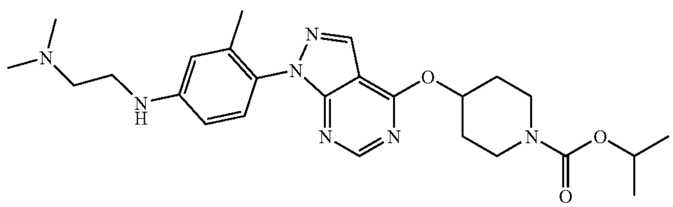 | 4-{1-[4-(2-Dimethylamino-ethylamino)-2-methyl-phenyl]-1H-pyrazolo[3,4-d]pyrimidin-4-yloxy}-piperidine-1-carboxylic acid isopropyl ester |
| A227 | 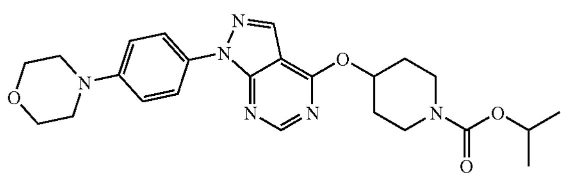 | 4-[1-(4-Morpholin-4-yl-phenyl)-1H-pyrazolo[3,4-]pyrimidin-4-yloxy]-piperidine-1-carboxylic acid isopropyl ester |
| A228 | 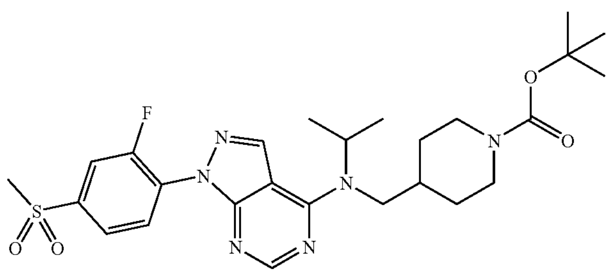 | 4-({[1-(2-Fluoro-4-methanesulfonyl-phenyl)-1H-pyrazolo[3,4-d]pyrimidin-4-yl]-isopropyl-amino}-methyl)-piperidine-1-carboxylic acid tert-butyl ester |
| A229 | 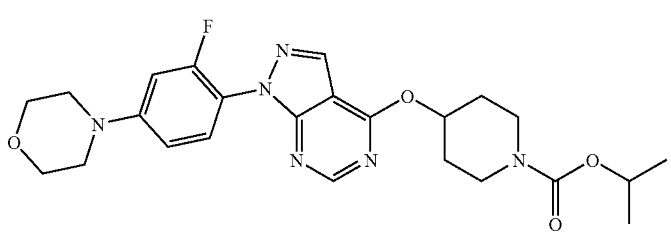 | 4-[1-(2-Fluoro-4-morpholin-4-yl-phenyl)-1H-pyrazolo[3,4-d]pyrimidin-4-yloxy]-piperidine-1-carboxylic acid isopropyl ester |
| A230 | 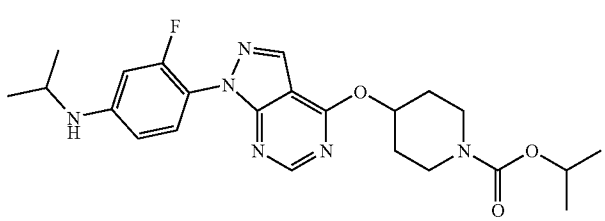 | 4-[1-(2-Fluoro-4-isopropylamino-phenyl)-1H-pyrazolo[3,4-d]pyrimidin-4-yloxy]-piperidine-1-carboxylic acid isopropyl ester |

TABLE A-continued

| Cmpd# | Structure | Chemical Name |
|---|---|---|
| A231 | 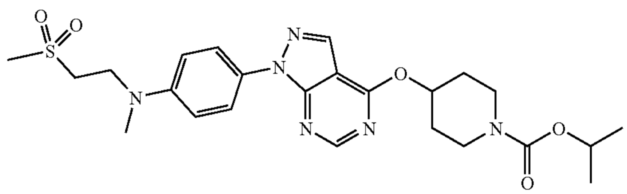 | 4-(1-{4-[(2-Methanesulfonyl-ethyl)-methyl-amino]-phenyl}-1H-pyrazolo[3,4-d]pyrimidin-4-yloxy)-piperidine-1-carboxylic acid isopropyl ester |
| A232 | 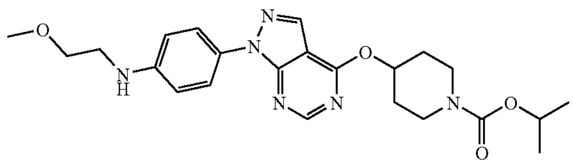 | 4-{1-[4-(2-Methoxy-ethylamino)-phenyl]-1H-pyrazolo[3,4-d]pyrimidin-4-yloxy}-piperidine-1-carboxylic acid isopropyl ester |
| A233 | 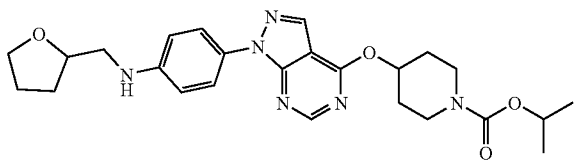 | 4-(1-{4-[(Tetrahydro-furan-2-ylmethyl)-amino]-phenyl}-1H-pyrazolo[3,4-d]pyrimidin-4-yloxy)-piperidine-1-carboxylic acid isopropyl ester |
| A234 | 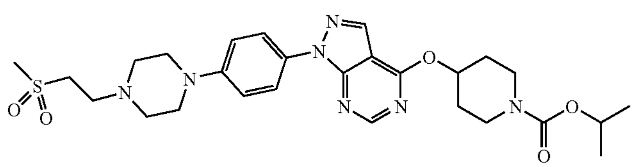 | 4-(1-{4-[4-(2-Methanesulfonyl-ethyl)-piperazin-1-yl]-phenyl}-1H-pyrazolo[3,4-d]pyrimidin-4-yloxy)-piperidine-1-carboxylic acid isopropyl ester |
| A235 | 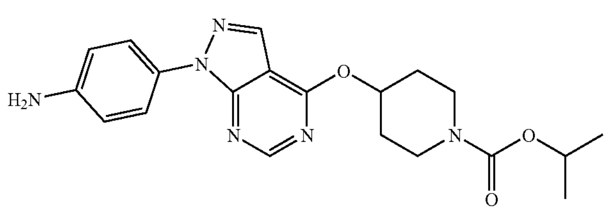 | 4-[1-(4-Amino-phenyl)-1H-pyrazolo[3,4-d]pyrimidin-4-yloxy]-piperidine-1-carboxylic acid isopropyl ester |
| A236 | 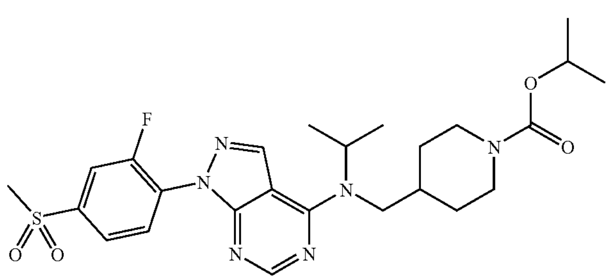 | 4-({[1-(2-Fluoro-4-methanesulfonyl-phenyl)-1H-pyrazolo[3,4-d]pyrimidin-4-yl]-isopropyl-amino}-methyl)-piperidine-1-carboxylic acid isopropyl ester |
| A237 | 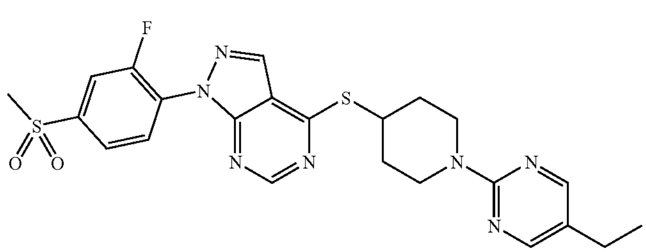 | 4-[1-(5-Ethyl-pyrimidin-2-yl)-piperidin-4-ylsulfanyl]-1-(2-fluoro-4-methanesulfonyl-phenyl)-1H-pyrazolo[3,4-d]pyrimidine |

TABLE A-continued

| Cmpd# | Structure | Chemical Name |
|---|---|---|
| A238 | 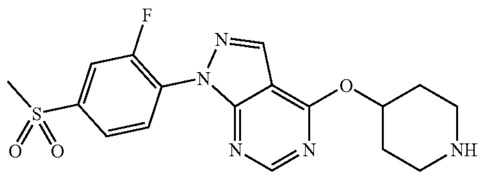 | 1-(2-Fluoro-4-methanesulfonyl-phenyl)-4-(piperidin-4-yloxy)-1H-pyrazolo[3,4-d]pyrimidine |
| A239 | 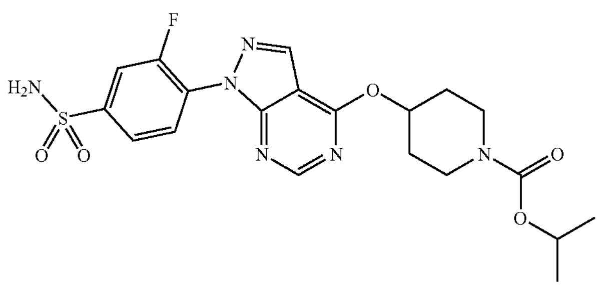 | 4-[1-(2-Fluoro-4-sulfamoyl-phenyl)-1H-pyrazolo[3,4-d]pyrimidin-4-yloxy]-piperidine-1-carboxylic acid isopropyl ester |
| A240 | 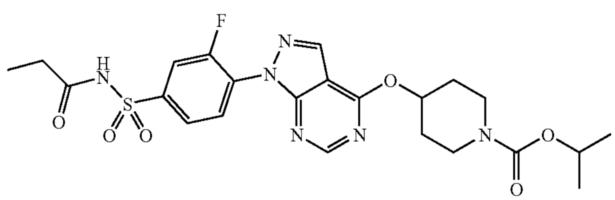 | 4-[1-(2-Fluoro-4-propionylsulfamoyl-phenyl)-1H-pyrazolo[3,4-d]pyrimidin-4-yloxy]-piperidine-1-carboxylic acid isopropyl ester |
| A241 | 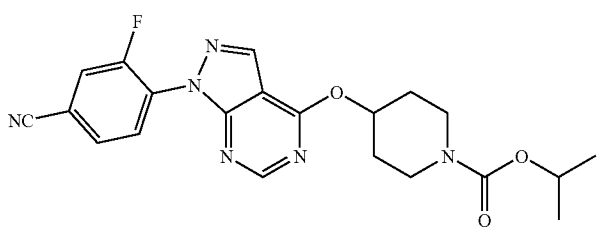 | 4-[1-(4-Cyano-2-fluoro-phenyl)-1H-pyrazolo[3,4-d]pyrimidin-4-yloxy]-piperidine-1-carboxylic acid isopropyl ester |
| A242 | 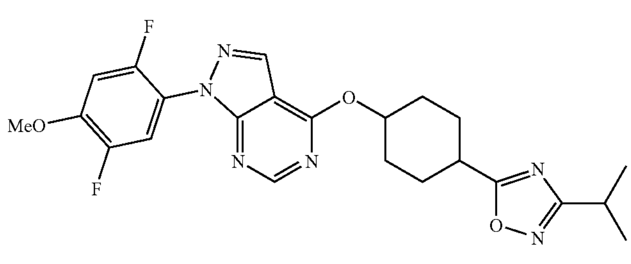 | 1-(2,5-Difluoro-4-methoxy-phenyl)-4-[4-(3-isopropyl-[1,2,4]oxadiazol-5-yl)-cyclohexyloxy]-1H-pyrazolo[3,4-d]pyrimidine |
| A243 | 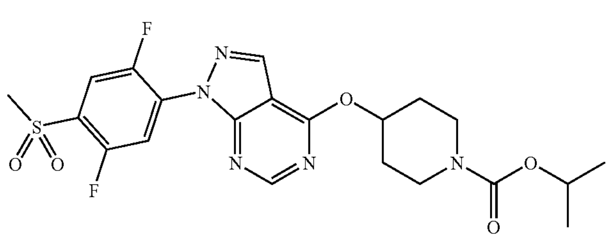 | 4-[1-(2,5-Difluoro-4-methanesulfonyl-phenyl)-1H-pyrazolo[3,4-d]pyrimidin-4-yloxy]-piperidine-1-carboxylic acid isopropyl ester |

TABLE A-continued

| Cmpd# | Structure | Chemical Name |
|---|---|---|
| A244 | 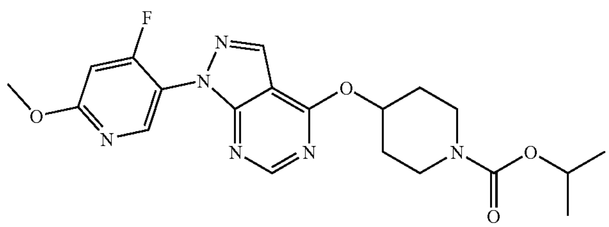 | 4-[1-(4-Fluoro-6-methoxy-pyridin-3-yl)-1H-pyrazolo[3,4-d]pyrimidin-4-yloxy]-piperidine-1-carboxylic acid isopropyl ester |
| A245 | 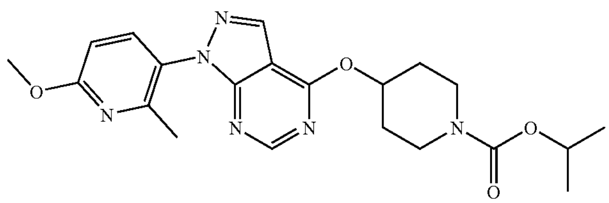 | 4-[1-(6-Methoxy-2-methyl-pyridin-3-yl)-1H-pyrazolo[3,4-d]pyrimidin-4-yloxy]-piperidine-1-carboxylic acid isopropyl ester |
| A246 | 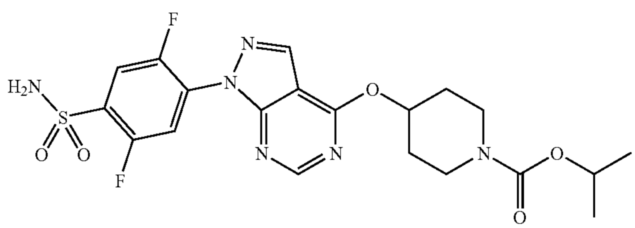 | 4-[1-(2,5-Difluoro-4-sulfamoyl-phenyl)-1H-pyrazolo[3,4-d]pyrimidin-4-yloxy]-piperidine-1-carboxylic acid isopropyl ester |
| A247 | 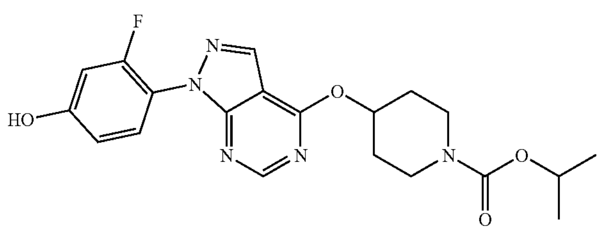 | 4-[1-(2-Fluoro-4-hydroxy-phenyl)-1H-pyrazolo[3,4-d]pyrimidin-4-yloxy]-piperidine-1-carboxylic acid isopropyl ester |
| A248 | 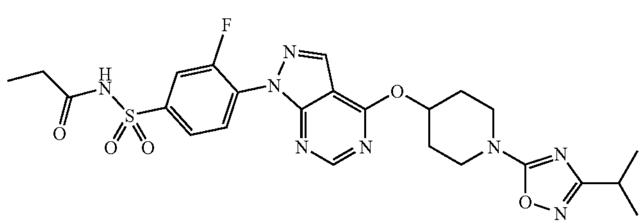 | 3-Fluoro-4-{4-[1-(3-isopropyl-[1,2,4]oxadiazol-5-yl)-piperidin-4-yloxy]-pyrazolo[3,4-d]pyrimidin-1-yl}-N-propionyl-benzenesulfonamide |
| A249 | 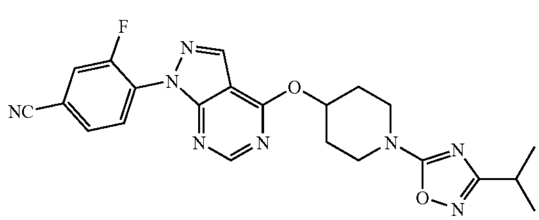 | 3-Fluoro-4-{4-[1-(3-isopropyl-[1,2,4]oxadiazol-5-yl)-piperidin-4-yloxy]-pyrazolo[3,4-d]pyrimidin-1-yl}-benzonitrile |
| A250 | 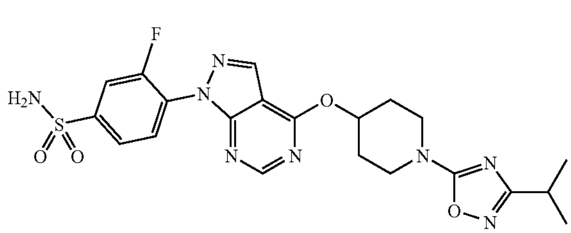 | 3-Fluoro-4-{4-[1-(3-isopropyl-[1,2,4]oxadiazol-5-yl)-piperidin-4-yloxy]-pyrazolo[3,4-d]pyrimidin-1-yl}-benzenesulfonamide |

TABLE A-continued

| Cmpd# | Structure | Chemical Name |
|---|---|---|
| A251 | 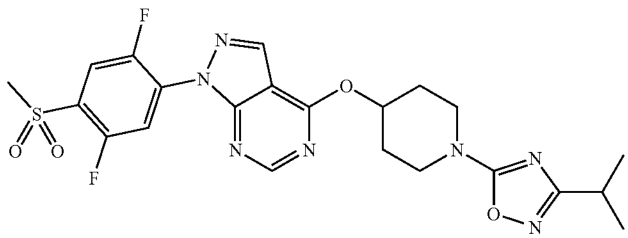 | 1-(2,5-Difluoro-4-methanesulfonyl-phenyl)-4-[1-(3-isopropyl-[1,2,4]oxadiazol-5-yl)-piperidin-4-yloxy]-1H-pyrazolo[3,4-d]pyrimidine |
| A252 | 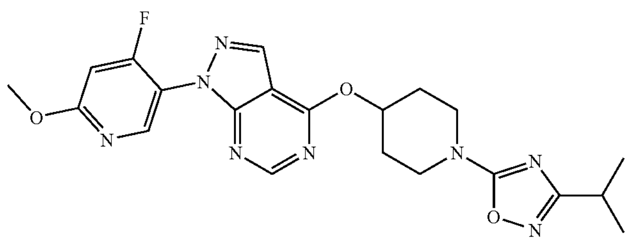 | 1-(4-Fluoro-6-methoxy-pyridin-3-yl)-4-[1-(3-isopropyl-[1,2,4]oxadiazol-5-yl)-piperidin-4-yloxy]-1H-pyrazolo[3,4-d]pyrimidine |
| A253 | 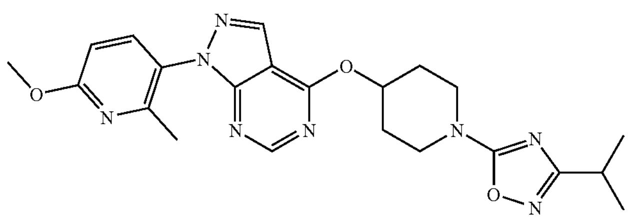 | 4-[1-(3-Isopropyl-[1,2,4]oxadiazol-5-yl)-piperidin-4-yloxy]-1-(6-methoxy-2-methyl-pyridin-3-yl)-1H-pyrazolo[3,4-d]pyrimidine |
| A254 | 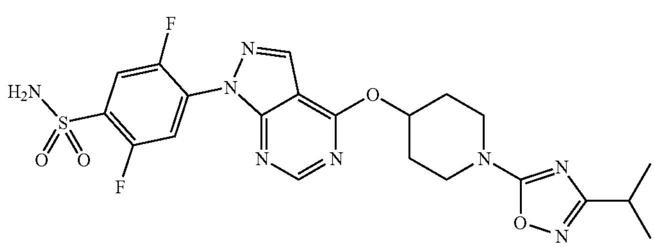 | 2,5-Difluoro-4-{4-[1-(3-isopropyl-[1,2,4]oxadiazol-5-yl)-piperidin-4-yloxy]-pyrazolo[3,4-d]pyrimidin-1-yl}-benzenesulfonamide |
| A255 | 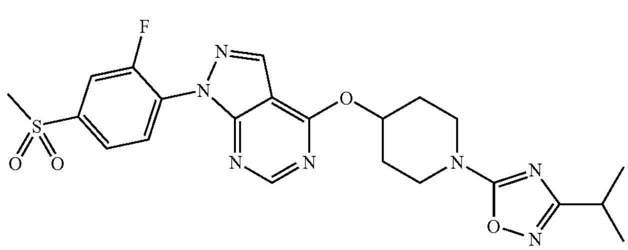 | 1-(2-Fluoro-4-methanesulfonyl-phenyl)-4-[4-(3-isopropyl-[1,2,4]oxadiazol-5-yl)-cyclohexyloxy]-1H-pyrazolo[3,4-d]pyrimidine |
| A256 | 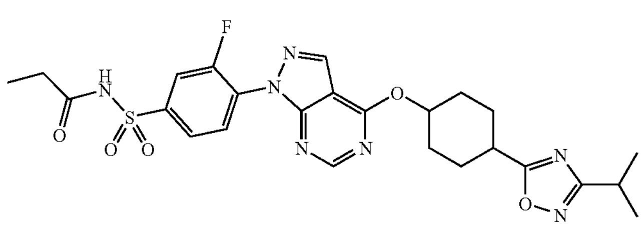 | 3-Fluoro-4-{4-[4-(3-isopropyl-[1,2,4]oxadiazol-5-yl)-cyclohexyloxy]-pyrazolo[3,4-d]pyrimidin-1-yl}-N-propionyl-benzenesulfonamide |

TABLE A-continued

| Cmpd# | Structure | Chemical Name |
|---|---|---|
| A257 | 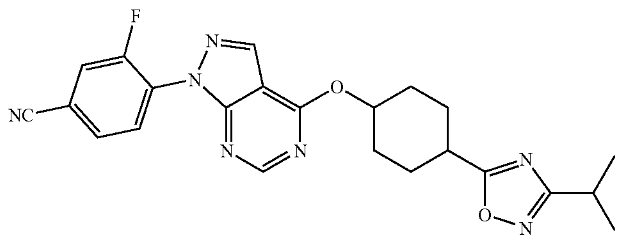 | 3-Fluoro-4-{4-[4-(3-isopropyl-[1,2,4]oxadiazol-5-yl)-cyclohexyloxy]-pyrazolo[3,4-d]pyrimidin-1-yl}-benzonitrile |
| A258 | 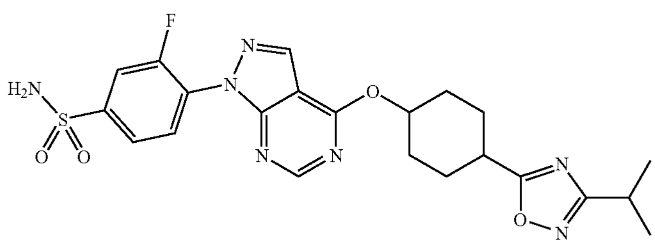 | 3-Fluoro-4-{4-[4-(3-isopropyl-[1,2,4]oxadiazol-5-yl)-cyclohexyloxy-pyrazolo[3,4-d]pyrimidin-1-yl}-benzenesulfonamide |
| A259 | 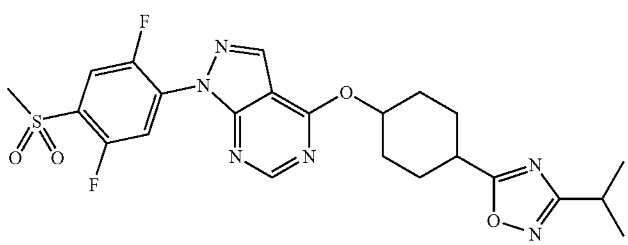 | 1-(2,5-Difluoro-4-methanesulfonyl-phenyl)-4-[4-(3-isopropyl-[1,2,4]oxadiazol-5-yl)-cyclohexyloxy]-1H-pyrazolo[3,4-d]pyrimidine |
| A260 | 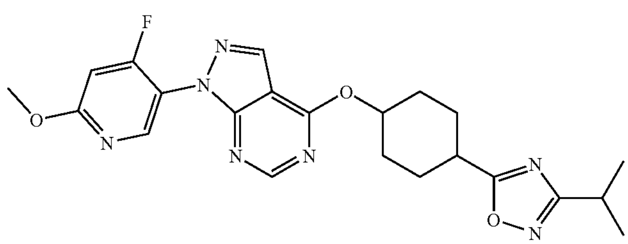 | 1-(4-Fluoro-6-methoxy-pyridin-3-yl)-4-[4-(3-isopropyl-[1,2,4]oxadiazol-5-yl)-cyclohexyloxy]-1H-pyrazolo[3,4-d]pyrimidine |
| A261 | 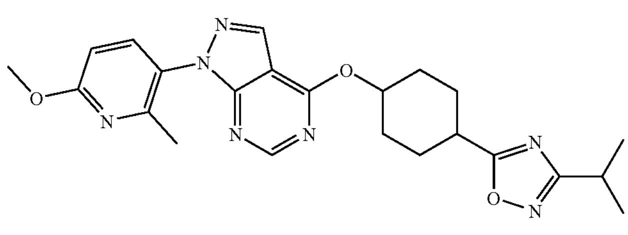 | 4-[4-(3-Isopropyl-[1,2,4]oxadiazol-5-yl)-cyclohexyloxy]-1-(6-methoxy-2-methyl-pyridin-3-yl)-1H-pyrazolo[3,4-d]pyrimidine |
| A262 | 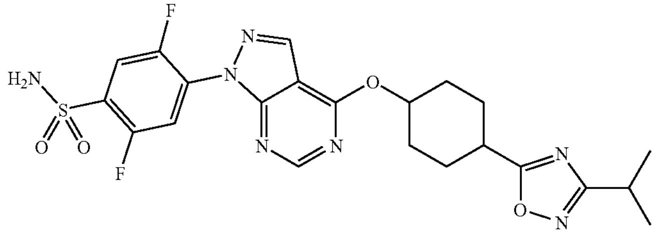 | 2,5-Difluoro-4-{4-[4-(3-isopropyl-[1,2,4]oxadiazol-5-yl)-cyclohexyloxy]-pyrazolo[3,4-d]pyrimidin-1-yl}-benzenesulfonamide |

TABLE A-continued

| Cmpd# | Structure | Chemical Name |
| --- | --- | --- |
| A263 | 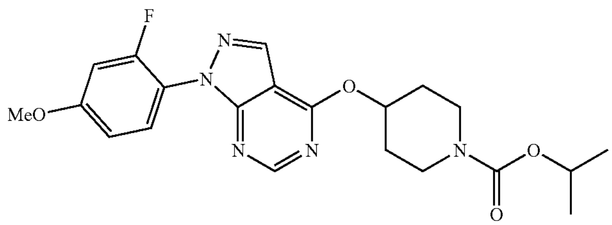 | 4-[1-(2-Fluoro-4-methoxy-phenyl)-1H-pyrazolo[3,4-d]pyrimidin-4-yloxy]-piperidine-1-carboxylic acid isopropyl ester |
| A264 | 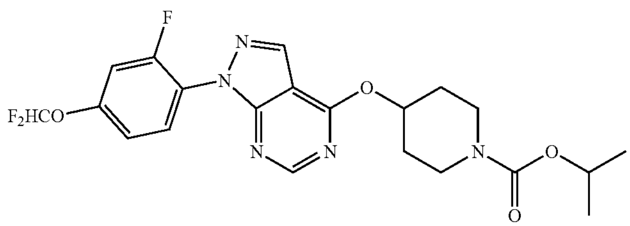 | 4-[1-(4-Difluoromethoxy-2-fluoro-phenyl)-1H-pyrazolol[3,4-d]pyrimidin-4-yloxy]-piperidine-1-carboxylic acid isopropyl ester |
| A265 | 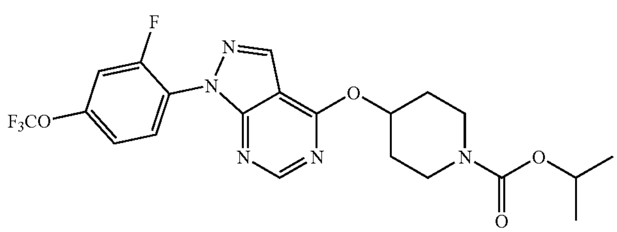 | 4-[1-(2-Fluoro-4-trifluoromethoxy-phenyl)-1H-pyrazolo[3,4-d]pyrimidin-4-yloxy]-piperidine-1-carboxylic acid isopropyl ester |
| A266 | 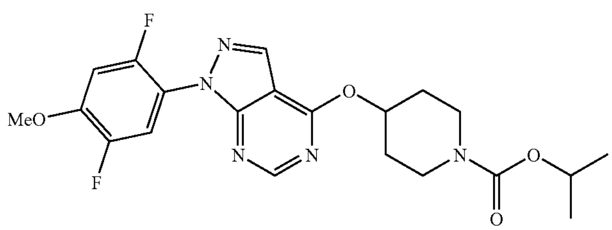 | 4-[1-(2,5-Difluoro-4-methoxy-phenyl)-1H-pyrazolo[3,4-d]pyrimidin-4-yloxy]-piperidine-1-carboxylic acid isopropyl ester |
| A267 | 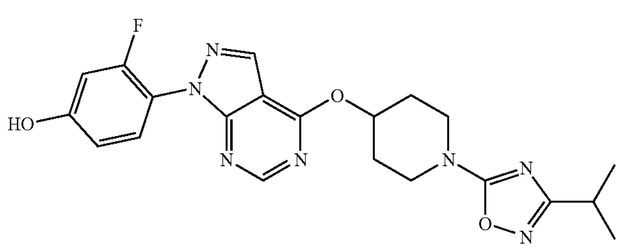 | 3-Fluoro-4-{4-[1-(3-isopropyl-[1,2,4]oxadiazol-5-yl)-piperidin-4-yloxy]-pyrazolo[3,4-d]pyrimidin-1-yl}-phenol |
| A268 | 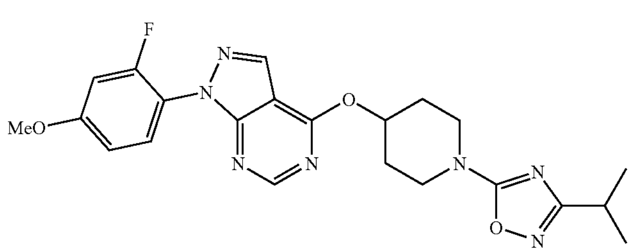 | 1-(2-Fluoro-4-methoxy-phenyl)-4-[1-(3-isopropyl-[1,2,4]oxadiazol-5-yl)-piperidin-4-yloxy]-1H-pyrazolo[3,4-d]pyrimidine |

TABLE A-continued

| Cmpd# | Structure | Chemical Name |
|---|---|---|
| A269 | 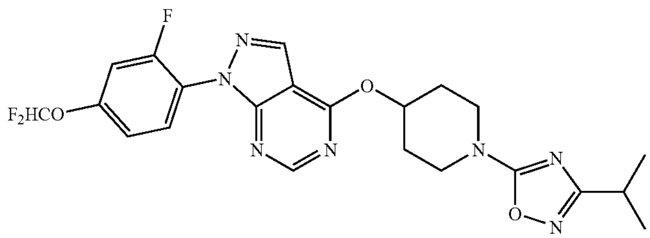 | 1-(4-Difluoromethoxy-2-fluoro-phenyl)-4-[1-(3-isopropyl-[1,2,4]oxadiazol-5-yl)-piperidin-4-yloxy]-1H-pyrazolo[3,4-d]pyrimidine |
| A270 | 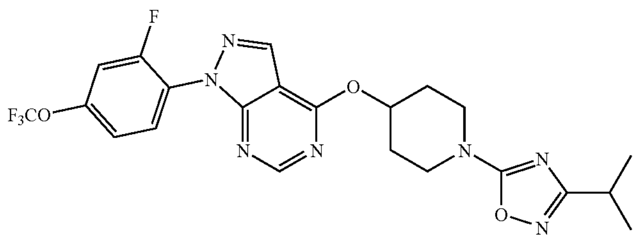 | 1-(2-Fluoro-4-trifluoromethoxy-phenyl)-4-[1-(3-isopropyl-[1,2,4]oxadiazol-5-yl)-piperidin-4-yloxy]-1H-pyrazolo[3,4-d]pyrimidine |
| A271 | 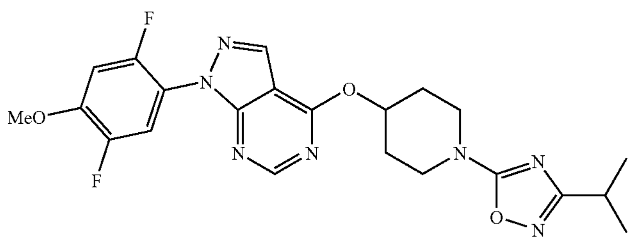 | 1-(2,5-Difluoro-4-methoxy-phenyl)-4-[1-(3-isopropyl-[1,2,4]oxadiazol-5-yl)-piperidin-4-yloxy]-1H-pyrazolo[3,4-d]pyrimidine |
| A272 | 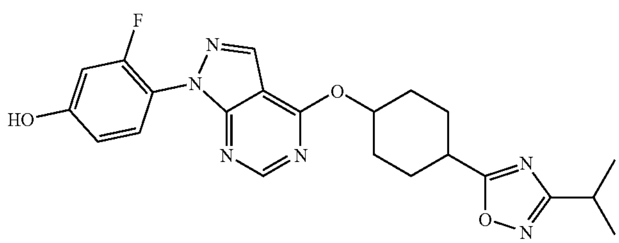 | 3-Fluoro-4-{4-[4-(3-isopropyl-[1,2,4]oxadiazol-5-yl)-cyclohexyloxy]-pyrazolo[3,4-d]pyrimidin-1-yl}-phenol |
| A273 | 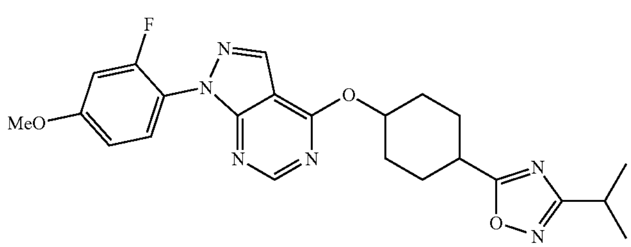 | 1-(2-Fluoro-4-methoxy-phenyl)-4-[4-(3-isopropyl-[1,2,4]oxadiazol-5-yl)-cyclohexyloxy]-1H-pyrazolo[3,4-d]pyrimidine |
| A274 | 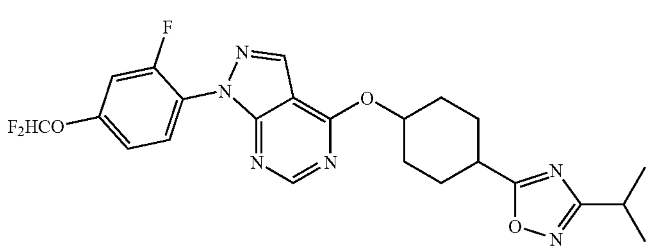 | 1-(4-Difluoromethoxy-2-fluoro-phenyl)-4-[4-(3-isopropyl-[1,2,4]oxadiazol-5-yl)-cyclohexyloxyl]-1H-pyrazolo[3,4-d]pyrimidine |

TABLE A-continued

| Cmpd# | Structure | Chemical Name |
|---|---|---|
| A275 | 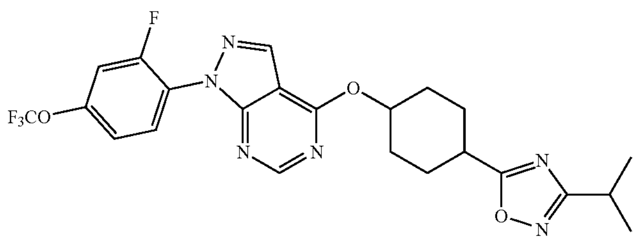 | 1-(2-Fluoro-4-trifluoromethoxy-phenyl)-4-[4-(3-isopropyl-[1,2,4]oxadiazol-5-yl)-cyclohexyloxy]-1H-pyrazolo[3,4-d]pyrimidine |

TABLE B

| Cmpd# | Structure | Chemical Name |
|---|---|---|
| B1 | 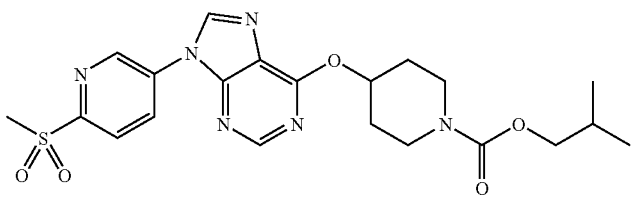 | 4-[9-(6-Methanesulfonyl-pyridin-3-yl)-9H-purin-6-yloxy]-piperidine-1-carboxylic acid isobutyl ester |
| B2 | 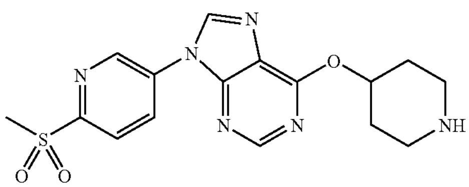 | 9-(6-Methanesulfonyl-pyridin-3-yl)-6-(piperidin-4-yloxy)-9H-purine |
| B3 | 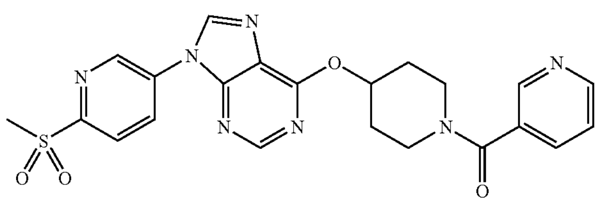 | {4-[9-(6-Methanesulfonyl-pyridin-3-yl)-9H-purin-6-yloxy]-piperidin-1-yl}-pyridin-3-yl-methanone |
| B4 | 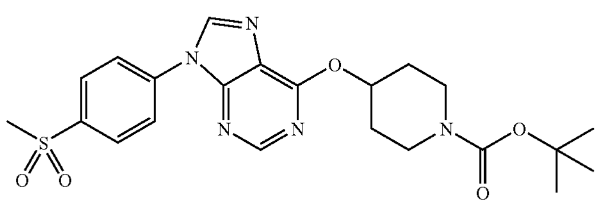 | 4-[9-(4-Methanesulfonyl-phenyl)-9H-purin-6-yloxy]-piperidine-1-carboxylic acid tert-butyl ester |
| B5 | 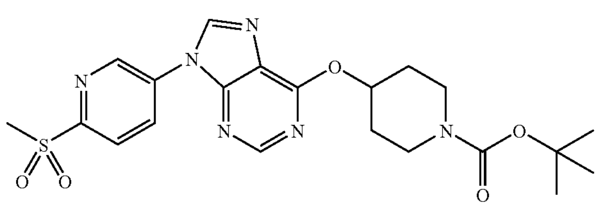 | 4-[9-(6-Methanesulfonyl-pyridin-3-yl)-9H-purin-6-yloxy]-piperidine-1-carboxylic acid tert-butyl ester |
| B6 | 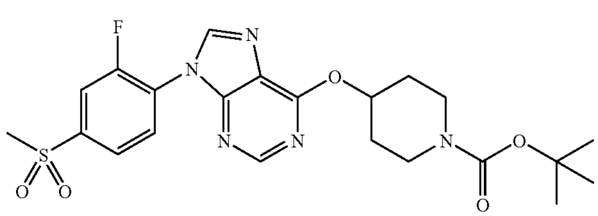 | 4-[9-(2-Fluoro-4-methanesulfonyl-phenyl)-9H-purin-6-yloxy]-piperidine-1-carboxylic acid tert-butyl ester |

TABLE B-continued

| Cmpd# | Structure | Chemical Name |
|---|---|---|
| B7 | 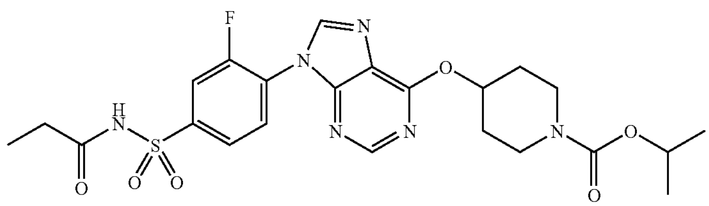 | 4-[9-(2-Fluoro-4-propionylsulfamoyl-phenyl)-9H-purin-6-yloxy]-piperidine-1-carboxylic acid isopropyl ester |
| B8 | 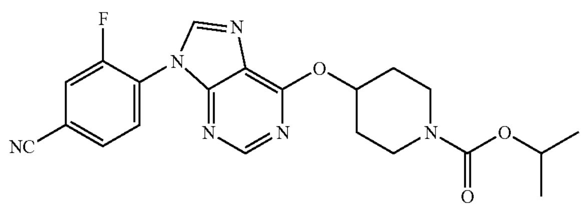 | 4-[9-(4-Cyano-2-fluoro-phenyl)-9H-purin-6-yloxy]-piperidine-1-carboxylic acid isopropyl ester |
| B9 | 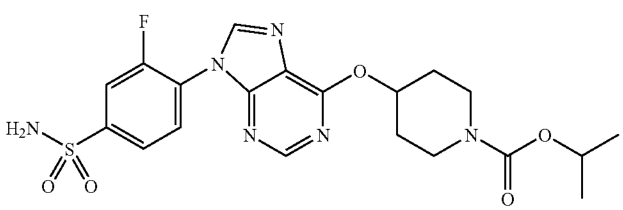 | 4-[9-(2-Fluoro-4-sulfamoyl-phenyl)-9H-purin-6-yloxy]-piperidine-1-carboxylic acid isopropyl ester |
| B10 | 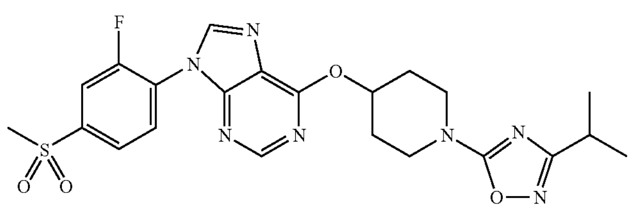 | 9-(2-Fluoro-4-methanesulfonyl-phenyl)-6-[1-(3-isopropyl-[1,2,4]oxadiazol-5-yl)-piperidin-4-yloxy]-9H-purine |
| B11 | 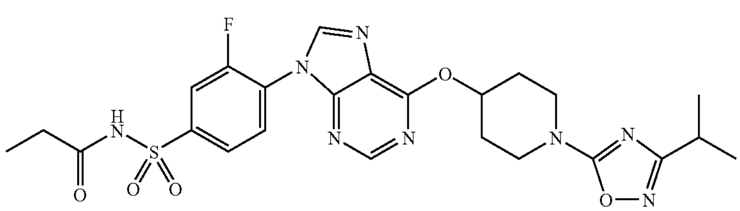 | 3-Fluoro-4-{6-[1-(3-isopropyl-[1,2,4]oxadiazol-5-yl)-piperidin-4-yloxy]-purin-9-yl}-N-propionyl-benzenesulfonamide |
| B12 | 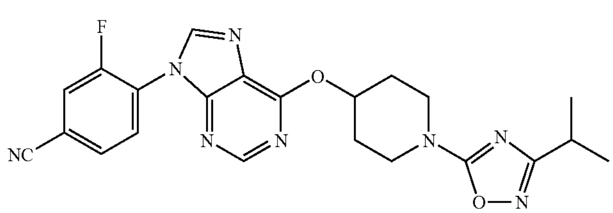 | 3-Fluoro-4-{6-[1-(3-isopropyl-[1,2,4]oxadiazol-5-yl)-piperidin-4-yloxy]-purin-9-yl}-benzonitrile |
| B13 | 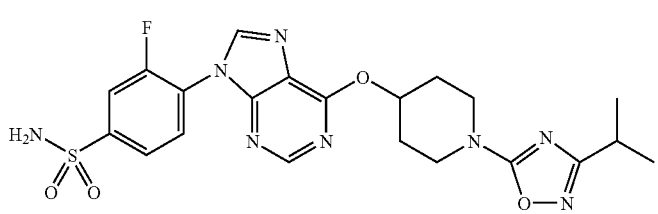 | 3-Fluoro-4-{6-[1-(3-isopropyl-[1,2,4]oxadiazol-5-yl)-piperidin-4-yloxy]-purin-9-yl}-benzenesulfonamide |

TABLE B-continued

| Cmpd# | Structure | Chemical Name |
|---|---|---|
| B14 | 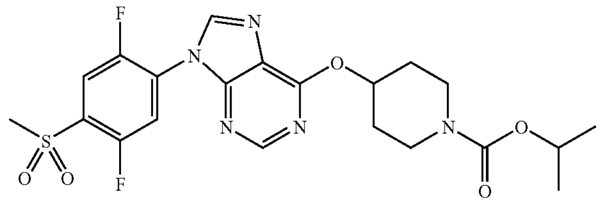 | 4-[9-(2,5-Difluoro-4-methanesulfonyl-phenyl)-9H-purin-6-yloxy]-piperidine-1-carboxylic acid isopropyl ester |
| B15 | 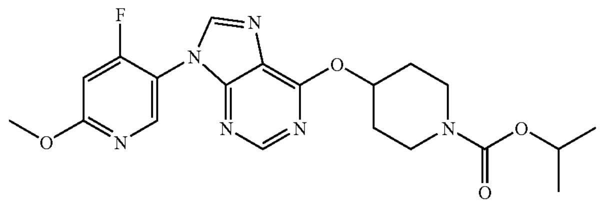 | 4-[9-(4-Fluoro-6-methoxy-pyridin-3-yl)-9H-purin-6-yloxy]-piperidine-1-carboxylic acid isopropyl ester |
| B16 | 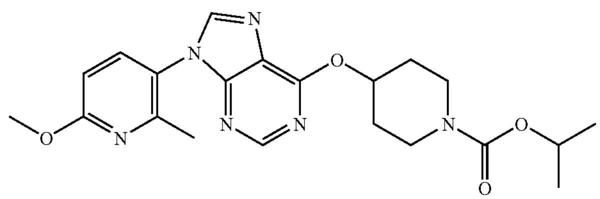 | 4-[9-(6-Methoxy-2-methyl-pyridin-3-yl)-9H-purin-6-yloxy]-piperidine-1-carboxylic acid isopropyl ester |
| B17 | 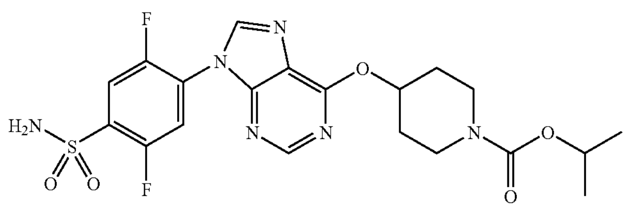 | 4-[9-(2,5-Difluoro-4-sulfamoyl-phenyl)-9H-purin-6-yloxy]-piperidine-1-carboxylic acid isopropyl ester |
| B18 | 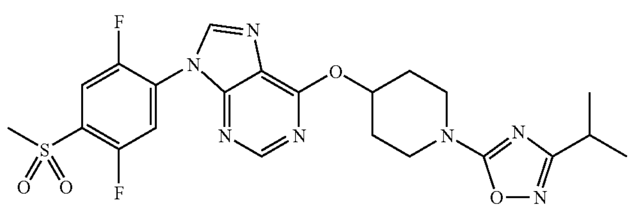 | 9-(2,5-Difluoro-4-methanesulfonyl-phenyl)-6-[1-(3-isopropyl-[1,2,4]oxadiazol-5-yl)-piperidin-4-yloxy]-9H-purine |
| B19 | 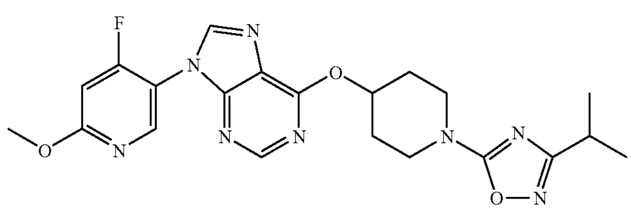 | 9-(4-Fluoro-6-methoxy-pyridin-3-yl)-6-[1-(3-isopropyl-[1,2,4]oxadiazol-5-yl)-piperidin-4-yloxy]-9H-purine |
| B20 | 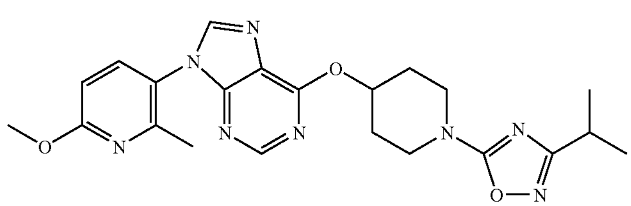 | 6-[1-(3-Isopropyl-[1,2,4]oxadiazol-5-yl)-piperidin-4-yloxy]-9-(6-methoxy-2-methyl-pyridin-3-yl)-9H-purine |

TABLE B-continued

| Cmpd# | Structure | Chemical Name |
|---|---|---|
| B21 | 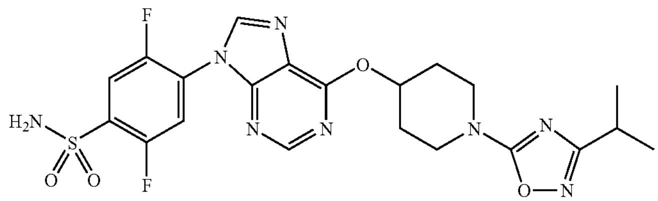 | 2,5-Difluoro-4-{6-[1-(3-isopropyl-[1,2,4]oxadiazol-5-yl)-piperidin-4-yloxy]-purin-9-yl}-benzenesulfonamide |
| B22 | 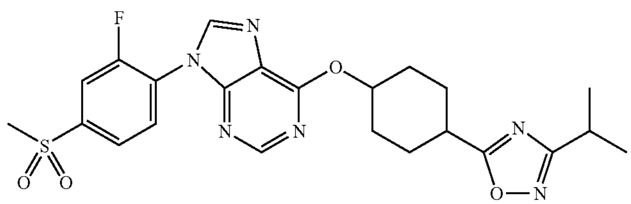 | 9-(2-Fluoro-4-methanesulfonyl-phenyl)-6-[4-(3-isopropyl-[1,2,4]oxadiazol-5-yl)-cyclohexyloxy]-9H-purine |
| B23 | 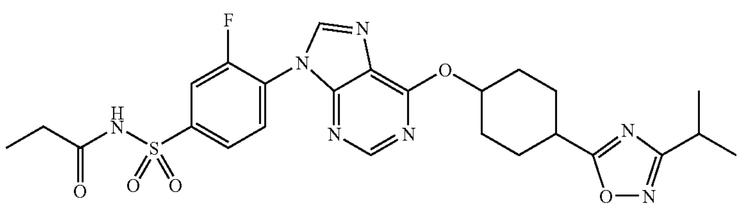 | 3-Fluoro-4-{6-[4-(3-isopropyl-[1,2,4]oxadiazol-5-yl)-cyclohexyloxy]-purin-9-yl}-N-propionyl-benzenesulfonamide |
| B24 | 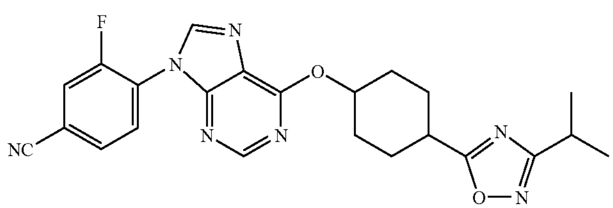 | 3-Fluoro-4-{6-[4-(3-isopropyl-[1,2,4]oxadiazol-5-yl)-cyclohexyloxy]-purin-9-yl}-benzonitrile |
| B25 | 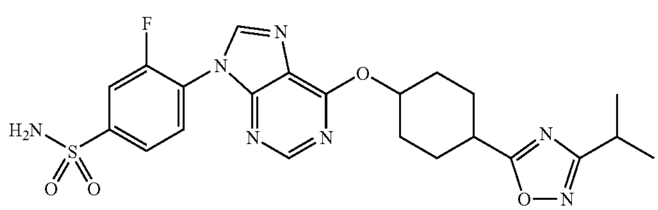 | 3-Fluoro-4-{6-[4-(3-isopropyl-[1,2,4]oxadiazol-5-yl)-cyclohexyloxy]-purin-9-yl}-benzenesulfonamide |
| B26 | 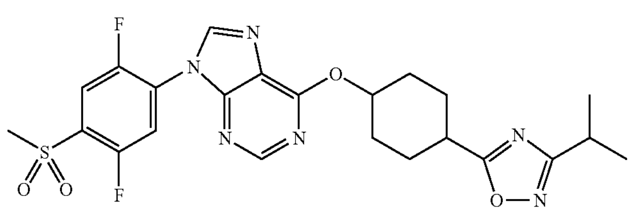 | 9-(2,5-Difluoro-4-methanesulfonyl-phenyl)-6-[4-(3-isopropyl-[1,2,4]oxadiazol-5-yl)-cyclohexyloxy]-9H-purine |
| B27 | 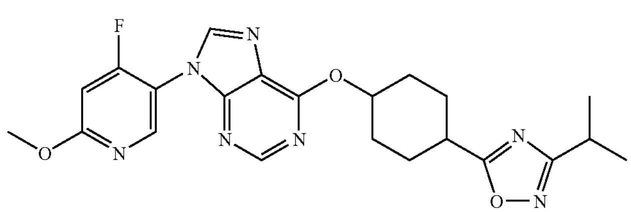 | 9-(4-Fluoro-6-methoxy-pyridin-3-yl)-6-[4-(3-isopropyl-[1,2,4]oxadiazol-5-yl)-cyclohexyloxy]-9H-purine |

TABLE B-continued

| Cmpd# | Structure | Chemical Name |
|---|---|---|
| B28 | 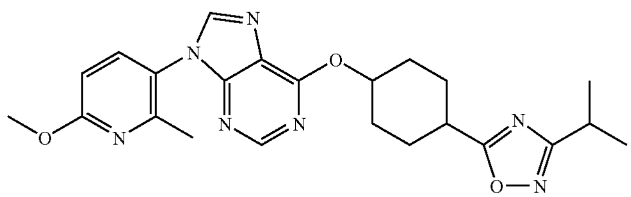 | 6-[4-(3-Isopropyl-[1,2,4]oxadiazol-5-yl)-cyclohexyloxy]-9-(6-methoxy-2-methyl-pyridin-3-yl)-9H-purine |
| B29 | 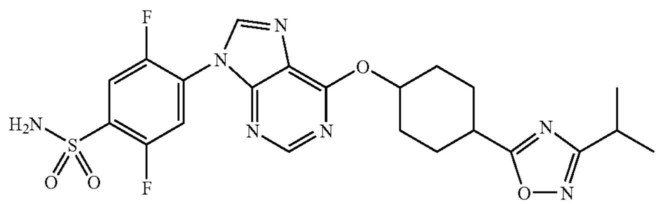 | 2,5-Difluoro-4-{6-[4-(3-isopropyl-[1,2,4]oxadiazol-5-yl)-cyclohexyloxy]-purin-9-yl}-benzenesulfonamide |

TABLE C

| Cmpd# | Structure | Chemical Name |
|---|---|---|
| C1 | 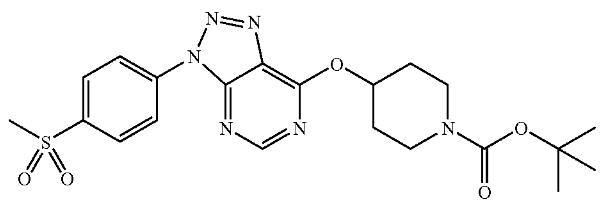 | 4-[3-(4-Methanesulfonyl-phenyl)-3H-[1,2,3]triazolo[4,5-d]pyrimidin-7-yloxy]-piperidine-1-carboxylic acid tert-butyl ester |
| C2 | 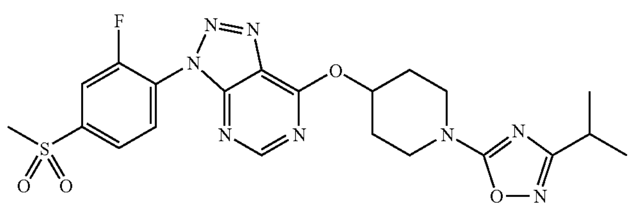 | 3-(2-Fluoro-4-methanesulfonyl-phenyl)-7-[1-(3-isopropyl-[1,2,4]oxadiazol-5-yl)-piperidin-4-yloxy]-3H-[1,2,3]triazolo[4,5-d]pyrimidine |
| C3 | 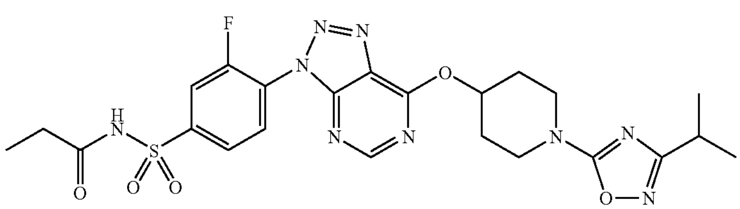 | 3-Fluoro-4-{7-[1-(3-isopropyl-[1,2,4]oxadiazol-5-yl)-piperidin-4-yloxy]-[1,2,3]triazolo[4,5-d]pyrimidin-3-yl}-N-propionyl-benzenesulfonamide |
| C4 | 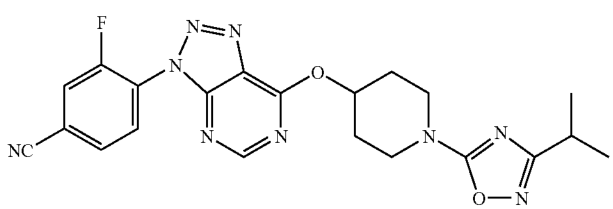 | 3-Fluoro-4-{7-[1-(3-isopropyl-[1,2,4]oxadiazol-5-yl)-piperidin-4-yloxy]-[1,2,3]triazolo[4,5-d]pyrimidin-3-yl}-benzonitrile |
| C5 | 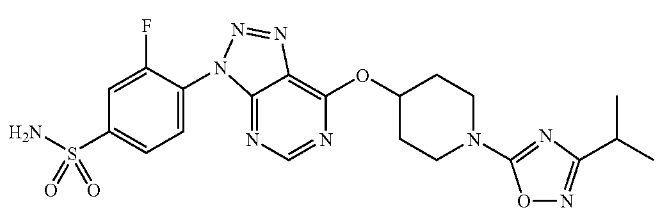 | 3-Fluoro-4-{7-[1-(3-isopropyl-[1,2,4]oxadiazol-5-yl)-piperidin-4-yloxy]-[1,2,3]triazolo[4,5-d]pyrimidin-3-yl}-benzenesulfonamide |

TABLE C-continued

| Cmpd# | Structure | Chemical Name |
|---|---|---|
| C6 | 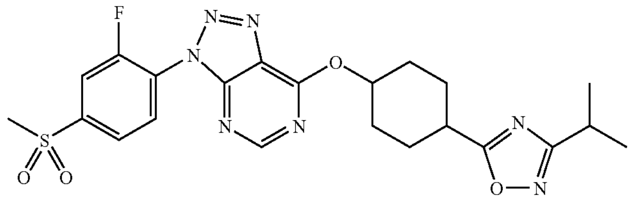 | 3-(2-Fluoro-4-methanesulfonyl-phenyl)-7-[4-(3-isopropyl-[1,2,4]oxadiazol-5-yl)-cyclohexyloxy]-3H-[1,2,3]triazolo[4,5-d]pyrimidine |
| C7 | 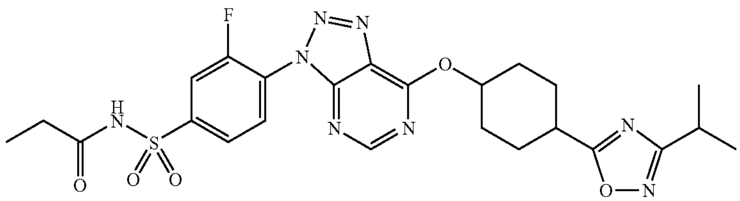 | 3-Fluoro-4-{7-[4-(3-isopropyl-[1,2,4]oxadiazol-5-yl)-cyclohexyloxy]-[1,2,3]triazolo[4,5-d]pyrimidin-3-yl}-N-propionyl-benzenesulfonamide |
| C8 | 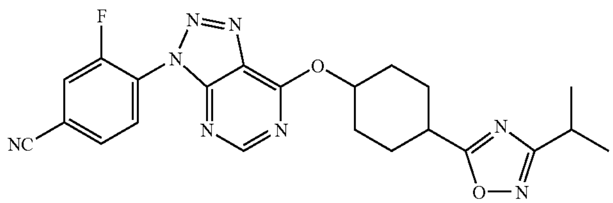 | 3-Fluoro-4-{7-[4-(3-isopropyl-[1,2,4]oxadiazol-5-yl)-cyclohexyloxy]-[1,2,3]triazolo[4,5-d]pyrimidin-3-yl}-benzonitrile |
| C9 | 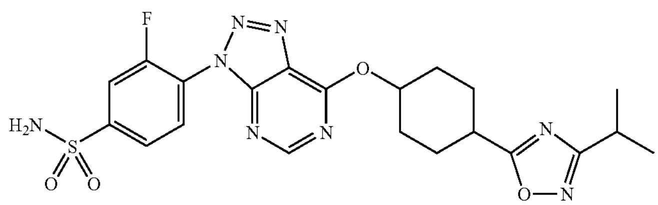 | 3-Fluoro-4-{7-[4-(3-isopropyl-[1,2,4]oxadiazol-5-yl)-cyclohexyloxy]-[1,2,3]triazolo[4,5-d]pyrimidin-3-yl}-benzenesulfonamide |
| C10 | 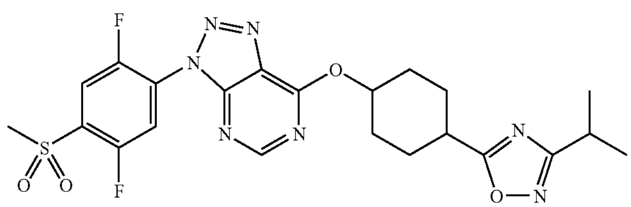 | 3-(2,5-Difluoro-4-methanesulfonyl-phenyl)-7-[4-(3-isopropyl-[1,2,4]oxadiazol-5-yl)-cyclohexyloxy]-3H-[1,2,3]triazolo[4,5-d]pyrimidine |
| C11 | 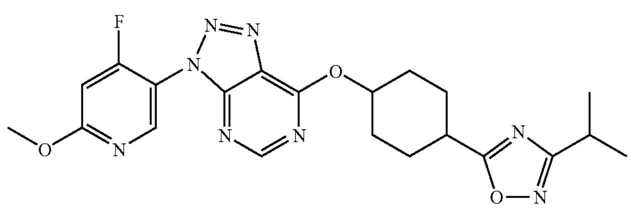 | 3-(4-Fluoro-6-methoxy-pyridin-3-yl)-7-[4-(3-isopropyl-[1,2,4]oxadiazol-5-yl)-cyclohexyloxy]-3H-[1,2,3]triazolo[4,5-d]pyrimidine |
| C12 | 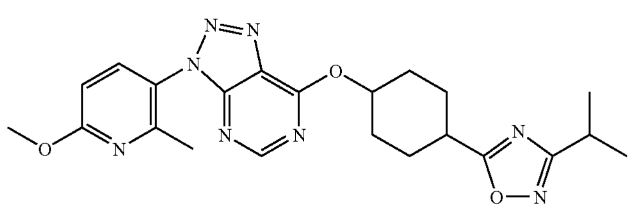 | 7-[4-(3-Isopropyl-[1,2,4]oxadiazol-5-yl)-cyclohexyloxy]-3-(6-methoxy-2-methyl-pyridin-3-yl)-3H-[1,2,3]triazolo[4,5-d]pyrimidine |

TABLE C-continued

| Cmpd# | Structure | Chemical Name |
| --- | --- | --- |
| C13 | 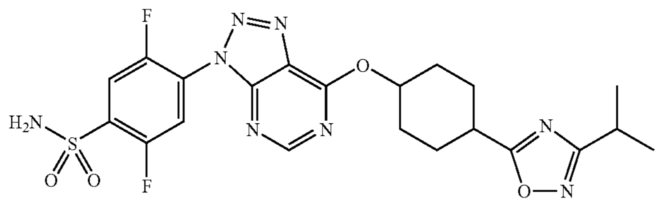 | 2,5-Difluoro-4-{7-[4-(3-isopropyl-[1,2,4]oxadiazol-5-yl)-cyclohexyloxy]-[1,2,3]triazolo[4,5-d]pyrimidin-3-yl}-benzenesulfonamide |
| C14 | 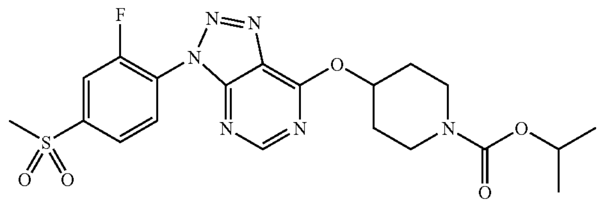 | 4-[3-(2-Fluoro-4-methanesulfonyl-phenyl)-3H-[1,2,3]triazolo[4,5-d]pyrimidin-7-yloxy]-piperidine-1-carboxylic acid isopropyl ester |
| C15 | 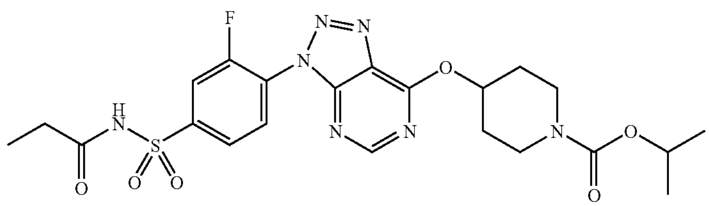 | 4-[3-(2-Fluoro-4-propionylsulfamoyl-phenyl)-3H-[1,2,3]triazolo[4,5-d]pyrimidin-7-yloxy]-piperidine-1-carboxylic acid isopropyl ester |
| C16 | 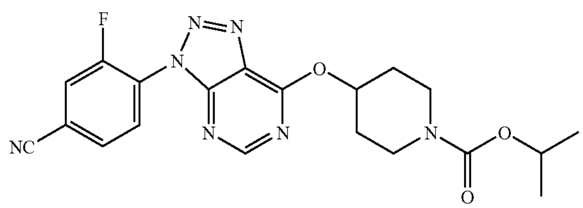 | 4-[3-(4-Cyano-2-fluoro-phenyl)-3H-[1,2,3]triazolo[4,5-d]pyrimidin-7-yloxy]-piperidine-1-carboxylic acid isopropyl ester |
| C17 | 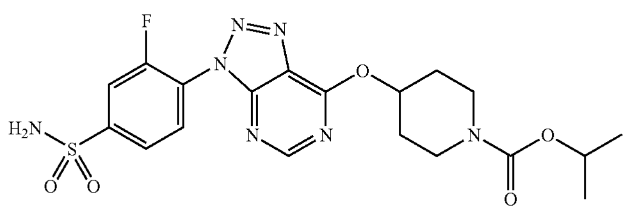 | 4-[3-(2-Fluoro-4-sulfamoyl-phenyl)-3H-[1,2,3]triazolo[4,5-d]pyrimidin-7-yloxy]-piperidine-1-carboxylic acid isopropyl ester |
| C18 | 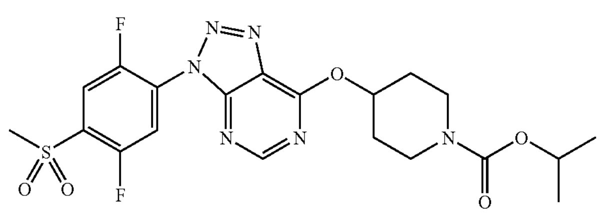 | 4-[3-(2,5-Difluoro-4-methanesulfonyl-phenyl)-3H-[1,2,3]triazolo[4,5-d]pyrimidin-7-yloxy]-piperidine-1-carboxylic acid isopropyl ester |
| C19 | 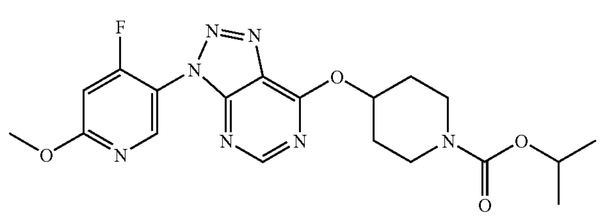 | 4-[3-(4-Fluoro-6-methoxy-pyridin-3-yl)-3H-[1,2,3]triazolo[4,5-d]pyrimidin-7-yloxy]-piperidine-1-carboxylic acid isopropyl ester |

TABLE C-continued

| Cmpd# | Structure | Chemical Name |
|---|---|---|
| C20 | 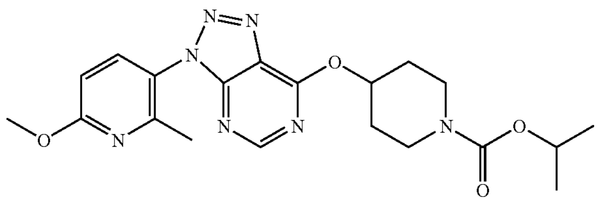 | 4-[3-(6-Methoxy-2-methyl-pyridin-3-yl)-3H-[1,2,3]triazolo[4,5-d]pyrimidin-7-yloxy]-piperidine-1-carboxylic acid isopropyl ester |
| C21 | 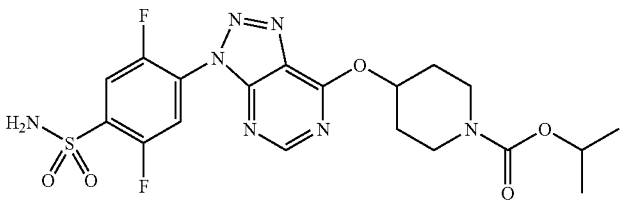 | 4-[3-(2,5-Difluoro-4-sulfamoyl-phenyl)-3H-[1,2,3]triazolo[4,5-d]pyrimidin-7-yloxy]-piperidine-1-carboxylic acid isopropyl ester |
| C22 | 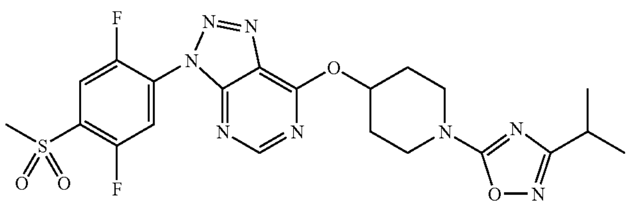 | 3-(2,5-Difluoro-4-methanesulfonyl-phenyl)-7-[1-(3-isopropyl-[1,2,4]oxadiazol-5-yl)-piperidin-4-yloxy]-3H-[1,2,3]triazolo[4,5-d]pyrimidine |
| C23 | 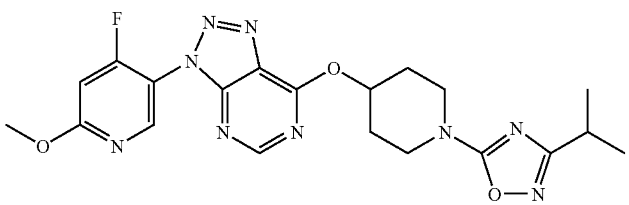 | 3-(4-Fluoro-6-methoxy-pyridin-3-yl)-7-[1-(3-isopropyl-[1,2,4]oxadiazol-5-yl)-piperidin-4-yloxy]-3H-[1,2,3]triazolo[4,5-d]pyrimidine |
| C24 | 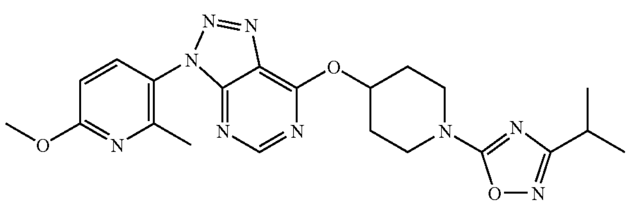 | 7-[1-(3-Isopropyl-[1,2,4]oxadiazol-5-yl)-piperidin-4-yloxy]-3-(6-methoxy-2-methyl-pyridin-3-yl)-3H-[1,2,3]triazolo[4,5-d]pyrimidine |
| C25 | 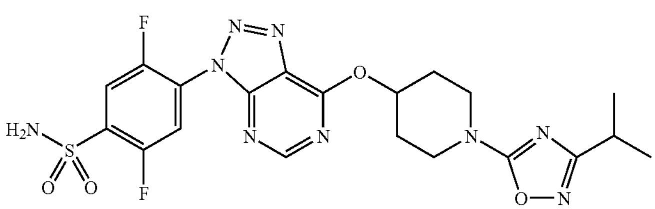 | 2,5-Difluoro-4-{7-[1-(3-isopropyl-[1,2,4]oxadiazol-5-yl)-piperidin-4-yloxy]-[1,2,3]triazolo[4,5-d]pyrimidin-3-yl}-benzenesulfonamide |

TABLE D

| Cmpd# | Structure | Chemical Name |
|---|---|---|
| D1 | 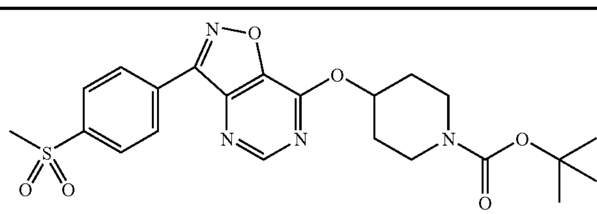 | 4-[3-(4-Methanesulfonyl-phenyl)-isoxazolo[4,5-d]pyrimidin-7-yloxy]-piperidine-1-carboxylic acid tert-butyl ester |

TABLE D-continued

| Cmpd# | Structure | Chemical Name |
|---|---|---|
| D2 | 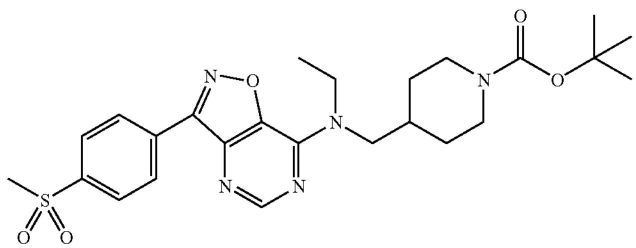 | 4-({Ethyl-[3-(4-methanesulfonyl-phenyl)-isoxazolo[4,5-d]pyrimidin-7-yl]-amino}-methyl)-piperidine-1-carboxylic acid tert-butyl ester |
| D3 | 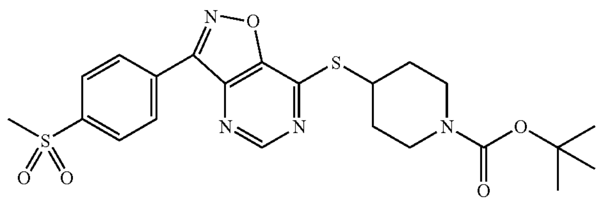 | 4-[3-(4-Methanesulfonyl-phenyl)-isoxazolo[4,5-d]pyrimidin-7-ylsulfanyl]-piperidine-1-carboxylic acid tert-butyl ester |
| D4 | 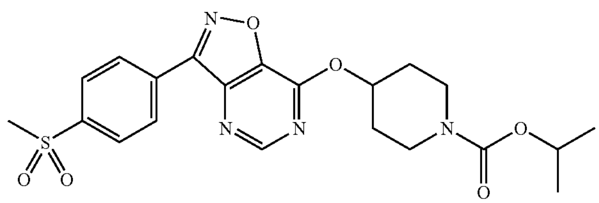 | 4-[3-(4-Methanesulfonyl-phenyl)-isoxazolo[4,5-d]pyrimidin-7-yloxy]-piperidine-1-carboxylic acid isopropyl ester |

TABLE E

| Cmpd# | Structure | Chemical Name |
|---|---|---|
| E1 | 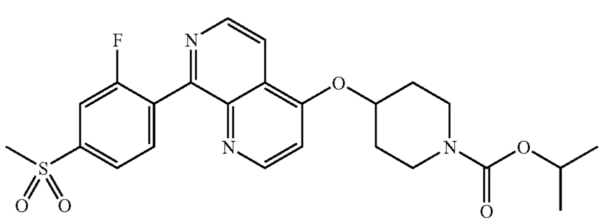 | 4-[8-(2-Fluoro-4-methanesulfonyl-phenyl)-[1,7]naphthyridin-4-yloxy]-piperidine-1-carboxylic acid isopropyl ester |

TABLE F

| Cmpd# | Structure | Chemical Name |
|---|---|---|
| F1 | 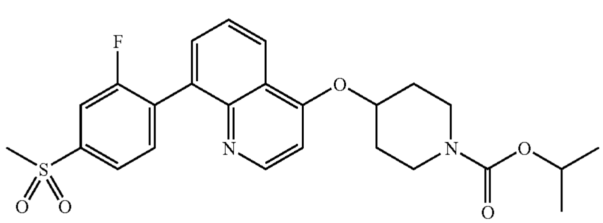 | 4-[8-(2-Fluoro-4-methanesulfonyl-phenyl)-quinolin-4-yloxy]-piperidine-1-carboxylic acid isopropyl ester |

TABLE F-continued

| Cmpd# | Structure | Chemical Name |
|---|---|---|
| F2 | 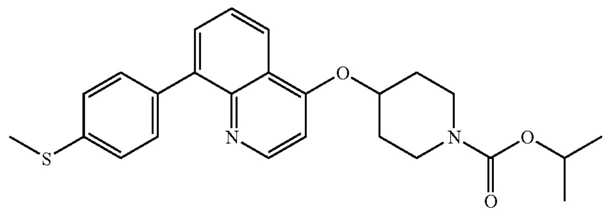 | 4-[8-(4-Methylsulfanyl-phenyl)-quinolin-4-yloxy]-piperidine-1-carboxylic acid isopropyl ester |
| F3 | 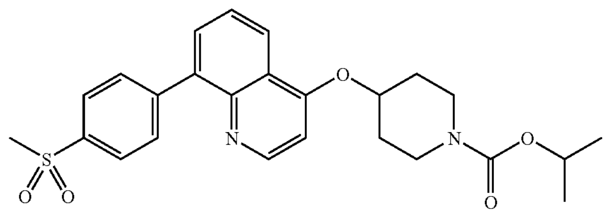 | 4-[8-(4-Methanesulfonyl-phenyl)-quinolin-4-yloxy]-piperidine-1-carboxylic acid isopropyl ester |
| F4 | 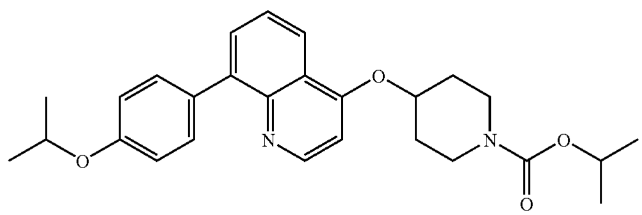 | 4-[8-(4-Isopropoxy-phenyl)-quinolin-4-yloxy]-piperidine-1-carboxylic acid isopropyl ester |
| F5 | 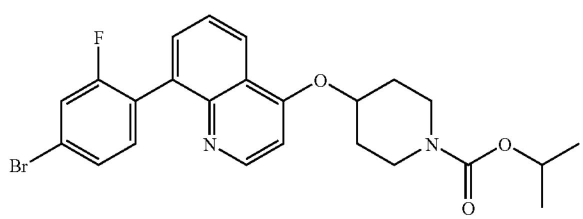 | 4-[8-(4-Bromo-2-fluoro-phenyl)-quinolin-4-yloxy]-piperidine-1-carboxylic acid isopropyl ester |
| F6 | 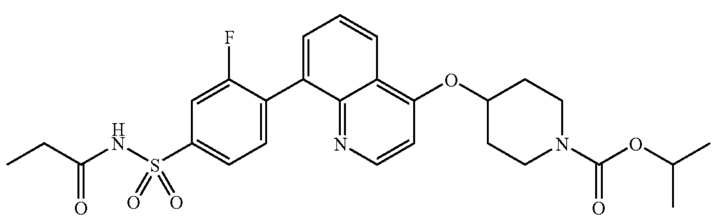 | 4-[8-(2-Fluoro-4-propionylsulfamoyl-phenyl)-quinolin-4-yloxy]-piperidine-1-carboxylic acid isopropyl ester |
| F7 | 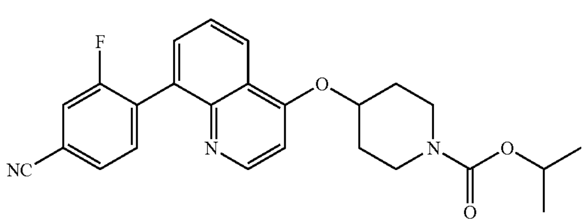 | 4-[8-(4-Cyano-2-fluoro-phenyl)-quinolin-4-yloxy]-piperidine-1-carboxylic acid isopropyl ester |
| F8 | 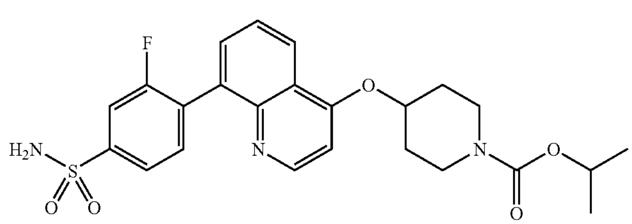 | 4-[8-(2-Fluoro-4-sulfamoyl-phenyl)-quinolin-4-yloxy]-piperidine-1-carboxylic acid isopropyl ester |

TABLE F-continued

| Cmpd# | Structure | Chemical Name |
|---|---|---|
| F9 | 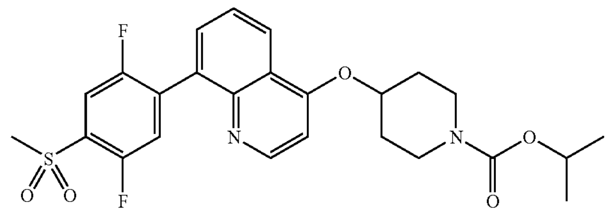 | 4-[8-(2,5-Difluoro-4-methanesulfonyl-phenyl)-quinolin-4-yloxy]-piperidine-1-carboxylic acid isopropyl ester |
| F10 | 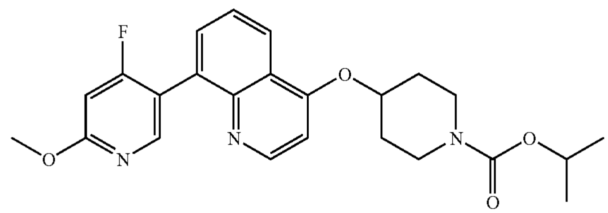 | 4-[8-(4-Fluoro-6-methoxy-pyridin-3-yl)-quinolin-4-yloxy]-piperidine-1-carboxylic acid isopropyl ester |
| F11 | 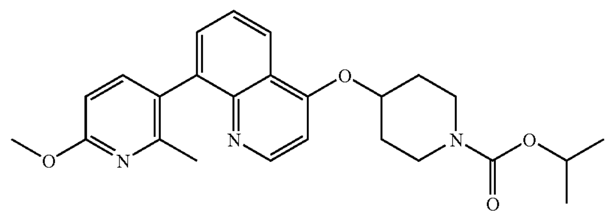 | 4-[8-(6-Methoxy-2-methyl-pyridin-3-yl)-quinolin-4-yloxy]-piperidine-1-carboxylic acid isopropyl ester |
| F12 | 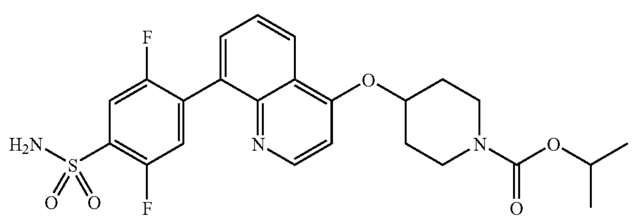 | 4-[8-(2,5-Difluoro-4-sulfamoyl-phenyl)-quinolin-4-yloxy]-piperdine-1-carboxylic acid isopropyl ester |
| F13 | 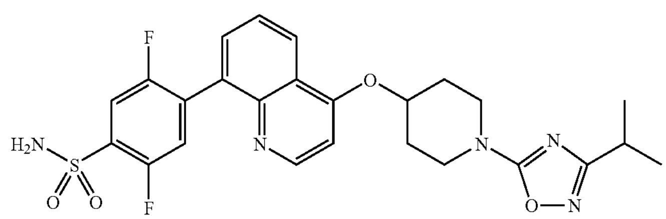 | 2,5-Difluoro-4-{4-[1-(3-isopropyl-[1,2,4]oxadiazol-5-yl)-piperidin-4-yloxy]-quinolin-8-yl}-benzenesulfonamide |
| F14 | 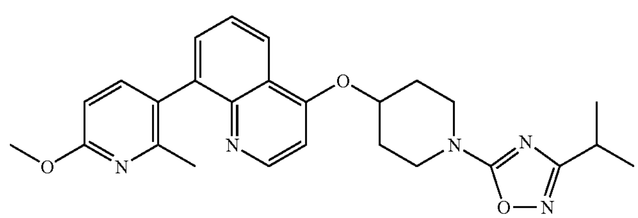 | 4-[1-(3-Isopropyl-[1,2,4]oxadiazol-5-yl)-piperidin-4-yloxy]-8-(6-methoxy-2-methyl-pyridin-3-yl)-quinoline |
| F15 | 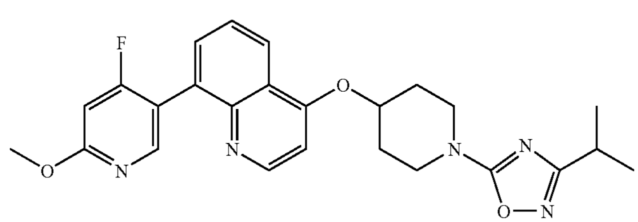 | 8-(4-Fluoro-6-methoxy-pyridin-3-yl)-4-[1-(3-isopropyl-[1,2,4]oxadiazol-5-yl)-piperidin-4-yloxy]-quinoline |

TABLE F-continued

| Cmpd# | Structure | Chemical Name |
|---|---|---|
| F16 | 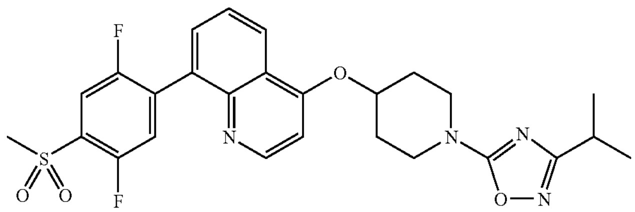 | 8-(2,5-Difluoro-4-methanesulfonyl-phenyl)-4-[1-(3-isopropyl-[1,2,4]oxadiazol-5-yl)-piperidin-4-yloxy]-quinoline |
| F17 | 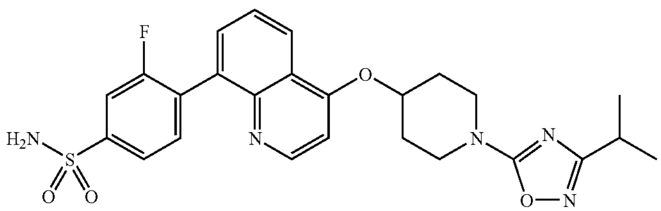 | 3-Fluoro-4-{4-[1-(3-isopropyl-[1,2,4]oxadiazol-5-yl)-piperidin-4-yloxy]-quinolin-8-yl}-benzenesulfonamide |
| F18 | 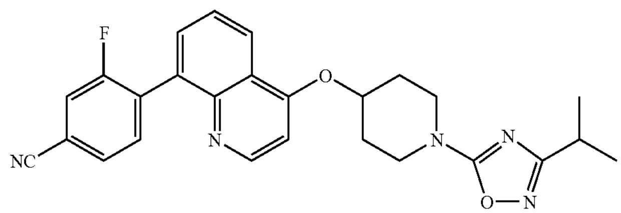 | 3-Fluoro-4-{4-[1-(3-isopropyl-[1,2,4]oxadiazol-5-yl)-piperidin-4-yloxy]-quinolin-8-yl}-benzonitrile |
| F19 | 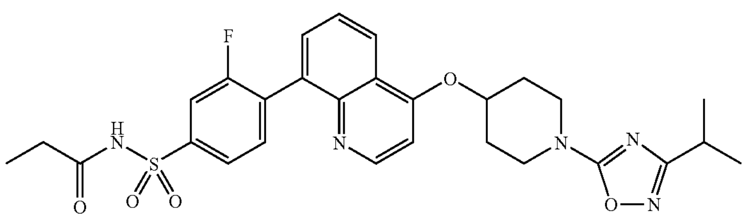 | 3-Fluoro-4-{4-[1-(3-isopropyl-[1,2,4]oxadiazol-5-yl)-piperidin-4-yloxy]-quinolin-8-yl}-N-propionyl-benzenesulfonamide |
| F20 | 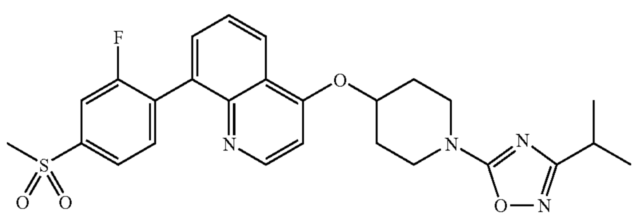 | 8-(2-Fluoro-4-methanesulfonyl-phenyl)-4-[1-(3-isopropyl-[1,2,4]oxadiazol-5-yl)-piperidin-4-yloxy]-quinoline |
| F21 | 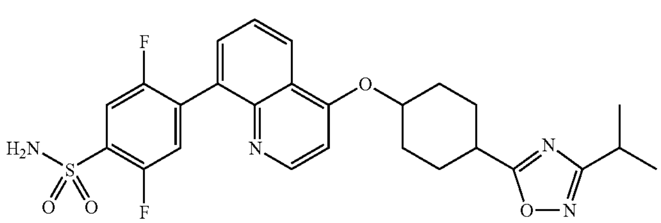 | 2,5-Difluoro-4-{4-[4-(3-isopropyl-[1,2,4]oxadiazol-5-yl)-cyclohexyloxy]-quinolin-8-yl}-benzenesulfonamide |
| F22 | 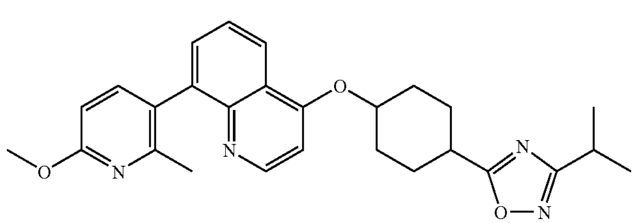 | 4-[4-(3-Isopropyl-[1,2,4]oxadiazol-5-yl)-cyclohexyloxy]-8-(6-methoxy-2-methyl-pyridin-3-yl)-quinoline |

TABLE F-continued

| Cmpd# | Structure | Chemical Name |
| --- | --- | --- |
| F23 | 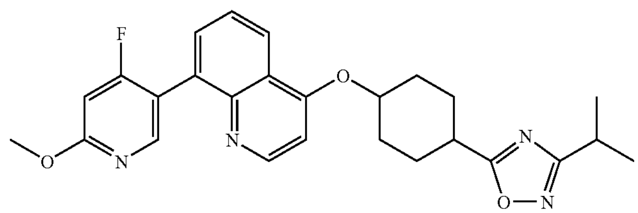 | 8-(4-Fluoro-6-methoxy-pyridin-3-yl)-4-[4-(3-isopropyl-[1,2,4]oxadiazol-5-yl)-cyclohexyloxy]-quinoline |
| F24 | 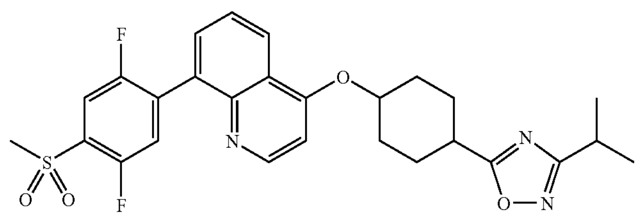 | 8-(2,5-Difluoro-4-methanesulfonyl-phenyl)-4-[4-(3-isopropyl-[1,2,4]oxadiazol-5-yl)-cyclohexyloxy]-quinoline |
| F25 | 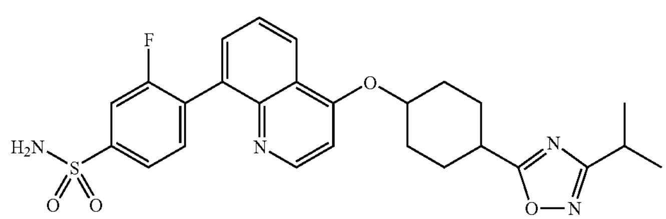 | 3-Fluoro-4-{4-[4-(3-isopropyl-[1,2,4]oxadiazol-5-yl)-cyclohexyloxy]-quinolin-8-yl}-benzenesulfonamide |
| F26 | 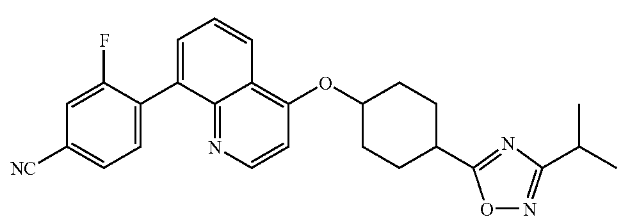 | 3-Fluoro-4-{4-[4-(3-isopropyl-[1,2,4]oxadiazol-5-yl)-cyclohexyloxy]-quinolin-8-yl}-benzonitrile |
| F27 | 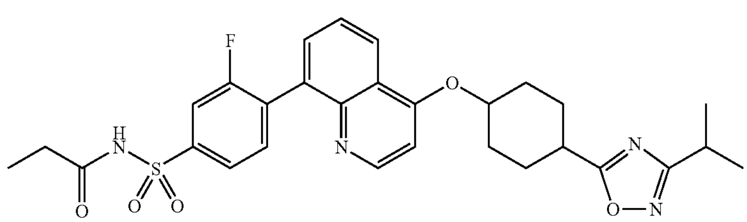 | 3-Fluoro-4-{4-[4-(3-isopropyl-[1,2,4]oxadiazol-5-yl)-cyclohexyloxy]-quinolin-8-yl}-N-propionyl-benzenesulfonamide |
| F28 | 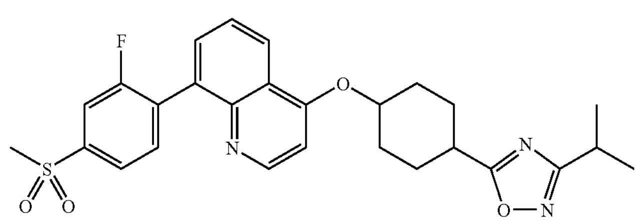 | 8-(2-Fluoro-4-methanesulfonyl-phenyl)-4-[4-(3-isopropyl-[1,2,4]oxadiazol-5-yl)-cyclohexyloxy]-quinoline |

TABLE G

| Cmpd# | Structure | Chemical Name |
|---|---|---|
| G1 | 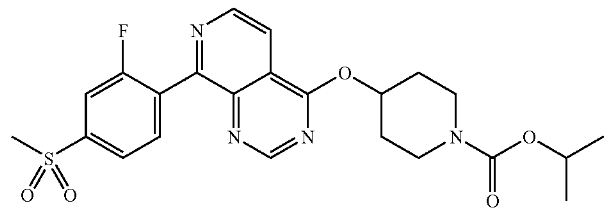 | 4-[8-(2-Fluoro-4-methanesulfonyl-phenyl)-pyrido[3,4-d]pyrimidin-4-yloxy]-piperidine-1-carboxylic acid isopropyl ester |
| G2 | 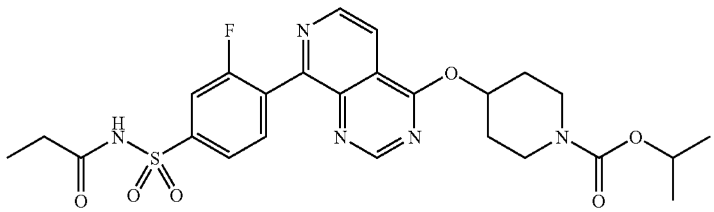 | 4-[8-(2-Fluoro-4-propionylsulfamoyl-phenyl)-pyrido[3,4-d]pyrimidin-4-yloxy]-piperidine-1-carboxylic acid isopropyl ester |
| G3 | 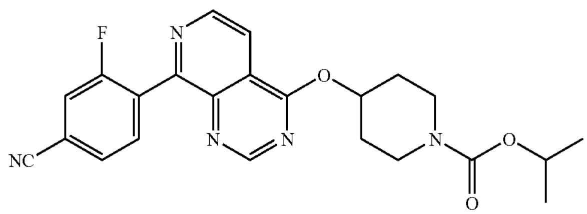 | 4-[8-(4-Cyano-2-fluoro-phenyl)-pyrido[3,4-d]pyrimidin-4-yloxy]-piperidine-1-carboxylic acid isopropyl ester |
| G4 | 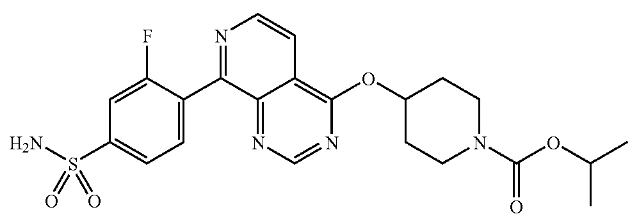 | 4-[8-(2-Fluoro-4-sulfamoyl-phenyl)-pyrido[3,4-d]pyrimidin-4-yloxy]-piperidine-1-carboxylic acid isopropyl ester |
| G5 | 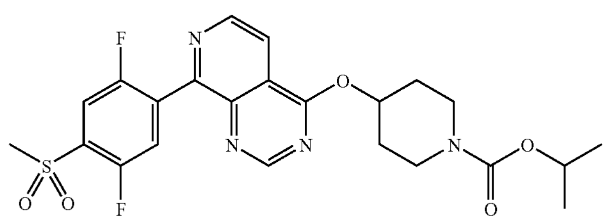 | 4-[8-(2,5-Difluoro-4-methanesulfonyl-phenyl)-pyrido[3,4-d]pyrimidin-4-yloxy]-piperidine-1-carboxylic acid isopropyl ester |
| G6 | 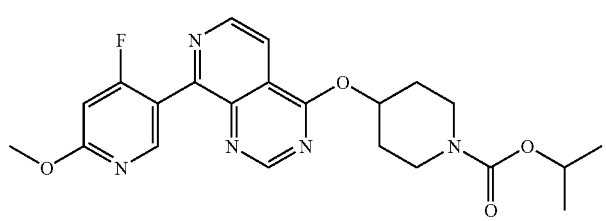 | 4-[8-(4-Fluoro-6-methoxy-pyridin-3-yl)-pyrido[3,4-d]pyrimidin-4-yloxy]-piperidine-1-carboxylic acid isopropyl ester |
| G7 | 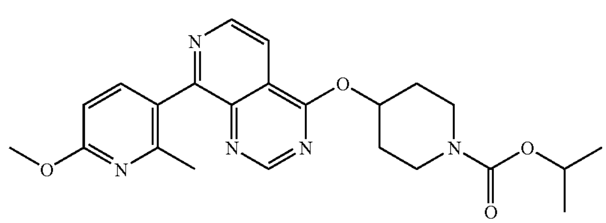 | 4-[8-(6-Methoxy-2-methyl-pyridin-3-yl)-pyrido[3,4-d]pyrimidin-4-yloxy]-piperidine-1-carboxylic acid isopropyl ester |

TABLE G-continued

| Cmpd# | Structure | Chemical Name |
|---|---|---|
| G8 | 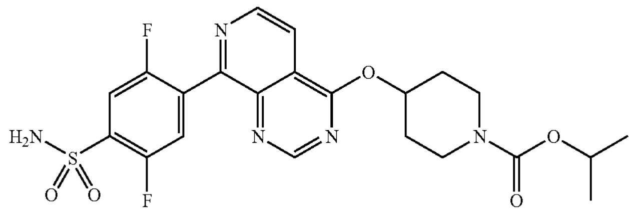 | 4-[8-(2,5-Difluoro-4-sulfamoyl-phenyl)-pyrido[3,4-d]pyrimidin-4-yloxy]-piperidine-1-carboxylic acid isopropyl ester |
| G9 | 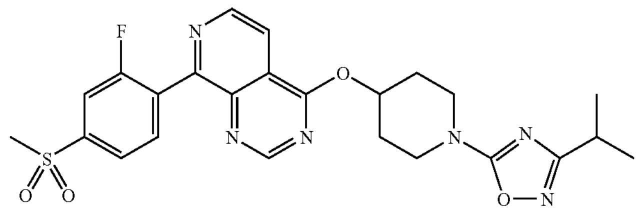 | 8-(2-Fluoro-4-methanesulfonyl-phenyl)-4-[1-(3-isopropyl-[1,2,4]oxadiazol-5-yl)-piperidin-4-yloxy]-pyrido[3,4-d]pyrimidine |
| G10 | 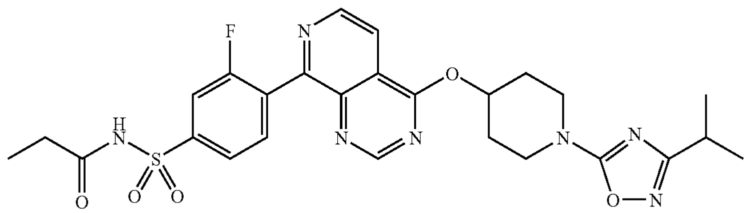 | 3-Fluoro-4-{4-[1-(3-isopropyl-[1,2,4]oxadiazol-5-yl)-piperidin-4-yloxy]-pyrido[3,4-d]pyrimidin-8-yl}-N-propionyl-benzenesulfonamide |
| G11 | 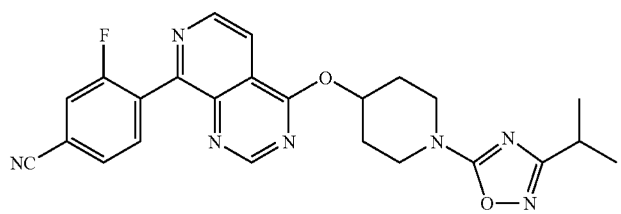 | 3-Fluoro-4-{4-[1-(3-isopropyl-[1,2,4]oxadiazol-5-yl)-piperidin-4-yloxy]-pyrido[3,4-d]pyrimidin-8-yl}-benzonitrile |
| G12 | 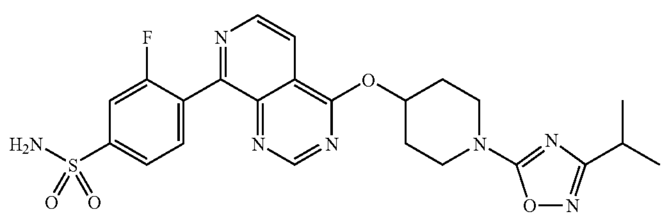 | 3-Fluoro-4-{4-[1-(3-isopropyl-[1,2,4]oxadiazol-5-yl)-piperidin-4-yloxy]-pyrido[3,4-d]pyrimidin-8-yl}-benzenesulfonamide |
| G13 | 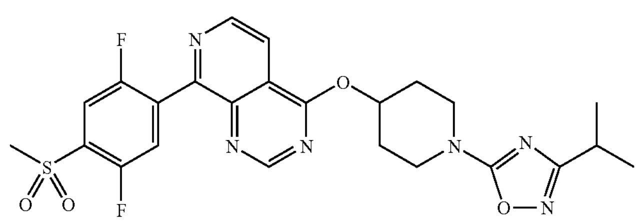 | 8-(2,5-Difluoro-4-methanesulfonyl-phenyl)-4-[1-(3-isopropyl-[1,2,4]oxadiazol-5-yl)-piperidin-4-yloxy]-pyrido[3,4-d]pyrimidine |
| G14 | 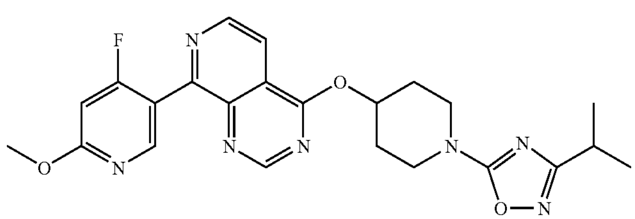 | 8-(4-Fluoro-6-methoxy-pyridin-3-yl)-4-[1-(3-isopropyl-[1,2,4]oxadiazol-5-yl)-piperidin-4-yloxy]-pyrido[3,4-d]pyrimidine |

TABLE G-continued

| Cmpd# | Structure | Chemical Name |
|---|---|---|
| G15 | 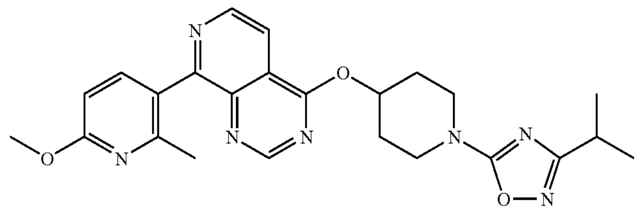 | 4-[1-(3-Isopropyl-[1,2,4]oxadiazol-5-yl)-piperidin-4-yloxy]-8-(6-methoxy-2-methyl-pyridin-3-yl)-pyrido[3,4-d]pyrimidine |
| G16 | 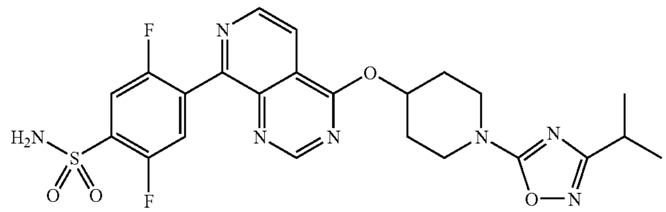 | 2,5-Difluoro-4-{4-[1-(3-isopropyl-[1,2,4]oxadiazol-5-yl)-piperidin-4-yloxy]-pyrido[3,4-d]pyrimidin-8-yl}-benzenesulfonamide |
| G17 | 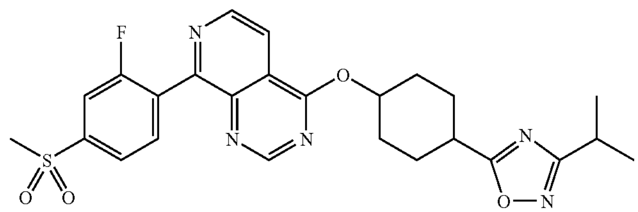 | 8-(2-Fluoro-4-methanesulfonyl-phenyl)-4-[4-(3-isopropyl-[1,2,4]oxadiazol-5-yl)-cyclohexyloxy]-pyrido[3,4-d]pyrimidine |
| G18 | 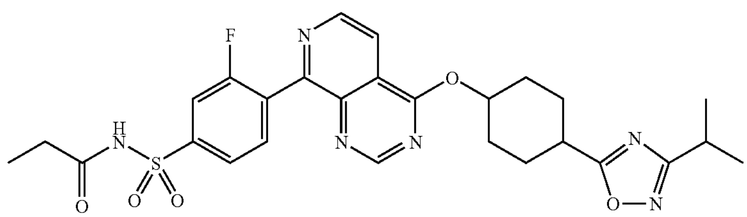 | 3-Fluoro-4-{4-[4-(3-isopropyl-[1,2,4]oxadiazol-5-yl)-cyclohexyloxy]-pyrido[3,4-d]pyrimidin-8-yl}-N-propionyl-benzenesulfonamide |
| G19 | 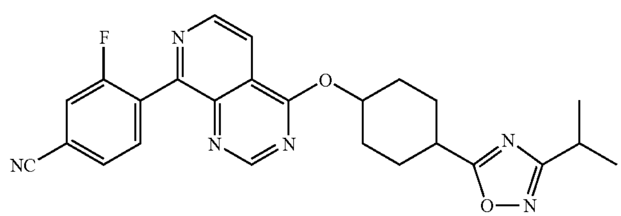 | 3-Fluoro-4-{4-[4-(3-isopropyl-[1,2,4]oxadiazol-5-yl)-cyclohexyloxy]-pyrido[3,4-d]pyrimidin-8-yl}-benzonitrile |
| G20 | 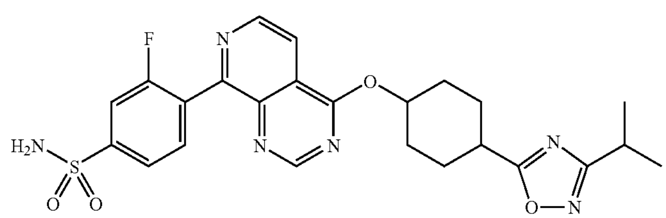 | 3-Fluoro-4-{4-[4-(3-isopropyl-[1,2,4]oxadiazol-5-yl)-cyclohexyloxy]-pyrido[3,4-d]pyrimidin-8-yl}-benzenesulfonamide |
| G21 | 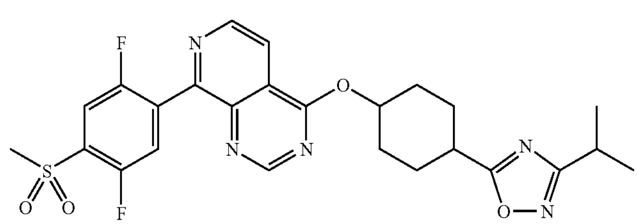 | 8-(2,5-Difluoro-4-methanesulfonyl-phenyl)-4-[4-(3-isopropyl-[1,2,4]oxadiazol-5-yl)-cyclohexyloxy]-pyrido[3,4-d]pyrimidine |

TABLE G-continued

| Cmpd# | Structure | Chemical Name |
|---|---|---|
| G22 | 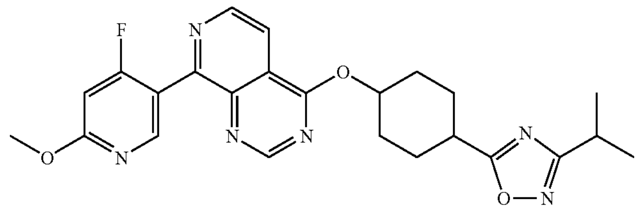 | 8-(4-Fluoro-6-methoxy-pyridin-3-yl)-4-[4-(3-isopropyl-[1,2,4]oxadiazol-5-yl)-cyclohexyloxy]-pyrido[3,4-d]pyrimidine |
| G23 | 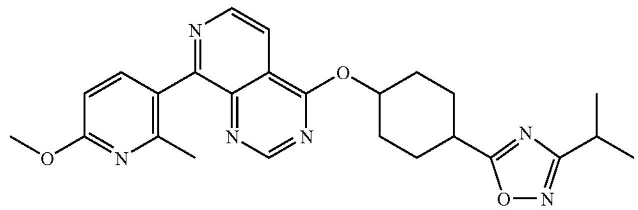 | 4-[4-(3-Isopropyl-[1,2,4]oxadiazol-5-yl)-cyclohexyloxy]-8-(6-methoxy-2-methyl-pyridin-3-yl)-pyrido[3,4-d]pyrimidine |
| G24 | 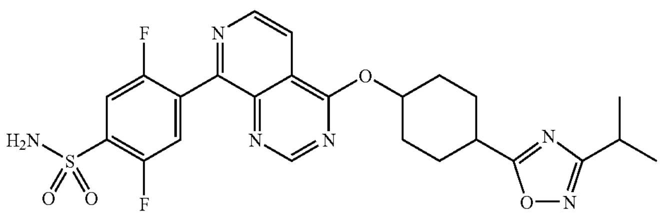 | 2,5-Difluoro-4-{4-[4-(3-isopropyl-[1,2,4]oxadiazol-5-yl)-cyclohexyloxy]-pyrido[3,4-d]pyrimidin-8-yl}-benzenesulfonamide |

TABLE I

| Cmpd# | Structure | Chemical Name |
|---|---|---|
| I1 | 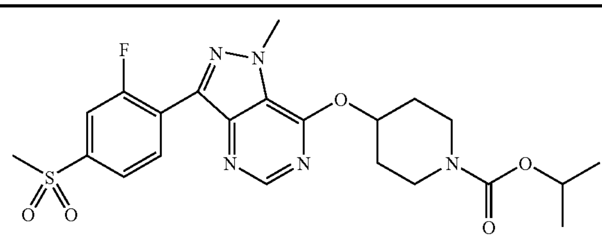 | 4-[3-(2-Fluoro-4-methanesulfonyl-phenyl)-1-methyl-1H-pyrazolo[4,3-d]pyrimidin-7-yloxy]-piperidine-1-carboxylic acid isopropyl ester |
| I2 | 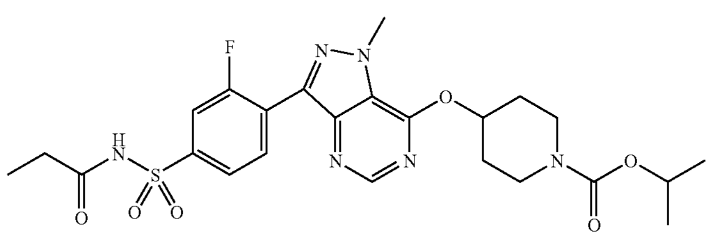 | 4-[3-(2-Fluoro-4-propionylsulfamoyl-phenyl)-1-methyl-1H-pyrazolo[4,3-d]pyrimidin-7-yloxy]-piperidine-1-carboxylic acid isopropyl ester |
| I3 | 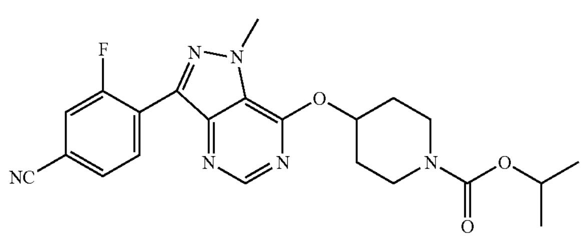 | 4-[3-(4-Cyano-2-fluoro-phenyl)-1-methyl-1H-pyrazolo[4,3-d]pyrimidin-7-yloxy]-piperidine-1-carboxylic acid isopropyl ester |

TABLE I-continued

| Cmpd# | Structure | Chemical Name |
|---|---|---|
| I4 | 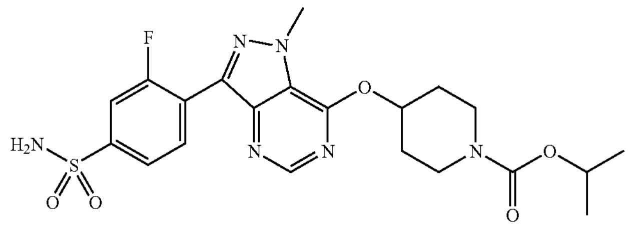 | 4-[3-(2-Fluoro-4-sulfamoyl-phenyl)-1-methyl-1H-pyrazolo[4,3-d]pyrimidin-7-yloxy]-piperidine-1-carboxylic acid isopropyl ester |
| I5 | 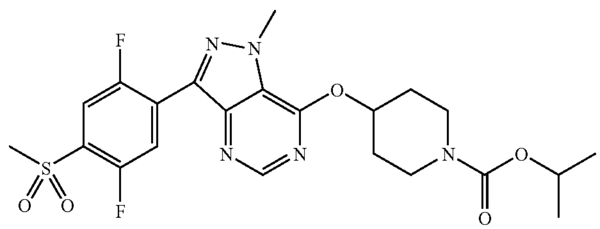 | 4-[3-(2,5-Difluoro-4-methanesulfonyl-phenyl)-1-methyl-1H-pyrazolo[4,3-d]pyrimidin-7-yloxy]-piperidine-1-carboxylic acid isopropyl ester |
| I6 | 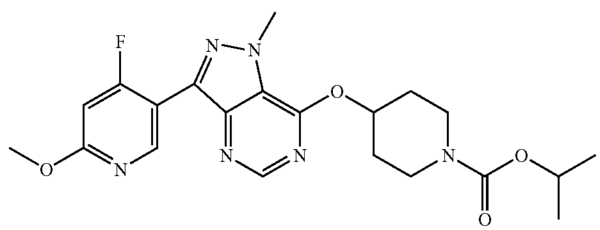 | 4-[3-(4-Fluoro-6-methoxy-pyridin-3-yl)-1-methyl-1H-pyrazolo[4,3-d]pyrimidin-7-yloxy]-piperidine-1-carboxylic acid isopropyl ester |
| I7 | 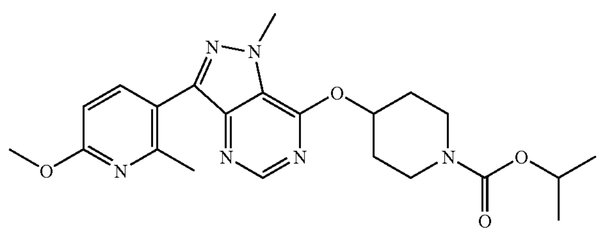 | 4-[3-(6-Methoxy-2-methyl-pyridin-3-yl)-1-methyl-1H-pyrazolo[4,3-d]pyrimidin-7-yloxy]-piperidine-1-carboxylic acid isopropyl ester |
| I8 | 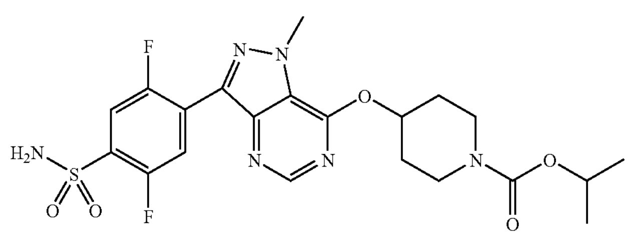 | 4-[3-(2,5-Difluoro-4-sulfamoyl-phenyl)-1-methyl-1H-pyrazolo[4,3-d]pyrimidin-7-yloxy]-piperidine-1-carboxylic acid isopropyl ester |
| I9 | 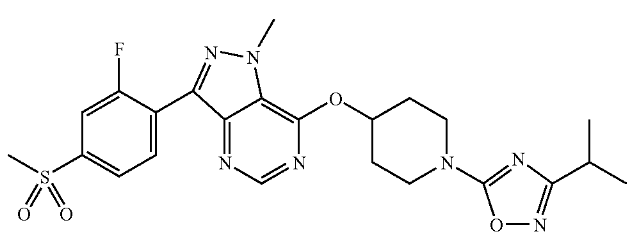 | 3-(2-Fluoro-4-methanesulfonyl-phenyl)-7-[1-(3-isopropyl-[1,2,4]oxadiazol-5-yl)-piperidin-4-yloxy]-1-methyl-1H-pyrazolo[4,3-d]pyrimidine |

TABLE I-continued

| Cmpd# | Structure | Chemical Name |
|---|---|---|
| I10 | 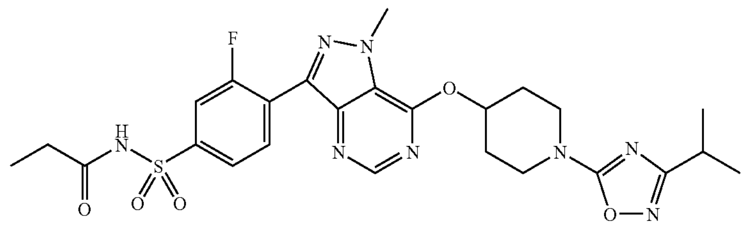 | 3-Fluoro-4-{7-[1-(3-isopropyl-[1,2,4]oxadiazol-5-yl)-piperidin-4-yloxy]-1-methyl-1H-pyrazolo[4,3-d]pyrimidin-3-yl}-N-propionyl-benzenesulfonamide |
| I11 | 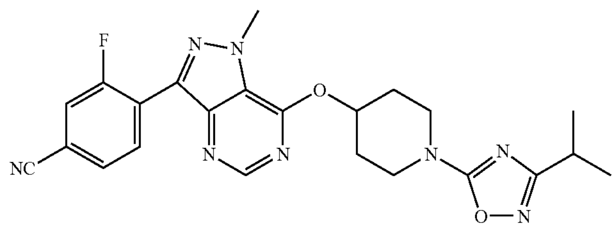 | 3-Fluoro-4-{7-[1-(3-isopropyl-[1,2,4]oxadiazol-5-yl)-piperidin-4-yloxy]-1-methyl-1H-pyrazolo[4,3-d]pyrimidin-3-yl}-benzonitrile |
| I12 | 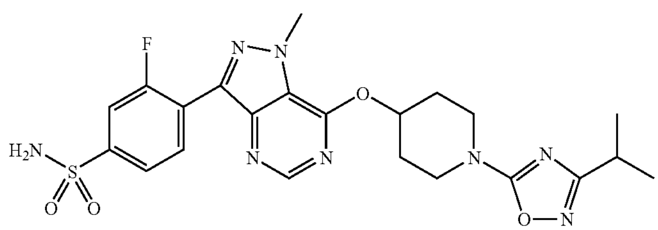 | 3-Fluoro-4-{7-[1-(3-isopropyl-[1,2,4]oxadiazol-5-yl)-piperidin-4-yloxy]-1-methyl-1H-pyrazolo[4,3-d]pyrimidin-3-yl}-benzenesulfonamide |
| I13 | 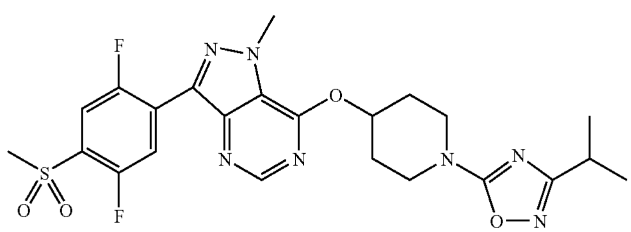 | 3-(2,5-Difluoro-4-methanesulfonyl-phenyl)-7-[1-(3-isopropyl-[1,2,4]oxadiazol-5-yl)-piperidin-4-yloxy]-1-methyl-1H-pyrazolo[4,3-d]pyrimidine |
| I14 | 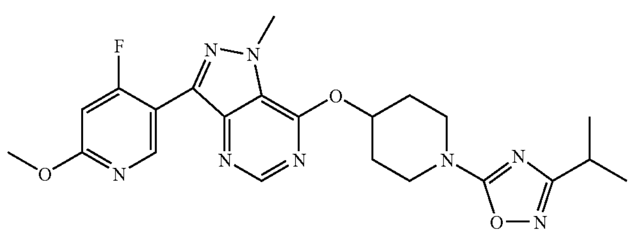 | 3-(4-Fluoro-6-methoxy-pyridin-3-yl)-7-[1-(3-isopropyl-[1,2,4]oxadiazol-5-yl)-piperidin-4-yloxy]-1-methyl-1H-pyrazolo[4,3-d]pyrimidine |
| I15 | 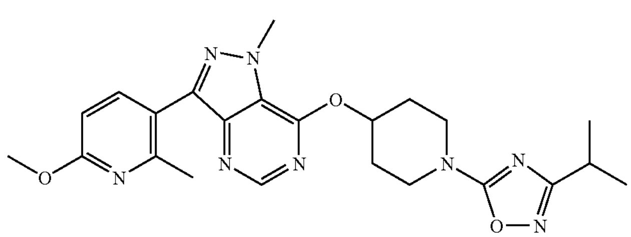 | 7-[1-(3-Isopropyl-[1,2,4]oxadiazol-5-yl)-piperidin-4-yloxy]-3-(6-methoxy-2-methyl-pyridin-3-yl)-1-methyl-1H-pyrazolo[4,3-d]pyrimidine |

TABLE I-continued

| Cmpd# | Structure | Chemical Name |
|---|---|---|
| I16 | 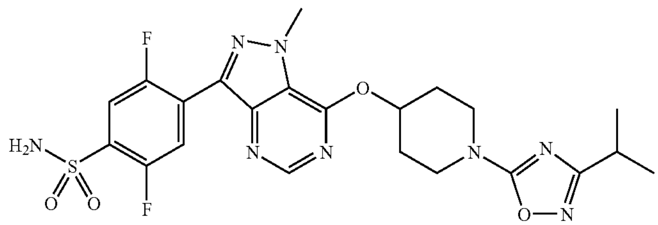 | 2,5-Difluoro-4-{7-[1-(3-isopropyl-[1,2,4]oxadiazol-5-yl)-piperidin-4-yloxy]-1-methyl-1H-pyrazolo[4,3-d]pyrimidin-3-yl}-benzenesulfonamide |
| I17 | 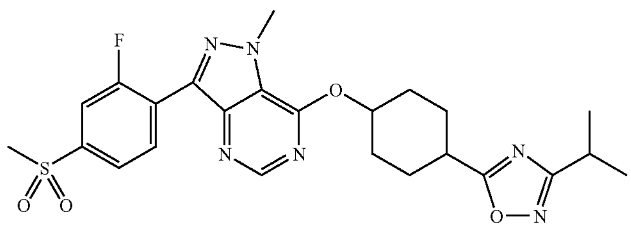 | 3-(2-Fluoro-4-methanesulfonyl-phenyl)-7-[4-(3-isopropyl-[1,2,4]oxadiazol-5-yl)-cyclohexyloxy]-1-methyl-1H-pyrazolo[4,3-d]pyrimidine |
| I18 | 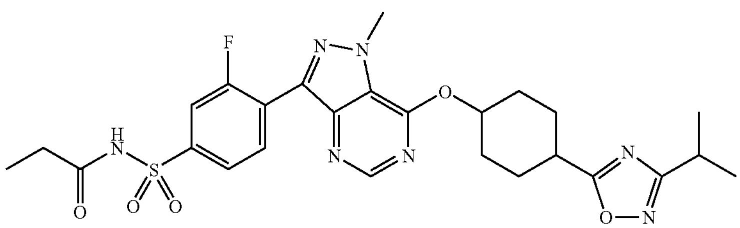 | 3-Fluoro-4-{7-[4-(3-isopropyl-[1,2,4]oxadiazol-5-yl)-cyclohexyloxy]-1-methyl-1H-pyrazolo[4,3-d]pyrimidin-3-yl}-N-propionyl-benzenesulfonamide |
| I19 | 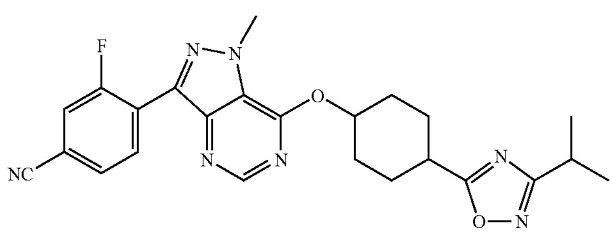 | 3-Fluoro-4-{7-[4-(3-isopropyl-[1,2,4]oxadiazol-5-yl)-cyclohexyloxy]-1-methyl-1H-pyrazolo[4,3-d]pyrimidin-3-yl}-benzonitrile |
| I20 | 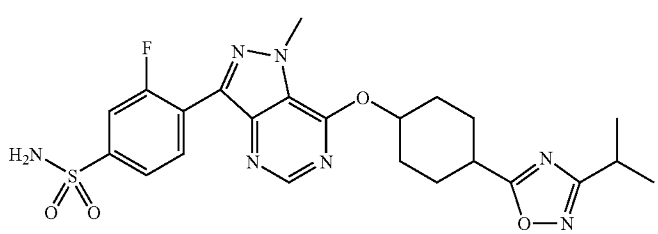 | 3-Fluoro-4-{7-[4-(3-isopropyl-[1,2,4]oxadiazol-5-yl)-cyclohexyloxy]-1-methyl-1H-pyrazolo[4,3-d]pyrimidin-3-yl}-benzenesulfonamide |
| I21 | 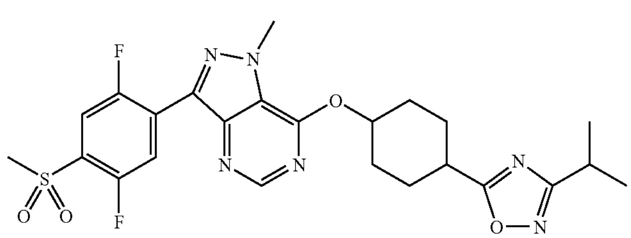 | 3-(2,5-Difluoro-4-methanesulfonyl-phenyl)-7-[4-(3-isopropyl-[1,2,4]oxadiazol-5-yl)-cyclohexyloxy]-1-methyl-1H-pyrazolo[4,3-d]pyrimidine |

TABLE I-continued

| Cmpd# | Structure | Chemical Name |
|---|---|---|
| I22 | 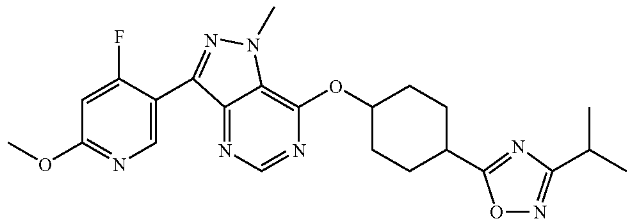 | 3-(4-Fluoro-6-methoxy-pyridin-3-yl)-7-[4-(3-isopropyl-[1,2,4]oxadiazol-5-yl)-cyclohexyloxy]-1-methyl-1H-pyrazolo[4,3-d]pyrimidine |
| I23 | 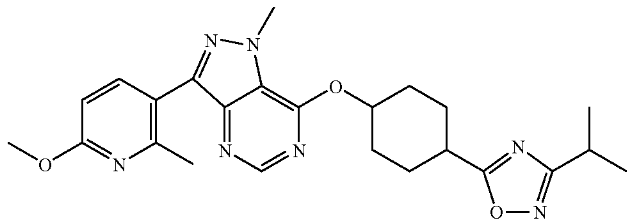 | 7-[4-(3-Isopropyl-[1,2,4]oxadiazol-5-yl)-cyclohexyloxy]-3-(6-methoxy-2-methyl-pyridin-3-yl)-1-methyl-1H-pyrazolo[4,3-d]pyrimidine |
| I24 | 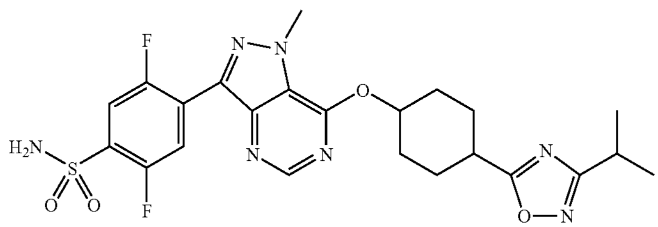 | 2,5-Difluoro-4-{7-[4-(3-isopropyl-[1,2,4]oxadiazol-5-yl)-cyclohexyloxy]-1-methyl-1H-pyrazolo[4,3-d]pyrimidin-3-yl}-benzenesulfonamide |

TABLE J

| Cmpd# | Structure | Chemical Name |
|---|---|---|
| J1 | 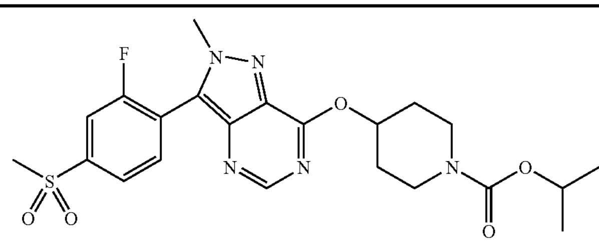 | 4-[3-(2-Fluoro-4-methanesulfonyl-phenyl)-2-methyl-2H-pyrazolo[4,3-d]pyrimidin-7-yloxy]-piperidine-1-carboxylic acid isopropyl ester |
| J2 | 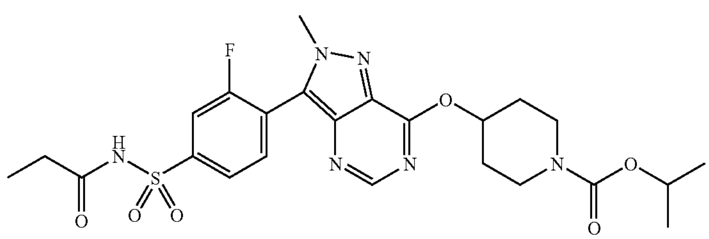 | 4-[3-(2-Fluoro-4-propionylsulfamoyl-phenyl)-2-methyl-2H-pyrazolo[4,3-d]pyrimidin-7-yloxy]-piperidine-1-carboxylic acid isopropyl ester |
| J3 | 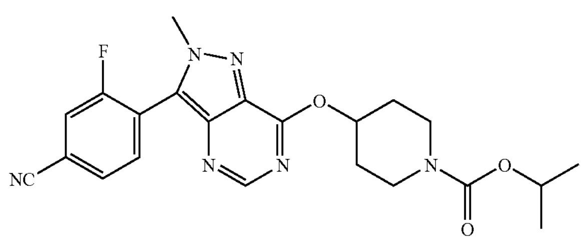 | 4-[3-(4-Cyano-2-fluoro-phenyl)-2-methyl-2H-pyrazolo[4,3-d]pyrimidin-7-yloxy]-piperidine-1-carboxylic acid isopropyl ester |

TABLE J-continued

| Cmpd# | Structure | Chemical Name |
|---|---|---|
| J4 | 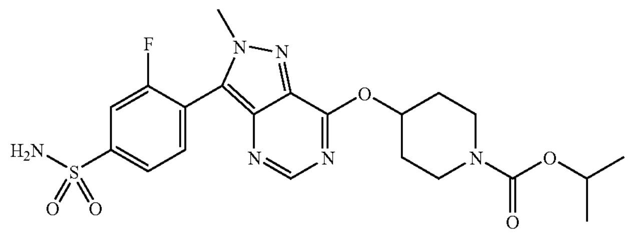 | 4-[3-(2-Fluoro-4-sulfamoyl-phenyl)-2-methyl-2H-pyrazolo[4,3-d]pyrimidin-7-yloxy]-piperidine-1-carboxylic acid isopropyl ester |
| J5 | 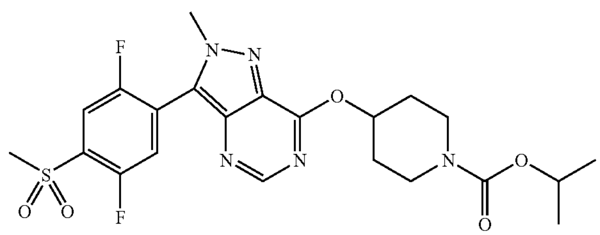 | 4-[3-(2,5-Difluoro-4-methanesulfonyl-phenyl)-2-methyl-2H-pyrazolo[4,3-d]pyrimidin-7-yloxy]-piperidine-1-carboxylic acid isopropyl ester |
| J6 | 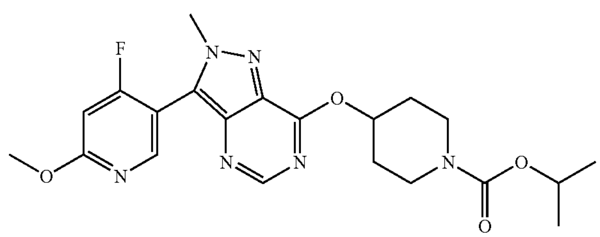 | 4-[3-(4-Fluoro-6-methoxy-pyridin-3-yl)-2-methyl-2H-pyrazolo[4,3-d]pyrimidin-7-yloxy]-piperidine-1-carboxylic acid isopropyl ester |
| J7 | 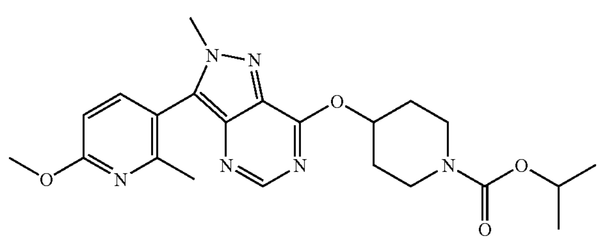 | 4-[3-(6-Methoxy-2-methyl-pyridin-3-yl)-2-methyl-2H-pyrazolo[4,3-d]pyrimidin-7-yloxy]-piperidine-1-carboxylic acid isopropyl ester |
| J8 | 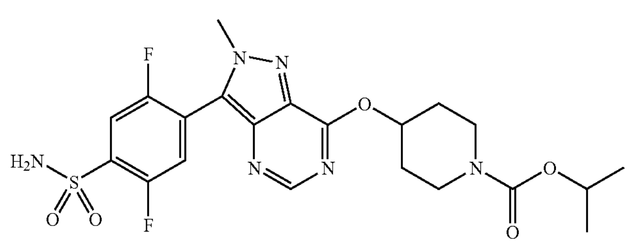 | 4-[3-(2,5-Difluoro-4-sulfamoyl-phenyl)-2-methyl-2H-pyrazolo[4,3-d]pyrimidin-7-yloxy]-piperidine-1-carboxylic acid isopropyl ester |
| J9 | 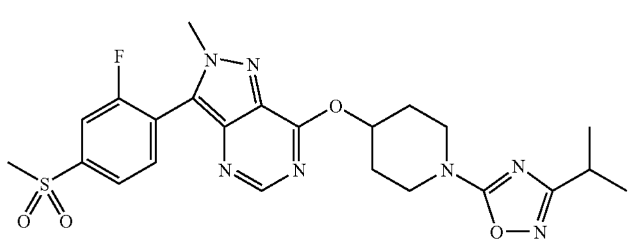 | 3-(2-Fluoro-4-methanesulfonyl-phenyl)-7-[1-(3-isopropyl-[1,2,4]oxadiazol-5-yl)-piperidin-4-yloxy]-2-methyl-2H-pyrazolo[4,3-d]pyrimidine |

TABLE J-continued

| Cmpd# | Structure | Chemical Name |
|---|---|---|
| J10 | 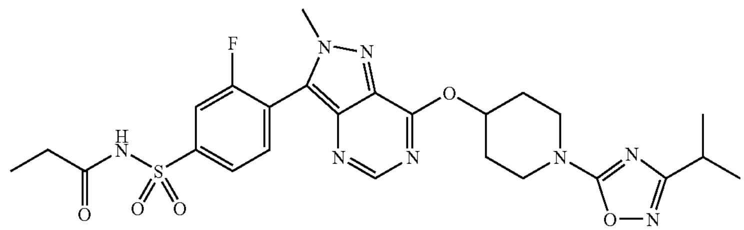 | 3-Fluoro-4-{7-[1-(3-isopropyl-[1,2,4]oxadiazol-5-yl)-piperidin-4-yloxy]-2-methyl-2H-pyrazolo[4,3-d]pyrimidin-3-yl}-N-propionyl-benzenesulfonamide |
| J11 | 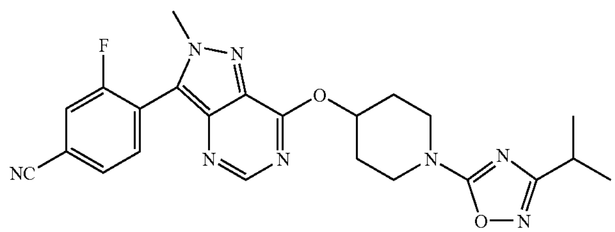 | 3-Fluoro-4-{7-[1-(3-isopropyl-[1,2,4]oxadiazol-5-yl)-piperidin-4-yloxy]-2-methyl-2H-pyrazolo[4,3-d]pyrimidin-3-yl}-benzonitrile |
| J12 | 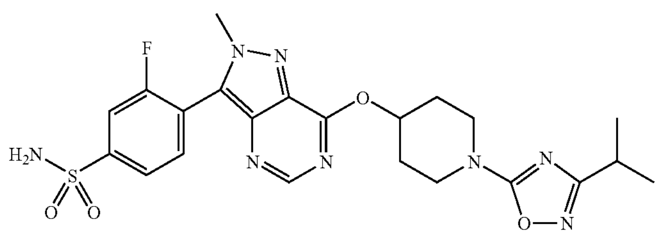 | 3-Fluoro-4-{7-[1-(3-isopropyl-[1,2,4]oxadiazol-5-yl)-piperidin-4-yloxy]-2-methyl-2H-pyrazolo[4,3-d]pyrimidin-3-yl}-benzenesulfonamide |
| J13 | 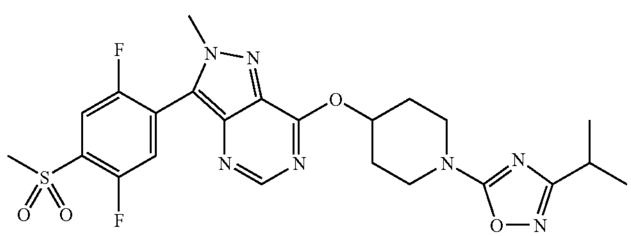 | 3-(2,5-Difluoro-4-methanesulfonyl-phenyl)-7-[1-(3-isopropyl-[1,2,4]oxadiazol-5-yl)-piperidin-4-yloxy]-2-methyl-2H-pyrazolo[4,3-d]pyrimidine |
| J14 | 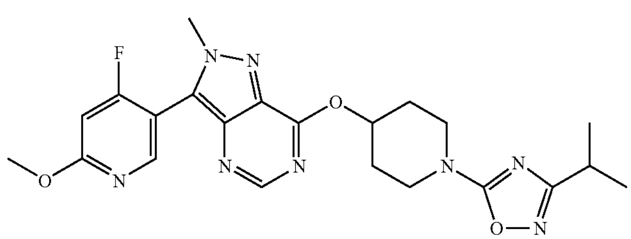 | 3-(4-Fluoro-6-methoxy-pyridin-3-yl)-7-[1-(3-isopropyl-[1,2,4]oxadiazol-5-yl)-piperidin-4-yloxy]-2-methyl-2H-pyrazolo[4,3-d]pyrimidine |
| J15 | 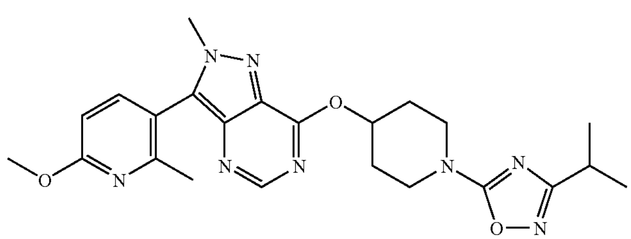 | 7-[1-(3-Isopropyl-[1,2,4]oxadiazol-5-yl)-piperidin-4-yloxy]-3-(6-methoxy-2-methyl-pyridin-3-yl)-2-methyl-2H-pyrazolo[4,3-d]pyrimidine |

US 7,625,906 B2

TABLE J-continued

| Cmpd# | Structure | Chemical Name |
|---|---|---|
| J16 | 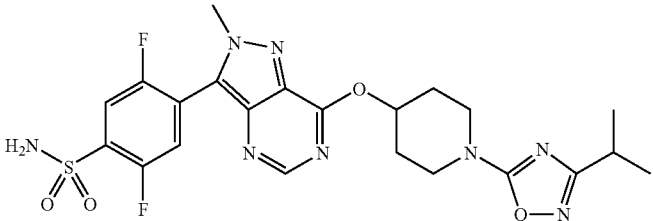 | 2,5-Difluoro-4-{7-[1-(3-isopropyl-[1,2,4]oxadiazol-5-yl)-piperidin-4-yloxy]-2-methyl-2H-pyrazolo[4,3-d]pyrimidin-3-yl}-benzenesulfonamide |
| J17 | 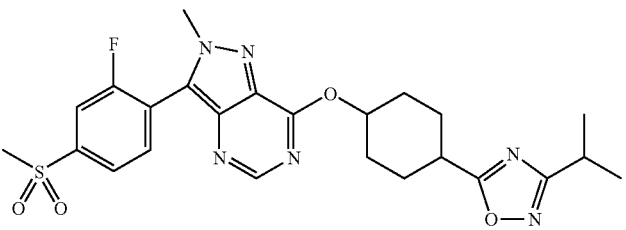 | 3-(2-Fluoro-4-methanesulfonyl-phenyl)-7-[4-(3-isopropyl-[1,2,4]oxadiazol-5-yl)-cyclohexyloxy]-2-methyl-2H-pyrazolo[4,3-d]pyrimidine |
| J18 | 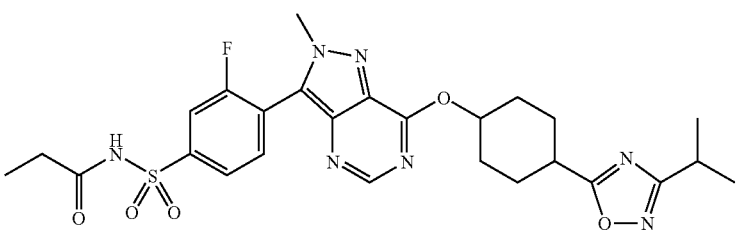 | 3-Fluoro-4-{7-[4-(3-isopropyl-[1,2,4]oxadiazol-5-yl)-cyclohexyloxy]-2-methyl-2H-pyrazolo[4,3-d]pyrimidin-3-yl}-N-propionyl-benzenesulfonamide |
| J19 | 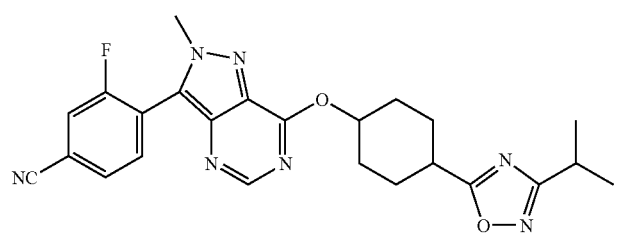 | 3-Fluoro-4-{7-[4-(3-isopropyl-[1,2,4]oxadiazol-5-yl)-cyclohexyloxy]-2-methyl-2H-pyrazolo[4,3-d]pyrimidin-3-yl}-benzonitrile |
| J20 | 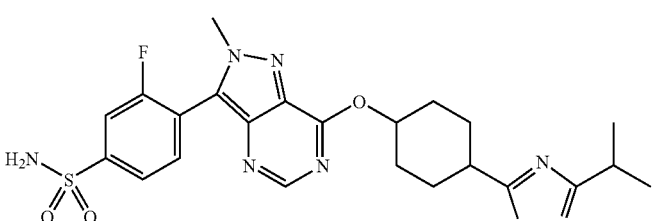 | 3-Fluoro-4-{7-[4-(3-isopropyl-[1,2,4]oxadiazol-5-yl)-cyclobexyloxy]-2-methyl-2H-pyrazolo[4,3-d]pyrimidin-3-yl}-benzenesulfonamide |
| J21 | 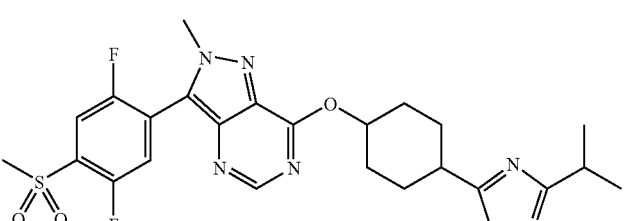 | 3-(2,5-Difluoro-4-methanesulfonyl-phenyl)-7-[4-(3-isopropyl-[1,2,4]oxadiazol-5-yl)-cyclohexyloxy]-2-methyl-2H-pyrazolo[4,3-d]pyrimidine |

TABLE J-continued

| Cmpd# | Structure | Chemical Name |
|---|---|---|
| J22 | 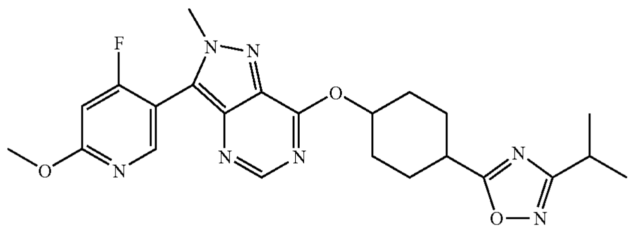 | 3-(4-Fluoro-6-methoxy-pyridin-3-yl)-7-[4-(3-isopropyl-[1,2,4]oxadiazol-5-yl)-cyclohexyloxy]-2-methyl-2H-pyrazolo[4,3-d]pyrimidine |
| J23 | 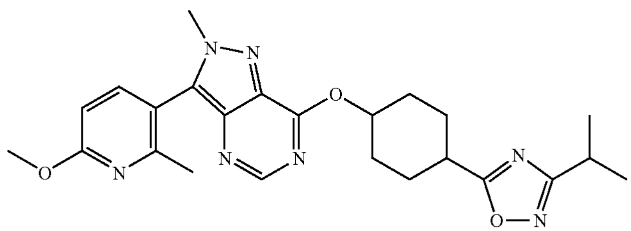 | 7-[4-(3-Isopropyl-[1,2,4]oxadiazol-5-yl)-cyclohexyloxy]-3-(6-methoxy-2-methyl-pyridin-3-yl)-2-methyl-2H-pyrazolo[4,3-d]pyrimidine |
| J24 | 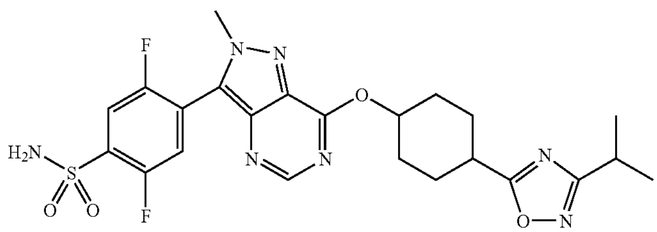 | 2,5-Difluoro-4-{7-[4-(3-isopropyl-[1,2,4]oxadiazol-5-yl)-cyclohexyloxy]-2-methyl-2H-pyrazolo[4,3-d]pyrimidin-3-yl}-benzenesulfonamide |

TABLE K

| Cmpd# | Structure | Chemical Name |
|---|---|---|
| K1 | 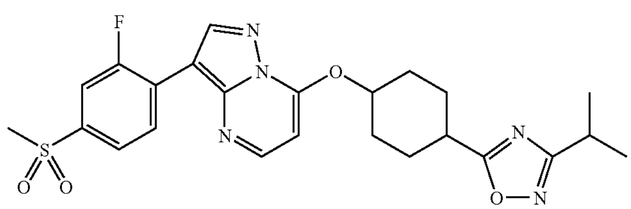 | 3-(2-Fluoro-4-methanesulfonyl-phenyl)-7-[4-(3-isopropyl-[1,2,4]oxadiazol-5-yl)-cyclohexyloxy]-pyrazolo[1,5-a]pyrimidine |
| K2 | 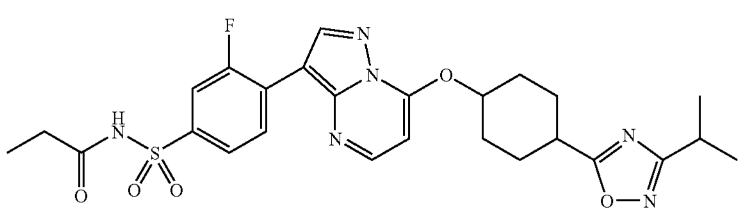 | 3-Fluoro-4-{7-[4-(3-isopropyl-[1,2,4]oxadiazol-5-yl)-cyclohexyloxy]-pyrazolo[1,5-a]pyrimidin-3-yl}-N-propionyl-benzenesulfonamide |
| K3 | 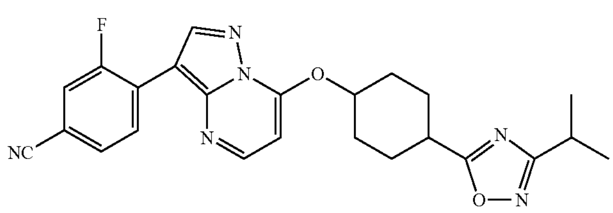 | 3-Fluoro-4-{7-[4-(3-isopropyl-[1,2,4]oxadiazol-5-yl)-cyclohexyloxy]-pyrazolo[1,5-a]pyrimidin-3-yl}-benzonitrile |

TABLE K-continued

| Cmpd# | Structure | Chemical Name |
|---|---|---|
| K4 | 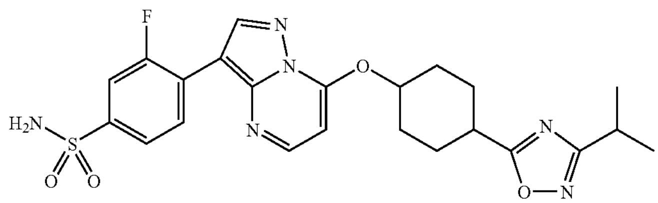 | 3-Fluoro-4-{7-[4-(3-isopropyl-[1,2,4]oxadiazol-5-yl)-cyclohexyloxy]-pyrazolo[1,5-a]pyrimidin-3-yl}-benzenesulfonamide |
| K5 | 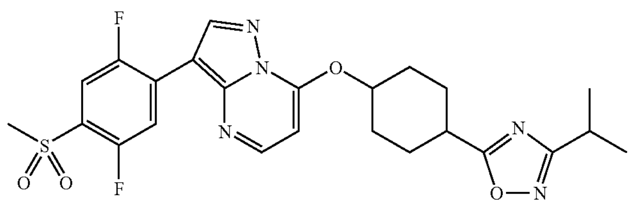 | 3-(2,5-Difluoro-4-methanesulfonyl-phenyl)-7-[4-(3-isopropyl-[1,2,4]oxadiazol-5-yl)-cyclohexyloxy]-pyrazolo[1,5-a]pyrimidine |
| K6 | 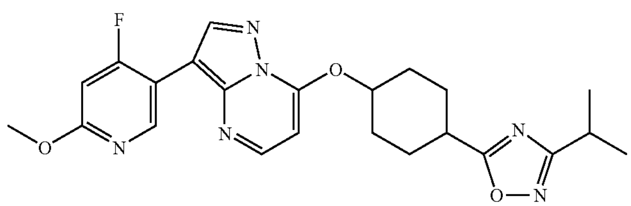 | 3-(4-Fluoro-6-methoxy-pyridin-3-yl)-7-[4-(3-isopropyl-[1,2,4]oxadiazol-5-yl)-cyclohexyloxy]-pyrazolo[1,5-a]pyrimidine |
| K7 | 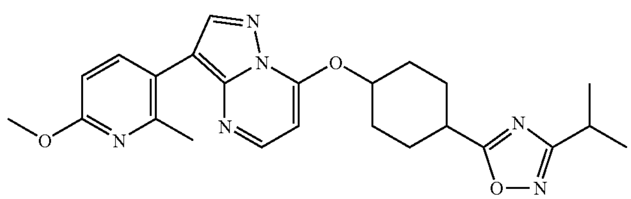 | 7-[4-(3-Isopropyl-[1,2,4]oxadiazol-5-yl)-cyclohexyloxy]-3-(6-methoxy-2-methyl-pyridin-3-yl)-pyrazolo[1,5-a]pyrimidine |
| K8 | 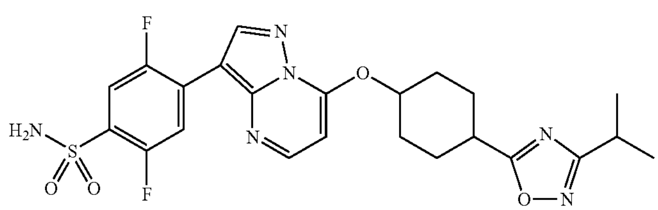 | 2,5-Difluoro-4-{7-[4-(3-isopropyl-[1,2,4]oxadiazol-5-yl)-cyclohexyloxy]-pyrazolo[1,5-a]pyrimidin-3-yl}-benzenesulfonamide |
| K9 | 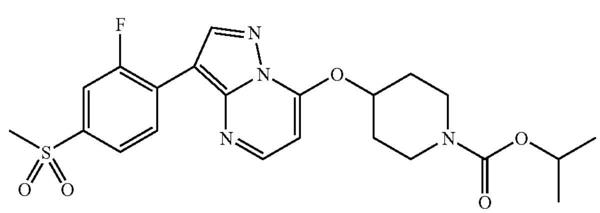 | 4-[3-(2-Fluoro-4-methanesulfonyl-phenyl)-pyrazolo[1,5-a]pyrimidin-7-yloxy]-piperidine-1-carboxylic acid isopropyl ester |
| K10 | 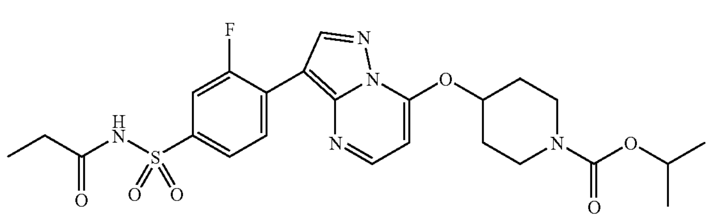 | 4-[3-(2-Fluoro-4-propionylsulfamoyl-phenyl)-pyrazolo[1,5-a]pyrimidin-7-yloxy]-piperidine-1-carboxylic acid isopropyl ester |

TABLE K-continued

| Cmpd# | Structure | Chemical Name |
|---|---|---|
| K11 | 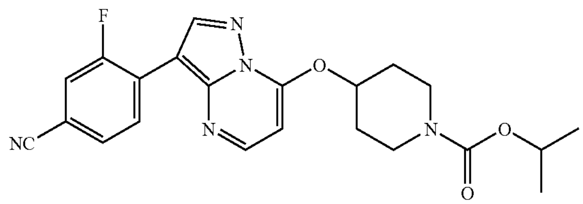 | 4-[3-(4-Cyano-2-fluoro-phenyl)-pyrazolo[1,5-a]pyrimidin-7-yloxy]-piperidine-1-carboxylic acid isopropyl ester |
| K12 | 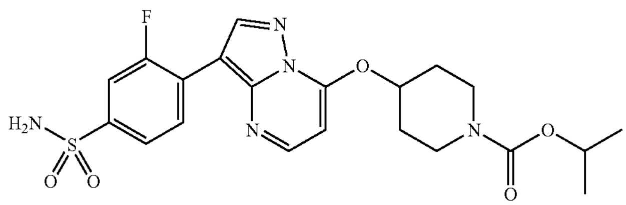 | 4-[3-(2-Fluoro-4-sulfamoyl-phenyl)-pyrazolo[1,5-a]pyrimidin-7-yloxy]-piperidine-1-carboxylic acid isopropyl ester |
| K13 | 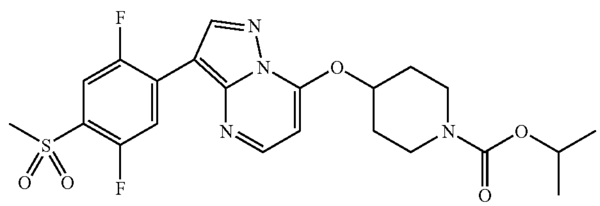 | 4-[3-(2,5-Difluoro-4-methanesulfonyl-phenyl)-pyrazolo[1,5-a]pyrimidin-7-yloxy]-piperidine-1-carboxylic acid isopropyl ester |
| K14 | 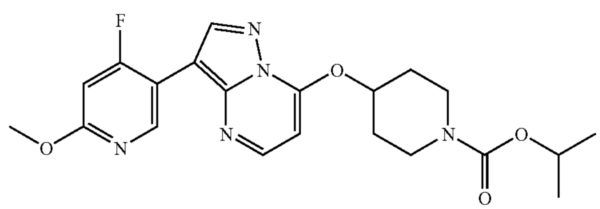 | 4-[3-(4-Fluoro-6-methoxy-pyridin-3-yl)-pyrazolo[1,5-a]pyrimidin-7-yloxy]-piperidine-1-carboxylic acid isopropyl ester |
| K15 | 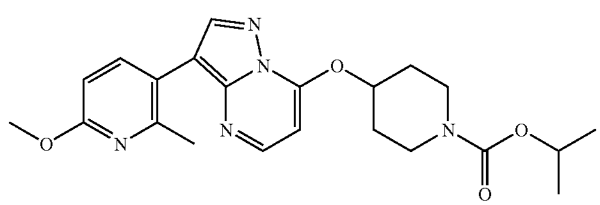 | 4-[3-(6-Methoxy-2-methyl-pyridin-3-yl)-pyrazolo[1,5-a]pyrimidin-7-yloxy]-piperidine-1-carboxylic acid isopropyl ester |
| K16 | 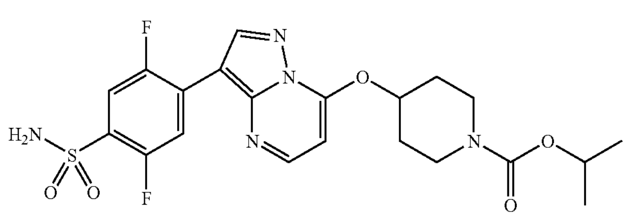 | 4-[3-(2,5-Difluoro-4-sulfamoyl-phenyl)-pyrazolo[1,5-a]pyrimidin-7-yloxy]-piperidine-1-carboxylic acid isopropyl ester |
| K17 | 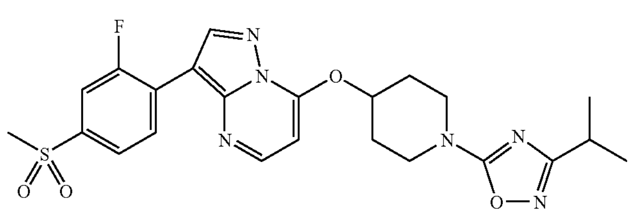 | 3-(2-Fluoro-4-methanesulfonyl-phenyl)-7-[1-(3-isopropyl-[1,2,4]oxadiazol-5-yl)-piperidin-4-yloxy]-pyrazolo[1,5-a]pyrimidine |

TABLE K-continued

| Cmpd# | Structure | Chemical Name |
|---|---|---|
| K18 | 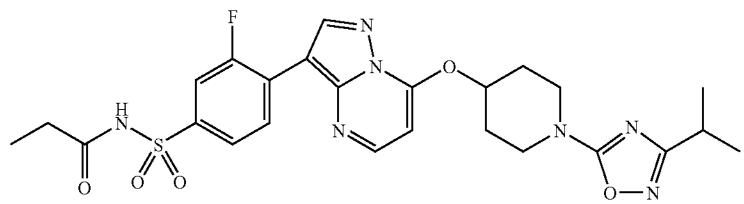 | 3-Fluoro-4-{7-[1-(3-isopropyl-[1,2,4]oxadiazol-5-yl)-piperidin-4-yloxy]-pyrazolo[1,5-a]pyrimidin-3-yl}-N-propionyl-benzenesulfonamide |
| K19 | 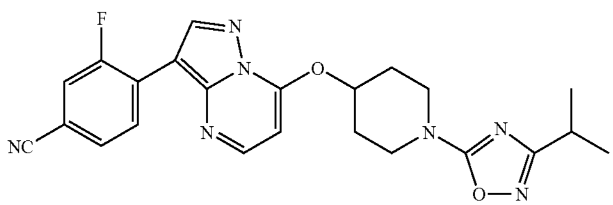 | 3-Fluoro-4-{7-[1-(3-isopropyl-[1,2,4]oxadiazol-5-yl)-piperidin-4-yloxy]-pyrazolo[1,5-a]pyrimidin-3-yl}-benzonitrile |
| K20 | 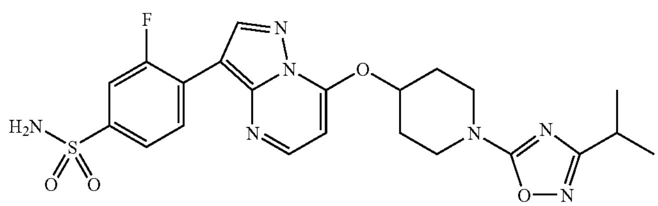 | 3-Fluoro-4-{7-[1-(3-isopropyl-[1,2,4]oxadiazol-5-yl)-piperidin-4-yloxy]-pyrazolo[1,5-a]pyrimidin-3-yl}-benzenesulfonamide |
| K21 | 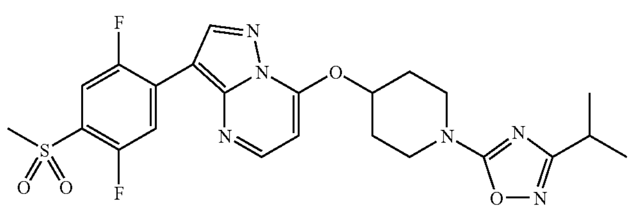 | 3-(2,5-Difluoro-4-methanesulfonyl-phenyl)-7-[1-(3-isopropyl-[1,2,4]oxadiazol-5-yl)-piperidin-4-yloxy]-pyrazolo[1,5-a]pyrimidine |
| K22 | 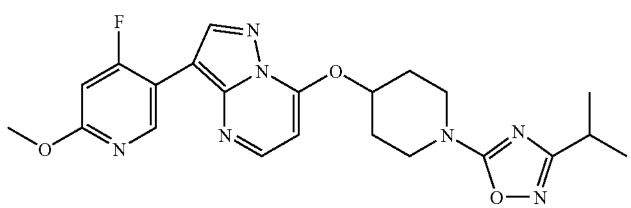 | 3-(4-Fluoro-6-methoxy-pyridin-3-yl)-7-[1-(3-isopropyl-[1,2,4]oxadiazol-5-yl)-piperidin-4-yloxy]-pyrazolo[1,5-a]pyrimidine |
| K23 | 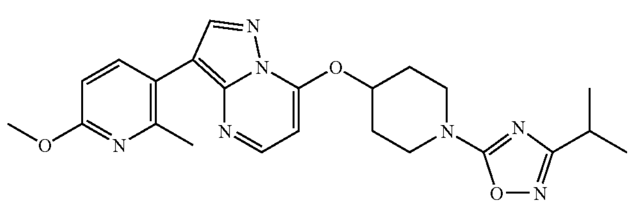 | 7-[1-(3-Isopropyl-[1,2,4]oxadiazol-5-yl)-piperidin-4-yloxy]-3-(6-methoxy-2-methyl-pyridin-3-yl)-pyrazolo[1,5-a]pyrimidine |
| K24 | 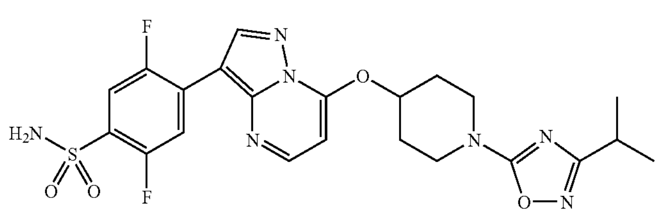 | 2,5-Difluoro-4-{7-[1-(3-isopropyl-[1,2,4]oxadiazol-5-yl)-piperidin-4-yloxy]-pyrazolo[1,5-a]pyrimidin-3-yl}-benzenesulfonamide |

TABLE K-continued

| Cmpd# | Structure | Chemical Name |
|---|---|---|
| K25 | 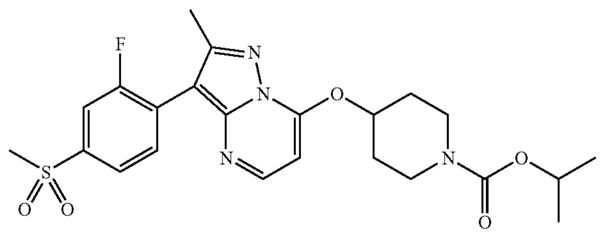 | 4-[3-(2-Fluoro-4-methanesulfonyl-phenyl)-2-methyl-pyrazolo[1,5-a]pyrimidin-7-yloxy]-piperidine-1-carboxylic acid isopropyl ester |
| K26 | 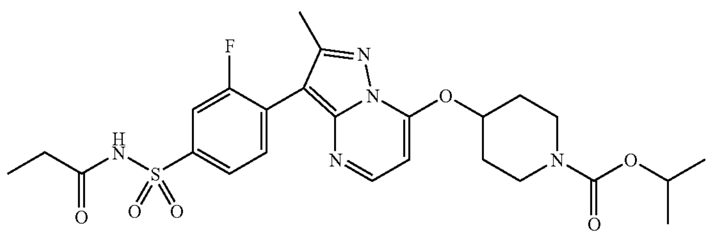 | 4-[3-(2-Fluoro-4-propionylsulfamoyl-phenyl)-2-methyl-pyrazolo[1,5-a]pyrimidin-7-yloxy]-piperidine-1-carboxylic acid isopropyl ester |
| K27 | 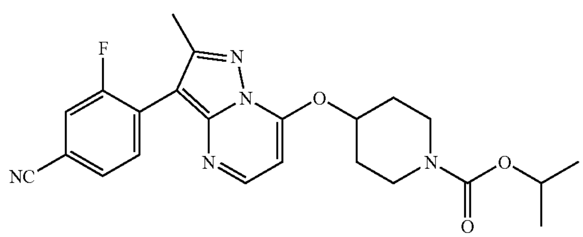 | 4-[3-(4-Cyano-2-fluoro-phenyl)-2-methyl-pyrazolo[1,5-a]pyrimidin-7-yloxy]-piperidine-1-carboxylic acid isopropyl ester |
| K28 | 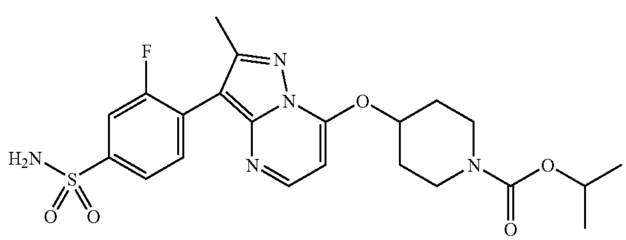 | 4-[3-(2-Fluoro-4-sulfamoyl-phenyl)-2-methyl-pyrazolo[1,5-a]pyrimidin-7-yloxy]-piperidine-1-carboxylic acid isopropyl ester |
| K29 | 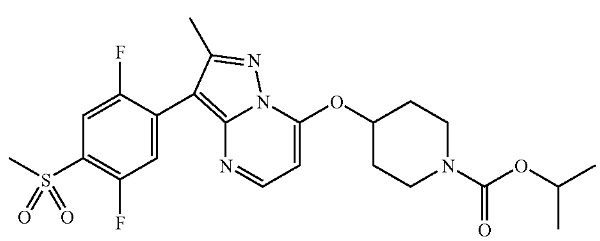 | 4-[3-(2,5-Difluoro-4-methanesulfonyl-phenyl)-2-methyl-pyrazolo[1,5-a]pyrimidin-7-yloxy]-piperidine-1-carboxylic acid isopropyl ester |
| K30 | 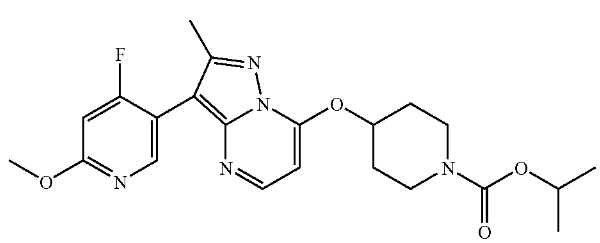 | 4-[3-(4-Fluoro-6-methoxy-pyridin-3-yl)-2-methyl-pyrazolo[1,5-a]pyrimidin-7-yloxy]-piperidine-1-carboxylic acid isopropyl ester |

TABLE K-continued

| Cmpd# | Structure | Chemical Name |
|---|---|---|
| K31 | 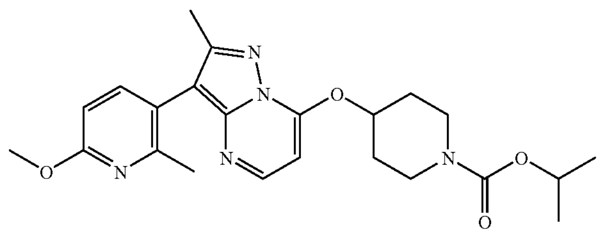 | 4-[3-(6-Methoxy-2-methyl-pyridin-3-yl)-2-methyl-pyrazolo[1,5-a]pyrimidin-7-yloxy]-piperidine-1-carboxylic acid isopropyl ester |
| K32 | 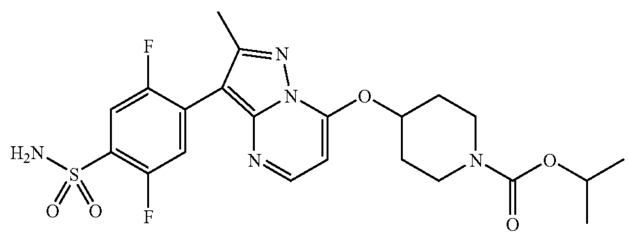 | 4-[3-(2,5-Difluoro-4-sulfamoyl-phenyl)-2-methyl-pyrazolo[1,5-a]pyrimidin-7-yloxy]-piperidine-1-carboxylic acid isopropyl ester |
| K33 | 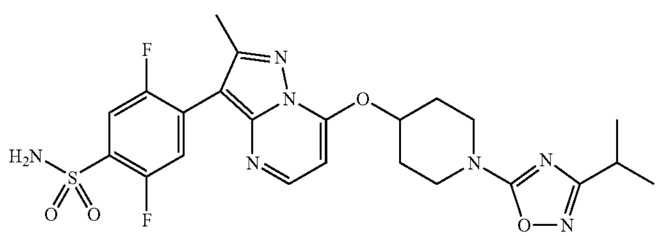 | 2,5-Difluoro-4-{7-[1-(3-isopropyl-[1,2,4]oxadiazol-5-yl)-piperidin-4-yloxy]-2-methyl-pyrazolo[1,5-a]pyrimidin-3-yl}-benzenesulfonamide |
| K34 | 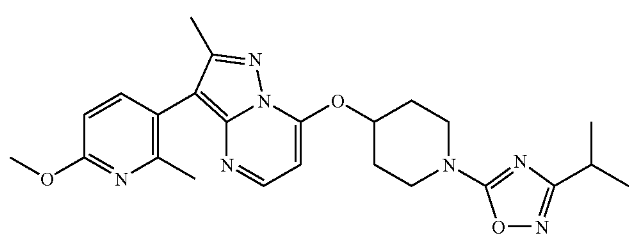 | 7-[1-(3-Isopropyl-[1,2,4]oxadiazol-5-yl)-piperidin-4-yloxy]-3-(6-methoxy-2-methyl-pyridin-3-yl)-2-methyl-pyrazolo[1,5-a]pyrimidine |
| K35 | 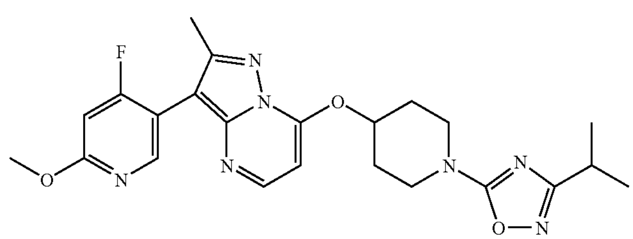 | 3-(4-Fluoro-6-methoxy-pyridin-3-yl)-7-[1-(3-isopropyl-[1,2,4]oxadiazol-5-yl)-piperidin-4-yloxy]-2-methyl-pyrazolo[1,5-a]pyrimidine |
| K36 | 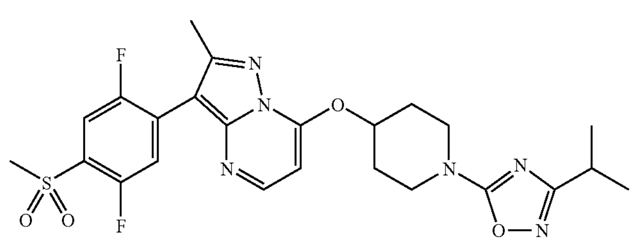 | 3-(2,5-Difluoro-4-methanesulfonyl-phenyl)-7-[1-(3-isopropyl-[1,2,4]oxadiazol-5-yl)-piperidin-4-yloxy]-2-methyl-pyrazolo[1,5-a]pyrimidine |

TABLE K-continued

| Cmpd# | Structure | Chemical Name |
| --- | --- | --- |
| K37 | 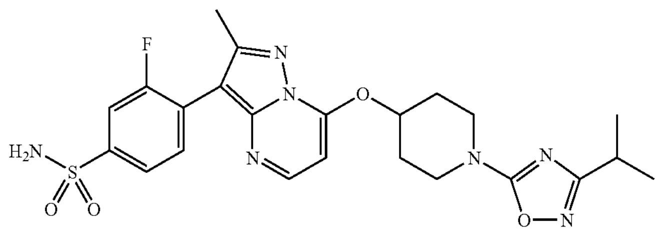 | 3-Fluoro-4-{7-[1-(3-isopropyl-[1,2,4]oxadiazol-5-yl)-piperidin-4-yloxy]-2-methyl-pyrazolo[1,5-a]pyrimidin-3-yl}-benzenesulfonamide |
| K38 | 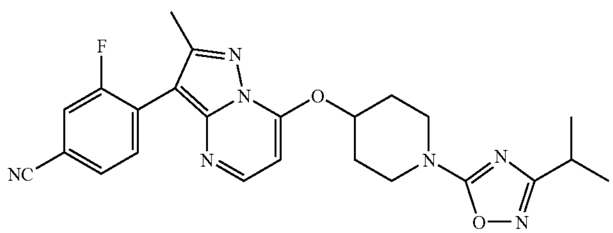 | 3-Fluoro-4-{7-[1-(3-isopropyl-[1,2,4]oxadiazol-5-yl)-piperidin-4-yloxy]-2-methyl-pyrazolo[1,5-a]pyrimidin-3-yl}-benzonitrile |
| K39 | 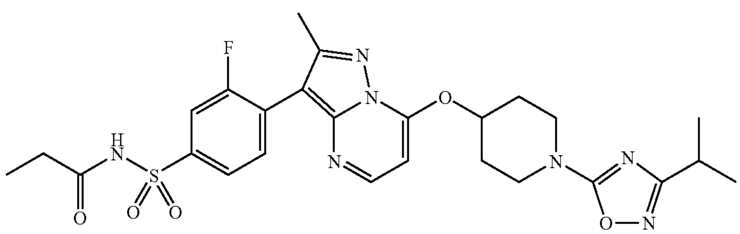 | 3-Fluoro-4-{7-[1-(3-isopropyl-[1,2,4]oxadiazol-5-yl)-piperidin-4-yloxy]-2-methyl-pyrazolo[1,5-a]pyrimidin-3-yl}-N-propionyl-benzenesulfonamide |
| K40 | 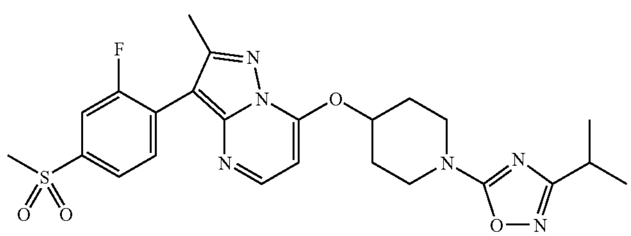 | 3-(2-Fluoro-4-methanesulfonyl-phenyl)-7-[1-(3-isopropyl-[1,2,4]oxadiazol-5-yl)-piperidin-4-yloxy]-2-methyl-pyrazolo[1,5-a]pyrimidine |
| K41 | 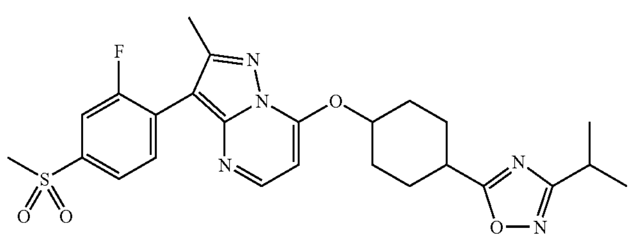 | 3-(2-Fluoro-4-methanesulfonyl-phenyl)-7-[4-(3-isopropyl-[1,2,4]oxadiazol-5-yl)-cyclohexyloxy]-2-methyl-pyrazolo[1,5-a]pyrimidine |
| K42 | 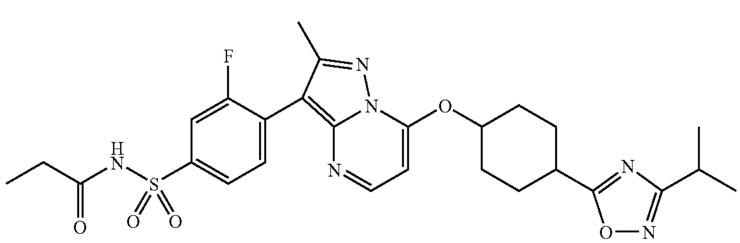 | 3-Fluoro-4-{7-[4-(3-isopropyl-[1,2,4]oxadiazol-5-yl)-cyclohexyloxy]-2-methyl-pyrazolo[1,5-a]pyrimidin-3-yl}-N-propionyl-benzenesulfonamide |

TABLE K-continued

| Cmpd# | Structure | Chemical Name |
|---|---|---|
| K43 | 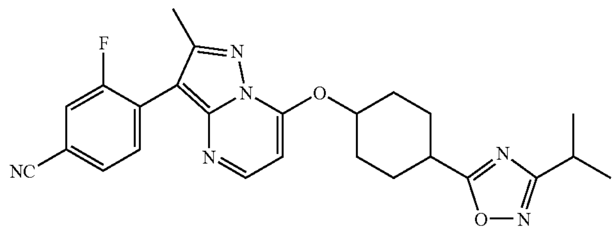 | 3-Fluoro-4-{7-[4-(3-isopropyl-[1,2,4]oxadiazol-5-yl)-cyclohexyloxy]-2-methyl-pyrazolo[1,5-a]pyrimidin-3-yl}-benzonitrile |
| K44 | 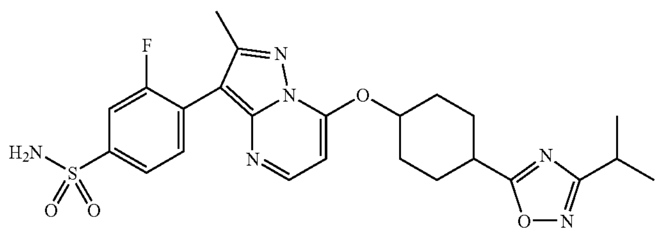 | 3-Fluoro-4-{7-[4-(3-isopropyl-[1,2,4]oxadiazol-5-yl)-cyclohexyloxy]-2-methyl-pyrazolo[1,5-a]pyrimidin-3-yl}-benzenesulfonamide |
| K45 | 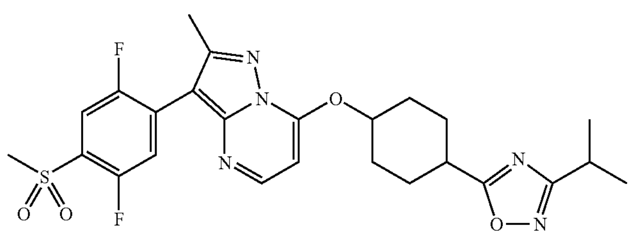 | 3-(2,5-Difluoro-4-methanesulfonyl-phenyl)-7-[4-(3-isopropyl-[1,2,4]oxadiazol-5-yl)-cyclohexyloxy]-2-methyl-pyrazolo[1,5-a]pyrimidine |
| K46 | 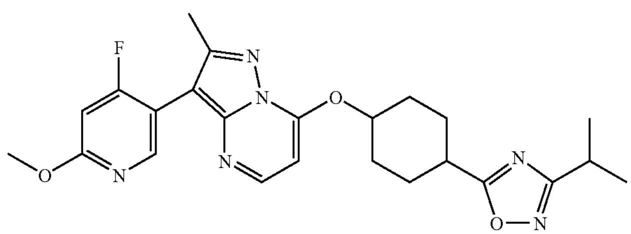 | 3-(4-Fluoro-6-methoxy-pyridin-3-yl)-7-[4-(3-isopropyl-[1,2,4]oxadiazol-5-yl)-cyclohexyloxy]-2-methyl-pyrazolo[1,5-a]pyrimidine |
| K47 | 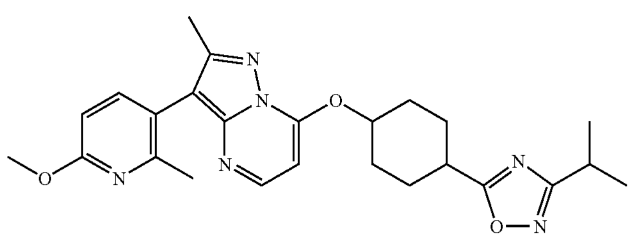 | 7-[4-(3-Isopropyl-[1,2,4]oxadiazol-5-yl)-cyclohexyloxy]-3-(6-methoxy-2-methyl-pyridin-3-yl)-2-methyl-pyrazolo[1,5-a]pyrimidine |
| K48 | 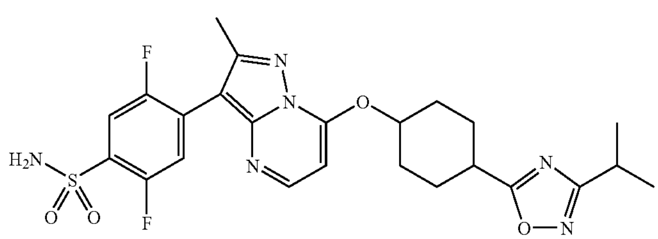 | 2,5-Difluoro-4-{7-[4-(3-isopropyl-[1,2,4]oxadiazol-5-yl)-cyclohexyloxy]-2-methyl-pyrazolo[1,5-a]pyrimidin-3-yl}-benzenesulfonamide |

Additionally, compounds of the present invention, such as Formula (I) and related Formulae, encompass all pharmaceutically acceptable salts, solvates, and particularly hydrates, thereof.

General Methods for the Preparation of Compounds of the Invention.

The novel compounds of the present invention can be readily prepared according to a variety of synthetic manipulations, all of which would be familiar to one skilled in the art. Certain methods for the preparation of compounds of the present invention include, but are not limited to, those described in Schemes, infra.

Many bicyclic heterocycles can be prepared using methods described or adapted from the literature. For example, the pyrazolopyrimidine of structure H7 in Table 6 may be prepared as follows (scheme 3)

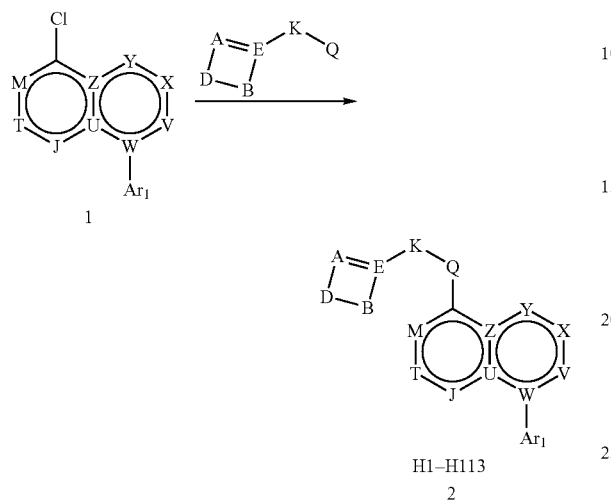

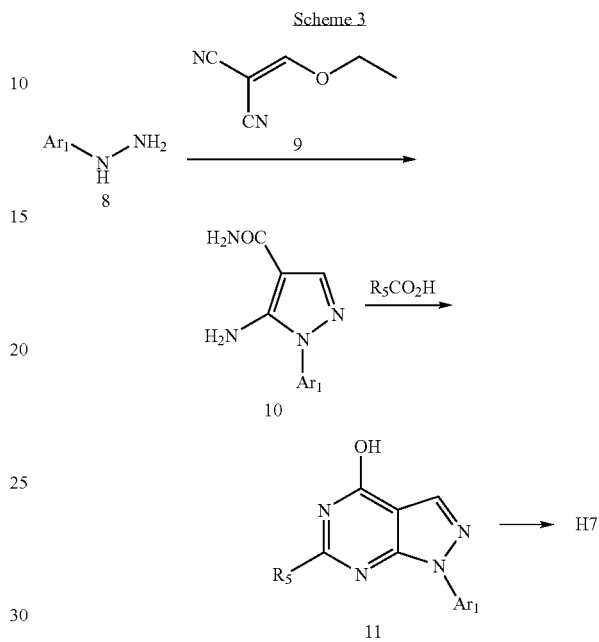

An appropriate nucleophilic species can be used to displace chloride, bromide or triflate from the bicyclic heterocycle. This conversion may be carried out under a range of conditions such as thermal heating and microwave heating and may or may not be catalyzed by addition of further reagents such as acid, base or transition metal salts etc (Scheme 1).

Bicyclic heterocycle halides may most conveniently be prepared by either direct halogenation of the parent heterocycle, for example with bromine or by radical bromination with N-bromo succinimide, or by conversion of the hydroxy compound (which may exist in the amide form when M=N and or J=N) to the chloride by treatment with a chlorinating agent such as but not limited to $POCl_3$, $PCl_5$ or some combination thereof (Scheme 2).

Subsequent treatment with $POCl_3$ and nucleophilic displacement with amino or alkoxide nucleophiles as outlined above can afford compounds of the invention in one of the embodiments.

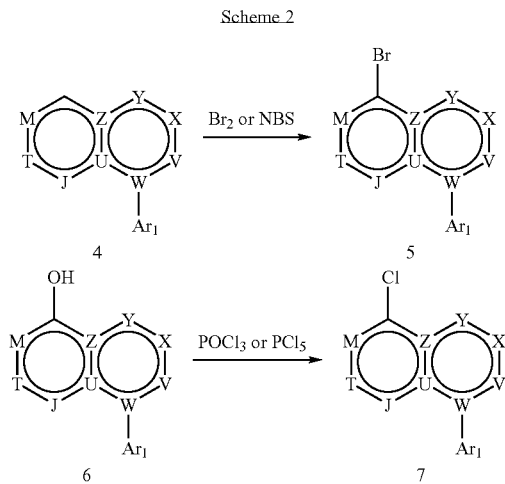

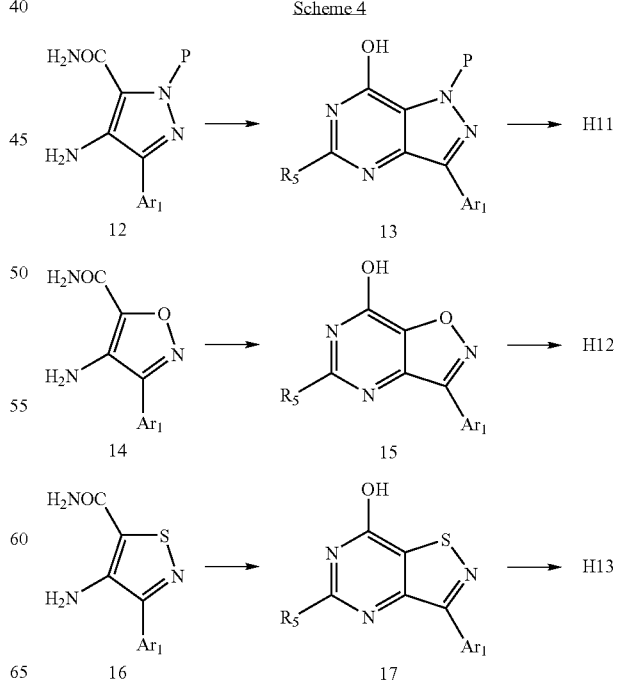

-continued

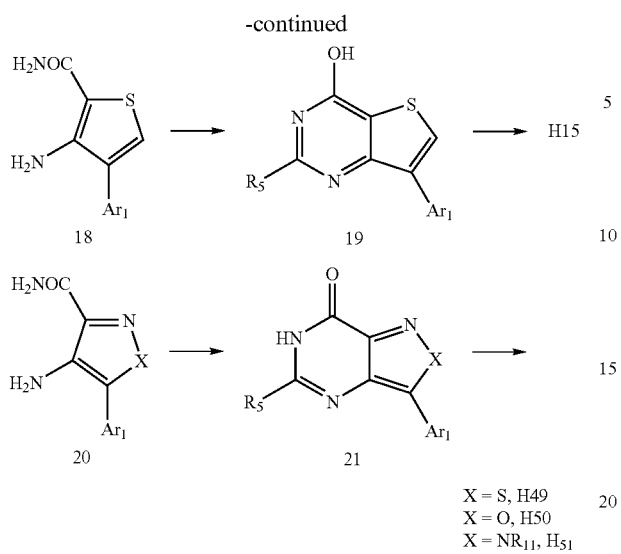

X = S, H49
X = O, H50
X = NR₁₁, H51

Similar approaches may be taken with other 6,5 fused systems (Scheme 4), wherein an amino carboxamide derivative may be condensed with other small carbon fragments. Compounds of the type shown by examples H11 (Bull Chem Soc. Jap. (1979) 52, 208; H12, H13 (*Leibigs Ann. Chim* (1979), 10, 1534), H15 (Indian J. Chem, Sec B. (1994), 33B, 436), H49, H50 and H51 (Bioorg Med Chem Lett, (2002), 12, 2133) may each be made by this general procedure by starting from the protected pyrazole, isoxazole, thiazole and thiophene respectively and cyclising by heating with either a small carboxylic acid, aldehyde or with a mixture of triethyl orthoformate and acetic anhydride (Scheme 4).

It is probable that other 6,5 fused heterocycles containing a pyrimidine ring (such as H6, H8, H9, H10 (see WO9749706, H12, H14, H46, H47 and H48) may also be prepared by analogous synthetic routes from the appropriate amido amine species. However, in some instances it may be more facile to fuse the 5-membered ring onto the already formed 6-membered ring rather than vice-versa. For example, compounds of example H8 and H9 may be formed from a common intermediate species (Scheme 5).

Scheme 5

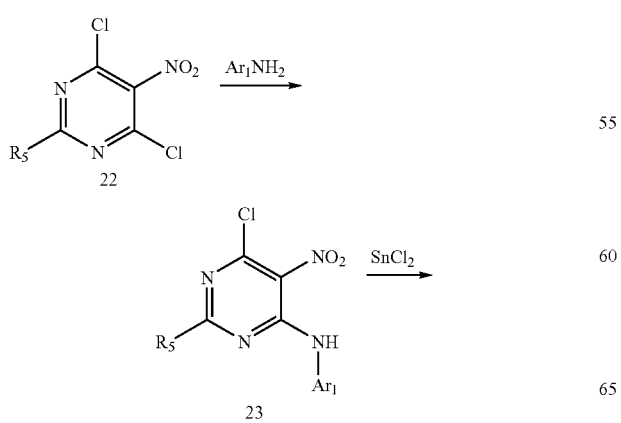

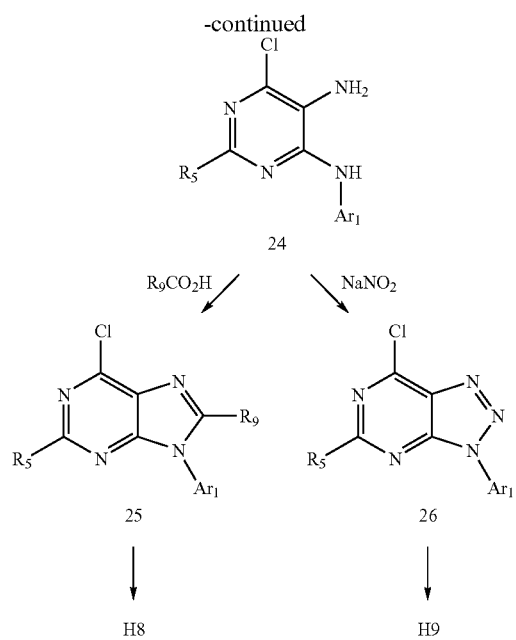

In some such cases it may be more useful to displace the chloride group with the appropriate nucleophilic component before completing the ring cyclization reaction.

Scheme 6

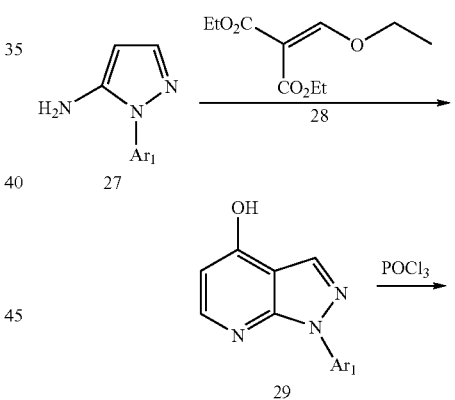

Similar strategies can be applied to the synthesis of pyridinyl 2,3-fused heterocycles. For example, heterocycles such as H22 may be prepared from the amino-5-membered heterocycle by condensation with an appropriate malonic ester 28 derivative (Heterocyclic communications, (2000), 6, 463)

Scheme 6 or as in Scheme 6b from aldhehydic substituted N-Aryl pyrazoles to form regioisomeric pyrazolo[4,3-c]pyridines. Heterocycles such as H21, H27 and H28 may be prepared by using similar strategies. Heterocycles such as H25 and H26 may be prepared as described in WO9635689 and WO 01087892 respectively (Scheme 6).

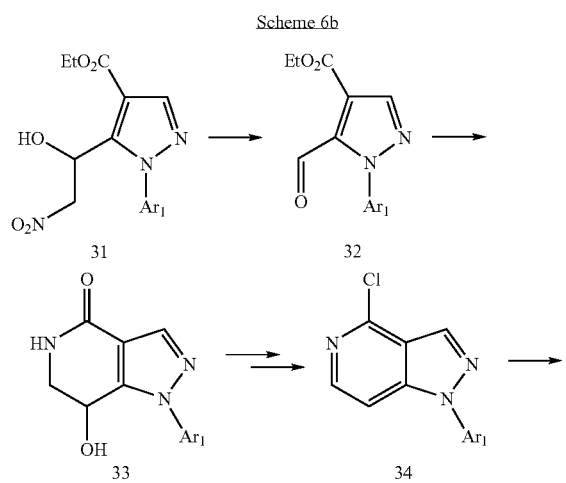

As with the fused pyrimidinyl series, it may sometimes be more prudent to allow the 5-membered ring to be formed second to produce the fused heterocycle.

For example heterocycles H23 (WO 01053263) and H24 (WO 9808847) (Scheme 7) may be prepared from a common intermediate:—

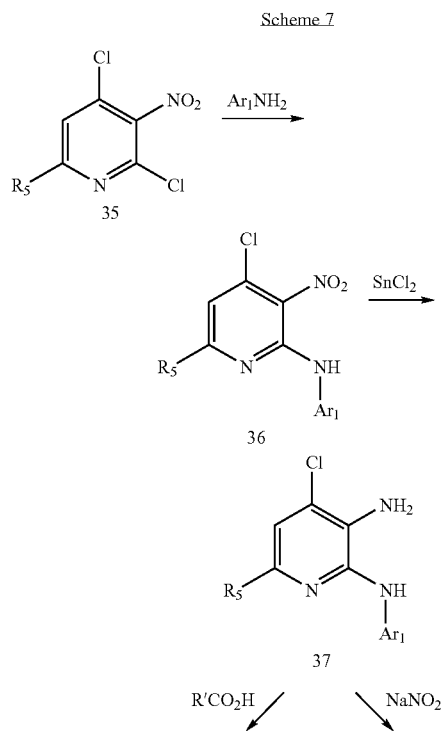

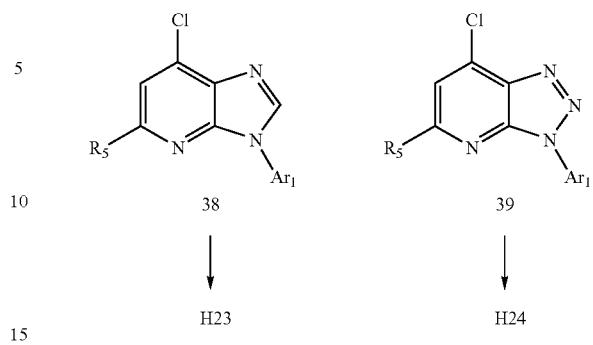

In addition, alternative condensation methods may be used, such as those described in J. Med Chem, (2003), 46, 4702 for the preparation of pyridylfurans: the same method would be adaptable for the synthesis of H30 which is also described in WO 9847903, if the thiol was used as the starting point in place of the alcohol.

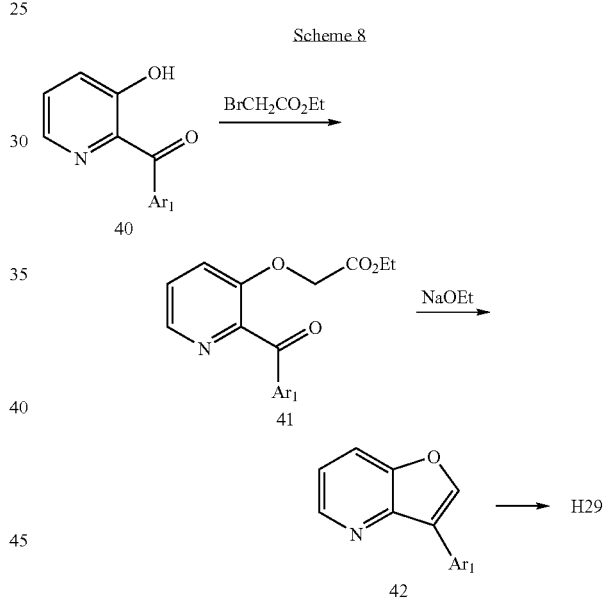

In addition, the same ketone intermediates may be used to prepare the analogous oximes which may be cyclised to the pyridylisoxazole (H27) and pyridylisothiazole (H28) respectively, by treatment with an appropriate acid catalyst, such as polyphosphoroic acid or by use of a acid catalyst and heating under Dean-Stark conditions (Scheme 9).

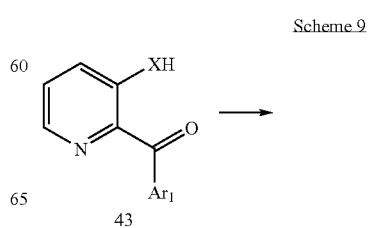

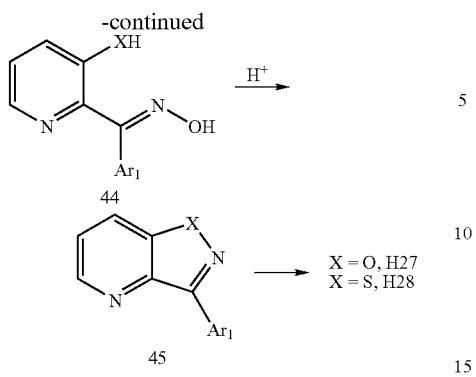

In some examples of 6,5-fused systems, in particular where the 5-membered ring is fused onto a 3-pyridyl ring it may be necessary to activate the ring system to be more reactive towards nucleophiles for the formation of an appropriate intermediate by, for example oxidation of the pyridyl nitrogen to the N-oxide, e.g. *Acta. Pol. Pharm.* (1984), 41, 601 enabling the formation of heterocycles H38 and H39 (Scheme 10).

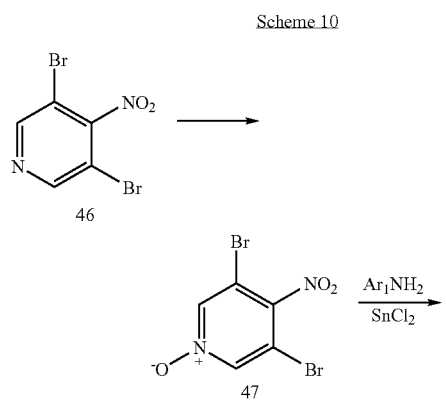

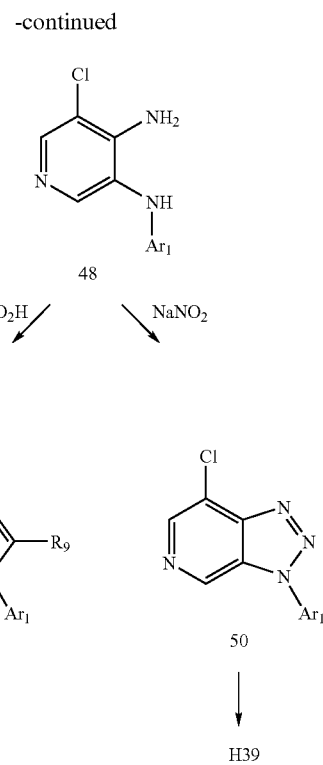

Alternatively, the position of this nitrogen may be used to advantage by enhancing nucleophilic reaction at the 4-position relative to the nitrogen in some examples, e.g. H41 may be prepared by nucleophilic reaction followed by cyclization, *J. Mol. Structure*, (1987), 158, 99, or H42 may be prepared by condensation with hydroxylamine followed by cyclization, a process enhanced by the presence of the nitrogen in the pyridyl ring portion (Scheme 11).

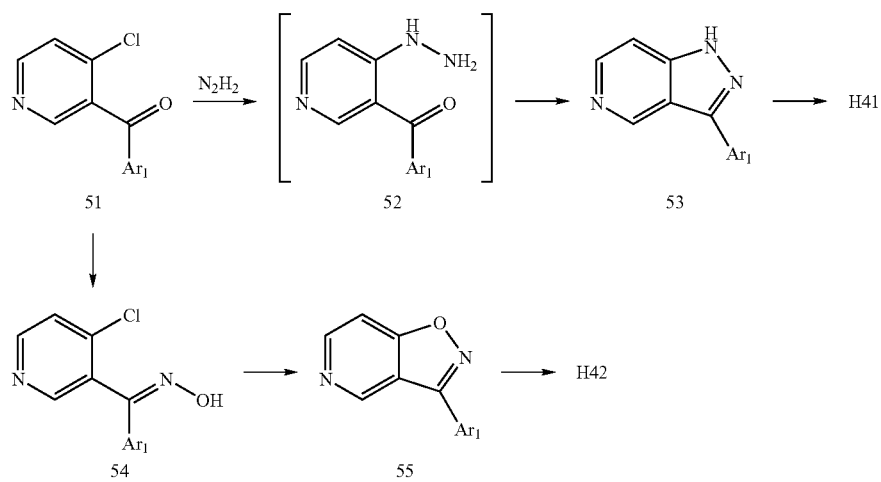

It is with a combination of several of the methods described above, that a range of 6,5-fused bicyclic templates may be prepared. In each case the templates serve to orientate the appropriate groups $Ar_1$ and the Q-K-(EBDA) portion around a central locus in the correct orientation for maximum biological activity. In the same way, the appropriate groups may also be arrayed around a 6,6-fused bicyclic core. Indeed, 6,6-fused pyrimidines may be prepared according to a similar strategy employed for the preparation of 6,5-fused pyrimidines, that is that the pyrimidine ring may be formed second, from the condensation of an aryl amino carboxamide derivative.

In this manner, heterocycles H1 (see: *Tetrahedron* (2000), 56, 5499; *J. Am. Chem. Soc.* (2002), 124, 1594), H2 (WO 0202549), H3 (WO 980820), H4 and H5 (*Montash fur Chemie*, (1978) 109, 527) may be prepared from the appropriately substituted phenyl or heterocyclic rings.

attached, in which case the ring system may be prepared from the appropriate aminopyridyl aryl ketone intermediate (where either M or T=N), a procedure in which the pyrimidine ring is formed by an intramolecular cyclisation process by nucleophilic displacement of a suitable leaving group, R, by an amino moiety formed by, for example, reduction of the oxime of the precursor ketone. Chlorination of the resultant urea-like intermediate and subsequent reduction provides the required ring system (*J. Heterocyclic Chem*, (1989) 26, 105) (Scheme 13).

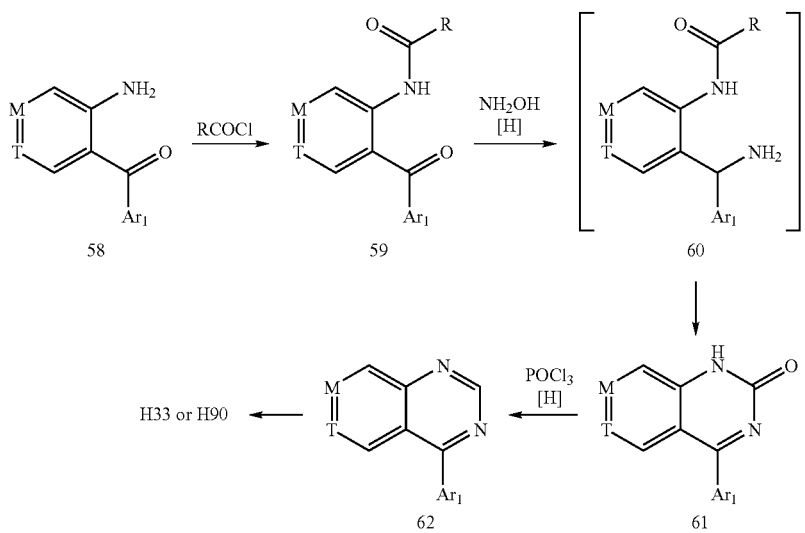

6,6-fused species wherein one of the 6-membered rings is a 2-pyridyl ring, which again may be formed by fusing an appropriate building block onto an existing amino substituted phenyl or heterocyclic ring, e.g.

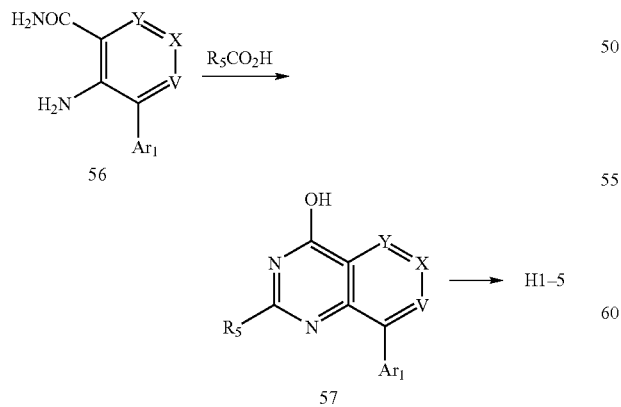

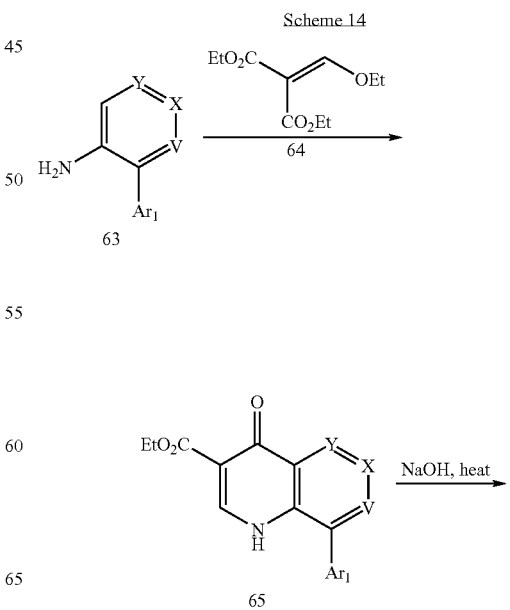

In an alternative embodiment, the pyrimidine ring may be the bicyclic ring component to which the aryl group $Ar_1$ is

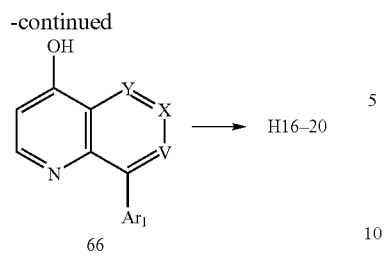

In this way heterocyclic templates of the type H16 (Yakugaku Zasshi (1987) 107, 123); H17 (WO 02040480); H18, H19 and H20 (WO 9835967) may be prepared. In a variant of the above method, the critical Ar₁ group may be optionally introduced at a later stage in the synthesis, via transition metal catalyzed biaryl coupling protocols well known to those in the art (Scheme 15). Other transition metal mediated N arylations of bicyclic heterocycles have been reported, such as those described in Tetrahedron Lett., 44, 2003, 3359-3362, wherein arylation is achieved with under mild conditions using aryl boronic acids in the presence of copper(II)acetate, molecular sieves and a base, which is preferably phenanthroline. In addition to this report other efficient exocyclic N—H arylations of heterocyclic functions have been developed. The most commonly used strategy is based on palladium, nickel or copper catalysis with aryl halides or aryl sulfonates.

Scheme 15

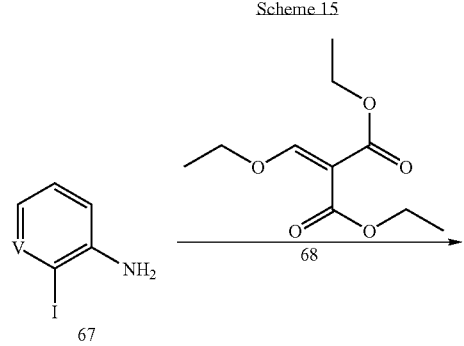

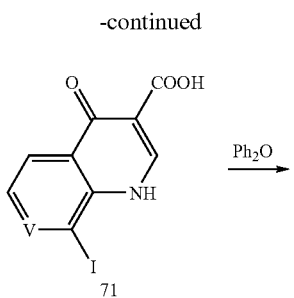

3-Aryl pyrazolo[4,3-d]pyrimidines, type H51, have been described in the literature (Bioorganic Medicinal Chemistry Lett. 12, 2002, 2133-2136). Treatment of N-alkyl pyrazole (74) with benzyl thioacetimidate hydrobromide in refluxing pyridine affords the intermediate pyrazolopyrimidinone (75) in moderate yield (Scheme 16).

Scheme 16

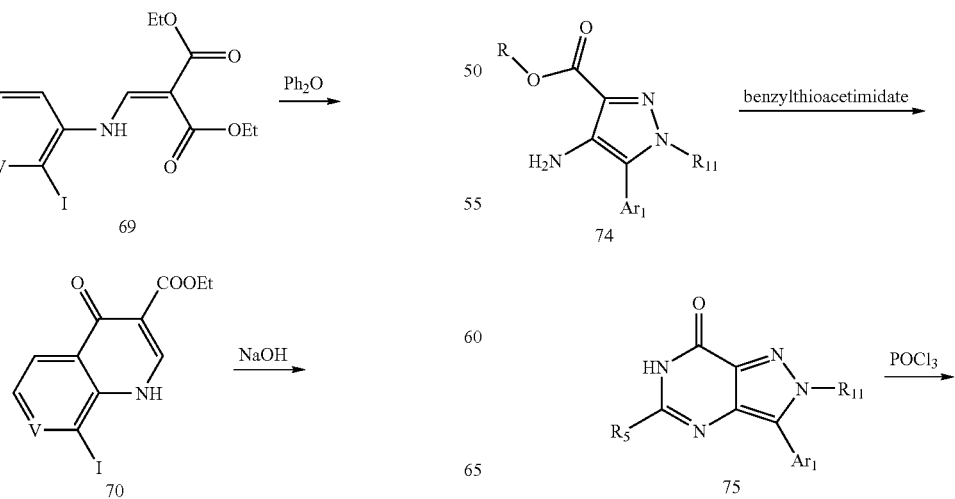

-continued

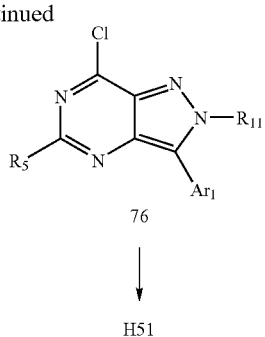
76

↓

H51

Again, target analogues retaining this bicyclic core are obtained via the standard halogenation, nucleophilic displacement sequence described in Scheme 1 and Scheme 20. In some embodiments one of the heteroatoms maybe incorporated into the 6:5 ring junction, such examples include heterocyclic cores H51-54, H61-63, H70-84 and H110-113 in Table 6.

3-Arylpyrazolo[1,5-a]pyrimidines of type H53 are well known in the art and may be obtained from arylacetonitriles as depicted in Scheme 17. Conversion to the intermediate ketonitriles (78, 79, 80) may be effected via a variety of synthetic methodologies as depicted. Cyclization to amino pyrazoles of all intermediates can be achieved thermally with hydrazine HCl in alcoholic solvents such as ethanol or isopropyl alcohol. Construction of the second 6 membered ring maybe undertaken using a variety of beta-keto esters in refluxing dioaxane or THF to afford pyrazolo[1,5-a]pyrimidinones of type 82 which are elaborated further via a standard halogenation nucleophilic displacement sequence. In an alternative embodiment the 3-Arylpyrazolo[1,5-a]pyrimidine (Scheme 18) core can be synthesized by the synthetic scheme outlined in Scheme 18, wherein $Ar_1$ is introduced via a key transition metal catalyst mediated Negishi or Suzuki type coupling. It is also noteworthy at this juncture to mention that 7-chloro-3-bromopyrazolo[1,5-a]pyrimidine (87) may also be prepared from the 7-chloro fused bicycle via direct bromination with N-bromosuccinimide (see for ref J. Med. Chem, 1976, vol. 19, No. 4, 512).

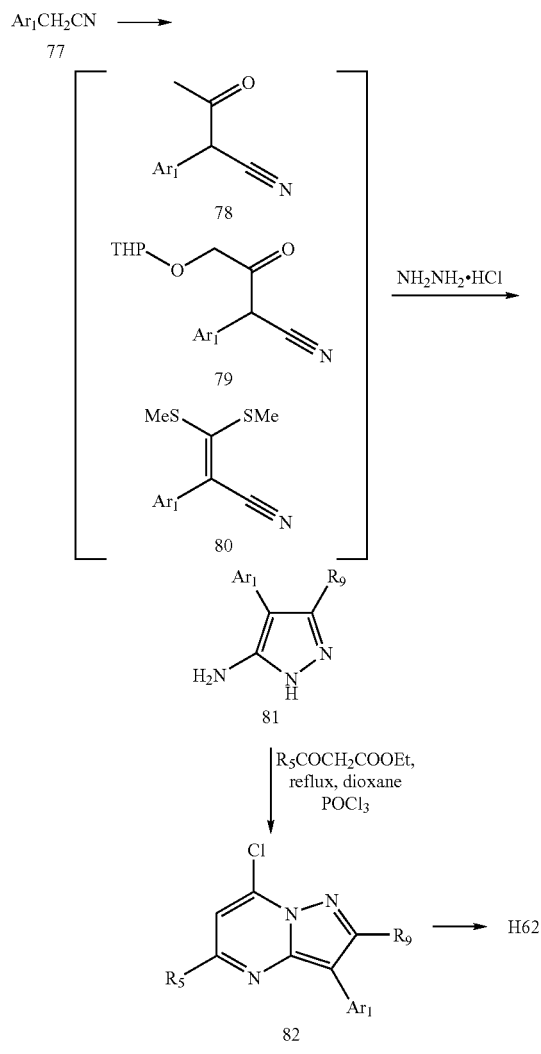

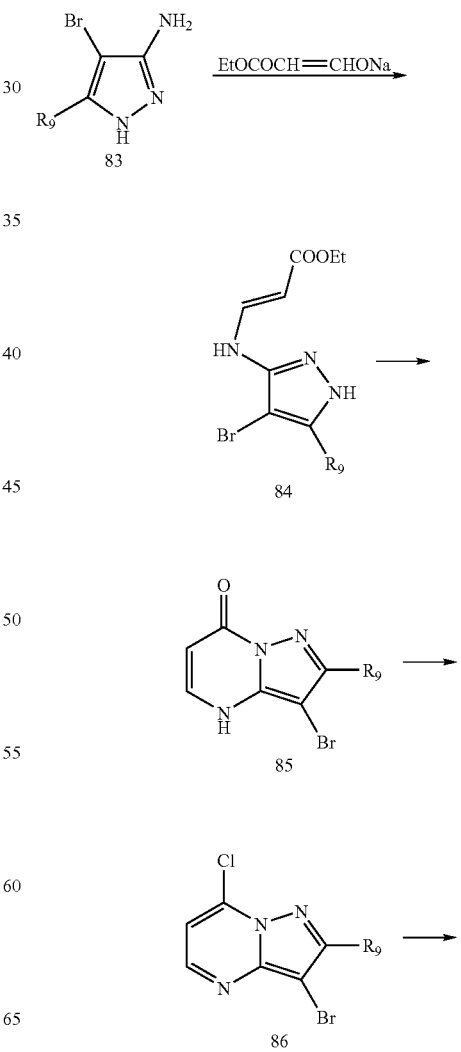

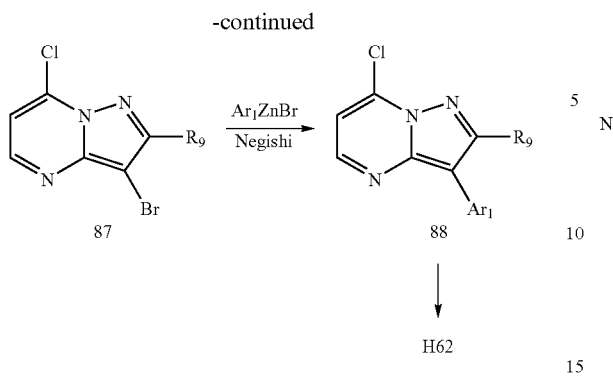

Other preferred core scaffolds of the present invention that contain heteroatoms at the ring junction positions include the pyrazolo[1,5-a]triazines and the pyrrolo[1,2-a]pyrimidines depicted in Scheme 18b below. Again, similar organic chemistry strategies can be harnessed to fuse a 6 membered ring on to the pyrazole or pyrrole core. Reaction of the 4-aryl-3-amino pyrazole with ethylacetimidate to produce an intermediate amidine is the key step in the construction of the pyrazolo[1,5-a]triazine 91, reaction of this intermediate with deiethyl carbonate in the presence of sodium ethoxide produces the 6:5 triazinone with can then be subjected to the standard chlorination, nucleophilic displacement steps to produce Rup-3 selective insuilin secretogogues of the present invention (for reference see J. Med. Chem. 2000, 43, 3, 449). Alternatively, pyrrolo[1,2-a]pyrimidines can be constructed from trisubstituted pyrroles by reaction with ethyl acetoacetate in refluxung dioxane (for reference see WO/9835967) (Scheme 18b).

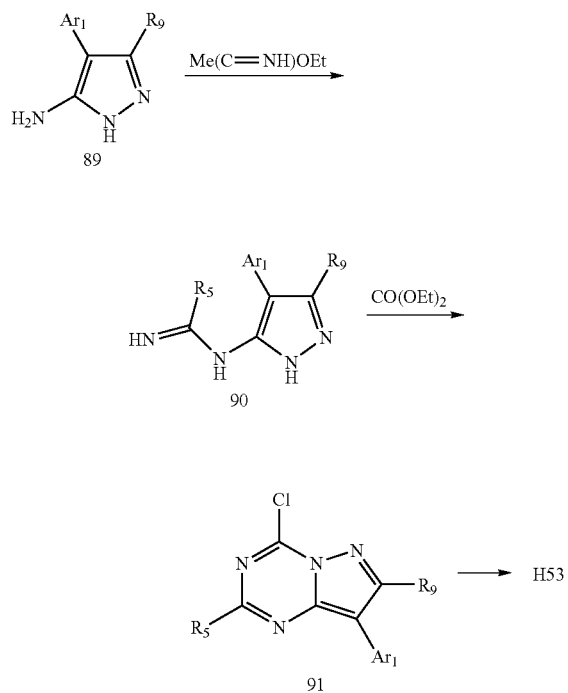

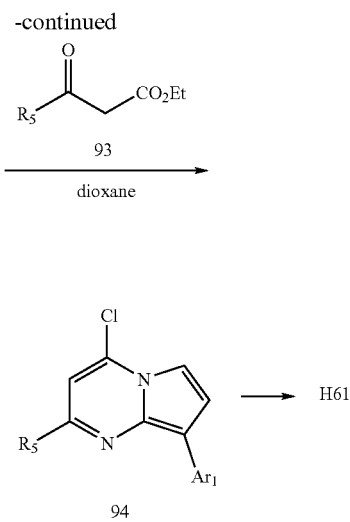

Pyrrolo[2,3-d]pyrimidine derivatives of the current invention may be obtained via methodologies depicted in Scheme 19a (J. Med. Chem, 1997, 40, 1749-1754). The Knoevenagel derived malonitrile derivative can be readily brominated with 1-1.3 equivalents of NBS in the presence of catalytic benzoyl peroxide. Subsequent reaction with $Ar_1NH_2$ affords aminopyrrole intermediate (97). Acylation followed by hydrolysis of the nitrile and phosphoric acid mediated cyclization is a proven strategy for synthesis of the pyrimidine ring.

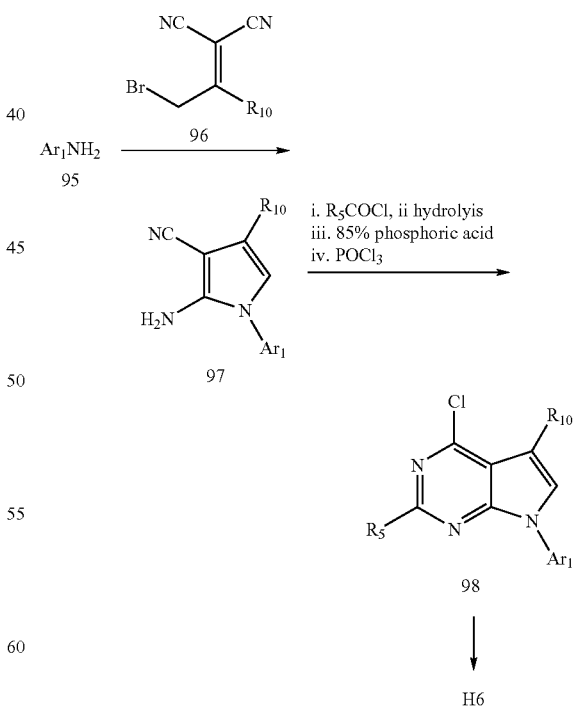

Alternative synthetic routes may be adopted such as the Heck mediated cyclization of 5-alkynyl-4-anilinopyrimidines as depicted in Scheme 19b.

Scheme 19b

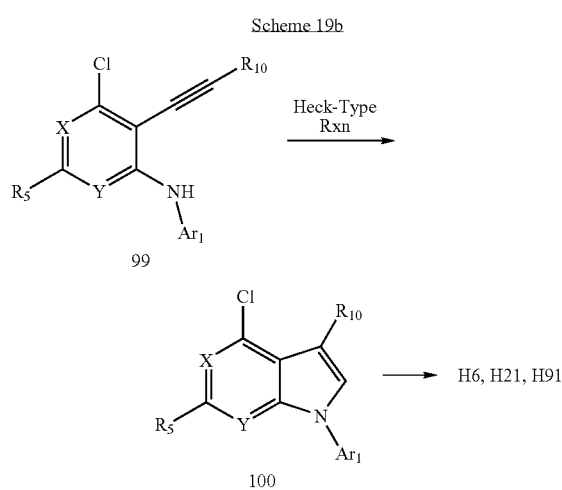

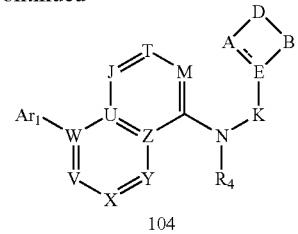

104

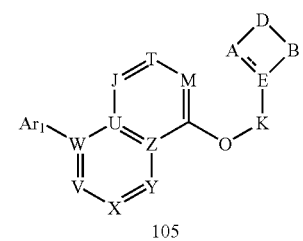

105

To facilitate rapid entry into many of the compounds of the invention microwave synthesis can be optionally utilized (Scheme 20). The Smith synthesizer from Personal Chemistry is a commercially available focused field heating instrument that provides safer and more uniform conditions for performing the base catalyzed substitution reactions depicted in Schemes. Bases employed for such conversions (whereby Q=NR$_4$) include tertiary amines such as triethylamine, Hunig's base (i.e. diisopropyl-ethylamine), N-methylmorpholine and the like. Alternatively, one skilled in the art can employ alkali metal hydrides, alkali metal carbonates (such as, Li$_2$CO$_3$, Na$_2$CO$_3$, K$_2$CO$_3$ and the like), an alkali metal hydrogencarbonate (such as, LiHCO$_3$, NaHCO$_3$, KHCO$_3$ and the like). Wherein Q=N, inert lower alkyl alcoholic solvent can be emplyed (such as, MeOH, EtOH, i-PrOH, n-BuOH and the like) or wherein Q=O, an ethereal solvent such as tetrahydrofuran, 1,4-dioxane, and the like can be used. Reaction times to access typical examples such as, 104 and 105, can range from about 300 s to about 3000 s and when conventional thermal methods are employed (wherein Q=O) about 20 mins to about 48 h.

Scheme 20

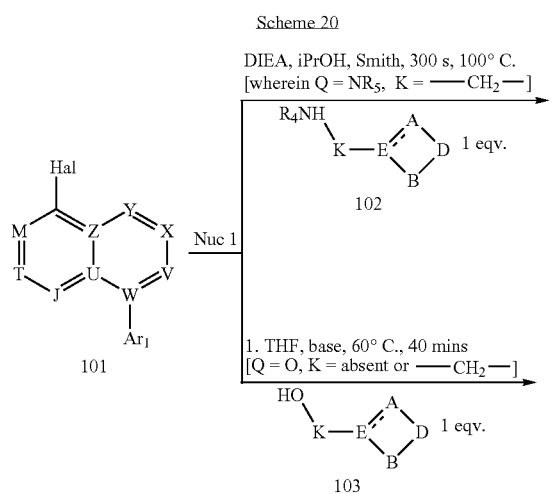

As illustrated in Scheme 21, a similar transition metal catalysed couplings were utilized to obtain molecules of general formula 107-111 (Scheme 21) wherein the "Ar$_1$" substituent (Hal=Br, I) of intermediate 106 is modified to give analogs with alkyl amino substituents (i.e., NR$_a$R$_b$, wherein R$_a$ and R$_b$ are each independently H, C$_{1-6}$ alkyl or a substituted C$_{1-6}$ alkyl, or R$_a$ and R$_b$ together with the nitrogen form a heterocyclic ring, as described herein). Alternatively, the linker atom can be oxygen by utilizing the CuI catalysed method for aromatic C—O formation described by Buchwald (see for reference S. L. Buchwald; Organic Lett., 2002, 4, 6, 973-976) by utilizing, for example, 10 mol % CuI, 20 mol % 1,10-phenanthroline, 2 equivalents of Cs$_2$CO$_3$, at 110° C. for 18 h (Scheme 21d), with an "Ar$_1$" iodo substitution in the substrate. Additional important organometallic transformations from halo intermediates 106 to active analogues of the current invention include the well know palladium catalyzed couplings of appropriately substituted aryl boronic acids via the "Suzuki coupling reaction" to introduce aryl or heteroaryl groups [Ar$_4$] (Scheme 21e).

The Suzuki coupling represents a widely used method for the synthesis of biaryl compounds and is already applied on industrial scale. Unfortunately, for a long time this reaction was limited to the use of aryl bromides, aryl iodides or electron-deficient aryl chlorides as starting materials. Thus, a general approach to the desired biaryl compounds using the cheap and easy available aryl chlorides was not available. In the last two years, however, several new protocols for the Suzuki coupling with aryl chlorides were developed. These methods allow an efficient synthesis of biaryls, independently of the substitution pattern and electronic properties of the starting materials. These concepts which were developed by the research groups of Fu, Buchwald, Guram, Beller as well as Trudell and Nolan are highlighted in "Modern methods of the Suzuki cross coupling: the long expected general synthetic routes using aryl chlorides. Groger, Harald, Journal fuer Praktische Chemie (Weinheim, Germany) (2000), 342 (4), 334-339. Alternatively additional functionality maybe introduced using other metal catalyzed transformations such as cyanation using zinc(II)cyanide under microwave irradiation conditions to obtain compounds of general formula 108 or the well documented Pd catalyzed "Sonogashira reaction" (Scheme 21c) for introduction of terminal alkynes. Most recently the Sonogashira Coupling has been described to produce almost quantitative yields of desired product using appropriate reaction conditions in the complete absence of palladium catalysts (for ref see "First Examples of Transition-Metal Free Sonogashira-Type Couplings" Leadbeater, Nicholas E.; Marco, Maria; Tominack, Bonnie J, Organic Letters (2003), 5(21), 3919-3922, and also transition-metal-free Sonogashira-type coupling reactions in water, Appukkuttan, Prasad; Dehaen, Wim; Van der Eycken, Erik, European Journal of Organic Chemistry (2003), (24), 4713-4716

-continued

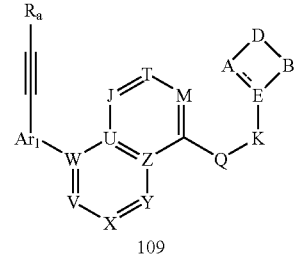
109

Scheme 21

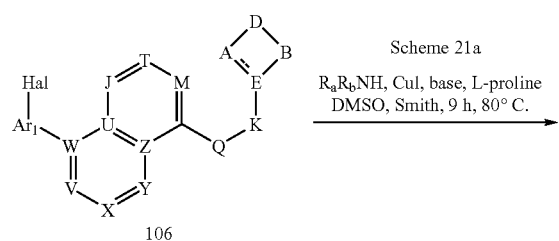
106

Scheme 21a
$R_aR_bNH$, CuI, base, L-proline
DMSO, Smith, 9 h, 80° C.

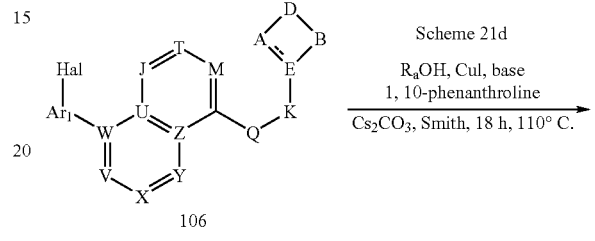
106

Scheme 21d
$R_aOH$, CuI, base
1, 10-phenanthroline
$Cs_2CO_3$, Smith, 18 h, 110° C.

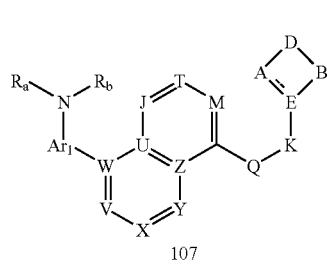
107

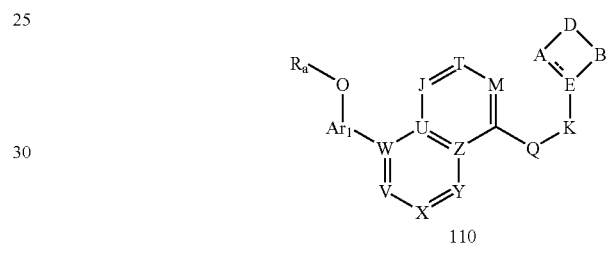
110

Scheme 21b
$Zn(CN)_2$, $Pd(PPh_3)_4$
DMF, Smith, 8', 180° C.
[Hal = I]

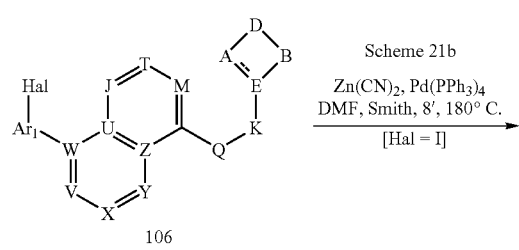
106

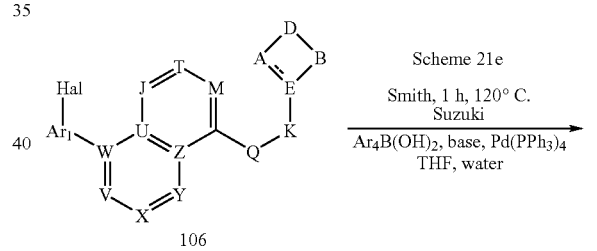
106

Scheme 21e
Smith, 1 h, 120° C.
Suzuki
$Ar_4B(OH)_2$, base, $Pd(PPh_3)_4$
THF, water

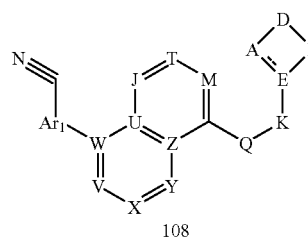
108

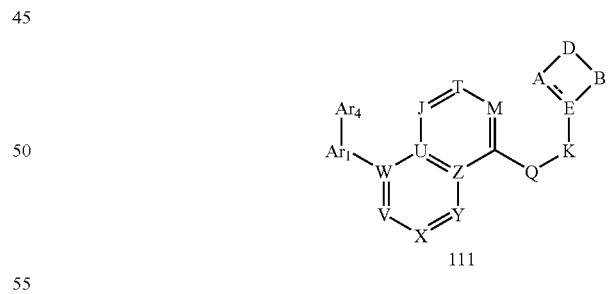
111

Scheme 21c
$R_aCCH$
Sonogashira

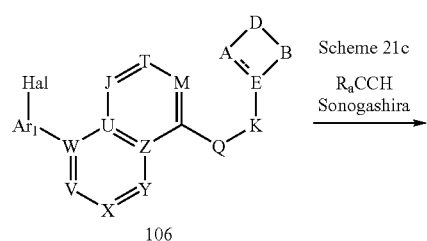
106

Scheme 21f
i. $NH_2OHHCl$, base
EtOH, $H_2O$
ii. Zinc dust, AcOH

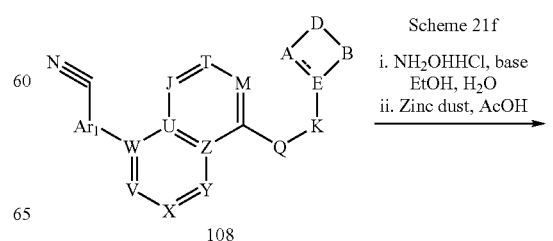
108

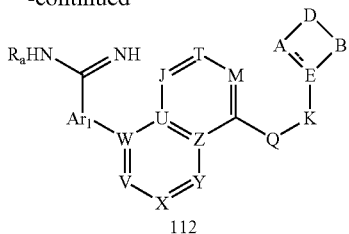

One particular embodiment is when the Hal group on "Ar₁" is located at the para position of a phenyl ring. In another particular emdodiment of the invention, the Hal group is chloro at the 2 position of a trisubstituted pyridyl moiety (intermediate 113). Organotransition metal catalysed methods for substitution of this halogen are depicted in Scheme 22.

A particular substitution for compounds of the present invention is wherein D=NCOOR$_c$ wherein R$_c$ is C$_{1-6}$ alkyl, or C$_{3-7}$ cycloalkyl and each can be further substituted. Urethanes of this type can be prepared directly from intermediates depicted in Schemes 20 and 21 when D=NH. In certain reactions, use of a suitable nitrogen protecting group (such as, 'Boc, Cbz, Moz, Alloc, Fmoc and the like) may be necessary during further chemical modification of the core. Deprotection maybe achieved using standard reagents familiar to one skilled in the art (these might include TFA, mineral acid, Palladium/hydrogen gas and the like in an alcoholic or ethereal solvent system chosen from methanol, ethanol, tert-butanol, THF, 1,4-dioxane, and the like). On occasion wherein the target molecule contains 2 protecting groups, an orthogonal protection strategy may be adopted. The deprotected secondary amine (D=NH) can subsequently be modified accordingly.

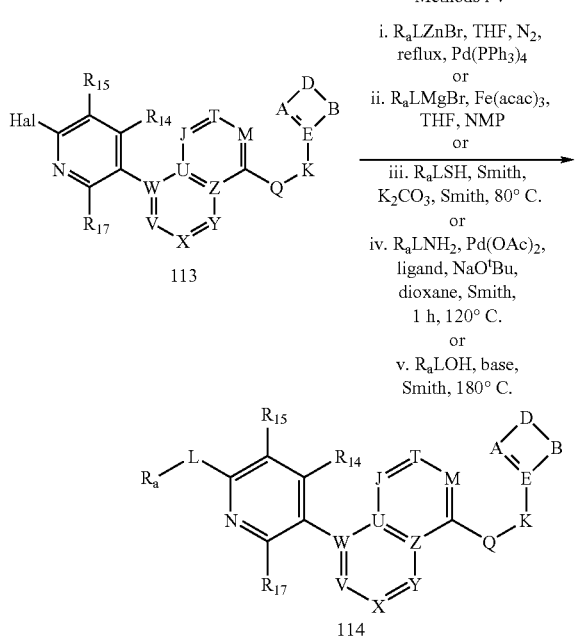

Schemes 23 and 24 and 25 illustrate such chemistries wherein generation of a carbamate, urea or amide can be executed using an appropriate reaction in the presence of a base, for example, a tertiary amine base such as TEA, DIEA and the like, in an inert solvent system.

As illustrated in Scheme 23, urethane 116 can be obtained by a urethane reaction using R$_c$OCO-halide (wherein R$_a$ is as described supra, and halide is chloro, bromo, or iodo, particularly useful is chloro) in an inert solvent with or without a base. Suitable bases include an alkali metal carbonate (such as, sodium carbonate, potassium carbonate, and the like), an alkali metal hydrogencarbonate (such as, sodium hydrogencarbonate, potassium hydrogencarbonate, and the like), an alkali hydroxide (such as, sodium hydroxide, potassium hydroxide, and the like), a tertiary amine (such as, N,N-diisopropylethylamine, triethylamine, N-methylmorpholine, and the like), or an aromatic amine (such as, pyridine, imidazole, poly-(4-vinylpyridine), and the like). The inert solvent includes lower halocarbon solvents (such as, dichloromethane, dichloroethane, chloroform, and the like), ethereal solvents (such as, tetrahydrofuran, dioxane, and the like), aromatic solvents (such as, benzene, toluene, and the like), or polar solvents (such as, N,N-dimethylformamide, dimethyl sulfoxide, and the like). Reaction temperature ranges from about –20° C. to 120° C., preferably about 0° C. to 100° C.

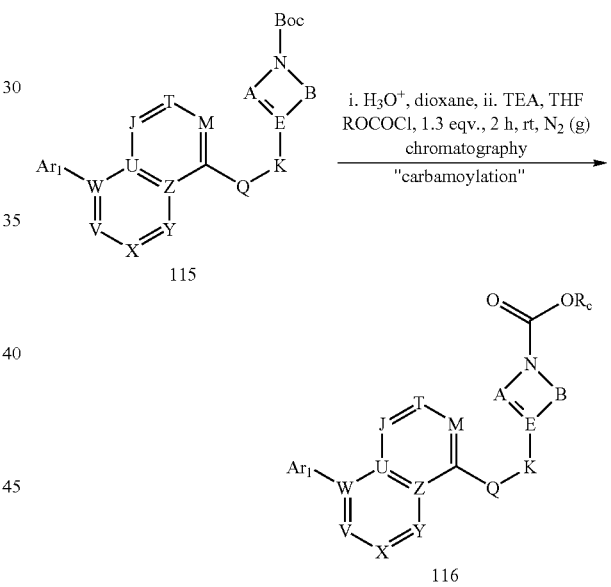

As shown in Scheme 24, the amine intermediate obtained from acidic deprotection of 117 can be functionalized to amides represented by species 118. Carbamate 117 is first reacted with 4N HCl in dioxane or alternatively TFA in dichloromethane and further reacted with a carboxylic acid (R$_d$CO$_2$H, wherein as used in Scheme 24, R$_d$ is Ar$_2$, or a C$_{1-6}$-alkylene-Ar$_2$; Ar$_{2/3}$ can be substituted or unsubstituted and has the same meaning as described herein) with a dehydrating condensing agent in an inert solvent with or without a base to provide the amide 118 of the present invention. The dehydrating condensing agent includes dicyclohexylcarbodiimide (DCC), 1,3-diisopropylcarbodiimide (DIC), 1-ethyl-3-(3-dimethylaminopropyl)carbodiimide hydrochloride (EDC.HCl), bromo-tris-pyrrolidino-phosphonium hexafluorophosphate (PyBroP), benzotriazoloyloxytris(dimethylamino)-phosphonium hexafluorophosphate (BOP), O-(7-azabenzo triazol-1-yl)-1,1,3,3-tetramethyluronium hexafluorophosphate (HATU), or 1-cyclohexyl-3-methylpolystyrene-carbodiimide. The base includes a tertiary amine (such as, N,N-diisopropylethylamine, triethylamine, and the like). The inert solvent includes lower halocarbon solvents (such as, dichloromethane, dichloroethane, chloroform, and the like), ethereal solvents (such as, tetrahydrofuran, dioxane, and the like), nitrile solvents (such as, acetonitrile, and the like), amide solvents (N,N-dimethylformamide, N,N-dimethylacetamide, and the like) and mixtures thereof. Optionally, 1-hydroxybenzotriazole (HOBT), HOBT-6-carboxaamidomethyl polystyrene, or 1-hydroxy-7-azabenzotriazole (HOAT) can be used as a reactant agent. Reaction temperature ranges from about −20° C. to 50° C., preferably about 0° C. to 40° C.

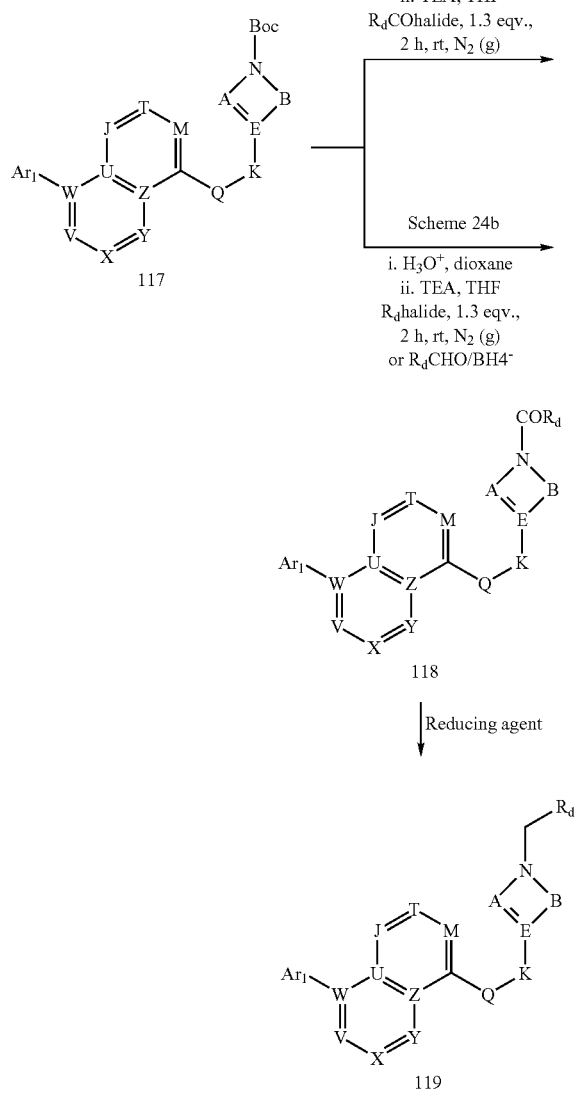

Alternatively, amides 118 of the present invention can be obtained by an amidation reaction using an acid halide (such as, $R_d$COCl) and a base in an inert solvent. The base includes an alkali metal carbonate (such as, sodium carbonate, potassium carbonate, and the like), an alkali metal hydrogencarbonate (such as, sodium hydrogencarbonate, potassium hydrogencarbonate, and the like), an alkali hydroxide (such as, sodium hydroxide or potassium hydroxide, and like), a tertiary amine (such as, N,N-diisopropylethylamine, triethylamine, N-methylmorpholine, and the like), or an aromatic amine (such as, pyridine, imidazole, poly-(4-vinylpyridine), and the like). The inert solvent includes lower halocarbon solvents (such as, dichloromethane, dichloroethane, chloroform, and the like), ethereal solvents (such as, tetrahydrofuran, dioxane, and the like), amide solvents (such as, N,N-dimethylacetamide, N,N-dimethylformamide, and the like), aromatic solvents (benzene, toluene, pyridine, and the like) and mixtures thereof. Reaction temperature ranges from about −20° C. to 50° C., preferably about 0° C. to 40° C.

Also illustrated in Scheme 24, amide 118 can be reacted with a reducing agent in an inert solvent to provide the amine 119 of the present invention. The reducing agent includes alkali metal aluminum hydrides (such as, lithium aluminum hydride, and the like), alkali metal borohydrides (such as, lithium borohydride, and the like), alkali metal trialkoxyaluminum hydrides (such as, lithium tri-tert-butoxyaluminum hydride, and the like), dialkylaluminum hydrides (such as, di-isobutylaluminum hydride, and the like), borane, dialkylboranes (such as, di-isoamyl borane, and the like), alkali metal trialkylboron hydrides (such as, lithium triethylboron hydride, and the like). The inert solvent includes ethereal solvents (such as, tetrahydrofuran, dioxane, and the like), aromatic solvents (such as, toluene, and the like) and mixtures thereof. Reaction temperature ranges from about −78° C. to 200° C., preferably about 50° C. to 120° C.

Alternatively, the amine 119 of the present invention can be obtained by a reductive amination reaction using the acid deprotected secondary amine intermediate with an aldehyde ($R_d$CHO) and a reducing agent in an inert solvent with or without an acid. The reducing agent includes sodium triacetoxyborohydride, sodium cyanoborohydride, sodium borohydride, borane-pyridine complex, and the like. The inert solvent includes lower alkyl alcohol solvents (such as, methanol, ethanol, and the like), lower halocarbon solvents (such as, dichloromethane, dichloroethane, chloroform, and the like), ethereal solvents (such as, tetrahydrofuran, dioxane, and the like), aromatic solvents (such as, benzene, toluene, and the like) and mixtures thereof. The acid includes an inorganic acid (such as, hydrochloric acid, sulfuric acid, and the like) or an organic acid (such as, acetic acid, and the like). Reaction temperature ranges from about −20° C. to 120° C., preferably about 0° C. to 100° C. In addition, this reaction can optionally be carried out under microwave conditions.

In an alternative manner, the intermediate amine product of acid deprotection of 117 can be alkylated directly with an alkylating agent, such as $R_d$-halide (wherein $R_d$ is substituted or unsubstituted $C_{1-6}$ alkyl, or substituted or unsubstituted $C_{1-6}$ alkyl-Ar, and halide is chloro, bromo and iodo), in the presence of a base and in an inert solvent to provide amine 119. The base includes an alkali metal carbonate (such as, sodium carbonate, potassium carbonate, and the like), an alkali metal hydride (such as, sodium hydride, potassium hydride, and the like), alkali metal alkoxide (such as, potassium tert-butoxide, sodium tert-butoxide, and the like); alkyl lithiums (such as, tert-butyl lithium, n-butyl lithium and the like). The inert solvents include, ethereal solvents (such as, tetrahydrofuran, dioxane), aromatic solvents (such as, benzene, toluene, and the like), amide solvents (such as, N,N-dimethylformamide, and the like) and mixtures thereof. Reaction temperature ranges from about −20° C. to 120° C., preferably about 0° C. to 100° C.

Also shown in Scheme 24 is the preparation of additional compounds of the invention via alkylating the nitrogen of ureas represented by 118 with an alkyl-halide (wherein halide is chloro, bromo and iodo) in the presence of a base in an inert solvent to provide di-substituted urea. The base includes an alkali metal hydride (such as, sodium hydride, potassium hydride, and the like), alkali metal alkoxide (such as, potassium tert-butoxide, sodium tert-butoxide, and the like); alkyl lithiums (such as, tert-butyl lithium, n-butyl lithium and the like). The inert solvents include, ethereal solvents (such as, tetrahydrofuran, dioxane), aromatic solvents (such as, benzene, toluene, and the like), amide solvents (such as, N,N-dimethylformamide, and the like) and mixtures thereof. Reaction temperature ranges from about −20° C. to 120° C., preferably about 0° C. to 100° C.

In addition, as illustrated in Scheme 25, urea 121 can be obtained from deprotecting common intermediate 120 and allowing the amine (i.e., D=NH) to react with a variety isocyanates ($R_aNCO$, wherein $R_a$ has the same meaning as described herein) in an inert solvent with or without a base. Suitable bases include an alkali metal carbonate (such as, sodium carbonate, potassium carbonate, and the like), an alkali metal hydrogencarbonate (such as, sodium hydrogencarbonate, potassium hydrogencarbonate, and the like), an alkali hydroxide (such as, sodium hydroxide, potassium hydroxide, and the like), a tertiary amine (such as, N,N-diisopropylethylamine, triethylamine, N-methylmorpholine, and the like), or an aromatic amine (such as, pyridine, imidazole, and the like). The inert solvent includes lower halocarbon solvents (such as, dichloromethane, dichloroethane, chloroform, and the like), ethereal solvents (such as, tetrahydrofuran, dioxane, and the like), aromatic solvents (such as, benzene, toluene, and the like), or polar solvents (such as, N,N-dimethylformamide, dimethyl sulfoxide, and the like). Reaction temperature ranges from about −20° C. to 120° C., preferably about 0° C. to 100° C.

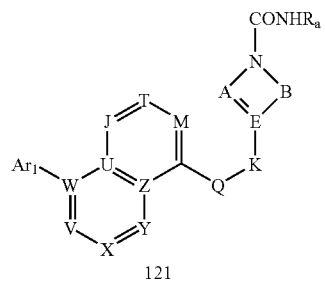

121

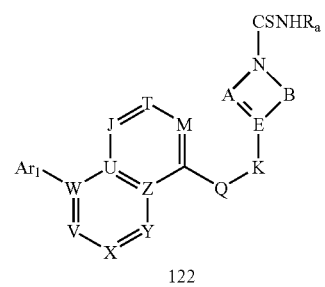

122

Further, as illustrated in Scheme 25b, thiourea 122 can be obtained from deprotecting common intermediate 120 and allowing the amine (i.e., D=NH) to react with a variety thioisocyanates ($R_aNCS$, wherein $R_a$ has the same meaning as described herein) in an inert solvent with or without a base. Suitable bases include an alkali metal carbonate (such as, sodium carbonate, potassium carbonate, and the like), an alkali metal hydrogencarbonate (such as, sodium hydrogencarbonate, potassium hydrogencarbonate, and the like), an alkali hydroxide (such as, sodium hydroxide, potassium hydroxide, and the like), a tertiary amine (such as, N,N-diisopropylethylamine, triethylamine, N-methylmorpholine, and the like), or an aromatic amine (such as, pyridine, imidazole, and the like). The inert solvent includes lower halocarbon solvents (such as, dichloromethane, dichloroethane, chloroform, and the like), ethereal solvents (such as, tetrahydrofuran, dioxane, and the like), aromatic solvents (such as, benzene, toluene, and the like), or polar solvents (such as, N,N-dimethylformamide, dimethyl sulfoxide, and the like). Reaction temperature ranges from about −20° C. to 120° C., preferably about 0° C. to 100° C.

Scheme 25

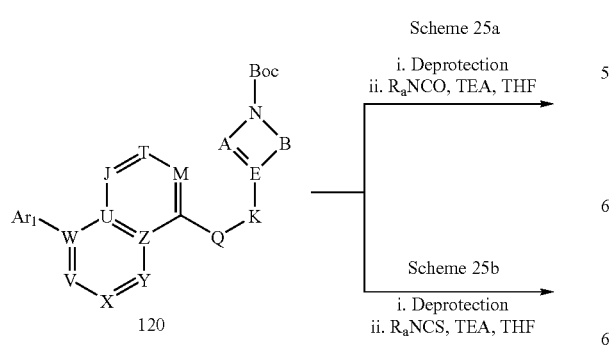

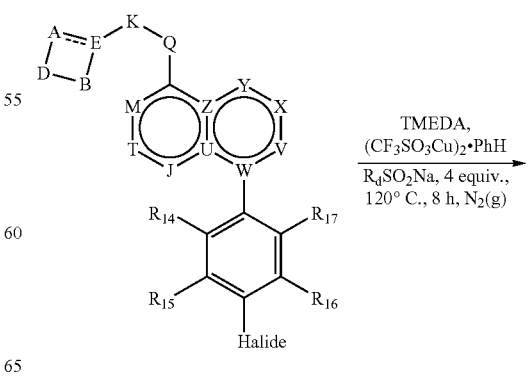

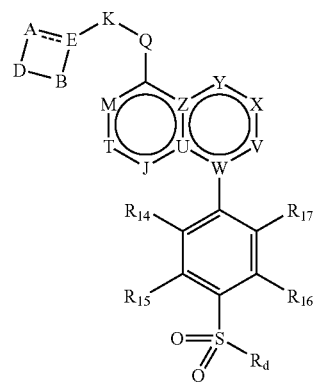

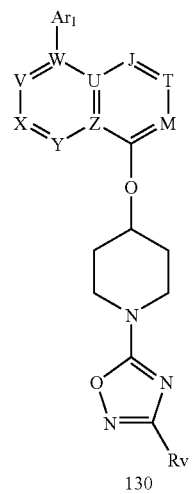

Scheme 26 illustrates the synthesis of para-alkyl sulfones (124) of the present invention, wherein $R_{10}$-$R_{13}$ have the same meaning as described herein where W=a heterocycle selected from Table 6 [H1-H116]. The common methods for preparing these sulfones include the oxidation of sulfides or the sulfonylation of arenes using aryl sulfonyl halides or aryl sulfonic acids in th presence of a strong acid catalyst (see for general reference: the Organic Chemistry of Sulfur; Oae S., Ed.; Plenum Press: New York, 1977). Optimal conversion to the arene 124 was achieved thermally wherein Hal is preferably iodo using 5 mol % (CuOTf)$_2$.PhH and 10 mol % N,N'-dimethylethylenediamine in DMSO by the method of Wang et al (see for reference Wang Z.; Baskin J. M., Org. Lett., 2002, 4, 25, 4423-4425). In some embodiments, $R_{10}$ and $R_{13}$ are each independently H, halogen, or $C_{1-6}$ alkyl; $R_{11}$ and $R_{12}$ are both H; Hal=Br, I.

Synthesis of the 3,5-oxadiazolo variant is depicted in Scheme 27. Zinc(II)chloride catalyzed coupling of amidoxime 126 with 4-hydroxypiperidine, CNBr derived 128 yielded building block 129 after acidic workup, which was subsequently utilized in reaction sequences depicted as illustrated in Schemes 1 & 20.

Scheme 27

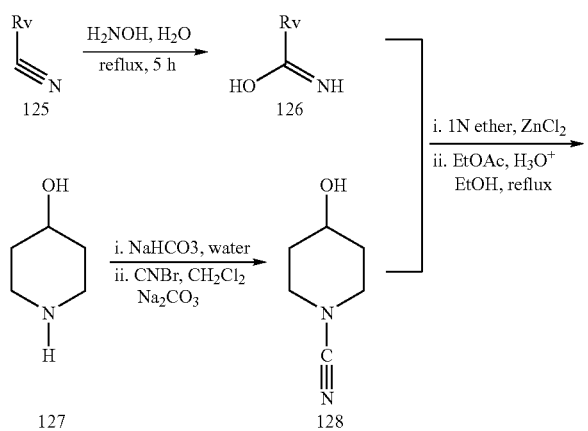

In a preferred embodiment of the present invention a sulfonamide group may be introduced into the meta or para Ar position. This can be accomplished via several amenable synthetic multi step manipulations including the reaction of ammonia with sulfonyl chlorides (Scheme 28A) or alternatively sulfonamides can be obtained by reacting sulfinic acid salts with an electrophilic nitrogen source such as hydroxylamine-O-sulfonic acid or bis-(2,2,2-trichloroethyl)-azodicarboxylate. Preferably 3-methoxy-3-oxapropane-1-sulfinate can serve as a sulfinate donor moiety through a simple alkylation and be subsequently removed via a beta-elimination reaction. Reaction of the resulting sulfinate with an electrophilic nitrogen source provides the primary sulfonamide analogue of the current invention. Such intermediates may be optionally further modified to amides such as those represented by general formulae 132. Acylsulfonamides of this type can be obtained by an amidation reaction using an acid halide or anhydride (such as, $R_g$COCl or $(R_gCO)_2O$) and a base in an inert solvent (Scheme 28C). The base includes an alkali metal carbonate (such as, sodium carbonate, potassium carbonate, and the like), an alkali metal hydrogencarbonate (such as, sodium hydrogencarbonate, potassium hydrogencarbonate, and the like), an alkali hydroxide (such as, sodium hydroxide or potassium hydroxide, and like), a tertiary amine (such as, N,N-diisopropylethylamine, triethylamine, N-methylmorpholine, and the like), or an aromatic amine (such as, pyridine, imidazole, poly-(4-vinylpyridine), and the like). The inert solvent includes lower halocarbon solvents (such as, dichloromethane, dichloroethane, chloroform, and the like), ethereal solvents (such as, tetrahydrofuran, dioxane, and the like), amide solvents (such as, N,N-dimethylacetamide, N,N-dimethylformamide, and the like), aromatic solvents (benzene, toluene, pyridine, and the like) and mixtures thereof. Reaction temperature ranges from about −20° C. to 50° C., preferably about 0° C. to 40° C.

Scheme 28

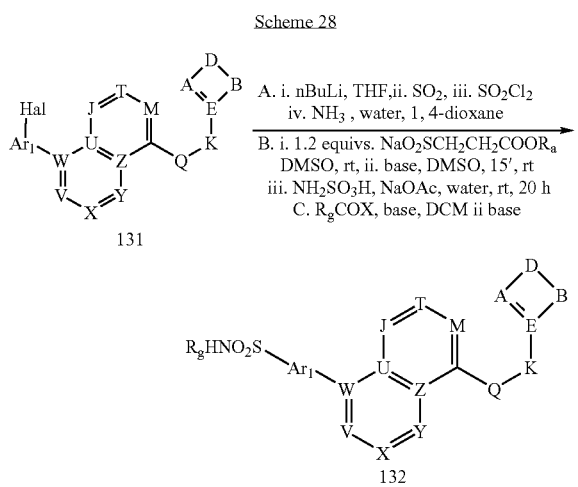

A. i. nBuLi, THF, ii. SO$_2$, iii. SO$_2$Cl$_2$
   iv. NH$_3$, water, 1,4-dioxane
B. i. 1.2 equivs. NaO$_2$SCH$_2$CH$_2$COOR$_a$
   DMSO, rt, ii. base, DMSO, 15', rt
   iii. NH$_2$SO$_3$H, NaOAc, water, rt, 20 h
C. R$_g$COX, base, DCM ii base Protecting groups may be required for various functionality or functionalities during the synthesis of some of the compounds of the invention. Accordingly, representative protecting groups that are suitable for a wide variety of synthetic transformations are disclosed in Greene and Wuts, *Protective Groups in Organic Synthesis*, 3rd edition, John Wiley & Sons, New York, 1999, the disclosure of which is incorporated herein by reference in its entirety.

The present invention also encompasses diastereomers as well as optical isomers, e.g. mixtures of enantiomers including racemic mixtures, as well as individual enantiomers and diastereomers, which arise as a consequence of structural asymmetry in certain compounds of Formula (I). Separation of the individual isomers or selective synthesis of the individual isomers is accomplished by application of various methods which are well known to practitioners in the art.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, disubstituted cycloalkyl groups (i.e., 1,4-cyclohexyl), and the like can also be present in the compounds described herein, and all such stable isomers are contemplated in the present invention. Cis and trans geometric isomers of the compounds of the present invention are described and may be isolated as a mixture of isomers or as separated isomeric forms.

Indications and Methods of Prophylaxis and/or Treatment

In addition to the foregoing beneficial uses for compounds of the present invention disclosed herein, compounds of the invention are useful in the treatment of additional diseases. Without limitation, these include the following.

The most significant pathologies in Type II diabetes are impaired insulin signaling at its target tissues ("insulin resistance") and failure of the insulin-producing cells of the pancreas to secrete an appropriate degree of insulin in response to a hyperglycemic signal. Current therapies to treat the latter include inhibitors of the β-cell ATP-sensitive potassium channel to trigger the release of endogenous insulin stores, or administration of exogenous insulin. Neither of these achieves accurate normalization of blood glucose levels and both carry the risk of inducing hypoglycemia. For these reasons, there has been intense interest in the development of pharmaceuticals that function in a glucose-dependent action, i.e. potentiators of glucose signaling. Physiological signaling systems which function in this manner are well-characterized and include the gut peptides GLP1, GIP and PACAP. These hormones act via their cognate G-protein coupled receptor to stimulate the production of cAMP in pancreatic β-cells. The increased cAMP does not appear to result in stimulation of insulin release during the fasting or preprandial state. However, a series of biochemical targets of cAMP signaling, including the ATP-sensitive potassium channel, voltage-sensitive potassium channels and the exocytotic machinery, are modified in such a way that the insulin secretory response to a postprandial glucose stimulus is markedly enhanced. Accordingly, agonists of novel, similarly functioning, β-cell GPCRs, including RUP3, would also stimulate the release of endogenous insulin and consequently promote normoglycemia in Type II diabetes.

It is also established that increased cAMP, for example as a result of GLP1 stimulation, promotes β-cell proliferation, inhibits β-cell death and thus improves islet mass. This positive effect on β-cell mass is expected to be beneficial in both Type II diabetes, where insufficient insulin is produced, and Type I diabetes, where β-cells are destroyed by an inappropriate autoimmune response.

Some β-cell GPCRs, including RUP3, are also present in the hypothalamus where they modulate hunger, satiety, decrease food intake, controlling or decreasing weight and energy expenditure. Hence, given their function within the hypothalamic circuitry, agonists or inverse agonists of these receptors mitigate hunger, promote satiety and therefore modulate weight.

It is also well-established that metabolic diseases exert a negative influence on other physiological systems. Thus, there is often the codevelopment of multiple disease states (e.g. type I diabetes, type II diabetes, inadequate glucose tolerance, insulin resistance, hyperglycemia, hyperlipidemia, hypertriglyceridemia, hypercholesterolemia, dyslipidemia, obesity or cardiovascular disease in "Syndrome X") or secondary diseases which clearly occur secondary to diabetes (e.g. kidney disease, peripheral neuropathy). Thus, it is expected that effective treatment of the diabetic condition will in turn be of benefit to such interconnected disease states.

In some embodiments of the present invention the metabolic-related disorder is hyperlipidemia, type 1 diabetes, type 2 diabetes mellitus, idiopathic type 1 diabetes (Type 1b), latent autoimmune diabetes in adults (LADA), early-onset type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction (e.g. necrosis and apoptosis), dyslipidemia, post-prandial lipemia, conditions of impaired glucose tolerance (IGT), conditions of impaired fasting plasma glucose, metabolic acidosis, ketosis, arthritis, obesity, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, coronary heart disease, angina pectoris, thrombosis, atherosclerosis, myocardial infarction, transient ischemic attacks, stroke, vascular restenosis, hyperglycemia, hyperinsulinemia, hyperlipidemia, hypertrygliceridemia, insulin resistance, impaired glucose metabolism, conditions of impaired glucose tolerance, conditions of impaired fasting plasma glucose, obesity, erectile dysfunction, skin and connective tissue disorders, foot ulcerations and ulcerative colitis, endothelial dysfunction and impaired vascular compliance.

One aspect of the present invention pertains to methods for treatment of a metabolic-related disorder in an individual comprising administering to the individual in need of such treatment a therapeutically effective amount of a compound as described herein or a pharmaceutical composition thereof. In some embodiments the metabolic-related disorder is type I diabetes, type II diabetes, inadequate glucose tolerance, insulin resistance, hyperglycemia, hyperlipidemia, hypertriglyceridemia, hypercholesterolemia, dyslipidemia or syndrome X. In some embodiments the metabolic-related disorder is type II diabetes. In some embodiments the metabolic-related disorder is hyperglycemia. In some embodiments the metabolic-related disorder is hyperlipidemia. In some embodiments the metabolic-related disorder is hypertriglyceridemia. In some embodiments the metabolic-related disorder is type I diabetes. In some embodiments the metabolic-related disorder is dyslipidemia. In some embodiments the metabolic-related disorder is syndrome X. In some embodiments the individual is a mammal. In some embodiments the mammal is a human.

One aspect of the present invention pertains to methods of decreasing food intake of an individual comprising administering to the individual in need thereof a therapeutically effective amount of a compound of the present invention or pharmaceutical composition thereof. In some embodiments the individual is a mammal. In some embodiments the mammal is a human.

One aspect of the present invention pertains to methods of inducing satiety in an individual comprising administering to the individual in need of such treatment a therapeutically effective amount of a compound of the present invention or pharmaceutical composition thereof. In some embodiments the individual is a mammal. In some embodiments the mammal is a human.

One aspect of the present invention pertains to methods of controlling or decreasing weight gain of an individual comprising administering to the individual in need of such treatment a therapeutically effective amount of a compound of the present invention or pharmaceutical composition thereof. In some embodiments the individual is a mammal. In some embodiments the mammal is a human.

Some embodiments of the present invention pertain to methods wherein the human has a body mass index of about 18.5 to about 45. In some embodiments, the human has a body mass index of about 25 to about 45. In some embodiments, the human has a body mass index of about 30 to about 45. In some embodiments, the human has a body mass index of about 35 to about 45.

One aspect of the present invention pertains to methods of modulating a RUP3 receptor in an individual comprising contacting the receptor with a compound of the present invention or a pharmaceutical composition thereof. In some embodiments, the compound is an agonist. In some embodiments, the compound is an inverse agonist. In some embodiments, the compound is an antagonist. In some embodiments, the modulation of the RUP3 receptor is treatment of a metabolic-related disorder and complications thereof. In some embodiments, the metabolic-related disorder is type I diabetes, type II diabetes, inadequate glucose tolerance, insulin resistance, hyperglycemia, hyperlipidemia, hypertriglyceridemia, hypercholesterolemia, dyslipidemia or syndrome X. In some embodiments, the metabolic-related disorder is type II diabetes. In some embodiments, the metabolic-related disorder is hyperglycemia. In some embodiments, the metabolic-related disorder is hyperlipidemia. In some embodiments, the metabolic-related disorder is hypertriglyceridemia. In some embodiments, the metabolic-related disorder is type I diabetes. In some embodiments, the metabolic-related disorder is dyslipidemia. In some embodiments, the metabolic-related disorder is syndrome X. In some embodiments, the individual is a mammal. In some embodiments, the mammal is a human.

Some embodiments of the present invention include a method of modulating a RUP3 receptor in an individual comprising contacting the receptor with a compound of the present invention wherein the modulation of the RUP3 receptor reduces food intake of the individual. In some embodiments the individual is a mammal. In some embodiments the mammal is a human. In some embodiments the human has a body mass index of about 18.5 to about 45. In some embodiments the human has a body mass index of about 25 to about 45. In some embodiments the human has a body mass index of about 30 to about 45. In some embodiments the human has a body mass index of about 35 to about 45.

Some embodiments of the present invention include a method of modulating a RUP3 receptor in an individual comprising contacting the receptor with a compound of the present invention wherein the modulation of the RUP3 receptor induces satiety in the individual. In some embodiments the individual is a mammal. In some embodiments the mammal is a human. In some embodiments the human has a body mass index of about 18.5 to about 45. In some embodiments the human has a body mass index of about 25 to about 45. In some embodiments the human has a body mass index of about 30 to about 45. In some embodiments the human has a body mass index of about 35 to about 45.

Some embodiments of the present invention include a method of modulating a RUP3 receptor in an individual comprising contacting the receptor with a compound of the present invention wherein the modulation of the RUP3 receptor controls or reduces weight gain of the individual. In some embodiments the individual is a mammal. In some embodiments the mammal is a human. In some embodiments the human has a body mass index of about 18.5 to about 45. In some embodiments the human has a body mass index of about 25 to about 45. In some embodiments the human has a body mass index of about 30 to about 45. In some embodiments the human has a body mass index of about 35 to about 45.

One aspect of the present invention pertains to use of a compound as described herein, for production of a medicament for use in treatment of a metabolic-related disorder. In some embodiments, the metabolic-related disorder is type II diabetes, inadequate glucose tolerance, insulin resistance, hyperglycemia, hyperlipidemia, hypertriglyceridemia, hypercholesterolemia, dyslipidemia or syndrome X.

One aspect of the present invention pertains to use of a compound as described herein, for production of a medicament for use in decreasing food intake of an individual. In some embodiments, the individual is a mammal. In some embodiments, the mammal is a human. In some embodiments, the human has a body mass index of about 18.5 to about 45. In some embodiments, the human has a body mass index of about 25 to about 45. In some embodiments, the human has a body mass index of about 30 to about 45. In some embodiments, the human has a body mass index of about 35 to about 45.

One aspect of the present invention pertains to use of a compound as described herein, for production of a medicament for use of inducing satiety in an individual. In some embodiments, the individual is a mammal. In some embodiments, the mammal is a human. In some embodiments, the human has a body mass index of about 18.5 to about 45. In some embodiments, the human has a body mass index of about 25 to about 45. In some embodiments, the human has a body mass index of about 30 to about 45. In some embodiments, the human has a body mass index of about 35 to about 45.

One aspect of the present invention pertains to use of a compound as described herein, for production of a medicament for use in controlling or decreasing weight gain in an individual. In some embodiments, the individual is a mammal. In some embodiments, the mammal is a human. In some embodiments, the human has a body mass index of about 18.5 to about 45. In some embodiments, the human has a body mass index of about 25 to about 45. In some embodiments, the human has a body mass index of about 30 to about 45. In some embodiments, the human has a body mass index of about 35 to about 45.

One aspect of the present invention pertains to a compound, as described herein, for use in a method of treatment of the human or animal body by therapy.

One aspect of the present invention pertains to a compound, as described herein, for use in a method of treatment of a metabolic-related disorder of the human or animal body by therapy.

One aspect of the present invention pertains to a compound, as described herein, for use in a method of decreasing food intake of the human or animal body by therapy.

One aspect of the present invention pertains to a compound, as described herein, for use in a method of inducing satiety of the human or animal body by therapy.

One aspect of the present invention pertains to a compound, as described herein, for use in a method of controlling or decreasing weight gain of the human or animal body by therapy.

Pharmaceutical Compositions

A further aspect of the present invention pertains to pharmaceutical compositions comprising one or more compound of the present invention and one or more pharmaceutically acceptable carriers. Some embodiments of the present invention pertain to pharmaceutical compositions comprising a compound of the present invention and a pharmaceutically acceptable carrier.

Some embodiments of the present invention include a method of producing a pharmaceutical composition comprising admixing at least one compound according to any of the compound embodiments disclosed herein and a pharmaceutically acceptable carrier.

Formulations may be prepared by any suitable method, typically by uniformly mixing the active compound(s) with liquids or finely divided solid carriers, or both, in the required proportions, and then, if necessary, forming the resulting mixture into a desired shape.

Conventional excipients, such as binding agents, fillers, acceptable wetting agents, tabletting lubricants, and disintegrants may be used in tablets and capsules for oral administration. Liquid preparations for oral administration may be in the form of solutions, emulsions, aqueous or oily suspensions, and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives, and flavorings and colorants may be added to the liquid preparations. Parenteral dosage forms may be prepared by dissolving the compound of the invention in a suitable liquid vehicle and filter sterilizing the solution before filling and sealing an appropriate vial or ampoule. These are just a few examples of the many appropriate methods well known in the art for preparing dosage forms.

A compound of the present invention can be formulated into pharmaceutical compositions using techniques well known to those in the art. Suitable pharmaceutically-acceptable carriers, outside those mentioned herein, are known in the art; for example, see Remington, The Science and Practice of Pharmacy, 20th Edition, 2000, Lippincott Williams & Wilkins, (Editors: Gennaro, A. R., et al.).

While it is possible that, for use in the prophylaxis or treatment, a compound of the invention may, in an alternative use, be administered as a raw or pure chemical, it is preferable however to present the compound or active ingredient as a pharmaceutical formulation or composition further comprising a pharmaceutically acceptable carrier.

The invention thus further provides pharmaceutical formulations comprising a compound of the invention or a pharmaceutically acceptable salt or derivative thereof together with one or more pharmaceutically acceptable carriers thereof and/or prophylactic ingredients. The carrier(s) must be "acceptable" in the sense of being compatible with the other ingredients of the formulation and not overly deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds of the invention, together with a conventional adjuvant, carrier, or diluent, may thus be placed into the form of pharmaceutical formulations and unit dosages thereof, and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

Compounds of the present invention or a solvate or physiologically functional derivative thereof can be used as active ingredients in pharmaceutical compositions, specifically as RUP3 receptor modulators. By the term "active ingredient" is defined in the context of a "pharmaceutical composition" and shall mean a component of a pharmaceutical composition that provides the primary pharmacological effect, as opposed to an "inactive ingredient" which would generally be recognized as providing no pharmaceutical benefit.

The dose when using the compounds of the present invention can vary within wide limits, and as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis is conducted or on whether further active compounds are administered in addition to the compounds of the present invention. Representative doses of the present invention include, but not limited to, about 0.001 mg to about 5000 mg, about 0.001 to about 2500 mg, about 0.001 to about 1000 mg, 0.001 to about 500 mg, 0.001 mg to about 250 mg, about 0.001 mg to 100 mg, about 0.001 mg to about 50 mg, and about 0.001 mg to about 25 mg. Multiple doses may be administered during the day, especially when relatively large amounts are deemed to be needed, for example 2, 3 or 4, doses. Depending on the individual and as deemed appropriate from the patient's physician or care-giver it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. Typically, animal models include, but are not limited to, the rodents diabetes models as described in Example 5, infra (as well as other animal models known in the art, such as those reported by Reed and Scribner in Diabetes, Obesity and Metabolism, 1, 1999, 75-86). In some circumstances, these extrapolations may merely be based on the weight of the animal in the respective model in comparison to another, such as a mammal, preferably a human, however, more often, these extrapolations are not simply based on weights, but rather incorporate a variety of factors. Representative factors include, but not limited to, the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis is conducted or on whether further active compounds are administered in addition to the compounds of the Formula (I) and as part of a drug combination. The dosage regimen for treating a disease condition with the compounds and/or compositions of this invention is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods of this invention.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4, part administrations. If appropriate, depending on individual behavior, it may be necessary to deviate upward or downward from the daily dose indicated.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, the selection of a suitable pharmaceutically acceptable carrier can be either solid, liquid or a mixture of both. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desire shape and size.

The powders and tablets may contain varying percentage amounts of the active compound. A representative amount in a powder or tablet may contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds of the Formula (I) or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds of the Formula (I) as an aerosol can be prepared by processes well-known to the person skilled in the art. For their preparation, for example, solutions or dispersions of the compounds of the Formula (I) in water, water/alcohol mixtures or suitable saline solutions can be employed using customary additives, for example benzyl alcohol or other suitable preservatives, absorption enhancers for increasing the bioavailability, solubilizers, dispersants and others, and, if appropriate, customary propellants, for example include carbon dioxide, CFC's, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

The compounds according to the invention may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfiric, tartaric, oxalic, p-toluenesulfonic and the like, such as those pharmaceutically acceptable salts listed in Journal of Pharmaceutical Science, 66, 2 (1977); incorporated herein by reference in its entirety.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent. The compounds of this invention may form solvates with standard low molecular weight solvents using methods known to the skilled artisan.

Compounds of the present invention can be converted to "pro-drugs." The term "pro-drugs" refers to compounds that have been modified with specific chemical groups known in the art and when administered into an individual these groups undergo biotransformation to give the parent compound. Pro-drugs can thus be viewed as compounds of the invention containing one or more specialized non-toxic protective groups used in a transient manner to alter or to eliminate a property of the compound. In one general aspect, the "pro-drug" approach is utilized to facilitate oral absorption. A thorough discussion is provided in T. Higuchi and V. Stella, "Pro-drugs as Novel Delivery Systems," Vol. 14 of the A.C.S. Symposium Series; and in Bioreversible Carriers in Drug Design, ed. Edward B. Roche, American Pharmaceutical Association and Pergamon Press, 1987, both of which are hereby incorporated by reference in their entirety.

Some embodiments of the present invention include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

In some embodiments the pharmaceutical agents is selected from the group consisting of: apolipoprotein-B secretion/microsomal triglyceride transfer protein (apo-B/MTP) inhibitors, MCR-4 agonists, cholescystokinin-A (CCK-A) agonists, serotonin and norepinephrine reuptake inhibitors (for example, sibutramine), sympathomimetic agensts, $\beta_3$ adrenergic receptor agonists, dopamine agonists (for example, bromocriptine), melanocyte-stimulating hormone receptor analogs, cannabinoid 1 receptor antagonists [for example, SR141716: N-(piperidin-1-yl)-5-(4-chlorophenyl)-1-(2,4-dichlorophenyl)-4-methyl-1H-pyrazole-3-carboxamide], melanin concentrating hormone antagonists, leptons (the OB protein), leptin analogues, leptin receptor agonists, galanin antagonists, lipase inhibitors (such as tetrahydrolipstatin, i.e., Orlistat), anorectic agents (such as a bombesin agonist), Neuropeptide-Y antagonists, thyromimetic agents, dehydroepiandrosterone or an analogue thereof, glucocorticoid receptor agonists or antagonists, orexin receptor antagonists, urocortin binding protein antagonists, glucagon-like peptide-1 receptor agonists, ciliary neutrotrophic factors (such as Axokine™), human agouti-related proteins (AGRP), ghrelin receptor antagonists, histamine 3 receptor antagonists or reverse agonists, neuromedin U receptor agonists, noradrenergic anorectic agents (for example, phentermine, mazindol and the like), appetite suppressants (for example, bupropion) and the like. In further embodiments, the pharmaceutical agent is selected from the group consisting of orlistat, sibutramine, bromocriptine, ephedrine, leptin, and pseudoephedrine.

In some embodiments the pharmaceutical agents is selected from the group consisting of: sulfonylureas, meglitinides, biguanides, α-glucosidase inhibitors, peroxisome proliferators-activated receptor-γ (i.e., PPAR-γ) agonists, insulin, insulin analogues, HMG-CoA reductase inhibitors, cholesterol-lowering drugs (for example, fibrates that include: fenofibrate, bezafibrate, gemfibrozil, clofibrate and the like; bile acid sequestrants which include: cholestyramine, colestipol and the like; and niacin), antiplatelet agents (for example, aspirin and adenosine diphosphate receptor antagonists that include: clopidogrel, ticlopidine and the like), angiotensin-converting enzyme inhibitors, angiotensin H receptor antagonists and adiponectin.

It is noted that when the RUP3 receptor modulators are utilized as active ingredients in a pharmaceutical composition, these are not intended for use only in humans, but in other non-human mammals as well. Indeed, recent advances in the area of animal health-care mandate that consideration be given for the use of active agents, such as RUP3 receptor modulators, for the treatment of obesity in domestic animals (e.g., cats and dogs), and RUP3 receptor modulators in other domestic animals where no disease or disorder is evident (e.g., food-oriented animals such as cows, chickens, fish, etc.). Those of ordinary skill in the art are readily credited with understanding the utility of such compounds in such settings.

Combination Therapy—Prophylaxis and Treatment

In the context of the present invention, a compound as desribed herein or pharmaceutical composition thereof can be utilized for modulating the activity of RUP3 receptor mediated diseases, conditions and/or disorders as described herein. Examples of modulating the activity of RUP3 receptor mediated diseases include the prophylaxis or treatment of metabolic related disorders such as, but not limited to, type I diabetes, type II diabetes, inadequate glucose tolerance, insulin resistance, hyperglycemia, hyperlipidemia, hypertriglyceridemia, hypercholesterolemia, dyslipidemia and syndrome X. Other examples of modulating the activity of RUP3 receptor mediated diseases include the prophylaxis or treatment of obesity and/or overweight by decreasing food intake, inducing satiation (i.e., the feeling of fullness), controlling weight gain, decreasing body weight and/or affecting metabolism such that the recipient loses weight and/or maintains weight.

While the compounds of the invention can be administered as the sole active pharmaceutical agent (i.e., mono-therapy), they can also be used in combination with other pharmaceutical agents (i.e., combination-therapy) for the treatment of the diseases/conditions/disorders described herein. Therefore, another aspect of the present invention includes methods of prophylaxis and/or treatment of a metabolic related disorder or a weight related disorder, such as obesity, comprising administering to an individual in need of prophylaxis and/or treatment a therapeutically effective amount of a compound of the present invention, for example Formula (I), in combination with one or more additional pharmaceutical agent as described herein.

Suitable pharmaceutical agents that can be used in combination with the compounds of the present invention include anti-obesity agents such as apolipoprotein-B secretion/microsomal triglyceride transfer protein (apo-B/MTP) inhibitors, MCR-4 agonists, cholescystokinin-A (CCK-A) agonists, serotonin and norepinephrine reuptake inhibitors (for example, sibutramine), sympathomimetic agents, β3 adrenergic receptor agonists, dopamine agonists (for example, bromocriptine), melanocyte-stimulating hormone receptor analogs, cannabinoid 1 receptor antagonists [for example, SR141716: N-(piperidin-1-yl)-5-(4-chlorophenyl)-1-(2,4-dichlorophenyl)-4-methyl-1H-pyrazole-3-carboxamide], melanin concentrating hormone antagonists, leptons (the OB protein), leptin analogues, leptin receptor agonists, galanin antagonists, lipase inhibitors (such as tetrahydrolipstatin, i.e., Orlistat), anorectic agents (such as a bombesin agonist), Neuropeptide-Y antagonists, thyromimetic agents, dehydroepiandrosterone or an analogue thereof, glucocorticoid receptor agonists or antagonists, orexin receptor antagonists, urocortin binding protein antagonists, glucagon-like peptide-1 receptor agonists, ciliary neutrotrophic factors (such as Axokine™ available from Regeneron Pharmaceuticals, Inc., Tarrytown, N.Y. and Procter & Gamble Company, Cincinnati, Ohio), human agouti-related proteins (AGRP), ghrelin receptor antagonists, histamine 3 receptor antagonists or reverse agonists, neuromedin U receptor agonists, noradrenergic anorectic agents (for example, phentermine, mazindol and the like) and appetite suppressants (for example, bupropion).

Other anti-obesity agents, including the agents set forth infra, are well known, or will be readily apparent in light of the instant disclosure, to one of ordinary skill in the art.

In some embodiments, the anti-obesity agents are selected from the group consisting of orlistat, sibutramine, bromocriptine, ephedrine, leptin, and pseudoephedrine. In a further embodiment, compounds of the present invention and combination therapies are administered in conjunction with exercise and/or a sensible diet.

It will be understood that the scope of combination-therapy of the compounds of the present invention with other anti-obesity agents, anorectic agents, appetite suppressant and related agents is not limited to those listed above, but includes in principle any combination with any pharmaceutical agent or pharmaceutical composition useful for the treatment of overweight and obese individuals.

Other suitable pharmaceutical agents, in addition to anti-obesity agents, that can be used in combination with the compounds of the present invention include agents useful in the treatment of metabolic related disorders and/or concomitant diseases thereof. For example, but not limited to, congestive heart failure, type I diabetes, type II diabetes, inadequate glucose tolerance, insulin resistance, hyperglycemia, hyperlipidemia, hypertriglyceridemia, hypercholesterolemia, dyslipidemia, syndrome X, retinopathy, nephropathy and neuropathy. Prophylaxis or treatment of one or more of the diseases cited herein include the use of one or more pharmaceutical agents known in the art belonging to the classes of drugs referred to, but not limited to, the following: sulfonylureas, meglitinides, biguanides, α-glucosidase inhibitors, peroxisome proliferators-activated receptor-γ (i.e., PPAR-γ) agonists, insulin, insulin analogues, HMG-CoA reductase inhibitors, cholesterol-lowering drugs (for example, fibrates that include: fenofibrate, bezafibrate, gemfibrozil, clofibrate and the like; bile acid sequestrants which include: cholestyramine, colestipol and the like; and niacin), antiplatelet agents (for example, aspirin and adenosine diphosphate receptor antagonists that include: clopidogrel, ticlopidine and the like), angiotensin-converting enzyme inhibitors, angiotensin II receptor antagonists, adiponectin and the like. In accordance to one aspect of the present invention, a compound of the present can be used in combination with a pharmaceutical agent or agents belonging to one or more of the classes of drugs cited herein.

It will be understood that the scope of combination-therapy of the compounds of the present invention with other pharmaceutical agents is not limited to those listed herein, supra or infra, but includes in principle any combination with any pharmaceutical agent or pharmaceutical composition useful for the prophylaxis or treatment of diseases, conditions or disorders that are linked to metabolic related disorders.

Some embodiments of the present invention include methods of prophylaxis or treatment of a disease, disorder, condition or complication thereof as described herein, comprising administering to an individual in need of such prophylaxis or treatment a therapeutically effective amount or dose of a compound of the present invention in combination with at least one pharmaceutical agent selected from the group consisting of: sulfonylureas, meglitinides, biguanides, α-glucosidase inhibitors, peroxisome proliferators-activated receptor-γ (i.e., PPAR-γ) agonists, insulin, insulin analogues, HMG-CoA reductase inhibitors, cholesterol-lowering drugs (for example, fibrates that include: fenofibrate, bezafibrate, gemfibrozil, clofibrate and the like; bile acid sequestrants which include: cholestyramine, colestipol and the like; and niacin), antiplatelet agents (for example, aspirin and adenosine diphosphate receptor antagonists that include: clopidogrel, ticlopidine and the like), angiotensin-converting enzyme inhibitors, angiotensin II receptor antagonists and adiponectin. In some embodiments, methods of the present invention include compounds of the present invention and the pharmaceutical agents are administered separately. In further embodiments, compounds of the present invention and the pharmaceutical agents are administered together.

Suitable pharmaceutical agents that can be used in conjunction with compounds of the present invention include sulfonylureas. The sulfonylureas (SU) are drugs which promote secretion of insulin from pancreatic β cells by transmitting signals of insulin secretion via SU receptors in the cell membranes. Examples of the sulfonylureas include glyburide, glipizide, glimepiride and other sulfonylureas known in the art.

Suitable pharmaceutical agents that can be used in conjunction with compounds of the present invention include the meglitinides. The meglitinides are benzoic acid derivatives represent a novel class of insulin secretagogues. These agents target postprandial hyperglycemia and show comparable efficacy to sulfonylureas in reducing HbA1c. Examples of meglitinides include repaglinide, nateglinide and other meglitinides known in the art.

Suitable pharmaceutical agents that can be used in conjunction with compounds of the present invention include the biguanides. The biguanides represent a class of drugs that stimulate anaerobic glycolysis, increase the sensitivity to insulin in the peripheral tissues, inhibit glucose absorption from the intestine, suppress of hepatic gluconeogenesis, and inhibit fatty acid oxidation. Examples of biguanides include phenformin, metformin, buformin, and biguanides known in the art.

Suitable pharmaceutical agents that can be used in conjunction with compounds of the present invention include the α-glucosidase inhibitors. The α-glucosidase inhibitors competitively inhibit digestive enzymes such as α-amylase, maltase, α-dextrinase, sucrase, etc. in the pancreas and or small intestine. The reversible inhibition by α-glucosidase inhibitors retard, diminish or otherwise reduce blood glucose levels by delaying the digestion of starch and sugars. Examples of α-glucosidase inhibitors include acarbose, N-(1,3-dihydroxy-2-propyl)valiolamine (generic name; voglibose), miglitol, and α-glucosidase inhibitors known in the art.

Suitable pharmaceutical agents that can be used in conjunction with compounds of the present invention include the peroxisome proliferators-activated receptor-γ (i.e., PPAR-γ) agonists. The peroxisome proliferators-activated receptor-γ agonists represent a class of compounds that activates the nuclear receptor PPAR-γ and therefore regulate the transcription of insulin-responsive genes involved in the control of glucose production, transport and utilization. Agents in the class also facilitate the regulation of fatty acid metabolism. Examples of PPAR-γ agonists include rosiglitazone, pioglitazone, tesaglitazar, netoglitazone, GW-409544, GW-501516 and PPAR-γ agonists known in the art.

Suitable pharmaceutical agents that can be used in conjunction with compounds of the present invention include the HMG-CoA reductase inhibitors. The HMG-CoA reductase inhibitors are agents also referred to as Statin compounds that belong to a class of drugs that lower blood cholesterol levels by inhibiting hydroxymethylglutalyl CoA (HMG-CoA) reductase. HMG-CoA reductase is the rate-limiting enzyme in cholesterol biosynthesis. The statins lower serum LDL concentrations by upregulating the activity of LDL receptors and are responsible for clearing LDL from the blood. Some representative examples the statin compounds include rosuvastatin, pravastatin and its sodium salt, simvastatin, lovastatin, atorvastatin, fluvastatin, cerivastatin, rosuvastatin, pitavastatin, BMS's "superstatin", and HMG-CoA reductase inhibitors known in the art.

Suitable pharmaceutical agents that can be used in conjunction with compounds of the present invention include the Fibrates. Fibrate compounds belong to a class of drugs that lower blood cholesterol levels by inhibiting synthesis and secretion of triglycerides in the liver and activating a lipoprotein lipase. Fibrates have been known to activate peroxisome proliferators-activated receptors and induce lipoprotein lipase expression. Examples of fibrate compounds include bezafibrate, beclobrate, binifibrate, ciplofibrate, clinofibrate, clofibrate, clofibric acid, etofibrate, fenofibrate, gemfibrozil, nicofibrate, pirifibrate, ronifibrate, simfibrate, theofibrate, and fibrates known in the art.

Suitable pharmaceutical agents that can be used in conjunction with compounds of the present invention include the angiotensin converting enzyme (ACE) inhibitors. The angiotensin converting enzyme inhibitors belong to the class of drugs that partially lower blood glucose levels as well as lowering blood pressure by inhibiting angiotensin converting enzymes. Examples of the angiotensin converting enzyme inhibitors include captopril, enalapril, alacepril, delapril; ramipril, lisinopril, imidapril, benazepril, ceronapril, cilazapril, enalaprilat, fosinopril, moveltopril, perindopril, quinapril, spirapril, temocapril, trandolapril, and angiotensin converting enzyme inhibitors known in the art.

Suitable pharmaceutical agents that can be used in conjunction with compounds of the present invention include the angiotensin II receptor antagonists. Angiotensin II receptor antagonists target the angiotensin II receptor subtype 1 (i.e., AT1) and demonstrate a beneficial effect on hypertension. Examples of angiotensin II receptor antagonists include losartan (and the potassium salt form), and angiotensin II receptor antagonists known in the art.

Other treatments for one or more of the diseases cited herein include the use of pharmaceutical agents known in the art belonging to the classes of drugs referred to, but not limited to, the following: amylin agonists (for example, pramlintide), insulin secretagogues (for example, GLP-1 agonists; exendin-4; insulinotropin (NN2211); dipeptyl peptidase inhibitors (for example, NVP-DPP-728), acyl CoA cholesterol acetyltransferase inhibitors (for example, Ezetimibe, eflucimibe, and like compounds), cholesterol absorption inhibitors (for example, ezetimibe, pamaqueside and like compounds), cholesterol ester transfer protein inhibitors (for example, CP-529414, JTT-705, CETi-1, and like compounds), microsomal triglyceride transfer protein inhibitors (for example, implitapide, and like compounds), cholesterol modulators (for example, NO-1886, and like compounds), bile acid modulators (for example, GT103-279 and like compounds) and squalene synthase inhibitors.

Squalene synthesis inhibitors belong to a class of drugs that lower blood cholesterol levels by inhibiting synthesis of squalene. Examples of the squalene synthesis inhibitors include (S)-α-[Bis[2,2-dimethyl-1-oxopropoxy)methoxy] phosphinyl]-3-phenoxybenzenebutanesulfonic acid, mono potassium salt (BMS-188494) and squalene synthesis inhibitors known in the art.

In accordance with the present invention, the combination can be used by mixing the respective active components either all together or independently with a physiologically acceptable carrier, excipient, binder, diluent, etc., as described herein above, and administering the mixture or mixtures either orally or non-orally as a pharmaceutical composition. When a compound or a mixture of compounds of Formula (I) are administered as a combination therapy with another active compound the therapeutic agents can be formulated as a separate pharmaceutical compositions given at the same time or at different times, or the therapeutic agents can be given as a single composition.

Other Utilities

Another object of the present invention relates to radio-labeled compounds of Formula (I) that would be useful not only in radio-imaging but also in assays, both in vitro and in vivo, for localizing and quantitating the RUP3 receptor in tissue samples, including human, and for identifying RUP3 receptor ligands by inhibition binding of a radio-labeled compound. It is a further object of this invention to develop novel RUP3 receptor assays of which comprise such radio-labeled compounds.

The present invention embraces isotopically-labeled compounds of Formula (I) and any subgenera herein, such as but not limited to, Formula (Ia) through Formula (IIIo). An "isotopically" or "radio-labeled" compounds are those which are identical to compounds disclosed herein, but for the fact that one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro RUP3 receptor labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound of the present invention that has incorporated at least one radionuclide; in some embodiments the radionuclide is selected from the group consisting of $^3$H, $^{14}$C, $^{125}$I, $^{35}$S and $^{82}$Br.

Certain isotopically-labeled compounds of the present invention are useful in compound and/or substrate tissue distribution assays. In some embodiments the radionuclide $^3$H and/or $^{14}$C isotopes are useful in these studies. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the present invention can generally be prepared by following procedures analogous to those disclosed in the Schemes supra and Examples infra, by substituting an isotopically labeled reagent for a non-isotopically labeled reagent. Other synthetic methods that are useful are discussed infra. Moreover, it should be understood that all of the atoms represented in the compounds of the invention can be either the most commonly occurring isotope of such atoms or the more scarce radio-isotope or nonradio-active isotope.

Synthetic methods for incorporating radio-isotopes into organic compounds are applicable to compounds of the invention and are well known in the art. These synthetic methods, for example, incorporating activity levels of tritium into target molecules, are as follows:

A. Catalytic Reduction with Tritium Gas—This procedure normally yields high specific activity products and requires halogenated or unsaturated precursors.

B. Reduction with Sodium Borohydride [$^3$H]—This procedure is rather inexpensive and requires precursors containing reducible functional groups such as aldehydes, ketones, lactones, esters, and the like.

C. Reduction with Lithium Aluminum Hydride [$^3$H]—This procedure offers products at almost theoretical specific activities. It also requires precursors containing reducible functional groups such as aldehydes, ketones, lactones, esters, and the like.

D. Tritium Gas Exposure Labeling—This procedure involves exposing precursors containing exchangeable protons to tritium gas in the presence of a suitable catalyst.

E. N-Methylation using Methyl Iodide [$^3$H]—This procedure is usually employed to prepare O-methyl or N-methyl ($^3$H) products by treating appropriate precursors with high specific activity methyl iodide ($^3$H). This method in general allows for higher specific activity, such as for example, about 70-90 Ci/mmol.

Synthetic methods for incorporating activity levels of $^{125}$I into target molecules include:

A. Sandmeyer and like reactions—This procedure transforms an aryl or heteroaryl amine into a diazonium salt, such as a tetrafluoroborate salt, and subsequently to $^{125}$I labeled compound using Na$^{125}$I. A represented procedure was reported by Zhu, D.-G. and co-workers in J. Org. Chem. 2002, 67, 943-948.

B. Ortho $^{125}$Iodination of phenols—This procedure allows for the incorporation of $^{125}$I at the ortho position of a phenol as reported by Collier, T. L. and co-workers in J. Labeled Compd Radiopharm. 1999, 42, S264-S266.

C. Aryl and heteroaryl bromide exchange with $^{125}$I— This method is generally a two step process. The first step is the conversion of the aryl or heteroaryl bromide to the corresponding tri-alkyltin intermediate using for example, a Pd catalyzed reaction [i.e. Pd(Ph$_3$P)4] or through an aryl or heteroaryl lithium, in the presence of a tri-alkyltinhalide or hexaalkylditin [e.g., (CH$_3$)$_3$SnSn (CH$_3$)$_3$]. A represented procedure was reported by Bas, M.-D. and co-workers in J. Labeled Compd Radiopharm. 2001, 44, S280-S282.

A radio-labeled RUP3 receptor compound of the present invention can be used in a screening assay to identify/evaluate compounds. In general terms, a newly synthesized or identified compound (i.e., test compound) can be evaluated for its ability to reduce binding of the "radio-labeled compound of the present invention" to the RUP3 receptor. Accordingly, the ability of a test compound to compete with the "radio-labeled compound of the present invention" for the binding to the RUP3 receptor directly correlates to its binding affinity.

The labeled compounds of the present invention bind to the RUP3 receptor. In one embodiment the labeled compound has an IC$_{50}$ less than about 500 μM, in another embodiment the labeled compound has an IC$_{50}$ less than about 100 μM, in yet another embodiment the labeled compound has an IC$_{50}$ less than about 10 μM, in yet another embodiment the labeled compound has an IC$_{50}$ less than about 1 μM, and in still yet another embodiment the labeled inhibitor has an IC$_{50}$ less than about 0.1 μM.

Other uses of the disclosed receptors and methods will become apparent to those in the art based upon, inter alia, a review of this disclosure.

As will be recognized, the steps of the methods of the present invention need not be performed any particular number of times or in any particular sequence. Additional objects, advantages, and novel features of this invention will become apparent to those skilled in the art upon examination of the following examples thereof, which are intended to be illustrative and not intended to be limiting.

EXAMPLES

The examples are provided to further define the invention without, however, limiting the invention to the specifics of these examples.

Example 1

96-well Cyclic AMP Membrane Assay for RUP3

Materials:
1) Adenlyl cyclase Activation Flashplate Assay kit from Perkin Elmer—96 wells (SMP004B) and $^{125}$I tracer (NEX130) which comes with the kit. Keep in refrigerator, in a box, and do not expose the Flashplates to light.
2) Phosphocreatine—Sigma P-7936
3) Creatine Phosphokinase—Sigma C-3755
4) GTP—Sigma G-8877
5) ATP—Sigma A-2383
6) IBMX—Sigma I-7018
7) Hepes—1M solution in distilled water—Gibco #15630080
8) MgCl2—Sigma M-1028—1M Solution
9) NaCl—Sigma—S6546—5M Solution
10) Bradford Protein Assay Kit—Biorad # 5000001
11) Proclin 300—Sigma #4-8126

Binding Buffer—filter through 45-micron Nalgene filter and keep in refrigerator. All buffers and membranes should be kept cold (in ice bucket) while performing assay.
20 mM Hepes, pH7.4
1 mM MgCl2
100 mM NaCl 2× Regeneration Buffer (Make in Binding Buffer):
20 mM Phosphocreatine (1.02 gm/200 mL binding buffer)
20 units Creatine phosphokinase (4 mg/200 mL)
20 μM GTP (make up 10.46 mg/mL in binding buffer and add 200 μL/200 mL)
0.2 mM ATP (22.04 mg/200 mL)
100 mM IBMX (44.4 mg IBMX dissolved in 1 mL 100% DMSO first and then add the entire amount to 200 mL of buffer).

Regeneration buffer can be aliquotted into 40-45 mL portions (in 50 mL sterile tubes) and kept frozen for up to 2 months. Simply put the tube in a beaker with room temperature water to thaw out the regeneration buffer on the day of the assay.

A. Assay Procedure
1) Pipet 50 μL regeneration buffer in all 96 wells using Matrix 1250 8-channel pipettor.
2) Pipet 5 μL DMSO in columns 1 and columns 11 and 12.
3) Pipet 50 μL cAMP standards in columns 11 and 12 in this format: 50 pmole/well for row A, 25 pmole/well for row B, 12.5 pmol/well for row C, 5 picomol/well for row D, 2.5 pmole/well for row E, 1.25 pmole/well for row F, 0.5 pmole/well for row G, and 0 pmole/well (buffer only) for row H.

4) Pipet 5 μL compounds from each well of a compound dilution plate, for IC50s, using the following dilution scheme:

Well H: 400 μM compound (final concentration of compound in reaction mix=5/100×400 μM=20 μM
Well G: 1:10 dilution of Well H (i.e. 5 μL compound from well H+45 μL 100% DMSO) (final concentration=2 μM)
Well F: 1:10 dilution of well G (final concentration=0.2 μM)
Well E: 1:10 dilution of well F (final concentration=0.02 μM)
Well D: 1:10 dilution of well E (final concentration=0.002 μM)
Well C: 1:10 dilution of well D (final concentration=0.0002 μM
Well B: 1:10 dilution of well C (final concentration=0.00002 μM)
Well A: 1:10 dilution of well B (final concentration=0.000002 μM)

$IC_{50}$s or $EC_{50}$s are done in triplicate. One Flashplate can therefore be set up to handle 3 compounds. (i.e., columns 2, 3, and 4 are for compound #1, columns 5, 6, and 7 are for compound #2, and columns 8, 9, and 10 are for compound #3.)

5) Add 50 μL of RUP3 membranes to all wells in Columns 2 to 10. (Prior to the start of the assay, the frozen membrane pellets for both RUP3 and CMV (cells transfected with an expression plasmid containing no RUP3 sequences), are suspended in binding buffer, usually 1 mL binding buffer for 1 plate of membranes. The membranes are kept in ice all the time, and a polytron (Brinkmann polytron, model # PT-3100) is used (setting 6-7, for 15-20 seconds) to obtain a homogeneous membrane suspension.) Protein concentration is determined by Bradford protein assay kit using instructions given in the kit, using the standard supplied with the kit as a reference. The protein concentration of the membranes is adjusted with binding buffer, so that 50 μL membranes=15 ug protein (i.e. 0.3 mg/mL protein).

6) In column 1, Wells A, B, C, and D, add 50 μL RUP3 membranes. To wells E, F, G, and H, add 50 μL CMV membranes, (CMV membranes being of the same protein concentration as the RUP3 membranes).

7) Incubate 1 hour at room temperature with agitation on a rotating platform shaker. Cover with foil while shaking.

8) After 1 hour, add (to all 96 wells), 100 μL of the $^{125}$I tracer in detection buffer supplied with the Flashplate kit plus proclin, made up in the following manner:

Pipet per 10 mL per Flashplate: 100 mL of detection buffer+1 mL $^{125}$I+0.2 mL of Proclin (the proclin helps to stop the production of cAMP). Make a smaller quantity of detection buffer mix if you have fewer plates.

9) Shake the plates on a rotating platform shaker for 2 hours, covering the plates with lead sheeting.
10) Seal the plates with the plastic film sealers provided with the Flashplate kit.
11) Count the plates using a TRILUX 1450 Microbeta Counter. See the door of the counter to determine which counting protocol to use.
12) Data is analyzed on the Arena Database according to the RUP3 non-fusion, $IC_{50}$ $EC_{50}$ for 96-well cAMP membrane assay, and the compound numbers and the concentrations of compounds must be entered by the user.

B. Membrane Cyclase Criteria

1) Signal to Noise:
An acceptable signal-to-noise ratio for RUP3 can vary from 4 to 6. The raw cpms are approximately 1800 to 2500 for RUP3 and 3500-4500 for CMV. The cpm (or ultimately pmoles of cAMP/well) cannot be outside the standard curve, and should not approach well A of the standard curve (50 pmole/well) and well H (no cAMP). Generally, the pmoles of cAMP produced by RUP3 receptor are around 11 to 13 pmole/well (for 15 ug/well protein), and for CMV are between 2 to 3 pmole/well (for 15 ug protein/well).

2) Standard Curve:
The slope should be linear and the error bars for duplicates should be very small. The receptor and CMV controls cannot be off scale of the standard curve, as described above. If the receptor controls are off the high end of the standard curve, i.e. 50 pmole/well or higher, one must repeat the experiment using less protein. However, such a case has not been observed with transiently transfected RUP3 membranes (10 ug DNA/15 cm plate, using 60 μL Lipofectamine, and preparing membranes after 24 hour of transfection.)

3) The $IC_{50}$ or $EC_{50}$ curve should be at 100% (+ or −20%) of control RUP3 membranes at the top, and should go down to 0 (or up to 20%) at the bottom. The standard error of the triplicate determinations should be + or −10%.

C. Stimulation of cAMP in HIT-T15 Cells

HIT-T15 (ATCC CRL#1777) is an immortalized hamster insulin-producing cell line. These cells express RUP3 and therefore can be used to assess the ability of RUP3 ligands to stimulate or inhibit cAMP accumulation via its endogenously expressed receptor. In this assay, cells are grown to 80% confluence and then distributed into a 96-well Flashplate (50,000 cells/well) for detection of cAMP via a "cAMP Flashplate Assay" (NEN, Cat # SMP004). Briefly, cells are placed into anti-cAMP antibody-coated wells that contain either vehicle, the test ligand(s) at a concentration of interest, or 1 μM forskolin. The latter is a direct activator of adenylyl cyclase and serves as a positive control for stimulation of cAMP in HIT-T15 cells. All conditions are tested in triplicate. After a 1 hour incubation to allow for stimulation of cAMP, a Detection Mix containing $^{125}$I-cAMP is added to each well and the plate is allowed to incubate for another 1 hour. The wells are then aspirated to remove unbound $^{125}$I-cAMP. Bound $^{125}$I-cAMP is detected using a Wallac Microbeta Counter. The amount of cAMP in each sample is determined by comparison to a standard curve, obtained by placing known concentrations of cAMP in some wells on the plate.

D. Stimulation of Insulin Secretion in HIT-T15 Cells

It is known that stimulation of cAMP in HIT-T15 cells causes an increase in insulin secretion when the glucose concentration in the culture media is changed from 3 mM to 15 mM. Thus, RUP3 ligands can also be tested for their ability to stimulate glucose-dependent insulin secretion (GSIS) in HIT-T15 cells. In this assay, 30,000 cells/well in a 12-well plate are incubated in culture media containing 3 mM glucose and no serum for 2 hours. The media is then changed; wells receive media containing either 3 mM or 15 mM glucose, and in both cases the media contains either vehicle (DMSO) or RUP3 ligand at a concentration of interest. Some wells receive media containing 1 μM forskolin as a positive control. All conditions are tested in triplicate. Cells are incubated for 30 minutes, and the amount of insulin secreted into the media is determined by ELISA, using a kit from either Peninsula Laboratories (Cat # ELIS-7536) or Crystal Chem Inc. (Cat # 90060).

E. Stimulation of Insulin Secretion in Isolated Rat Islets

As with HIT-T15 cells, it is known that stimulation of cAMP in isolated rat islets causes an increase in insulin secretion when the glucose concentration in the culture media is changed from 60 mg/dl to 300 mg/dl. RUP3 is an endogenously expressed GPCR in the insulin-producing cells of rat islets. Thus, RUP3 ligands can also be tested for their ability to stimulate GSIS in rat islet cultures. This assay is performed as follows:

A. Select 75-150 islet equivalents (IEQ) for each assay condition using a dissecting microscope. Incubate overnight in low-glucose culture medium. (Optional.)

B. Divide the islets evenly into triplicate samples of 25-40 islet equivalents per sample. Transfer to 40 μm mesh sterile cell strainers in wells of a 6-well plate with 5 mL of low (60 mg/dl) glucose Krebs-Ringers Buffer (KRB) assay medium.

C. Incubate 30 minutes (1 hour if overnight step skipped) at 37° C. and 5% $CO_2$. Save the supernatants if a positive control for the RIA is desired.

D. Move strainers with islets to new wells with 5 mL/well low glucose KRB. This is the second pre-incubation and serves to remove residual or carryover insulin from the culture medium. Incubate 30 minutes.

E. Move strainers to next wells (Low 1) with 4 or 5 mL low glucose KRB. Incubate @ 37° C. for 30 minutes. Collect supernatants into low-binding polypropylene tubes pre-labelled for identification and keep cold.

F. Move strainers to high glucose wells (300 mg/dl, which is equivalent to 16.7 mM). Incubate and collect supernatants as before. Rinse islets in their strainers in low-glucose to remove residual insulin. If the rinse if to be collected for analysis, use one rinse well for each condition (i.e. set of triplicates.)

G. Move strainers to final wells with low-glucose assay medium (Low 2). Incubate and collect supernatants as before.

H. Keeping cold, centrifuge supernatants at 1800 rpm for 5 minutes @ 4-8° C. to remove small islets/islet pieces that escape the 40 mm mesh. Remove all but lower 0.5-1 mL and distribute in duplicate to pre-labelled low-binding tubes. Freeze and store at <−20° C. until insulin concentrations can be determined.

I. Insulin determinations are done as above, or by Linco Labs as a custom service, using their rat insulin RIA (Cat. # RI-13K).

Example 2

A. RT-PCR Analysis of RUP3 Expression in Human Tissues (FIG. 1A).

RT-PCR was applied to determine the tissue distribution of RUP3. Oligonucleotides used for PCR had the following sequences:

```
ZC47:
                                        (SEQ ID NO:3)
5'-CATTGCCGGGCTGTGGTTAGTGTC-3' (forward primer),;

ZC48:
                                        (SEQ ID NO:4)
5'-GGCATAGATGAGTGGGTTGAGCAG-3' (reverse primer),;
``` and the human multiple tissue cDNA panels (MTC, Clontech) were used as templates (1 ng cDNA per PCR amplification). Twenty-two (22) human tissues were analyzed. PCR was performed using Platinum PCR SuperMix (Life Technologies, Inc.; manufacture instructions were followed) in a 50 μl reaction by the following sequences: step 1, 95° C. for 4 min; step 2, 95° C. for 1 min; step 3, 60° C. for 30 sec; step 4, 72° C. for 1 min; and step 5, 72° C. for 7 min. Steps 2 through 4 were repeated 35 times.

The resulting PCR reactions (15 μl) were loaded on a 1.5% agarose gel to analyze the RT-PCR products, and a specific 466 base-pair DNA fragment representing RUP3 was specifically amplified from cDNA of pancreas origin. Low expression was also evident in subregions of brain.

B. cDNA Dot-Blot Analysis of RUP3 Expression in Human Tissues (FIG. 1B).

Results from RT-PCR analysis were further confirmed in cDNA dot-blot analysis. In this assay, a dot-blot membrane containing cDNA from 50 human tissues (Clontech) was hybridized with a $^{32}$P-radiolabelled DNA probe having sequences derived from human RUP3. Hybridyzation signals were seen in pancreas and fetal liver, suggesting these tissues express RUP3. No significant expression was detected in other tissues analyzed.

C. Analysis of RUP3 by RT-PCR with Isolated Human Pancreatic Islets of Langerhans (FIG. 1C).

Further analysis of RUP3 by RT-PCR with isolated human pancreatic islets of Langerhans showed robust expression of RUP3 in islet cells but not in control samples.

D. Analysis of RUP3 Expression with cDNAs of Rat Origin by RT-PCR (FIG. 1D).

RUP3 expression was further analyzed with cDNAs of rat origin by RT-PCR technique. Tissue cDNAs used for this assay were obtained from Clontech except those for hypothalamus and islets, which were prepared in house. Concentrations of each cDNA sample were normalized via a control RT-PCR analysis of the house-keeping gene GAPDH before assaying for RUP3 expression. Oligonucleotides used for PCR had the following sequences:

```
rat RUP3 ("rRUP3") forward:
                                        (SEQ ID NO:5)
5'-CATGGGCCCTGCACCTTCTTTG-3';

rRUP3 reverse:
                                        (SEQ ID NO:6)
5'-GCTCCGGATGGCTGATGATAGTGA-3'.
```

PCR was performed using Platinum PCR SuperMix (Life Technologies, Inc.; manufacture instructions were followed) in a 50 μl reaction by the following sequences: step 1, 95° C. for 4 min; step 2, 95° C. for 1 min; step 3, 60° C. for 30 sec; step 4, 72° C. for 1 min; and step 5, 72° C. for 7 min. Steps 2 through 4 were repeated 35 times.

The resulting PCR reactions (15 μl) were loaded on a 1.5% agarose gel to analyze the RT-PCR products, and a specific 547 base-pair DNA fragment representing rat RUP3 was specifically amplified from cDNA of pancreas origin, revealing a similar expression profile with human. Of particular note, robust expression was seen in isolated islets and hypothalamus.

Example 3

Figure 2:
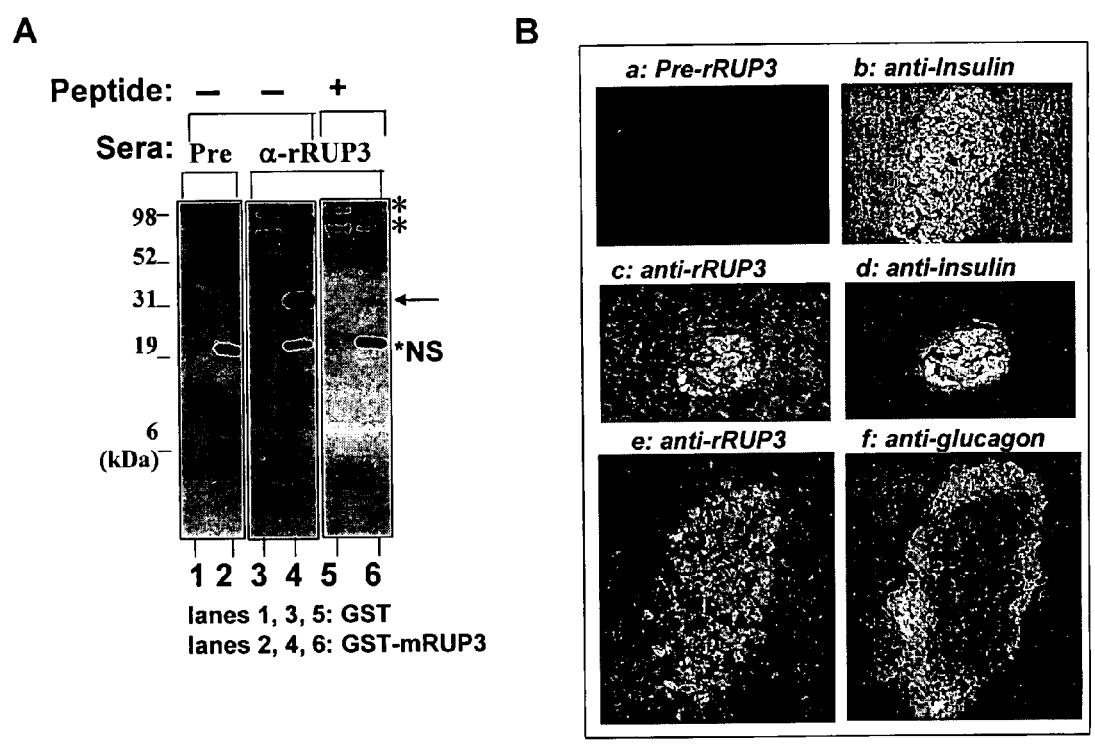
FIG. 2A shows a polyclonal anti-RUP3 antibody prepared in Rabbits.
FIG. 2B shows the expression of RUP3 in insulin-producing β cells of pancreatic islets.

RUP3 Protein Expression is Restricted to β Cell Lineage of Pancreatic Islets (FIG. 2).

A. A Polyclonal Anti-RUP3 Antibody was Prepared in Rabbits (FIG. 2A).

Rabbits were immunized with an antigenic peptide with sequence derived from rat RUP3 ("rRUP3"). The peptide sequence was RGPERTRESAYHIVTISHPELDG and shared 100% identity with mouse RUP3 in the corresponding region. A cysteine residue was incorporated at the N-terminal end of this antigenic peptide to facilitate KLH crosslinking before injecting into rabbits. The resulting antisera ("anti-rRUP3") and the corresponding preimmune sera ("pre-rRUP3") were tested for immune reactivity to mouse RUP3 in immunobloting assays (lanes 1 though 4). In this assay, the GST-RUP3 fusion protein was readily recognized by the anti-rRUP3 antisera (lane 4), but not by the preimmune sera (lane 2). The immunoreactive signal could be efficiently eliminated when the immunobloting assay was performed in the presence of excess antigenic peptide (lane 6).

B. RUP3 Expression in Insulin-Producing β Cells of Pancreatic Islets (FIG. 2B).

Rat pancreas was perfused with 4% paraformaldehyde (PFA) in PBS and embedded in OCT embedding medium. Ten micron sections were prepared, fixed on glass slides, and immunostained with either pre-rRUP3 (FIG. 2B, panel a) or with anti-rRUP3 antisera (FIG. 2B, panels c and e) followed by secondary staining with donkey anti-rabbit IgG conjugated to the fluorochrome Cy-3. Each section was also co-immunostained with a monoclonal anti-insulin antibody (Santa Cruz, FIG. 2B, panels b and d) in primary staining followed by a secondary staining with donkey anti-mouse IgG conjugated with FITC, or with a goat anti-glucagon antibody (Santa Cruz, FIG. 2B, panel f) and donkey anti-goat IgG coupled to FITC. Immunofluorescent signals were examined under a fluorescent microscope. RUP3 was found expressed in insulin producing cells (panels c and d), but not in glucagons producing cells (panels e and f). These data demonstrated that RUP3 is expressed in β cells but not in β cells of the rat pancreatic islets. Analogous results were obtained when mouse pancreatic sections were investigated for RUP3 expression.

Example 4

Figure 3:
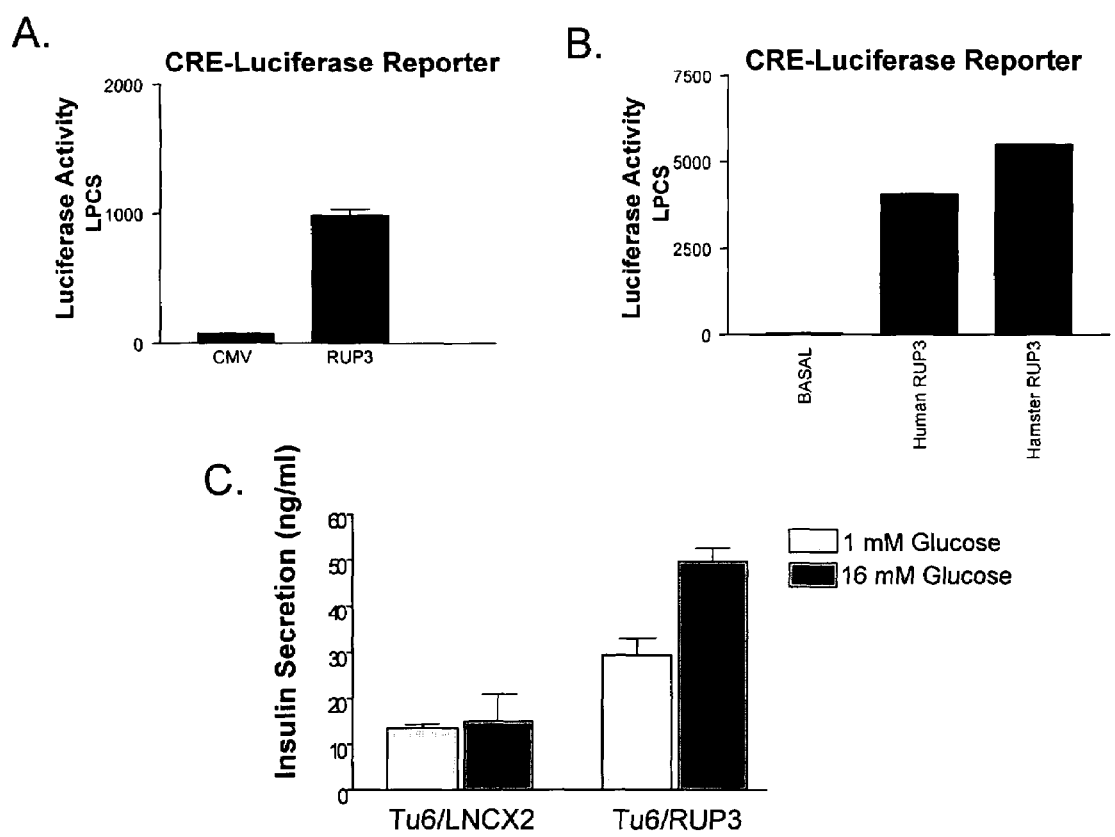
FIGS. 3A,3B, and 3C shows in vitro functional activities of RUP3.
Figure 4:
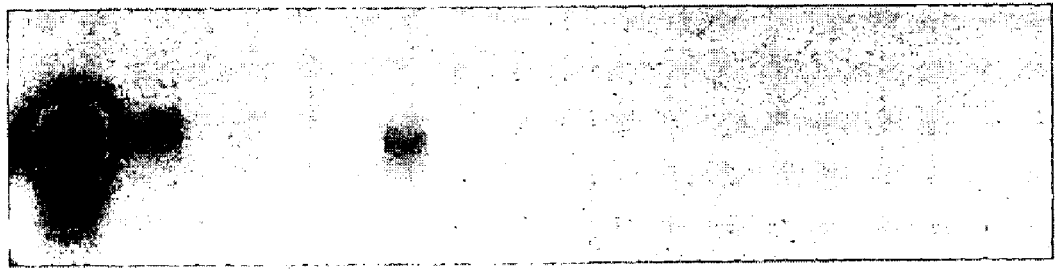
FIG. 4 shows a RUP3 RNA blot.

Functional Activities of RUP3 In Vitro (FIG. 3).

It was established that RUP3 stimulates the production of cAMP by cotransfection of 293 cells with: (1) a CRE-Luciferase reporter, wherein the ability to stimulate the production of firefly luciferase depends on increased cAMP in cells, and (2) an expression plasmid encoding the human form of RUP3 (FIG. 3A). Note that cells co-transfected with an expression plasmid containing no RUP3 sequences ("CMV" in FIG. 3A) produce very little luciferase activity, whereas cells transfected with an expression plasmid encoding RUP3 ("RUP3" in FIG. 3A) have at least a 10-fold increase in luciferase activity. This indicates that RUP3 stimulates the production of cAMP when introduced into 293 cells. This property of RUP3 is conserved across species, because hamster RUP3 stimulates luciferase activity when introduced into 293 cells in a manner analogous to that described for human RUP3 (FIG. 3B).

It is established that, when cAMP is increased in insulin-producing cells of the pancreas, these cells exhibit an enhanced ability to secrete insulin when glucose concentrations rise. To test whether RUP3 might impart enhanced glucose-dependent insulin release, retrovirus containing human RUP3 was used to generate Tu6 cells that express high levels of RUP3. Tu6 cells produce insulin, but do not express appreciable levels of RUP3 and do not normally exhibit an increase in insulin release when increased glucose is present in the culture media. As shown in FIG. 3C, Tu6 cells transduced with a control virus that contains no receptor are still able to produce insulin, but do not show an increase in insulin secretion when the concentration of glucose in the culture media is shifted from 1 mM to 16 mM. By contrast, Tu6 cells transduced with RUP3-containing retrovirus display significant glucose-dependent insulin secretion (FIG. 3C).

Example 5

In Vivo Effects of RUP3 Agonists on Glucose Homeostasis in Rats.

A. Oral Glucose Tolerance Test (oGTT)

Male Sprague Dawley rats weighing approximately 200 g-250 g were fasted for 15 hours and randomly grouped (n=6) to receive a RUP3 agonist (Compounds A194, A214 or D4) at 3, 10 or 30 mg/kg. Compounds were delivered orally via a gavage needle (p.o., volume 3 mL/kg). At time 0, levels of blood glucose were assessed using a glucometer (Elite XL, Bayer), and rats were administered either vehicle (20% hydroxypropyl-beta-cyclodextrin) or test compound. Thirty minutes after administration of test compound, levels of blood glucose were again assessed, and rats were administered dextrose orally at a dose of 2 g/kg. Blood glucose measurements were then taken 30 min, 60 min, and 120 min after this time. Table 8 shows the mean percentage inhibition of glucose excursion for each test compound, averaged across the six animals in the treatment group. These results demonstrated that the RUP3 agonists, Compounds A194, A214 and D4 lowered blood glucose after challenge with glucose.

TABLE 8

Mean % Inhibition of Glucose Excursion

| Compound | % inhibition of glucose excursion (dose, mg/kg) |
|---|---|
| A194 | 15%, (30) |
| A214 | 33%, (10) |
| D4 | 12%, (30) |

Example 6

Generation of Tu6/RUP3 Stable Lines

To produce Tu6 cells that express RUP3 at high levels, a retrovirus bearing an expression cassette for RUP3 was generated. Briefly, RUP3 coding sequence was cloned into the retroviral vector pLNCX2 (Clontech, Cat # 6102-1). The amphotropic packaging cell line PT-67 (Clontech, K1060-D) was then transfected with either the parental vector pLNCX2 or pLNCX2/RUP3 using Lipofectamine and stable lines were established using guidelines provided by the PT-67 vendor. Retrovirus-containing supernatant was obtained by collecting media from the resultant stables according to the manufacturer's directions. Tu6 cells, in a 10 cm dish, were then infected with retrovirus by incubating in a solution of 1 mL viral supernatant/9 mL culture media containing 40 ug/mL polybrene for 24 hours. The medium was then changed to culture media containing 300 ug/mL G418. G418-resistant clones were ultimately created by virtue of the neomycin-resistance gene cassette present in the pLNCX2 vector, thus indicating the successful integration of retrovirus into the Tu6 genome. The expression of RUP3 in the Tu6/RUP3 G418-resistant colonies was confirmed by Northern blot.

Example 7

Insulin Secretion, Tu6 Stables

To measure insulin secretion from rodent insulin-producing cell lines, cells were first cultured overnight in serum-free, glucose-deficient media. The following morning, the cells were then placed in the same media supplemented with either 1 mM or 16 mM glucose. After an incubation of 4 hours, the media was collected and analyzed for insulin content using a Rat Insulin Enzyme-Immunoassay (EIA) System (Amersham Pharmacia Biotech, Cat. # RPN 2567). Typically, the assay was performed using multiple dilutions of sample media in order to ensure that the sample measurements fell within the boundaries of the standard curve (generated using known amounts of insulin), as recommended by the manufacturer.

Example 8

Receptor Binding Assay

In addition to the methods described herein, another means for evaluating a test compound is by determining binding affinities to the RUP3 receptor. This type of assay generally requires a radiolabelled ligand to the RUP3 receptor. Absent the use of known ligands for the RUP3 receptor and radiolabels thereof, compounds of Formula (I) can be labelled with a radioisotope and used in an assay for evaluating the affinity of a test compound to the RUP3 receptor.

A radiolabelled RUP3 compound of the present invention can be used in a screening assay to identify/evaluate compounds. In general terms, a newly synthesized or identified compound (i.e., test compound) can be evaluated for its ability to reduce binding of the "radiolabelled compound of the present invention" to the RUP3 receptor. Accordingly, the ability to compete with the "radio-labelled compound of the present invention" or Radiolabelled RUP3 Ligand for the binding to the RUP3 receptor directly correlates to its binding affinity of the test compound to the RUP3 receptor.

Assay Protocol for Determining Receptor Binding for RUP3:

A. RUP3 Receptor Preparation 293 cells (human kidney, ATCC), transiently transfected with 10 ug human RUP3 receptor and 60 µL Lipofectamine (per 15-cm dish), were grown in the dish for 24 hours (75% confluency) with a media change and removed with 10 mL/dish of Hepes-EDTA buffer (20 mM Hepes+10 mM EDTA, pH 7.4). The cells were then centrifuged in a Beckman Coulter centrifuge for 20 minutes, 17,000 rpm (JA-25.50 rotor). Subsequently, the pellet was resuspended in 20 mM Hepes+1 mM EDTA, pH 7.4 and homogenized with a 50-mL Dounce homogenizer and again centrifuged. After removing the supernatant, the pellets were stored at −80° C., until used in binding assay. When used in the assay, membranes were thawed on ice for 20 minutes and then 10 mL of incubation buffer (20 mM Hepes, 1 mM $MgCl_2$, 100 mM NaCl, pH 7.4) added. The membranes were then vortexed to resuspend the crude membrane pellet and homogenized with a Brinkmann PT-3100 Polytron homogenizer for 15 seconds at setting 6. The concentration of membrane protein was determined using the BRL Bradford protein assay.

B. Binding Assay

For total binding, a total volume of 50 µL of appropriately diluted membranes (diluted in assay buffer containing 50 mM Tris HCl (pH 7.4), 10 mM $MgCl_2$, and 1 mM EDTA; 5-50 ug protein) is added to 96-well polyproylene microtiter plates followed by addition of 100 µL of assay buffer and 50 µL of Radiolabelled RUP3 Ligand. For nonspecific binding, 50 µL of assay buffer is added instead of 100 µL and an additional 50 µL of 10 µM cold RUP3 is added before 50 µL of Radiolabelled RUP3 Ligand is added. Plates are then incubated at room temperature for 60-120 minutes. The binding reaction is terminated by filtering assay plates through a Microplate Devices GF/C Unifilter filtration plate with a Brandell 96-well plate harvestor followed by washing with cold 50 mM Tris HCl, pH 7.4 containing 0.9% NaCl. Then, the bottom of the filtration plate are sealed, 50 µL of Optiphase Supermix is added to each well, the top of the plates are sealed, and plates are counted in a Trilux MicroBeta scintillation counter. For compound competition studies, instead of adding 100 µL of assay buffer, 100 µL of appropriately diluted test compound is added to appropriate wells followed by addition of 50 µL of Radiolabelled RUP3 Ligand.

C. Calculations

The test compounds are initially assayed at 1 and 0.1 µM and then at a range of concentrations chosen such that the middle dose would cause about 50% inhibition of a Radio-RUP3 Ligand binding (i.e., $IC_{50}$). Specific binding in the absence of test compound ($B_O$) is the difference of total binding ($B_T$) minus non-specific binding (NSB) and similarly specific binding (in the presence of test compound) (B) is the difference of displacement binding ($B_D$) minus non-specific binding (NSB). $IC_{50}$ is determined from an inhibition response curve, logit-log plot of % $B/B_O$ vs concentration of test compound.

$K_i$ is calculated by the Cheng and Prustoff transformation:

$$K_i = IC_{50}/(1+[L]/K_D)$$

where [L] is the concentration of a Radio-RUP3 Ligand used in the assay and $K_D$ is the dissociation constant of a Radio-RUP3 Ligand determined independently under the same binding conditions.

CHEMISTRY EXAMPLES

Syntheses of Compounds of the Present Invention

The compounds of the invention and their synthesis are further illustrated by the following examples. The following examples are provided to further define the invention without, however, limiting the invention to the particulars of these examples. The compounds described herein, supra and infra, are named according to the CS Chem Draw Ultra Version 7.0.1, AutoNom version 2.2. In certain instances common names are used and it is understood that these common names would be recognized by those skilled in the art.

Chemistry: Proton nuclear magnetic resonance ($^1$H NMR) spectra were recorded on a Varian Mercury Vx-400 equipped with a 4 nucleus auto switchable probe and z-gradient or a Bruker Avance-400 equipped with a QNP (Quad Nucleus Probe) or a BBI (Broad Band Inverse) and z-gradient. Chemical shifts are given in parts per million (ppm) with the residual solvent signal used as reference. NMR abbreviations are used as follows: s=singlet, d=doublet, t=triplet, q=quartet, m=multiplet, br=broad. Microwave irradiations were carried out using the Emyrs Synthesizer (Personal Chemistry). Thin-layer chromatography (TLC) was performed on silica gel 60 $F_{254}$ (Merck), preparatory thin-layer chromatography (prep TLC) was preformed on PK6F silica gel 60 A 1 mm plates (Whatman), and column chromatography was carried out on a silica gel column using Kieselgel 60, 0.063-0.200 mm (Merck). Evaporation was done in vacuo on a Buchi rotary evaporator. Celite 545® was used during palladium filtrations.

LCMS specs: 1) PC: HPLC-pumps: LC-10AD VP, Shimadzu Inc.; HPLC system controller: SCL-10A VP, Shimadzu Inc; UV-Detector: SPD-10A VP, Shimadzu Inc; Autosampler: CTC HTS, PAL, Leap Scientific; Mass spectrometer: API 150EX with Turbo Ion Spray source, AB/MDS

Example 9

Example 9.1

Preparation of 4-[1-(4-methanesulfonyl-phenyl)-1H-pyrazolo[3,4-d]pyrimidin-4-yloxy]-piperidine-1-carboxylic acid tert-butyl ester (Compound A1)

Step 1: Preparation of 5-amino-1-(4-methanesulfonyl-phenyl)-1H-pyrazole-4-carbonitrile A round-bottomed flask (100 mL), equipped with a reflux condenser and $N_2$ inlet septum, was charged with 4-(methylsulfonyl)phenylhydrazine hydrochloride (2 g, 9 mmol), and sodium methoxide (0.49 g, 9 mmol). Methanol (20 mL) was added under a stream of nitrogen at room temperature. The reaction mixture was stirred for 15-20 minutes until the purple color disappeared and a white precipitate was formed. This was followed by the addition of ethoxymethylenemalononitrile (1.1 g, 9 mmol) and stirring at room temperature for an additional 10 mins, subsequently the reaction mixture was brought to reflux for 150 mins. The cooled reaction mixture was filtered and concentrated under reduced pressure to afford the crude product. The solid residue was dissolved in EtOAc/$H_2O$. The EtOAc layer was collected, washed with saturated aqueous NaCl, dried over $NaSO_4$ and concentrated to give second portion of the crude product. The crude product was purified by flash chromatography (10% $CH_3OH$/$CH_2Cl_2$) and recrystallized from methanol to give a yellow crystalline product (625 mg, 26%). $^1H$ NMR (DMSO-$d_6$, 400 MHz) δ 3.27 (s, 3H), 6.98 (s, 2H), 7.81 (d, 2H), 7.88 (s, 1H), 8.06 (s, 2H). LCMS: calculated for $C_{11}H_{10}N_4O_2S$ 262.05, observed 262.9 ($MH^+$)

Step 2: Preparation of 1-(4-methanesulfonyl-phenyl)-1H-pyrazolo[3,4-d]pyrimidin-4-ol A mixture of 5-amino-1-(4-methanesulfonyl-phenyl)-1H-pyrazole-4-carbonitrile (540 mg), formic acid (10 mL) and 1 mL $H_2O$ was refluxed overnight at 102° C. After cooling to room temperature, a white precipitate was observed. The mixture was diluted with $H_2O$ (10 mL), filtered through a funnel and washed thoroughly with $H_2O$, $CH_3OH$, and diethyl ether. The white solid was collected and dried under vacuum to give a crude product (300 mg, 50% yield). $^1H$ NMR (DMSO-$d_6$, 400 MHz) δ 3.26 (s, 3H), 8.12 (d, 2H), 8.29 (s, 1H), 8.42 (d, 2H), 8.44 (d, 1H), 12.61 (s, 1H). LCMS: calculated $C_{12}H_{10}N_4O_3S$ 290.05, observed 291.2 ($MH^+$).

Step 3: Preparation of 4-Chloro-1-(4-methanesulfonyl-phenyl)-1H-pyrazolo[3,4-d]pyrimidine Into a 50 mL round-bottomed equipped with a reflux condenser and $N_2$ inlet septum was place a stir bar, 1-(4-methanesulfonyl-phenyl)-1H-pyrazolo[3,4-d]pyrimidin-4-ol (93 mg, 0.32 mmol), dimethylaniline (0.3 mL) and $POCl_3$ (10 mL). The reaction mixture was stirred at room temperature under $N_2$ for 5 minutes and brought to reflux for 6 hrs. After cooling down to room temperature, the reaction mixture was poured into ice and extracted with $CH_2Cl_2$ quickly. The crude product was then purified by flash chromatography (EtOAc:Hex=1:1), 24 mg of product was obtained (27% yield). $^1H$ NMR (DMSO-$d_6$, 400 MHz) δ 3.29 (s, 3H), 8.19 (d, 2H), 8.53 (d, 2H), 8.89 (s, 1H), 9.08 (s, 1H). LCMS calculated $C_{12}H_9ClN_4O_2S$ 308.01, observed 309.1 ($MH^+$).

Step 4: Preparation of 4-[1-(4-Methanesulfonyl-phenyl)-1H-pyrazolo[3,4-d]pyrimidin-4-yloxy]-piperidine-1-carboxylic acid tert-butyl ester (Compound A1)

Into a 16 mL reaction vial was placed sodium hydride (7.8 mg, 60% in oil, 0.195 mmol) and 0.5 mL of THF. 4-Hydroxy-piperidine-1-carboxylic acid tert-butyl ester (10 mg, 0.0487 mmol) was added to the suspension and the mixture was stirred 20 min under $N_2$ at room temperature, followed by the slow addition of 4-chloro-1-(4-methanesulfonyl-phenyl)-1H-pyrazolo[3,4-d]pyrimidine (10 mg, 0.0325 mmol). After stirring overnight under $N_2$ at room temperature, all of the starting chloropyrazolopyrimidine had been converted as indicated by LCMS. The reaction mixture was then concentrated under vacuum and purified by flash column chromatography using 50% EtOAc/Hex as eluent. $^1H$ NMR ($CDCl_3$, 400 MHz) δ 1.49 (s, 9H), 1.85 (m, 2H), 2.09 (m, 2H), 3.10 (s, 3H), 3.32 (m, 2H), 3.86 (m, 2H), 5.60 (m, 1H), 8.09 (d, 2H), 8.26 (s, 1H), 8.61 (d, 2H), 8.66 (s, 1H). LCMS: calculated for $C_{22}H_{27}N_5O_5S$ 473.17, observed 474.4 ($MH^+$)

Example 9.2

Preparation of 4-[1-(4-Methanesulfonyl-phenyl)-3-methyl-1H-pyrazolo[3,4-d]pyrimidin-4-yloxy]-piperidine-1-carboxylic acid tert-butyl ester (Compound A2)

Step 1: Preparation of 5-Amino-1-(4-methanesulfonyl-phenyl)-3-methyl-1H-pyrazole-4-carbonitrile Following the above general procedure in Example 9.1, the title compound, 5-amino-1-(4-methanesulfonyl-phenyl)-3-methyl-1H-pyrazole-4-carbonitrile, was synthesized using 1-ethoxyethylidenemalononitrile and 4-(methylsulfonyl)phenylhydrazine hydrochloric acid as a yellow solid. $^1H$ NMR (DMSO-$d_6$, 400 MHz) δ 2.18(s, 3H), 3.26(s, 3H), 6.94 (s, 2H), 7.9(d, 2H), 8.03(s, 2H). LCMS: calculated $C_{12}H_{12}N_4O_2S$ 276.07, observed 277.1 ($MH^+$)

Step 2: Preparation of 1-(4-Methanesulfonyl-phenyl)-3-methyl-1H-pyrazolo[3,4-d]pyrimidin-4-ol Following the general procedure described in Example 9.1, the title compound, 1-(4-methanesulfonyl-phenyl)-3-methyl-1H-pyrazolo[3,4-d]pyrimidin-4-ol, was prepared and isolated. $^1H$ NMR (DMSO-$d_6$/$CDCl_3$, 400 MHz) δ 2.54 (s, 3H), 3.13 (s, 3H), 8.02 (d, 2H), 8.05 (s, 1H), 8.42 (d, 2H), 12.41(s, 1H). LCMS: calculated $C_{13}H_{12}N_4O_3S$ 304.06, observed 305.1 ($MH^+$).

Step 3: Preparation of 4-Chloro-1-(4-methanesulfonyl-phenyl)-3-methyl-1H-pyrazolo[3,4-d]pyrimidine Following general procedure in Example 9.1, the title compound was isolated and purified by flash column chromatography. $^1H$ NMR ($CDCl_3$, 400 MHz) δ 2.84 (s, 3H), 3.011 (s, 3H), 8.11 (d, 2H), 8.60 (d, 2H), 8.87 (s, 1H). LCMS: calcdated for $C_{14}H_{13}ClN_4O_2S$ 336.04, observed 337.2 ($MH^+$).

Step 4: Preparation of 4-[1-(4-Methanesulfonyl-phenyl)-3-methyl-1H-pyrazolo[3,4-d]pyrimidin-4-yloxy]-piperidine-1-carboxylic acid tert-butyl ester (Compound A2)

Compound A2 was prepared by general procedure in Example 9.1. $^1$H NMR (CDCl$_3$, 400 MHz) δ 1.49 (s, 9H), 1.89 (m, 2H), 2.07 (m, 2H), 2.70 (s, 3H), 3.09 (s, 3H), 3.49 (m, 2H), 3.88 (m, 2H), 5.62 (m, 1H), 8.08 (d, 2H), 8.58 (s, 2H), 8.61 (s, 1H). LCMS calculated for C$_{23}$H$_{29}$N$_5$O$_5$S 487.19, observed 488.4 (MH$^+$).

Example 9.3

Preparation of 4-[1-(4-Methanesulfonyl-phenyl)-3,6-dimethyl-1H-pyrazolo[3,4-d]pyrimidin-4-yloxy]-piperidine-1-carboxylic acid tert-butyl ester (Compound A3)

Step 1: Preparation of N-[4-Cyano-2-(4-methanesulfonyl-phenyl)-5-methyl-2H-pyrazol-3-yl]-acetamide To a 50 mL round-bottomed equipped with a reflux condenser and N$_2$ inlet septum was placed a stir bar, 5-amino-1-(4-methanesulfonyl-phenyl)-3-methyl-1H-pyrazole-4-carbonitrile (85 mg, 0.31 mmol), and acetyl chloride (5 mL). The reaction mixture was stirred under N$_2$ for 24 hrs at 60° C. The acetyl chloride was removed under reduced pressure and solid residue washed with CH$_2$Cl$_2$ and EtOAc and collected by filtration. The crude product was then purified by flash chromatography (EtOAc:Hex=1:1) and recrystalized from methanol. 55 mg of product was obtained (56% yield). $^1$H NMR (DMSO-d$_6$, 400 MHz) δ 2.07 (s, 3H), 2.36 (s, 3H), 3.29 (s, 3H), 7.81 (d, 2H), 8.09 (d, 2H), 10.7 (s, 1H). LCMS: calculted C$_{14}$H$_{14}$N$_4$O$_3$S 318.08, observed 319.1 (MH$^+$)

Step 2: Preparation of 1-(4-Methanesulfonyl-phenyl)-3,6-dimethyl-1,5-dihydro-pyrazolo[3,4-d]pyrimidin-4-one In to a 50 mL round-bottomed equipped with a stir bar and a reflux condenser was added, N-[4-cyano-2-(4-methanesulfonyl-phenyl)-5-methyl-2H-pyrazol-3-yl]-acetamide (30 mg, 0.079 mmol), H$_2$O (0.6 mL), and ethanol (1 mL) followed by 20% aqouus KOH (0.33 mL). The reaction mixture turned purple and the solid dissolved after addition of KOH. Hydrogen peroxide (0.25 mL) was then added to the above solution. After stirring 15 min at room temperature, the reaction mixture was heated at 75° C. overnight. After cooled to room temperature acetic acid was added slowly until the pH attained a range between 6-6.5. The mixture was then diluted with H$_2$O and methanol. The resulting precipitate was collected by filtration and washed with H$_2$O, methanol, diethyl ether and dried under vacuum. The crude product was used directly in the next step without further purification. $^1$H NMR (DMSO-d$_6$, 400 MHz) δ 1.71 (s, 2H), 2.39 (s, 3H), 2.51 (s, 1H), 3.25 (s, 3H), 8.05 (d, 2H), 8.46 (d, 2H). LCMS: calculated C$_{14}$H$_{14}$N$_4$O$_3$S 318.08, observed 319.1 (MH$^+$)

Step 3: Preparation of 4-Chloro-1-(4-methanesulfonyl-phenyl)-3,6-dimethyl-1H-pyrazolo[3,4-d]pyrimidine Following the general procedure in Example 9.1, the title compound was isolated and purified by flash column chromatography. $^1$H NMR (CDCl$_3$, 400 MHz) δ 2.79 (s, 3H), 2.86 (s, 3H), 3.09 (s, 3H), 8.10 (d, 2H), 8.61 (d, 2H). LCMS: calculated for C$_{14}$H$_{13}$ClN$_4$O$_2$S 336.04, observed 337.2 (MH$^+$).

Step 4: Preparation of 4-[1-(4-methanesulfonyl-phenyl)-3,6-dimethyl-1H-pyrazolo[3,4-d]pyrimidin-4-yloxy]-piperidine-1-carboxylic acid tert-butyl ester (Compound A3)

Compound A3 was prepared using general procedure in Example 9.1. $^1$H NMR (CDCl$_3$, 400 MHz) δ 1.49 (s, 9H), 1.89 (m, 2H), 2.07 (m, 2H), 2.66 (s, 3H), 2.70 (s, 3H), 3.08 (s, 3H), 3.49 (m, 2H), 3.68 (m, 2H), 5.65 (m, 1H), 8.05 (d, 2H), 8.59 (d, 2H). LCMS: calculated for C$_{24}$H$_{31}$N$_5$O$_5$S 501.2, observed 502.4 (MH$^+$).

Example 9.4

Preparation of 4-[1-(4-Methanesulfonyl-phenyl)-1H-pyrazolo[3,4-d]pyrimidin-4-yloxy]-piperidine-1-carboxylic acid isobutyl ester (Compound A4)

General Procedure for Carbamate Formation

A mixture of Compound A6 (150 mg, 0.367 mmol), isobutylchloroformate (0.057 mL, 0.44 mmol) and triethyl amine (0.1 mL) in DMF (8 mL) was stirred at rt for 1 hour. Water was added to the mixture and precipitate was collected. Compound A4 was obtained as a solid (88%). $^1$H NMR (CDCl$_3$, 400 MHz) δ 0.95 (d, 6H), 1.86-1.98 (m, 3H), 2.11-2.13 (m, 2H), 3.10 (s, 3H), 3.37-3.43 (m, 2H), 3.89-3.95 (m, 4H), 5.64-5.68 (m, 1H), 8.09-8.12 (m, 2H), 8.26 (s, 1H), 8.60-8.63 (m, 2H), 8.67 (s, 1H). Exact mass calculated for C$_{22}$H$_{27}$N$_5$O$_5$S 473.2, found 474.3 (MH$^+$).

Example 9.5

Preparation of 4-[1-(4-Methanesulfonyl-phenyl)-1H-pyrazolo[3,4-d]pyrimidin-4-yloxy]-piperidine-1-carboxylic acid isopropyl ester (Compound A5)

Compound A5 was obtained via general procedure described in Example 9.4 as a solid (95%). $^1$H NMR (CDCl$_3$, 400 MHz) δ 1.26 (d, 6H), 1.82-1.86 (m, 2H), 2.01-2.10 (m, 2H), 3.10 (s, 3H), 3.34-3.45 (m, 2H), 3.90-3.93 (m, 2H), 4.94 (sept, 1H), 5.44-5.48 (m, 1H), 8.09-8.12 (m, 2H), 8.26 (s, 1H), 8.60-8.62 (m, 2H), 8.67 (s, 1H). Exact mass calculated for C$_{21}$H$_{25}$N$_5$O$_5$S 459.2, found 460.3 (MH$^+$).

Example 9.6

Preparation of 1-(4-Methanesulfonyl-phenyl)-4-(piperidin-4-yloxy)-1H-pyrazolo[3,4-d]pyrimidine (Compound A6)

General Deprotection Method

Into a 200 mL round-bottomed flask was placed a stir bar, Compound A1 (1.2 g), anhydrous acetonitrile (50 mL), and dichloromethane (15 mL). 4M HCl in 1,4-dioxane (15 mL) was added under nitrogen and the mixture was stirred at 40° C. for 10 minutes. The solution turned cloudy. The precipitate was isolated and purified by HPLC to give Compound A6. $^1$H NMR (DMSO-d$_6$, 400 MHz) δ 2.04 (m, 2H), 2.25 (m, 2H), 3.21 (m, 2H), 3.28 (s, 3H), 3.32 (m, 2H), 5.60 (m, 1H), 8.16 (d, 2H), 8.61 (d, 2H), 8.70 (s, 1H), 8.79 (s, 1H). LCMS: calculated for C$_{17}$H$_{19}$N$_5$O$_3$S 373.12, observed 374.1 (MH$^+$).

Example 9.7

Preparation of {4-[1-(4-Methanesulfonyl-phenyl)-1H-pyrazolo[3,4-d]pyrimidin-4-yloxy]-piperidin-1-yl}-pyridin-3-yl-methanone (Compound A7)

General Amide Formation Method

Into a 500 mL round-bottomed flask was placed Compound A6 (146 mg, 0.36 mmol) and triethylamine (300 µL). DMF (15 mL) was added to completely dissolve the solid material. Nicotinoyl chloride hydrochloride (96 mg, 0.54 mmol) was added to the solution and the mixture was stirred overnight under $N_2$ at room temperature. After all of the starting amine was completely converted as indicated by LCMS, the reaction was stopped by quenching with water. The reaction mixture was then concentrated under vacuum and purified by preparative HPLC to give Compound A7. $^1$H NMR (CDCl$_3$, 400 MHz) δ 2.06 (m, 2H), 2.22 (m, 2H), 3.09 (s, 3H), 3.55 (m, 1H), 3.79 (m, 2H), 4.15 (m, 1H), 5.76 (m, 1H), 7.86 (m,1H), 8.11 (d, 2H), 8.28 (s,1H), 8.33 (d,1H), 8.61 (d, 2H), 8.68 (s, 1H), 8.84 (m, 1H), 8.92 (m, 1H). LCMS calculated for $C_{23}H_{22}N_6O_4S$ 478.14, observed 479.1 (MH$^+$)

Example 9.8

Preparation of 4-[1-(4-Methanesulfonyl-phenyl)-1H-pyrazolo[3,4-d]pyrimidin-4-yloxy]-piperidine-1-carboxylic acid butyl ester (Compound A48)

1-(4-Methanesulfonyl-phenyl)-4-(piperidin-4-yloxy)-1H-pyrazolo[3,4-d]pyrimidine hydrochloride (0.17 mmol, 60 mg), n-butyl chloroformate (0.19 mmol, 24 µL) and triethylamine (0.51 mmol, 71 µL) were dissolved in DMF (2 mL) and stirred for 60 minutes at room temperature. The reaction mixture was quenched with water followed by an extraction with ethylacetate. Removal of organic solvents in vacuo provided Compound A48 as a white solid (40 mg, 50%). $^1$H NMR (400 MHz, CDCl$_3$) δ (ppm): 8.67 (s, 1H); 8.62 (d, 2H); 8.26 (s, 1H); 8.11 (d, 2H); 5.62 (h, 1H); 4.12 (t, 2H); 3.92 (m, 2H); 3.39 (m, 2H); 3.10 (s, 3H); 2.11 (m, 2H); 1.65 (m, 2H), 1.56 (p, 2H); 1.42 (s, 2H); 0.97 (t, 3H). Exact mass calculated for $C_{22}H_{27}N_5O_5S$ 473.55, found 474.4 (MH$^+$).

Example 9.9

Preparation of 4-[1-(2-Fluoro-4-methanesulfonyl-phenyl)-1H-pyrazolo[3,4-d]pyrimidin-4-ylsulfanyl]-piperidine-1-carboxylic acid cyclopropylmethyl ester (Compound A112)

Di-imidazol-1-yl-methanone (0.25 mmol, 41 mg), and cyclopropylmethanol (0.25 mmol, 20 µL) were dissolved in DMSO (2 mL) and stirred for 30 minutes at room temperature. Then, 1-(2-fluoro-4-methanesulfonyl-phenyl)-4-(piperidin-4-ylsulfanyl)-1H-pyrazolo[3,4-d]pyrimidine hydrochloride (0.18 mmol, 80 mg) and triethylamine (0.54 mmol, 75 µL) were added. The mixture was heated in a microwave for 5 minutes at 120° C. The progress of the reaction was monitored by thin layer chromatography and LCMS. Purification by RPLC provided Compound A112 as a white solid (26 mg, 29%). $^1$H NMR (400 MHz, CDCl$_3$) δ (ppm): 8.72 (s, 1H); 8.41 (s, 1H); 7.87 (m, 3H); 4.40 (h, 1H); 4.01 (m, 2H); 3.87 (d, 2H); 3.19 (m, 2H); 3.06 (s, 3H); 2.17 (m, 2H); 1.73 (m, 2H); 1.07 (m, 1H); 0.51 (m, 2H); 0.25 (m, 2H). Exact mass calculated for $C_{22}H_{24}FN_5O_4S_2$ 505.59, found 506.20 (MH$^+$).

Example 9.10

Preparation of 4-[1-(2-Fluoro-4-methanesulfonyl-phenyl)-1H-pyrazolo[3,4-d]pyrimidin-4-ylsulfanyl]-piperidine-1-carboxylic acid cyclobutylmethyl ester (Compound A113)

Di-imidazol-1-yl-methanone (0.25 mmol, 41 mg), and cyclobutyl methanol (0.25 mmol, 24 µL) were dissolved in DMSO (2 mL) and stirred for 30 minutes at room temperature. Then, 1-(2-fluoro-4-methanesulfonyl-phenyl)-4-(piperidin-4-ylsulfanyl)-1H-pyrazolo[3,4-d]pyrimidine hydrochloride (0.18 mmol, 80 mg) and triethylamine (0.54 mmol, 75 µL) were added. The mixture was heated in a microwave for 5 minutes at 120° C. The progress of the reaction was monitored by thin layer chromatography and LCMS. Purification by HPLC provided Compound A113 as a white solid (29 mg, 31%). $^1$H NMR (400 MHz, CDCl$_3$) δ (ppm): 8.71 (s, 1H); 8.22 (s, 1H); 7.87 (m, 3H); 4.37 (h, 1H); 4.00 (m, 4H); 3.16 (m, 2H); 3.05 (s, 3H); 2.56 (m, 1H); 2.12 (m, 2H); 2.01 (m, 2H); 1.85 (m, 2H); 1.73 (m, 4H). Exact mass calculated for $C_{23}H_{26}FN_5O_4S_2$ 519.61, found 520.3 (MH$^+$).

Example 9.11

Preparation of 4-[1-(2-Fluoro-4-methanesulfonyl-phenyl)-1H-pyrazolo[3,4-d]pyrimidin-4-ylsulfanyl]-piperidine-1-carboxylic acid 2-cyclopropyl-ethyl ester (Compound A114)

Di-imidazol-1-yl-methanone (0.25 mmol, 41 mg), and 2-cyclopropyl-ethanol (0.25 mmol, 32 µL) were dissolved in DMSO (2 mL) and stirred for 30 minutes at room temperature. Then, 1-(2-fluoro-4-methanesulfonyl-phenyl)-4-(piperidin-4-ylsulfanyl)-1H-pyrazolo[3,4-d]pyrimidine hydrochloride (0.18 mmol, 80 mg) and triethylamine (0.54 mmol, 75 µL) were added. The mixture was heated in a microwave for 5 minutes at 120° C. The progress of the reaction was monitored by thin layer chromatography and LCMS. Purification by HPLC provided Compound A114 as a white solid (35 mg, 36%). $^1$H NMR (400 MHz, CDCl$_3$) δ (ppm): 8.71 (s, 1H); 8.21 (s, 1H); 7.86 (m, 3H); 4.37 (m, 1H); 4.10 (t, 2H); 3.96 (s broad, 2H); 3.19 (m, 2H); 3.04 (s, 3H); 2.12 (m, 2H); 1.72 (m, 2H); 1.48 (m, 2H); 1.39 (m, 2H); 1.00 (m, 2H); 0.65 (m, 1H). Exact mass calculated for $C_{23}H_{26}FN_5O_4S_2$ 519.61, found 520.3 (MH$^+$).

Example 9.12

Preparation of (5-Bromo-furan-2-yl)-{4-[1-(2-fluoro-4-methanesulfonyl-phenyl)-1H-pyrazolo[3,4-d]pyrimidin-4-ylsulfanyl]-piperidin-1-yl}-methanone (Compound A115)

Oxalyl chloride (0.51 mmol, 45 µL) and DMF (catalytic amount) were added to 5-bromo-furan-2-carboxylic acid (0.18 mmol, 36 mg) in dichloromethane (3 mL). The reaction mixture was stirred for 40 minutes at room temperature. The organic solvents were removed in vaccuo. The concentrate was re-dissolved in dichloromethane and 1-(2-fluoro-4-methanesulfonyl-phenyl)-4-(piperidin-4-ylsulfanyl)-1H-pyrazolo[3,4-d]pyrimidine hydrochloride (0.16 mmol, 70 mg) and triethylamine (0.47 mmol, 66 µL) were added and stirred for 1.5 hours at room temperature. The progress of the reaction was monitored by thin layer chromatography and LCMS. Purification by HPLC provided Compound A115 as a white solid (45 mg, 41%). $^1$H NMR (400 MHz, CDCl$_3$) δ

(ppm): 8.74 (s, 1H); 8.25 (s, 1H); 7.87 (m, 3H); 7.00 (d, 1H); 6.49 (s, 1H); 4.50 (h, 1H); 4.34 (m, 2H); 3.42 (s broad, 2H); 2.70 (s, 3H); 2.28 (m, 2H); 1.85 (m, 2H). Exact mass calculated for $C_{22}H_{19}BrFN_5O_4S_2$ 580.45, found 582.3 (MH$^+$).

Example 9.13

Preparation of 4-[1-(4-Methanesulfonyl-phenyl)-1H-pyrazolo[3,4-d]pyrimidin-4-yloxy]-piperidine-1-carboxylic acid pentyl ester (Compound A117)

Di-imidazol-1-yl-methanone (0.51 mmol, 83 mg), and n-pentanol (0.51 mmol, 56 µL) were dissolved in DMSO (1 mL) and stirred for 30 minutes at room temperature. Then, 1-(4-methanesulfonyl-phenyl)-4-(piperidin-4-yloxy)-1H-pyrazolo[3,4-d]pyrimidine (0.17 mmol, 70 mg) and triethylamine (0.51 mmol, 72 µL) were added and heated in a microwave at 120° C. for 6 minutes. The progress of the reaction was monitored by LCMS. The reaction mixture was quenched with water and the product was extracted with ethylacetate. Removal of organic solvents in vacuo and purification by HPLC provided Compound A117 as a white solid (33 mg, 32%). Exact mass calculated for $C_{23}H_{29}N_5O_5S$ 487.57, found 488.20 (MH$^+$).

Example 9.14

Preparation of 4-[1-(4-Methanesulfonyl-phenyl)-1H-pyrazolo[3,4-d]pyrimidin-4-yloxy]-piperidine-1-carboxylic acid 1-ethyl-propyl ester (Compound A118)

Di-imidazol-1-yl-methanone (0.51 mmol, 83 mg), and pentan-3-ol (0.51 mmol, 56 µL) were dissolved in DMSO (1 mL) and stirred for 30 minutes at room temperature. Then, 1-(4-methanesulfonyl-phenyl)-4-(piperidin-4-yloxy)-1H-pyrazolo[3,4-d]pyrimidine (0.17 mmol, 70 mg) and triethylamine (0.51 mmol, 72 µL) were added and heated in a microwave at 120° C. for 6 minutes. The progress of the reaction was monitored by LCMS. The reaction mixture was quenched with water and the product was extracted with ethylacetate. Removal of organic solvents in vacuo and purification by HPLC provided Compound A118 as a white solid (14 mg, 14%). Exact mass calculated for $C_{23}H_{29}N_5O_5S$ 487.57, found 488.20 (MH$^+$).

Example 9.15

Preparation of 4-[1-(4-Methanesulfonyl-phenyl)-1H-pyrazolo[3,4-d]pyrimidin-4-yloxy]-piperidine-1-carboxylic acid 2-ethyl-butyl ester (Compound A119)

Di-imidazol-1-yl-methanone (0.51 mmol, 83 mg), and 2-ethyl-butan-1-ol (0.51 mmol, 52 mg) were dissolved in DMSO (1 mL) and stirred for 30 minutes at room temperature. Then, 1-(4-methanesulfonyl-phenyl)-4-(piperidin-4-yloxy)-1H-pyrazolo[3,4-d]pyrimidine (0.17 mmol, 70 mg) and triethylamine (0.51 mmol, 72 µL) were added and heated in a microwave at 120° C. for 6 minutes. The progress of the reaction was monitored by LCMS. The reaction mixture was quenched with water and the product was extracted with ethylacetate. Removal of organic solvents in vacuo and purification by HPLC provided Compound A119 as a white solid (38 mg, 36%). Exact mass calculated for $C_{24}H_{31}N_5O_5S$ 501.60, found 502.3 (MH$^+$).

Example 9.16

Preparation of 4-[1-(4-Methanesulfonyl-phenyl)-1H-pyrazolo[3,4-d]pyrimidin-4-yloxy]-piperidine-1-carboxylic acid cyclopentylmethyl ester (Compound A120)

Di-imidazol-1-yl-methanone (0.51 mmol, 83 mg), and cyclopentyl-methanol (0.51 mmol, 51 mg) were dissolved in DMSO (1 mL) and stirred for 30 minutes at room temperature. Then, 1-(4-methanesulfonyl-phenyl)-4-(piperidin-4-yloxy)-1H-pyrazolo[3,4-d]pyrimidine (0.17 mmol, 70 mg) and triethylamine (0.51 mmol, 72 µL) were added and heated in a microwave at 120° C. for 6 minutes. The progress of the reaction was monitored by LCMS. The reaction mixture was quenched with water and the product was extracted with ethylacetate. Removal of organic solvents in vacuo and purification by HPLC provided Compound A120 as a white solid (30 mg, 29%). Exact mass calculated for $C_{24}H_{29}N_5O_5S$ 499.58, found 500.4 (MH$^+$).

Example 9.17

Preparation of 4-[1-(4-Methanesulfonyl-phenyl)-1H-pyrazolo[3,4-d]pyrimidin-4-yloxy]-piperidine-1-carboxylic acid 2,2-dimethyl-propyl ester (Compound A124)

1-(4-Methanesulfonyl-phenyl)-4-(piperidin-4-yloxy)-1H-pyrazolo[3,4-d]pyrimidine hydrochloride (0.17 mmol, 70 mg), neopentyl chloroformate (0.25 mmol, 37 µL) and triethylamine (0.51 mmol, 72 µL) were dissolved in DMF (2 mL) and stirred for 60 minutes at room temperature. Progress of the reaction was monitored by TLC and LCMS. The reaction mixture was quenched with water. The product was extracted with ethyl acetate. Removal of organic solvents in vacuo and purification by HPLC provided Compound A124 as a white solid (28 mg, 27%). Exact mass calculated for $C_{23}H_{29}N_5O_5S$ 487.57, found 488.20 (MH$^+$).

Example 9.18

Preparation of (5-Butyl-pyridin-2-yl)-{4-[1-(4-methanesulfonyl-phenyl)-1H-pyrazolo[3,4-d]pyrimidin-4-yloxy]-piperidin-1-yl}-methanone (Compound A125)

5-Butyl-pyridine-2-carboxylic acid (92 mg, 0.51 mmol) and isopropyl chloroformate (70 µL, 0.51 mmol) were dissolved in DMF and stirred at room temperature for 40 min. 1-(4-Methanesulfonyl-phenyl)-4-(piperidin-4-yloxy)-1H-pyrazolo[3,4-d]pyrimidine hydrochloride (70 mg, 0.17 mmol) and triethylamine (72 µL, 0.51 mmol) were added next and continued to stir for 24 hours. Progress of the reaction was monitored by TLC and LCMS. Removal of organic solvents in vacuo and purification by HPLC afforded Compound A125 as a white solid (13 mg, 13%). Exact mass calculated for $C_{27}H_{30}N_6O_4S$ 534.63, found 535.20 (MH$^+$).

Example 9.19

Preparation of (4-Difluoromethoxy-phenyl)-{4-[1-(2-fluoro-4-methanesulfonyl-phenyl)-1H-pyrazolo[3,4-d]pyrimidin-4-yloxy]-piperidin-1-yl}-methanone (Compound A193)

4-Difluoromethoxy-benzoic acid (527 mg, 2.8 mmol) and HATU (1.06 g, 2.8 mmol) were stirred together in DMF at room temperature for 30 min. 1-(2-Fluoro-4-methanesulfonyl-phenyl)-4-(piperidin-4-yloxy)-1H-pyrazolo[3,4-d]pyrimidine hydrochloride (800 mg, 1.87 mmol) and triethylamine (785 μL, 5.61 mmol) were added next. The resulting mixture was allowed to stir for 24 hours. Progress of the reaction was monitored by TLC and LCMS. Removal of organic solvents in vacuo and purification by HPLC afforded Compound A193 as a beige solid (127 mg, 32%). Exact mass calculated for $C_{25}H_{22}F_2N_5O_5S$ 561.53, found 562.2 ($MH^+$)

Example 9.20

Preparation of 1-(2-Fluoro-4-methanesulfonyl-phenyl)-4-[1-(3-isopropyl-[1,2,4]oxadiazol-5-yl)-piperidin-4-yloxy]-1H-pyrazolo[3,4-d]pyrimidine (Compound A198)

Step 1: Preparation of N-hydroxy-isobutyramidine

A solution of isobutyronitrile (276 g, 4.0 mol) in EtOH (2.0 L) was combined with hydroxylamine (50% aqueous solution, 1.1 L, 16 mol), and refluxed for 5 h. The solvent was then removed in vacuo, and the residual water was azeotropically removed with toluene. The residue was then taken up in $CH_2Cl_2$, dried over $MgSO_4$, and the solvent was removed to afford a white solid (402 g, 98% yield). $^1H$ NMR ($CDCl_3$) δ 7.94 (br s, 1H), 4.55 (br s, 2H), 2.47 (m, 1H), 1.20 (d, 6H, J=7.1 Hz).

Step 2: Preparation of 1-cyano-4-hydroxypiperidine

A 5-liter, 3-neck flask was equipped with mechanical stirring, a reflux condenser, and a powder addition funnel. Sodium bicarbonate (840 g, 10 mmol) was added via the powder funnel while stirring, then water (ca. 300-400 mL) was gradually added while vigorously stirring to form a thick, uniform slurry. The flask was then placed in an ice bath, and a solution of 4-hydroxypiperidine (506 g, 5.00 mol) in $CH_2Cl_2$ (1.0 L) was added, and the contents were vigorously mixed while cooling. A solution of cyanogen bromide (640 g, 6.0 mol) in $CH_2Cl_2$ (600 mL) was added in a dropwise fashion over 2 h, and stirring was continued for an additional 30 min. The ice bath was removed, and the mechanical stirrer was replaced by a magnetic stirrer, and the reaction mixture was stirred for 16 h. The flask was once again placed under mechanical stirring, and sodium carbonate (100 g) was added in order to ensure complete neutralization. $MgSO_4$ (500 g) was added, and vigorous stirring was continued for 15 min. The resulting suspension was filtered, rinsing with $CH_2Cl_2$ (2.0 L). A light amber, viscous oil was obtained upon solvent removal to give 1-cyano-4-hydroxypiperidine (574 g, 91% yield). $^1H$ NMR ($CDCl_3$) δ 3.80 (m, 1H), 3.39 (m, 2H), 3.05 (m, 2H), 1.87 (m, 2H), 1.70 (br s, 1H), 1.62 (m, 2H); MS m/z 212.1 ($M^+$).

Step 3: Preparation of 1-(3-isopropyl-[1,2,4]oxadiazol-5-yl)-piperidin-4-ol

In a variation of the method described by Yarovenko et al, (Bull. Acad. Sci. USSR, Div. Chem. Sci. 1991, 40, 1924) $ZnCl_2$, (1 N in ether, 120 mL, 120 mmol) was added in a dropwise fashion over 15 min to a magnetically stirred solution of N-hydroxy-isobutyramidine (12.2 g, 120 mmol) and 4-hydroxy-piperidine-1-carbonitrile (12.6 g, 100 mmol) in ethyl acetate (500 mL). Precipitate formed immediately upon addition, and at a point the stirring bar became immobilized in the matrix, requiring the reaction to be manually shaken for the remainder of addition. After standing for 15 min, the supernatant was decanted and filtered, and the residue was rinsed twice with ether, furnishing a hard white precipitate which was collected by filtration. This material was taken up in conc. HCl (50 mL), diluted to 4N with EtOH (100 mL), and refluxed for 1 h. Upon cooling, a white precipitate was removed by filtration, then the filtrate was reduced to 50 mL and diluted with 100 mL water. Solid $Na_2CO_3$ was added until the mixture was basic, $CH_2Cl_2$ was added, and the resulting mixture was filtered, rinsing with $CH_2Cl_2$. The organic extract was separated, dried over $MgSO_4$, and the solvent was removed to afford a viscous, amber oil as 1-(3-isopropyl-[1,2,4]oxadiazol-5-yl)-piperidin-4-ol (15.0 g, 71% yield): $^1H$ NMR ($CDCl_3$) δ 3.95 (m, 3H), 3.37 m, 2H), 2.88 (m, 1H), 2.34 (br s, 1H), 1.93 (m, 2H), 1.63 (m, 2H), 1.28 (d, 6H, J=7.1 Hz); MS m/z 212.3 ($M^+$).

Step 4: Preparation of 1-(2-Fluoro-4-methanesulfonyl-phenyl)-4-[1-(3-isopropyl-[1,2,4]oxadiazol-5-yl)-piperidin-4-yloxy]-1H-pyrazolo[3,4-d]pyrimidine (Compound A198)

1-(3-Isopropyl-[1,2,4]oxadiazol-5-yl)-piperidin-4-ol (338 mg, 1.6 mmol) and sodium hydride (87 mg, 3.66 mmol) were stirred together in dry THF (2 mL) at room temperature for 30 minutes. 4-Chloro-1-(2-fluoro-4-methanesulfonyl-phenyl)-1H-pyrazolo[3,4-d]pyrimidine was then added and the reaction continued to stir at room temperature for 45 minutes. Its progress was monitored by thin layer chromatography and LCMS. The reaction was treated with water and the desired compound was extracted with ethyl acetate. Organic layer was evaporated in vacuo. Purification by HPLC provided the desired Compound A198 as a white solid (600 mg, 98%). Exact mass calculated for $C_{22}H_{24}FN_7O_4S$ 501.53, found 502.2 ($MH^+$).

Example 9.21

Preparation of 2-{4-[1-(2-Fluoro-4-methanesulfonyl-phenyl)-1H-pyrazolo[3,4-d]pyrimidin-4-yloxy]-piperidin-1-yl}-1-(4-trifluoromethoxy-phenyl)-ethanone (Compound A94)

General Alkylation Method

In a 10 mL round-bottomed flask fitted with a $N_2$ inlet was placed a stir bar, 1-(2-fluoro-4-methanesulfonyl-phenyl)-4-(piperidin-4-yloxy)-1H-pyrazolo[3,4-d]pyrimidine (43 mg, 0.1 mmol), $K_2CO_3$. (138 mg, 1 mmol) and DMF (1 mL). 2-Bromo-1-(4-trifluoromethoxy-phenyl)-ethanone (30 mg, 0.1 mmol) was added in one portion. The reaction mixture was stirred at room temperature for 30 minutes. The resulting suspension was filtered and concentrated under vacuum. The crude was purified by preparative HPLC to give Compound A94. $^1H$ NMR ($CDCl_3$, 400MHz) δ 2.43 (m, 2H), 2.59 (m, 2H), 3.14 (s, 3H), 3.68 (m, 2H), 3.78 (m, 2H), 4.78 (s, 2H), 5.81 (m, 1H), 7.35 (d, 2H), 7.96 (m, 3H), 8.01 (m, 2H), 8.42 (s, 1H), 8.65 (s, 1H). Exact mass calculated for $C_{26}H_{23}F_4N_5O_5S$ 593.14, found 594.3 (MH+).

Example 9.22

Preparation of 2-{4-[1-(2-Fluoro-4-methanesulfonyl-phenyl)-1H-pyrazolo[3,4-d]pyrimidin-4-yloxy]-piperidin-1-yl}-1-(3-fluoro-phenyl)-ethanone (Compound A95)

Compound A95 was prepared in a similar manner as described in Example 9.21; purified by preparative HPLC. $^1$H NMR (CDCl$_3$, 400MHz) δ 2.43 (m, 2H), 2.59 (m, 2H), 3.14 (s, 3H), 3.73 (m, 4H), 4.78 (s, 2H), 5.81 (m, 1H), 7.37 (m, 1H), 7.51 (m, 1H), 7.63 (m, 1H), 7.71 (m, 1H), 7.96 (m, 3H), 8.01 (m, 2H), 8.41 (s, 1H), 8.65 (s, 1H). Exact mass calculated for $C_{25}H_{23}F_2N_5O_4S$ 527.14, found 528.3 (MH+).

Example 9.23

Preparation of 2-{4-[1-(2-Fluoro-4-methanesulfonyl-phenyl)-1H-pyrazolo[3,4-d]pyrimidin-4-yloxy]-piperidin-1-yl}-1-pyridin-2-yl-ethanone (Compound A96)

Compound A96 was prepared in a similar manner as described in Example 9.21; purified by preparative HPLC. $^1$H NMR (CDCl$_3$, 400MHz) δ 2.46 (m, 2H), 2.53 (m, 2H), 3.14 (s, 3H), 3.60 (m, 2H), 3.80 (m, 2H), 4.99 (s, 2H), 5.86 (m, 1H), 7.61 (m, 1H), 7.91 (m, 1H), 7.96 (m, 3H), 8.11 (m, 1H), 8.40 (s, 1H), 8.65 (s, 1H), 8.68 (m, 1H). Exact mass calculated for $C_{24}H_{23}FN_6O_4S$ 510.15, found 511.3 (MH+).

Example 9.24

Preparation of 4-[1-(2-Fluoro-4-methanesulfonyl-phenyl)-1H-pyrazolo[3,4-d]pyrimidin-4-yloxy]-piperidine-1-carboxylic acid tert-butyl ester (Compound A74); and 4-[1-(2-Fluoro-4-methanesulfonyl-phenyl)-1H-pyrazolo[3,4-d]pyrimidin-4-yloxy]-piperidine-1-carboxylic acid isopropyl ester (Compound A129)

Step 1: Preparation of 5-Amino-1-(2-fluoro-4-methanesulfonyl-phenyl)-1H-pyrazole-4-carbonitrile (2-Fluoro-4-methanesulfonyl-phenyl)-hydrazine (1 g, 4.89 mmol) and sodium methoxide (30 mg, 0.489 mmol) were dissolved in methanol under N$_2$ at room temperature. The mixture was stirred for 10. min and 2-ethoxymethylene-malononitrile (0.6 g, 4.91 mmol) was added. The reaction mixture was stirred for 30 min and then brought to reflux for 2 hours. The solvent was removed under reduced pressure; the residue was suspended in water and extracted with ethyl acetate. The organic layer was washed with water, brine and was dried over sodium sulfate. The solvent was concentrated, affording 5-amino-1-(2-fluoro-4-methanesulfonyl-phenyl)-1H-pyrazole-4-carbonitrile as a yellow solid (1.2 g, 87.5%). $^1$H NMR (400MHz DMSO-d$_6$) δ (ppm): 7.96 (d, 1H); 7.93 (m, 1H); 7.80 (s, 1H); 7.74 (m, 1H); 6.89 (s, 2H); 3.24(s, 3H). Exact mass calculated for $C_{11}H_9FN_4O_2S$ 280.04, found 281.30 (MH+, 100%).

Step 2: Preparation of 1-(2-Fluoro-4-methanesulfonyl-phenyl)-1H-pyrazolo[3,4-d]pyrimidin-4-ol 5-Amino-1-(2-fluoro-4-methanesulfonyl-phenyl)-1H-pyrazole-4-carbonitrile (1.2 g, 4.28 mmol) was suspended in formic acid (20 mL, 530 mmol) and water (2 mL) and the mixture brought to reflux for 18 h. The reaction mixture was cooled down and 15 mL of water were added, causing the precipitation of 1-(2-fluoro-4-methanesulfonyl-phenyl)-1H-pyrazolo[3,4-d]pyrimidin-4-ol (0.774 g, 58.6%) as a white solid. The solid was retrieved by filtration and thoroughly washed with water, methanol and ether. The powder was kept under high vacuum overnight. $^1$H NMR (400MHz DMSO-d$_6$) δ (ppm): 12.4 (s, 1H); 8.29 (s, 1H); 8.00 (d, 1H); 7.97 (m, 1H); 7.82 (m, 2H); 3.21(s, 3H). Exact mass calculated for $C_{12}H_9FN_4O_3S$ 308.04, found 309.30 (MH+, 100%).

Step 3: Preparation of 4-Chloro-1-(2-fluoro-4-methanesulfonyl-phenyl)-1H-pyrazolo[3,4-d]pyrimidine 1-(2-Fluoro-4-methanesulfonyl-phenyl)-1H-pyrazolo[3,4-d]pyrimidin-4-ol (0.774 g, 2.51 mmol) was suspended in POCl$_3$ (23 mL, 251 mmol) and dimethylaniline (0.69 mL) and the mixture brought to reflux for 18 h. The solvent was concentrated under reduced pressure and the residue loaded to a column of silica gel. The product was eluted using 5% ethyl acetate/dichloromethane. Removal of solvent afforded 4-chloro-1-(2-fluoro-4-methanesulfonyl-phenyl)-1H-pyrazolo[3,4-d]pyrimidine as a white solid (0.781 g, 95%). $^1$H NMR (400MHz DMSO-d$_6$) δ (ppm): 9.14 (s, 1H); 9.07 (s, 1H); 8.34 (d, 1H); 8.24 (m, 1H); 8.20 (m, 1H); 3.55(s, 3H). Exact mass calculated for $C_{12}H_8ClFN_4O_2S$ 326, found 327.2 (MH+, 100%).

Step 4: Preparation of 4-[1-(2-Fluoro-4-methanesulfonyl-phenyl)-1H-pyrazolo[3,4-d]pyrimidin-4-yloxy]-piperidine-1-carboxylic acid tert-butyl ester (Compound A74)

In a 500 mL round-bottomed flask equipped with a N$_2$ inlet septum was placed a stir bar, NaH (60% in mineral oil, 1.8 g, 45.6 mmol) and 4-hydroxy-piperidine-1-carboxylic acid tert-butyl ester (1.53 g, 7.6 mmol). THF (anhydrous, 80 mL) was added to the mixture. The resulting suspension was stirred about 30 min at room temperature. 4-Chloro-1-(2-fluoro-4-methanesulfonyl-phenyl)-1H-pyrazolo[3,4-d]pyrimidine (2.5 g, 7.6 mmol) was then added in one portion. The mixture was stirred overnight under N$_2$ at room temperature and the resulting slurry turned slightly yellowish. The slurry was added CH$_2$Cl$_2$ and filtered. The filtrate was concentrated under vacuum to give the crude product. Column chromatography purification using 50% EtOAc/Hexane gave Compound A74 as an off-white solid. Exact mass calculated for $C_{22}H_{26}FN_5O_5S$: 491.16, found 492.1 (MH+).

Step 5: Preparation of 1-(2-Fluoro-4-methanesulfonyl-phenyl)-4-(piperidin-4-yloxy)-1H-pyrazolo[3,4-d]pyrimidine (Compound A238)

In a 500 mL round-bottomed flask was placed a stir bar, Compound A74 (4.00 g), acetonitrile (80 mL), and dichloromethane (24 mL). 4M HCl in 1,4-dioxane (24 mL) was added under nitrogen and the mixture was stirred at room temperature for 20 minutes. The solution turned cloudy. The precipitate was isolated and dried under vacuum to give 1-(2-fluoro-4-methanesulfonyl-phenyl)-4-(piperidin-4-yloxy)-

1H-pyrazolo[3,4-d]pyrimidine. Exact mass calculated for $C_{17}H_{18}FN_5O_3S$: 391.11, found 392.1 (MH$^+$).

Step 6: Preparation of 4-[1-(2-Fluoro-4-methanesulfonyl-phenyl)-1H-pyrazolo[3,4-d]pyrimidin-4-yloxy]-piperidine-1-carboxylic acid isopropyl ester (Compound A129)

In a 50 mL round-bottom flask was placed 1-(2-fluoro-4-methanesulfonyl-phenyl)-4-(piperidin-4-yloxy)-1H-pyrazolo[3,4-d]pyrimidine (80 mg, 0.2 mmol) and triethylamine (200 µl). DMF (3 mL) was added to completely dissolve the solid material. The reaction flask was immersed in an ice-bath. Isopropyl chloroformate (1.0M in toluene, 0.22 mL) was added to the solution and the mixture was stirred 2 h under $N_2$ at 0° C. After all of the starting amine was completely converted as indicated by LCMS, the reaction was stopped by quenching with water. The reaction mixture was then concentrated under vacuum and purified by preparative HPLC to give 4-[1-(2-fluoro-4-methanesulfonyl-phenyl)-1H-pyrazolo[3,4-d]pyrimidin-4-yloxy]-piperidine-1-carboxylic acid isopropyl ester (Compound A129). $^1$H NMR (CDCl$_3$, 400MHz) δ 1.27 (d, 6H), 1.9 (m, 2H), 2.12 (m, 2H), 3.13 (s, 3H), 3.40 (m, 2H), 3.91 (m, 2H), 4.97 (m, 1H), 5.63 (m, 1H), 7.95 (m, 3H), 8.34 (s, 1H), 8.63 (s, 1H). Exact mass calculated for $C_{21}H_{24}FN_5O_5S$: 477.15, found 478.2 (MH$^+$).

Example 9.25

Preparation of (4-Ethyl-pyridin-2-yl)-{4-[1-(2-fluoro-4-methanesulfonyl-phenyl)-1H-pyrazolo[3,4-d]pyrimidin-4-yloxy]-piperidin-1-yl}-methanone (Compound A135)

General Procedure for the Preparation of Amides.

In a 50 mL reaction vial fitted with a $N_2$ inlet was placed a stir bar, 4-ethyl-pyridine-2-carboxylic acid, O-(7-Azabenzotriazol-1-yl)-N,N,N',N'-tetramethyluronium hexafluorophosphate (180 mg) and DMF (15 mL). The mixture was stirred 20 min at room temperature under $N_2$. 1-(2-Fluoro-4-methanesulfonyl-phenyl)-4-(piperidin-4-yloxy)-1H-pyrazolo[3,4-d]pyrimidine (310 mg) and triethylamine (403 µl) was added. After stirred 3-8 hours at room temperature under $N_2$, the reaction mixture was filtered through a syringe filter. The filtrate was concentrated to give crude Compound A135. The crude product was further purified by preparative HPLC. $^1$H NMR (CDCl$_3$, 400MHz) δ 1.35 (s, 3H), 2.04 (m, 1H), 2.13 (m, 2H), 2.25 (m, 1H), 2.88 (m, 2H), 3.13 (s, 3H), 3.45 (m, 1H), 3.71 (m, 3H), 3.87 (m, 1H), 4.12 (m, 1H), 5.76 (m, 1H), 7.60 (d, 1H), 7.64 (s, 1H), 7.95 (m, 1H), 8.35 (s, 1H), 8.63 (s, 1H), 8.73 (d, 1H). Exact mass calculated for $C_{25}H_{25}FN_6O_4S$ 524.16, found 525.2 (MH$^+$).

Example 9.26

Preparation of (5-Bromo-pyridin-3-yl)-{4-[1-(2-fluoro-4-methanesulfonyl-phenyl)-1H-pyrazolo[3,4-d]pyrimidin-4-yloxy]-piperidin-1-yl}-methanone (Compound A139)

Compound A139 was prepared in a similar manner as described in Example 9.25, and purified by preparative HPLC. Exact mass calculated for $C_{23}H_{20}BrFN_6O_4S$ 574.04, found 575.2 (MH$^+$).

Example 9.27

Preparation of (5-Ethyl-pyridin-2-yl)-{4-[1-(2-fluoro-4-methanesulfonyl-phenyl)-1H-pyrazolo[3,4-d]pyrimidin-4-yloxy]-piperidin-1-yl}-methanone (Compound A183)

Compound A183 was prepared in a similar manner as described in Example 9.25, and purified by preparative HPLC. $^1$H NMR (CDCl$_3$, 400MHz) δ 1.37 (t, 3H), 2.02 (m, 1H), 2.15 (m, 2H), 2.26 (m, 1H), 2.87 (m, 2H), 3.14 (s, 3H), 3.45 (m, 1H), 3.71 (m, 1H), 3.87 (m, 1H), 4.13 (m, 1H), 5.76 (m, 1H), 7.75 (d, 1H), 7.94 (m, 3H), 8.06 (m, 1H), 8.36 (s, 1H), 8.65 (s, 1H), 8.72 (s, 1H). Exact mass calculated for $C_{25}H_{25}FN_6O_4S$ 524.16, found 525.2 (MH$^+$).

Example 9.28

Preparation of (4-Ethoxy-phenyl)-{4-[1-(2-fluoro-4-methanesulfonyl-phenyl)-1H-pyrazolo[3,4-d]pyrimidin-4-yloxy]-piperidin-1-yl}-methanone (Compound A184)

In a 50 mL round-bottomed flask fitted with N2 inlet was placed 1-(2-fluoro-4-methanesulfonyl-phenyl)-4-(piperidin-4-yloxy)-1H-pyrazolo[3,4-d]pyrimidine (50 mg, 0.117 mmol) and triethylamine (65. µl) and THF (0.8 mL). The reaction flask was immersed in an ice-bath. 4-Ethoxy-benzoyl chloride (24 mg, 0.129 mmol) was added to the solution and the mixture was stirred 2 h under $N_2$ at 0° C. After all of the starting amine was completely converted as indicated by LCMS, the reaction was stopped by quenching with water. The reaction mixture was then concentrated under vacuum and purified by column chromatography using EtOAc as eluent to give Compound A184. $^1$H NMR (CDCl$_3$, 400MHz) δ 1.43 (t, 3H), 1.96 (m, 2H), 2.17 (m, 2H), 3.13 (s, 3H), 3.55 (m, 2H), 4.06 (m, 2H), 4.12 (m, 2H), 5.71 (m, 1H), 6.92 (d, 2H), 7.43 (d, 2H), 7.92 (m, 3H), 8.33 (s, 1H), 8.62 (s, 1H). Exact mass calculated for $C_{26}H_{26}FN_5O_5S$ 539.16, found 540.2 (MH$^+$).

Example 9.29

Preparation of (5-Butyl-pyridin-2-yl)-{4-[1-(2-fluoro-4-methanesulfonyl-phenyl)-1H-pyrazolo[3,4-d]pyrimidin-4-yloxy]-piperidin-1-yl}-methanone (Compound A190)

Compound A190 was prepared in a similar manner as described in Example 9.25, and purified by preparative HPLC. $^1$H NMR (CDCl$_3$, 400MHz) δ 0.96 (t, 3H), 1.41 (m, 2H), 1.67 (m, 2H), 2.00 (m, 1H), 2.14 (m, 2H), 2.26 (m, 1H), 2.76 (t, 2H), 3.13 (s, 3H), 3.46 (m, 1H), 3.74 (m, 3H), 3.83 (m, 1H), 4.16 (m, 1H), 5.75 (m, 1H), 7.68 (d, 1H), 7.89 (m, 1H), 7.95 (m, 3H), 8.34 (s, 1H), 8.62 (s, 1H), 8.63 (s, 1H). Exact mass calculated for $C_{27}H_{29}FN_6O_4S$ 552.20, found 553.4 (MH$^+$).

Example 9.30

Preparation of {4-[1-(2-Fluoro-4-methanesulfonyl-phenyl)-1H-pyrazolo[3,4-d]pyrimidin-4-yloxy]-piperidin-1-yl}-(5-isopropoxymethyl-pyridin-2-yl)-methanone (Compound A192)

Step 1: Preparation of 5-Isopropoxymethyl-pyridine-2-carbonitrile

In a microwave reaction tube was placed 2-chloro-5-isopropoxymethyl-pyridine (0.12 g, 0.66 mmol), $Zn(CN)_2$ (0.077 g, 0.66 mmol), tetrakis(triphenylphosphino)dipalladium (76 mg, 0.066 mmol), DMF (2 mL). The reaction mixture was heated at 180° C. for 5 minutes. The resulted mixture was worked up by $CH_2Cl_2/H_2O$. The $CH_2Cl_2$ layer was dried and concentrated to give the crude product. The crude was purified by column chromatography by using 30% EtOAc/Hexane. $^1$H NMR (CDCl$_3$, 400MHz) δ 1.26 (d, 6H), 3.73 (m, 1H), 4.59 (s, 2H), 7.68 (d, 1H), 7.85 (m, 1H), 8.67 (s, 1H). Exact mass calculated for $C_{10}H_{12}N_2O$ 176.09, found 177.2 (MH$^+$).

Step 2: Preparation of 5-Isopropoxymethyl-pyridine-2-carboxylic acid

In a 25 mL round-bottom flask was place ethanol (4 mL) solution of 5-isopropoxymethyl-pyridine-2-carbonitrile (1 g, 5.7 mmol). A solution of KOH (1.6 g, 28.36 mmol) in ethanol (6 mL) was added. The mixture was refluxed overnight and cooled down to room temperature. The resulted gel like mixture was added $H_2O$ and acidified with 6 mL of 10% HCl. The aqueous solution was extracted with EtOAc. The organic extracts were dried and concentrated to give the crude 5-isopropoxymethyl-pyridine-2-carboxylic acid. The crude product was further purified by column chromatography using 20% MeOH/$CH_2Cl_2$. $^1$H NMR (CDCl$_3$, 400MHz) δ 1.26 (d, 6H), 3.74 (m, 1H), 4.63 (s, 2H), 7.94 (d, 1H), 8.21 (m, 1H), 8.60 (s, 1H). Exact mass calculated for $C_{10}H_{13}NO_3$ 195.09, found 196.2 (MH$^+$).

Step 3: Preparation of {4-[1-(2-Fluoro-4-methane-sulfonyl-phenyl)-1H-pyrazolo[3,4-d]pyrimidin-4-yloxy]-piperidin-1-yl}-(5-isopropoxymethyl-pyridin-2-yl)-methanone (Compound A192)

Compound A192 was prepared in a similar manner as described in Example 9.25, and purified by preparative HPLC. $^1$H NMR (CDCl$_3$, 400MHz) δ 1.25 (d, 6H), 1.96 (m, 1H), 2.07 (m, 1H), 2.15 (m, 1H), 2.25 (m, 1H), 3.13 (s, 3H), 3.55 (m, 1H), 3.73 (m, 3H), 3.90 (m, 1H), 4.22 (m, 1H), 4.58 (s, 2H), 5.73 (m, 1H), 7.68 (d, 1H), 7.86 (m, 1H), 7.95 (m, 3H), 8.33 (s, 1H), 8.60 (d, 1H), 8.63 (s, 1H). Exact mass calculated for $C_{28}H_{30}FN_5O_5S$ 567.20, found 568.4 (MH$^+$).

Example 9.31

Preparation of {4-[1-(2-Fluoro-4-methanesulfonyl-phenyl)-1H-pyrazolo[3,4-d]pyrimidin-4-yloxy]-piperidin-1-yl}-(5-isopropoxy-pyridin-2-yl)-methanone (Compound A194)

Step 1: Preparation of 5-Isopropoxy-pyridine-2-carboxylic acid

5-Isopropoxy-pyridine-2-carboxylic acid was prepared in a similar manner as described in Example 9.30 and purified by column chromatography. $^1$H NMR (CDCl$_3$, 400MHz) δ 1.41 (d, 6H), 4.70 (m, 1H), 7.33 (m, 1H), 8.16 (d, 1H), 8.24 (d, 1H). Exact mass calculated for $C_9H_{11}NO_3$ 181.07, found 182.2 (MH$^+$).

Step 2: Preparation of {4-[1-(2-Fluoro-4-methane-sulfonyl-phenyl)-1H-pyrazolo[3,4-d]pyrimidin-4-yloxy]-piperidin-1-yl}-(5-isopropoxy-pyridin-2-yl)-methanone (Compound A194)

Compound A194 was prepared in a similar manner as described in Example 9.25, and purified by preparative HPLC. $^1$H NMR (CDCl$_3$, 400MHz) δ 1.42 (d, 6H), 2.06 (m, 1H), 2.09 (m, 1H), 2.18 (m, 1H), 2.25 (m, 1H), 3.13 (s, 3H), 3.56 (m, 1H), 3.83 (m, 2H), 4.16 (m, 1H), 4.70 (m, 2H), 5.75 (m, 1H), 7.45 (d, 1H), 7.71 (d, 1H), 7.95 (m, 3H), 8.34 (s, 1H), 8.38 (d, 1H), 8.64 (s, 1H). Exact mass calculated for $C_{26}H_{27}FN_6O_5S$ 554.17, found 555.4 (MH$^+$).

Example 9.32

Preparation of 4-[1-(2-Fluoro-4-methanesulfonyl-phenyl)-1H-pyrazolo[3,4-d]pyrimidin-4-yloxy]-5'-isopropoxy-3,4,5,6-tetrahydro-2H-[1,2']bipyridinyl (Compound A201)

In a 50 mL round-bottomed flask equipped with a $N_2$ inlet septum was placed a stir bar, NaH (60% in mineral oil, 364 mg, 0.91 mmol) and 5'-isopropoxy-3,4,5,6-tetrahydro-2H-[1,2']bipyridinyl-4-ol (215 mg, 0.91 mmol). THF (anhydrous, 3 mL) was added to the mixture. The resulting suspension was stirred about 30 min at room temperature. 4-Chloro-1-(2-fluoro-4-methanesulfonyl-phenyl)-1H-pyrazolo[3,4-d]pyrimidine (297 mg, 0.91 mmol) was then added in one portion. The mixture was stirred overnight under $N_2$ at room temperature and the resulting slurry turned slightly yellowish. The slurry was added $CH_2Cl_2$ and filtered. The filtrate was concentrated under vacuum to give the crude product. Purification by preparative HPLC gave the desired product as an off-white solid. $^1$H NMR (CDCl$_3$, 400 MHz) δ 1.36 (d, 6H), 2.17 (m, 2H), 2.30 (m, 2H), 3.13 (s, 3H), 3.74 (m, 2H), 3.97 (m, 2H), 4.50 (m, 1H), 5.76 (m, 1H), 7.04 (d, 1H), 7.60 (m, 1H), 7.87 (m, 1H), 7.94 (m, 3H), 8.34 (s, 1H), 8.64 (s, 1H). Exact mass calculated for $C_{26}H_{28}FN_5O_4S$ 525.18, found 526.2 (MH$^+$)

Example 9.33

Preparation of 1-(2-Fluoro-4-methanesulfonyl-phenyl)-4-[1-(4-trifluoromethoxy-phenyl)-piperidin-4-yloxy]-1H-pyrazolo[3,4-d]pyrimidine (Compound A203)

Compound A203 was prepared in a similar manner as described in Example 9.32 and purified by preparative HPLC. $^1$H NMR (CDCl$_3$, 400MHz) δ 2.46 (m, 2H), 2.50 (m, 2H), 3.14 (s, 3H), 3.60 (m, 2H), 3.78 (m, 2H), 5.79 (m, 1H), 7.36 (d, 2H), 7.57 (d, 2H), 7.95 (m, 3H), 8.40 (s, 1H), 8.66 (s, 1H), 11.15 (m, 2H). Exact mass calculated for $C_{24}H_{21}F_4N_5O_4S$ 551.13, found 552.2 (MH$^+$).

Example 9.34

Preparation of 1-(2-Fluoro-4-methanesulfonyl-phenyl)-4-[1-(3-trifluoromethoxy-phenyl)-piperidin-4-yloxy]-1H-pyrazolo[3,4-d]pyrimidine (Compound A207)

Compound A207 was prepared in a similar manner as described in Example 9.32 and purified by preparative HPLC. $^1$H NMR (CDCl$_3$, 400MHz) δ 2.29 (m, 2H), 2.49 (m, 2H), 3.14 (s, 3H), 3.48 (m, 2H), 3.73 (m, 2H), 5.74 (m, 1H), 7.06 (d, 1H), 7.14 (s, 1H), 7.27 (m, 1H), 7.45 (t, 1H), 7.95 (m, 3H), 8.38 (s, 1H), 8.66 (s, 1H), 8.82 (m, 2H). Exact mass calculated for C$_{24}$H$_{21}$F$_4$N$_5$O$_4$S 551.13, found 552.2 (MH$^+$).

Example 9.35

Preparation of 5'-Fluoro-4-[1-(4-methanesulfonyl-phenyl)-1H-pyrazolo[3,4-d]pyrimidin-4-yloxy]-3,4,5,6-tetrahydro-2H-[1,2']bipyridinyl (Compound A130)

General Procedure for Palladium Catalyzed Amination of Aryl Bromides with the Nitrogen of Piperidine To a 5 mL conical microwave vial was added sequentially Pd$_2$(dba)$_3$ (2.5 mol %), 1,3-bis(2,6-di-i-propylphenyl)-4,5-dihydroimidazolium tetrafluoroborate (5 mol %), dioxane (anhydrous, 1 mL added per 0.3 mmol of piperdine substrate), piperidine substrate (1.0 equiv.), aryl bromide (0.9-1.3 equiv.), and KOt-Bu (1.0M soln in THF, 3.5 equiv.). The vial was sealed under N$_2$ and heated by microwave irradiation at 120° C. to 130° C. for 10-40 min (as monitored by LC/MS). The reaction mixture was cooled to rt and diluted with EtOAc (25 mL) and H$_2$O (25 mL). The layers were mixed and separated and the aqueous phase was back-extracted with EtOAc (25 mL). The combined organics were dried over MgSO$_4$, filtered and concentrated. The products were purified by reverse-phase HPLC: Phenomenex® Luna C18 column (10μ, 250×21.2 mm), 5% (v/v) CH$_3$CN (containing 1% v/v TFA) in H$_2$O (containing 1% v/v TFA) gradient to 95% H$_2$O, 20 mL/min, λ=280 nm.

HPLC/MS for 5'-Fluoro-4-[1-(4-methanesulfonyl-phenyl)-1H-pyrazolo[3,4-d]pyrimidin-4-yloxy]-3,4,5,6-tetrahydro-2H-[1,2']bipyridinyl (Compound A130): Waters® YMC™ ODS-A C18 column (5μ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=1.79 min, ESI$^+$=387.3 (M+H).

Example 9.36

Preparation of 4-[1-(4-Methanesulfonyl-phenyl)-1H-pyrazolo[3,4-d]pyrimidin-4-yloxy]-5'-methyl-3,4,5,6-tetrahydro-2H-[1,2']bipyridinyl (Compound A131)

Compound A131 was prepared in a similar manner as described in Example 9.35 and purified by preparative HPLC. HPLC/MS: Alltech® Prevail C18 column (5μ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=1.82 min, ESI$^+$=465.2 (M+H).

Example 9.37

Preparation of 4-[1-(4-Methanesulfonyl-phenyl)-1H-pyrazolo[3,4-d]pyrimidin-4-yloxy]-6'-trifluoromethyl-3,4,5,6-tetrahydro-2H-[1,2']bipyridinyl (Compound A132)

Compound A132 was prepared in a similar manner as described in Example 9.35 and purified by preparative HPLC. HPLC/MS: Alltech® Prevail C18 column (5μ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=3.00 min, ESI$^+$=519.3 (M+H).

Example 9.38

Preparation of (5'-Fluoro-3,4,5,6-tetrahydro-2H-[1,2']bipyridinyl-4-yl)-[1-(4-methanesulfonyl-phenyl)-1H-pyrazolo[3,4-d]pyrimidin-4-yl]-amine (Compound A138)

Compound A138 was prepared in a similar manner as described in Example 9.35 and purified by preparative HPLC. HPLC/MS: Discovery® C18 column (5μ, 50×2.1 mm), 5% v/v CH$_3$CN (containing 1% v/v TFA) in H$_2$O (containing 1% v/v TFA) gradient to 99% v/v CH$_3$CN in H$_2$O, 0.75 mL/min, t$_r$=1.62 min, ESI$^+$=468.3 (M+H).

Example 9.39

Preparation of (6-Chloro-pyridin-3-yl)-{4-[1-(4-methanesulfonyl-phenyl)-1H-pyrazolo[3,4-d]pyrimidin-4-yloxy]-piperidin-1-yl}-methanone (Compound A143)

General Procedure for Coupling 1-(4-methanesulfonyl-phenyl)-4-(piperidin-4-yloxy)-1H-pyrazolo[3,4-d]pyrimidine hydrochloride with carboxylic acids To a solution of 1-(4-methanesulfonyl-phenyl)-4-(piperidin-4-yloxy)-1H-pyrazolo[3,4-d]pyrimidine hydrochloride (35 mg, 0.086 mmol) in DMF (1.5 mL) and Et$_3$N (45 μL, 0.33 mmol) was added the desired carboxylic acid, for Compound A143 the desired acid was 6-chloro-nicotinic acid (0.11 mmol, 1.3 equiv), followed by HATU (49 mg, 0.129 mmol). The reactions were stirred at rt overnight diluted with CH$_3$CN and filtered. The compounds were purified directly by reverse-phase HPLC: Phenomenex® Luna C18 column (10μ, 250×21.2 mm), 5% (v/v) CH$_3$CN (containing 1% v/v TFA) in H$_2$O (containing 1% v/v TFA) gradient to 95% H$_2$O, 20 mL/min, λ=280 nm.

HPLC/MS for (6-chloro-pyridin-3-yl)-{4-[1-(4-methanesulfonyl-phenyl)-1H-pyrazolo[3,4-d]pyrimidin-4-yloxy]-piperidin-1-yl}-methanone (Compound A143); Waters® YMC™ ODS-A C18 column (5μ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=2.56 min, ESI$^+$=513.0 (M+H).

Example 9.40

Preparation of (5-Chloro-pyridin-3-yl)-{4-[1-(4-methanesulfonyl-phenyl)-1H-pyrazolo[3,4-d]pyrimidin-4-yloxy]-piperidin-1-yl}-methanone (Compound A144)

Compound A144 was prepared in a similar manner as described in Example 9.39 and purified by preparative HPLC. HPLC/MS: Waters® YMC™ ODS-A C18 column (5µ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=2.61 min, ESI$^+$=513.0 (M+H).

Example 9.41

Preparation of {4-[1-(4-Methanesulfonyl-phenyl)-1H-pyrazolo[3,4-d]pyrimidin-4-yloxy]-piperidin-1-yl}-(1-methyl-3-trifluoromethyl-1H-pyrazol-4-yl)-methanone (Compound A145)

Compound A145 was prepared in a similar manner as described in Example 9.39 and purified by preparative HPLC. HPLC/MS: Waters® YMC™ ODS-A C18 column (5µ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=2.58 min, ESI$^+$=550.1 (M+H).

Example 9.42

Preparation of (2-Chloro-pyridin-4-yl)-{4-[1-(4-methanesulfonyl-phenyl)-1H-pyrazolo[3,4-d]pyrimidin-4-yloxy]-piperidin-1-yl}-methanone (Compound A146)

Compound A146 was prepared in a similar manner as described in Example 9.39 and purified by preparative HPLC. HPLC/MS: Waters® YMC™ ODS-A C18 column (5µ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=2.58 min, ESI$^+$=513.1 (M+H).

Example 9.43

Preparation of (4-Hydroxy-3-methoxy-phenyl)-{4-[1-(4-methanesulfonyl-phenyl)-1H-pyrazolo[3,4-d]pyrimidin-4-yloxy]-piperidin-1-yl}-methanone (Compound A147)

Compound A147 was prepared in a similar manner as described in Example 9.39 and purified by preparative HPLC. HPLC/MS: Waters® YMC™ ODS-A C18 column (5µ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=2.35 min, ESI$^+$=524.3 (M+H).

Example 9.44

Preparation of (4-Chloro-3-nitro-phenyl)-{4-[1-(4-methanesulfonyl-phenyl)-1H-pyrazolo[3,4-d]pyrimidin-4-yloxy]-piperidin-1-yl}-methanone (Compound A148)

Compound A148 was prepared in a similar manner as described in Example 9.39 and purified by preparative HPLC. HPLC/MS: Waters® YMC™ ODS-A C18 column (5µ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=2.83 min, ESI$^+$=557.3 (M+H).

Example 9.45

Preparation of 1-{4-[1-(4-Methanesulfonyl-phenyl)-1H-pyrazolo[3,4-d]pyrimidin-4-yloxy]-piperidin-1-yl}-3-methyl-butan-1-one (Compound A149)

Compound A149 was prepared in a similar manner as described in Example 9.39 and purified by preparative HPLC. HPLC/MS: Waters® YMC™ ODS-A C18 column (5µ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=2.75 min, ESI$^+$=458.0 (M+H).

Example 9.46

Preparation of {4-[1-(4-Methanesulfonyl-phenyl)-1H-pyrazolo[3,4-d]pyrimidin-4-yloxy]-piperidin-1-yl}-(6-pyrazol-1-yl-pyridin-3-yl)-methanone (Compound A150)

Compound A150 was prepared in a similar manner as described in Example 9.39 and purified by preparative HPLC. HPLC/MS: Waters® YMC™ ODS-A C18 column (5µ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=2.70 min, ESI$^+$=545.4 (M+H).

Example 9.47

Preparation of (2-Hydroxy-pyridin-3-yl)-{4-[1-(4-methanesulfonyl-phenyl)-1H-pyrazolo[3,4-d]pyrimidin-4-yloxy]-piperidin-1-yl}-methanone (Compound A151)

Compound A151 was prepared in a similar manner as described in Example 9.39 and purified by preparative HPLC. HPLC/MS: Waters® YMC™ ODS-A C18 column (5µ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=1.95 min, ESI$^+$=495.3 (M+H).

Example 9.48

Preparation of (5,6-Dichloro-pyridin-3-yl)-{4-[1-(4-methanesulfonyl-phenyl)-1H-pyrazolo[3,4-d]pyrimidin-4-yloxy]-piperidin-1-yl}-methanone (Compound A152)

Compound A152 was prepared in a similar manner as described in Example 9.39 and purified by preparative HPLC. HPLC/MS: Waters® YMC™ ODS-A C18 column (5µ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=2.81 min, ESI$^+$=546.9 (M+H).

Example 9.49

Preparation of (5-Bromo-pyridin-3-yl)-{4-[1-(4-methanesulfonyl-phenyl)-1H-pyrazolo[3,4-d]pyrimidin-4-yloxy]-piperidin-1-yl}-methanone (Compound A153)

Compound A153 was prepared in a similar manner as described in Example 9.39 and purified by preparative HPLC.

HPLC/MS: Waters® YMC™ ODS-A C18 column (5μ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=2.66 min, ESI$^+$=559.2 (M+H).

Example 9.50

Preparation of 5-{4-[1-(4-Methanesulfonyl-phenyl)-1H-pyrazolo[3,4-d]pyrimidin-4-yloxy]-piperidine-1-carbonyl}-nicotinic acid (Compound A154)

Compound A154 was prepared in a similar manner as described in Example 9.39 and purified by preparative HPLC. HPLC/MS: Waters® YMC™ ODS-A C18 column (5μ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=2.04 min, ESI$^+$=523.3 (M+H).

Example 9.51

Preparation of (1H-Imidazol-4-yl)-{4-[1-(4-methanesulfonyl-phenyl)-1H-pyrazolo[3,4-d]pyrimidin-4-yloxy]-piperidin-1-yl}-methanone (Compound A155)

Compound A155 was prepared in a similar manner as described in Example 9.39 and purified by preparative HPLC. HPLC/MS: Waters® YMC™ ODS-A C18 column (5μ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=1.73 min, ESI$^+$=468.3 (M+H).

Example 9.52

Preparation of {4-[1-(4-Methanesulfonyl-phenyl)-1H-pyrazolo[3,4-d]pyrimidin-4-yloxy]-piperidin-1-yl}-(6-pyrrolidin-1-yl-pyridin-3-yl)-methanone (Compound A157)

Compound A157 was prepared in a similar manner as described in Example 9.39 and purified by preparative HPLC. HPLC/MS: Waters® YMC™ ODS-A C18 column (5μ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=2.08 min, ESI$^+$=548.3 (M+H).

Example 9.53

Preparation of (6-Isobutylamino-pyridin-3-yl)-{4-[1-(4-methanesulfonyl-phenyl)-1H-pyrazolo[3,4-d]pyrimidin-4-yloxy]-piperidin-1-yl}-methanone (Compound A158)

Compound A158 was prepared in a similar manner as described in Example 9.39 and purified by preparative HPLC. HPLC/MS: Waters® YMC™ ODS-A C18 column (5μ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=2.58 min, ESI$^+$=550.1 (M+H).

Example 9.54

Preparation of (6-Ethylamino-pyridin-3-yl)-{4-[1-(4-methanesulfonyl-phenyl)-1H-pyrazolo[3,4-d]pyrimidin-4-yloxy]-piperidin-1-yl}-methanone (Compound A159)

Compound A159 was prepared in a similar manner as described in Example 9.39 and purified by preparative HPLC. HPLC/MS: Waters® YMC™ ODS-A C18 column (5μ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=1.96 min, ESI$^+$=522.3 (M+H).

Example 9.55

Preparation of (6-Cyclobutylamino-pyridin-3-yl)-{4-[1-(4-methanesulfonyl-phenyl)-1H-pyrazolo[3,4-d]pyrimidin-4-yloxy]-piperidin-1-yl}-methanone (Compound A160)

Compound A160 was prepared in a similar manner as described in Example 9.39 and purified by preparative HPLC. HPLC/MS: Waters® YMC™ ODS-A C18 column (5μ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=2.15 min, ESI$^+$=548.4 (M+H).

Example 9.56

Preparation of (6-Isopropylamino-pyridin-3-yl)-{4-[1-(4-methanesulfonyl-phenyl)-1H-pyrazolo[3,4-d]pyrimidin-4-yloxy]-piperidin-1-yl}-methanone (Compound A161)

Compound A161 was prepared in a similar manner as described in Example 9.39 and purified by preparative HPLC. HPLC/MS: Waters® YMC™ ODS-A C18 column (5μ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=2.05 min, ESI$^+$=536.2 (M+H).

Example 9.57

Preparation of [6-(1-Ethyl-propylamino)-pyridin-3-yl]-{4-[1-(4-methanesulfonyl-phenyl)-1H-pyrazolo[3,4-d]pyrimidin-4-yloxy]-piperidin-1-yl}-methanone (Compound A162)

Compound A162 was prepared in a similar manner as described in Example 9.39 and purified by preparative HPLC. HPLC/MS: Waters® YMC™ ODS-A C18 column (5μ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=2.13 min, ESI$^+$=550.2 (M+H).

Example 9.58

Preparation of {4-[1-(4-Methanesulfonyl-phenyl)-1H-pyrazolo[3,4-d]pyrimidin-4-yloxy]-piperidin-1-yl}-[6-(1-propyl-butylamino)-pyridin-3-yl]-methanone (Compound A163)

Compound A163 was prepared in a similar manner as described in Example 9.39 and purified by preparative HPLC. HPLC/MS: Waters® YMC™ ODS-A C18 column (5μ, 50×4.6 mm), 5% v/v CH$_3$CN (containing 1% v/v TFA) in $H_2O$ (containing 1% v/v TFA) gradient to 99% v/v $CH_3CN$ in $H_2O$, 3.5 mL/min, $t_r$=2.40 min, $ESI^+$=578.5 (M+H).

Example 9.59

Preparation of 5-Benzyloxy-2-{4-[1-(4-methanesulfonyl-phenyl)-1H-pyrazolo[3,4-d]pyrimidin-4-yloxy]-piperidine-1-carbonyl}-pyran-4-one (Compound A164)

Compound A164 was prepared in a similar manner as described in Example 9.39 and purified by preparative HPLC. HPLC/MS: Waters® YMC™ ODS-A C18 column (5µ, 50×4.6 mm), 5% v/v $CH_3CN$ (containing 1% v/v TFA) in $H_2O$ (containing 1% v/v TFA) gradient to 99% v/v $CH_3CN$ in $H_2O$, 3.5 mL/min, $t_r$=2.64 min, $ESI^+$=602.3 (M+H).

Example 9.60

Preparation of Benzo[c]isoxazol-3-yl-{4-[1-(4-methanesulfonyl-phenyl)-1H-pyrazolo[3,4-d]pyrimidin-4-yloxy]-piperidin-1-yl}-methanone (Compound A165)

Compound A165 was prepared in a similar manner as described in Example 9.39 and purified by preparative HPLC. HPLC/MS: Waters® YMC™ ODS-A C18 column (5µ, 50×4.6 mm), 5% v/v $CH_3CN$ (containing 1% v/v TFA) in $H_2O$ (containing 1% v/v TFA) gradient to 99% v/v $CH_3CN$ in $H_2O$, 3.5 mL/min, $t_r$=2.85 min, $ESI^+$=519.4 (M+H).

Example 9.61

Preparation of (4-Chloro-pyridin-2-yl)-{4-[1-(4-methanesulfonyl-phenyl)-1H-pyrazolo[3,4-d]pyrimidin-4-yloxy]-piperidin-1-yl}-methanone (Compound A166)

Compound A166 was prepared in a similar manner as described in Example 9.39 and purified by preparative HPLC. HPLC/MS: Alltech® Prevail C18 column (5µ, 50×4.6 mm), 5% v/v $CH_3CN$ (containing 1% v/v TFA) in $H_2O$ (containing 1% v/v TFA) gradient to 99% v/v $CH_3CN$ in $H_2O$, 3.5 mL/min, $t_r$=2.62 min, $ESI^+$=513.2 (M+H).

Example 9.62

Preparation of 1-{4-[1-(4-Methanesulfonyl-phenyl)-1H-pyrazolo[3,4-d]pyrimidin-4-yloxy]-piperidin-1-yl}-butan-2-one (Compound A168)

To a solution of 1-(4-methanesulfonyl-phenyl)-4-(piperidin-4-yloxy)-1H-pyrazolo[3,4-d]pyrimidine hydrochloride (30.0 mg, 0.073 m mmol) and $Et_3N$ (35 µL) in dioxane (1.5 mL) was added bromomethyl ethyl ketone (22 µL, 0.219 mmol). The mixture was heated by microwave irradiation at 100° C. for 10 min. The mixture was diluted with $CH_3CN$ (3 mL) and purified by reverse-phase HPLC: Phenomenex® Luna C18 column (10µ, 250×21.2 mm), 5% (v/v) $CH_3CN$ (containing 1% v/v TFA) in $H_2O$ (containing 1% v/v TFA) gradient to 95% $H_2O$, 20 mL/min, λ=214 nm to give Compound A168 (7.8 mg, 0.014 mmol, 19% yield) isolated as a white solid. HPLC/MS: Alltech® Prevail C18 column (5µ, 50×4.6 mm), 5% v/v $CH_3CN$ (containing 1% v/v TFA) in $H_2O$ (containing 1% v/v TFA) gradient to 99% v/v $CH_3CN$ in $H_2O$, 3.5 mL/min, $t_r$=1.69 min, $ESI^+$=444.3 (M+H).

Example 9.63

Preparation of 2-{4-[1-(4-Methanesulfonyl-phenyl)-1H-pyrazolo[3,4-d]pyrimidin-4-yloxy]-piperidine-1-carbonyl}-pyran-4-one (Compound A182)

Compound A182 was prepared in a similar manner as described in Example 9.39 and purified by preparative HPLC. HPLC/MS: Alltech® Prevail C18 column (5µ, 50×4.6 mm), 5% v/v $CH_3CN$ (containing 1% v/v TFA) in $H_2O$ (containing 1% v/v TFA) gradient to 99% v/v $CH_3CN$ in $H_2O$, 3.5 mL/min, $t_r$=2.14 min, $ESI^+$=496.2 (M+H).

Example 9.64

Preparation of 5'-Bromo-4-[1-(4-methanesulfonyl-phenyl)-1H-pyrazolo[3,4-d]pyrimidin-4-yloxy]-3,4,5,6-tetrahydro-2H-[1,2']bipyridinyl (Compound A206); and 4-[1-(4-Methanesulfonyl-phenyl)-1H-pyrazolo[3,4-d]pyrimidin-4-yloxy]-5'-trifluoromethyl-3,4,5,6-tetrahydro-2H-[1,2']bipyridinyl (Compound A208)

Step 1: Preparation of General Procedure for Aromatic Substitution of 2-chloropyridines with 4-hydroxypiperidine A solution of piperidin-4-ol (100 mg, 0.99 mmol), desired 2-chlorpyridine (0.99 mmol, 1.0 equiv.), and DIPEA (345 µL, 1.98 mmol) in isopropanol (1.5 mL) was heated by microwave irradiation at 160° C. for 2.5 h. The reaction was purified directly by silica gel chromatography to give the desired 3,4,5,6-tetrahydro-2H-[1,2']bipyridinyl-4-ol (using 5-bromo-2-chloropyridine, 5'-bromo-3,4,5,6-tetrahydro-2H-[1,2']bipyridinyl-4-ol was isolated in 27% yield, 69.1 mg, 0.27 mmol; using 5-trifluoromethyl-2-chloropyridine, 5'-trifluoromethyl-3,4,5,6-tetrahydro-2H-[1,2']bipyridinyl-4-ol was isolated in 62% yield, 150.1 mg, 0.61 mmol).

HPLC/MS for 5'-bromo-3,4,5,6-tetrahydro-2H-[1,2']bipyridinyl-4-ol: Alltech® Prevail C18 column (5µ, 50×4.6 mm), 5% v/v $CH_3CN$ (containing 1% v/v TFA) in $H_2O$ (containing 1% v/v TFA) gradient to 99% v/v $CH_3CN$ in $H_2O$, 3.5 mL/min, $t_r$=1.17 min, $ESI^+$=258.9 (M+H).

HPLC/MS for 5'-trifluoromethyl-3,4,5,6-tetrahydro-2H-[1,2']bipyridinyl-4-ol: Alltech® Prevail C18 column (5µ, 50×4.6 mm), 5% v/v $CH_3CN$ (containing 1% v/v TFA) in $H_2O$ (containing 1% v/v TFA) gradient to 99% v/v $CH_3CN$ in $H_2O$, 3.5 mL/min, $t_r$=1.47 min, $ESI^+$=247.1 (M+H).

Step 2: Preparation of General Addition Procedure of a hydroxyl piperidine to 4-Chloro-1-(4-methanesulfonyl-phenyl)-1H-pyrazolo[3,4-d]pyrimidine To a solution of desired 5'-bromo-3,4,5,6-tetrahydro-2H-[1,2']bipyridinyl-4-ol (69 mg, 0.27 mmol, 1.0 equiv.) in THF (1.5 mL) under $N_2$ at rt was added NaH (60% wt/wt dispersion in mineral oil, 25 mg, 0.62 mmol, 2.3 equiv.). After stirring for 5 min 4-chloro-1-(4-methanesulfonyl-phenyl)-1H-pyrazolo[3,4-d]pyrimidine (64.1 mg, 0.21 mmol) was added and the reaction was stirred at rt for 2 h. The mixture was diluted with $H_2O$ (0.5 mL) and $CH_3CN$ (3.0 mL) and purified directly by by reverse-phase HPLC: Phenomenex® Luna C18 column (10µ, 250×21.2 mm), 5% (v/v) $CH_3CN$ (containing 1% v/v TFA) in $H_2O$ (containing 1% v/v TFA) gradient to 95% $H_2O$, 20 mL/min, λ=214 nm to give Compound A206 (2.5 mg, 0.0056 mmol, 3% yield) as a white solid.

Compound A206: Preparation of HPLC/MS: Alltech® Prevail C18 column (5µ, 50×4.6 mm), 5% v/v CH$_3$CN (containing 1% v/v TFA) in H$_2$O (containing 1% v/v TFA) gradient to 99% v/v CH$_3$CN in H$_2$O, 3.5 mL/min, t$_r$=2.78 min, ESI$^+$=531.2 (M+H).

Compound A208: Preparation of HPLC/MS: Discovery® C18 column (5µ, 50×2.1 mm), 5% v/v CH$_3$CN (containing 1% v/v TFA) in H$_2$O (containing 1% v/v TFA) gradient to 99% v/v CH$_3$CN in H$_2$O, 0.75 mL/min, t$_r$=2.86 min, ESI$^+$=519.3 (M+H).

Example 9.65

Preparation of 1-[2-Fluoro-4-(methanesulfonyl)phenyl]-4-[[1-(3-isopropyl-1,2,4-oxadiazol-5-yl)-3-pyrrolidinyl]oxy]-1H-pyrazolo-[3,4-d]pyrimidine hydrochloride (Compound A136)

Step 1: Preparation of (RS)-3-Hydroxy-1-[(3-isopropyl-1,2,4-oxadiazol-5-yl)methyl]pyrrolidine A mixture of 5-chloromethyl-3-isopropyl-[1,2,4]oxadiazole (1.6 g, 10 mmol) and (RS)-3-hydroxypyrrolidine (960 mg, 11 mmol) were combined neat, diluted with MeCN (10 mL), and K$_2$CO$_3$ (2.75 g, 20 mmol) was added. The mixture was heated at 65° C. for 1 h, and was filtered upon cooling. The solvent was removed and the residue was taken up in CH$_2$Cl$_2$ and rinsed with water. The organic extract was dried over MgSO$_4$, the solvent was removed, and the residue was taken up in ether and filtered in order to remove a small amount of quaternary ammonium byproduct. Solvent removal from the filtrate gave (RS)-3-hydroxy-1-[(3-isopropyl-1,2,4-oxadiazol-5-yl)methyl]pyrrolidine as an amber oil (1.72 g, 82% yield): $^1$H NMR (DMSO-d$_6$) δ 4.76 (d, 1H, J=4.5 Hz), 4.19 (m, 1H), 3.90 (s, 2H), 3.05 (m, 1H), 2.79 (m, 1H), 2.69 (m, 1H), 2.53 (m, 1H), 2.43 (m, 1H), 1.98 (m, 1H), 1.54 (m, 1H), 1.25 (d, 6H, J=6.8 Hz); MS m/z 212.1 (M$^+$).

Step 2: Preparation of 1-[2-Fluoro-4-(methanesulfonyl)phenyl]-4-[[1-(3-isopropyl-1,2,4-oxadiazol-5-yl)-3-pyrrolidinyl]oxy]-1H-pyrazolo-[3,4-d]pyrimidine hydrochloride (Compound A136)

A solution of 1-(3-isopropyl-[1,2,4]oxadiazol-5-ylmethyl)-pyrrolidin-3-ol (422 mg, 2.0 mmol) in anhydrous THF (5 mL) was added to a stirred suspension of NaH (60% mineral oil dispersion, 480 mg, 12 mmol) in anhydrous THF under N$_2$. After stirring for 10 min, 4-chloro-1-(2-fluoro-4-methanesulfonyl-phenyl)-1H-pyrazolo[3,4-d]pyrimidine (654 mg, 2.0 mmol) was added, and the reaction mixture was stirred for 18 h. The reaction was then quenched with water and extracted with ether. The organic extract was rinsed with brine, dried over MgSO$_4$, and the solvent was removed. The residue was triturated in hot ether (3×10 mL), and the ether rinses decanted, combined, and reduced in volume. Crystallization from ether/CH$_2$Cl$_2$ 4:1 gave 425 mg of a white solid. The filtrate was combined with the residue from the ether rinses and subjected to flash chromatography (0.5% 7N NH$_3$/MeOH in CH$_2$Cl$_2$) to furnish an additional 100 mg of product, for a total yield of 525 mg (53% yield). The product was taken up in CH$_2$Cl$_2$ and treated with 1N HCl/ether (3.0 mL), then the solvent was removed to furnish Compound A136 as a white powder (570 mg): $^1$H NMR (CDCl$_3$) δ 8.62 (s, 1H), 8.34 (s, 1H), 7.95 (m, 3H), 5.81 (m, 1H), 4.02 (m, 2H), 3.24 (m, 1H), 3.15 (s, 3H), 3.10 (m, 3H), 2.79 (m, 1H), 2.54 (m, 1H), 2.20 (m, 1H), 1.35 (d, 6H, J=6.8 Hz); MS m/z 502.0 (M$^+$).

Example 9.66

Preparation of 1-[4-(Methanesulfonyl)phenyl]-4-[[1-[(4-trifluoromethoxy)phenyl]-4-piperidinyl]oxy]-1H-pyrazolo-[3,4-d]pyrimidine (Compound A202)

Step 1: Preparation of 4-Hydroxy-1-(4-trifluoromethoxy-)-phenylpiperidine

A mixture of 4-(trifluoromethoxy)bromobenzene (2.41 g, 10.0 mmol), 4-hydroxypiperidine (1.21 g, 12.0 mmol), tris(dibenzylideneacetone)dipalladium(0) (137 mg, 0.15 mmol), and 2-(di-t-butylphosphino)biphenyl (107 mg, 0.36 mmol) under N$_2$ was combined with lithium bis(trimethylsilyl)amide (1.0M in THF, 22 mL, 22 mmol). The reaction mixture was heated at 65° C. for 2 h, and then was cooled to ambient temperature and quenched with 1N HCl (35 mL) to pH 7. The resulting mixture was extracted with EtOAc (20 mL), and the organic extract was rinsed with brine, dried over MgSO$_4$, and the solvent was removed. The residue was subjected to flash chromatography (2% 7N methanolic ammonia in CH$_2$Cl$_2$), and a waxy, amber solid was obtained upon solvent removal (1.4 g, 54% yield): $^1$H NMR (CDCl$_3$) δ 7.02 (d, 2H, J=8.7 Hz), 6.83 (d, 2H, J=8.4 Hz), 3.79 (m, 1H), 3.45 (m, 2H), 2.86 (m, 2H), 1.94 (m, 2H), 1.62 (m, 2H), 1.49 (s, 1H); MS m/z 261.9 (M$^+$).

Step 2: Preparation of 1-[4-(Methanesulfonyl)phenyl]-4-[[1-[(4-trifluoromethoxy) phenyl]-4-piperidinyl]oxy]-1H-pyrazolo-[3,4-d]pyrimidine (Compound A202)

Compound A202 was synthesized from 4-hydroxy-1-(4-trifluoromethoxy-)-phenylpiperidine and 4-chloro-1-(4-methanesulfonyl-phenyl)-1H-pyrazolo[3,4-d]pyrimidine by a similar method as described in Example 9.65, however after stirring overnight at room temperature, heating at 65° C. for 1 h was required to drive the reaction to completion. The reaction was worked up in the same manner, but isolation of the free base was accomplished by crystallization from EtOAc. Upon preparation of the HCl salt a white solid was obtained (570 mg, 50% yield): $^1$H NMR (DMSO-d$_6$) δ 8.82 (s, 1H), 8.70 (s, 1H), 8.56 (d, 2H, J=9.4 Hz), 8.16 (d, 2H, J=9.4 Hz), 7.55 (m, 2H), 7.41 (d, 2H, J=8.2 Hz), 5.71 (m, 1H), 3.71 (m, 2H), 3.46 (m, 2H), 3.29 (s, 3H), 2.36 (m, 2H), 2.19 (m, 2H); MS m/z 534.2 (M$^+$).

Example 9.67

Preparation of (Compound A238)

Compound A203 was prepared in a similar manner as described in Example 9.6 as a solid. Exact mass calculated for C$_{17}$H$_{18}$FN$_5$O$_3$S 391.1, found 392.2 (MH$^+$).

Example 9.68

Preparation of 4-[-(2-Fluoro-4-methanesulfonyl-phenyl)-1H-pyrazolo[3,4-d]-pyrimidin-4-ylsulfanyl]-piperidine-1-carboxylic acid tert-butyl ester (Compound 107)

To a solution of 4-mercapto-piperidine-1-carboxylic acid tert-butyl ester (3.09 g, 14.22 mmol) in DMF (50 mL) was added K$_2$CO$_3$. After 45 minutes stirring at room temperature, 4-chloro-1-(2-fluoro-4-methanesulfonyl-phenyl)-1H-pyrazolo[3,4-d]pyrimidine (4.65 g, 14.22 mmol) was added. After 1 hour stirring reaction was extracted with ethyl acetate and washed with water. Some product crashed out in the organic layer. This was collected by filtration. Remaining organic layer was dried over anhydrous MgSO$_4$, filtered and concentrated to provide Compound A107 as a white solid. $^1$H NMR (CDCl$_3$, 400 MHz) δ 1.48 (9H, s), 1.77 (2H, m), 2.18 (2H, m), 3.20-3.13 (5H, m), 3.99 (2H, m), 4.42 (1H, m), 7.95 (3H, m), 8.30 (1H, s), 8.78 (1H, s). Exact mass calculated for C$_{22}$H$_{26}$FN$_5$O$_4$S$_2$ 507.1, found 508.3 (MH$^+$).

Example 9.69

Preparation of 4-[-(2-Fluoro-4-methanesulfonyl-phenyl)-1H-pyrazolo[3,4-d]-pyrimidin-4-ylsulfanyl]-piperidine-1-carboxylic acid isopropyl ester (Compound A214)

4-[1-(2-Fluoro-4-methanesulfonyl-phenyl)-1H-pyrazolo[3,4-d]pyrimidin-4-ylsulfanyl]-piperidine-1-carboxylic acid tert-butyl ester (3.54 g, 6.97 mmol) was treated with 4M HCl in 1,4-dioxanes (40 mL). After 2 hours stirring at room temperature, 1-(2-fluoro-4-methanesulfonyl-phenyl)-4-(piperidin-4-ylsulfanyl)-1H-pyrazolo[3,4-d]pyrimidine hydrochloride was collected by filtration. To a mixture of 1-(2-fluoro-4-methanesulfonyl-phenyl)-4-(piperidin-4-ylsulfanyl)-1H-pyrazolo[3,4-d]pyrimidine hydrochloride (3.0 g, 6.76 mmol) in DMF (27 mL) was added triethyl amine (2.05 g, 20.28 mmol). After 30 minutes stirring, isopropyl chloroformate (7.44 mmol) as a 1.0M solution in toluene was added to the reaction and reaction was stirred for two hours. HCl salts had crashed out and were removed by filtration. Filtrate was extracted with ethyl acetate (100 mL) and washed with water (4×100 mL). Organic was dried over anhydrous MgSO$_4$, filtered and concentrated in vacuo to yield Compound A214 as a white solid. $^1$H NMR(CDCl$_3$, 400MHz) δ 1.27 (d, J=6.3 Hz, 6H), 1.77 (2H, m), 2.18 (2H, m), 3.13 (3H, s), 3.21 (2H, m), 4.04 (2H, m), 4.48-4.40 (1H, m), 4.99-4.90 (1H, m), 7.98-7.92 (3H, m), 8.30 (1H, s), 8.79 (1H, s). Exact mass calculated for C$_{21}$H$_{24}$FN$_5$O$_4$S$_2$ 493.1, found 494.3 (MH$^+$).

Example 9.70

Preparation of General Procedure of Coupling Acids with Amine

A solution of the carboxylic acid (0.139 mmol) and HATU (53 mg, 0.139 mmol) in DMF (6 mL) was stirred at room temperature for one hour. To the solution was added triethyl amine (34 mg, 0.332 mmol) and the amine, such as, 1-(4-methanesulfonyl-phenyl)-4-(piperidin-4-yloxy)-1H-pyrazolo[3,4-d]pyrimidine (40 mg, 0.107 mmol). After overnight stirring at room temperature, the reaction were extracted with DCM (5 mL), washed with 1M aq citric acid (5 mL), followed by water (3×5 mL). Organics were dried over anhydrous Na$_2$SO$_4$. Organics were concentrated in vacuo and purified by HPLC to provide the desired compound as a TFA salt.

The following representative compounds of the present invention were prepared in a manner similar to that described above in this general procedure:

{4-[1-(4-Methanesulfonyl-phenyl)-1H-pyrazolo[3,4-d] pyrimidin-4-yloxy]-piperidin-1-yl}-(5-methyl-pyridin-3-yl)-methanone (Compound A18);

{4-[1-(4-Methanesulfonyl-phenyl)-1H-pyrazolo[3,4-d] pyrimidin-4-yloxy]-piperidin-1-yl}-(6-trifluoromethyl-pyridin-3-yl)-methanone (Compound A34);

2-(5-Bromo-pyridin-3-yl)1-{4-[1-(4-methanesulfonyl-phenyl)-1H-pyrazolo[3,4-d]pyrimidin-4-yloxy]-piperidin-1-yl}-ethanone (Compound A169);

(6-Fluoro-pyridin-2-yl)-{4-[1-(4-methanesulfonyl-phenyl)-1H-pyrazolo[3,4-d]pyrimidin-4-yloxy]-piperidin-1-yl}-methanone (Compound A170);

(6-Chloro-pyridin-2-yl)-{4-[1-(4-methanesulfonyl-phenyl)-1H-pyrazolo[3,4-d]pyrimidin-4-yloxy]-piperidin-1-yl}-methanone (Compound A172);

{4-[1-(4-Methanesulfonyl-phenyl)-1H-pyrazolo[3,4-d] pyrimidin-4-yloxy]-piperidin-1-yl}-[5-(2-methyl-pyrrolidin-1-ylmethyl)-pyridin-3-yl]-methanone (Compound A174);

5-{4-[1-(4-Methanesulfonyl-phenyl)-1H-pyrazolo[3,4-d] pyrimidin-4-yloxy]-piperidine-1-carbonyl}-nicotinonitrile (Compound A176); and 5-{4-[1-(4-Methanesulfonyl-phenyl)-1H-pyrazolo[3,4-d] pyrimidin-4-yloxy]-piperidine-1-carbonyl}-pyridine-2-carboxylic acid methyl ester (Compound A195).

The table below shows the corresponding MS data for Compounds A18, A34, A169, A170, A172, A174, A176, and A195.

| Compound No. | Formula | Exact Mass | Found Mass (MH$^+$) |
|---|---|---|---|
| | MS Data | | |
| A18 | C$_{24}$H$_{24}$N$_6$O$_4$S | 492.16 | 493.4 |
| A34 | C$_{24}$H$_{21}$F$_3$N$_6$O$_4$S | 546.13 | 547.3 |
| A169 | C$_{24}$H$_{23}$BrN$_6$O$_4$S | 570.07 | 573.2 |
| A170 | C$_{23}$H$_{21}$FN$_6$O$_4$S | 496.13 | 497.1 |
| A172 | C$_{23}$H$_{21}$ClN$_6$O$_4$S | 512.1 | 513.2 |
| A174 | C$_{29}$H$_{33}$N$_7$O$_4$S | 575.23 | 576.3 |
| A176 | C$_{24}$H$_{21}$N$_7$O$_4$S | 503.14 | 504.2 |
| A195 | C$_{25}$H$_{24}$N$_6$O$_6$S | 536.15 | 537.2 |

Example 9.71

Preparation of General Alkylation Procedure

To a mixture of 1-(4-methanesulfonyl-phenyl)-4-(piperidin-4-yloxy)-1H-pyrazolo[3,4-d]pyrimidine (50 mg, 0.122 mmol) in DMF (1.5 mL) was added triethyl amine (38 mg, 0.379 mmol) and the desired alkyl bromide (0.159 mmol). After stirring overnight at room temperature, the reaction was diluted in CH$_3$CN, CH$_3$OH, and H$_2$O and purified by HPLC to provide the desired Compound as a TFA salt.

The following representative compounds of the present invention were prepared in a manner similar to that described above in this general procedure:

{4-[1-(4-Methanesulfonyl-phenyl)-1H-pyrazolo[3,4-d] pyrimidin-4-yloxy]-piperidin-1-yl}-acetic acid ethyl ester (Compound A196);

1-(4-Chloro-phenyl)-2-{4-[1-(4-methanesulfonyl-phenyl)-1H-pyrazolo[3,4-d]pyrimidin-4-yloxy]-piperidin-1-yl}-ethanone (Compound A199);

2-{4-[1-(4-Methanesulfonyl-phenyl)-1H-pyrazolo[3,4-d] pyrimidin-4-yloxy]-piperidin-1-yl}-1-(3-trifluoromethyl-phenyl)-ethanone (Compound A200);

1-(4-Chloro-3-methyl-phenyl)-2-{4-[1-(4-methanesulfonyl-phenyl)-1H-pyrazolo[3,4-d]pyrimidin-4-yloxy]-piperidin-1-yl}-ethanone (Compound A204);

1-(3,4-Dichloro-phenyl)-2-{4-[1-(4-methanesulfonyl-phenyl)-1H-pyrazolo[3,4-d]pyrimidin-4-yloxy]-piperidin-1-yl}-ethanone (Compound A205);

1-(2,4-Dimethoxy-phenyl)-2-{4-[1-(4-methanesulfonyl-phenyl)-1H-pyrazolo[3,4-d]pyrimidin-4-yloxy]-piperidin-1-yl}-ethanone (Compound A209);

1-(4-Difluoromethoxy-phenyl)-2-{4-[1-(4-methanesulfonyl-phenyl)-1H-pyrazolo[3,4-d]pyrimidin-4-yloxy]-piperidin-1-yl}-ethanone (Compound A210); and 1-(4-Diethylamino-phenyl)-2-{4-[1-(4-methanesulfonyl-phenyl)-1H-pyrazolo[3,4-d]pyrimidin-4-yloxy]-piperidin-1-yl}-ethanone (Compound A211).

The table below shows the corresponding MS data for Compounds A196, A199, A200, A204, A205, A209, A210, and A211.

| | MS Data | | |
|---|---|---|---|
| Compound No. | Formula | Exact Mass | Found Mass (MH$^+$) |
| A196 | $C_{21}H_{25}N_5O_5S$ | 459.16 | 460.3 |
| A199 | $C_{25}H_{24}ClN_5O_4S$ | 525.12 | 526.4 |
| A200 | $C_{26}H_{24}F_3N_5O_4S$ | 559.15 | 560.3 |
| A204 | $C_{26}H_{26}ClN_5O_4S$ | 539.14 | 540.1 |
| A205 | $C_{25}H_{23}Cl_2N_5O_4S$ | 559.08 | 560.2 |
| A209 | $C_{27}H_{29}N_5O_6S$ | 551.18 | 552.3 |
| A210 | $C_{26}H_{25}F_2N_5O_5S$ | 557.15 | 558.3 |
| A211 | $C_{29}H_{34}N_6O_4S$ | 562.24 | 563.2 |

Example 9.72

Preparation of (5-Amino-pyridin-2-yl)-{4-[1-(4-methanesulfonyl-phenyl)-1H-pyrazolo[3,4-d]pyrimidin-4-yloxy]-piperidin-1-yl}-methanone (Compound A186)

To a solution of 3-aminopicloinic acid (245 mg, 1.77 mmol) in 30 mL DMF, HATU (673 mg, 1.77 mmol) and triethylamine (1 mL, 7.72 mmol) were added. After 5 minutes, 1-(4-methanesulfonyl-phenyl)-4-(piperidin-4-yloxy)-1H-pyrazolo[3,4-d]pyrimidine (HCl salt, 660 mg, 1.61 mmol) was added and mixture was stirred for 45 minutes. Mixture was extracted with 1M NaOH solution and methylene chloride; organic phases were dried over MgSO$_4$, filtered, and concentrated. Residue was purified by HPLC to give Compound A186 as a white solid (TFA salt, 389 mg, 36%). Exact mass calculated for $C_{23}H_{23}N_7O_4S$ 493.15, found 494.4 (MH$^+$).

Example 9.73

Preparation of (5-Amino-pyridin-2-yl)-{4-[1-(2-fluoro-4-methanesulfonyl-phenyl)-1H-pyrazolo[3,4-d]pyrimidin-4-yloxy]-piperidin-1-yl}-methanone (Compound A187)

To a solution of 3-aminopicloinic acid (290 mg, 2.10 mmol) in 40 mL DMF, HATU (801 mg, 2.11 mmol) and triethylamine (1.17 mL, 8.44 mmol) were added. After 5 minutes, 1-(2-fluoro-4-methanesulfonyl-phenyl)-4-(piperidin-4-yloxy)-1H-pyrazolo[3,4-d]pyrimidine (HCl salt, 660 mg, 1.91 mmol) was added and mixture was stirred for 45 minutes. Mixture was purified by HPLC to give Compound A187 as a white solid (TFA salt, 1.03 g, 79%). Exact mass calculated for $C_{23}H_{22}FN_7O_4S$ 511.14, found 512.2 (MH$^+$).

Example 9.74

Preparation of (5-Ethylamino-pyridin-2-yl)-{4-[1-(2-fluoro-4-methanesulfonyl-phenyl)-1H-pyrazolo[3,4-d]pyrimidin-4-yloxy]-piperidin-1-yl}-methanone (Compound A191)

A mixture of (5-amino-pyridin-2-yl)-{4-[1-(2-fluoro-4-methanesulfonyl-phenyl)-1H-pyrazolo[3,4-d]pyrimidin-4-yloxy]-piperidin-1-yl}-methanone (Compound A187-TFA salt, 500 mg, 0.799 mmol), bromoethane (60 μl, 0.80 mmol), and potassium carbonate (331 mg, 2.39 mmol) in 7 mL acetonitrile were stirred at room temperature. After 1 hour, mixture was continued to be stirred under reflux. After 45 min, there was still no product formation observed. Mixture was cooled to r.t., sodium hydride dispersion (70 mg, 1.75 mmol) was added, and stirred at room temperature. After 90 minutes, more sodium hydride dispersion (70 mg, 1.75 mmol) was added and mixture was stirred under reflux for 90 minutes. Mixture was purified by HPLC to give Compound A191 as an oil (TFA salt, 10 mg, 2%). Exact mass calculated for $C_{25}H_{26}FN_7O_4S$ 539.18, found 540.3 (MH$^+$).

Example 9.75

Preparation of {4-[1-(2-Fluoro-4-methanesulfonyl-phenyl)-1H-pyrazolo[3,4-d]pyrimidin-4-yloxy]-piperidin-1-yl}-[5-(3-methyl-butylamino)-pyridin-2-yl]-methanone (Compound A188)

Compound A188 was prepared in a similar manner as described in Example 9.74 as an oil (TFA salt, 6.6 mg, 1%). Exact mass calculated for $C_{28}H_{32}FN_7O_4S$ 581.22, found 582.6 (MH$^+$).

Example 9.76

Preparation of 4-[1-(4-Bromo-phenyl)-1H-pyrazolo[3,4-d]pyrimidin-4-yloxy]-piperidine-1-carboxylic acid isopropyl ester (Compound A220)

A mixture of 4-hydroxy-piperidine-1-carboxylic acid isopropyl ester (727 mg, 3.88 mmol), and sodium hydride (465 mg, 19.4 mmol) in THF (12 mL) was stirred for 30 min at 60° C. 1-(4-Bromo-phenyl)-4-chloro-1H-pyrazolo[3,4-d]pyrimidine was added to the mixture at room temperature and stirred for 1.0 hr at RT. The reaction was quenched with water and the product extracted in ethyl acetate. The organic layer was concentrated in vacuo to provide Compound A220 as a white solid (1.3 g, 81%). $^1$H NMR (CDCl$_3$, 400MHz) δ 1.19 (d, 6H), 1.73-1.85 (m, 2H), 1.98-2.08 (m, 2H), 3.26-3.34 (m, 2H), 3.78-3.87 (m, 2H), 4.88 (h, 1H), 5.54 (h, 1H), 7.57 (d, 2H), 8.07 (d, 2H), 8.13 (s, 1H), 8.55 (s, 1H). Exact mass calculated for $C_{20}H_{22}BrN_5O_3$ 460.3, found 462.3 (MH$^+$).

Example 9.77

Preparation of 4-[1-(4-Propylamino-phenyl)-1H-pyrazolo[3,4-d]pyrimidin-4-yloxy]-piperidine-1-carboxylic acid isopropyl ester (Compound A221)

General Amination Method

A mixture of 4-[1-(4-bromo-phenyl)-1H-pyrazolo[3,4-d]pyrimidin-4-yloxy]-piperidine-1-carboxylic acid isopropyl ester (Compound A220, 100 mg, 0.22 mmol), n-propylamine (130 mg, 2.2 mmol), L-proline (46 mg, 0.40 mmol), copper iodide (42 mg, 0.22 mmol) and potassium carbonate (71 mg, 0.51 mmol) in DMSO (2.5 mL) was heated under microwave irradiation for 50 min at 100° C. The crude mixture was concentrated in vacuo and purified by HPLC to provide Compound A221 as a white solid (6 mg, 6%). $^1$H NMR (CDCl$_3$, 400MHz) δ 0.95 (t, 3H), 1.20 (d, 6H), 1.54-1.56 (m, 2H), 1.80-1.89 (m, 2H), 1.97-2.07 (m, 2H), 3.07 (t, 2H), 3.25-3.34 (m, 2H), 3.76-3.87 (m, 2H), 4.88 (h, 1H), 5.51 (h, 1H), 6.67 (d, 2H), 7.71 (d, 2H), 8.08 (s, 1H), 8.50 (s, 1H). Exact mass calculated for $C_{23}H_{30}N_6O_3$ 438.52, found 439.4 (MH$^+$).

Example 9.78

Preparation of 4-[1-(4-Isopropylamino-phenyl)-1H-pyrazolo[3,4-d]pyrimidin-4-yloxy]-piperidine-1-carboxylic acid isopropyl ester (Compound A222)

Compound A222 was prepared in a similar manner as described in Example 9.77. $^1$H NMR (CDCl$_3$, 400MHz) δ 1.20 (d, 6H), 1.28 (d, 6H), 1.74-1.85 (m, 2H), 1.99-2.09 (m, 2H), 3.26-3.36 (m, 2H), 3.52-3.60 (m, 2H), 3.79-3.89 (m, 2H), 4.88 (h, 1H), 5.51 (h, 1H), 7.46 (d, 2H), 7.99 (s, 1H), 8.21 (d, 2H), 8.49 (s, 1H). Exact mass calculated for C$_{23}$H$_{30}$N$_6$O$_3$ 438.52, found 439.4 (MH$^+$).

Example 9.79

Preparation of 4-[1-(4-Morpholin-4-yl-phenyl)-1H-pyrazolo[3,4-d]pyrimidin-4-yloxy]-piperidine-1-carboxylic acid isopropyl ester (Compound A227)

Compound A227 was prepared in a similar manner as described in Example 9.77. $^1$H NMR (CDCl$_3$, 400MHz) δ 1.19 (d, 6H), 1.73-1.84 (m, 2H), 1.97-2.06 (m, 2H), 3.12-3.19 (m, 4H), 3.25-3.35 (m, 2H), 3.76-3.87 (m, 6H), 4.87 (h, 1H), 5.52 (h, 1H), 6.99 (d, 2H), 7.90 (d, 2H), 8.10 (s, 1H), 8.51 (s, 1H). Exact mass calculated for C$_{23}$H$_{30}$N$_6$O$_4$ 466.53, found 467.3 (MH$^+$).

Example 9.80

Preparation of 4-[1-(2-Fluoro-4-isopropylamino-phenyl)-1H-pyrazolo[3,4-d]pyrimidin-4-yloxy]-piperidine-1-carboxylic acid isopropyl ester (Compound A230)

A mixture of 4-[1-(2-fluoro-4-iodo-phenyl)-1H-pyrazolo[3,4-d]pyrimidin-4-yloxy]-piperidine-1-carboxylic acid isopropyl ester (263 mg, 0.50 mmol), isopropylamine (450 μL, 5.0 mmol), L-proline (86 mg, 0.75 mmol), copper iodide (95 mg, 0.50 mmol) and potassium carbonate (207 mg, 1.50 mmol) in DMSO (4.0 mL) was heated under microwave irradiation for 50 min at 100° C. The crude mixture was concentrated in vacuo and purified by HPLC to provide Compound A230 as a white solid (80 mg, 35%). $^1$H NMR (CDCl$_3$, 400MHz) δ 1.20 (d, 6H), 1.26 (d, 6H), 1.75-1.88 (m, 2H), 1.98-2.09 (m, 2H), 3.28-3.37 (m, 2H), 3.55-3.63 (m, 1H), 3.78-3.87 (m, 2H), 4.88 (h, 1H), 5.55 (h, 1H), 6.90-7.08 (m, 2H), 7.44-7.50 (m, 1H), 8.17 (s, 1H), 8.53 (s, 1H). Exact mass calculated for C$_{23}$H$_{29}$FN$_6$O$_3$ 456.51, found 457.3 (MH$^+$).

Example 9.81

Preparation of 4-[1-(2-Fluoro-4-morpholin-4-yl-phenyl)-1H-pyrazolo[3,4-d]pyrimidin-4-yloxy]-piperidine-1-carboxylic acid isopropyl ester (Compound A229)

Compound A229 was prepared in a similar manner as described in Example 9.80. $^1$H NMR (CDCl$_3$, 400MHz) δ 1.20 (d, 6H), 1.74-1.86 (m, 2H), 1.97-2.07 (m, 2H), 3.13-3.19 (m, 4H), 3.25-3.36 (m, 2H), 3.76-3.87 (m, 6H), 4.87 (h, 1H), 5.52 (h, 1H), 6.66-6.76 (m, 2H), 7.33-7.43 (m, 1H), 8.15 (s, 1H), 8.50 (s, 1H). Exact mass calculated for C$_{24}$H$_{29}$FN$_6$O$_4$ 484.52, found 485.4 (MH$^+$).

Example 9.82

Preparation of 4-(1-{4-[4-(2-Methanesulfonyl-ethyl)-piperazin-1-yl]-2-methyl-phenyl}-1H-pyrazolo[3,4-d]pyrimidin-4-yloxy)-piperidine-1-carboxylic acid isopropyl ester (Compound A223)

General Amination Procedure.

A solution of 4-[1-(4-iodo-2-methyl-phenyl)-1H-pyrazolo[3,4-d]pyrimidin-4-yloxy]-piperidine-1-carboxylic acid isopropyl ester (78 mg, 0.15 mmol), 1-(2-methanesulfonyl-ethyl)-piperazine (0.75 mmol, 5.0 eq), CuI (0.15 mmol, 1 eq), L-proline (0.27 mmol, 1.8 eq), and potassium carbonate (0.15 mmole, 1 eq) in DMSO (2 mL) was heated at 120° C. for 1 hour under microwave conditions. The crude was purified through prep-LCMS 5-95% to provide Compound A223 as a brown sticky oil (5 mg, 6%). Exact mass calculated for C$_{28}$H$_{39}$N$_7$O$_5$S 585.3, found LCMS (ESI) m/z 586.6 (M+H$^+$, 90%).

Example 9.83

Preparation of 4-(1-{2-Methyl-4-[(tetrahydro-furan-2-ylmethyl)-amino]-phenyl}-1H-pyrazolo[3,4-d]pyrimidin-4-yloxy)-piperidine-1-carboxylic acid isopropyl ester (Compound A224)

Compound A224 was prepared in a similar manner as described in Example 9.82 as a peach powder (36.8 mg, 50%). Exact mass calculated for C$_{26}$H$_{34}$N$_5$O$_4$ 494.3, found LCMS (ESI) m/z 495.6 (M+H$^+$, 71%).

Example 9.84

Preparation of 4-[1-(4-Cyclopropylamino-2-methyl-phenyl)-1H-pyrazolo[3,4-d]pyrimidin-4-yloxy]-piperidine-1-carboxylic acid isopropyl ester (Compound A225)

Compound A225 was prepared in a similar manner as described in Example 9.82 as an off-white powder. Exact mass calculated for C$_{24}$H$_{30}$N$_6$O$_3$ 450.2, found LCMS (ESI) m/z 451.4 (M+H+, 97%).

Example 9.85

Preparation of 4-{1-[4-(2-Dimethylamino-ethylamino)-2-methyl-phenyl-1H-pyrazolo[3,4-d]pyrimidin-4-yloxy}-piperidine-1-carboxylic acid isopropyl ester (Compound A226)

Compound A226 was prepared in a similar manner as described in Example 9.82 as a white powder (8.4 mg, 12%). Exact mass calculated for C$_{25}$H$_{35}$N$_7$O$_3$ 481.3, found LCMS (ESI) m/z 482.4 (M+H$^+$, 100%).

Example 9.86

Preparation of 4-(1-{4-[(2-Methanesulfonyl-ethyl)-methyl-amino]-phenyl}-1H-pyrazolo [3,4-d]pyrimidin-4-yloxy)-piperidine-1-carboxylic acid isopropyl ester (Compound A231)

Compound A231 was prepared in a similar manner as described in Example 9.82 as an off-white powder. Exact mass calculated for C$_{24}$H$_{32}$N$_6$O$_5$S 516.2, found LCMS (ESI) m/z 517.6 (M+H$^+$, 78%).

Example 9.87

Preparation of 4-{1-[4-(2-Methoxy-ethylamino)-phenyl]-1H-pyrazolo[3,4-d]pyrimidin-4-yloxy}-piperidine-1-carboxylic acid isopropyl ester (Compound A232)

Compound A232 was prepared in a similar manner as described in Example 9.82 as an off-white powder. Exact mass calculated for $C_{23}H_{30}N_6O_4$ 454.2, found LCMS (ESI) m/z 455.5 (M+H$^+$, 89%).

Example 9.88

Preparation of 4-(1-{4-[(Tetrahydro-furan-2-ylmethyl)-amino]-phenyl}-1H-pyrazolo[3,4-d]pyrimidin-4-yloxy)-piperidine-1-carboxylic acid isopropyl ester (Compound A233)

Compound A233 was prepared in a similar manner as described in Example 9.82 as a yellow powder (5.3 mg, 7%). Exact mass calculated for $C_{25}H_{32}N_6O_4$ 480.2, found LCMS (ESI) m/z 481.6. (M+H$^+$, 92%).

Example 9.89

Preparation of 4-(1-{4-[4-(2-Methanesulfonyl-ethyl)-piperazin-1-yl]-phenyl}-1H-pyrazolo[3,4-d]pyrimidin-4-yloxy)-piperidine-1-carboxylic acid isopropyl ester (Compound A234)

Compound A234 was prepared in a similar manner as described in Example 9.82 as a brown powder. Exact mass calculated for $C_{27}H_{37}N_7O_5S$ 571.3, found LCMS (ESI) m/z 572.6 (M+H$^+$, 74%).

Example 9.90

Preparation of 4-[1-(4-Amino-phenyl)-1H-pyrazolo[3,4-d]pyrimidin-4-yloxy]-piperidine-1-carboxylic acid isopropyl ester (Compound A235)

Compound A235 was prepared in a similar manner as described in Example 9.82 as an off-white powder (7.3 mg, 12%). Exact mass calculated for $C_{20}H_{24}N_6O_3$ 396, found LCMS (ESI) m/z 397.1 (M+H$^+$, 70%).

Example 9.91

Preparation of 4-[1-(5-Ethyl-pyrimidin-2-yl)-piperidin-4-ylsulfanyl]-1-(2-fluoro-4-methanesulfonyl-phenyl)-1H-pyrazolo[3,4-d]pyrimidine (Compound A237)

A mixture of 1-(2-fluoro-4-methanesulfonyl-phenyl)-4-(piperidin-4-ylsulfanyl)-1H-pyrazolo[3,4-d]pyrimidine hydrochloride (250 mg, 0.56 mmol), 2-chloro-5-ethyl-pyrimidine (680 µL, 5.6 mmol), and triethylamine (315 µL, 2.24 mmol) in isopropanol (4 mL) was heated under microwave irradiation for 15 min at 150° C. The crude mixture was concentrated in vacuo and purified by HPLC to provide Compound A237 as a white solid (100 mg, 35%). $^1$H NMR (CDCl$_3$, 400MHz) δ 1.18 (t, 3H), 1.82-1.94 (m, 2H), 2.28-2.37 (m, 2H), 2.53 (q, 2M), 3.06 (s, 3H), 3.55-3.64 (m, 2H), 4.41-4.55 (m, 3H), 7.82 (m, 3H), 8.24 (s, 1H), 8.37 (s, 2H), 8.74 (s, 1H). Exact mass calculated for $C_{23}H_{24}FN_7O_2S_2$ 513.61, found 514.4 (MH$^+$).

Example 9.92

Preparation of 3-tert-Butoxy-1-{4-[1-(4-methanesulfonyl-phenyl)-1H-pyrazolo[3,4-d]pyrimidin-4-yloxy]-piperidin-1-yl}-propan-1-one (Compound A32)

Compound A32 was prepared in a similar manner as described in Example 9.25 as a solid (95%). $^1$H NMR (CDCl$_3$, 400MHz) δ 1.26 (d, 6H), 1.82-1.86 (m, 2H), 2.01-2.10 (m, 2H), 3.10 (s, 3H), 3.34-3.45 (m, 2H), 3.90-3.93 (m, 2H), 4.94 (sept, 1H), 5.44-5.48 (m, 1H), 8.09-8.12 (m, 2H), 8.26 (s, 1H), 8.60-8.62 (m, 2H), 8.67 (s, 1H). Exact mass calculated for $C_{21}H_{25}N_5O_5S$ 459.2, found 460.3 (MH$^+$).

Example 9.93

Preparation of (3-{4-[1-(4-Methanesulfonyl-phenyl)-1H-pyrazolo[3,4-d]pyrimidin-4-yloxy]-piperidin-1-yl}-3-oxo-propyl)-methyl-carbamic acid tert-butyl ester (Compound A33)

Compound A33 was prepared in a similar manner as described in Example 9.25 as a solid (37%). Exact mass calculated for $C_{26}H_{34}N_6O_6S$ 558.2, found 559.3 (MH$^+$).

Example 9.94

Preparation of {4-[1-(4-Methanesulfonyl-phenyl)-1H-pyrazolo[3,4-d]pyrimidin-4-ylamino]-cyclohexyl}-carbamic acid tert-butyl ester (Compound A35)

A mixture of 4-chloro-1-(4-methanesulfonyl-phenyl)-1H-pyrazolo[3,4-d]pyrimidine (308 mg, 1 mmol), (4-amino-cyclohexyl)-carbamic acid tert-butyl ester (257 mg, 1.2 mmol) and potassium carbonate (166 mg, 1.2 mmol) in THF (10 mL) was stirred at rt overnight. The mixture was purified by column chromatography to provide Compound A35 as a solid (76%). $^1$H NMR (CDCl$_3$, 400MHz) δ 1.46 (s, 9H), 1.74-2.04 (m, 8H), 3.09 (s, 3H), 3.73 (s, 1H), 4.62 (s, 1H), 8.07-8.09 (m, 3H), 8.49 (s, 1H), 8.57-8.59 (m, 2H). Exact mass calculated for $C_{23}H_{30}N_6O_4S$ 486.2, found 487.2 (MH$^+$).

Example 9.95

Preparation of N-[1-(4-Methanesulfonyl-phenyl)-1H-pyrazolo[3,4-d]pyrimidin-4-yl]-cyclohexane-1,4-diamine (Compound A36)

Compound A36 was prepared in a similar manner as described in Example 9.6 as a solid (98%). Exact mass calculated for $C_{18}H_{22}N_6O_2S$ 386.2, found 387.1 (MH$^+$).

Example 9.96

Preparation of N-{4-[1-(4-Methanesulfonyl-phenyl)-1H-pyrazolo[3,4-d]pyrimidin-4-ylamino]-cyclohexyl}-nicotinamide (Compound A42)

Compound A42 was prepared in a similar manner as described in Example 9.25 as a solid (65%). Exact mass calculated for $C_{24}H_{25}N_7O_3S$ 491.2, found 492.3 (MH$^+$).

Example 9.97

Preparation of 3-tert-Butoxy-N-{4-[1-(4-methanesulfonyl-phenyl)-1H-pyrazolo[3,4-d]pyrimidin-4-ylamino]-cyclohexyl)-propionamide (Compound A43)

Compound A43 was prepared in a similar manner as described in Example 9.25 as a solid (24%). $^1$H NMR (CDCl$_3$, 400MHz) δ 1.23 (s, 9H), 1.89-1.90 (m, 4H), 2.02-2.03 (m, 4H), 2.51 (t, 2H), 3.12 (s, 3H), 3.64 (t, 2H), 4.09 (s, 2H), 7.35-7.37 (m, 1H), 8.13 (d, 2H), 8.26 (s, 1H), 8.32 (s, 1H), 8.45 (d, 2H), 11.5-11.6 (m, 1H). Exact mass calculated for $C_{25}H_{34}N_6O_5S$ 514.2, found 515.6 (MH$^+$).

Example 9.98

Preparation of (4-{[1-(4-Methanesulfonyl-phenyl)-1H-pyrazolo[3,4-d]pyrimidin-4-ylamino]-methyl}-cyclohexyl)-carbamic acid tert-butyl ester (Compound A71)

Compound A71 was prepared in a similar manner as described in Example 9.94 as a solid (100%). $^1$H NMR (CDCl$_3$, 400MHz) δ 1.35-1.85 (m, 19H), 3.09 (s, 3H), 3.61 (s, 2H), 3.73-3.76 (m, 1H), 4.64 (s, 1H), 8.07-8.11 (m, 3H), 8.50 (s, 1H), 8.57-8.60 (m, 2H). Exact mass calculated for $C_{24}H_{32}N_6O_4S$ 500.2, found 501.3 (MH$^+$).

Example 9.99

Preparation of N-{4-[1-(4-Methanesulfonyl-phenyl)-1H-pyrazolo[3,4-d]pyrimidin-4-ylamino]-cyclohexylmethyl}-nicotinamide (Compound A72)

Compound A72 was prepared in a similar manner as described in Example 9.25 as a solid (91%). Exact mass calculated for $C_{25}H_{27}N_7O_3S$ 505.2, found 506.3 (MH$^+$).

Example 9.100

Preparation of N-{4-[1-(4-Methanesulfonyl-phenyl)-1H-pyrazolo[3,4-d]pyrimidin-4-ylamino]-cyclohexylmethyl}-6-methyl-nicotinamide (Compound A73)

Compound A73 was prepared in a similar manner as described in Example 9.25 as a solid (94%). Exact mass calculated for $C_{26}H_{29}N_7O_3S$ 519.2, found 520.5 (MH$^+$).

Example 9.101

Preparation of 4-(2-{Ethyl-1-(4-methanesulfonyl-phenyl)-1H-pyrazolo[3,4-d]pyrimidin-4-yl]-amino}-ethyl)-piperazine-1-carboxylic acid tert-butyl ester (Compound A101)

Compound A101 was prepared in a similar as described in Example 9.94 as a solid (9%). Exact mass calculated for $C_{25}H_{35}N_7O_4S$ 529.3, found 530.3 (MH$^+$).

Example 9.102

Preparation of 4-({[1-(2-Fluoro-4-methanesulfonyl-phenyl)-1H-pyrazolo[3,4-d]pyrimidin-4-yl]-isopropyl-amino}-methyl)-piperidine-1-carboxylic acid tert-butyl ester (Compound A228)

Compound A228 was prepared in a similar manner as described in Example 9.94 as a solid (120 mg, 71%). Exact mass calculated for $C_{26}H_{35}FN_6O_4S$ 546.2, found 547.7 (MH$^+$).

Example 9.103

Preparation of 4-({[1-(2-Fluoro-4-methanesulfonyl-phenyl)-1H-pyrazolo[3,4-d]pyrimidin-4-yl]-isopropyl-amino}-methyl)-piperidine-1-carboxylic acid isopropyl ester (Compound A236)

Compound A236 was prepared in a similar manner as described in Example 9.4 as a sticky oil (509 mg, 80%). Exact mass calculated for $C_{25}H_{33}FN_6O_4S$ 532.2, found 533.3 (MH$^+$).

Example 9.104

Preparation of 4-[1-(2-Fluoro-4-sulfamoyl-phenyl)-1H-pyrazolo[3,4-d]pyrimidin-4-yloxy]-piperidine-1-carboxylic acid isopropyl ester (Compound A239)

Step 1: Preparation of 3-fluoro-4-hydrazino-benzenesulfonamide

In a 500 mL round-bottomed flask fitted with a condenser and N$_2$ inlet septum was placed a stir bar, 3,4-difluoro-benzenesulfonamide (10 g, 52 mmol), anhydrous hydrazine (10.56 mL, 336 mmol), and acetonitrile (180 mL). The mixture was refluxed for 6 h under N$_2$. The solvent was then removed under vacuum and the residue was treated with H$_2$O. The separated solid was filtered and washed with H$_2$O to give the desired product. Exact mass calculated for $C_6H_8FN_3O_2S$ 205.03, found 206.1 (MH$^+$).

Step 2: 4-[1-(2-Fluoro-4-sulfamoyl-phenyl)-1H-pyrazolo[3,4-d]pyrimidin-4-yloxy]-piperidine-1-carboxylic acid isopropyl ester (Compound A239)

Compound A239 was made in a similar manner as described in Example 9.24; purified by HPLC. $^1$H NMR (CDCl$_3$, 400MHz) δ 1.26 (d, 6H), 1.87 (m, 2H), 2.10 (m, 2H), 3.37 (m, 2H), 3.91 (m, 2H), 4.91 (m, 1H), 5.01 (s, 2H), 5.62 (m, 1H), 7.91 (m, 3H), 8.31 (s, 1H), 8.61 (s, 1H). Exact mass calculated for $C_{20}H_{23}FN_6O_5S$ 478.14, found 479.3 (MH$^+$).

Example 9.105

Preparation of (1-tert-Butyl-5-methyl-1H-pyrazol-4-yl)-{4-[1-(4-methanesulfonyl-phenyl)-1H-pyrazolo[3,4-d]pyrimidin-4-yloxy]-piperidin-1-yl}-methanone (Compound A9)

Compound A9 were prepared the same way as described in Example 9.104. $^1$H NMR (CDCl$_3$, 400MHz) δ 1.62 (s, 9H), 2.01 (m, 2H), 2.22 (m, 2H), 2.47 (s, 3H), 3.09 (s, 3H), 3.65 (m, 1H), 3.96 (m, 1H), 4.23 (m, 1H), 4.55 (m, 1H), 5.72 (m, 1H), 6.50 (s, 1H), 8.10 (d, 2H), 8.28 (s, 1H), 8.62 (d, 2H), 8.68 (s, 1H). Exact mass calculated for $C_{26}H_{31}N_7O_4S$ 537.22, found 538.4 (MH$^+$)

Example 9.106

Preparation of (5-tert-Butyl-2-methyl-2H-pyrazol-3-yl)-{4-[1-(4-methanesulfonyl-phenyl)-1H-pyrazolo[3,4-d]pyrimidin-4-yloxy]-piperidin-1-yl}-methanone (Compound A10)

Compound A10 were prepared the same way as described in Example 9.104. $^1$H NMR (CDCl$_3$, 400MHz) δ 1.30 (s, 9H), 1.97 (m, 2H), 2.20 (m, 2H), 3.11 (s, 3H), 3.63 (m, 2H), 3.86 (s, 1H), 3.94 (s, 3H), 4.13 (m, 1H), 5.72 (m, 1H), 6.18 (s, 1H), 8.10 (d, 2H), 8.28 (s, 1H), 8.62 (d, 2H), 8.68 (s, 1H). Exact mass calculated for C$_{26}$H$_{31}$N$_7$O$_4$S 537.22, found 538.4 (MH$^+$)

Example 9.107

Preparation of (3-Fluoro-phenyl)-{4-[1-(4-methanesulfonyl-phenyl)-1H-pyrazolo[3,4-d]pyrimidin-4-yloxy]-piperidin-1-yl}-methanone (Compound A8)

In a 16 mL reaction vial was placed sodium hydride (48 mg, 60% in oil, 1.2 mmol) and 5 mL of THF. (3-Fluoro-phenyl)-(4-hydroxy-piperidin-1-yl)-methanone (66 mg, 0.3 mmol) was added to the suspension and the mixture was stirred 60 min under N$_2$ at room temperature, followed by the addition of 4-chloro-1-(4-methanesulfonyl-phenyl)-1H-pyrazolo[3,4-d]pyrimidine (60 mg, 0.2 mmol). After stir another 2 hrs under N$_2$ at room temperature, all of the starting chloropyrozolepyrimidines was completely converted as indicated by LCMS. The reaction mixture was then filtered through a syringe filter and purified HPLC to give Compound A8. $^1$H NMR (CDCl$_3$, 400MHz) δ 1.95 (m, 2H), 2.21 (m, 2H), 3.11 (s, 3H), 3.45 (m, 1H), 3.68 (m, 1H), 3.75 (m, 1H), 4.20 (s, 1H), 5.72 (m, 1H), 7.12 (m, 1H), 7.16 (m, 1H), 7.22 (m, 1H), 7.41 (m, 1H), 8.11 (d, 2H), 8.27 (s, 1H), 8.62 (d, 2H), 8.67 (s, 1H). Exact mass calculated for C$_{24}$H$_{22}$FN$_5$O$_4$S 495.14, found 496.3 (MH$^+$)

Example 9.108

Preparation of 1-(2-Fluoro-4-methanesulfonyl-phenyl)-4-[1-(3-isopropyl-[1,2,4]oxadiazol-5-ylmethyl)-piperidin-4-yloxy]-1H-pyrazolo[3,4-d]pyrimidine (Compound A137)

Compound A137 were prepared the same way as described in Example 9.107. $^1$H NMR (CDCl3, 400MHz) δ 1.35 (d, 6H), 2.06 (m, 2H), 2.19 (m, 2H), 2.60 (m, 2H), 2.92 (m, 2H), 3.13 (m, 2H), 3.90 (s, 2H), 5.47 (m, 1H), 7.94 (m, 3H), 8.32 (s, 1H), 8.61 (s, 1H). Exact mass calculated for C$_{23}$H$_{26}$FN$_7$O$_4$S 515.18, found 516.4 (MH$^+$)

Example 9.109

Preparation of 4-[1-(4-Methanesulfonyl-phenyl)-1H-pyrazolo[3,4-d]pyrimidin-4-ylamino]-piperidine-1-carboxylic acid tert-butyl ester (Compound A11)

Compound A11 was prepared in a similar manner as described in Example 9.94 as a white solid. $^1$H NMR (DMSO-d$_6$, 400MHz) δ 1.42 (s, 9H), 1.48 (m, 2H), 1.97 (m, 2H), 2.92 (m, 2H), 3.26 (s, 3H), 3.99 (m, 2H), 4.33 (m, 1H), 8.10 (d, 2H), 8.45 (s, 2H), 8.50 (s, 1H), 8.56 (d, 2H). Exact mass calculated for C$_{22}$H$_{28}$N$_6$O$_4$S 472.19, found 473.4 (MH$^+$)

Example 9.110

Preparation of 3-[1-(4-Methanesulfonyl-phenyl)-1H-pyrazolo[3,4-d]pyrimidin-4-ylamino]-piperidine-1-carboxylic acid tert-butyl ester (Compound A24)

Compound A24 were prepared in a similar manner as described in Example 9.94. $^1$H NMR (CDCl3, 400MHz) δ 1.40 (m, 2H), 1.47 (s, 9H), 1.66 (m, 1H), 1.79 (m, 1H), 3.09 (s, 3H), 3.49 (m, 3H), 3.79 (m, 1H), 4.31 (m, 1H), 5.83 (m, 1H), 8.08 (d, 2H), 8.19 (s, 1H), 8.51 (s, 1H), 8.59 (d, 2H). Exact mass calculated for C$_{22}$H$_{28}$N$_6$O$_4$S 472.19, found 473.4 (MH$^+$)

Example 9.111

Preparation of 4-[1-(4-Methanesulfonyl-phenyl)-1H-pyrazolo[3,4-d]pyrimidin-4-ylamino]-piperidine-1-carboxylic acid isopropyl ester (Compound A12)

Step 1: Preparation of [1-(4-methanesulfonyl-phenyl)-1H-pyrazolo[3,4-d]pyrimidin-4-yl]-piperidin-4-yl-amine In a 100 mL round-bottomed flask was placed a stir bar, compound A11 (1 g), acetonitrile (40 mL), and dichloromethane (12 mL). After the compound was dissolved, 4M HCl in 1,4-dioxane (12 mL) was added under nitrogen and the mixture was stirred at room temperature for 20 minutes. The solution was concentrated to about 60% of the original volume. The precipitate was isolated to give [1-(4-methanesulfonyl-phenyl)-1H-pyrazolo[3,4-d]pyrimidin-4-yl]-piperidin-4-yl-amine. $^1$H NMR (DMSO-d$_6$, 400MHz) δ 1.98 (m, 2H), 2.11 (m, 2H), 3.02 (m, 2H), 3.26 (s, 3H), 3.36 (m, 2H), 4.44 (m, 1H), 8.11 (d, 2H), 8.47 (s, 1H), 8.56 (d, 2H), 8.79 (s, 1H). Exact mass calculated for C$_{17}$H$_{20}$N$_6$O$_2$S 372.14, found 373.2 (MH$^+$)

Step 2: Preparation of 4-[1-(4-Methanesulfonyl-phenyl)-1H-pyrazolo[3,4-d]pyrimidin-4-ylamino]-piperidine-1-carboxylic acid isopropyl ester (Compound A12)

Compound A12 was prepared in a similar manner as described in Example 9.4. $^1$H NMR (CDCl$_3$, 400MHz) δ 1.27 (d, 6H), 1.89 (m, 2H), 2.14 (m, 2H), 2.92 (m, 2H), 3.12 (s, 3H), 4.01 (m, 2H), 4.26 (m, 2H), 4.95 (m, 1H), 8.14 (d, 2H), 8.23 (s, 1H), 8.33 (s, 1H), 8.46 (d, 2H), 11.88 (s, 1H). Exact mass calculated for C$_{21}$H$_{26}$N$_6$O$_4$S 458.17 found 459.4 (MH$^+$).

Example 9.112

Preparation of 4-[1-(4-Methanesulfonyl-phenyl)-1H-pyrazolo[3,4-d]pyrimidin-4-ylamino]-piperidine-1-carboxylic acid isobutyl ester (Compound A13)

Compound A13 was prepared in a similar manner as described in Example 9.4. $^1$H NMR (CDCl$_3$, 400MHz) δ 0.96 (d, 6H), 1.57 (m, 2H), 1.97 (m, 2H), 2.22 (m, 2H), 3.01 (m, 2H), 3.12 (s, 3H), 3.90 (d, 2H), 4.25 (m, 2H), 4.38 (m, 1H), 8.09 (d, 2H), 8.15 (s, 1H), 8.49 (s, 1H), 8.57 (d, 2H), 11.88 (s, 1H). Exact mass calculated for C$_{22}$H$_{28}$N$_6$O$_4$S 472.19 found 473.4 (MH$^+$).

Example 9.113

Preparation of {3-[1-(4-Methanesulfonyl-phenyl)-1H-pyrazolo[3,4-d]pyrimidin-4-ylamino]-piperidin-1-yl}-(6-methyl-pyridin-3-yl)-methanone (Compound A55)

Step 1: Preparation of [1-(4-methanesulfonyl-phenyl)-1H-pyrazolo[3,4-d]pyrimidin-4-yl]-piperidin-3-yl-amine In a 20 mL round-bottomed flask was placed a stir bar, compound A24 (215 mg) and acetonitrile (8 mL). After the compound was dissolved, 4M HCl in 1,4-dioxane (2 mL) was added under nitrogen and the mixture was stirred at room temperature for 20 minutes. The solution was concentrated to about 60% of the original volume. The precipitate was isolated to give [1-(4-methanesulfonyl-phenyl)-1H-pyrazolo[3,4-d]pyrimidin-4-yl]-piperidin-3-yl-amine. $^1$H NMR (DMSO-$d_6$, 400MHz) δ 1.98 (m, 2H), 2.11 (m, 2H), 3.02 (m, 2H), 3.26 (s, 3H), 3.36 (m, 2H), 4.44 (m, 1H), 8.11 (d, 2H), 8.47 (s, 1H), 8.56 (d, 2H), 8.79 (s, 1H). Exact mass calculated for $C_{17}H_{20}N_6O_2S$ 372.14, found 373.2 (MH$^+$)

Step 2: Preparation of {3-[1-(4-Methanesulfonyl-phenyl)-1H-pyrazolo[3,4-d]pyrimidin-4-ylamino]-piperidin-1-yl}-(6-methyl-pyridin-3-yl)-methanone (Compound A55)

Compound A55 was prepared in a similar manner as described in Example 9.25. $^1$H NMR (DMSO-$d_6$, 400MHz) δ 1.67 (m, 1H), 1.77 (m, 1H), 1.97 (m, 1H), 2.11 (m, 1H), 2.55 (s, 3H), 3.20 (m, 1H), 3.26 (s, 3H), 3.50 (m, 1H), 3.80 (m, 1H), 4.05 (m, 1H), 4.19 (m, 1H), 4.34 (m, 1H), 4.61 (m, 1H), 7.53 (m, 1H), 8.05 (m, 1H), 8.11 (d, 2H), 8.32 (m, 1H), 8.41 (m, 1H), 8.55 (m, 2H), 8.64 (m, 1H). Exact mass calculated for $C_{24}H_{25}N_7O_3S$ 491.17, found 492.3 (MH$^+$).

Example 9.114

Preparation of {3-[1-(4-Methanesulfonyl-phenyl)-1H-pyrazolo[3,4-d]pyrimidin-4-ylamino]-piperidin-1-yl}-(2-methyl-pyridin-3-yl)-methanone (Compound A56)

Compound A56 was prepared in a similar manner as described in Example 9.25. $^1$H NMR (DMSO-$d_6$, 400MHz) δ 1.70 (m, 1H), 1.77 (m, 1H), 1.97 (m, 1H), 2.11 (m, 1H), 2.33 (m, 1H), 2.55 (m, 1H), 3.10 (m, 2H), 3.26 (s, 3H), 3.50 (m, 1H), 4.05 (m, 1H), 4.10 (m, 1H), 4.34 (m, 1H), 4.56 (m, 1H), 7.53 (m, 1H), 8.11 (d, 2H), 8.13 (m, 1H), 8.40 (m, 1H), 8.51 (m, 1H), 8.55 (m, 2H), 8.57 (m, 2H). Exact mass calculated for $C_{24}H_{25}N_7O_3S$ 491.17, found 492.3 (MH$^+$).

Example 9.115

Preparation of {3-[1-(4-Methanesulfonyl-phenyl)-1H-pyrazolo[3,4-d]pyrimidin-4-ylamino]-piperidin-1-yl}-(5-methyl-pyridin-3-yl)-methanone (Compound A57)

Compound A57 was prepared in a similar manner as described in Example 9.25. $^1$H NMR (DMSO-$d_6$, 400MHz) δ 1.67 (m, 1H), 1.80 (m, 1H), 1.97 (m, 1H), 2.09 (m, 1H), 2.33 (m, 1H), 2.40 (m, 1H), 2.69 (m, 2H), 3.26 (s, 3H), 3.40 (m, 1H), 3.70 (m, 1H), 4.17 (m, 2H), 4.10 (m, 1H), 4.34 (m, 1H), 4.56 (m, 1H), 7.64 (m, 1H), 8.11 (d, 2H), 8.20 (m, 1H), 8.35 (m, 1H), 8.45 (m, 1H), 8.55 (m, 2H), 8.57 (m, 2H). Exact mass calculated for $C_{24}H_{25}N_7O_3S$ 491.17, found 492.3 (MH$^+$).

Example 9.116

Preparation of {3-[1-(4-Methanesulfonyl-phenyl)-1H-pyrazolo[3,4-d]pyrimidin-4-ylamino]-piperidin-1-yl}-pyridin-3-yl-methanone (Compound A58)

Compound A58 was prepared in a similar manner as described in Example 9.25. $^1$H NMR (DMSO-$d_6$, 400MHz) δ 1.67 (m, 1H), 1.80 (m, 1H), 1.97 (m, 1H), 2.09 (m, 1H), 2.33 (m, 1H), 2.40 (m, 1H), 2.69 (m, 2H), 3.26 (s, 3H), 3.40 (m, 1H), 3.70 (m, 1H), 4.17 (m, 2H), 4.10 (m, 1H), 4.34 (m, 1H), 4.56 (m, 1H), 7.64 (m, 1H), 8.11 (d, 2H), 8.20 (m, 1H), 8.35 (m, 1H), 8.45 (m, 1H), 8.55 (m, 2H), 8.57 (m, 2H). Exact mass calculated for $C_{23}H_{23}N_7O_3S$ 477.16, found 478.3 (MH$^+$).

Example 9.117

Preparation of {3-[1-(4-Methanesulfonyl-phenyl)-1H-pyrazolo[3,4-d]pyrimidin-4-ylamino]-piperidin-1-yl}-(1-methyl-1H-pyrrol-3-yl)-methanone (Compound A59)

Compound A59 was prepared in a similar manner as described in Example 9.25. $^1$H NMR (DMSO-$d_6$, 400MHz) δ 1.60 (m, 1H), 1.69 (m, 1H), 1.87 (m, 1H), 2.11 (m, 1H), 2.69 (m, 2H), 3.11 (m, 2H), 3.26 (s, 3H), 3.62 (s, 3H), 4.10 (m, 1H), 4.20 (m, 1H), 4.39 (m, 1H), 6.01 (m, 1H), 6.49 (m, 1H), 6.83 (s, 1H), 8.11 (d, 2H), 8.46 (s, 1H), 8.48 (s, 1H), 8.35 (m, 1H), 8.56 (d, 2H), 8.57 (s, 1H). Exact mass calculated for $C_{23}H_{25}N_7O_3S$ 479.17, found 480.3 (MH$^+$).

Example 9.118

Preparation of {4-[1-(4-Methanesulfonyl-phenyl)-1H-pyrazolo[3,4-d]pyrimidin-4-yloxy]-piperidin-1-yl}-(4-trifluoromethyl-pyridin-3-yl)-methanone (Compound A62)

Compound A62 was prepared in a similar manner as described in Example 9.25. $^1$H NMR (DMSO-$d_6$, 400MHz) δ 1.86 (m, 1H), 1.90 (m, 1H), 2.08 (m, 1H), 2.20 (m, 1H), 3.28 (s, 3H), 3.60 (m, 1H), 3.69 (m, 1H), 4.04 (m, 1H), 4.13 (m, 1H), 5.71 (m, 1H), 7.89 (d, 1H), 8.15 (d, 2H), 8.18 (m, 1H), 8.56 (d, 2H), 8.71 (s, 1H), 8.80 (s, 1H), 8.85 (m, 1H), 8.93 (m, 1H). Exact mass calculated for $C_{24}H_{21}F_3N_6O_4S$ 546.13, found 547.2 (MH$^+$).

Example 9.119

Preparation of (6-tert-Butyl-pyridin-3-yl)-{4-[1-(4-methanesulfonyl-phenyl)-1H-pyrazolo[3,4-d]pyrimidin-4-yloxy]-piperidin-1-yl}-methanone (Compound A70)

Step 1: Preparation of 6-tert-butyl-nicotinonitrile

In an oven dried 500 mL round-bottomed flask equipped with $N_2$ inlet was placed 3-cyanopyridine (2 g) dissolved completely in 100 mL of anhydrous $Et_2O$. To the above solution under $N_2$ was added drop-wise 1.7M t-BuLi in pentane using a syringe. The addition was completed in about 30 min. The resulting mixture was stirred for 20 hrs under $N_2$ at room temperature. The mixture was then cooled in an ice-bath for 20 min. Ice cooled water (300 mL) was added dropwise. The dark greenish suspension cleared out and became light yellowish solution. The solution was extracted with EtOAc/H$_2$O. The organic extracts was concentrated, and purified by column chromatography on silica gel using 15% EtOAc/Hex. $^1$H NMR (CDCl$_3$, 400MHz) δ 1.38 (s, 9H), 7.46 (d, 1H), 7.88 (m, 1H), 8.82 (s, 1H). Exact mass calculated for C$_{10}$H$_{12}$N$_2$ 160.10, found 161.2 (MH$^+$).

Step 2: Preparation of 6-tert-butyl-nicotinic acid

In a 5 mL reaction vial was placed 6-tert-butyl-nicotinonitrile (160 mg) and 1.5 mL of conc. HCl. The mixture was heated overnight at 80° C. The resulting mixture was concentrated under vacuum. The residue was purified by HPLC. $^1$H NMR (CDCl$_3$, 400MHz) δ 1.49 (s, 9H), 7.81 (d, 1H), 8.76 (m, 1H), 9.48 (s, 1H). Exact mass calculated for C$_{10}$H$_{13}$NO$_2$ 179.09, found 180.2 (MH$^+$).

Step 3: Preparation of (6-tert-Butyl-pyridin-3-yl)-{4-[1-(4-methanesulfonyl-phenyl)-1H-pyrazolo[3,4-d]pyrimidin-4-yloxy]-piperidin-1-yl}-methanone (Compound A70)

In a 20 mL reaction vial was placed a stir bar, 4-t-butylnictinic acid (30 mg), O-(7-Azabenzotriazol-1-yl)-N,N,N',N'-tetramethyluronium hexafluorophosphate (60 mg) and DMF (1 mL). The mixture was stirred 10 min at room temperature under N$_2$. 1-(4-Methanesulfonyl-phenyl)-4-(piperidin-4-yloxy)-1H-pyrazolo[3,4-d]pyrimidine (17.2 mg) and triethylamine (100 μl) was added. After stirred 3 hours at room temperature under N$_2$, the reaction mixture was filtered through a syringe filter. The filtrate was concentrated and purified by HPLC. $^1$H NMR (DMSO-d$_6$, 400MHz) δ 1.34 (s, 9H), 1.88 (m, 2H), 2.14 (m, 2H), 3.28 (s, 3H), 3.62 (m, 3H), 4.06 (m, 1H), 5.72 (m, 1H), 7.53 (d, 1H), 7.84 (m, 1H), 8.15 (d, 2H), 8.18 (m, 1H), 8.55 (d, 2H), 8.60 (m, 1H), 8.66 (s, 1H), 8.81 (s, 1H). Exact mass calculated for C$_{27}$H$_{30}$N$_6$O$_4$S 534.20, found 535.4 (MH$^+$).

Example 9.120

Preparation of 4-{[1-(4-Methanesulfonyl-phenyl)-1H-pyrazolo[3,4-d]pyrimidin-4-ylamino]-methyl}-piperidine-1-carboxylic acid tert-butyl ester (Compound A76)

Compound A76 were prepared the same way as described in Example 9.94. $^1$H NMR (CDCl$_3$, 400MHz) δ 1.41 (s, 9H), 1.77 (m, 2H), 1.86 (m, 1H), 2.69 (m, 2H), 3.07 (s, 3H), 3.54 (m, 3H), 4.12 (m, 2H), 6.44 (m, 1H), 8.03 (d, 2H), 8.16 (s, 1H), 8.45 (s, 1H), 8.55 (d, 2H). Exact mass calculated for C$_{23}$H$_{30}$N$_6$O$_4$S 486.20, found 487.4 (MH$^+$)

Example 9.121

Preparation of 4-({[1-(4-Methanesulfonyl-phenyl)-1H-pyrazolo[3,4-d]pyrimidin-4-yl]-methyl-amino}-methyl)-piperidine-1-carboxylic acid tert-butyl ester (Compound A75)

Step 1: Preparation of 4-methylcarbamoyl-piperidine-1-carboxylic acid tert-butyl ester To a stirred solution of 1-t-butoxycarbonyl-iso-nipecotic acid (10 g) and Et$_3$N (5.92 mL) in THF (32 mL) was added drop-wise iso-butylchloroformate (5.66 mL) at 0° C. The resulting mixture was stirred at 0° C. for 30 min before diluted with THF (120 mL) and added 2M methylamine (80 mL). The reaction mixture was stirred overnight at room temperature. Excess THF was removed under vacuum. The residue was taken into H$_2$O and extracted into EtOAc. The organic extracts were washed with 1N NaOH, followed by brine. After dried over Na$_2$SO$_4$, it was concentrated to give the crude product.

Step 2: Preparation of 4-Methylaminomethyl-piperidine-1-carboxylic acid tert-butyl ester In a 32 mL reaction vial was placed a stir bar and 4-methylcarbamoyl-piperidine-1-carboxylic acid tert-butyl ester (0.97 g) dissolved in 12.8 mL anhydrous THF. The solution was cooled to 0° C. with an ice-bath. A 65% toluene solution of Red-Al (3.66 mL) was added dropwise at 0° C. After the addition was completed, the mixture was stirred under N$_2$ at room temperature until all the starting materials were just consumed. The reaction mixture was worked up with H$_2$O at 0° C., extracted with EtOAc (×3). The EtOAc extract was washed with saturated NaCl solution. After drying over Na$_2$SO$_4$, the organic layer was concentrated to give 550 mg of crude product.

Step 3: Preparation of 4-({[1-(4-Methanesulfonyl-phenyl)-1H-pyrazolo[3,4-d]pyrimidin-4-yl]-methyl-amino}-methyl)-piperidine-1-carboxylic acid tert-butyl ester (Compound A75)

Compound A75 was prepared the in a similar manner as described in 9.94 by using 4-chloro-1-(4-methanesulfonyl-phenyl)-1H-pyrazolo[3,4-d]pyrimidine and methylaminomethyl-piperidine-1-carboxylic acid tert-butyl ester and purified by preparative thin layer chromatography. $^1$H NMR (CDCl$_3$, 400MHz) δ 1.27 (m, 2H), 1.44 (s, 9H), 1.63 (m, 2H), 2.03 (m, 1H), 2.69 (m, 2H), 3.09 (s, 3H), 3.49 (s, 3H), 4.12 (m, 2H), 8.08 (d, 2H), 8.18 (s, 1H), 8.49 (s, 1H), 8.57 (d, 2H). Exact mass calculated for C$_{24}$H$_{32}$N$_6$O$_4$S 500.22, found 501.4 (MH$^+$).

Example 9.122

Preparation of 3-{[1-(4-Methanesulfonyl-phenyl)-1H-pyrazolo[3,4-d]pyrimidin-4-ylamino]-methyl}-piperidine-1-carboxylic acid tert-butyl ester (Compound A77)

Compound A77 was prepared in a similar manner as described in Example 9.94 and purified by preparative thin layer chromatography using 50% EtOAc/Hex. $^1$H NMR (CDCl$_3$, 400MHz) δ 1.44 (s, 9H), 1.83 (m, 2H), 1.91 (m, 2H), 2.73 (m, 2H), 3.10 (s, 3H), 3.59 (s, 3H), 4.13 (m, 2H), 8.08 (d, 2H), 8.15 (s, 1H), 8.49 (s, 1H), 8.57 (d, 2H). Exact mass calculated for C$_{23}$H$_{30}$N$_6$O$_4$S 486.20, found 487.4 (MH$^+$).

Example 9.123

Preparation of 4-({[1-(2-Fluoro-4-methanesulfonyl-phenyl)-1H-pyrazolo[3,4-d]pyrimidin-4-yl]-isopropyl-amino}-methyl)-piperidine-1-carboxylic acid isopropyl ester (Compound A236)

Compound A236 was prepared in a similar manner as described in Example 9.121 as a sticky oil (509 mg, 80%). Exact mass calculated for C$_{25}$H$_{33}$FN$_6$O$_4$S 532.2, found 533.3 (MH$^+$).

Example 9.124

Preparation of 4-({Ethyl-[1-(4-methanesulfonyl-phenyl)-1H-pyrazolo[3,4-d]pyrimidin-4-yl]-amino}-methyl)-piperidine-1-carboxylic acid tert-butyl ester (Compound A78)

Step 1: Preparation of 4-(acetylamino-methyl)-piperidine-1-carboxylic acid tert-butyl ester In a 32 mL reaction vial was placed a stir bar, $Et_3N$ (0.5 mL) and 4-aminomethyl-piperidine-1-carboxylic acid tert-butyl ester (1.3 g) dissolved in 10 mL anhydrous THF. Acetic acid chloride (0.48 g) was added dropwise through a syringe at 0° C. The mixture was stirred 2 hrs at room temperature. After worked up with $H_2O$ at 0° C., it was extracted with EtOAc. The organic extracts were washed with 2M NaOH solution, $NaHSO_4$ and saturated NaCl solution. After dried over $Na_2SO_4$, it was concentrated to give crude 4-(acetylamino-methyl)-piperidine-1-carboxylic acid tert-butyl ester. $^1H$ NMR ($CDCl_3$, 400 MHz) δ 1.14 (m, 2H), 1.45 (s, 9H), 1.65 (m, 2H), 1.68 (m, 1H), 1.99 (s, 3H), 2.66 (m, 2H), 3.14 (m, 2H), 4.12 (m, 2H), 5.51 (m, 1H). Exact mass calculated for $C_{13}H_{24}N_2O_3$ 256.18, found 257.4 ($MH^+$).

Step 2: Preparation of 4-Ethylaminomethyl-piperidine-1-carboxylic acid tert-butyl ester 4-Ethylaminomethyl-piperidine-1-carboxylic acid tert-butyl ester was prepared in a similar manner as described in Example 9.121. $^1H$ NMR ($CDCl_3$, 400MHz) δ 1.11 (m, 3H), 1.26 (m, 2H), 1.45 (s, 9H), 1.64 (m, 1H), 1.71 (m, 2H), 2.50 (m, 2H), 2.65 (m, 4H), 4.12 (m, 2H). Exact mass calculated for $C_{13}H_{26}N_2O_2$ 242.20, found 243.4 ($MH^+$).

Step 3: Preparation of 4-({Ethyl-[1-(4-methanesulfonyl-phenyl)-1H-pyrazolo[3,4-d]pyrimidin-4-yl]-amino}-methyl)-piperidine-1-carboxylic acid tert-butyl ester (Compound A78)

Compound A78 was prepared in a similar manner as described in Example 9.121. $^1H$ NMR ($CDCl_3$, 400MHz) δ 1.26 (m, 3H), 1.36 (m, 2H), 1.40 (s, 9H), 1.63 (m, 2H), 2.03 (m, 1H), 2.69 (m, 2H), 3.09 (s, 3H), 3.68 (m, 2H), 3.82 (m, 2H), 4.12 (m, 2H), 8.08 (d, 2H), 8.09 (s, 1H), 8.46 (s, 1H), 8.57 (d, 2H). Exact mass calculated for $C_{25}H_{34}N_6O_4S$ 514.24, found 515.4 ($MH^+$).

Example 9.125

Preparation of 4-({Ethyl-[1-(2-fluoro-4-methane-sulfonyl-phenyl)-1H-pyrazolo[3,4-d]pyrimidin-4-yl]-amino}-methyl)-piperidine-1-carboxylic acid tert-butyl ester (Compound A88)

Compound A88 was prepared in a similar manner as described in Example 9.121. $^1H$ NMR ($CDCl_3$, 400MHz) δ 1.26 (m, 3H), 1.36 (m, 2H), 1.40 (s, 9H), 1.63 (m, 2H), 2.03 (m, 1H), 2.69 (m, 2H), 3.09 (s, 3H), 3.68 (m, 2H), 3.82 (m, 2H), 4.12 (m, 2H), 7.90 (m, 1H), 7.93 (m, 1H), 7.96 (m, 1H), 8.12 (s, 1H), 8.41 (s, 1H). Exact mass calculated for $C_{25}H_{33}FN_6O_4S$ 532.23, found 533.4 ($MH^+$).

Example 9.126

Preparation of 4-{1-[2-(2-Dimethylamino-ethoxy)-4-methanesulfonyl-phenyl]-1H-pyrazolo[3,4-d]pyrimidin-4-yloxy}-piperidine-1-carboxylic acid tert-butyl ester (Compound A79)

Step 1: Preparation of 1-[2-(2-dimethylamino-ethoxy)-4-methanesulfonyl-phenyl]-1H-pyrazolo[3,4-d]pyrimidin-4-ol In a reaction vial was placed a stir bar and NaH (60% in oil, 90 mg). Dimethylaminoethanol (200 mg) was dissolved in dioxane (1.5 mL) and added to the reaction vial under $N_2$. The mixture was stirred at room temperature for 1 hour before 1-(2-fluoro-4-methanesulfonyl-phenyl)-1H-pyrazolo[3,4-d]pyrimidin-4-ol (50 mg) was added. The reaction mixture was heated at 70° C. for 60 hours. The resulting solution was concentrated under vacuum and 1-[2-(2-dimethylamino-ethoxy)-4-methanesulfonyl-phenyl]-1H-pyrazolo[3,4-d]pyrimidin-4-ol was purified by preparative HPLC. $^1H$ NMR (DMSO-$d_6$, 400MHz) δ 2.68 (s, 6H), 3.36 (s, 3H), 3.40 (m, 2H), 4.54 (m, 2H), 7.74 (m, 1H), 7.78 (m, 1H), 7.85 (m, 1H), 8.10 (s, 1H), 8.37 (s, 1H), 9.75 (s, 1H), 12.5 (s, 1H). Exact mass calculated for $C_{16}H_{19}N_5O_4S$ 377.12, found 377.9 ($MH^+$).

Step 2: Preparation of {2-[2-(4-chloro-pyrazolo[3,4-d]pyrimidin-1-yl)-5-methanesulfonyl-phenoxy]-ethyl}-dimethyl-amine In a reaction vial was placed a stir bar, 1-[2-(2-dimethy-lamino-ethoxy)-4-methanesulfonyl-phenyl]-1H-pyrazolo[3,4-d]pyrimidin-4-ol (50 mg), $POCl_3$ (0.5 mL) and N,N-dimethylaniline (15 μl). The reaction mixture was stirred at 100° C. for 1 hour. Upon cooling the reaction mixture to the room temperature, a white precipitate formed. The mixture was left sealed over the weekend at room temperature. After concentrated under the vacuum, the residue was washed with $Et_2O$ and filtered to give {2-[2-(4-chloro-pyrazolo[3,4-d]pyrimidin-1-yl)-5-methanesulfonyl-phenoxy]-ethyl}-dimethyl-amine as a white solid. Exact mass calculated for $C_{16}H_{18}ClN_5O_3S$ 395.08, found 396 ($MH^+$).

Step 3: Preparation of 4-{1-[2-(2-Dimethylamino-ethoxy)-4-methanesulfonyl-phenyl]-1H-pyrazolo[3,4-d]pyrimidin-4-yloxy}-piperidine-1-carboxylic acid tert-butyl ester (Compound A79)

In a reaction vial was place a stir bar, NaH (60% in oil, 110 mg), 4-hydroxy-piperidine-1-carboxylic acid tert-butyl ester (70 mg) and THF (3 mL). The mixture was stirred at room temperature for 15 min under $N_2$. {2-[2-(4-Chloro-pyrazolo[3,4-d]pyrimidin-1-yl)-5-methanesulfonyl-phenoxy]-ethyl}-dimethyl-amine was then added. The mixture was stirred at 80° C. for 30 min. After cooled down to room temperature, the reaction was quenched with $H_2O$ and product was extracted with $CH_2Cl_2$. The organic extracts were concentrated under vacuum. The residue was purified by silica column chromatography using 20% MeOH/$CH_2Cl_2$ as eluent to give 4-{1-[2-(2-dimethylamino-ethoxy)-4-methanesulfonyl-phenyl]-1H-pyrazolo[3,4-d]pyrimidin-4-yloxy}-piperidine-1-carboxylic acid tert-butyl ester. $^1H$ NMR ($CDCl_3$, 400MHz) δ 1.49 (s, 9H), 1.88 (m, 2H), 2.10 (m, 2H), 2.20 (s, 6H), 2.67 (t, 2H), 3.10 (s, 3H), 3.32 (m, 2H), 3.87 (m, 2H), 4.28 (t, 2H), 5.59 (m, 1H), 7.70 (m, 3H), 8.25 (s, 1H), 8.54 (s, 1H). Exact mass calculated for $C_{26}H_{36}N_6O_6S$ 560.24, found 561.4 ($MH^+$).

Example 9.127

Preparation of 4-({(2-Dimethylamino-ethyl)-[1-(4-methanesulfonyl-phenyl)-1H-pyrazolo[3,4-d]pyrimidin-4-yl]-amino}-methyl)-piperidine-1-carboxylic acid tert-butyl ester (Compound A98)

Step 1: Preparation of 4-(2-dimethylamino-ethylcarbamoyl)-piperidine-1-carboxylic acid tert-butyl ester 4-(2-Dimethylamino-ethylcarbamoyl)-piperidine-1-carboxylic acid tert-butyl ester was prepared from 1-t-butoxycarbonyl-iso-nipecotic acid (5 g), iso-butylchloroformate (2.83 mL) and N,N-dimethyl-1,2-ethylenediamine (2.63 mL). Exact mass calculated for $C_{15}H_{29}N_3O_3$ 299.22, found 300.4 (MH$^+$).

Step 2: Preparation of 4-[(2-dimethylamino-ethylamino)-methyl]-piperidine-1-carboxylic acid tert-butyl ester 4-[(2-Dimethylamino-ethylamino)-methyl]-piperidine-1-carboxylic acid tert-butyl ester was made in a similar manner as described in Example 9.121. Exact mass calculated for $C_{15}H_{31}N_3O_2$ 285.24, found 286.4 (MH$^+$).

Step 3: Preparation of 4-({(2-Dimethylamino-ethyl)-[1-(4-methanesulfonyl-phenyl)-1H-pyrazolo[3,4-d]pyrimidin-4-yl]-amino}-methyl)-piperidine-1-carboxylic acid tert-butyl ester (Compound A98)

Compound A98 was prepared in a similar manner as described in Example 9.121. $^1$H NMR (CDCl$_3$, 400MHz) δ 1.28 (m, 2H), 1.46 (s, 9H), 1.72 (m, 2H), 2.04 (m, 4H), 2.66 (m, 2H), 3.01 (s, 6H), 3.10 (s, 3H), 3.44 (m, 2H), 3.68 (m, 2H), 4.22 (m, 2H), 8.05 (s, 1H), 8.08 (d, 2H), 8.47 (s, 1H), 8.53 (d, 2H), 12.0 (s, 1H). Exact mass calculated for $C_{27}H_{39}N_7O_4S$ 557.28, found 558.4 (MH$^+$).

Example 9.128

Preparation of 4-({(2-Dimethylamino-ethyl)-[1-(2-fluoro-4-methanesulfonyl-phenyl)-1H-pyrazolo[3,4-d]pyrimidin-4-yl]-amino}-methyl)-piperidine-1-carboxylic acid tert-butyl ester (Compound A99)

Compound A99 was prepared in a similar manner as described in Example 9.127. $^1$H NMR (CDCl$_3$, 400MHz) δ 1.28 (m, 2H), 1.47 (s, 9H), 1.72 (m, 2H), 2.04 (m, 2H), 2.66 (m, 2H), 3.01 (s, 6H), 3.13 (s, 3H), 3.46 (m, 2H), 3.69 (m, 2H), 4.22 (m, 4H), 8.05 (s, 1H), 7.88 (m, 1H), 7.91 (m, 1H), 7.94 (m, 1H), 8.11 (s, 1H), 8.44 (s, 1H), 12.0 (s, 1H). Exact mass calculated for $C_{27}H_{38}FN_7O_4S$ 575.27, found 576.4 (MH$^+$).

Example 9.129

Preparation of {4-[1-(2-Fluoro-4-methanesulfonyl-phenyl)-1H-pyrazolo[3,4-d]pyrimidin-4-yloxy]-piperidin-1-yl}-(4-trifluoromethoxy-phenyl)-methanone (Compound A189)

In a 50 mL round-bottomed flask was placed 1-(2-fluoro-4-methanesulfonyl-phenyl)-4-(piperidin-4-yloxy)-1H-pyrazolo[3,4-d]pyrimidine (300 mg, 0.7 mmol) and triethylamine (584 μl). DMF (6 mL) was added to completely dissolve the solid material. The reaction flask was immersed in an ice-bath. Trifluoromethoxybenzoyl chloride (180 mg, 0.8 mmol) was added to the solution and the mixture was stirred 2 h under N$_2$ at 0° C. After all of the starting amine was completely converted as indicated by LCMS, the reaction was stopped by quenching with water. The reaction mixture was then concentrated under vacuum and purified by preparative HPLC. $^1$H NMR (CDCl$_3$, 400MHz) δ 1.98 (m, 1H), 2.12 (m, 2H), 2.27 (m, 1H), 3.13 (s, 3H), 3.51 (m, 1H), 3.79 (m, 2H), 4.21 (m, 1H), 5.76 (m, 1H), 7.31 (d, 2H), 7.52 (d, 2H), 7.95 (m, 3H), 8.36 (s, 1H), 8.65 (s, 1H). Exact mass calculated for $C_{25}H_{21}F_4N_5O_5S$ 579.12, found 580.2 (MH$^+$).

Example 9.130

Preparation of {4-[1-(3,5-Bis-trifluoromethyl-phenyl)-1H-pyrazolo[3,4-d]pyrimidin-4-ylamino]-cyclohexyl}-carbamic acid tert-butyl ester (Compound A44)

1-(3,5-Bis-trifluoromethyl-phenyl)-4-chloro-1H-pyrazolo[3,4-d]pyrimidine (147 mg, 0.4 mmol), (4-amino-cyclohexyl)-carbamic acid tert-butyl ester (0.44 mmole, 1.1 eq) and diisopropylethyl amine (0.44 mmol, 1.1 eq) were dissolved in THF (3 mL) and then stirred at room temperature over night. THF was removed in vacuo and the solid residue was re-dissolved in 30/70 mixture of water and ACN gave yellow solid. The solid was washed with water and dried in vacuo provided compound A44 as creamy green solid (179 mg, 82%). $^1$H NMR (CDCl$_3$, 400MHz) δ 1.43 (s, 9H), 1.75 (m, 2H), 1.98-1.97 (m, 2H), 2.04 (m, 2H), 2.95 (sb, 2H), 4.12 (q, 1H), 4.62 (m, 1H), 7.80 (s, 1H), 8.09 (s, 1H), 8.50 (s, 1H), 8.94 (s, 2H). Exact mass calculated for $C_{24}H_{26}F_6N_6O_2$ 544.2, Found 545.5 (MH$^+$).

Example 9.131

Preparation of 4-[1-(3,5-Bis-trifluoromethyl-phenyl)-1H-pyrazolo[3,4-d]pyrimidin-4-yloxy]-piperidine-1-carboxylic acid tert-butyl ester (Compound A46)

1-(3,5-Bis-trifluoromethyl-phenyl)-4-chloro-1H-pyrazolo[3,4-d]pyrimidine (73 mg, 0.2 mmole), 4-hydroxy-piperidine-1-carboxylic acid tert-butyl ester (0.3 mmole, 1.5 eq) and NaH (1.2 mmol, 6 eq) were dissolved in THF (3 mL) and then stirred at room temperature overnight. THF solvent was removed in vacuo and the oily solid residue was re-dissolved in water and extracted with ethyl acetate provided compound A46 as greenish yellow oil (111 mg, 90%). $^1$H NMR (CDCl$_3$, 400MHz) δ 1.48 (s, 9H), 1.88-1.84 (m, 2H), 2.09 (m, 2H), 3.35-3.29 (m, 2H), 3.87-3.80 (m, 2H), 5.62-5.59 (m, 1H), 7.81 (s, 1H), 8.26 (s, 1H), 8.69 (s, 1H), 8.96 (s, 2H). Exact mass calculated for $C_{23}H_{23}F_6N_5O_3$ 531.17, found 532.2 (MH$^+$).

Example 9.132

Preparation of 4-{1-[4-(2-Methanesulfonyl-ethyl)-phenyl]-1H-pyrazolo[3,4-d]pyrimidin-4-yloxy}-piperidine-1-carboxylic acid tert-butyl ester (Compound A45).

Compound A45 was prepared in a similar manner as described in Example 9.1 as creamy yellow solid (75 mg, 100%). $^1$H NMR (CDCl$_3$, 400 MHz) δ 1.50 (s, 9H), 1.87-1.85 (m, 2H), 2.11-2.09 (m, 2H), 2.88 (s, 3H), 3.28-3.23 (m, 2H), 3.36-3.31 (m, 4H), 3.88 (m, 2H), 5.62-5.59 (m, 1H), 7.41 (d, 2H), 8.18 (d, 2H), 8.21 (s, 1H), 8.62 (s, 1H). Exact mass calculated for $C_{24}H_{31}N_5O_5S$ 501.2, found 502.3 (MH$^+$).

Example 9.133

Preparation of 4-[1 (3-Fluoro-phenyl)-1H-pyrazolo[3,4-d]pyrimidin-4-yloxy]-piperidine-1-carboxylic acid tert-butyl ester (Compound A50)

Compound A50 was prepared in a similar manner as described in Example 9.1 as a yellow solid (86 mg, 100%). $^1$H NMR (CDCl$_3$, 400MHz) δ 1.49 (s, 9H), 1.89-1.84 (m, 2H), 2.09 (m, 2H), 3.36-3.29 (m, 2H), 3.85 (m, 2H), 5.59 (m, 1H), 7.07-7.03 (m, 1H), 7.52-7.46 (m, 1H), 8.08 (t, 2H), 8.21 (s, 1H), 8.64 (s, 1H). Exact mass calculated for C$_{21}$H$_{24}$FN$_5$O$_3$ 413.19, found 414.4 (MH$^+$).

Example 9.134

Preparation of {4-[1-(3-Fluoro-phenyl)-1H-pyrazolo[3,4-d]pyrimidin-4-ylamino]-cyclohexyl}-carbamic acid tert-butyl ester (Compound A53)

Compound A53 was made in a similar manner as described in Example 9.130 as a white solid (108 mg, 100%). $^1$H NMR (CDCl$_3$, 400MHz) δ 1.47 (s, 9H), 1.93-1.85 (m, 4H), 2.00-1.97 (m, 4H), 3.79 (sb, 1H), 4.02 (sb, NH), 4.85 (sb, 1H), 7.14 (t, 1H), 7.52 (tt, 1H), 7.90 (d, 1H), 7.95 (d, 1H), 8.19 (s, 1H), 8.26 (s, 1H), 11.5 (s, NH). Exact mass calculated for C$_{22}$H$_{27}$FN$_6$O$_2$ 426.22, found 427.4 (MH$^+$).

Example 9.135

Preparation of {4-[1-(2,4-Difluoro-phenyl)-1H-pyrazolo[3,4-d]pyrimidin-4-ylamino]-cyclohexyl}-carbamic acid tert-butyl ester (Compound A52)

Compound A52 was prepared in a similar manner as described in Example 9.130 as white solid (63 mg, 71%). $^1$H NMR (CDCl$_3$, 400MHz) δ 1.47 (s, 9H), 1.93-1.87 (m, 4H), 2.01-1.98 (m, 4H), 3.79 (sb, 1H), 4.03 (sb, 1H), 4.88 (sb, 1H), 7.10 (t, 2H), 7.59-7.53 (m, 1H), 8.20 (s, 1H), 8.23 (s, 1H), 11.5 (s, 1H). Exact mass calculated for C$_{22}$H$_{26}$F$_2$N$_6$O$_2$ 444.2, found 445.5 (MH$^+$).

Example 9.136

Preparation of 4-[1-(2,4-Difluoro-phenyl)-1H-pyrazolo[3,4-d]pyrimidin-4-yloxy]-piperidine-1-carboxylic acid tert-butyl ester (Compound A51)

Compound A51 was prepared in a similar manner as described in Example 9.131 as a white solid (89 mg, 99%). $^1$H NMR (CDCl$_3$, 400MHz) δ 1.49 (s, 9H), 1.88-1.84 (m, 2H), 2.09 (m, 2H), 3.36-3.30 (m, 2H), 3.86 (m, 2H), 5.60-5.58 (m, 1H), 7.10-7.05 (m, 2H), 7.61 (m, 1H), 8.26 (s, 1H), 8.58 (s, 1H). Exact mass calculated for C$_{21}$H$_{23}$F$_2$N$_5$O$_3$ 431.2, found 432.2 (MH$^+$).

Example 9.137

Preparation of N-[1-(4-Methanesulfonyl-phenyl)-1H-pyrazolo[3,4-d]pyrimidin-4-yl]-cyclohexane-1,4-diamine (Compound A54)

{4-[1-(4-Methanesulfonyl-phenyl)-1H-pyrazolo[3,4-d]pyrimidin-4-ylamino]-cyclohexyl}-carbamic acid tert-butyl ester (30 mg, 0.06 mmol) was dissolved in 4M HCl in dioxane (2 mL) and then stirred overnight at 40° C. The resulting solution was evaporated to provide compound A54 as a white solid (24 mg, 100%). Exact mass calculated for C$_{18}$H$_{22}$N$_6$O$_2$S 386.2, found 387.2 (MH$^+$).

Example 9.138

Preparation of {4-[1-(4-Methanesulfonyl-phenyl)-1H-pyrazolo[3,4-d]pyrimidin-4-yloxy]-cyclohexyl}-carbamic acid tert-butyl ester (Compound A60)

Compound A60 was prepared in a similar manner as described in Example 9.131 as a white solid (45 mg, 46%). $^1$H NMR (CDCl$_3$, 400MHz) δ 1.21-1.12 (m, 2H), 1.44 (s, 9H), 1.72-1.67 (m, 2H), 2.14 (db, 2H), 2.25 (db, 2H), 3.10 (s, 3H), 3.46-3.42 (m, 1H), 4.47 (sb, 1H), 5.38-5.33 (m, 1H), 8.10 (d, 2H), 8.25 (s, 1H), 8.60 (d, 2H), 8.65 (s, 1H). Exact mass calculated for C$_{23}$H$_{29}$N$_5$O$_5$S 487.2, found 488.4 (MH$^+$).

Example 9.139

Preparation of N-[1-(2,4-Difluoro-phenyl)-1H-pyrazolo[3,4-d]pyrimidin-4-yl]-cyclohexane-1,4-diamine (Compound A61)

Following the general deprotection method in Example 9.6, compound A61 was obtained as yellow solid (11 mg, 100%). Exact mass calculated for C$_{17}$H$_{18}$F$_2$N$_6$ 344.2, found 345.2 (MH$^+$).

Example 9.140

Preparation of 4-[1-(2,5-Difluoro-phenyl)-1H-pyrazolo[3,4-d]pyrimidin-4-yloxy]-piperidine-1-carboxylic acid tert-butyl ester (Compound A86)

Compound A86 was prepared in a similar manner as described in Example 9.131 as a white solid (29 mg, 45%). $^1$H NMR (CDCl$_3$, 400MHz) δ 1.49 (s, 9H), 1.89-1.84 (m, 2H), 2.12-2.07 (m, 2H), 3.36-3.29 (m, 2H), 3.89-3.58 (m, 2H), 5.60-5.58 (m, 1H), 7.19-7.17 (m, 1H), 7.31-7.28 (m, 1H), 7.43-7.39 (m, 1H), 8.27 (s, 1H), 8.60 (s, 1H). Exact mass calculated for C$_{21}$H$_{23}$F$_2$N$_5$O$_3$ 431.18, found 432.3 (MH$^+$).

Example 9.141

Preparation of 4-[({1-[4-(2-Methanesulfonyl-ethyl)-phenyl]-1H-pyrazolo[3,4-d]pyrimidin-4-yl}-methyl-amino)-methyl]-piperidine-1-carboxylic acid tert-butyl ester (Compound A92)

Compound A92 was prepared in a similar manner as described in Example 9.94 as a yellow solid (33 mg, 42%). $^1$H NMR (CDCl$_3$, 400MHz) δ 1.33-1.28 (m, 2H), 1.47 (s, 9H), 1.73 (m, 1H), 2.07 (m, 1H), 2.81 (m, 2H), 2.90 (s, 3H), 3.27-3.23 (m, 2H), 3.36-3.33 (m, 2H), 3.50 (sb, 3H), 3.79 (m, 2H), 4.15 (m, 2H), 7.41 (d, 2H), 8.13-1.11 (m, 3H), 8.50 (sb, 1H). Exact mass calculated for C$_{26}$H$_{36}$N$_6$O$_4$S 528.2, found 529.3 (MH$^+$).

Example 9.142

Preparation of 4-({[1-(2,5-Difluoro-phenyl)-1H-pyrazolo[3,4-d]pyrimidin-4-yl]-methyl-amino}-methyl)-piperidine-1-carboxylic acid tert-butyl ester (Compound A93)

Compound A93 was prepared in a similar manner as described in Example 9.94 as a yellow solid (7 mg, 10%). $^1$H NMR (CDCl$_3$, 400MHz) δ 1.30 (m, 2H), 1.46 (s, 9H), 1.72 (m, 2H), 2.11-2.07 (m, 1H), 2.71 (m, 2H), 3.58 (s, 3H), 3.81 (m, 2H), 4.15 (m, 2H), 7.24-7.20 (m, 1H), 7.36-7.27 (m, 2H), 8.28 (s, 1H), 8.51 (s, 1H). Exact mass calculated for C$_{23}$H$_{28}$F$_2$N$_6$O$_2$ 458.2, found 459.4 (MH$^+$).

Example 9.143

Preparation of 4-[1-(2-Methyl-4-propylamino-phenyl)-1H-pyrazolo[3,4-d]pyrimidin-4-yloxy]-piperidine-1-carboxylic acid isopropyl ester (Compound A215)

4-[1-(4-Iodo-2-methyl-phenyl)-1H-pyrazolo[3,4-d]pyrimidin-4-yloxy]-piperidine-1-carboxylic acid isopropyl ester (78 mg, 0.15 mmol), propyl amine (0.75 mmole, 5 eq), proline (0.27 mole, 1.8 eq), copper iodide (0.15 mmole, 1 eq), and potassium carbonate (0.15 mmole, 1 eq) were dissolved in DMSO (2 mL) and then stirred at 100° C. for 30 mins in microwave. The crude was purified through Prep-TLC (Hexane:EthylAcetate=1:1, Rf=0.7) to provid compound A215 as white solid (36 mg, 53%). $^1$H NMR 400MHz CDCl$_3$ δ (ppm): 8.51 (s, 1H); 8.20 (s, 1H); 7.40-7.36 (m, 1H); 7.30-7.21 (m, 2H); 5.63-5.58 (m, 1H); 4.95 (sep, 1H); 3.89 (m, 2H); 3.41-3.35 (m, 2H); 3.23-3.19 (m, 2H); 2.16-2.03 (m, 4H); 1.89-1.86 (m, 2H); 1.27 (d, 6H); 1.04 (t, 2H). Exact mass calculated for C$_{24}$H$_{32}$N$_6$O$_3$ 452.2, found LCMS (ESI) m/z 453.4 (M+H$^+$, 100%).

Example 9.144

Preparation of 4-[1-(4-Isopropylamino-2-methyl-phenyl)-1H-pyrazolo[3,4-d]pyrimidin-4-yloxy]-piperidine-1-carboxylic acid isopropyl ester (Compound A216)

Compound A216 was prepared in a similar manner as described in Example 9.143 as yellow oil (25 mg, 38%). $^1$H NMR (CDCl$_3$, 400MHz) δ 1.28 (d, 6H), 1.42 (d, 6H), 1.93-1.88 (m, 2H), 2.14-2.11 (m, 2H), 2.21 (s, 3H), 3.44-3.37 (m, 2H), 3.69 (sep, 1H), 3.93-3.89 (m, 2H), 4.96 (sep, 1H), 5.63 (m, 1H), 7.50 (s, 2H), 7.54 (s, 1H), 8.24 (s, 1H), 8.57 (s, 1H). Exact mass calculated for C$_{24}$H$_{32}$N$_6$O$_3$ 452.2, found 453.4 (MH$^+$).

Example 9.145

Preparation of 4-[1-(2-Methyl-4-morpholin-4-yl-phenyl)-1H-pyrazolo[3,4-d]pyrimidin-4-yloxy]-piperidine-1-carboxylic acid isopropyl ester (Compound A217)

Compound A217 was prepared in a similar manner as described in Example 9.143 as yellow oil (47 mg, 65%). $^1$H NMR (CDCl$_3$, 400MHz) δ 1.28 (d, 6H), 1.94-1.89 (m, 2H), 2.15-2.09 (m, 2H), 2.19 (s, 3H), 3.45-3.39 (m, 2H), 3.53-3.50 (m, 4H), 3.94-3.88 (m, 2H), 4.12-4.10 (m, 4H), 4.96 (sep, 1H), 5.64 (m, 1H), 7.35 (d, 1H), 7.42 (s, 1H), 7.47 (d, 1H), 8.29 (s, 1H), 8.59 (s, 1H). Exact mass calculated for C$_{25}$H$_{32}$N$_6$O$_4$ 480.3, found 481.4 (MH$^+$).

Example 9.146

Preparation of 4-{1-[4-(2-Methoxy-ethylamino)-2-methyl-phenyl]-1H-pyrazolo[3,4-d]pyrimidin-4-yloxy}-piperidine-1-carboxylic acid isopropyl ester (Compound A218)

Compound A218 was prepared in a similar manner as described in Example 9.143 as yellow oil (25 mg, 36%). $^1$H NMR (CDCl$_3$, 400MHz) δ 1.27 (d, 6H), 1.90-1.86 (m, 2H), 2.12-2.03 (m, 2H), 2.12 (s, 3H), 3.40 (s, 3H), 3.45-3.35 (m, 4H), 3.71-3.66 (m, 2H), 3.90 (m, 2H), 4.95 (sep, 1H), 5.62-5.59 (m, 1H), 7.10 (sb, 2H), 7.33 (d, 1H), 8.20 (s, 1H). Exact mass calculated for C$_{24}$H$_{32}$N$_6$O$_4$ 468.3, found 469.4 (MH$^+$).

Example 9.147

Preparation of 4-(1-{4-[(2-Methanesulfonyl-ethyl)-methyl-amino]-2-methyl-phenyl}-1H-pyrazolo[3,4-d]pyrimidin-4-yloxy)-piperidine-1-carboxylic acid isopropyl ester (Compound A219)

Compound A219 was prepared in a similar manner as described in Example 9.143 as white gummy solid (6 mg, 7.5%). Exact mass calculated for C$_{25}$H$_{34}$N$_6$O$_5$S 530.2, found 531.5 (MH$^+$).

Example 9.148

Preparation of (2-{4-[1-(2-Fluoro-4-methanesulfonyl-phenyl)-1H-pyrazolo[3,4-d]pyrimidin-4-yloxy]-piperidin-1-yl}-5-methyl-pyrimidin-4-yl)-dimethyl-amine (Compound A212)

1-(2-Fluoro-4-methanesulfonyl-phenyl)-4-(piperidin-4-yloxy)-1H-pyrazolo[3,4-d]pyrimidine HCl salt (0.3 g, 0.97 mmol) and (2-chloro-6-methyl-pyrimidin-4-yl)-dimethyl-amine (285 mg, 0.97 mmol) were dissolved in DMF (10 mL). The solution was treated with K$_2$CO$_3$ (398 mg, 2.91 mmol) at an ambient temperature. After stirring at 65° C. for five hours, the reaction was poured into H$_2$O (20 mL). The organic compound was extracted with ethyl acetate (30 mL) and washed with brine. The ethyl acetate layer was dried over MgSO$_4$ and concentrated under vacuum. The residue was purified over SiO$_2$ to afford Compound A212 (312 mg, 65.2%). $^1$H NMR (400Mz, DMSO-d$_6$) δ 8.69 (s, 1H), 8.64 (s, 1H), 8.17 (dd, J=8.4, 1.8, 1H), 8.08 (d, J=4.2, 1H), 8.01 (dd, J=8.4, 1.8, 1H), 7.72 (s, 1H), 5.65 (m, 1H), 4.23~4.20 (m, 2H), 3.50~3.46 (m, 2H), 3.39 (s, 3H), 3.00 (s, 6H), 2.13 (s, 3H), 2.10~2.09 (m, 2H), 1.77~1.72 (m, 2H). LCMS 527.5 [M+1].

Example 9.149

Preparation of 1-(2-Fluor-4-methanesulfonyl-phenyl)-4-[1-(4-methyl-6-pyrrolidin-1-yl-pyrimidin-2-yl)-piperidin-4-ylmethyl]-1H-pyrazolo[3,4-d]pyrimidine. (Compound A213)

1-(2-Fluoro-4-methanesulfonyl-phenyl)-4-(piperidin-4-yloxy)-1H-pyrazolo[3,4-d]pyrimidine HCl salt (0.3 g, 0.97 mmol) and (2-chloro-6-methyl-pyrimidin-4-yl)-dimethyl-amine (285 mg, 0.97 mmol) were dissolved in DMF (10 mL). The solution was treated with K$_2$CO$_3$ (398 mg, 2.91 mmol) at an ambient temperature. After stirring at 65° C. for five hours, the reaction was poured into H$_2$O (20 mL). The organic compound was extracted with ethyl acetate (30 mL) and washed with brine. The ethyl acetate layer was dried over MgSO$_4$ and concentrated under vacuum. The residue was purified over SiO$_2$ to afford Compound A213 (312 mg, 65.2%) as a white crystal. $^1$H NMR (400Mz, DMSO-d$_6$) δ 8.68 (s, 1H), 8.64 (s, 1H), 8.17 (dd, J=8.4, 1.8, 1H), 8.08 (d, J=4.2, 1H), 8.01 (dd, J=8.4, 1.8, 1H), 7.62 (s, 1H), 5.68 (m, 1H), 4.23~4.19 (m, 2H), 3.62~3.58 (m, 4H), 3.50~3.46 (m, 2H), 3.39 (s, 3H), 3.00 (s, 6H), 2.13 (s, 1H), 2.10~2.09 (m, 2H), 1.86~1.83 (m, 4H), 1.77~1.72 (m, 2H). LCMS 563.4 [M+1].

Example 9.150

Preparation of Furan-2-yl-{4-[1-(4-methanesulfonyl-phenyl)-1H-pyrazolo[3,4-d]pyrimidin-4-yloxy]-piperidin-1-yl}-methanone (Compound A14)

Compound A14 was prepared in a similar manner as described in Example 9.104 as an off-white solid (25 mg, 59%). $^1$H NMR 400MHz CDCl$_3$ δ (ppm): 2.25 (m, 2H); 2.48 (m, 2H); 3.35 (s, 3H); 3.95 (m, 2H); 4.42 (m, 2H); 5.97 (m, 1H); 6.75 (m, 1H); 7.28 (d, 1H); 7.75 (d, 1H); 8.35 (d, 2H); 8.52 (s, 1H); 8.86 (d, 2H); 8.93 (s, 1H). Exact mass calculated for C$_{22}$H$_{21}$N$_5$O$_5$S 467.13, found 468.4 (MH$^+$, 100%).

Example 9.151

Preparation of {4-[1-(4-Methanesulfonyl-phenyl)-1H-pyrazolo[3,4-d]pyrimidin-4-yloxy]-piperidin-1-yl}-(1-methyl-1H-pyrrol-2-yl)-methanone (Compound A15)

Compound A15 was prepared in a similar manner as described in Example 9.25 as a grayish solid (22 mg, 54%). $^1$H NMR 400MHz CDCl$_3$ δ (ppm): 8.68 (s, 1H); 8.63 (d, 2H); 8.28 (s, 1H); 8.11 (d, 2H); 6.73 (t, 1H); 6.38 (m, 1H); 6.10 (m, 1H); 5.71 (m, 1H); 4.20 (m, 2H); 3.81 (s, 3H); 3.65 (m, 2H); 3.10 (s, 3H); 2.19 (m, 2H); 1.96 (m, 2H). Exact mass calculated for C$_{23}$H$_{24}$N$_6$O$_4$S 480.16, found 481.3 (MH$^+$, 100%).

Example 9.152

Preparation of 2-{4-[1-(4-Methanesulfonyl-phenyl)-1H-pyrazolo[3,4-d]pyrimidin-4-yloxy]-piperidin-1-yl}-1-pyridin-3-yl-ethanone (Compound A16)

Compound A16 was prepared in a similar manner as described in Example 9.21 as a yellow solid (27 mg, 45%). $^1$H NMR 400MHz CDCl$_3$ δ (ppm): 9.12 (d, 1H); 8.73 (d, 1H); 8.72 (s, 1H); 8.56 (s, 1H); 8.50 (d, 2H); 8.28 (m, 1H); 8.08 (d, 2H); 7.50 (m, 1H); 5.38 (m, 1H); 3.87 (s, 2H); 3.21 (s, 3H); 2.81 (m, 2H); 2.46 (m, 2H); 2.04 (m, 2H); 1.76 (m, 2H). Exact mass calculated for C$_{24}$H$_{24}$N$_6$O$_4$S 492.16, found 493.3 (MH$^+$, 100%).

Example 9.153

Preparation of 2-{4-[1-(4-Methanesulfonyl-phenyl)-1H-pyrazolo[3,4-d]pyrimidin-4-yloxy]-piperidin-1-yl}-1-thiophen-2-yl-ethanone (Compound A22)

Compound A22 was prepared in a similar manner as described in Example 9.21 as an off-white solid (24 mg, 32%). $^1$H NMR 400MHz CDCl$_3$ δ (ppm): 8.75 (s, 1H); 8.60 (d, 1H); 8.49 (d, 2H); 8.16 (m, 1H); 8.09 (d, 2H); 8.02 (m, 1H); 7.32 (m, 1H); 5.55 (m, 1H); 5.05 (m, 2H); 3.46 (m, 4H); 3.20 (s, 3H); 2.25 (m, 4H). Exact mass calculated for C$_{23}$H$_{23}$N$_5$O$_4$S$_2$ 497.12, found 498.3 (MH$^+$, 100%).

Example 9.154

Preparation of 1-{4-[1-(4-Methanesulfonyl-phenyl)-1H-pyrazolo[3,4-d]pyrimidin-4-yloxy]-piperidin-1-yl}-3,3-dimethyl-butan-2-one (Compound A25)

Compound A25 was prepared in a similar manner as described in Example 9.21 as an off-white solid (29 mg, 55%). $^1$H NMR 400MHz CDCl$_3$ δ (ppm): 8.69 (s, 1H); 8.49 (d, 1H); 8.40 (d, 2H); 8.01 (m, 2H); 5.48 (m, 1H); 4.49 (m, 2H); 3.40 (m, 1H); 3.12 (s, 3H); 2.98 (m, 3H); 2.12 (m, 4H); 1.03 (s, 9H). Exact mass calculated for C$_{23}$H$_{29}$N$_5$O$_4$S 471.19, found 472.4 (MH$^+$, 100%).

Example 9.155

Preparation of {4-[1-(4-Methanesulfonyl-phenyl)-1H-pyrazolo[3,4-d]pyrimidin-4-yloxy]-piperidin-1-yl}-(5-methyl-pyridin-3-yl)-methanone (Compound A18)

Compound A18 was prepared in a similar manner as described in Example 9.25 as a solid (39 mg, 66%). $^1$H NMR 400MHz CDCl$_3$ δ (ppm): 8.82 (s, 1H); 8.67 (s, 1H); 8.58 (m, 2H); 8.51 (m, 1H); 8.46 (m, 1H); 8.17 (m, 2H); 7.71 (m, 1H); 5.71 (m, 1H); 4.06 (m, 1H); 3.62 (m, 2H); 3.29 (s, 3H); 2.36 (s, 3H); 2.17 (m, 2H); 1.89 (m, 2H). Exact mass calculated for C$_{24}$H$_{24}$N$_6$O$_4$S 492.16, found 493.3 (MH$^+$, 100%).

Example 9.156

Preparation of {4-[1-(4-Methanesulfonyl-phenyl)-1H-pyrazolo[3,4-d]pyrimidin-4-yloxy]-piperidin-1-yl}-(2-methyl-pyridin-3-yl)-methanone (Compound A19)

Compound A19 was obtained in a similar manner as described in Example 9.25 as an off-white solid (35 mg, 48%). $^1$H NMR 400MHz CDCl$_3$ δ (ppm): 8.74 (s, 1H); 8.58 (s, 1H); 8.55 (m, 1H); 8.49 (m, 2H); 8.08 (m, 2H); 7.87 (m, 1H); 7.44 (m, 1H); 5.63 (m, 1H); 3.59 (m, 2H); 3.38 (m, 1H); 3.24 (m, 1H); 3.21 (s, 3H); 2.45 (s, 3H); 2.16 (m, 1H); 1.98 (m, 1H); 1.84 (m, 1H); 1.72 (m, 1H). Exact mass calculated for C$_{24}$H$_{24}$N$_6$O$_4$S 492.16, found 493.3 (MH$^+$, 100%).

Example 9.157

Preparation of {4-[1-(4-Methanesulfonyl-phenyl)-1H-pyrazolo[3,4-d]pyrimidin-4-yloxy]-piperidin-1-yl}-(6-methyl-pyridin-3-yl)-methanone (Compound A20)

Compound A20 was obtained in a similar manner as described in Example 9.25 as an off-white solid (40 mg, 55%). $^1$H NMR 400MHz CDCl$_3$ δ (ppm): 8.59 (s, 1H); 8.43 (s, 1H); 8.42 (m, 1H); 8.34 (m, 2H); 7.94 (m, 2H); 7.75 (m, 1H); 7.29 (m, 1H); 5.49 (m, 1H); 3.31 (m, 4H); 3.06 (s, 3H); 2.35 (s, 3H); 1.93 (m, 2H); 1.65 (m, 2H). Exact mass calculated for C$_{24}$H$_{24}$N$_6$O$_4$S 492.16, found 493.3 (MH$^+$, 100%).

Example 9.158

Preparation of {4-[1-(4-Methanesulfonyl-phenyl)-1H-pyrazolo[3,4-d]pyrimidin-4-yloxy]-piperidin-1-yl}-(5-methyl-isoxazol-3-yl)-methanone (Compound A21)

Compound A21 was obtained in a similar manner as described in Example 9.25 as a brownish solid (18 mg, 24%). $^1$H NMR 400MHz CDCl$_3$ δ (ppm): 8.46 (s, 1H); 8.40 (d, 2H); 8.06 (s, 1H); 7.89 (d, 2H); 6.11 (s, 1H); 5.52 (m, 1H); 3.98 (m, 2H); 3.55 (m, 2H); 2.89 (s, 3H); 2.28 (s, 3H); 1.97 (m, 2H); 1.82 (m, 2H). Exact mass calculated for $C_{22}H_{22}N_6O_5S$ 482.14, found 483.2 (MH$^+$, 100%).

Example 9.159

Preparation of {4-[1-(4-Methanesulfonyl-phenyl)-1H-pyrazolo[3,4-d]pyrimidin-4-yloxy]-piperidin-1-yl}-(6-methyl-pyridin-3-yl)-methanone (Compound A80)

Compound A80 was obtained in a similar manner as described in Example 9.94 as a yellowish solid (75 mg, 58%). Exact mass calculated for $C_{22}H_{27}FN_6O_4S$ 490.18, found 491.3 (MH$^+$, 100%).

Example 9.160

Preparation of 4-[1-(2-Fluoro-4-methanesulfonyl-phenyl)-1H-pyrazolo[3,4-d]pyrimidin-4-yloxy]-piperidine-1-carboxylic acid tert-butyl ester (Compound A74)

Compound A74 was obtained in a similar manner as described in Example 9.1 as a white solid (30 mg, 23%). $^1$H NMR 400MHz CDCl$_3$ δ (ppm): 8.56 (s, 1H); 8.26 (s, 1H); 7.88 (m, 3H); 5.54 (m, 1H); 3.81 (m, 2H); 3.27 (m, 2H); 3.06 (s, 3H); 2.03 (m, 2H); 1.80 (m, 2H); 1.43 (s, 9H). Exact mass calculated for $C_{22}H_{26}FN_5O_5S$ 491.16, found 492.4 (MH$^+$, 100%).

Example 9.161

Preparation of 4-[6-Dimethylamino-1-(4-methanesulfonyl-phenyl)-1H-pyrazolo[3,4-d]pyrimidin-4-yloxy]-piperidine-1-carboxylic acid tert-butyl ester (Compound A89)

Step 1: Preparation of 1-chloro-N'-[4-cyano-2-(4-methanesulfonyl-phenyl)-2H-pyrazol-3-yl]-N,N-dimethyl-formamidine A solution of 5-amino-1-(4-methanesulfonyl-phenyl)-1H-pyrazole-4-carbonitrile (1.2 g, 4.57 mmol) and phosgeniminium chloride (0.900 g, 7.08 mmol) in dry 1,2-dichloroethane was refluxed for 4 h. The solvent was removed under reduced pressure and the residue was purified by flash chromatography (30 to 50% ethyl acetate/hexanes) to yield 1-chloro-N'-[4-cyano-2-(4-methanesulfonyl-phenyl)-2H-pyrazol-3-yl]-N,N-dimethyl-formamidine (1.3 g, 80%) as a yellowish solid. Exact mass calculated for $C_{14}H_{14}ClN_5O_2S$ 351.06, found 352.20 (MH$^+$, 100%).

Step 2: Preparation of [4-Chloro-1-(4-methanesulfonyl-phenyl)-1H-pyrazolo[3,4-d]pyrimidin-6-yl]-dimethyl-amine A stream of dry hydrogen chloride was passed through a solution of 1-chloro-N'-[4-cyano-2-(4-methanesulfonyl-phenyl)-2H-pyrazol-3-yl]-N,N-dimethyl-formamidine (0.600 g, 1.70 mmol) in 1,2-dichloroethane (20 mL) for 1 h. The solution was stirred at rt for 3 days. The solvent was removed under reduced pressure and the crude washed several times with dichloromethane. [4-Chloro-1-(4-methanesulfonyl-phenyl)-1H-pyrazolo[3,4-d]pyrimidin-6-yl]-dimethyl-amine recrystalized in dichloromethane and it was retrieved by filtration as an off-white solid (0.4 g, 67%). Exact mass calculated for $C_{14}H_{14}ClN_5O_2S$ 351.06, found 352.20 (MH$^+$, 100%).

Step 3: Preparation of 4-[6-Dimethylamino-1-(4-methanesulfonyl-phenyl)-1H-pyrazolo[3,4-d]pyrimidin-4-yloxy]-piperidine-1-carboxylic acid tert-butyl ester (Compound A89)

Compound A89 was made in a similar manner as described in Example 9.1 as a white solid (100 mg, 90%). $^1$H NMR (400MHz DMSO-d$_6$) δ (ppm): 8.37 (d, 2H); 8.02 (s, 1H); 7.88 (d, 2H); 5.26 (m, 1H); 3.49 (m, 2H); 3.12 (m, 5H); 3.05 (s, 6H); 1.79 (m, 2H); 1.50 (m, 2H); 1.22 (s, 9H). Exact mass calculated for $C_{24}H_{32}N_6O_5S$ 516.22, found 517.3 (MH$^+$, 100%).

Example 9.162

Preparation of 4-({Ethyl-[1-(2-fluoro-4-methanesulfonyl-phenyl)-1H-pyrazolo[3,4-d]pyrimidin-4-yl]-amino}-methyl)-piperidine-1-carboxylic acid isopropyl ester (Compound A87)

Compounds A87 was made in a similar manner as described in Example 9.24 by using Compound A88. It was obtained as a white solid (32 mg, 50%). $^1$H NMR 400MHz CDCl$_3$ δ (ppm): 8.41 (s, 1H); 8.13 (s, 1H); 7.86 (m, 2H); 7.79 (m, 1H); 4.85 (m, 1H); 4.41 (s, 2H); 3.66 (m, 4H); 3.05 (s, 3H); 2.67 (m, 2H); 2.08 (d, 1H); 1.65 (s, 2H); 1.39 (m, 4H); 1.18 (d, 6H). Exact mass calculated for $C_{24}H_{31}FN_6O_4S$ 518.21, found 519.5 (MH$^+$, 100%).

Example 9.163

Preparation of 4-[1-(2-Dimethylamino-4-methanesulfonyl-phenyl)-1H-pyrazolo[3,4-d]pyrimidin-4-yloxy]-piperidine-1-carboxylic acid tert-butyl ester (Compound A100)

Step 1: Preparation of 1-(2-dimethylamino-4-methanesulfonyl-phenyl)-1H-pyrazolo[3,4-d]pyrimidin-4-ol 1-(2-Fluoro-4-methanesulfonyl-phenyl)-1H-pyrazolo[3,4-d]pyrimidin-4-ol (0.520 g, 1.68 mmol) was dissolved in DMSO (3 mL) and dimethylamine (2M solution in THF) (4 mL, 150 mmol) was added. The mixture was heated at 120° C. for 15 h. The solvent was removed under reduced pressure and the crude was purified by HPLC, yielding 1-(2-dimethylamino-4-methanesulfonyl-phenyl)-1H-pyrazolo[3,4-d]pyrimidin-4-ol as an off-white solid (0.500 g, 89%). Exact mass calculated for $C_{14}H_{15}N_5O_3S$ 333.09, found 334.4 (MH$^+$, 100%).

Step 2: Preparation of 4-[1-(2-Dimethylamino-4-methanesulfonyl-phenyl)-1H-pyrazolo[3,4-d]pyrimidin-4-yloxy]-piperidine-1-carboxylic acid tert-butyl ester (Compound A100)

1-(2-Dimethylamino-4-methanesulfonyl-phenyl)-1H-pyrazolo[3,4-d]pyrimidin-4-ol (66 mg, 0.200 mmol), 4-hydroxy-piperidine-1-carboxylic acid tert-butyl ester (61 mg, 0.300 mmol) and triphenylphosphine (52 mg, 0.200 mmol) were dissolved in toluene (5 mL) and the mixture stirred at 0° C. for 15 min. Diisopropyl azodicarboxylate (28 µL, 0.200 mmol) was then added and the reaction kept going at rt for 16 h. The solvent was removed under reduced pressure and the crude was purified by HPLC. Compound A100 was obtained as a yellowish solid. Exact mass calculated for $C_{24}H_{32}N_6O_5S$ 516.22, found 517.3 (MH$^+$, 100%). $^1$H NMR (400MHz CDCl$_3$) δ (ppm): 8.50 (s, 1H); 8.22 (s, 1H); 7.42 (m, 3H); 5.52 (m, 1H); 3.81 (m, 2H); 3.26 (m, 2H); 3.03 (s, 3H); 2.47 (s, 6H); 2.03 (m, 2H); 1.80 (m, 2H); 1.42 (s, 9H).

Example 9.164

Preparation of 4-2-[1-(4-Methanesulfonyl-phenyl)-1H-pyrazolo[3,4-d]pyrimidin-4-yloxy]-ethyl}-piperazine-1-carboxylic acid ethyl ester (Compound A103)

Compound A103 was made in a similar manner as described in Example 9.131 as a white solid (46 mg, 49%). $^1$H NMR (400MHz DMSO-d$_6$). δ (ppm): 8.78 (s, 1H); 8.66 (s, 1H); 8.50 (m, 2H); 8.10 (m, 2H); 4.90 (s, 2H); 4.00 (m, 4H); 3.49 (m, 5H); 3.12 (s, 3H); 3.02 (m, 3H); 1.14 (t, 3H). Exact mass calculated for $C_{21}H_{26}N_6O_5S$ 474.17, found 475.3 (MH$^+$, 100%).

Example 9.165

Preparation of 4-{2-[1-(4-Methanesulfonyl-phenyl)-1H-pyrazolo[3,4-d]pyrimidin-4-yloxy]-propyl}-piperazine-1-carboxylic acid ethyl ester (Compound A104)

Compound A104 was obtained in a similar manner as described in Example 9.131 as a white solid (47 mg, 48%). $^1$H NMR (400MHz DMSO-d$_6$) δ (ppm): 8.66 (s, 1H); 8.45 (s, 1H); 8.37 (m, 2H); 7.98 (m, 2H); 5.73 (m, 1H); 3.87 (m, 4H); 3.37 (m, 5H); 3.06 (s, 3H); 3.02 (m, 3H); 1.30 (d, 3H); 1.14 (t, 3H). Exact mass calculated for $C_{22}H_{28}N_6O_5S$ 488.18, found 489.30 (MH$^+$, 100%).

Example 9.166

Preparation of (5-Fluoro-pyridin-2-yl)-{4-[1-(4-methanesulfonyl-phenyl)-1H-pyrazolo[3,4-d]pyrimidin-4-yloxy]-piperidin-1-yl}-methanone (Compound A171)

Compound A171 was prepared in a similar manner as described in Example 9.25 as an orange solid (15.5 mg; 50.7%). Exact mass calculated for $C_{23}H_{21}FN_6O_4S$ 496.13, found 497.10 (MH$^+$, 100%).

Example 9.167

Preparation of (2-Chloro-5-fluoro-pyridin-3-yl)-{4-[1-(4-methanesulfonyl-phenyl)-1H-pyrazolo[3,4-d]pyrimidin-4-yloxy]-piperidin-1-yl}-methanone (Compound A173)

Compound A173 was obtained in a similar manner as described in Example 9.25 as a brownish solid (14.9 mg, 46.2%). Exact mass calculated for $C_{23}H_{20}ClFN_6O_4S$ 530.09, found 531.10 (MH$^+$, 100%).

Example 9.168

Preparation of {4-[1-(4-Methanesulfonyl-phenyl)-1H-pyrazolo[3,4-d]pyrimidin-4-yloxy]-piperidin-1-yl}-(4-methoxy-pyridin-2-yl)-methanone (Compound A177)

Compound A177 was obtained in a similar manner as described in Example 9.25 as an off-white solid (11.7 mg, 37.6%). Exact mass calculated for $C_{24}H_{24}N_6O_5S$ 508.15, found 509.1 (MH$^+$, 100%).

Example 9.169

Preparation of (2-Fluoro-pyridin-3-yl)-{4-[1-(4-methanesulfonyl-phenyl)-1H-pyrazolo[3,4-d]pyrimidin-4-yloxy]-piperidin-1-yl}-methanone (Compound A179)

Compound A179 was obtained in a similar manner as described in Example 9.25 as an orange solid (11.7 mg, 37.6%). Exact mass calculated for $C_{23}H_{21}FN_6O_4S$ 496.13, found 497.10 (MH$^+$, 100%).

Example 9.170

Preparation of (6-Fluoro-pyridin-3-yl)-{4-[1-(4-methanesulfonyl-phenyl)-1H-pyrazolo[3,4-d]pyrimidin-4-yloxy]-piperidin-1-yl}-methanone (Compound A180)

Compound A180 was obtained in a similar manner as described in Example 9.25 as a brownish solid (15.5 mg, 50%). Exact mass calculated for $C_{23}H_{21}FN_6O_4S$ 496.13, found 497.10 (MH$^+$, 100%).

Example 9.171

Preparation of (4-Iodo-pyridin-2-yl)-{4-[1-(4-methanesulfonyl-phenyl)-1H-pyrazolo[3,4-d]pyrimidin-4-yloxy]-piperidin-1-yl}-methanone (Compound A167)

Compound A167 was obtained in a similar manner as described in Example 9.25 as a brownish solid (15.5 mg, 50%). Exact mass calculated for $C_{23}H_{21}N_6O_4S$ 604.04, found 605.1 (MH$^+$, 100%).

Example 9.172

Preparation of {4-[1-(4-Methanesulfonyl-phenyl)-1H-pyrazolo[3,4-d]pyrimidin-4-yloxy]-piperidin-1-yl}-(4-methoxy-thiophen-3-yl)-methanone (Compound A181)

Compound A181 was obtained in a similar manner as described in Example 9.25 as a white solid (7.2 mg, 23%). Exact mass calculated for $C_{23}H_{23}N_5O_5S_2$ 513.11, found 514.2 (MH+, 100%).

Example 9.173

Preparation of 4-(1-Benzyl-azetidin-3-yloxy)-1-(4-methanesulfonyl-phenyl)-1H-pyrazolo[3,4-d]pyrimidine (Compound A23)

1-Benzyl-azetidin-3-ol hydrochloride salt (0.59 mmol, 117 mg) and sodium hydride were dissolved in dimethyl acetamide (2 mL) and stirred at room temperature for 30 minutes. 4-Chloro-1-(4-methanesulfonyl-phenyl)-1H-pyrazolo[3,4-d]pyrimidine (0.49 mmol, 150 mg) was added slowly and the mixture was stirred at 70° C. for 20 minutes. The reaction mixture was quenched with water followed by an extraction with ethyl acetate. Removal of organic solvents in vacuo and purification by flash chromatography provided compound A23 as a white solid (88 mg, 41%). $^1$H NMR (400MHz, DMSO-d$_6$) δ (ppm): 8.90 (s, 1H); 8.53 (s, 1H); 8.30 (d, 2H); 8.16 (d, 2H); 7.43 (m, 5H); 6.19 (m, 1H); 4.59 (m, 2H); 4.42 (d, 1H); 4.00 (d, 1H); 3.65 (d, 1H); 3.35 (m, 1); 3.30 (s, 3H).

Example 9.174

Preparation of 3-[1-(4-Methanesulfonyl-phenyl)-1H-pyrazolo[3,4-d]pyrimidin-4-yloxy]-azetidine-1-carboxylic acid isopropyl ester (Compound A47)

Step 1: Preparation of 4-(azetidin-3-yloxy)-1-(4-methanesulfonyl-phenyl)-1H-pyrazolo[3,4-d]pyrimidine 4-(1-Benzyl-azetidin-3-yloxy)-1-(4-methanesulfonyl-phenyl)-1H-pyrazolo[3,4-d]pyrimidine (0.01 mmol, 46 mg) was dissolved in a mixture of ethyl acetate (5 mL) and methanol (5 mL). Palladium catalyst (30 mg, 65% by wt) was added to the reaction. The mixture was exposed to hydrogen gas for 60. minutes at room temperature and atmospheric pressure. The mixture was passed through celite to remove palladium catalyst. Removal of organic solvents in vacuo and purification by flash chromatography provided 4-(azetidin-3-yloxy)-1-(4-methanesulfonyl-phenyl)-1H-pyrazolo[3,4-d]pyrimidine as a white solid (11 mg, 5%). $^1$H NMR (400MHz, MeOH-d$_4$) δ (ppm): 8.45 (m, 2H); 8.37 (d, 2H); 8.05 (d, 2H); 4.54 (m, 1H); 4.35 (dd, 2H); 3.69 (m, 2H); 3.09 (s, 3H). LCMS (ESI), m/z 346.2 (M+H+, 100%).

Step 2: Preparation of 3-[1-(4-Methanesulfonyl-phenyl)-1H-pyrazolo[3,4-d]pyrimidin-4-yloxy]-azetidine-1-carboxylic acid isopropyl ester (Compound A47)

Compound A47 was made in a similar manner as described in Example 9.24 as a white solid (26 mg, 55%). $^1$H NMR (400MHz, CDCl$_3$) δ (ppm): 8.66 (s, 1H); 8.62 (d, 2H); 8.31 (s, 1H); 8.11 (d, 2H); 5.65 (m, 1H); 4.93 (h, 1H); 4.48 (m, 2H); 4.18 (m, 2H); 3.11 (s, 3H); 1.25 (d, 6H). LCMS (ESI), m/z 432.3 (M+H+, 100%)

Example 9.175

Preparation of {4-[1-(2-Fluoro-4-methanesulfonyl-phenyl)-1H-pyrazolo[3,4-d]pyrimidin-4-yloxy]-piperidin-1-yl}-(3-trifluoromethoxy-phenyl)-methanone (Compound A197)

Compound A197 was made in a similar manner as described in Example 9.28 as a white solid (221 mg, 46%). Exact mass calculated for $C_{25}H_{22}F_3N_5O_2S$ 579.56, found 580.4 (MH+).

Example 9.176

Preparation of 4-[1-(4-Methanesulfonyl-phenyl)-1H-pyrazolo[3,4-d]pyrimidin-4-yloxy]-piperidine-1-carboxylic acid propyl ester (Compound A49)

Compound A49 was made in a similar manner as described in Example 9.24 as a white solid (36 mg, 46%). $^1$H NMR (400MHz, CDCl$_3$) δ (ppm): 8.69 (s, 1H); 8.62 (d, 2H); 8.26 (s, 1H); 8.10 (d, 2H); 5.61 (h, 1H); 4.22 (t, 2H); 4.08 (m, 2H); 3.40 (m, 2H); 3.10 (s, 3H); 2.11 (m, 2H); 1.87 (m, 2H), 1.64 (s, 2H); 0.97 (t, 3). LCMS (ESI), m/z 460.3 (MH+, 100%)

Example 9.177

Preparation of 4-[1-(4-Methanesulfonyl-phenyl)-1H-pyrazolo[3,4-d]pyrimidin-4-yloxy]-piperidine-1-carboxylic acid cyclohexyl ester (Compound A63)

Carbonyldiimidizole (0.28 mmol, 46 mg), and cyclohexanol (0.28 mmol, 34 µL) were dissolved in DMF (2 mL) and stirred for 30 minutes at room temperature. Then, 1-(4-Methanesulfonyl-phenyl)-4-(piperidin-4-yloxy)-1H-pyrazolo[3,4-d]pyrimidine hydrochloride salt (0.16 mmol, 60 mg) and triethylamine (0.84 mmol, 118 µL) were added and continued to stir at 60° C. for 24 hours. The reaction mixture was quenched with water followed by an extraction with ethylacetate. Removal of organic solvents in vacuo and purification by HPLC provided compound A63 as a white solid. $^1$H NMR (400 MHz, CDCl$_3$) δ (ppm): 8.67 (s, 1H); 8.61 (d, 2H); 8.26 (s, 1H); 8.11 (d, 2H); 5.62 (h, 1H); 4.71 (h, 1H); 3.91 (m, 2H); 3.38 (m, 2H); 3.10 (s, 3H); 2.10 (m, 2H); 1.87 (m, 4H), 1.65 (m, 6H); 1.28 (m, 2H). LCMS (ESI), m/z 500.4 (MH+, 100%)

Example 9.178

Preparation of 4-[1-(4-Methanesulfonyl-phenyl)-1H-pyrazolo[3,4-d]pyrimidin-4-yloxy]-piperidine-1-carboxylic acid tetrahydro-pyran-4-yl ester (Compound A64)

Compound A64 was made in a similar manner as described in Example 9.177 as a white solid (7 mg, 9%). $^1$H NMR (400MHz, CDCl$_3$) δ (ppm): 8.67 (s, 1H); 8.62 (d, 2H); 8.26 (s, 1H); 8.11 (d, 2H); 5.13 (h, 1H); 4.89 (h, 1H); 3.92 (m, 4H); 3.58 (m, 2H); 3.40 (m, 2H); 3.11 (s, 3H); 2.12 (m, 2H), 1.90 (m, 4H); 1.71 (m, 2H). LCMS (ESI), m/z 502.3 (MH+, 100%)

Example 9.179

Preparation of 4-[1-(4-Methanesulfonyl-phenyl)-1H-pyrazolo[3,4-d]pyrimidin-4-yloxy]-piperidine-1-carboxylic acid cyclopentyl ester (Compound A65)

Compound A65 was made in a similar manner as described in Example 9.177 as a white solid (13 mg, 18%). $^1$H NMR (400MHz, CDCl$_3$) δ (ppm): 8.67 (s, 1H); 8.62 (d, 2H); 8.26 (s, 1H); 8.11 (d, 2H); 5.61 (h, 1H); 5.14 (m, 1H); 3.89 (m, 2H); 3.36 (m, 2H); 3.10 (s, 314); 2.10 (m, 2H); 1.88 (m, 4H), 1.74 (m, 4H); 1.61 (m, 2H). LCMS (ESI), m/z 486.3 (MH+, 100%)

Example 9.180

Preparation of 4-[1-(4-Methanesulfonyl-phenyl)-1H-pyrazolo[3,4-d]pyrimidin-4-yloxy]-piperidine-1-carboxylic acid tetrahydro-furan-3-yl ester (Compound A67)

Compound A67 was made in a similar manner as described in Example 9.177 as a white solid (12 mg, 16%). $^1$H NMR (400MHz, CDCl$_3$) δ (ppm): 8.67 (s, 1H); 8.61 (d, 2H); 8.26 (s, 1H); 8.10 (d, 2H); 5.63 (h, 1H); 5.30 (m, 1H); 3.91 (m, 6H); 3.41 (m, 2H); 3.11 (s, 3H); 2.18 (m, 4H); 1.95 (m, 2H). LCMS (ESI), m/z 488.3 (MH+, 100%)

Example 9.181

Preparation of 4-[1-(4-Methanesulfonyl-phenyl)-1H-pyrazolo[3,4-d]pyrimidin-4-yloxy]-piperidine-1-carboxylic acid tetrahydro-furan-3-yl ester (Compound A66)

Compound A65 was made in a similar manner as described in Example 9.177 as a white solid (11 mg, 15%). $^1$H NMR (400MHz, CDCl$_3$) δ (ppm): 8.67 (s, 1H); 8.61 (d, 2H); 8.26 (s, 1H); 8.11 (d, 2H); 5.63 (h, 1H); 5.29 (m, 1H); 3.90 (m, 6H); 3.41 (m, 2H); 3.11 (s, 3H); 2.18 (m, 4H); 1.97 (m, 2H). LCMS (ESI), m/z 488.2 (MH+, 100%)

Example 9.182

Preparation of 4-[1-(4-Methanesulfonyl-phenyl)-1H-pyrazolo[3,4-d]pyrimidin-4-yloxy]-piperidine-1-carboxylic acid tetrahydro-thiopyran-4-yl ester (Compound A68)

Compound A68 was made in a similar manner as described in Example 9.177 as a white solid (4 mg, 5%). $^1$H NMR (400MHz, CDCl$_3$) δ (ppm): 8.67 (s, 1H); 8.61 (d, 2H); 8.26 (s, 1H); 8.11 (d, 2H); 5.63 (h, 1H); 4.80 (h, 1H); 4.22 (m, 2H); 3.41 (m, 2H); 3.11 (s, 3H); 2.79 (m, 2H); 2.64 (m, 2H); 2.15 (m, 4H); 1.91 (m, 4H). LCMS (ESI), m/z 518.2 (MH+, 100%)

Example 9.183

Preparation of 4-[1-(4-Methanesulfonyl-phenyl)-1H-pyrazolo[3,4-d]pyrimidin-4-yloxy]-piperidine-1-carboxylic acid cyclobutyl ester (Compound A69)

Compound A65 was made in a similar manner as described in Example 9.177 as a white solid (13 mg, 19%). $^1$H-NMR (400MHz, CDCl$_3$) δ (ppm): 8.67 (s, 1H); 8.6 (d, 2H); 8.26 (s, 1H); 8.10 (d, 2H); 5.632 (h, 1H); 4.97 (p, 1H); 3.89 (m, 2H); 3.40 (m, 2H); 3.10 (s, 3H); 2.36 (m, 2H); 2.10 (m, 4H); 1.88 (m, 4H). LCMS (ESI), m/z 472.4 (MH+, 100%)

Example 9.184

Preparation of 4-[1-(4-Methanesulfonyl-phenyl)-1H-pyrazolo[3,4-d]pyrimidin-4-yloxy]-piperidine-1-carboxylic acid pyridin-3-ylmethyl ester (Compound A81).

Compound A81 was made in a similar manner as described in Example 9.177 as a white solid (31 mg, 28%). $^1$H NMR (400 MHz, CDCl$_3$) δ (ppm): 8.93 (s, 1H); 8.81 (d, 1H); 8.67 (s, 1H); 8.61 (d, 2H); 8.30 (d, 1H); 8.26 (s, 1H); 8.11 (d, 2H); 7.84 (m, 1H); 5.65 (h, 1H); 5.33 (s, 2H); 3.91 (m, 2H); 3.50 (m, 2H); 3.11 (s, 3H); 2.15 (m, 2H); 1.91 (m, 2H). LCMS (ESI), m/z 509.0 (MH+, 100%)

Example 9.185

Preparation of 4-[1-(4-Methanesulfonyl-phenyl)-1H-pyrazolo[3,4-d]pyrimidin-4-yloxy]-piperidine-1-carboxylic acid 2-pyridin-3-yl-ethyl ester (Compound A82)

Compound A82 was made in a similar manner as described in Example 9.177 as a white solid (35 mg, 30%). $^1$H NMR (400MHz, MeOH-d$_4$) δ (ppm): 7.54 (s broad, 1H); 7.44 (m, 1H); 7.36 (m, 3H); 7.24 (d, 1H); 7.09 (s, 1H); 6.85 (d, 2H); 6.71 (m, 1H); 4.37 (h, 1H); 3.4 (t, 2H); 2.52 (m, 2H); 2.10 (m, 2H); 1.97 (t, 2H); 1.94 (s, 3); 0.81 (m, 2H); 0.56 (m, 2H). LCMS (ESI), m/z 523.2 (MH+, 100%)

Example 9.186

Preparation of 4-1[-(4-Methanesulfonyl-phenyl)-1H-pyrazolo[3,4-d]pyrimidin-4-yloxy]-piperidine-1-carboxylic acid 3-pyridin-3-yl-propyl ester (Compound A83)

Compound A83 was made in a similar manner as described in Example 9.177 as a white solid (28 mg, 24%). $^1$H NMR (400MHz, MeOH-d$_4$) δ (ppm): 7.64 (s broad, 1H); 7.38 (m, 4H); 7.16 (d, 1H); 7.10 (s, 1H); 6.84 (d, 2H); 6.66 (m, 1H); 4.38 (h, 1H); 2.89 (t, 2H); 2.57 (m, 2H); 2.12 (m, 2H); 1.89 (s, 3H); 1.68 (t, 2H); 0.81 (m, 4H); 0.59 (m, 2H). LCMS (ESI), m/z 537.2 (MH+, 100%)

Example 9.187

Preparation of 4-[1-(4-Methanesulfonyl-phenyl)-1H-pyrazolo[3,4-d]pyrimidin-4-yloxy]-piperidine-1-carboxylic acid 2-dimethylamino-ethyl (Compound A84)

Compound A84 was made in a similar manner as described in Example 9.177 as a white solid (16 mg, 15%). $^1$H NMR (400MHz, CDCl$_3$) δ (ppm): 7.37 (m, 3H); 7.11 (s, 1H); 6.83 (d, 2H); 4.39 (h, 1H); 2.95 (t, 2H); 2.61 (m, 2H); 2.03 (m, 2H); 1.89 (s, 3H); 1.37 (t, 2H); 1.03 (s, 6H); 0.86 (m, 2H); 0.60 (m, 2H). LCMS (ESI), m/z 489.2 (MH+, 100%)

Example 9.188

Preparation of 4-{[1-(4-Methanesulfonyl-phenyl)-1H-pyrazolo[3,4-d]pyrimidin-4-yl]-methyl-amino}-piperidine-1-carboxylic acid tert-butyl ester (Compound A85)

Compound A85 was made in a similar manner as described in Example 9.130 as a yellow solid (750 mg, 95%). $^1$H NMR (400MHz, CDCl$_3$) δ (ppm): 8.59 (d, 2H); 8.51 (s broad, 1H); 8.12 (s, 1H); 8.08 (d, 2H); 4.18 (m, 2H); 3.59 (s broad, 2H); 3.10 (s, 3H); 2.73 (m, 2H); 1.91 (m, 1H); 1.79 (m, 2); 1.70 (s broad, 3H); 1.43 (s, 9H). LCMS (ESI), m/z 487.1 (MH+, 100%)

Example 9.189

Preparation of 1-(4-{[1-(4-Methanesulfonyl-phenyl)-1H-pyrazolo[3,4-d]pyrimidin-4-yl]-methyl-amino}-piperidin-1-yl)-3,3-dimethyl-butan-2-one (Compound A90)

Compound A90 was made in a similar manner as described in Example 9.21 as a white solid (14 mg, 12%). $^1$H NMR (400MHz, CDCl$_3$) δ (ppm): 8.58 (d, 2H); 8.09 (t, 3H); 3.59 (s broad, 2H); 3.39 (s, 2H); 3.09 (s, 3H); 2.95 (m, 2H); 2.05 (m, 2H); 1.79 (m, 3H); 1.66 (m, 4H); 1.16 (s, 9H). LCMS (ESI), m/z 485.3 (MH+, 100%).

Example 9.190

Preparation of 4-{[1-(4-Methanesulfonyl-phenyl)-1H-pyrazolo[3,4-d]pyrimidin-4-yl]-methyl-amino}-piperidine-1-carboxylic acid cyclobutyl ester (Compound A91)

Compound A91 was made in a similar manner as described in Example 9.177 as a white solid (62 mg, 35%). $^1$H NMR (400MHz, CDCl$_3$) δ (ppm): 8.60 (d, 2H); 8.57 (s broad, 1H); 8.13 (s, 1H); 8.07 (d, 2H); 4.93 (p, 1H); 4.22 (m, 2H); 3.58 (s broad, 2H); 3.10 (s, 3H); 2.75 (s broad, 2H); 2.34 (m, 2H); 2.06 (m, 2H), 1.93 (m, 1H); 1.75 (m, 7H). LCMS (ESI), m/z 485.2 (MH+, 100%).

Example 9.191

Preparation of 4-[1-(4-Methanesulfonyl-phenyl)-1H-pyrazolo[3,4-d]pyrimidin-4-ylsulfanyl]-piperidine-1-carboxylic acid tert-butyl ester (Compound A102)

4-Chloro-1-(4-methanesulfonyl-phenyl)-1H-pyrazolo[3,4-d]pyrimidine (1.23 mmol, 250 mg), 4-mercapto-piperidine-1-carboxylic acid tert-butyl ester (1.23 mmol, 268 mg) and potassium carbonate (1.4 mmol, 203 mg) were dissolved in DMF (10 mL) and stirred for 60 minutes at room temperature. Its progress was followed by thin layer chromatography and LCMS. The reaction mixture was quenched with water followed by an extraction with ethylacetate. Removal of organic solvents in vacuo and purification by column chromatography provided compound A102 as a white solid (264 mg, 66%). $^1$H NMR (400MHz, CDCl$_3$) δ (ppm): 8.83 (s, 1H); 8.61 (d, 2H); 8.24 (s, 1H); 8.11 (d, 2H); 4.42 (h, 1H); 4.00 (m, 2H); 3.20 (m, 2H); 3.15 (s, 3H); 2.19 (m, 2H); 1.77 (m, 2H); 1.46 (s, 9H). LCMS (ESI), m/z 490.3 (MH+, 100%)

Example 9.192

Preparation of 4-[1-(4-Methanesulfonyl-phenyl)-1H-pyrazolo[3,4-d]pyrimidine-4-sulfinyl]-piperidine-1-carboxylic acid tert-butyl ester (Compound A105)

Compound A102 (0.51 mmol, 250 mg) was dissolved in 1,2-dichloroethane (15 mL). To this was added MCPBA (0.51 mmol, 88 mg). The mixture was allowed to stir overnight at room temperature. Its progress was monitored by thin layer chromatography and LCMS. The reaction mixture was washed with a solution of ammonium chloride in water (pH10) and a solution of sodium bicarbonate in water. The product was extracted with dichloromethane. Removal of organic solvents in vacuo and purification by HPLC provided compound A105 as a white solid (29 mg, 12%). $^1$H NMR (400MHz, CDCl$_3$) δ (ppm): 9.12 (s, 1H); 9.03 (s, 1H); 8.66 (d, 2H); 8.15 (d, 2H); 4.22 (m, 1H); 4.20 (m, 2H); 3.43 (m, 1H); 3.13 (s, 3H); 2.74 (m, 2H); 2.26 (m, 1H); 2.00 (m, 2H), 1.57 (s, 9H). LCMS (ESI), m/z 506.2 (MH+, 100%)

Example 9.193

Preparation of 4-[1-(4-Methanesulfonyl-phenyl)-1H-pyrazolo[3,4-d]pyrimidine-4 sulfonyl]-piperidine-1-carboxylic acid tert-butyl ester (Compound A106)

Compound A102 (0.31 mmol, 150 mg) was dissolved in 1,2-dichloroethane (15 mL). To this was added MCPBA in excess (1.5 mmol, 268 mg). The mixture was refluxed for 1.0 hour. Its progress was monitored by thin layer chromatography and LCMS. The reaction mixture was washed with a solution of ammonium chloride in water (pH10) and a solution of sodium bicarbonate in water. The product was extracted in dichloromethane. Removal of organic solvents in vacuo and purification by HPLC provided compound A106 as a white solid (46 mg, 25%). $^1$H NMR (400MHz, CDCl$_3$) δ (ppm): 9.31 (s, 1H); 8.86 (s, 1H); 8.65 (d, 2H); 8.17 (d, 2H); 4.25 (m, 3H); 3.90 (m, 1H); 3.13 (s, 3H); 2.80 (m, 1H); 2.03 (m, 2H); 1.86 (m, 2H); 1.70 (s, 9H). LCMS (ESI), m/z 522.3 (MH+, 100%)

Example 9.194

Preparation of 4-[1-(2-Fluoro-4-methanesulfonyl-phenyl)-1H-pyrazolo[3,4-d]pyrimidin-4-ylsulfanyl]-piperidine-1-carboxylic acid butyl ester (Compound A108)

Step 1: Preparation of 1-(2-fluoro-4-methanesulfonyl-phenyl)-4-(piperidin-4-ylsulfanyl)-1H-pyrazolo[3,4-d]pyrimidine Compound A107 (1.22 mmol, 620 mg) was dissolved in dichloromethane (15 mL). To this was added a solution of 4M HCl in dioxane (8 mL) at room temperature. The reaction was stirred for 30 minutes at 40° C. The progress of the reaction was monitored by LCMS. Evaporation of organic solvents in vacuo provided 1-(2-fluoro-4-methanesulfonyl-phenyl)-4-(piperidin-4-ylsulfanyl)-1H-pyrazolo[3,4-d]pyrimidine as a white solid. (530 mg, 98%). LCMS (ESI), m/z 408.2 (MH+, 100%).

Step 2: Preparation of 4-[1-(2-Fluoro-4-methanesulfonyl-phenyl)-1H-pyrazolo[3,4-d]pyrimidin-4-ylsulfanyl]-piperidine-1-carboxylic acid butyl ester (Compound A108)

Compound A108 was made in a similar manner as described in Example 9.177 as a white solid (43 mg, 54%). $^1$H NMR (400MHz, CDCl$_3$) δ (ppm): 8.72 (s, 1H); 8.23 (s, 1H); 7.87 (m, 3H); 4.36 (h, 1H); 4.01 (m, 4H); 3.16 (m, 2H); 3.05 (s, 3H); 2.12 (m, 2H); 1.70 (m, 2H); 1.58 (m, 2H); 1.35 (s, 2H); 0.88 (t, 3H). LCMS (ESI), m/z 508.4 (MH+, 100%)

Example 9.195

Preparation of 4-1-(2-Fluoro-4-methanesulfonyl-phenyl)-1H-pyrazolo[3,4-d]pyrimidin-4-ylsulfanyl]-piperidine-1-carboxylic acid 2-methoxy-ethyl ester (Compound A109)

Compound A109 was made in a similar manner as described in Example 9.177 as a white solid (4 mg, 5%). $^1$H NMR (400MHz, CDCl$_3$) δ (ppm): 8.71 (s, 1H); 8.24 (s, 1H); 7.87 (m, 3H); 4.37 (m, 1H); 4.20 (m, 2H); 3.99 (m, 2H); 3.56 (m, 2H); 3.33 (s, 3H); 3.17 (m, 2H); 3.06 (s, 3H); 2.12 (m, 2H); 1.72 (m, 2H). LCMS (ESI), m/z 510.3 (MH+, 100%)

Example 9.196

Preparation of 4-[1-(2-Fluoro-4-methanesulfonyl-phenyl)-1H-pyrazolo[3,4-d]pyrimidin-4-ylsulfanyl]-piperidine-1-carboxylic acid 3,3-dimethyl-butyl ester (Compound A110)

Compound A110 was made in a similar manner as described in Example 9.177 as a white solid (22 mg, 24%). $^1$H NMR (400MHz, CDCl$_3$) δ (ppm): 8.71 (s, 1H); 8.23 (s, 1H); 7.87 (m, 3H); 4.36 (h, 1H); 4.10 (t, 2H); 3.96 (s broad, 2H); 3.15 (m, 2H); 3.04 (s, 3H); 2.12 (m, 2H); 1.71 (m, 2H); 1.51 (t, 2H); 0.85 (s, 9H). LCMS (ESI), m/z 536.2 (MH+, 100%).

Example 9.197

Preparation of 4-[1-(2-Fluoro-4-methanesulfonyl-phenyl)-1H-pyrazolo[3,4-d]pyrimidin-4-ylsulfanyl]-piperidine-1-carboxylic acid 4-methyl-pentyl ester (Compound A111)

Compound A111 was made in a similar manner as described in Example 9.177 as a white solid. LCMS (ESI), m/z 536.2 (MH+, 100%).

Example 9.198

Preparation of {4-[1-(4-Methanesulfonyl-phenyl)-1H-pyrazolo[3,4-d]pyrimidin-4-yloxy]-piperidin-1-yl}-(5-morpholin-4-ylmethyl-furan-2-yl)-methanone (Compound A116)

5-Morpholin-4-ylmethyl-furan-2-carboxylic acid (0.12 mmol, 25 mg), and isopropylchloroformate (0.12 mmol, 17 μL) and triethylamine (0.12 mmol, 17 μL) were dissolved in DMSO (2 mL) and stirred for 30 minutes at room temperature. Then, 1-(4-methanesulfonyl-phenyl)-4-(piperidin-4-yloxy)-1H-pyrazolo[3,4-d]pyrimidine (0.12 mmol, 50 mg) and excess triethylamine were added. The mixture was heated in a microwave for 5 minutes at 120° C. The progress of the reaction was monitored by thin layer chromatography and LCMS. Purification by HPLC provided compound A116 as a white solid. LCMS (ESI), m/z 567.3 (MH+, 100%).

Example 9.199

Preparation of 4-[1-(4-Methanesulfonyl-phenyl)-1H-pyrazolo[3,4-d]pyrimidin-4-yloxy]-piperidine-1-carboxylic acid 2-pyrrolidin-1-yl-ethyl ester (Compound A121)

Compound A121 was made in a similar manner as described in Example 9.177 as a white solid (29 mg, 27%). LCMS (ESI), m/z 515.3 (MH+, 100%)

Example 9.200

Preparation of 4-[1-(4-Methanesulfonyl-phenyl)-1H-pyrazolo[3,4-d]pyrimidin-4-yloxy]-piperidine-1-carboxylic acid 2-morpholin-4-yl-ethyl ester (Compound A122)

Compound A122 was made in a similar manner as described in Example 9.177 as a white solid (20 mg, 20%). LCMS (ESI), m/z 531.3 (MH+, 100%)

Example 9.201

Preparation of 4-[1-(4-Methanesulfonyl-phenyl)-1H-pyrazolo[3,4-d]pyrimidin-4-yloxy]-piperidine-1-carboxylic acid ethyl ester (Compound A123)

1-(4-methanesulfonyl-phenyl)-4-(piperidin-4-yloxy)-1H-pyrazolo[3,4-d]pyrimidine hydrochloride salt (0.17 mmol, 70 mg), ethylchloroformate (0.25 mmol, 25 μL) and triethylamine (0.51 mmol, 72 μL) were dissolved in DMF (2 mL) and stirred for 60 minutes at room temperature. Progress of the reaction was monitored by TLC and LCMS. The reaction mixture was quenched with water. The product was extracted with ethyl acetate. Removal of organic solvents in vacuo and purification by HPLC provided compound A123 as a white solid (14 mg, 15%). Exact mass calculated for $C_{20}H_{23}N_5O_5S$ 445.49, found 446.10 (MH$^+$).

Example 9.202

Preparation of Ethyl-[1-(2-fluoro-4-methanesulfonyl-phenyl)-1H-pyrazolo[3,4-d]pyrimidin-4-yl]-(3,4,5,6-tetrahydro-2H-[1,2']bipyridinyl-4-ylmethyl)-amine (Compound A126)

A mixture of ethyl-[1-(2-fluoro-4-methanesulfonyl-phenyl)-1H-pyrazolo[3,4-d]pyrimidin-4-yl]-piperidin-4-ylmethyl-amine hydrochloride salt (30 mg, 0.064 mmol), 2-bromopyridine (0.62 μL, 0.64 mmol), and triethylamine (26 μL, 0.19 mmol) in DMF (1.0 mL) was heated under microwave irradiation for 30 minutes at 165° C. The crude mixture was purified by HPLC to provide compound A126 as a white solid (5 mg, 15%). Exact mass calculated for $C_{25}H_{28}FN_7O_2S$ 509.2, found 510.5 (MH$^+$).

Example 9.203

Preparation of Ethyl-[1-(2-fluoro-4-methanesulfonyl-phenyl)-1H-pyrazolo[3,4-d]pyrimidin-4-yl]-(5'-trifluoromethyl-3,4,5,6-tetrahydro-2H-[1,2']bipyridinyl-4-ylmethyl)-amine (Compound A127)

A mixture of ethyl-[1-(2-fluoro-4-methanesulfonyl-phenyl)-1H-pyrazolo[3,4-d]pyrimidin-4-yl]-piperidin-4-ylmethyl-amine hydrochloride salt (30 mg, 0.064 mmol), 2-bromo-5-trifluoromethylpyridine (188 mg, 0.83 mmol), and triethylamine (27 µL, 0.19 mmol) in DMF (1.0 mL) was heated under microwave irradiation for 20 minutes at 165° C. The crude mixture was purified by HPLC to provide compound A127 as a white solid (19 mg, 51%). Exact mass calculated for $C_{26}H_{27}F_4N_7O_2S$ 557.19, found 578.3 (MH$^+$).

Example 9.204

Preparation of [1-(4-Methanesulfonyl-phenyl)-1H-pyrazolo[3,4-d]pyrimidin-4-yl]-(5'-trifluoromethyl-3,4,5,6-tetrahydro-2H-[1,2']bipyridinyl-4-yl)-amine (Compound A128)

A mixture of [1-(4-methanesulfonyl-phenyl)-1H-pyrazolo[3,4-d]pyrimidin-4-yl]-piperidin-4-yl-amine (100 mg, 0.24 mmol), 2-bromo-4-trifluoromethylpyridine (166 mg, 0.73 mmol), and potassium carbonate (102 mg, 0.73 mmol) in DMF (1.0 mL) was heated under microwave irradiation for 20 minutes at 165° C. The crude mixture was purified by HPLC to provide compound A128 as a white solid (41 mg, 32%). Exact mass calculated for $C_{23}H_{22}F_3N_7O_2S$ 517.15, found 518.2 (MH$^+$).

Example 9.205

Preparation of [1-(2-Fluoro-4-methanesulfonyl-phenyl)-1H-pyrazolo[3,4-d]pyrimidin-4-yl]-[1-(3-isopropyl-[1,2,4]oxadiazol-5-ylmethyl)-pyrrolidin-3-yl]-amine (Compound A133)

A mixture of 1-(3-isopropyl-[1,2,4]oxadiazol-5-ylmethyl)-pyrrolidin-3-ylamine (354 mg, 1.68 mmol), 4-chloro-1-(2-fluoro-4-methanesulfonyl-phenyl)-1H-pyrazolo[3,4-d]pyrimidine (500 mg, 1.53 mmol), and potassium carbonate (3.18 g, 23 mmol) in THF (20 mL) was refluxed for 2 hours. Water was added to the reaction mixture and the product was extracted with ethylacetate. The ethylacetate layer was dried over MgSO$_4$. The organic layer was concentrated in vacuo to afford compound A133 as a white solid (700 mg, 91%). Exact mass calculated for $C_{22}H_{25}FN_8O_3S$ 500.18, found 501.1 (MH$^+$).

Example 9.206

Preparation of [1-(2-Fluoro-4-methanesulfonyl-phenyl)-1H-pyrazolo[3,4-d]pyrimidin-4-yl]-[1-(3-isopropyl-[1,2,4]oxadiazol-5-ylmethyl)-pyrrolidin-3-yl]-amine (Compound A134)

Compound A134 was made in a similar manner as described in Example 9.205 as a white solid (712 mg, 93%). Exact mass calculated for $C_{22}H_{25}FN_8O_3S$ 500.18, found 501.1 (MH$^+$).

Example 9.207

Preparation of 3-[1-(2-Fluoro-4-methanesulfonyl-phenyl)-1H-pyrazolo[3,4-d]pyrimidin-4-yloxy]-pyrrolidine-1-carboxylic acid tert-butyl ester (Compound A140)

A mixture of 3-hydroxy-pyrrolidine-1-carboxylic acid tert-butyl ester (431 mg, 2.3 mmol) and sodium hydride (92 mg, 3.82 mmol) in THF (10 mL) was stirred for 30 minutes at room temperature. Then 4-chloro-1-(2-fluoro-4-methanesulfonyl-phenyl)-1H-pyrazolo[3,4-d]pyrimidine (500 mg, 1.53 mmol) was added and stirred overnight at room temperature. The reaction mixture was quenched with water and the product extracted with ethyl acetate. The ethylacetate layer was dried over MgSO$_4$, concentrated in vacuo, and purified by flash chromatography to afford compound A140 as a white solid (495 mg, 45%). Exact mass calculated for $C_{21}H_{24}FN_5O_5S$ 477.15, found 478.2 (MH$^+$).

Example 9.208

Preparation of 3-[1-(4-Methanesulfonyl-phenyl)-1H-pyrazolo[3,4-d]pyrimidin-4-ylamino]-pyrrolidine-1-carboxylic acid tert-butyl ester (Compound A141)

Compound A141 was made in a similar manner as described in Example 9.205 as a white solid (723 mg, 49%). Exact mass calculated for $C_{21}H_{26}N_6O_4S$ 458.17, found 459.2 (MH$^+$).

Example 9.209

Preparation of 3-[1-(2-Fluoro-4-methanesulfonyl-phenyl)-1H-pyrazolo[3,4-d]pyrimidin-4-ylamino]-pyrrolidine-1-carboxylic acid isopropyl ester (Compound A142)

A mixture of [1-(2-fluoro-4-methanesulfonyl-phenyl)-1H-pyrazolo[3,4-d]pyrimidin-4-yl]-pyrrolidin-3-yl-amine (20 mg, 0.048 mmol), isopropylchloroformate (7.2 µL, 0.52 mmol), and triethylamine (20 µL, 0.144 mmol) in DMF (500 µL) was stirred for 2 hours at room temperature. The reaction was purified by HPLC to afford compound A142 as a white solid (9 mg, 41%). Exact mass calculated for $C_{20}H_{23}FN_6O_4S$ 462.15 found 463.3 (MH$^+$).

Example 9.210

Preparation of 3-[1-(4-Methanesulfonyl-phenyl)-1H-pyrazolo[3,4-d]pyrimidin-4-yloxy]-pyrrolidine-1-carboxylic acid tert-butyl ester (Compound A156)

Compound A156 was made in a similar manner as described in Example 9.207 as a white solid (758 mg, 68%). Exact mass calculated for $C_{21}H_{25}N_5O_5S$ 459.16, found 460.2 (MH$^+$).

Example 9.211

Preparation of {4-[1-(4-Methanesulfonyl-phenyl)-1H-pyrazolo[3,4-d]pyrimidin-4-yloxy]-piperidin-1-yl}-(5-pyridin-2-yl-thiophen-2-yl)-methanone (Compound A185)

Compound A185 was made in a similar manner as described in Example 9.25 as a white solid (5 mg, 9%). Exact mass calculated for $C_{27}H_{24}N_6O_4S_2$ 560.13, found 561.4 (MH$^+$).

Example 10

Example 10.1

Preparation of 4-[9-(6-Methanesulfonyl-pyridin-3-yl)-9H-purin-6-yloxy]-piperidine-1-carboxylic acid isobutyl ester (Compound B1)

General Method for Addition of a Chloroformate

Compound B2, see Example 10.2, (75 mg, 0.17 mmol) and TEA (0.34 mmol, 2 equiv.) were dissolved in anhydrous DMF (3 mL) and isobutyl chloroformate was added into the solution then stirred at room temp for 30 minutes. The crude product was purified through HPLC provided Compound B1 as a white solid (46 mg, 57%). $^1$H NMR 400MHz CDCl$_3$ δ (ppm): 9.23 (s, 1H), 8.62 (s, 1H), 8.55 (d, 1H), 8.34 (d, 1H), 8.32 (s, 1H), 5.65 (m, 1H), 3.98-3.95 (m, 2H), 3.90 (d, 2H), 3.43-3.37 (m, 2H), 3.31 (s, 3H), 2.13 (m, 2H), 2.00-1.93 (m, 3H), 0.955 (d, 6H). Exact mass calculated for C$_{21}$H$_{26}$N$_6$O$_5$S 474.17, LCMS (ESI) m/z 475.4 (M+H$^+$, 100%)

Example 10.2

Preparation of 9-(6-Methanesulfonyl-pyridin-3-yl)-6-(piperidin-4-yloxy)-9H-purine (Compound B2)

Prepared using a similar procedure as described in Example 9.6 to give Compound B2 as a tan solid (171 mg, 95%). $^1$H NMR 400MHz CDCl$_3$ δ (ppm): 9.41 (s, 1H); 9.07 (s, 1H); 8.79 (d, 1H); 8.70 (s, 1H); 8.34 (d, 1H); 5.64 (m, 1H); 3.36 (s, 3H); 3.32 (m, 2H); 3.23 (m, 2H); 2.26 (m, 2H); 2.08 (m, 2H). Exact mass calculated for C$_{16}$H$_{18}$N$_6$O$_3$S 374.12, observed LCMS (ESI) m/z 375.2 (M+H$^+$, 100%).

Example 10.3

Preparation of {4-[9-(6-Methanesulfonyl-pyridin-3-yl)-9H-purin-6-yloxy]-piperidin-1-yl}-pyridin-3-yl-methanone (Compound B3)

Using a similar procedure as described in Example 9.7, Compound B3 was prepared and isolated as a cream solid (47 mg, 58%). $^1$H NMR 400MHz CDCl$_3$ δ (ppm): 9.23 (s, 1H); 8.70 (m, 2H); 8.62 (s, 1H); 8.55 (d, 1H); 8.54 (d, 1H); 7.80 (m, 1H); 5.76 (m, 1H); 4.18 (bs, 1H); 3.79 (m, 2H); 3.47 (m, 1H); 3.31 (s, 3H); 2.25 (m, 1H); 2.12 (m, 1H); 2.00 (1H). LCMS: calculated for C$_{22}$H$_{21}$N$_7$O$_4$S 479.14, observed 480.3 (M+H$^+$, 100%)

Example 10.4

Preparation of 4-[9-(4-Methanesulfonyl-phenyl)-9H-purin-6-yloxy]-piperidine 1-carboxylic acid tert-butyl ester (Compound B4)

General Procedure of Purine Formation

Step 1: Preparation of 4-[5-amino-6-(4-methanesulfonyl-phenylamino)-pyrimidin-4-yloxy]-piperidine-1-carboxylic acid tert-butyl ester 4-[6-(4-Methanesulfonyl-phenylamino)-5-nitro-pyrimidin-4-yloxy]-piperidine-1-carboxylic acid tert-butyl ester (647 mg, 1.3 mmol) was dissolved in ethyl acetate under nitrogen and then 10% Pd/C was added. The mixture was stirred at room temperature for 4 hours to afford 4-[5-amino-6-(4-methanesulfonyl-phenylamino)-pyrimidin-4-yloxy]-piperidine-1-carboxylic acid tert-butyl ester as a tan solid (535 mg, 89%). $^1$H NMR(CDCl$_3$, 400MHz) δ 1.77-1.67 (m, 4H), 1.48 (s, 9H), 3.04 (s, 3H), 3.31-3.24 (m, 2H), 3.82 (m, 2H), 5.32 (m, 1H), 6.96 (s, NH), 7.53 (t, NH), 7.70 (t, 1H), 7.71 (d, 2H), 8.16 (s, 1H). Exact mass calculated for C$_{21}$H$_{29}$N$_5$O$_5$S 463.19, found 464.3 (MH$^+$).

Step 2: Preparation of 4-[9-(4-Methanesulfonyl-phenyl)-9H-purin-6-yloxy]-piperidine-1-carboxylic acid tert-butyl ester (Compound B4)

4-[5-Amino-6-(4-methanesulfonyl-phenylamino)-pyrimidin-4-yloxy]-piperidine-1-carboxylic acid tert-butyl ester (300 mg, 0.6 mmol) was dissolved in mixture of triethyl orthoformate (4 mL) and acetic anhydride (4 mL), and then the mixture was refluxed at 140° C. for 15 hours. The crude product was quenched with saturated sodium bicarbonate and extracted with ethyl acetate, then dried in vacuo. Solid was precipitated out in acetonitrile/water and provided Compound B4 as a peach solid (205 mg, 67%). $^1$H NMR (CDCl$_3$, 400MHz) δ 1.48 (s, 9H), 1.95-1.91 (m, 2H), 2.14-2.11 (m, 2H), 3.12 (s, 3H), 3.34-3.27 (m, 2H), 3.94-3.91 (m, 2H), 5.61 (m, 1H), 8.06 (d, 2H), 8.19 (d, 2H), 8.29 (s, 1H), 8.61 (s, 1H). Exact mass calculated for C$_{22}$H$_{27}$N$_5$O$_5$S 473.17, found 474.3 (MH+).

Example 10.5

Preparation of 4-[9-(6-Methanesulfonyl-pyridin-3-yl)-9H-purin-6-yloxy]-piperidine-1-carboxylic acid tert-butyl ester (Compound B5)

Compound B5 was prepared in a similar manner as described in Example 10.4 except using 4-[5-amino-6-(6-methanesulfonyl-pyridin-3-ylamino)-pyrimidin-4-yloxy]-piperidine-1-carboxylic acid tert-butyl ester and was obtained as a peach solid (502 mg, 81%). $^1$H NMR (CDCl$_3$, 400MHz) δ 1.49 (s, 9H), 1.95-1.91 (m, 2H), 2.14-2.11 (m, 2H), 3.31 (s, 3H), 3.35-3.25 (m, 2H), 3.94-3.90 (m, 2H), 5.61 (m, 1H), 8.32 (s, 1H), 8.33 (d, 1H), 8.55 (d, 1H), 8.61 (s, 1H), 9.22 (s, 1H). Exact mass calculated for C$_{21}$H$_{26}$N$_6$O$_5$S 474.17, found 475.3 (MH$^+$).

Example 10.6

Preparation of 4-[9-(2-Fluoro-4-methanesulfonyl-phenyl)-9H-purin-6-yloxy]-piperidine-1-carboxylic acid tert-butyl ester (Compound B6)

Using a similar procedure as described in Example 10.4 afforded Compound B6 as a yellow solid (75 mg, 25%). $^1$H NMR 400MHz CDCl$_3$ δ (ppm): 8.59 (s, 1H); 8.26 (s, 1H); 8.19 (d, 2H); 8.15 (t, 1H); 7.98 (d, 1H); 5.62 (m, 1H); 3.93-3.81 (m, 2H); 3.35-3.27 (m, 2H); 3.14 (s, 3H); 2.10 (m, 2H); 1.97-1.92 (m, 2H); 1.49 (s, 9H). LCMS: calculated for C$_{22}$H$_{26}$FN$_5$O$_5$S 491.16, observed 492.3 (M+H+, 100%).

Example 11

Example 11.1

Preparation of 4-[3-(4-Methanesulfonyl-phenyl)-3H-[1,2,3]triazolo[4,5-d]pyrimidin-7-yloxy]-piperidine-1-carboxylic acid tert-butyl ester (Compound C1)

Step 1: Preparation of 7-chloro-3-(4-methanesulfonyl-phenyl)-3H-[1,2,3]triazolo[4,5-d]pyrimidine To a solution of (6-chloro-5-nitro-pyrimidin-4-yl)-(4-methanesulfonyl-phenyl)-amine in dichloromethane (8 mL) and 50% aqueous acetic acid (6 mL) was added sodium nitrite (64.6 mg, 0.937 mmol) in water (1 mL) dropwise at room temperature. After the addition was complete, the reaction was stirred for additional 15 minutes at room temperature. The organic layer was then separated, washed with water, and dried over anhydrous magnesium sulfate. Filtration followed by removal of volatiles under high vacuum afforded the desired product as a yellow solid (205 mg, 77.8%).

Step 2: Preparation of 4-[3-(4-Methanesulfonyl-phenyl)-3H-[1,2,3]triazolo[4,5-d]pyrimidin-7-yloxy]-piperidine-1-carboxylic acid tert-butyl ester (Compound C1)

Compound C1 was obtained as a yellow solid. (101.1 mg, 66%) via a similar procedure as described in Example 9.1 using 7-chloro-3-(4-methanesulfonyl-phenyl)-3H-[1,2,3]triazolo[4,5-d]pyrimidine and 4-hydroxy-piperidine-1-carboxylic acid tert-butyl ester. $^1$H NMR (400MHz DMSO-d$_6$) δ (ppm): 8.92 (s, 1H); 8.52 (d, 2H); 8.24 (d, 2H); 5.68 (m, 1H); 3.78 (m, 2H); 3.31 (s, 3H); 3.26 (m, 2H); 2.12 (m, 2H); 1.76 (m, 2H); 1.42 (s, 9H). LCMS (ESI) calculated for $C_{21}H_{26}N_6O_5S$: observed m/z 475.3 (MH$^+$, 100%).

Example 12

Example 12.1

Preparation of 4-[3-(4-Methanesulfonyl-phenyl)-isoxazolo[4,5-d]pyrimidin-7-yloxy]-piperidine-1-carboxylic acid tert-butyl ester (Compound D1)

Step 1: Preparation of 4-Methanesulfonyl-benzoic acid phenyl ester.

To a solution of the 4-methanesulfonyl-benzoic acid (20 g, 99.9 mmol) in $CH_2Cl_2$ (150 mL), was oxalyl chloride (13.1 mL, 149.9 mmol) added. The reaction mixture was cooled to 0° C. and treated with DMF (2 mL). The reaction was warmed to room temperature and maintained for 10 h. The reaction was concentrated under vacuum and dissolved with $CH_2Cl_2$ (200 mL). The reaction was treated with phenol (10.5 mL, 120 mmol) followed by Et$_3$N (16.7 mL, 120 mmol) at 0° C. The reaction was warmed to room temperature and stirred for 7 hr. The reaction was extracted with $CH_2Cl_2$ (500 mL), dried and concentrated under vacuum. The desired compound, 4-methanesulfonyl-benzoic acid phenyl ester, was obtained by recrystallization from methanol (200 mL) as a white crystal in 78% yield (21.5 g). $^1$H NMR (400Mz, DMSO-d$_6$) δ 8.41 (d, J=7.1, 2H), 8.39 (d, J=7.1, 2H), 7.55~7.51 (m, 2H), 7.37~7.35 (m, 3H), 3.35 (s, 3H). LCMS 277.0 [M+H].

Step 2: Preparation of 1-(4-Methanesulfonyl-phenyl)-2-nitro-ethanone

To a suspension of potassium tert-butoxide (24.3 g, 217.1 mmol) in DMSO (150 mL), was added $CH_3NO_2$ (11.7 mL, 217.1 mmol) added at 0° C. After stirring for 1 h, 4-methanesulfonyl-benzoic acid phenyl ester (20.0 g, 72.4 mmol) was added in one portion at 0° C. The reaction was warmed to room temperature and stirred for 5 hr. The reaction was poured into ice-water (200 mL) and followed by adding urea (2.17 g, 36.2 mmol). The reaction was acidified with 5.0M HCl to pH=5 at 0° C. The reaction was added to water (1L) and stirred for 1 h. The pale yellow solid was filtered and dried under vacuum to afford the desired compound (13.2 g, 75.2%). $^1$H NMR (400Mz, DMSO-d$_6$) δ 8.19 (m, 4H), 6.63 (s, 2H), 3.35 (s, 3H). LCMS 244.5 [M+H].

Step 3: Preparation of 1-(4-Methanesulfonyl-phenyl)-2-nitro-ethanone oxime

To a solution of 1-(4-methanesulfonyl-phenyl)-2-nitro-ethanone (12.5 g, 51.4 mmol) in ethanol (100 mL), was added NH$_2$OH.HCl (3.57 g, 51.4 mmol) and acetic acid (33 mL) at room temperature. The reaction was refluxed for 3 h and cooled to room temperature. The reaction was concentrated under vacuum and extracted with ethyl acetate (200 mL). The reaction was concentrated to afford the crude compound which was recrystallized from petroleum ether/hexane (1/3) as white crystals (10.3 g, 83.4%). $^1$H NMR (400Mz, DMSO-d$_6$) δ 12.81 (s, 1H), 8.03 (m, 4H), 5.93 (s, 2H), 3.28 (s, 3H). LCMS 259.2[M+H].

Step 4: Preparation of 3-(4-Methanesulfonyl-phenyl)-4-nitro-isoxazole-5-carboxylic acid ethyl ester To a solution of 1-(4-methanesulfonyl-phenyl)-2-nitro-ethanone oxime (10.0 g, 38.7 mmol) in ether (100 mL) and THF (50 mL) was added ethyl chloro ethyloxalate (4.29 mL, 38.7 mmol) at ambient temperature. The reaction was stirred for 16 h and concentrated under vacuum. The residue was washed with ether (100 mL). The solid was filtered and washed with ether. The compound was dissolved in THF (50 mL) and ether (100 mL) and treated with a solution of Et$_3$N (~1.5 mL) in THF (10 mL). The completion of the reaction was determined by TLC. The reaction was poured into H$_2$O (200 mL). The organic layer was dried over MgSO$_4$ and concentrated to afford the crude desired compound as a solid. The compound was recrystallized in Ethyl acetate/Hexane (50 mL/150 mL) to afford the desired compound (6.2 g, 47%) as a yellowish crystal. $^1$H NMR (400Mz, DMSO) δ 8.40 (d, J=7.1, 2H), 8.21 (d, J=7.1, 2H), 3.35 (s, 3H), 2.63 (q, 2H), 1.05 (t, 3H).

Step 5: Preparation of 4-Amino-3-(4-methanesulfonyl-phenyl)-isoxazole-5-carboxylic acid ethyl ester 3-(4-Methanesulfonyl-phenyl)-4-nitro-isoxazole-5-carboxylic acid ethyl ester (6.2 g) was suspended in sat. NH$_4$Cl (100 mL) and treated with Zn (10.0 g) at room temperature.

The reaction was stirred for 3 h and ethyl acetate (100 mL) was added. After stirring for 1 h, zinc was filtered off. The ethyl acetate was taken and washed with $H_2O$, dried over $MgSO_4$ and concentrated under vacuum to afford the crude product (4.3 g, 77%). The product was crystallized in ethyl acetate/hexane (1/3) to afford the desired compound. LCMS 311.1 [M+H].

Step 6: Preparation of 4-Amino-3-(4-methanesulfonyl-phenyl)-isoxazole-5-carboxylic acid amide To a solution of 4-amino-3-(4-methanesulfonyl-phenyl)-isoxazole-5-carboxylic acid ethyl ester (4.0 g, 12.9 mmol) in methanol (50 mL) and THF (50 mL), was added a $NH_4OH$ solution (100 mL) at room temperature. The reaction was stirred for 24 h. The precipitates were filtered and washed with $H_2O$ (100 mL). The compound was dried in vacuo to afford the crude product which was used for the next step without further purification. LCMS 282.1 [M+H].

Step 7: Preparation of 3-(4-methanesulfonyl-phenyl)-isoxazolo[4,5-d]pyrimidin-7-ol To a suspension of 4-amino-3-(4-methanesulfonyl-phenyl)-isoxazole-5-carboxylic acid amide (2.5 g, 8.9 mmol) in $CH(OEt)_3$ (30 mL), was added acetic anhydride (10 mL) at ambient temperature. The reaction was heated to reflux for 5 h and cooled to room temperature. The reaction was concentrated under vacuum and poured into $H_2O$ (50 mL). The organic material was extracted with ethyl acetate (50 mL), dried over $MgSO_4$ and concentrated under vacuum. The crude product was used for the next step without further purification. LCMS 292.0 [M+H].

Step 8: Preparation of 7-chloro-3-(4-methanesulfonyl-phenyl)-isoxazolo[4,5-d]pyrimidine 3-(4-Methanesulfonyl-phenyl)-isoxazolo[4,5-d]pyrimidin-7-ol (0.5 g, 1.7 mmol) was suspended in $POCl_3$ (10 mL) and refluxed for 12 h. The reaction was poured into ice carefully and precipitates filtered. The solid was dissolved in ethyl acetate (15 mL) and purified under $SiO_2$ with 30% ethyl acetate in hexane to afford the desired compound (0.42 g, 80.1%).

Step 9: Preparation of 4-[3-(4-Methanesulfonyl-phenyl)-isoxazolo[4,5-d]pyrimidin-7-yloxy]-piperidine-1-carboxylic acid tert-butyl ester (Compound D1)

4-hydroxy-piperidine-1-carboxylic acid tert-butyl ester (0.1 g, 0.49 mmol) was dissolved in anhydrous THF (5 mL) and treated with NaH, 60% oil dispersion (20 mg, 0.49 mmol) at ambient temperature. After stirring for 10 min, 7-chloro-3-(4-methanesulfonyl-phenyl)-isoxazolo[4,5-d]pyrimidine (0.15 g, 0.49 mmol) was added. The reaction was stirred for 3 h and concentrated under vacuum. The residue was purified by column chromatography using ethyl acetate and hexane (1/1) to afford 4-[3-(4-methanesulfonyl-phenyl)-isoxazolo[4,5-d]pyrimidin-7-yloxy]-piperidine-1-carboxylic acid tert-butyl ester (0.14 g, 61%). $^1$H NMR (400Mz, DMSO-$d_6$) δ 8.51 (s, 1H), 8.42 (d, J=7.1, 2H), 8.34 (d, J=7.1, 2H), 4.11~3.83 (m, 4H), 3.52 (m, 1H), 3.26 (s, 3H), 1.41~1.22 (m, 4H). LCMS 475.3[M+H].

Example 12.2

Preparation of 4-({ethyl-[3-(4-methanesulfonyl-phenyl)-isoxazolo[4,5-d]pyrimidin-7-yl]-amino}-methyl)-piperidine-1-carboxylic acid tert-butyl ester (Compound D2)

4-Ethylaminomethyl-piperidine-1-carboxylic acid tert-butyl ester (0.12 g, 0.49 mmol) was dissolved in anhydrous THF (5 mL) and treated with NaH, 60% oil dispersion (20 mg, 0.49 mmol) at ambient temperature. After stirring for 10 min, 7-chloro-3-(4-methanesulfonyl-phenyl)-isoxazolo[4,5-d]pyrimidine (0.15 g, 0.49 mmol) was added. The reaction was stirred for 3 h and concentrated under vacuum. The residue was subjected to $SiO_2$ with ethyl acetate and hexane (1/1) to afford Compound D2 (0.82 g, 61%). $^1$H NMR (400Mz, DMSO-$d_6$) δ 8.49 (s, 1H), 8.41 (d, J=7.1, 2H), 8.34 (d, J=7.1, 2H), 4.10~3.74 (m, 7H), 3.52 (m, 1H), 3.25 (t, 3H), 1.41~1.22 (m, 4H). LCMS 516.3[M+H].

Example 12.3

Preparation of 4-[3-(4-Methanesulfonyl-phenyl)-isoxazolo[4,5-d]pyrimidin-7-ylsulfanyl]-piperidine-1-carboxylic acid tert-butyl ester (Compound D3)

7-Chloro-3-(4-methanesulfonyl-phenyl)-isoxazolo[4,5-d]pyrimidine (0.19 mmol, 60 mg), 4-mercapto-piperidine-1-carboxylic acid tert-butyl ester (0.25 mmol, 54 mg) and potassium carbonate (0.28 mmol, 35 mg) were dissolved in DMF (10 mL) and stirred for 90 minutes at room temperature. Its progress was monitored by thin layer chromatography and LCMS. The reaction was treated with water and the desired compound was extracted with ethyl acetate. The organic layer was evaporated in vacuo. Purification by HPLC provided compound D3 as a white solid (40 mg, 35%). $^1$H NMR (400Mz, CDCl$_3$) δ 9.03 (s, 1H); 8.71 (d, 2H); 8.15 (d, 2H); 4.44 (h, 1H); 4.02 (m, 2H); 3.22 (m, 2H); 3.13 (s, 3H); 2.19 (m, 2H); 1.82 (m, 2H); 1.47 (s, 9H). LCMS (ESI), m/z 491.1 (MH+, 100%)

Example 12.4

Preparation of 4-[3-(4-methanesulfonyl-phenyl)-isoxazolo[4,5-d]pyrimidin-7-yloxy]-piperidine-1-carboxylic acid isopropyl ester (Compound D4)

4-[3-(4-Methanesulfonyl-phenyl)-isoxazolo[4,5-d]pyrimidin-7-yloxy]-piperidine-1-carboxylic acid tert-butyl ester (1.2 g, 2.53 mmol) was dissolved in $CH_2Cl_2$ (5 mL) and cooled to 0° C. The reaction was treated with 4.0M HCl in dioxane (2.0 mL) at the same temperature. The reaction was warmed to room temperature and stirred for five hours. The reaction was concentrated under vacuum and crystallized in methanol (10 mL). The precipitate was filtrated and dried to afford the HCl salt of the amine. The salt was stirred in $CH_2Cl_2$ (20 mL) and treated with $Et_3N$ and chloro isopropylchloroformate at 0° C. After stirring for five hours, the reaction was poured into $H_2O$ (20 mL). The organic compound was extracted with $CH_2Cl_2$ (30 mL) and washed with brine. The ethyl acetate layer was dried over $MgSO_4$ and concentrated under vacuum. The residue was purified over $SiO_2$ to afford Compound D4 (970 mg, 83.4%). $^1$H NMR (400Mz, DMSO-$d_6$) δ 8.50 (s, 1H), 8.41 (d, J=7.0, 2H), 8.35 (d, J=7.0, 2H), 4.11~3.83 (m, 4H), 3.52 (m, 1H), 3.47 (m, 1H), 3.25 (d, 6H), 1.41~1.22 (m, 4H). LCMS 461.6[M+H].

Example 13.1

Preparation of 4-[8-(4-Bromo-2-fluoro-phenyl)-quinolin-4-yloxy]-piperidine-1-carboxylic acid isopropyl ester (Compound F5)

Step 1: Preparation of 2-[(2-iodo-phenylamino)-methylene]-malonic acid diethyl ester 2-Iodoaniline (50 g, 228.3 mmol) and 2-ethoxymethylene-malonic acid diethyl ester (50 mL, 251.1 mmol) were mixed and the solution was stirred at 110° C. for 3 h. The crude was dissolved in dichloromethane and it was purified by silica plug. The product was eluted with ethyl acetate/hexanes (10-50%) and the solvent removed under reduced pressure to afford 2-[(2-iodo-phenylamino)-methylene]-malonic acid diethyl ester as an off-white powder (81.4 g, 91.6%). $^1$H NMR (CDCl$_3$, 400 MHz) δ 1.49 (t, 3H), 1.54 (t, 3H), 4.40 (q, 2H), 4.52 (q, 2H), 7.01-7.05 (m, 1H), 7.36-7.39 (m, 1H), 7.52-7.56 (m, 1H), 8.59 (d, 1H). Exact mass calculated for $C_{14}H_{16}INO_4$ 389.01, found 390.1 (MH$^+$).

Step 2: Preparation of 8-iodo-4-oxo-1,4-dihydro-quinoline-3-carboxylic acid ethyl ester In a 2-neck round bottomed flask (250 mL), phenylether (60 mL) was put to reflux on a heating mantel. When it started boiling, p-toluenesulfonic acid (0.140 g) was added. 2-[(2-iodo-phenylamino)-methylene]-malonic acid diethyl ester was dissolved in phenylether (20 mL) and the mixture was poured into the boiling solvent. The mixture was refluxed for 3 h. The crude was transferred to a bequer and cooled to room temperature. Hexanes (600 mL) were added and a precipitate was observed. The mixture was stirred for 5 min, followed by filtration of the solid and thorough wash with hexanes to afford 8-iodo-4-oxo-1,4-dihydro-quinoline-3-carboxylic acid ethyl ester as a grayish solid (2 g, 46%). $^1$H NMR (DMSO-d$_6$, 400MHz) δ 1.43 (t, 3H), 4.39 (q, 2H), 7.36 (t, 1H), 8.32 (d, 1H), 8.37 (d, 1H), 8.63 (s, 1H), 11.4 (s, 1H). Exact mass calculated for $C_{12}H_{10}INO_3$ 342.97, found 343.9 (MH$^+$).

Step 3: Preparation of 8-iodo-4-oxo-1,4-dihydro-quinoline-3-carboxylic acid

8-Iodo-4-oxo-1,4-dihydro-quinoline-3-carboxylic acid ethyl ester (2 g, 5.83 mmol) was suspended in 10% NaOH in water (20 mL). The mixture was stirred under reflux for 1 h. The crude was cooled to room temperature and acidified with concentrated HCl. The solid was filtered off and thoroughly washed with water to afford 8-iodo-4-oxo-1,4-dihydro-quinoline-3-carboxylic acid as a pinkish solid (1.5 g, 81.6%). $^1$H NMR (DMSO-d$_6$, 400MHz) δ 7.04 (t, 1H), 8.12-8.16 (m, 2H), 8.71 (s, 1H). Exact mass calculated for $C_{10}H_6INO_3$ 314.94, found 316 (MH$^+$).

Step 4: Preparation of 8-iodo-1H-quinolin-4-one

8-Iodo-4-oxo-1,4-dihydro-quinoline-3-carboxylic acid (15.69 g, 49.8 mmol) was suspended in phenylether (40 mL) and the mixture heated to boiling. After 30 min, reaction was completed by LCMS. The crude was transferred to a bequer and cooled to room temperature. Hexanes (500 mL) were added and the mixture was stirred for 10 min. The solid was retrieved by filtration, thoroughly washed with hexanes and purified by HPLC to afford 8-iodo-1H-quinolin-4-one as a brownish solid (4.4 g, 23%). $^1$H NMR (DMSO-d$_6$, 400MHz) δ 6.14 (d, 1H), 7.09 (t, 1H), 7.88 (d, 1H), 8.08 (dd, 1H), 8.16 (dd, 1H). Exact mass calculated for $C_9H_6INO$ 270.95, found 271.8 (MH$^+$).

Step 5: Preparation of 4-chloro-8-iodo-quinoline

8-Iodo-1H-quinolin-4-one (3.36 g, 8.72 mmol) was suspended in POCl$_3$ (8 mL, 87.2 mmol) and catalytic anhydrous DMF (6.72 μL) was added. The mixture was refluxed for 1 h. The hot crude was poured over ice and the mixture stirred until ice was completely melted. Solid was filtered off, thoroughly washed with water and kept in the vacuum oven overnight to afford 4-chloro-8-iodo-quinoline as a grayish solid (2.47 g, 98%). $^1$H NMR (DMSO-d$_6$, 400MHz) δ 7.45 (t, 1H), 7.81 (d, 1H), 8.19 (dd, 1H), 8.45 (dd, 1H), 8.87 (d, 1H). Exact mass calculated for $C_9H_5ClIN$ 288.92, found 289.9 (MH$^+$).

Step 6: Preparation of 8-(4-bromo-2-fluoro-phenyl)-4-chloro-quinoline

To a solution of 4-chloro-8-iodo-quinoline (14 5 mg, 0.5 mmol) and tetrakis(triphenylphosphine)palladium (57 mg, 0.05 mmol) in THF (1 mL) was added 0.5M THF solution of 2-fluoro-4-bromozinciodide (1 mL) under N$_2$. The reaction mixture was heated overnight at 65° C. The resulting mixture was diluted with CH$_2$Cl$_2$ and filtered through a syringe filter. The filtrate was concentrated and the residue was purified by column chromatography using 15% EtOAc/Hexane to give 8-(4-bromo-2-fluoro-phenyl)-4-chloro-quinoline. $^1$H NMR (CDCl$_3$, 400MHz) δ 7.41 (m, 3H), 7.52 (d, 1H), 7.74 (m, 2H), 8.34 (m, 1H), 8.78 (d, 1H). Exact mass calculated for $C_{15}H_8BrClFN$ 334.95, found 336.2 (MH$^+$).

Step 7: Preparation of 4-[8-(4-bromo-2-fluoro-phenyl)-quinolin-4-yloxy]-piperidine-1-carboxylic acid isopropyl ester (Compound F5)

In a 10 mL reaction vial equipped with a N$_2$ inlet septum was placed a stir bar, NaH (60% in mineral oil, 40 mg, 1 mmol) and 4-hydroxy-piperidine-1-carboxylic acid isopropyl ester (37 mg, 0.2 mmol). THF (anhydrous, 1.2 mL) was added to the mixture. The resulting suspension was stirred about 30 min at room temperature. 8-(4-Bromo-2-fluoro-phenyl)-4-chloro-quinoline (1 g, 0.5 mmol) was then added in one portion. The mixture was stirred overnight under N$_2$ at 65° C. and the resulting slurry turned slightly yellowish. The slurry was added CH$_2$Cl$_2$ and filtered. The filtrate was concentrated under vacuum to give the crude product. Purification by column chromatography gave the desired Compound F5 as an off-white solid. $^1$H NMR (CDCl$_3$, 400MHz) δ 1.27 (d, 6H), 1.97 (m, 2H), 2.05 (m, 2H), 3.59 (m, 2H), 3.75 (m, 2H), 4.84 (m, 1H), 4.94 (m, 1H), 6.76 (d, 1H), 7.39 (m, 3H), 7.56 (t, 1H), 7.67 (d, 1H), 8.31 (d, 1H), 8.74 (d, 1H). Exact mass calculated for $C_{24}H_{24}BrFN_2O_3$ 486.10, found 487.2 (MH$^+$).

Example 13.2

Preparation of 4-[8-(4-Methylsulfanyl-phenyl)-quinolin-4-yloxy]-piperidine-1-carboxylic acid isopropyl ester (Compound F2)

Step 1: Preparation of 4-(8-chloro-quinolin-4-yloxy)-piperidine-1-carboxylic acid isopropyl ester In a 50 mL round-bottomed flask equipped with a $N_2$ inlet septum was placed a stir bar, NaH (60% in mineral oil, 1.1 g, 30 mmol) and 4-hydroxy-piperidine-1-carboxylic acid isopropyl ester (0.93 g, 5 mmol). THF (anhydrous, 20 mL) was added to the mixture. The resulting suspension was stirred about 30 min at room temperature. 4,8-Dichloro-quinoline (1 g, 0.5 mmol) was then added in one portion. The mixture was stirred overnight under $N_2$ at 80° C. and the resulting slurry turned slightly yellowish. The slurry was added $CH_2Cl_2$ and filtered. The filtrate was concentrated under vacuum to give the crude product. Purification by column chromatography gave 4-(8-chloro-quinolin-4-yloxy)-piperidine-1-carboxylic acid isopropyl ester as an off-white solid. $^1$H NMR ($CDCl_3$, 400MHz) δ 1.26 (d, 6H), 1.97 (m, 2H), 2.05 (m, 2H), 3.58 (m, 2H), 3.73 (m, 2H), 4.82 (m, 1H), 4.94 (m, 1H), 6.81 (d, 1H), 7.42 (t, 1H), 7.84 (d, 1H), 8.16 (d, 1H), 8.87 (d, 1H). Exact mass calculated for $C_{18}H_{21}ClN_2O_3$ 348.12, found 349.2 ($MH^+$)

Step 2: Preparation of 4-[8-(4-methylsulfanyl-phenyl)-quinolin-4-yloxy]-piperidine-1-carboxylic acid isopropyl ester In a 25 mL round-bottomed flask equipped with a reflux condenser and N2 inlet septum was placed a stir bar, 4-(8-chloro-quinolin-4-yloxy)-piperidine-1-carboxylic acid isopropyl ester (198 mg, 0.57 mmol), 4-methylthiophenylboronic acid (287 mg, 1.7 mmol), tetrakis(triphenylphosphine) palladium (98 mg, 0.085 mmol), 2M sodium carbonate (0.6 mL) and toluene (4 mL). The mixture was refluxed 36 h under N2. The resulting mixture was diluted with ethyl acetate and extracted with $H_2O$. The organic extract was dried and concentrated to give the crude product. The crude product was purified by column chromatography to using 50% EtOAc/Hexane and preparative HPLC to give the desired product. $^1$H NMR ($CDCl_3$, 400MHz) δ 1.27 (d, 6H), 2.04 (m, 2H), 2.17 (m, 2H), 2.55 (s, 3H), 3.59 (m, 2H), 3.83 (m, 2H), 4.97 (m, 1H), 5.09 (m, 1H), 7.14 (s, 1H), 7.41 (m, 4H), 7.81 (t, 1H), 7.90 (d, 1H), 8.38 (d, 1H), 9.11 (s, 1H). Exact mass calculated for $C_{25}H_{28}N_2O_3S$ 436.18, found 437.2 ($MH^+$).

Example 13.3

Preparation of 4-[8-(4-Methanesulfonyl-phenyl)-quinolin-4-yloxy]-piperidine-1-carboxylic acid isopropyl ester (Compound F3)

In a 25 mL round-bottomed flask immersed in an ice-bath was placed a stir bar and Compound F2 (16 mg, 0.037 mmol) in $CH_2Cl_2$ (5 mL). A solution of mCPBA (19 mg, 0.081 mmol) dissolved in $CH_2Cl_2$ (1 mL) was added at 0° C. The mixture was stirred at 0° C. for 30 min. A solution of sodium bisulfite was added. The organic phase was separated, dried and concentrated to give the crude product. The crude was purified by HPLC. $^1$H NMR ($CDCl_3$, 400MHz) δ 1.29 (d, 6H), 2.04 (m, 2H), 2.20 (m, 2H), 3.16 (s, 3H), 3.59 (m, 2H), 3.85 (m, 2H), 4.97 (m, 1H), 5.14 (m, 1H), 7.23 (s, 1H), 7.66 (d, 2H), 7.92 (m, 2H), 8.12 (d, 2H), 8.48 (d, 1H), 9.08 (d, 1H). Exact mass calculated for $C_{25}H_{28}N_2O_5S$ 468.17, found 469.2 ($MH^+$).

Example 13.4

Preparation of 4-[8-(4-Isopropoxy-phenyl)-quinolin-4-yloxy]-piperidine-1-carboxylic acid isopropyl ester (Compound F4)

In a 25 mL round-bottomed flask equipped with a reflux condenser and N2 inlet septum was placed a stir bar, 4-(8-chloro-quinolin-4-yloxy)-piperidine-1-carboxylic acid isopropyl ester (200 mg, 0.57 mmol), 4-isopropoxyphenylboronic acid (304 mg, 1.7 mmol), 2M sodium carbonate (0.6 mL) and toluene (4 mL). The mixture was degassed for a few minutes. Tetrakis(triphenylphosphine) palladium (98 mg, 0.085 mmol) was added to the above mixture. The reaction mixture was refluxed overnight under N2. The resulting mixture was diluted with ethyl acetate and extracted with $H_2O$. The organic extract was dried and concentrated to give the crude product. The crude product was purified by column chromatography to using 50% EtOAc/Hexane and preparative HPLC to give the desired product. $^1$H NMR ($CDCl_3$, 400MHz) δ 1.28 (d, 6H), 1.39 (d, 6H), 2.03 (m, 2H), 2.17 (m, 2H), 3.59 (m, 2H), 3.85 (m, 2H), 4.63 (m, 1H), 4.97 (m, 1H), 5.12 (m, 1H), 7.04 (s, 1H), 7.22 (d, 1H), 7.37 (d, 2H), 7.81 (t, 1H), 7.90 (d, 1H), 8.36 (d, 1H), 9.06 (d, 1H). Exact mass calculated for $C_{27}H_{32}N_2O4$ 448.24, found 449.4 ($MH^+$).

Example 14

Protocol for RUP3Dose Responses in Melanophores

Melanophores are maintained in culture as reported by Potenza, M. N. and Lerner, M. R., in Pigment Cell Research, Vol. 5, 372-378, 1992 and transfected with the RUP3 expression vector (pCMV) using electroporation. Following electroporation, the transfected cells are plated into 96 well plates for the assay. The cells are then allowed to grow for 48 hours in order to both recover from the electroporation procedure and attain maximal receptor expression levels.

On the assay day, the growth medium on the cells is replaced with serum-free buffer containing 10 nM melatonin. The melatonin acts via an endogenous Gi-coupled GPCR in the melanophores to lower intracellular cAMP levels. In response to lowered cAMP levels, the melanophores translocate their pigment to the center of the cell. The net effect of this is a significant decrease in the absorbance reading of the cell monolayer in the well, measured at 600-650 nM.

After a 1-hour incubation in melatonin, the cells become completely pigment-aggregated. At this point a baseline absorbance reading is collected. Serial dilutions of test compounds are then added to the plate and compounds that stimulate RUP3 produce increases in intracellular cAMP levels. In response to these increased cAMP levels, the melanophores translocate their pigment back into the cell periphery. After one hour, stimulated cells are fully pigment-dispersed. The cell monolayer in the dispersed state absorbs much more light in the 600-650 nm range. The measured increase in absorbance compared to the baseline reading allows one to quantitate the degree of receptor stimulation and plot a dose-response curve.

The compounds in the above examples were screened using the melanophore assay. Representative compounds and their corresponding $EC_{50}$ values are shown in Table 10 below:

TABLE 10

| Compound | RUP3 (EC$_{50}$) (nM) |
|---|---|
| A5 | 12.7 |
| B5 | 59.1 |
| C1 | 13.0 |

Other compounds in the Examples showed EC$_{50}$ activities in the melanophore assay of less than about 10 µM. Each of the embodiments of the present invention may in the alternative be limited to relate to those compounds that demonstrate about 100 fold or greater binding to RUP3 compared to the corticotrophin-releasing factor-1 (CRF-1) receptor; a recent review of CRF-1 compounds can be found in Expert Opin. Ther. Patents 2002, 12 (11), 1619-1630, incorporated herein by reference in its entirety.

Example 15

Food Intake Study

Male ZDF (Zucker diabetic fatty) rats weighing 350 g-400 g were dosed independently with two structurally divergent chemotypes exhibiting agonism to the RUP3 receptor. Rats were dosed daily via oral gavage with either vehicle (100% PEG 400), First Compound (30 mg/kg, 100 mg/kg), or Second Compound (10 mg/kg, 30 mg/kg) at a volume of 3 ml/kg. Body weight and food intake were monitored and recorded daily. Table 11 shown below illustrates the body weight (g) and cumulative food intake (g) taken after both seven days and 14 days of dosing.

TABLE 11

| Substance | Dose (mg/Kg) | Cumulative Food Intake (g) | | Body Weight (g) | |
|---|---|---|---|---|---|
| | | Week 1 | Week 2 | Week 1 | Week 2 |
| First Compound | Vehicle | 321 | 672 | 390 | 395 |
| | 30 mg/Kg | 271 | 557 | 383 | 383 |
| | 100 mg/Kg | 211 | 457 | 361 | 376 |
| Second Compound | Vehicle | 261 | 563 | 393 | 393 |
| | 10 mg/Kg | 217 | 459 | 388 | 390 |
| | 30 mg/Kg | 159 | 307 | 377 | 373 |

Those skilled in the art will recognize that various modifications, additions, substitutions, and variations to the illustrative examples set forth herein can be made without departing from the spirit of the invention and are, therefore, considered within the scope of the invention. All documents referenced above, including, but not limited to, printed publications, and provisional and regular patent applications, are incorporated herein by reference in their entirety.

We claim:

1. A compound of Formula (I):

$$\text{(I)}$$

or a pharmaceutically acceptable salt, hydrate or solvate thereof;
wherein:
A and B are each independently $C_{1-3}$ alkylene optionally substituted with 1 to 4 substituents selected from the group consisting of $C_{1-3}$ alkyl, $C_{1-4}$ alkoxy, carboxy, cyano, $C_{1-3}$ haloalkyl and halogen;
D is $CR_1R_2$ or $N—R_2$, wherein $R_1$ is selected from the group consisting of H, $C_{1-8}$ alkyl, $C_{1-4}$ alkoxy, halogen and hydroxyl;
E is N, C or $CR_3$, wherein $R_3$ is H or $C_{1-8}$ alkyl;
----- is a single bond when E is N or $CR_3$, or a double bond when E is C;
K is a $C_{3-6}$ cycloalkylene or $C_{1-3}$ alkylene wherein each are optionally substituted with 1 to 4 substituents selected from the group consisting of $C_{1-3}$ alkyl, $C_{1-4}$ alkoxy, carboxy, cyano, $C_{1-3}$ haloalkyl and halogen; or K is a bond;
Q is O, S, S(O) or $S(O)_2$;
T is $CR_5$;
M is N;
J is N;
U is C;
V is a bond;
W is N or C;
X is N, $CR_9$ or $NR_{11}$;
Y is N, $CR_{10}$ or $NR_{12}$;
Z is C;
$R_5$, $R_9$ and $R_{10}$ are each independently selected from the group consisting of H, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-4}$ alkylamino, $C_{2-8}$ dialkylamino, carboxamide, cyano, $C_{3-6}$ cycloalkyl, $C_{2-6}$ dialkylcarboxamide, $C_{2-6}$ dialkylsulfonamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl, hydroxylamino and nitro; wherein said $C_{2-6}$ alkenyl, $C_{1-8}$ alkyl, $C_{2-6}$ alkynyl and $C_{3-6}$ cycloalkyl are optionally substituted with 1, 2, 3 or 4 substituents selected from the group consisting of $C_{1-5}$ acyl, $C_{1-5}$ acyloxy, $C_{1-4}$ alkoxy, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{2-8}$ dialkylamino, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, hydroxyl, hydroxylamino and nitro;

$R_{11}$ and $R_{12}$ are each independently selected from $C_{2-6}$ alkenyl, $C_{1-8}$ alkyl, $C_{2-6}$ alkynyl or $C_{3-6}$ cycloalkyl each optionally substituted with 1, 2, 3 or 4 substituents selected from the group consisting of $C_{1-5}$ acyl, $C_{1-5}$ acyloxy, $C_{1-4}$ alkoxy, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{2-8}$ dialkylamino, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, hydroxyl, hydroxylamino and nitro;

$Ar_1$ is aryl or heteroaryl each optionally substituted with $R_{13}$, $R_{14}$, $R_{15}$, $R_{16}$, and $R_{17}$; wherein $R_{13}$ is selected from the group consisting of $C_{1-5}$ acyl, $C_{1-6}$ acylsulfonamide, $C_{1-5}$ acyloxy, $C_{2-6}$ alkenyl, $C_{1-4}$ alkoxy, $C_{1-8}$ alkyl, $C_{1-4}$ alkylamino, $C_{1-6}$ alkylcarboxamide, $C_{1-4}$ alkylthiocarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, arylsulfonyl, carbamimidoyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, $C_{2-6}$ dialkylthiocarboxamide, guanidinyl, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heterocyclic, heterocyclic-oxy, heterocyclicsulfonyl, heterocyclic-carbonyl, heteroaryl, heteroarylcarbonyl, hydroxyl, nitro, $C_{4-7}$ oxo-cycloalkyl, phenoxy, phenyl, sulfonamide, sulfonic acid, and thiol, and wherein said $C_{1-5}$ acyl, $C_{1-6}$ acylsulfonamide, $C_{1-4}$ alkoxy, $C_{1-8}$ alkyl, $C_{1-4}$ alkylamino, $C_{1-6}$ alkylsulfonamide, $C_{1-4}$ alkylsulfonyl, $C_{1-4}$ alkylthio, arylsulfonyl, carbamimidoyl, $C_{2-6}$ dialkylamino, heterocyclic, heterocyclic-carbonyl, heteroaryl, phenoxy and phenyl are optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{3-7}$ cycloalkyloxy, $C_{2-6}$ dialkylamino, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heteroaryl, heterocyclic, hydroxyl, nitro, phenyl, and phosphonooxy, and wherein said $C_{1-7}$ alkyl and $C_{1-4}$ alkylcarboxamide are each optionally substituted with 1 to 5 substituents selected from the group consisting of $C_{1-4}$ alkoxy and hydroxy; or $R_{13}$ is a group of Formula (A):

$$\text{(A)}$$

wherein:
"p" and "r" are independently 0, 1, 2 or 3; and
$R_{18}$ is H, $C_{1-5}$ acyl, $C_{2-6}$ alkenyl, $C_{1-8}$ alkyl, $C_{1-4}$ alkylcarboxamide, $C_{2-6}$ alkynyl, $C_{1-4}$ alkylsulfonamide, carbo-$C_{1-6}$-alkoxy, carboxamide, carboxy, cyano, $C_{3-7}$ cycloalkyl, $C_{2-6}$ dialkylcarboxamide, halogen, heteroaryl or phenyl, and wherein said heteroaryl or phenyl optionally substituted with 1 to 5 substituents selected independently from the group consisting of $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl;

$R_{14}$, $R_{15}$, $R_{16}$, and $R_{17}$ are each independently selected form the group consisting of H, $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-7}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl and nitro; or two adjacent $R_{14}$, $R_{15}$, $R_{16}$ and $R_{17}$ together with the atoms to which they are attached form a 5, 6 or 7 member cycloalkyl, cycloalkenyl or heterocyclic group fused with $Ar_1$ wherein the 5, 6 or 7 member group is optionally substituted with halogen; and $R_2$ is selected from the group consisting of $C_{1-8}$ alkyl, $C_{2-6}$ alkynyl, amino, aryl, carboxamide, carboxy, cyano, $C_{3-6}$-cycloalkyl, $C_{1-4}$ haloalkoxy, $C_{1-4}$ haloalkyl, halogen, heteroaryl and hydroxyl; and wherein said $C_{1-8}$ alkyl, aryl and heteroaryl are each optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{3-6}$-cycloalkyl-$C_{1-3}$-heteroalkylene, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, halogen, heterocyclic, hydroxyl, hydroxylamino and nitro; or $R_2$ is —$Ar_2$—$Ar_3$ wherein $Ar_2$ and $Ar_3$ are each independently aryl or heteroaryl each optionally substituted with 1 to 5 substituents selected from the group consisting of H, $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, $C_{1-4}$ alkylamino, carbo-$C_{1-6}$-alkoxy, carboxamide, carboxy, cyano, $C_{3-6}$-cycloalkyl, $C_{2-8}$ dialkylamino, $C_{2-6}$ dialkylcarboxamide, $C_{1-4}$ haloalkoxy, $C_{1-4}$ haloalkyl, halogen, hydroxyl and nitro; or $R_2$ is a group of Formula (B):

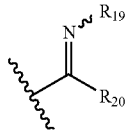

(B)

wherein:
$R_{19}$ is H, $C_{1-8}$ alkyl, $C_{3-7}$ cycloalkyl, aryl, heteroaryl or $OR_{21}$; and $R_{20}$ is F, Cl, Br, CN or $NR_{22}R_{23}$; where $R_{21}$ is H, $C_{1-8}$ alkyl or $C_{3-7}$ cycloalkyl, and $R_{22}$ and $R_{23}$ are independently H, $C_{1-8}$ alkyl, $C_{3-7}$ cycloalkyl, aryl or heteroaryl;

or
$R_2$ is a group of Formula (C):

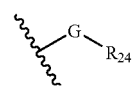

(C)

wherein:
G is:
i) —C(O)—, —C(O)NR$_{25}$—, —NR$_{25}$C(O)—, —NR$_{25}$—, —NR$_{25}$C(O)O—, —OC(O)NR$_{25}$—, —CR$_{25}$R$_{26}$NR$_{27}$C(O)—, —CR$_{25}$R$_{26}$C(O)NR$_{27}$—, —C(O)O—, —OC(O)—, —C(S)—, —C(S)NR$_{25}$—, —C(S)O—, —OC(S)—, —CR$_{25}$R$_{26}$—, —O—, —S—, —S(O)—, —S(O)$_2$— or a bond when D is CR$_2$R$_3$; or
ii) —CR$_{25}$R$_{26}$C(O)—, —C(O)—, —CR$_{25}$R$_{26}$C(O)NR$_{27}$—, —C(O)NR$_{25}$—, —C(O)O—, —C(S)—, —C(S)NR$_{25}$—, —C(S)O—, —CR$_{25}$R$_{26}$—, —S(O)$_2$—, or a bond when D is NR$_2$;

wherein $R_{25}$, $R_{26}$ and $R_{27}$ are each independently H or $C_{1-8}$ alkyl; and $R_{24}$ is H, $C_{1-8}$ alkyl, $C_{3-7}$ cycloalkyl, phenyl, heteroaryl, or heterocyclic each optionally substituted with 1 to 5 substituents selected from the group consisting of $C_{1-5}$ acyl, $C_{1-5}$ acyloxy, $C_{2-6}$ alkenyl, $C_{1-4}$ alkoxy, $C_{1-7}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, heterocyclic, hydroxyl, hydroxylamino, nitro, phenyl, phenoxy, and sulfonic acid, wherein said $C_{1-4}$ alkoxy, $C_{1-7}$ alkyl, $C_{1-4}$ alkylamino, heteroaryl, phenyl and phenoxy are each optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-7}$ cycloalkyl, $C_{2-8}$ dialkylamino, $C_{2-6}$ dialkylcarboxamide, $C_{2-6}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, halogen, heterocyclic, hydroxyl, hydroxylamino, nitro, and phenyl;

provided that Z and U are not both N.

2. The compound according to claim 1, or a pharmaceutically acceptable salt, hydrate or solvate thereof, wherein:
M, J, X, and W are all N;
T is CR$_5$;
Y is CR$_{10}$;
V is a bond; and
Z and U are both C.

3. The compound according to claim 1, or a pharmaceutically acceptable salt, hydrate or solvate thereof, wherein:
M, J, X, and W are all N;
T is CR$_5$, wherein R$_5$ is —H, —CH$_3$, or —N(CH$_3$)$_2$;
Y is CR$_{10}$, wherein R$_{10}$ is —H or —CH$_3$;

V is a bond; and
Z and U are both C.

4. The compound according to claim 1, or a pharmaceutically acceptable salt, hydrate or solvate thereof, wherein:
M, J, X, and W are all N;
T is C—H;
Y is C—H;
V is a bond; and
Z and U are both C.

5. The compound according to claim 1, or a pharmaceutically acceptable salt, hydrate or solvate thereof, wherein ----- is a single bond.

6. The compound according to claim 1, or a pharmaceutically acceptable salt, hydrate or solvate thereof, wherein Q is O.

7. The compound according to claim 1, or a pharmaceutically acceptable salt, hydrate or solvate thereof, wherein Q is S, S(O) or S(O)$_2$.

8. The compound according to claim 1, or a pharmaceutically acceptable salt, hydrate or solvate thereof, wherein K is selected from the group consisting of —CH$_2$—, —CH$_2$CH$_2$—, and —CH(CH$_3$)CH$_2$—.

9. The compound according to claim 1, or a pharmaceutically acceptable salt, hydrate or solvate thereof, wherein both A and B are —CH$_2$—.

10. The compound according to claim 1, or a pharmaceutically acceptable salt, hydrate or solvate thereof, wherein A is —CH$_2$CH$_2$— and B is —CH$_2$—.

11. The compound according to claim 1, or a pharmaceutically acceptable salt, hydrate or solvate thereof, wherein both A and B are —CH$_2$CH$_2$—.

12. The compound according to claim 1, or a pharmaceutically acceptable salt, hydrate or solvate thereof, wherein A is —CH$_2$— and B is —CH$_2$CH$_2$CH$_2$—.

13. The compound according to claim 1, or a pharmaceutically acceptable salt, hydrate or solvate thereof, wherein E is CH and D is CHR$_2$.

14. The compound according to claim 1, or a pharmaceutically acceptable salt, hydrate or solvate thereof, wherein R$_2$ is a group of Formula (C):

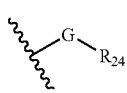

(C)

wherein G is:
—NHC(O)—, —NH—, —NHC(O)O—, —CH$_2$NHC(O)—, or a bond; and R$_{24}$ is C$_{1-8}$ alkyl, or heteroaryl, each optionally substituted with 1 to 2 substituents selected from the group consisting of C$_{1-4}$ alkoxy, and C$_{1-7}$ alkyl.

15. The compound according to claim 1, or a pharmaceutically acceptable salt, hydrate or solvate thereof, wherein R$_2$ is —C(O)OR$_{24}$ and R$_{24}$ is C$_{1-8}$ alkyl, or C$_{3-7}$ cycloalkyl each optionally substituted with 1 to 5 substituents selected from the group consisting of C$_{1-4}$ alkoxy, C$_{1-7}$ alkyl, C$_{1-4}$ alkylsulfonyl, carboxy, cyano, C$_{3-7}$ cycloalkyl, C$_{2-8}$ dialkylamino, C$_{1-4}$ haloalkoxy, C$_{1-4}$ haloalkyl, halogen, heteroaryl, heterocyclic, hydroxyl, phenyl, phenoxy, and sulfonic acid.

16. The compound according to claim 1, or a pharmaceutically acceptable salt, hydrate or solvate thereof, wherein R$_2$ is —C(O)OR$_{24}$ and R$_{24}$ is C$_{1-8}$ alkyl, or C$_{3-7}$ cycloalkyl wherein said C$_{3-7}$ cycloalkyl is optionally substituted with 1 to 5 substituents selected from the group consisting of C$_{1-4}$ alkoxy, C$_{1-7}$ alkyl, carboxy, C$_{2-8}$ dialkylamino, and halogen.

17. The compound according to claim 1, or a pharmaceutically acceptable salt, hydrate or solvate thereof, wherein R$_2$ is —C(O)OR$_{24}$ and R$_{24}$ is C$_{1-8}$ alkyl, or C$_{3-7}$ cycloalkyl.

18. The compound according to claim 1, or a pharmaceutically acceptable salt, hydrate or solvate thereof, wherein R$_2$ is —C(O)R$_{24}$ and R$_{24}$ is C$_{1-8}$ alkyl, C$_{3-7}$ cycloalkyl, phenyl, heteroaryl, or heterocyclic each optionally substituted with 1 to 5 substituents selected from the group consisting of C$_{2-6}$ alkenyl, C$_{1-4}$ alkoxy, C$_{1-7}$ alkyl, C$_{1-4}$ alkylsulfonyl, amino, carbo-C$_{1-6}$-alkoxy, carboxy, cyano, C$_{3-7}$ cycloalkyl, C$_{2-8}$ dialkylamino, C$_{1-4}$ haloalkoxy, C$_{1-4}$ haloalkyl, halogen, heteroaryl, heterocyclic, hydroxyl, phenyl, phenoxy, and sulfonic acid, wherein said C$_{1-7}$ alkyl, phenyl and phenoxy are each optionally substituted with 1 to 5 substituents selected from the group consisting of amino, C$_{1-4}$ haloalkoxy, and heterocyclic.

19. The compound according to claim 1, or a pharmaceutically acceptable salt, hydrate or solvate thereof, wherein R$_2$ is —C(O)R$_{24}$ and R$_{24}$ is C$_{1-8}$ alkyl, heteroaryl, or heterocyclic each optionally substituted with 1 to 5 substituents selected from the group consisting of H, C$_{1-4}$ alkoxy, C$_{1-8}$ alkyl, amino, carboxy, halogen, heteroaryl, hydroxyl, phenoxy, and sulfonic acid, wherein said alkyl and phenoxy are optionally substituted with 1 to 5 substituents selected from the group consisting of amino, C$_{1-4}$ haloalkoxy, and heterocyclic.

20. The compound according to claim 1, , or a pharmaceutically acceptable salt, hydrate or solvate thereof, wherein Ar$_1$ is aryl or heteroaryl optionally substituted with R$_{13}$, R$_{14}$, R$_{15}$, R$_{16}$, and R$_{17}$;
wherein R$_{13}$ is selected from the group consisting of C$_{1-6}$ acylsulfonamide, C$_{1-4}$ alkoxy, C$_{1-8}$ alkyl, C$_{1-4}$ alkylamino, C$_{1-6}$ alkylcarboxamide, C$_{1-4}$ alkylsulfonamide, C$_{1-4}$ alkylsulfonyl, C$_{1-4}$ alkylthio, amino, carbamimidoyl, carboxamide, carboxy, cyano, C$_{2-6}$ dialkylamino, halogen, heterocyclic, heterocyclic-oxy, heterocyclic-carbonyl, heteroaryl, heteroarylcarbonyl, and sulfonamide, and wherein said C$_{1-6}$ acylsulfonamide, C$_{1-4}$ alkoxy, C$_{1-8}$ alkyl, C$_{1-4}$ alkylamino, C$_{1-4}$ alkylsulfonamide, alkylsulfonyl, C$_{1-4}$ alkylthio, carbamimidoyl, C$_{2-6}$ dialkylamino, heterocyclic, heterocyclic-carbonyl, and heteroaryl are each optionally substituted with 1 to 5 substituents selected independently from the group consisting of C$_{1-6}$ acylsulfonamide, C$_{1-4}$ alkoxy, C$_{1-7}$ alkyl, C$_{1-4}$ alkylcarboxamide, C$_{1-4}$ alkylsulfonyl, carboxy, C$_{3-7}$ cycloalkyloxy, C$_{2-6}$ dialkylamino, C$_{2-6}$ dialkylcarboxamide, heteroaryl, heterocyclic, hydroxyl, phenyl, and phosphonooxy, and wherein said C$_{1-7}$ alkyl and C$_{1-4}$ alkylcarboxamide are each optionally substituted with 1 to 5 substituents selected from the group consisting of C$_{1-4}$ alkoxy and hydroxy; and
R$_{14}$, R$_{15}$, R$_{16}$, and R$_{17}$ are each independently selected form the group consisting of C$_{1-4}$ alkoxy, C$_{1-8}$ alkyl, C$_{1-4}$ alkylcarboxamide, C$_{1-4}$ alkylsulfonamide, C$_{1-4}$ alkylsulfonyl, C$_{1-4}$ alkylthio, carboxamide, cyano, and halogen.

21. The compound according to claim 1, or a pharmaceutically acceptable salt, hydrate or solvate thereof, wherein Ar$_1$ is phenyl optionally substituted with R$_{13}$, R$_{14}$, R$_{15}$, R$_{16}$, and R$_{17}$;
wherein R$_{13}$ is selected from the group consisting of C$_{1-6}$ acylsulfonamide, C$_{1-4}$ alkoxy, C$_{1-8}$ alkyl, C$_{1-4}$ alkylamino, C$_{1-6}$ alkylcarboxamide, C$_{1-4}$ alkylsulfonamide, C$_{1-4}$ alkylsulfonyl, C$_{1-4}$ alkylthio, amino, carbamimidoyl, carboxamide, carboxy, cyano, C$_{2-6}$ dialkylamino, C$_{1-4}$ haloalkyl, halogen, heterocyclic, heterocyclic-oxy, heterocyclic-carbonyl, heteroaryl, heteroarylcarbonyl, and sulfonamide, and wherein said $C_{1-6}$ acylsulfonamide, $C_{1-4}$ alkoxy, $C_{1-8}$ alkyl, $C_{1-4}$ alkylamino, $C_{1-4}$ alkylsulfonamide, $C_{1-4}$ alkylsulfonyl, $C_{1-4}$ alkylthio, carbamimidoyl, $C_{2-6}$ dialkylamino, heterocyclic, heterocyclic-carbonyl, and heteroaryl are each optionally substituted with 1 to 5 substituents selected independently from the group consisting of $C_{1-6}$ acylsulfonamide, $C_{1-4}$ alkoxy, $C_{1-7}$ alkyl, $C_{1-4}$ alkylcarboxamide, $C_{1-4}$ alkylsulfonyl, carboxy, $C_{3-7}$ cycloalkyloxy, $C_{2-6}$ dialkylamino, $C_{2-6}$ dialkylcarboxamide, heteroaryl, heterocyclic, hydroxyl, phenyl, and phosphonooxy, and wherein said $C_{1-7}$ alkyl and $C_{1-4}$ alkylcarboxamide are each optionally substituted with 1 to 5 substituents selected from the group consisting of $C_{1-4}$ alkoxy and hydroxy; and $R_{14}$, $R_{15}$, $R_{16}$, and $R_{17}$ are each independently selected form the group consisting of $C_{1-4}$ alkoxy, $C_{1-8}$ alkyl, $C_{1-4}$ alkylcarboxamide, $C_{1-4}$ alkylsulfonamide, $C_{1-4}$ alkylsulfonyl, $C_{1-4}$ alkylthio, carboxamide, cyano, $C_{1-4}$ haloalkyl, and halogen.

22. The compound according to claim 1, or a pharmaceutically acceptable salt, hydrate or solvate thereof, wherein $Ar_1$ is phenyl optionally substituted with $R_{13}$, $R_{14}$, $R_{15}$, $R_{16}$, and $R_{17}$;
wherein $R_{13}$ is selected from the group consisting of $C_{1-6}$ acylsulfonamide, $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, carbamimidoyl, carboxamide, carboxy, cyano, $C_{2-6}$ dialkylamino, halogen, heterocyclic, heterocyclic-oxy, heterocyclic-carbonyl, heteroaryl, heteroarylcarbonyl, and sulfonamide, and wherein said $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, carbamimidoyl, $C_{2-6}$ dialkylamino, heterocyclic, heterocyclic-carbonyl, and heteroaryl are each optionally substituted with 1 to 5 substituents selected independently from the group consisting of $C_{1-6}$ acylsulfonamide, $C_{1-4}$ alkoxy, $C_{1-7}$ alkyl, $C_{1-4}$ alkylcarboxamide, $C_{1-4}$ alkylsulfonyl, carboxy, $C_{2-6}$ dialkylamino, $C_{2-6}$ dialkylcarboxamide, heteroaryl, heterocyclic, hydroxyl, phenyl, and phosphonooxy, and wherein said $C_{1-7}$ alkyl and $C_{1-4}$ alkylcarboxamide are each optionally substituted with 1 to 5 substituents selected from the group consisting of $C_{1-4}$ alkoxy and hydroxy; and $R_{14}$, $R_{15}$, $R_{16}$, and $R_{17}$ are each independently selected form the group consisting of $C_{1-4}$ alkoxy, $C_{1-8}$ alkyl, $C_{1-4}$ alkylcarboxamide, $C_{1-4}$ alkylsulfonamide, $C_{1-4}$ alkylsulfonyl, $C_{1-4}$ alkylthio, carboxamide, cyano, and halogen.

23. The compound according to claim 1, or a pharmaceutically acceptable salt, hydrate or solvate thereof, wherein $Ar_1$ is phenyl optionally substituted with $R_{13}$, $R_{14}$, $R_{15}$, $R_{16}$, and $R_{17}$;
wherein $R_{13}$ is selected from the group consisting of $C_{1-6}$ acylsulfonamide, $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, carbamimidoyl, carboxamide, carboxy, cyano, $C_{2-6}$ dialkylamino, halogen, heterocyclic, heterocyclic-oxy, heterocyclic-carbonyl, heteroaryl, heteroarylcarbonyl, and sulfonamide, and wherein said $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, carbamimidoyl, $C_{2-6}$ dialkylamino, heterocyclic, heterocyclic-carbonyl, and heteroaryl are each optionally substituted with 1 to 5 substituents selected independently from the group consisting of $C_{1-6}$ acylsulfonamide, $C_{1-4}$ alkoxy, $C_{1-7}$ alkyl, $C_{1-4}$ alkylcarboxamide, $C_{1-4}$ alkylsulfonyl, carboxy, $C_{2-6}$ dialkylamino, $C_{2-6}$ dialkylcarboxamide, heteroaryl, heterocyclic, hydroxyl, phenyl, and phosphonooxy, and wherein said $C_{1-7}$ alkyl and $C_{1-4}$ alkylcarboxamide are each optionally substituted with 1 to 5 substituents selected from the group consisting of $C_{1-4}$ alkoxy and hydroxy; and $R_{14}$, $R_{15}$, $R_{16}$, and $R_{17}$ are each independently selected form the group consisting of $C_{1-8}$ alkyl, and halogen.

24. The compound according to claim 1, or a pharmaceutically acceptable salt, hydrate or solvate thereof, wherein $Ar_1$ is pyridyl optionally substituted with $R_{13}$, $R_{14}$, $R_{15}$, and $R_{16}$;
wherein $R_{13}$ is selected from the group consisting of $C_{1-6}$ acylsulfonamide, $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, amino, carbamimidoyl, carboxamide, carboxy, cyano, $C_{2-6}$ dialkylamino, halogen, heterocyclic, heterocyclic-oxy, heterocyclic-carbonyl, heteroaryl, and sulfonamide, and wherein said $C_{1-6}$ acylsulfonamide, $C_{1-4}$ alkoxy, $C_{1-8}$ alkyl, $C_{1-4}$ alkylamino, $C_{1-4}$ alkylsulfonamide, alkylsulfonyl, $C_{1-4}$ alkylthio, carbamimidoyl, $C_{2-6}$ dialkylamino, heterocyclic, heterocyclic-carbonyl, and heteroaryl are each optionally substituted with 1 to 5 substituents selected independently from the group consisting of $C_{1-6}$ acylsulfonamide, $C_{1-4}$ alkoxy, $C_{1-7}$ alkyl, $C_{1-4}$ alkylcarboxamide, $C_{1-4}$ alkylsulfonyl, carboxy, $C_{3-7}$ cycloalkyloxy, $C_{2-6}$ dialkylamino, $C_{2-6}$ dialkylcarboxamide, heteroaryl, heterocyclic, hydroxyl, phenyl, and phosphonooxy, and wherein said $C_{1-7}$ alkyl and $C_{1-4}$ alkylcarboxamide are each optionally substituted with 1 to 5 substituents selected from the group consisting of $C_{1-4}$ alkoxy and hydroxy; and $R_{14}$, $R_{15}$, and $R_{16}$ are each independently selected form the group consisting of $C_{1-4}$ alkoxy, $C_{1-8}$ alkyl, $C_{1-4}$ alkylcarboxamide, $C_{1-4}$ alkylsulfonamide, $C_{1-4}$ alkylsulfonyl, $C_{1-4}$ alkylthio, carboxamide, cyano, and halogen.

25. The compound according to claim 1, or a pharmaceutically acceptable salt, hydrate or solvate thereof, wherein $Ar_1$ is pyridyl optionally substituted with $R_{13}$, $R_{14}$, $R_{15}$, and $R_{16}$;
wherein $R_{13}$ is selected from the group consisting of $C_{1-6}$ acylsulfonamide, $C_{1-4}$ alkoxy, $C_{1-8}$ alkyl, $C_{1-4}$ alkylamino, $C_{1-4}$ alkylsulfonyl, $C_{1-4}$ alkylthio, amino, $C_{2-6}$ dialkylamino, halogen, heterocyclic, and sulfonamide, and wherein said $C_{1-4}$ alkoxy, $C_{1-8}$ alkyl, $C_{1-4}$ alkylamino, alkylsulfonyl, $C_{1-4}$ alkylthio, $C_{2-6}$ dialkylamino, and heterocyclic are each optionally substituted with 1 to 5 substituents selected independently from the group consisting of $C_{1-6}$ acylsulfonamide, $C_{1-4}$ alkoxy, $C_{1-4}$ alkylsulfonyl, $C_{3-7}$ cycloalkyloxy, heteroaryl, hydroxyl, phenyl, and phosphonooxy; and $R_{14}$, $R_{15}$, and $R_{16}$ are each independently selected form the group consisting of $C_{1-4}$ alkoxy, $C_{1-8}$ alkyl, $C_{1-4}$ alkylcarboxamide, $C_{1-4}$ alkylsulfonamide, $C_{1-4}$ alkylsulfonyl, $C_{1-4}$ alkylthio, carboxamide, cyano, and halogen.

26. The compound according to claim 1, or a pharmaceutically acceptable salt, hydrate or solvate thereof, wherein $Ar_1$ is pyridyl optionally substituted with $R_{13}$, $R_{14}$, $R_{15}$, and $R_{16}$;
wherein $R_{13}$ is selected from the group consisting of $C_{1-6}$ acylsulfonamide, $C_{1-4}$ alkoxy, $C_{1-8}$ alkyl, $C_{1-4}$ alkylamino, $C_{1-4}$ alkylsulfonyl, $C_{1-4}$ alkylthio, amino, $C_{2-6}$ dialkylamino, halogen, heterocyclic, and sulfonamide, and wherein said $C_{1-4}$ alkoxy, $C_{1-8}$ alkyl, $C_{1-4}$ alkylamino, alkylsulfonyl, $C_{1-4}$ alkylthio, $C_{2-6}$ dialkylamino, and heterocyclic are each optionally substituted with 1 to 5 substituents selected independently from the group consisting of $C_{1-6}$ acylsulfonamide, $C_{1-4}$ alkoxy, $C_{1-4}$ alkylsulfonyl, $C_{3-7}$ cycloalkyloxy, heteroaryl, hydroxyl, phenyl, and phosphonooxy; and $R_{14}$, $R_{15}$, and $R_{16}$ are each independently selected form the group consisting of $C_{1-8}$ alkyl, and halogen.

27. The compound according to claim 1 is of Formula (H7):

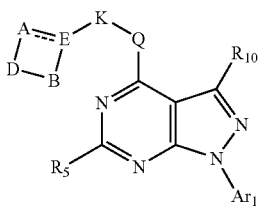

(H7)

or a pharmaceutically acceptable salt, hydrate or solvate thereof, wherein:

A is —$CH_2$—, or —$CH_2CH_2$—;
B is —$CH_2$—, —$CH_2CH_2$—, or —$CH_2CH_2CH_2$—;
E is CH;
----- is a single bond;
D is N—$R_2$;
K is —$CH_2$—, —$CH_2CH_2$—, —$CH(CH_3)CH_2$—, or a bond;
Q is O, S, S(O), or $S(O)_2$;
$R_5$ is H, $CH_3$ or $N(CH_3)_2$;
$R_{10}$ is H or $CH_3$;
$R_2$ is —$CR_{25}R_{26}C(O)R_{24}$, —$C(O)R_{24}$, —$C(O)NR_{25}R_{24}$, —$R_{24}$, —$C(O)OR_{24}$, —$C(S)NR_{25}R_{24}$, or —$CR_{25}R_{26}R_{24}$, wherein $R_{24}$ is $C_{1-8}$ alkyl, $C_{3-7}$ cycloalkyl, phenyl, heteroaryl, or heterocyclic each optionally substituted with 1 to 5 substituents selected from the group consisting of $C_{2-6}$ alkenyl, $C_{1-4}$ alkoxy, $C_{1-7}$ alkyl, $C_{1-4}$ alkylsulfonyl, amino, carbo-$C_{1-6}$-alkoxy, carboxy, cyano, $C_{3-7}$ cycloalkyl, $C_{2-8}$ dialkylamino, $C_{1-4}$ haloalkoxy, $C_{1-4}$ haloalkyl, halogen, heteroaryl, heterocyclic, hydroxyl, phenyl, phenoxy, and sulfonic acid, wherein said $C_{1-7}$ alkyl, phenyl and phenoxy are each optionally substituted with 1 to 5 substituents selected from the group consisting of amino, $C_{1-4}$ haloalkoxy, and heterocyclic; and $R_{25}$ and $R_{26}$ are each independently H or $C_{1-8}$ alkyl; and $Ar_1$ is aryl or heteroaryl optionally substituted with $R_{13}$, $R_{14}$, $R_{15}$, $R_{16}$, and $R_{17}$; wherein $R_{13}$ is selected from the group consisting of $C_{1-6}$ acylsulfonamide, $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, amino, carbamimidoyl, carboxamide, carboxy, cyano, $C_{2-6}$ dialkylamino, halogen, heterocyclic, heterocyclic-oxy, heterocyclic-carbonyl, heteroaryl, and sulfonamide, and wherein said $C_{1-6}$ acylsulfonamide, $C_{1-4}$ alkoxy, $C_{1-8}$ alkyl, $C_{1-4}$ alkylamino, $C_{1-4}$ alkylsulfonamide, alkylsulfonyl, $C_{1-4}$ alkylthio, carbamimidoyl, $C_{2-6}$ dialkylamino, heterocyclic, heterocyclic-carbonyl, and heteroaryl are each optionally substituted with 1 to 5 substituents selected independently from the group consisting of $C_{1-6}$ acylsulfonamide, $C_{1-4}$ alkoxy, $C_{1-7}$ alkyl, $C_{1-4}$ alkylcarboxamide, $C_{1-4}$ alkylsulfonyl, carboxy, $C_{3-7}$ cycloalkyloxy, $C_{2-6}$ dialkylamino, $C_{2-6}$ dialkylcarboxamide, heteroaryl, heterocyclic, hydroxyl, phenyl, and phosphonooxy; and wherein said $C_{1-7}$ alkyl and $C_{1-4}$ alkylcarboxamide are each optionally substituted with 1 to 5 substituents selected from the group consisting of $C_{1-4}$ alkoxy and hydroxy; and $R_{14}$, $R_{15}$, $R_{16}$, and $R_{17}$ are each independently selected form the group consisting of $C_{1-4}$ alkoxy, $C_{1-8}$ alkyl, $C_{1-4}$ alkylcarboxamide, $C_{1-4}$ alkylsulfonamide, $C_{1-4}$ alkylsulfonyl, $C_{1-4}$ alkylthio, carboxamide, cyano, and halogen.

28. The compound according to claim 1, or a pharmaceutically acceptable salt, hydrate or solvate thereof, wherein:

A and B are both —$CH_2CH_2$—;
E is CH;
----- is a single bond;
D is N—$R_2$
K is a bond;
Q is O;
$R_5$ and $R_{10}$ are both H;
$R_2$ is —$C(O)OR_{24}$ wherein $R_{24}$ is $C_{1-8}$ alkyl or $C_{3-7}$ cycloalkyl;
$Ar_1$ is phenyl, 3-pyridyl, or 2-pyridyl each optionally substituted with $R_{13}$, $R_{14}$, $R_{15}$, $R_{16}$, and $R_{17}$,
wherein $R_{11}$ is selected from the group consisting of $C_{1-6}$ acylsulfonamide, $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, carbamimidoyl, carboxamide, carboxy, cyano, $C_{2-6}$ dialkylamino, halogen, heterocyclic, heterocyclic-oxy, heterocyclic-carbonyl, heteroaryl, heteroarylcarbonyl, and sulfonamide, and wherein said $C_{1-4}$ alkoxy, $C_{1-8}$ alkyl, $C_{1-4}$ alkylamino, $C_{1-6}$ alkylcarboxamide, $C_{1-4}$ alkylsulfonamide, $C_{1-4}$ alkylsulfonyl, $C_{1-4}$ alkylthio, carbamimidoyl, $C_{2-6}$ dialkylamino, heterocyclic, heterocyclic-carbonyl, and heteroaryl are each optionally substituted with 1 to 5 substituents selected independently from the group consisting of $C_{1-6}$ acylsulfonamide, $C_{1-4}$ alkoxy, $C_{1-7}$ alkyl, $C_{1-4}$ alkylcarboxamide, $C_{1-4}$ alkylsulfonyl, carboxy, $C_{2-6}$ dialkylamino, $C_{2-6}$ dialkylcarboxamide, heteroaryl, heterocyclic, hydroxyl, phenyl, and phosphonooxy, and wherein said $C_{1-7}$ alkyl and $C_{1-4}$ alkylcarboxamide are each optionally substituted with 1 to 5 substituents selected from the group consisting of $C_{1-4}$ alkoxy and hydroxy; and $R_{14}$, $R_{15}$, $R_{16}$, and $R_{17}$ are each independently $CH_3$, or F.

29. The compound according to claim 28, or a pharmaceutically acceptable salt, hydrate or solvate thereof, wherein $R_2$ is selected from the group consisting of methoxycarbonyl, ethoxycarbonyl, iso-propoxycarbonyl, n-propoxycarbonyl, n-butoxycarbonyl, tert-butoxycarbonyl, iso-butoxycarbonyl, and n-pentyloxycarbonyl.

30. The compound according to claim 28, or a pharmaceutically acceptable salt, hydrate or solvate thereof, wherein $R_{13}$ is selected from the group consisting of sulfamoyl, acetylsulfamoyl, propionylsulfamoyl, butyrylsulfamoyl, pentanoylsulfamoyl, methanesulfonyl, ethanesulfonyl, propane-1-sulfonyl, hydroxymethyl, 2-hydroxyethyl, 3-hydroxypropyl, 4-hydroxy-butyl, phosphonooxymethyl, 2-phosphonooxyethyl, 3-phosphonooxy-propyl, and 4-phosphonooxy-butyl.

31. The compound according to claim 1 wherein said compound is selected from the group consisting of:
4-(1-Benzyl-azetidin-3-yloxy)-1-(4-methanesulfonyl-phenyl)-1H-pyrazolo[3,4-d]pyrimidine;
3-[1-(4-Methanesulfonyl-phenyl)-1H-pyrazolo[3,4-d]pyrimidin-4-yloxy]-azetidine-1-carboxylic acid isopropyl ester; and
{4-[1-(4-Methanesulfonyl-phenyl)-1H-pyrazolo[3,4-d]pyrimidin-4-yloxy]-cyclohexyl}-carbamic acid tert-butyl ester;
or a pharmaceutically acceptable salt, hydrate or solvate thereof.

32. The compound according to claim 1 wherein said compound is selected from the group consisting of:
- 1-(2-Fluoro-4-methanesulfonyl-phenyl)-4-[1-(3-isopropyl-[1,2,4]oxadiazol-5-ylmethyl)-pyrrolidin-3-yloxy]-1H-pyrazolo[3,4-d]pyrimidine;
- 3-[1-(2-Fluoro-4-methanesulfonyl-phenyl)-1H-pyrazolo[3,4-d]pyrimidin-4yloxy]-pyrrolidine-1-carboxylic acid tert-butyl ester;
- 3-[1-(4-Methanesulfonyl-phenyl)-1H-pyrazolo[3,4-d]pyrimidin-4-yloxy]-pyrrolidine-1-carboxylic acid tert-butyl ester;
- 4-[1-(2-Fluoro-4-morpholin-4-yl-phenyl)-1H-pyrazolo[3,4-d]pyrimidin-4yloxy]-piperidine-1-carboxylic acid isopropyl ester;
- 4-[1-(2-Fluoro-4-isopropylamino-phenyl)-1H-pyraznlo[3,4d]pyrimidin-4-yloxy]-piperidine-1-carboxylic acid isopropyl ester;
- 1-(2,5-Difluoro-4-methoxy-phenyl)-4-[4-(3-isopropyl-[1,2,4]oxadiazol-5-yl)-cyclohexyloxy]-1H-pyrazolo[3,4-d]pyrimidine;
- 4-[1-(4-Fluoro-6-methoxy-pyridin-3-yl)-1H-pyrazolo[3,4-d]pyrimidin-4-yloxy]-piperidine-1-carboxylic acid isopropyl ester;
- 4-[1-(6-Methoxy-2-methyl-pyridin-3-yl)-1H-pyrazolo[3,4-d]pyrimidin-4-yloxy]-piperidine-1-carboxylic acid isopropyl ester;
- 1-(4-Fluoro-6-methoxy-pyridin-3-yl)-4-[1-(3-isopropyl-[1,2,4]oxadiazol-5-yl)-piperidin-4-yloxy]-1H-pyrazolo[3,4-d]pyrimidine;
- 4-[1-(3-Isopropyl-[1,2,4]oxadiazol-5-yl)-piperidin-4-yloxy]-1-(6-methoxy-2-methyl-pyridin-3-yl)-1H-pyrazolo[3,4-d]pyrimidine;
- 1-(2-Fluoro-4-methanesulfonyl-phenyl)-4-[4-(3-isopropyl-[1,2,4]oxadiazol-5-yl)-cyclohexyloxy]-1H-pyrazolo[3,4-d]pyrimidine;
- 3-Fluoro-4-{4-[4-(3-isopropyl-[1,2,4]oxadiazol-5-yl)-cyclohexyloxy]-pyrazolo[3,4-d]pyrimidin-1-yl}—N-propionyl-benzenesulfonamide;
- 3-Fluoro-4-{4-[4-(3-isopropyl-[1,2,4]oxadiazol-5-yl)-cyclohexyloxy]-pyrazolo[3,4-d]pyrimidin-1-yl}-benzonitrile;
- 3-Fluoro-4-{4-[4-(3isopropyl-[1,2,4]oxadiazol-5-yl)-cyclohexyloxy]-pyrazolo[3,4-d]pyrimidin-1-yl}-benzenesulfonamide;
- 1-(2,5-Difluoro-4-methanesulfonyl-phenyl)-4-[4-(3-isopropyl-[1,2,4]oxadiazol-5-yl)-cyclohexyloxy]-1H-pyrazolo[3,4-d]pyrimidine;
- 1-(4-Fluoro-6-methoxy-pyridin-3-yl)-4-[4-(3-isopropyl-[1,2,4]oxadiazol-5-yl)-cyclohexyloxy]-1H-pyrazolo[3,4-d]pyrimidine;
- 4-[4-(3-Isopropyl-[1,2,4]oxadiazol-5-yl)-cyclohexyloxy]-1-(6-methoxy-2-methyl-pyridin-3-yl)-1H-pyrazolo[3,4-d]pyrimidine;
- 2,5-Difluoro-4-{4-[4-(3-isopropyl-[1,2,4]oxadiazol-5-yl)-cyclohexyloxy]-pyrazolo[3,4-d]pyrimidin-1-yl}-benzenesulfonamide;
- 3-Fluoro-4-{4-[4-(3-isopropyl-[1,2,4]oxadiazol-5-yl)-cyclohexyloxy]-pyrazolo[3,4-d]pyrimidin-1-yl}-phenol;
- 1-(2-Fluoro-4-methoxy-phenyl)-4-[4-(3-isopropyl-[1,2,4]oxadiazol-5-yl)-cyclohexyloxy]-1H-pyrazolo[3,4-d]pyrimidine;
- 1-(4-Difluoromethoxy-2-fluoro-phenyl)-4-[4-(3-isopropyl-[1,2,4]oxadiazol-5-yl)-cyclohexyloxy]-1H-pyrazolo[3,4-d]pyrimidine; and
- 1-(2-Fluoro-4-trifluoromethoxy-phenyl)-4-[4-(3-isopropyl-[1,2,4]oxadiazol-5-yl)-cyclohexyloxy]-1H-pyrazolo[3,4-d]pyrimidine; or a pharmaceutically acceptable salt, hydrate or solvate thereof.

33. The compound according to claim 1 wherein said compound is selected from the group consisting of:
- 4-[9-(6-Methanesulfonyl-pyridin-3-yl)-9H-purin-6-yloxy]-piperidine-1-carboxylic acid isobutyl ester;
- {4-[9-(6-Methanesulfonyl-pyridin-3-yl)-9H-purin-6-yloxy]-piperidin-1-yl}-pyridin-3-yl-methanone;
- 4-[9-(4-Methanesulfonyl-phenyl)-9H-purin-6-yloxy]-piperidine-1-carboxylic acid tert-butyl ester;
- 4-[9-(6-Methanesulfonyl-pyridin-3-yl)-9H-purin-6-yloxy]-piperidine-1-carboxylic acid tert-butyl ester and
- 4-[9-(2-Fluoro-4-methanesulfonyl-phenyl)-9H-purin-6-yloxy]-piperidine-1-carboxylic acid tert-butyl ester; or a pharmaceutically acceptable salt, hydrate or solvate thereof.

34. The compound according to claim 1 wherein said compound is selected from the group consisting of:
- 4-[9-(2-Fluoro-4-propionylsulfamoyl-phenyl)-9H-purin-6-yloxy]-piperidine-1-carboxylic acid isupropyl ester;
- 4-[9-(4-Cyano-2-fluoro-phenyl)-9H-purin-6-yloxy]-piperidine-1-carboxylic acid isopropyl ester;
- 4-[9-(2-Fluoro-4-sulfamoyl-phenyl)-9H-purin-6-yloxy]-piperidine-1-carboxylic acid isopropyl ester;
- 9-(2-Fluoro-4-methanesulfonyl-phenyl)-6-[1-(3-isopropyl-[1,2,4]oxadiazol-5-yl)-piperidin-4-yloxy]-9H-purine;
- 3-Fluoro-4-{6-[1-(3-isopropyl-[1,2,4]oxadiazol-5-yl)-piperidin-4-yloxy]-purin-9-yl}—N-propionyl-benzenesulfonamide;
- 3-Fluoro-4-{6-[1-(3-isopropyl-[1,2,4]oxadiazol-5-yl)-piperidin-4-yloxy]-purin-9-yl}-benzonitrile;
- 3-Fluoro-4-{6-[1-(3-isopropyl-[1,2,4]oxadiazol-5-yl)-piperidin-4-yloxy]-purin-9-yl}-benzenesulfonamide;
- 4-[9-(2,5-Difluoro-4-meshanesulfonyl-phenyl)-9H-purin-6-yloxy]-piperidine-1-carboxylic acid isopropyl ester;
- 4-[9-(4-Fluoro-6-methoxy-pyridin-3-yl)-9H-purin-6-yloxy]-piperidine-1-carboxylic acid isopropyl ester;
- 4-[9-(6-Methoxy-2-methyl-pyridin-3-yl)-9H-purin-6-yloxy]-piperidine-1-carboxylic acid isopropyl ester;
- 4-[9-(2,5-Difluoro-4-sulfamoyl-phenyl)-9H-purin-6-yloxy]-piperidine-1-carboxylic acid isoprupyl ester;
- 9-(2,5-Difluoro-4-meshanesulfonyl-phenyl)-6-[1-(3-isopropyl-[1,2,4]oxadiazol-5-yl)-piperidin-4-yloxy]-9H-purine;
- 9-(4-Fluoro-6-methoxy-pyridin-3-yl)-6-[1-(3-isopropyl-[1,2,4]oxadiazol-5-yl)-piperidin-4-yloxy]-9H-purine;
- 6-[1-(3-Isopropyl-[1,2,4]oxadiazol-5-yl)-piperidin-4-yloxy]-9-(6-methoxy-2-methyl-pyridin-3-yl)-9H-purine;
- 2,5-Difluoro-4-{6-[1-(3-isopropyl-[1,2,4]oxadiazol-5-yl)-piperidin-4-yloxy]-purin-9-yl}-benzenesulfonamide;
- 9-(2-Fluoro-4-methanesulfonyl-phenyl)-6-[4-(3-isopropyl-[1,2,4]oxadiazol-5-yl)-cyclohexyloxy]-9H-purine;
- 3-Fluoro-4-{6-[4-(3-isopropyl-[1,2,4]oxadiazol-5-yl)-cyclohexyloxy]-purin-9-yl}—N-propionyl-benzenesulfonamide;
- 3-Fluoro-4-{6-[4-(3-isopropyl-[1,2,4]oxadiazol-5-yl)-cyclohexyloxy]-purin-9-yl}-benzonitrile
- 3-Fluoro-4-{6-[4-(3-isopropyl-[1,2,4]oxadiazol-5-yl)-cyclohexyloxy]-purin-9-yl}-benzenesulfonamide;
- 9-(2,5-Difluoro-4-methanesulfonyl-phenyl)-6-[4-(3-isopropyl-[1,2,4]oxadiazol-5-yl)-cyclohexyloxy]-9H-purine;
- 9-(4-Fluoro-6-methoxy-pyridin-3-yl)-6-[4-(3-isopropyl-[1,2,4]oxadiazol-5-yl)-cyclohexyloxy]-9H-purine;

6-[4-(3-Isopropyl-[1,2,4]oxadiazol-5-yl)-cyclohexyloxy]-9-(6-methoxy-2-methyl-pyridin-3-yl)-9H-purine; and 2,5-Difluoro-4-{6-[4-(3-isopropyl-[1,2,4]oxadiazol-5-yl)-cyclohexyloxy]-purin-9-yl}-benzenesulfonamide; or a pharmaceutically acceptable salt, hydrate or solvate thereof.

35. The compound according to claim 1 wherein said compound is 4-[3-(4-Methanesulfonyl-phenyl)-3H-[1,2,3]triazolo[4,5-d]pyrimidin-7-yloxy]-piperidine-1-carboxylic acid tert-butyl ester;

or a pharmaceutically acceptable salt, hydrate or solvate thereof.

36. The compound according to claim 1 wherein said compound is selected from the group consisting of:

3-(2-Fluoro-4-methanesulfonyl-phenyl)-7-[1-(3-isopropyl-[1,2,4]oxadiazol-5-yl)-piperidin-4-yloxy]-3H-[1,2,3]triazolo[4,5-d]pyrimidine;

3-Fluoro-4-{7-[1-(3-isopropyl-[1,2,4]oxadiazol-5-yl)-piperidin-4-yloxy]-[1,2,3]triazolo[4,5-d]pyrimidin-3-yl}—N-propionyl-benzenesulfonamide;

3-Fluoro-4-{7-[1-(3-isopropyl-[1,2,4]oxadiazol-5-yl)-piperidin-4-yloxy]-[1,2,3]triazolo[4,5-d]pyrimidin-3-yl}-benzonitrile;

3-Fluoro-4-{7-[1-(3-isopropyl-[1,2,4]oxadiazol-5-yl)-piperidin-4-yloxy]-[1,2,3]triazolo[4,5-d]pyrimidin-3-yl}-benzenesulfonamide;

3-(2-Fluoro-4-methanesulfonyl-phenyl)-7-[4-(3-isopropyl-[1,2,4]oxadiazol-5-yl)-cyclohexyloxy]-3H-[1,2,3]triazolo[4,5-d]pyrimidine;

3-Fluoro-4-{7-[4-(3-isopropyl-[1,2,4]oxadiazol-5-yl)-cyclohexyloxy]-[1,2,3]triazolo[4,5-d]pyrimidin-3-yl}—N-propionyl-benzenesulfonamide;

3-Fluoro-4-{7-[4-(3-isopropyl-[1,2,4]oxadiazol-5-yl)-cyclohexyloxy]-[1,2,3]triazolo[4,5-d]pyrimidin-3-yl}-beozonitrile;

3-Fluoro-4-{7-[4-(3-isopropyl-[1,2,4]oxadiazol-5-yl)-cyclohexyloxy]-[1,2,3]triazolo[4,5-d]pyrimidin-3-yl}-benzenesulfonamide;

3-(2,5-Difluoro-4-methanesulfonyl-phenyl)-7-[4-(3-isopropyl-[1,2,4]oxadiazol-5-yl)-cyclohexyloxy]-3H-[1,2,3]triazolo[4,5-d]pyrimidine;

3-(4-Fluoro-6-methoxy-pyridin-3-yl)-7-[4-(3-isopropyl-[1,2,4]oxadiazol-5-yl)-cyclohexyloxy]-3H-[1,2,3]triazolo[4,5-d]pyrimidine;

7-[4-(3-Isopropyl-[1,2,4]oxadiazol-5-yl)-cyclohexyloxy]-3-(6-methoxy-2-methyl-pyridin-3-yl)-3H-[1,2,3]triazolo[4,5-d]pyrimidine;

2,5-Difluoro-4-{7-[4-(3-isopropyl-[1,2,4]oxadiazol-5-yl)-cycloliexyloxy]-[1,2,3]triazolo[4,5-d]pyrimidin-3-yl}-benzenesulfonamide;

4-[3-(2-Fluoro-4-methanesulfonyl-phenyl)-3H-[1,2,3]triazolo[4,5-d]pyrimidin-7-yloxy]-piperidine-1-carboxylic acid isopropyl ester;

4-[3-(2-Fluoro-4-propionylsulfamoyl-phenyl)-3H-[1,2,3]triazolo[4,5-d]pyrimidin-7-yloxy]-piperidine-1-carboxylic acid isopropyl ester;

4-[3-(4-Cyano-2-fluoro-phenyl)-3H-[1,2,3]triazolo[4,5-d]pyrimidin-7-yloxy]-piperidine-1-carboxylic acid isopropyl ester;

4-[3-(2-Fluoro-4-sulfamoyl-phenyl)-3H-[1,2,3]triazolo[4,5-d]pyrimidin-7-yloxy]-piperidine-1-carboxylic acid isopropyl eater;

4-[3-(2,5-Difluoro-4-methanesulfonyl-phenyl)-3H-[1,2,3]triazolo[4,5-d]pyrimidin-7-yloxy]-piperidine-1-carboxylic acid isopropyl ester;

4-[3-(4-Fluoro-6-methoxy-pyridin-3-yl)-3H-[1,2,3]triazolo[4,5-d]pyrimidin-7-yloxy]-piperidine-1-carboxylic acid isopropyl ester;

4-[3-(6-Methoxy-2-methyl-pyridin-3-yl)-3H-[1,2,3]triazolo[4,5-d]pyrimidin-7-yloxy]-piperidine-1-carboxylic acid isopropyl ester;

4-[3-(2,5-Difluoro-4-sulfamoyl-phenyl)-3H-[1,2,3]triazolo[4,5-d]pyrimidin-7-yloxy]-piperidine-1-carboxylic acid isopropyl ester;

3-(2,5-Difluoro-4-methanesulfonyl-phenyl)-7-[1-(3-isopropyl-[1,2,4]oxadiazol-5-yl)-piperidin-4-yloxy]-3H-[1,2,3]triazolo[4,5-d]pyrimidine;

3-(4-Fluoro-6-methoxy-pyridin-3-yl)-7-[1-(3-isopropyl-[1,2,4]oxadiazol-5-yl)-piperidin-4-yloxy]-3H-[1,2,3]triazolo[4,5-d]pyrimidine;

7-[1-(3-Isopropyl-[1,2,4]oxadiazol-5-yl)-piperidin-4-yloxy]-3-(6-methoxy-2-methyl-pyridin-3-yl)-3H-[1,2,3]triazolo[4,5-d]pyrimidine; and 2,5-Difluoro-4-{7-[1-(3-isopropyl-[1,2,4]oxadiazol-5-yl)-piperidin-4-yloxy]-[1,2,3]triazolo[4,5-d]pyrimidin-3-yl}-benzenesulfonamide; or a pharmaceutically acceptable salt, hydrate or solvate thereof.

37. The compound according to claim 1 wherein said compound is selected from the group consisting of:

4-(1-{4-[(2-Methanesulfonyl-ethyl)-methyl-amino]-phenyl}-1H-pyrazolo[3,4-d]pyrimidin-4-yloxy)-piperidine-1-carboxylic acid isopronyl ester; and 4-[1-(2-Fluoro-4-propionylsulfamoyl-phenyl)-1H-pyrazolo[3,4-d]pyrimidin-4-yloxy]-piperidine-1-carboxylic acid isopropyl ester; or a pharmaceutically acceptable salt, hydrate or solvate thereof.

38. The compound according to claim 1 wherein said compound is selected from the group consisting of:

4-[3-(2-Fluoro-4-methanesulfonyl-phenyl)-1-methyl-1H-pyrazolo[4,3-d]pyrimidin-7-yloxy]-piperidine-1-carboxylic acid isopropyl ester;

4-[3-(2-Fluoro-4-propionylsulfamoyl-phenyl)-1-methyl-1H-pyrazolo[4,3-d]pyrimidin-7-yloxy]-piperidine-1-carboxylic acid isopropyl eater;

4-[3-(4-Cyano-2-fluoro-phenyl)-1-methyl-1H-pyrazolo[4,3-d]pyrimidin-7-yloxy]-piperidine-1-carboxylic acid isopropyl ester;

4-[3-(2-Fluoro-4-sulfamoyl-phenyl)-1-methyl-1H-pyrazolo[4,3-d]pyrimidin-7-yloxy]-piperidine-1-carboxylic acid isopropyl ester;

4-[3-(2,5-Difluoro-4-methanesulfonyl-phenyl)-1-methyl-1H-pyrazolo[4,3-d]pyrimidin-7-yloxy]-piperidine-1-carboxylic acid isopropyl ester;

4-[3-(4-Fluoro-6-methoxy-pyridin-3-yl)-1-methyl-1H-pyrazolo[4,3-d]pyrimidin-7-yloxy]-piperidine-1-carboxylic acid isopropyl ester;

4-[3-(6-Methoxy-2-methyl-pyridin-3-yl)-1-methyl-1H-pyrazolo[4,3-d]pyrimidin-7-yloxy]-piperidine-1-carboxylic acid isopropyl ester;

4-[3-(2,5-Difluoro-4-sulfamoyl-phenyl)-1-methyl-1H-pyrazolo[4,3-d]pyrimidin-7-yloxy]-piperidine-1-carboxylic acid isopropyl ester;

3-(2-Fluoro-4-methanesulfonyl-phenyl)-7-[1-(3-isopropyl-[1,2,4]oxadiazol-5-yl)-piperidin-4-yloxy]-1-methyl-1H-pyrazolo[4,3-d]pyrimidine;

3-Fluoro-4-{7-[1-(3-isopropyl-[1,2,4]oxadiazol-5-yl)-piperidin-4-yloxy]-1-methyl-1H-pyrazolo[4,3-d]pyrimidin-3-yl}—N-propionyl-benzenesulfonamide;

3-Fluoro-4-{7-[1-(3-isopropyl-[1,2,4]oxadiazol-5-yl)-piperidin-4-yloxy]-1-methyl-1H-pyrazolo[4,3-d]pyrimidin-3-yl}-benzonitrile;

3-Fluoro-4-{7-[1-(3-isopropyl-1,2,4]oxadiazol-5-yl)-piperidin-4-yloxy]-1-methyl-1H-pyrazolo[4,3-d]pyrimidin-3-yl}-benzenesulfonamide;

3-(2,5-Difluoro-4-methanesulfonyl-phenyl)-7-[1-(3-isopropyl-[1,2,4]oxadiazol-5-yl)-piperidin-4-yloxy]-1-methyl-1H-pyrazolo[4,3-d]pyrimidine;

3-(4-Fluoro-6-methoxy-pyridin-3-yl)-7-1-(3-isopropyl-[1,2,4]oxadiazol-5-yl)-piperidin-4-yloxy]-1-methyl-1H-pyrazolo[4,3-d]pyrimidine;

7-[1-(3-Isopropyl-[1,2,4]oxadiazol-5-yl)-piperidin-4-yloxy]-3-(6-methoxy-2-methyl-pyridin-3-yl)-1-methyl-1H-pyrazolo[4,3-d]pyrimidine;

2,5-Difluoro-4-{7-[1-(3-isopropyl-[1,2,4]oxadiazol-5-yl)-piperidin-4-yloxy]-1-methyl-1H-pyrazolo[4,3 d]pyrimidin-3-yl}-benzenesulfonamide;

3-(2-Fluoro-4-methanesulfonyl-phenyl)-7-[4-(3-isopropyl-[1,2,4]oxadiazol-5-yl)-cyclohexyloxy]-1-methyl-1H-pyrazolo[4,3-d]pyrimidine;

3-Fluoro-4-{7-[4-(3-isopropyl-[1,2,4]oxadiazol-5-yl)-cyclohcxyloxy]-1-methyl-1H-pyrazolo[4,3-d]pyrimidin-3-yl}—N-propionyl-benzenesulfonamide;

3-Fluoro-4-{7-[4-(3-isopropyl-[1,2,4]oxadiazol-5-yl)-cyclohexyloxy]-1-methyl-1H-pyrazolo[4,3-d]pyrimidin-3-yl}-benzonitrile;

3-Fluoro-4-{7-[4-(3-isopropyl-[1,2,4]oxadiazol-5-yl)-cyclohexyloxy]-1-methyl-1H-pyrazolo[4,3-d]pyrimidin-3-yl}-benzenesulfonamide;

3-(2,5-Difluoro-4-methanesulfonyl-phenyl)-7-[4-(3-isopropyl-[1,2,4]oxadiazol-5-yl)-cyclohexyloxy]-1-methyl-1H-pyrazolo[4,3-d]pyrimidine;

3-(4-Fluoro-6-methoxy-pyridin-3-yl)-7-[4-(3-isopropyl-[1,2,4]oxadiazol-5-yl)-cyclohexyloxy]-1-methyl-1H-pyrazolo[4,3-d]pyrimidine;

7-[4-(3-Isopropyl-[1,2,4]oxadiazol-5-yl)-cyclohexyloxy]-3-(6-methoxy-2-methyl-pyridin-3-yl)-1-methyl-1H-pyrazoio[4,3-d]pyrimidine; and 2,5-Difluoro-4-{7-[4-(3-isopropyl-[1,2,4]oxadiazol-5-yl)-cyclohexyloxy]-1-methyl-1H-pyrazolo[4,3-d]pyrimidin-3-yl}-benzenesulfonamide; or a pharmaceutically acceptable salt, hydrate or solvate thereof.

39. The compound according to claim 1 wherein said compound is selected from the group consisting of:

4-[3-(2-Fluoro-4-methanesulfonyl-phenyl)-2-methyl-2H-pyrazolo[4,3-d]pyrimidin-7-yloxy]-piperidine-1-carboxylic acid isopropyl ester;

4-3-(2-Fluoro-4-propionylsulfamoyl-phenyl)-2-methyl-2H-pyrazolo[4,3-d]pyrimidin-7-yloxy]-piperidine-1-carboxylic acid isopropyl ester;

4-[3-(4-Cyano-2-fluoro-phenyl)-2-methyl-2H-pyrazolo[4,3-d]pyrimidin-7-yloxy]-piperidine-1-carboxylic acid isopropyl ester;

4-[3-(2-Fluoro-4-sulfamoyl-phenyl)-2-methyl-2H-pyrazolo[4,3-d]pyrimidin-7-yloxy]-piperidine-1-carboxylic acid isopropyl ester;

4-[3-(2,5-Difluoro-4-methanesulfonyl-phenyl)-2-methyl-2H-pyrazolo[4,3-d]pyrimidin-7-yloxy]-piperidine-1-carboxylic acid isopropyl ester;

4-[3-(4-Fluoro-6-methoxy-pyridin-3-yl)-2-methyl-2H-pyrazolo[4,3-d]pyrimidin-7-yloxy]-piperidine-1-carboxylic acid isopropyl ester;

4-[3-(6-Methoxy-2-methyl-pyridin-3-yl)-2-methyl-2H-pyrazolo[4,3-d]pyrimidin-7-yloxy]-piperidine-1-carboxylic acid isopropyl ester;

4-[3-(2,5-Difluoro-4-sulfamoyl-phenyl)-2-methyl-2H-pyrazolo[4,3-d]pyrimidin-7-yloxy]-piperidine-1-carboxylic acid isopropyl ester;

3-(2-Fluoro-4-methanesulfonyl-phenyl)-7-[1-(3-isopropyl-[1,2,4]oxadiazol-5-yl) -piperidin-4-yloxy]-2-methyl-2H-pyrazolo[4,3-d]pyrimidine;

3-Fluoro-4-{7-[1-(3-isopropyl-[1,2,4]oxadiazol-5-yl)-piperidin-4-yloxy]-2-methyl-2H-pyrazolo[4,3-d]pyrimidin-3-yl}—N-propionyl-benzenesulfonamide;

3-Fluoro-4-{7-[1-(3-isopropyl-[1,2,4]oxadiazol-5-yl)-piperidin-4-yloxy]-2-methyl-2H-pyrazolo[4,3-d]pyrimidin-3-yl}-benzonitrile;

3-Fluoro-4-{7-[1-(3-isopropyl-[1,2,4]oxadiazol-5-yl)-piperidin-4-yloxy]-2-methyl-2H-pyrazolo[4,3-d]pyrimidin-3-yl}-benzenesulfonamide;

3-(2,5-Difluoro-4-methanesulfonyl-phenyl)-7-[1-(3-isopropyl-[1,2,4]oxadiazol-5-yl)-piperidin-4-yloxy]-2-methyl-2H-pyrazolo[4,3-d]pyrimidine;

3-(4-Fluoro-6-methoxy-pyridin-3-yl)-7-[1-(3-isopropyl-[1,2,4]oxadiazol-5-yl)-piperidin-4-yloxy]-2-methyl-2H-pyrazolo[4,3-d]pyrimidine;

7-[1-(3-Isopropyl-[1,2,4]oxadiazol-5-yl)-piperidin-4-yloxy]-3-(6-methoxy-2-methyl-pyridin-3-yl)-2-methyl-2H-pyrazolo[4,3-d]pyrimidine;

2,5-Difluoro-4-{7-[1-(3-isopropyl-[1,2,4]oxadiazol-5-yl)-piperidin-4-yloxy]-2-methyl-2H-pyrazolo[4,3-d]pyrimidin-3-yl}-benzenesulfonamide;

3-(2-Fluoro-4-methanesulfonyl-phenyl)-7-[4-(3-isopropyl-[1,2,4]oxadiazol-5-yl)-cyclohexyloxy]-2-methyl-2H-pyrazolo[4,3-d]pyrimidine;

3-Fluoro-4-{7-[4-(3-isopropyl-[1,2,4]oxadiazol-5-yl)-cyclohexyloxy]-2-methyl-2H-pyrazolo[4,3-d]pyrimidin-3-yl}—N-propionyl-benzenesulfonamide;

3-Fluoro-4-{7-[4-(3-isopropyl-[1,2,4]oxadiazol-5-yl)-cyclohexyloxy]-2-methyl-2H-pyrazolo[4,3-d]pyrimidin-3-yl}-benzonitrile;

3-Fluoro-4-{7-[4-(3-isopropyl-[1,2,4]oxadiazol-5-yl)-cyclohexyloxy]-2-methyl-2H-pyrazolo[4,3-d]pyrimidin-3-yl}-benzenesulfonamide;

3-(2,5-Difluoro-4-methanesulfonyl-phenyl)-7-[4-(3-isopropyl-[1,2,4]oxadiazol-5-yl)-cyclohexyloxy]-2-methyl-2H-pyrazolo[4,3-d]pyrimidine;

3-(4-Fluoro-6-methoxy-pyridin-3-yl)-7-[4-(3-isopropyl-[1,2,4]oxadiazol-5-yl)-cyclohexyloxy]-2-methyl-2H-pyrazolo[4,3-d]pyrimidine;

7-[4-(3-Isopropyl-[1,2,4]oxadiazol-5-yl)-cyclohexyloxy]-3-(6-methoxy-2-methyl-pyridin-3-yl)-2-methyl-2H-pyrazolo[4,3-d]pyrimidine; and 2,5-Difluoro-4-{7-[4-(3-isopropyl-[1,2,4]oxadiazol-5-yl)-cyclohexyloxy]-2-methyl-2H-pyrazolo[4,3-d]pyrimidin-3-yl}-benzenesulfonamide; or a pharmaceutically acceptable salt, hydrate or solvate thereof.

40. A pharmaceutical composition comprising at least one compound according to claim 1, or a pharmaceutically acceptable salt or solvate thereof, and a pharmaceutically acceptable carrier.

41. The compound according to claim 1, or a pharmaceutically acceptable salt, hydrate or solvate thereof, having Formula (IIIc):

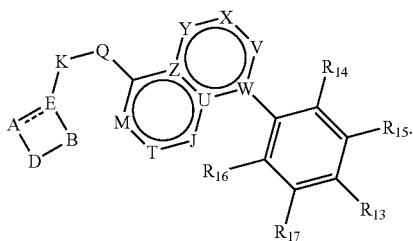

42. The compound according to claim 1, or a pharmaceutically acceptable salt, hydrate or solvate thereof, having Formula (IIId-1):

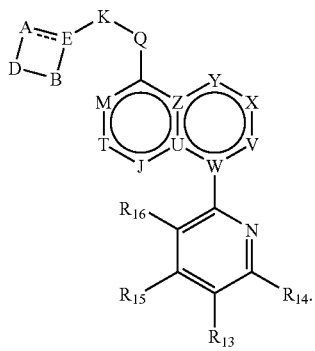

43. The compound according to claim 1, or a pharmaceutically acceptable salt, hydrate or solvate thereof, having Formula (IIId-2):

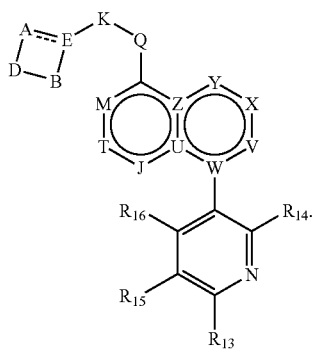

44. The compound according to any one of claims 1, 41, 42, and 43, or a pharmaceutically acceptable salt, hydrate or solvate thereof, wherein:

⋯⋯ is a single bond;
Q is O;
K is a bond; and
$R_2$ is of Formula (C):

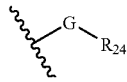

wherein:
G is $-CR_{25R26}C(O)-$, $-C(O)-$, $-C(O)NR_{25}-$, $-C(O)O-$, $-C(S)NR_{25}-$, $-CR_{25}R_{26}-$, or a bond, wherein $R_{25}$, and $R_{26}$ are each independently H or $C_{1-8}$ alkyl; and $R_{24}$ is $C_{1-8}$ alkyl, $C_{3-7}$ cycloalkyl, phenyl, heteroaryl, or heterocyclic each optionally substituted with 1 to 5 substituents selected from the group consisting of $C_{1-4}$ alkoxy, $C_{1-7}$ alkyl, $C_{1-4}$ alkylamino, amino, carbo-$C_{1-6}$-alkoxy, carboxy, $C_{3-7}$ cycloalkyl, $C_{2-8}$ dialkylamino, $C_{1-4}$ haloalkoxy, $C_{1-4}$ haloalkyl, halogen, heteroaryl, heterocyclic, hydroxyl, and nitro, wherein said $C_{1-4}$ alkoxy, $C_{1-7}$ alkyl, $C_{1-4}$ alkylamino, heteroaryl, and phenyl are each optionally substituted with 1 to 5 substituents selected from the group consisting of $C_{1-4}$ alkoxy, carbo-$C_{1-6}$-alkoxy, carboxamide, carboxy, $C_{3-7}$ cycloalkyl, halogen, heterocyclic, and phenyl.

45. The pharmaceutical composition according to claim 40, wherein said compound is selected from the group consisting of:
  4-[1-(4-Methanesulfonyl-phenyl)-1H-pyrazolo[3,4-d]pyrimidin-4-yloxy]-piperidine-1-carboxylic acid tert-butyl ester;
  4-[1-(4-Methanesulfonyl-phenyl)-1H-pyrazolo[3,4-d]pyrimidin-4yloxy]-piperidine-1-carboxylic acid isopropyl ester;
  (3,5-Dimethyl-isoxazol-4-yl)-{4-[1-(4-methanesulfonyl-phenyl)-1H-pyrazolo[3,4-d]pyrimidin-4-yloxy]-piperidin-1-yl}-methanone;
  4-[1-(2-Fluoro-4-methanesulfonyl-phenyl)-1H-pyrazolo[3,4-d]pyrimidin-4-ylsulfanyl]-piperidine-1-carboxylic acid tert-butyl ester;
  4-[1-(2-Fluoro-4-methanesulfonyl-phenyl)-1H-pyrazolo[3,4-d]pyrimidin-4-yloxy]-piperidine-1-carboxylic acid isopropyl ester;
  4-[1-(2-Fluoro-4-methanesulfonyl-phenyl)-1H-pyrazolo[3,4-d]pyrimidin-4-ylsulfanyl]-piperidine-1-carboxylic acid isopropyl ester;
  4-[1(2-Fluoro-4-sulfamoyl-phenyl)-1H-pyrazolo[3,4-d]pyrimidin-4-yloxy]-piperidine-1-carboxylic acid isopropyl ester;
  4-[1-(4-Cyano-2-fluoro-phenyl)-1H-pyrazolo[3,4-d]pyrimidin-4-yloxy]-piperidine-1-carboxylic acid isopropyl ester;
  3-Fluoro-4-{4-[1-(3-isopropyl-[1,2,4]oxadiazol-5-yl)-piperidin-4-yloxy]-pyrazolo[3,4-d]pyrimidin-1-yl}-benzonitrile; and
  3-Fluoro-4-{4-[1-(3-isopropyl-[1,2,4]oxadiazol-5-yl)-piperidin-4-yloxy]-pyrazolo[3,4-d]pyrimidin-1-yl}-benzenesulfonamide;
  or a pharmaceutically acceptable salt, hydrate or solvate thereof.

46. The compound according to any one of claims 1, 41, 42, and 43, or a pharmaceutically acceptable salt, hydrate or solvate thereof, wherein K is a bond.

47. The compound according to any one of claims 1, 41, 42, and 43, or a pharmaceutically acceptable salt, hydrate or solvate thereof, wherein E is CH and D is N—$R_2$.

48. The compound according to anyone of claims 1, 41, 42, and 43, or a pharmaceutically acceptable salt, hydrate or solvate thereof, wherein $R_2$ is of Formula (C):

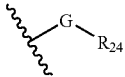

(C)

wherein:

G is —$CR_{25}R_{26}C(O)$—, —$C(O)$—, —$C(O)NR_{25}$—, —$C(O)O$—, —$C(S)NR_{25}$-, —$CR_{25}R_{26}$—, or a bond, wherein $R_{25}$, and $R_{26}$ are each independently H or $C_{1-8}$ alkyl; and $R_{24}$ is $C_{1-8}$ alkyl, $C_{3-7}$ cycloalkyl, phenyl, heteroaryl, or heterocyclic each optionally substituted with 1 to 5 substituents selected from the group consisting of $C_{1-4}$ alkoxy, $C_{1-7}$ alkyl, $C_{1-4}$ alkylamino, amino, carbo-$C_{1-6}$-alkoxy, carboxy, $C_{3-7}$ cycloalkyl, $C_{2-8}$ dialkylamino, $C_{1-4}$ haloalkoxy, $C_{1-4}$ haloalkyl, halogen, heteroaryl, heterocyclic, hydroxyl, and nitro, wherein said $C_{1-4}$ alkoxy, $C_{1-7}$ alkyl, $C_{1-4}$ alkylamino, heteroaryl, and phenyl are each optionally substituted with 1 to 5 substituents selected from the group consisting of $C_{1-4}$ alkoxy, carbo-$C_{1-6}$-alkoxy, carboxamide, carboxy, $C_{3-7}$ cycloalkyl, halogen, heterocyclic, and phenyl.

49. The compound according to any one of claims 1, 41, 42, and 43, or a pharmaceutically acceptable salt, hydrate or solvate thereof, wherein $R_2$ is —$C(O)OR_{24}$ and $R_{24}$ is $C_{1-8}$ alkyl, $C_{3-7}$ cycloalkyl, phenyl, heteroaryl, or heterocyclic each optionally substituted with 1 to 5 substituents selected from the group consisting of $C_{1-4}$ alkoxy, $C_{1-7}$ alkyl, $C_{1-4}$ alkylsulfonyl, amino, carbo-$C_{1-6}$-alkoxy, carboxy, cyano, $C_{3-7}$cycloalkyl, $C_{2-8}$ dialkylamino, $C_{1-4}$ haloalkoxy, haloalkyl, halogen, heteroaryl, heterocyclic, hydroxyl, phenyl, phenoxy, and sulfonic acid, wherein said $C_{1-7}$ alkyl, phenyl and phenoxy are each optionally substituted with 1 to 5 substituents selected from the group consisting of amino, $C_{1-4}$ haloalkoxy, and heterocyclic.

50. A compound selected from:
(6-Cyclobutylamino-pyridin-3-yl)-{4-[1-(4-methanesulfonyl-phenyl)-1H-pyrazolo[3,4-d]pyrimidin-4-yloxy]-piperidin-1-yl}-methanone;
{4-[1-(4-Mechanesulfonyl-phenyl)-1H-pyrazolo[3,4-d]pyrimidin-4-yloxy]-piperidin-1-yl}-[5-(2-methyl-pyrrolidin-1-ylmethyl)-pyridin-3-yl]-methanone;
4-(1-{4-[4-(2-Methanesulfonyl-ethyl)-piperazin-1-yl]-2-methyl-phenyl}-1H-pyrazolo[3,4-d]pyrimidin-4-yloxy)-piperidine-1-carboxylic acid isopropyl ester;
4-[1-(4-Cyclopropylamino-2-methyl-phenyl)-1H-pyrazolo[3,4-d]pyrimidin-4-yloxy]-piperidine-1-carboxylic acid isopropyl ester; and
4-(1-{4-[4-(2-Methanesulfonyl-ethyl)-piperazin-1-yl]-phenyl}-1H-pyrazolo[3,4-d]pyrimidin-4-yloxy)-piperidine-1-carboxylic acid isopropyl ester; or
a pharmaceutically acceptable salt, hydrate or solvate thereof.

* * * * *

UNITED STATES PATENT AND TRADEMARK OFFICE
CERTIFICATE OF CORRECTION

PATENT NO. : 7,625,906 B2
APPLICATION NO. : 11/355785
DATED : December 1, 2009
INVENTOR(S) : Robert M. Jones et al.

It is certified that error appears in the above-identified patent and that said Letters Patent is hereby corrected as shown below:

Title page, item (75), Column 1, line 4 (Inventors), delete "San Digeo, CA (US);" and insert -- San Diego, CA (US); --, therefor.

Title page, item (75), Column 1, line 7 (Inventors), after "Tucson, AZ (US):" insert -- Jin Sun Karoline Choi, San Diego, CA (US); --.

Title page, item (56), Column 2, lines 7-8 (Foreign Patent Documents), below "JP 2000-038350 2/2000" delete
"JP 2000 038350 2/2000
JP    200038350 2/2000".

First page, Column 2, line 3 (Other Publications), delete "quinoiones,"" and insert -- quinolones," --, therefor.

Column 387, line 28, in Claim 1, delete "$C_{3-6}$cycloalkylene" and insert -- $C_{3-6}$ cycloalkylene --, therefor.

Column 390, line 24, in Claim 1, after "$R_{24}$ is" delete "H,".

Column 390, line 63, in Claim 3, delete "Claim 1,or" and insert -- Claim 1, or --, therefor.

Column 392, line 28, in Claim 20, delete "Claim 1, , or" and insert -- Claim 1, or --, therefor.

Column 395, line 5, in Claim 27, delete "is of" and insert -- having --, therefor.

Column 396, lines 51-52, in Claim 30, delete "butyrylsulfamoyl,pentanoylsulfamoyl,"
and insert -- butyrylsulfamoyl, pentanoylsulfamoyl, --, therefor.

Column 396, line 59, in Claim 31, below "pyrimidine;" insert -- 4-{1-[4-(Methanesulfonyl-ethyl)-phenyl]-1H-pyrazolo[3,4-d]pyrimidin-4-yloxy}piperidine-1-carboxylic acid tert-butyl ester; --.

Signed and Sealed this

Sixteenth Day of November, 2010

David J. Kappos
*Director of the United States Patent and Trademark Office*

CERTIFICATE OF CORRECTION (continued)
U.S. Pat. No. 7,625,906 B2

Column 397, line 7, in Claim 32, delete "4yloxy]" and insert -- 4-yloxy] --, therefor.

Column 397, line 13, in Claim 32, delete "4yloxy]" and insert -- 4-yloxy] --, therefor.

Column 397, lines 15-16, in Claim 32, delete "pyraznlo[3,4d]" and insert -- pyrazolo[3,4-d] --, therefor.

Column 397, line 42, in Claim 32, delete "(3isopropyl" and insert -- (3-isopropyl --, therefor.

Column 398, line 20, in Claim 34, delete "isupropyl" and insert -- isopropyl --, therefor.

Column 398, line 35, in Claim 34, delete "meshanesulfonyl" and insert -- methanesulfonyl --, therefor.

Column 398, line 42, in Claim 34, delete "isoprupyl" and insert -- isopropyl --, therefor.

Column 398, line 43, in Claim 34, delete "meshanesulfonyl" and insert -- methanesulfonyl --, therefor.

Column 398, line 60, in Claim 34, delete "benzonitrile" and insert -- benzonitrile; --, therefor.

Column 399, line 37, in Claim 36, delete "beozonitrile;" and insert -- benzonitrile; --, therefor.

Column 399, line 51, in Claim 36, delete "cycloliexyloxy]" and insert -- cyclohexyloxy] --, therefor.

Column 399, line 64, in Claim 36, delete "eater;" and insert -- ester; --, therefor.

Column 400, line 29, in Claim 37, delete "isopronyl" and insert -- isopropyl --, therefor.

Column 400, line 43, in Claim 38, delete "eater;" and insert -- ester' --, therefor.

Column 401, lines 23-24, in Claim 38, delete "cyclohcxyloxy]" and insert -- cyclohexyloxy] --, therefor.

Column 401, line 41, in Claim 38, delete "pyrazoio" and insert -- pyrazolo --, therefor.

Column 404, line 13, in Claim 44, delete "-CR$_{25R26}$C(O)-," and insert -- -CR$_{25}$R$_{26}$C(O)-, --, therefor.

Column 404, line 37, in Claim 45, delete "4yloxy]" and insert -- 4-yloxy] --, therefor.

Column 404, line 51, in Claim 45, delete "4-[1(2-Flouro" and insert -- 4-[1-(2-Flouro --, therefor.

Column 405, line 4, in Claim 48, delete "anyone" and insert -- any one --, therefor.

Column 406, line 1, in Claim 49, delete "$R_2$, is" and insert -- $R_2$ is --, therefor.

Column 406, line 6, in Claim 49, delete "$C_{3-7}$cycloalkyl," and insert -- $C_{3-7}$ cycloalkyl, --, therefor.

Column 406, line 7, in Claim 49, before "haloalkyl," insert -- $C_{1-4}$ --.

Column 406, line 16, in Claim 50, delete "Mechanesulfonyl" and insert -- Methanesulfonyl --, therefor.

```
SEQUENCE LISTING

<160> NUMBER OF SEQ ID NOS: 7

<210> SEQ ID NO 1
<211> LENGTH: 1191
<212> TYPE: DNA
<213> ORGANISM: Homo sapiens

<400> SEQUENCE: 1
atgtacccat acgacgtccc agactacgct ggaagcttgg aatcatcttt ctcatttgga      60
gtgatccttg ctgtcctggc ctccctcatc attgctacta acacactagt ggctgtggct     120
gtgctgctgt tgatccacaa gaatgatggt gtcagtctct gcttcacctt gaatctggct     180
gtggctgaca ccttgattgg tgtggccatc tctggcctac tcacagacca gctctccagc     240
ccttctcggc ccacacagaa gacccgtgtgc agcctgcgga tggcatttgt cacttcctcc     300
gcagctgcct ctgtcctcac ggtcatgctg atcacctttg acaggtacct tgccatcaag     360 cagccttcc gctacttgaa gatcatgagt gggttcgtgg ccgggggcctg cattgccggg     420 ctgtggttag tgtcttacct cattggcttc ctcccactcg gaatccccat gttccagcag     480
actgcctaca aagggcagtg cagcttcttt gctgtatttc accctcactt cgtgctgacc     540
ctctcctgcg ttggcttctt cccagccatg ctcctctttg tcttcttcta ctgcgacatg     600
ctcaagattg cctccatgca cagccagcag attcgaaaga tggaacatgc aggagccatg     660
gctggaggtt atcgatcccc acggactccc agcgacttca aagctctccg tactgtgtct     720
gttctcattg ggagctttgc tctatcctgg acccccttcc ttatcactgg cattgtgcag     780
gtggcctgcc aggagtgtca cctctaccta gtgctggaac ggtacctgtg gctgctcggc     840
gtgggcaact ccctgctcaa cccactcatc tatgcctatt ggcagaagga ggtgcgactg     900
cagctctacc acatggccct aggagtgaag aaggtgctca cctcattcct cctctttctc     960
```

-continued

```
tcggccagga attgtggccc agagaggccc agggaaagtt cctgtcacat cgtcactatc    1020
tccagctcag agtttgatgg cgaattcgga tccaagggca attctgcaga tatccagcac    1080
agtggcggcc gctcgagtct agagggcccg cggttcgaag gtaagcctat ccctaaccct    1140
ctcctcggtc tcgattctac gcgtaccggt catcatcacc atcaccattg a             1191
```

<210> SEQ ID NO 2
<211> LENGTH: 396
<212> TYPE: PRT
<213> ORGANISM: Homo sapiens

<400> SEQUENCE: 2

```
Met Tyr Pro Tyr Asp Val Pro Asp Tyr Ala Gly Ser Leu Glu Ser Ser
1               5                   10                  15

Phe Ser Phe Gly Val Ile Leu Ala Val Leu Ala Ser Leu Ile Ile Ala
            20                  25                  30

Thr Asn Thr Leu Val Ala Val Ala Val Leu Leu Leu Ile His Lys Asn
        35                  40                  45

Asp Gly Val Ser Leu Cys Phe Thr Leu Asn Leu Ala Val Ala Asp Thr
    50                  55                  60

Leu Ile Gly Val Ala Ile Ser Gly Leu Leu Thr Asp Gln Leu Ser Ser
65                  70                  75                  80

Pro Ser Arg Pro Thr Gln Lys Thr Leu Cys Ser Leu Arg Met Ala Phe
                85                  90                  95

Val Thr Ser Ser Ala Ala Ala Ser Val Leu Thr Val Met Leu Ile Thr
            100                 105                 110

Phe Asp Arg Tyr Leu Ala Ile Lys Gln Pro Phe Arg Tyr Leu Lys Ile
        115                 120                 125

Met Ser Gly Phe Val Ala Gly Ala Cys Ile Ala Gly Leu Trp Leu Val
    130                 135                 140

Ser Tyr Leu Ile Gly Phe Leu Pro Leu Gly Ile Pro Met Phe Gln Gln
145                 150                 155                 160

Thr Ala Tyr Lys Gly Gln Cys Ser Phe Phe Ala Val Phe His Pro His
                165                 170                 175

Phe Val Leu Thr Leu Ser Cys Val Gly Phe Phe Pro Ala Met Leu Leu
            180                 185                 190

Phe Val Phe Phe Tyr Cys Asp Met Leu Lys Ile Ala Ser Met His Ser
        195                 200                 205

Gln Gln Ile Arg Lys Met Glu His Ala Gly Ala Met Ala Gly Gly Tyr
    210                 215                 220

Arg Ser Pro Arg Thr Pro Ser Asp Phe Lys Ala Leu Arg Thr Val Ser
225                 230                 235                 240

Val Leu Ile Gly Ser Phe Ala Leu Ser Trp Thr Pro Phe Leu Ile Thr
                245                 250                 255

Gly Ile Val Gln Val Ala Cys Gln Glu Cys His Leu Tyr Leu Val Leu
            260                 265                 270

Glu Arg Tyr Leu Trp Leu Leu Gly Val Gly Asn Ser Leu Leu Asn Pro
        275                 280                 285

Leu Ile Tyr Ala Tyr Trp Gln Lys Glu Val Arg Leu Gln Leu Tyr His
    290                 295                 300

Met Ala Leu Gly Val Lys Lys Val Leu Thr Ser Phe Leu Leu Phe Leu
305                 310                 315                 320

Ser Ala Arg Asn Cys Gly Pro Glu Arg Pro Arg Glu Ser Ser Cys His
                325                 330                 335
```

```
Ile Val Thr Ile Ser Ser Glu Phe Asp Gly Glu Phe Gly Ser Lys
                340                 345                 350

Gly Asn Ser Ala Asp Ile Gln His Ser Gly Gly Arg Ser Ser Leu Glu
            355                 360                 365

Gly Pro Arg Phe Glu Gly Lys Pro Ile Pro Asn Pro Leu Leu Gly Leu
        370                 375                 380

Asp Ser Thr Arg Thr Gly His His His His His His
385                 390                 395

<210> SEQ ID NO 3
<211> LENGTH: 24
<212> TYPE: DNA
<213> ORGANISM: Artificial
<220> FEATURE:
<223> OTHER INFORMATION: Homo sapiens Primer

<400> SEQUENCE: 3
cattgccggg ctgtggttag tgtc                                      24

<210> SEQ ID NO 4
<211> LENGTH: 24
<212> TYPE: DNA
<213> ORGANISM: Artificial
<220> FEATURE:
<223> OTHER INFORMATION: Homo sapiens Primer

<400> SEQUENCE: 4
ggcatagatg agtgggttga gcag                                      24

<210> SEQ ID NO 5
<211> LENGTH: 22
<212> TYPE: DNA
<213> ORGANISM: Artificial
<220> FEATURE:
<223> OTHER INFORMATION: Rat Primer

<400> SEQUENCE: 5 catgggcect gcaccttctt tg                                        22

<210> SEQ ID NO 6
<211> LENGTH: 24
<212> TYPE: DNA
<213> ORGANISM: Artificial
<220> FEATURE:
<223> OTHER INFORMATION: Rat Primer

<400> SEQUENCE: 6
gctccggatg gctgatgata gtga                                      24

<210> SEQ ID NO 7
<211> LENGTH: 23
<212> TYPE: PRT
<213> ORGANISM: Artificial
<220> FEATURE:
<223> OTHER INFORMATION: Chemically synthesized peptide

<400> SEQUENCE: 7

Arg Gly Pro Glu Arg Thr Arg Glu Ser Ala Tyr His Ile Val Thr Ile
1               5                   10                  15

Ser His Pro Glu Leu Asp Gly
            20
```